US012790347B2

(12) United States Patent
Zhao et al.

(10) Patent No.: US 12,790,347 B2
(45) Date of Patent: Nov. 10, 2026

(54) CLASS OF FUSED RING COMPOUNDS, AND PREPARATION AND USE THEREOF

(71) Applicant: CSPC Zhongqi Pharmaceutical Technology (Shijiazhuang) Co., Ltd, Shijiazhuang (CN)

(72) Inventors: Chuanwu Zhao, Shijiazhuang (CN); Zhenyu Wang, Shijiazhuang (CN); Chaozai Zhang, Shijiazhuang (CN); Fei Qi, Shijiazhuang (CN); Liqian Chen, Shijiazhuang (CN); Chunhua Jiang, Shijiazhuang (CN); Lixue Fan, Shijiazhuang (CN); Xiaoling Chai, Shijiazhuang (CN); Chunna Li, Shijiazhuang (CN); Yan Zhang, Shijiazhuang (CN)

(73) Assignee: CSPC Zhongqi Pharmaceutical Technology (Shijiazhuang) Co., Ltd, Shijiazhuang (CN)

( * ) Notice: Subject to any disclaimer, the term of this patent is extended or adjusted under 35 U.S.C. 154(b) by 702 days.

(21) Appl. No.: 18/028,960

(22) PCT Filed: Sep. 27, 2021

(86) PCT No.: PCT/CN2021/121023

§ 371 (c)(1),
(2) Date: Mar. 28, 2023

(87) PCT Pub. No.: WO2022/063303

PCT Pub. Date: Mar. 31, 2022

(65) Prior Publication Data

US 2024/0294545 A1 Sep. 5, 2024

(30) Foreign Application Priority Data

Sep. 28, 2020 (CN) ......................... 202011044828.9
Aug. 5, 2021 (CN) ......................... 202110905531.5

(51) Int. Cl.

| | |
|---|---|
| ***C07D 498/16*** | (2006.01) |
| ***A61K 31/4745*** | (2006.01) |
| ***A61K 31/551*** | (2006.01) |
| ***A61K 31/553*** | (2006.01) |
| ***A61K 31/554*** | (2006.01) |
| ***A61K 45/06*** | (2006.01) |
| ***A61P 35/00*** | (2006.01) |
| ***C07D 471/16*** | (2006.01) |
| ***C07D 498/22*** | (2006.01) |
| ***C07D 513/16*** | (2006.01) |
| ***C07D 519/00*** | (2006.01) |

(52) U.S. Cl.

CPC ........ *C07D 498/16* (2013.01); *A61K 31/4745* (2013.01); *A61K 31/551* (2013.01); *A61K 31/553* (2013.01); *A61K 31/554* (2013.01); *A61K 45/06* (2013.01); *A61P 35/00* (2018.01); *C07D 471/16* (2013.01); *C07D 498/22* (2013.01); *C07D 513/16* (2013.01); *C07D 519/00* (2013.01)

(58) Field of Classification Search

CPC .. C07D 498/16; C07D 471/16; C07D 498/22; C07D 513/16; C07D 519/00; A61K 31/4745; A61K 31/551; A61K 31/553; A61K 31/554; A61K 45/06; A61P 35/00

See application file for complete search history.

(56) References Cited

U.S. PATENT DOCUMENTS

| | | | |
|---|---|---|---|
| 10,745,399 | B2 | 8/2020 | Fuchss |
| 2020/0165254 | A1 | 5/2020 | Zhao et al. |
| 2023/0286981 | A1 | 9/2023 | Barlaam et al. |

FOREIGN PATENT DOCUMENTS

| | | | |
|---|---|---|---|
| AU | 2016323399 | A1 | 5/2018 |
| AU | 2021349904 | B2 | 2/2024 |
| CN | 102372711 | A | 3/2012 |

(Continued)

OTHER PUBLICATIONS

Pike, K. G. et al. The Identification of Potent, Selective, and Orally Available Inhibitors of Ataxia Telangiectasia Mutated (ATM) Kinase: The Discovery of AZDO156. J. Med. Chem. 2018, 61, 3823-3841. (Year: 2018).*

(Continued)

*Primary Examiner* — Jeffrey H Murray
*Assistant Examiner* — Kristen W Romero
(74) *Attorney, Agent, or Firm* — McCarter & English, LLP; Wei Song

(57) ABSTRACT

The present invention relates to a class of fused ring compounds that have a structure represented by formula (I')

(I')

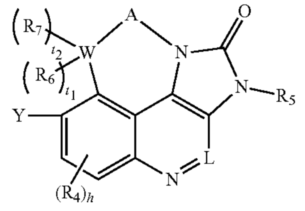

wherein the variables are defined in the description, and the preparation and use of the compounds thereof. Test results demonstrate that the compounds significantly inhibit the Ataxia-Telangiectasia Mutated (ATM) kinase activity, exhibit good selectivity for the ATM target, and are useful for treating cancer.

36 Claims, No Drawings

(56) References Cited

FOREIGN PATENT DOCUMENTS

| | | | |
|---|---|---|---|
| CN | 102399218 | A | 4/2012 |
| CN | 108137576 | A | 6/2018 |
| CN | 111747952 | A | 10/2020 |
| EP | 4219499 | A1 | 8/2023 |
| JP | 2016-531226 | A | 10/2016 |
| RU | 2017138100 | A | 5/2019 |
| WO | 2017/046216 | A1 | 3/2017 |
| WO | 2022/063303 | A1 | 3/2022 |

OTHER PUBLICATIONS

Johnson, T. W. et al. Design and Synthesis of Novel N-Hydroxy-Dihydronaphthyridinones as Potent and Orally Bioavailable HIV-1 Integrase Inhibitors J. Med. Chem. 2011, 54, 3393-3417. (Year: 2011).*

Wolff, et al. Burger's Medicinal Chemistry and Drug Discovery. 5th Ed. Part 1, 1995. p. 975-977. (Year: 1995).*

Banker, G. S. Modern Pharmaceutics, 3rd ed. 1996. p. 596. (Year: 1996).*

STN search. RN 1315370-90-1. Entered into STN on Aug. 8, 2011. See examiner's search results. (Year: 2011).*

Zheng et al., Palladium-catalyzed intermolecular oxidative cyclization of N-aryl enamines with isocyanides through double sp(2) C—H bonds cleavage: facile synthesis of 4-aminoquinoline derivatives. Org Biomol Chem. Apr. 28, 2015;13(16):4657-60.

International Search Report and Written Opinion for Application No. PCT/CN2021/121023, dated Dec. 29, 2021, 13 pages.

Savitsky et al., A single ataxia telangiectasia gene with a product similar to PI-3 kinase. Science. Jun. 23, 1995;268(5218):1749-53.

* cited by examiner

CLASS OF FUSED RING COMPOUNDS, AND PREPARATION AND USE THEREOF

CROSS-REFERENCE TO RELATED APPLICATION

The present disclosure is a U.S. National Stage Application filed under 35 U.S.C. § 371, based on International Patent Application No. PCT/CN2021/121023, filed on Sep. 27, 2021, which claims priority to Chinese patent application No. 202011044828.9, filed on Sep. 28, 2020, and entitled "A CLASS OF FUSED RING COMPOUNDS, AND PREPARATION AND USE THEREOF", and to Chinese patent application No. 202110905531.5, filed on Aug. 5, 2021, and entitled "A CLASS OF FUSED RING COMPOUNDS, AND PREPARATION AND USE THEREOF", each of which is incorporated by reference herein in its entirety.

TECHNICAL FIELD

The present disclosure belongs to the technical field of medicines, and specifically relates to a class of novel compounds with ATM protein kinase inhibitory activity and use of the compounds or the pharmaceutical compositions comprising thereof in the preparation of medicaments.

BACKGROUND

Ataxia-telangiectasia (A-T) is an autosomal recessive hereditary disease, which mostly shows clinical features like progressive cerebellar ataxia beginning in early childhood, facial telangiectasia, increased sensitivity to radiation exposure, an enhanced frequency of malignancy and so on (Taylor A M, Harnden D G, Arlett C F, et al. Ataxia telangiectasia: a human mutation with abnormal radiation sensitivity. Nature, 1975, 258: 427-429). At present, it is known that it is caused by a mutation in ataxia telangiectasia mutated gene (ATM gene). The ATM gene is mapped to chromosome 11q22-23 with a length of 150 kb and 66 exons, which is one of human genes with the most exons found so far (Savitsky K, Bar Shira A, Gilad S, et al. A single ataxia telangiectasia gene with a product similar to PI-3 kinase. Science, 1995, 268 (5218): 1749-1753).

ATM protein kinase is a product encoded by the ATM gene, which is a serine/threonine protein kinase consisting of 3056 amino acids with a relative molecular weight of about 350 kDa (CHEN G, LEE E. The product of the ATM gene is a 370-kDa nuclear phosphoprotein. J Biol Chem, 1996, 271(52): 33693-33697), as a member of the phosphatidylinositol 3-kinase-related kinase (PIKK) family (Watters D, Khanna K K, Beamish H, et al. Cellular localisation of the ataxia-telangiectasia (ATM) gene product and discrimination between mutated and normal forms. Oncogene, 1997, 14: 1911-1921). It is distributed in nucleus and cytoplasm, and ubiquitously in higher eukaryotic tissues and cells, and highly expressed in tissues and cells, such as testis, spleen, and thymus. The ATM participates in regulation of cell cycle and identification and repair of DNA damage through its functional domain at the C terminal, and plays a role in cell signal transduction pathway, including activation of cell cycle checkpoints (Canman C E, Lim D S, Cimprich K A et al. Activation of the ATM kinase by ionizing radiation and phosphorylation of p53. Science, 1998, 281:1677-1679), regulation of DNA damage repair (matsuoka S, huang M, elledge S J. linkage of ATM to cell cycle regulation by the Chk2 protein kinase. Science 1998; 282: 1893-1897), regulation of telomeres (Kishi S, Lu K P. A critical role for Pin2/TRF1 in ATM-dependent regulation. Inhibition of Pin2/TRF1 function complements telomere shortening, radio sensitivity, and the G(2)/M checkpoint defect of ataxia-telangiectasia cells. Journal Bio Chem. 2002, 277(9): 7420-7429), and regulation of apoptosis (Lee Y, Barnes D E, Lindahl T, et al. Defective neurogenesis resulting from DNAligase IV deficiency requires Atm. Genes Dev. 2000, 14: 2576-2580).

The ATM protein kinase mainly plays a role in repairing DNA double-strand breaks, and maintains DNA stability by mediating phosphorylation of downstream effectors. DNA double-strand break (DSB) occurs when DNA double-strand damage is induced by ionizing radiation or ultraviolet radiation. MRE11-RAD50-NBS1 (MRN) complex senses the DSB and initiates the DNA repair, thereby recruiting the ATM protein kinases. The ATM protein kinase, as a main sensor in DSB repair, is recruited and subjected to interaction with other proteins. A homodimer of ATM is dissociated into active monomers at a DSB site, and the monomer is catalytically activated through autophosphorylation and acetylation, thereby promoting the repair of broken DNA in cooperation with other proteins (Lee J H, Paull T T, Activation and regulation of ATM kinase activity in response to DNA double-strand breaks. Oncogene. 2007, 26(56): 7741-7748).

The ATM may also regulate the cell cycle through Chk2-p53/AKT pathway to affect the proliferation and apoptosis of tumor cells (Lazzaro F, Giannattasio M, Puddu F, et al. Checkpoint mechanisms at the interaction between DNA damage and repair. DNARepair, 2009, 8 (9): 1055-1067). At the same time, the activated ATM may also affect the occurrence, migration, and invasion of a tumor via ATM-AKT-GSK-3β pathway, transcription regulatory factor NF-κB, and interleukin-8, and participate in DNA damage response through different mechanisms, thus leading to an increase in tolerance and resistance of tumor cells to radiotherapy and chemotherapy (Bo Peng, Janice Ortega, et al. Phosphorylation of proliferating cell nuclear antigen promotes cancer progression by activating the ATM/AKT/GSK3P/Snail signaling pathway. JBC, 2019 (295) 9767).

In the present clinical researches, ATM inhibitors are mostly combined with radiotherapy and chemotherapy. Among the molecules under clinical research are AZD-1390 (AstraZeneca) and M-3541 (Merck, Germany).

The related diseases that ATM kinase inhibitors are capable of treating are solid tumors or hematological tumors.

AZD-1390

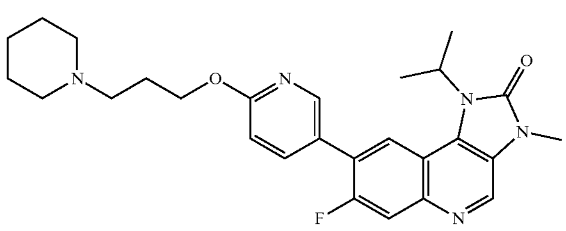

SUMMARY

[Fused Ring Compound]

The present disclosure provides a class of compounds with novel structures as ATM kinase inhibitors.

Specifically, the present disclosure provides a compound as represented by formula (I') or a prodrug, tautomer, optical isomer, geometric isomer, solvate, isotopic derivative, or pharmaceutically acceptable salt thereof, having the following structure:

(I')

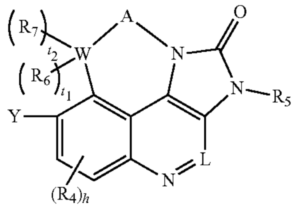

wherein

Y is

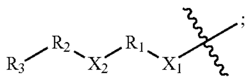

;

$X_1$ is selected from the group consisting of a bond, hydrogen, deuterium, halogen, hydroxyl, amino, nitro, cyano, —O—, S—, —C(O)—, —C(O)O—, —OC(O)—, —N(R)$_{1x}$C(O)—, —C(O)N($R_{1x}$)—, and —N($R_{1x}$)—; $R_{1x}$ is selected from the group consisting of hydrogen and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said optionally substituted means that hydrogen on a group to be substituted is not substituted or hydrogen on one or more substitution sites of the group to be substituted is independently substituted by a substituent selected from the group consisting of halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $X_1$ is hydrogen, deuterium, halogen, hydroxyl, amino, nitro, or cyano, $R_1$, $X_2$, $R_2$, and $R_3$ are absent;

$R_1$ is absent or selected from the group consisting of a bond, hydrogen, deuterium, and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocyclyl, $C_{6-14}$ aryl, 5- to 12-membered heteroaryl, 4- to 12-membered bridged ring group, 4- to 12-membered heterobridged ring group, monospiro ring group, heteromonospiro ring group, condensed ring group, and heterocondensed ring group; said optionally substituted means that hydrogen on a group to be substituted is not substituted or hydrogen on one or more substitution sites of the group to be substituted is independently substituted by $R_{1a}$; $R_{1a}$ is, for each presence, independently selected from the group consisting of deuterium, halogen, hydroxyl, amino, nitro, mercapto, cyano, oxo, —$R_{1b}$, —O$R_{1b}$, —S$R_{1b}$, —S(O)$R_{1b}$, —$SO_2$($R_{1b}$), —C(O)$R_{1b}$, —C(O)O$R_{1b}$, —OC(O)$R_{1b}$, —NH($R_{1b}$), —N($R_{1b}$)($R_{1c}$), —C(O)NH($R_{1b}$), —C(O)N($R_{1b}$)($R_{1c}$), —NHC(O)($R_{1b}$), —N($R_{1b}$)C(O)($R_{1c}$), —S(O)NH($R_{1b}$), —S(O)N($R_{1b}$)($R_{1c}$), —$SO_2$NH($R_{1b}$), —$SO_2$N($R_{1b}$)($R_{1c}$), —NHS(O)($R_{1b}$), —N($R_{1b}$)S(O)($R_{1c}$), —NH$SO_2$($R_{1b}$), and —N($R_{1b}$)$SO_2$($R_{1c}$); $R_{1b}$ and $R_{1c}$ are, for each presence, independently selected from the group consisting of hydrogen, deuterium, and any one of $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl which is optionally substituted by one or more of deuterium, halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{1b}$ and $R_{1c}$ are linked to the same nitrogen atom, $R_{1b}$ and $R_{1c}$, together with the nitrogen atom linked thereto, form 3- to 10-membered heterocycloalkyl or 5- to 12-membered heteroaryl which is optionally substituted by one or more of deuterium, halogen, hydroxyl, amino, nitro, mercapto, cyano, oxo, $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $R_1$ is hydrogen or deuterium, $X_2$, $R_2$, and $R_3$ are absent;

$X_2$ is absent or selected from the group consisting of a bond, hydrogen, deuterium, halogen, hydroxyl, amino, nitro, mercapto, cyano, —O—, —S—, —P—, —C(O)—, —C(S)—, —C(=N—$R_{2x}$)—, —CH=N—, —C(O)O—, —C(O)C(O)—, —OC(O)—, —OC(S)—, —O—$SO_2$—, —O—P(O)—, —N=CH—, —C(O)N($R_{2x}$)—, —N($R_{2x}$)C(O)—, —N($R_{2x}$)—, —S(O)—, —$SO_2$—, —S(O)N($R_{2x}$)—, —$SO_2$N($R_{2x}$)—, and —P(O)—; $R_{2x}$ is selected from the group consisting of hydrogen, deuterium, and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said optionally substituted means that hydrogen on a group to be substituted is not substituted or hydrogen on one or more substitution sites of the group to be substituted is independently substituted by a substituent selected from the group consisting of deuterium, halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $X_2$ is hydrogen, deuterium, halogen, hydroxyl, amino, nitro, mercapto, or cyano, $R_2$ and $R_3$ are absent;

$R_2$ is absent or selected from the group consisting of a bond, hydrogen, deuterium, and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, $C_{6-14}$ aryl, 3- to 10-membered heterocycloalkyl, 5- to 12-membered heteroaryl, 4- to 12-membered bridged ring group, 4- to 12-membered heterobridged ring group, monospiro ring group, heteromonospiro ring group, condensed ring group, and heterocondensed ring group; said optionally substituted means that hydrogen on a group to be substituted is not substituted or hydrogen on one or more substitution sites of the group to be substituted is independently substituted by $R_{2a}$; $R_{2a}$ is, for each presence, independently selected from the group consisting of deuterium, halogen, hydroxyl, amino, nitro, mercapto, cyano, oxo, —$R_{2b}$, —$OR_{2b}$, —$SR_{2b}$, —S(O)($R_{2b}$), —$SO_2$($R_{2b}$), —C(O)$R_{2b}$, —C(O)O$R_{2b}$, —OC(O)$R_{2b}$, —NH($R_{2b}$), —N($R_{2b}$)($R_{2c}$), —C(O)NH($R_{2b}$), —C(O)N($R_{2b}$)($R_{2c}$), —NHC(O)($R_{2b}$), —N($R_{2b}$)C(O)($R_{2c}$), —S(O)NH($R_{2b}$), —S(O)N($R_{2b}$)($R_{2c}$), —$SO_2$NH($R_{2b}$), —$SO_2$N($R_{2b}$)($R_{2c}$), —NHS(O)($R_{2b}$), —N($R_{2b}$)S(O)($R_{2c}$), —NH$SO_2$($R_{2b}$), and —N($R_{2b}$)$SO_2$($R_{2c}$); $R_{2b}$ and $R_{2c}$ are, for each presence, independently selected from the group consisting of hydrogen, any one of $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl which is optionally substituted by one or more of deuterium, halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{2b}$ and $R_{2e}$ are linked to the same nitrogen atom, $R_{2b}$ and $R_{2c}$, together with the nitrogen atom linked thereto, form 3- to 10-membered heterocycloalkyl or 5- to 12-membered heteroaryl which is optionally substituted by one or more of deuterium, halogen, hydroxyl, amino, nitro, mercapto, cyano, oxo, $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $R_2$ is hydrogen or deuterium, $R_3$ is absent;

$R_3$ is absent or selected from the group consisting of hydrogen, deuterium, halogen, hydroxyl, amino, nitro, mercapto, cyano, oxo, —$R_{3b}$, —$OR_{3b}$, —$SR_{3b}$, —S(O)($R_{3b}$), —$SO_2$($R_{3b}$), —C(O)$R_{3b}$, —C(O)O$R_{3b}$, —OC(O)$R_{3b}$, —NH($R_{3b}$), —N($R_{3b}$)($R_{3c}$), —C(O)NH($R_{3b}$), —C(O)N($R_{3b}$)($R_{3c}$), —NHC(O)($R_{3b}$), —N($R_{3b}$)C(O)($R_{3c}$), —S(O)NH($R_{3b}$), —S(O)N($R_{3b}$)($R_{3c}$), —$SO_2$NH($R_{3b}$), —$SO_2$N($R_{3b}$)($R_{3c}$), —NHS(O)($R_{3b}$), —N($R_{3b}$)S(O)($R_{3c}$), —NH$SO_2$($R_{3b}$), and —N($R_{3b}$)$SO_2$($R_{3c}$); $R_{3b}$ and $R_{3c}$ are, for each presence, independently selected from the group consisting of hydrogen, deuterium, and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{3b}$ and $R_{3c}$ are linked to the same nitrogen atom, $R_{3b}$ and $R_{3c}$, together with the nitrogen atom linked thereto, form an optionally substituted group selected from 3- to 20-membered heterocyclyl and 5- to 12-membered heteroaryl; said optionally substituted means that hydrogen on a group to be substituted is not substituted or hydrogen on one or more substitution sites of the group to be substituted is independently substituted by $R_{3d}$; $R_{3d}$ is, for each presence, independently selected from the group consisting of deuterium, halogen, hydroxyl, amino, nitro, mercapto, cyano, oxo, —$R_{3e}$, —$OR_{3e}$, —$SR_{3e}$, —S(O)($R_{3e}$), —$SO_2$($R_{3e}$), —C(O)$R_{3e}$, —C(O)O$R_{3e}$, —OC(O)$R_{3e}$, —NH($R_{3e}$), —N($R_{3e}$)($R_{3f}$), —C(O)NH($R_{3e}$), —C(O)N($R_{3e}$)($R_{3f}$), —NHC(O)($R_{3e}$), —N($R_{3e}$)C(O)($R_{3f}$), —S(O)NH($R_{3e}$), —S(O)N($R_{3e}$)($R_{3f}$), —$SO_2$NH($R_{3e}$), —$SO_2$N($R_{3e}$)($R_{3f}$), —NHS(O)($R_{3e}$), —N($R_{3e}$)S(O)($R_{3f}$), —NH$SO_2$($R_{3e}$), and —N($R_{3e}$)$SO_2$($R_{3f}$); $R_{3e}$ and $R_{3f}$ are, for each presence, independently selected from the group consisting of hydrogen, deuterium, and any one of $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl which is optionally substituted by one or more of halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{3e}$ and $R_{3f}$ are linked to the same nitrogen atom, $R_{3e}$ and $R_{3f}$, together with the nitrogen atom linked thereto, form 3- to 10-membered heterocycloalkyl or 5- to 12-membered heteroaryl which is optionally substituted by one or more of deuterium, halogen, hydroxyl, amino, nitro, mercapto, cyano, oxo, $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

$R_4$ is, for each presence, independently selected from the group consisting of hydrogen, deuterium, halogen, nitro, amino, cyano, hydroxyl, carboxyl, mercapto, and any one of $C_{1-6}$ alkyl, $C_{1-6}$ alkoxy, and $C_{1-6}$ alkthio which is optionally substituted by one or more of deuterium, halogen, hydroxyl, and amino;

h is equal to 1 or 2;

$R_5$ is, for each presence, independently selected from the group consisting of hydrogen, deuterium, halogen, hydroxyl, and any one of $C_{1-6}$ alkyl, $C_{1-6}$ alkoxy, $C_{1-6}$ alkthio, $C_{3-10}$ cycloalkyl, $C_{6-14}$ aryl, 3- to 10-membered heterocycloalkyl, and 5- to 12-membered heteroaryl which is optionally substituted by one or more of deuterium, halogen, hydroxyl, amino, and cyano;

L is C($R_L$) or N;

$R_L$ is, for each presence, independently selected from the group consisting of hydrogen, deuterium, halogen, nitro, amino, cyano, hydroxyl, carboxyl, mercapto, $C_{1-6}$ alkyl, $C_{1-6}$ alkoxy, and $C_{1-6}$ alkthio;

A is

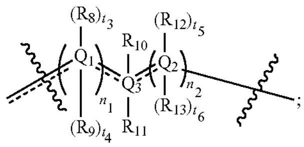
;

wherein ------ represents a single bond or a double bond; $Q_1$ is linked to W;

$t_1$, $t_2$, $t_3$, $t_4$, $t_5$, and $t_6$ are independently equal to 0 or 1;

$n_1$ and $n_2$ are independently equal to 0, 1, or 2, and $n_1$ and $n_2$ are not simultaneously equal to 0, wherein $n_1$ represents sequentially linked chain of $Q_1$ with $n_1$ repeat units, and $n_2$ represents sequentially linked chain of $Q_2$ with $n_2$ repeat units; two adjacent $Q_1$ are linked by a single bond or a double bond; two adjacent $Q_2$ are linked by a single bond or a double bond;

W, $Q_1$, and $Q_2$ are independently selected from the group consisting of C, O, N, and S;

$Q_3$ is C; when one of the bonds linked to $Q_3$ is a double bond, $R_{10}$ or $R_{11}$ is absent;

$R_6$, $R_7$, $R_8$, $R_9$, $R_{10}$, $R_{11}$, $R_{12}$, and $R_{13}$ are, for each presence, independently selected from the group consisting of hydrogen, deuterium, halogen, hydroxyl, amino, cyano, nitro, —$R_{6a}$, —$OR_{6a}$, —$SR_{6a}$, —S(O)($R_{6a}$), —$SO_2$($R_{6a}$), —C(O)$R_{6a}$, —C(O)O$R_{6a}$, —OC(O)$R_{6a}$, —NH($R_{6a}$), —N($R_{6a}$)($R_{6b}$), —C(O)NH($R_{6a}$), —C(O)N($R_{6a}$)($R_{6b}$), —NHC(O)($R_{6a}$), —N($R_{6a}$)C(O)($R_{6b}$), —S(O)NH($R_{6a}$), —S(O)N($R_{6a}$)($R_{6b}$), —$SO_2$NH ($R_{6a}$), —$SO_2N(R_{6a})(R_{6b})$, —$NHS(O)(R_{6a})$, —$N(R_{6a})S(O)(R_{6b})$, —$NHSO_2(R_{6a})$, and —$N(R_{6a})SO_2(R_{6b})$; or any two substituents linked to the same atom among $R_6$, $R_7$, $R_8$, $R_9$, $R_{10}$, $R_{11}$, $R_{12}$, and $R_{13}$ form =O, =N—$R_{6a}$, or =CH—$R_{6a}$; or any two adjacent atoms among W, each present $Q_1$, each present $Q_2$, and $Q_3$, together with the substituents linked thereto, form $C_{3-10}$ carbocyclyl, 3- to 10-membered heterocyclyl, $C_{6-14}$ aryl, 5- to 12-membered heteroaryl, 4- to 12-membered bridged ring group, 4- to 12-membered heterobridged ring group, monospiro ring group, heteromonospiro ring group, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl, 3- to 10-membered heterocyclyl, $C_{6-14}$ aryl, 5- to 12-membered heteroaryl, monospiro ring group, or heteromonospiro ring group which is optionally substituted by $R_{6c}$;

$R_{6a}$ and $R_{6b}$ are, for each presence, independently selected from the group consisting of hydrogen, deuterium, and any one of $C_{1-6}$ alkyl, $C_{2-6}$ alkenyl, $C_{2-6}$ alkynyl, $C_{1-6}$ alkoxy, $C_{3-10}$ carbocyclyl, 3- to 10-membered heterocyclyl, $C_{6-14}$ aryl, 5- to 12-membered heteroaryl, 4- to 12-membered bridged ring group, 4- to 12-membered heterobridged ring group, monospiro ring group, heteromonospiro ring group, condensed ring group, and heterocondensed ring group which is optionally substituted by $R_{6c}$; or when $R_{6a}$ and $R_{6b}$ are linked to the same nitrogen atom, $R_{6a}$ and $R_{6b}$, together with the nitrogen atom linked thereto, form 3- to 10-membered heterocyclyl or 5- to 12-membered heteroaryl which is optionally substituted by $R_{6c}$;

$R_{6c}$ is, for each presence, independently selected from the group consisting of hydrogen, deuterium, halogen, hydroxyl, amino, cyano, nitro, azido, oxo, —$R_{6d}$, —$OR_{6d}$, —$N(R_{6d})R_{6e}$, —$C(O)R_{6d}$, —$C(O)N(R_{6d})R_{6e}$, —$N(R_{6d})C(O)R_{6e}$, —$C(O)OR_{6d}$, —$OC(O)R_{6d}$, —$S(O)N(R_{6d})(R_{6e})$, —$SO_2N(R_{6d})(R_{6e})$, —$N(R_{6d})S(O)(R_{6e})$, —$N(R_{6d})SO_2(R_{6e})$, =N—$R_{6d}$, and =CH—$R_{6d}$; said oxo means that two hydrogens on the same substitution site are replaced by the same oxygen to form a double bond; said =N—$R_{6d}$ means that two hydrogens on the same substitution site are replaced by the same nitrogen to form a double bond, and said nitrogen is substituted by $R_{6d}$; said =CH—$R_{6d}$ means that two hydrogens on the same substitution site are replaced by the same carbon to form a double bond, and said carbon is substituted by $R_{6d}$;

$R_{6d}$ and $R_{6e}$ are, for each presence, independently selected from the group consisting of hydrogen, deuterium, halogen, hydroxyl, amino, nitro, cyano, and an optionally substituted group selected from $C_{1-6}$ alkyl, $C_{2-6}$ alkenyl, $C_{2-6}$ alkynyl, $C_{1-6}$ alkoxy, $C_{3-10}$ carbocyclyl, 3- to 10-membered heterocycloalkyl, $C_{6-14}$ aryl, 5- to 12-membered heteroaryl, monospiro ring group, heteromonospiro ring group, condensed ring group, and heterocondensed ring group; or when $R_{6d}$ and $R_{6e}$ are linked to the same nitrogen atom, $R_{6d}$ and $R_{6e}$, together with the nitrogen atom linked thereto, form an optionally substituted group selected from 3- to 10-membered heterocyclyl and 5- to 12-membered heteroaryl; said optionally substituted means that hydrogen on a group to be substituted is not substituted or hydrogen on one or more substitution sites of the group to be substituted is independently substituted by $R_{6f}$; $R_{6f}$ is, for each presence, independently selected from the group consisting of hydrogen, deuterium, halogen, hydroxyl, amino, nitro, mercapto, cyano, oxo, —$C(O)C_{1-6}$ alkyl, —C(O)O—$C_{1-6}$ alkyl, —OC(O)—$C_{1-6}$ alkyl, —NH($C_{1-6}$ alkyl), —N($C_{1-6}$ alkyl)($C_{1-6}$ alkyl), —C(O)NH—$C_{1-6}$ alkyl, —NHC(O)—$C_{1-6}$ alkyl, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when the heterocycloalkyl, heteroaryl, heterocyclyl, heteromonospiro ring group, heterocondensed ring group and/or heterobridged ring group is present, the heteroatom thereof is independently selected from the group consisting of O, N, and S, and the number of the heteroatom is 1, 2, 3, or 4.

The present disclosure further provides a compound as represented by formula (I) or a prodrug, tautomer, optical isomer, geometric isomer, solvate, isotopic derivative, or pharmaceutically acceptable salt thereof, having the following structure:

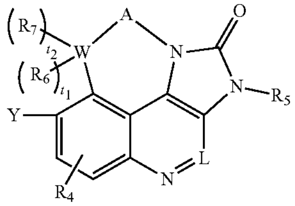

(I)

wherein

Y is

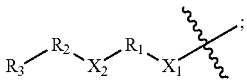

$X_1$ is selected from the group consisting of a bond, hydrogen, halogen, hydroxyl, amino, nitro, cyano, —O—, —S—, —C(O)—, —C(O)O—, —OC(O)—, —$N(R_{1x})C(O)$—, —$C(O)N(R_{1x})$—, and —$N(R_{1x})$—; $R_{1x}$ is selected from the group consisting of hydrogen and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said optionally substituted means that hydrogen on a group to be substituted is not substituted or hydrogen on one or more substitution sites of the group to be substituted is independently substituted by a substituent selected from the group consisting of halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $X_1$ is hydrogen, halogen, hydroxyl, amino, nitro, or cyano, $R_1$, $X_2$, $R_2$, and $R_3$ are absent;

$R_1$ is absent or selected from the group consisting of a bond, hydrogen, and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, 5- to 12-membered heteroaryl, 4- to 12-membered bridged ring group, 4- to 12-membered heterobridged ring group, monospiro ring group, heteromonospiro ring group, condensed ring group, and heterocondensed ring group; said optionally substituted means that hydrogen on a group to be substituted is not substituted or hydrogen on one or more substitution sites of the group to be substituted is independently substituted by $R_{1a}$; $R_{1a}$ is, for each presence, independently selected from the group consisting of halogen, hydroxyl, amino, nitro, mercapto, cyano, oxo, —$R_{1b}$, —$OR_{1b}$, —$SR_{1b}$, —$S(O)R_{1b}$, —$SO_2(R_{1b})$, —$C(O)R_{1b}$, —$C(O)OR_{1b}$, —$OC(O)R_{1b}$, —$NH(R_{1b})$, —$N(R_{1b})(R_{1c})$, —$C(O)NH(R_{1b})$, —$C(O)N(R_{1b})(R_{1c})$, —$NHC(O)(R_{1b})$, —$N(R_{1b})C(O)(R_{1c})$, —$S(O)NH(R_{1b})$, —$S(O)N(R_{1b})(R_{1c})$, —$SO_2NH(R_{1b})$, —$SO_2N(R_{1b})(R_{1c})$, —$NHS(O)(R_{1b})$, —$N(R_{1b})S(O)(R_{1c})$, —$NHSO_2(R_{1b})$, and —$N(R_{1b})SO_2(R_{1c})$; $R_{1b}$ and $R_{1c}$ are, for each presence, independently selected from the group consisting of hydrogen and any one of $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl which is optionally substituted by one or more of halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{1b}$ and $R_{1c}$ are linked to the same nitrogen atom, $R_{1b}$ and $R_{1c}$, together with the nitrogen atom linked thereto, form 3- to 10-membered heterocycloalkyl or 5- to 12-membered heteroaryl which is optionally substituted by one or more of halogen, hydroxyl, amino, nitro, mercapto, cyano, oxo, $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $R_1$ is hydrogen, $X_2$, $R_2$, and $R_3$ are absent;

$X_2$ is absent or selected from the group consisting of a bond, hydrogen, halogen, hydroxyl, amino, nitro, mercapto, cyano, —O—, —S—, —P—, —C(O)—, —C(S)—, —C(=N—$R_{2x}$)—, —CH=N—, —C(O)O—, —C(O)C(O)—, —OC(O)—, —OC(S)—, —O—$SO_2$—, —O—P(O)—, —N=CH—, —C(O)N($R_{2x}$)—, —N($R_{2x}$)C(O)—, —N($R_{2x}$)—, —S(O)—, —$SO_2$—, —S(O)N($R_{2x}$)—, —$SO_2N(R_{2x})$—, and —P(O)—; $R_{2x}$ is selected from the group consisting of hydrogen and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said optionally substituted means that hydrogen on a group to be substituted is not substituted or hydrogen on one or more substitution sites of the group to be substituted is independently substituted by a substituent selected from the group consisting of halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $X_2$ is hydrogen, halogen, hydroxyl, amino, nitro, mercapto, or cyano, $R_2$ and $R_3$ are absent;

$R_2$ is absent or selected from the group consisting of a bond, hydrogen and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, $C_{6-14}$ aryl, 3- to 10-membered heterocycloalkyl, 5- to 12-membered heteroaryl, 4- to 12-membered bridged ring group, 4- to 12-membered heterobridged ring group, monospiro ring group, heteromonospiro ring group, condensed ring group, and heterocondensed ring group; said optionally substituted means that hydrogen on a group to be substituted is not substituted or hydrogen on one or more substitution sites of the group to be substituted is independently substituted by $R_{2a}$; $R_{2a}$ is, for each presence, independently selected from the group consisting of halogen, hydroxyl, amino, nitro, mercapto, cyano, oxo, —$R_{2b}$, —$OR_{2b}$, —$SR_{2b}$, —$S(O)(R_{2b})$, —$SO_2(R_{2b})$, —$C(O)R_{2b}$, —$C(O)OR_{2b}$, —$OC(O)R_{2b}$, —$NH(R_{2b})$, —$N(R_{2b})(R_{2c})$, —$C(O)NH(R_{2b})$, —$C(O)N(R_{2b})(R_{2c})$, —$NHC(O)(R_{2b})$, —$N(R_{2b})C(O)(R_{2c})$, —$S(O)NH(R_{2b})$, —$S(O)N(R_{2b})(R_{2c})$, —$SO_2NH(R_{2b})$, —$SO_2N(R_{2b})(R_{2c})$, —$NHS(O)(R_{2b})$, —$N(R_{2b})S(O)(R_{2c})$, —$NHSO_2(R_{2b})$, and —$N(R_{2b})SO_2(R_{2c})$; $R_{2b}$ and $R_{2e}$ are, for each presence, independently selected from the group consisting of hydrogen, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl which is optionally substituted by one or more of halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{2b}$ and $R_{2c}$ are linked to the same nitrogen atom, $R_{2b}$ and $R_{2c}$, together with the nitrogen atom linked thereto, form 3- to 10-membered heterocycloalkyl or 5- to 12-membered heteroaryl which is optionally substituted by one or more of halogen, hydroxyl, amino, nitro, mercapto, cyano, oxo, $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when $R_2$ is hydrogen, $R_3$ is absent;

$R_3$ is absent or selected from the group consisting of hydrogen, halogen, hydroxyl, amino, nitro, mercapto, cyano, oxo, —$R_{3b}$, —$OR_{3b}$, —$SR_{3b}$, —$S(O)(R_{3b})$, —$SO_2(R_{3b})$, —$C(O)R_{3b}$, —$C(O)OR_{3b}$, —$OC(O)R_{3b}$, —$NH(R_{3b})$, —$N(R_{3b})(R_{3c})$, —$C(O)NH(R_{3b})$, —$C(O)N(R_{3b})(R_{3c})$, —$NHC(O)(R_{3b})$, —$N(R_{3b})C(O)(R_{3c})$, —$S(O)NH(R_{3b})$, —$S(O)N(R_{3b})(R_{3c})$, —$SO_2NH(R_{3b})$, —$SO_2N(R_{3b})(R_{3c})$, —$NHS(O)(R_{3b})$, —$N(R_{3b})S(O)(R_{3c})$, —$NHSO_2(R_{3b})$, and —$N(R_{3b})SO_2(R_{3c})$; $R_{3b}$ and $R_{3c}$ are, for each presence, independently selected from the group consisting of hydrogen and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{3b}$ and $R_{3c}$ are linked to the same nitrogen atom, $R_{3b}$ and $R_{3c}$, together with the nitrogen atom linked thereto, form an optionally substituted group selected from 3- to 10-membered heterocycloalkyl and 5- to 12-membered heteroaryl; said optionally substituted means that hydrogen on a group to be substituted is not substituted or hydrogen on one or more substitution sites of the group to be substituted is independently substituted by $R_{3d}$; $R_{3d}$ is, for each presence, independently selected from the group consisting of halogen, hydroxyl, amino, nitro, mercapto, cyano, oxo, —$R_{3e}$, —$OR_{3e}$, —$SR_{3e}$, —S(O)($R_{3e}$), —$SO_2$($R_{3e}$), —C(O)$R_{3e}$, —C(O)O$R_{3e}$, —OC(O)$R_{3e}$, —NH($R_{3e}$), —N($R_{3e}$)($R_{3f}$), —C(O)NH($R_{3e}$), —C(O)N($R_{3e}$)($R_{3f}$), —NHC(O)($R_{3e}$), —N($R_{3e}$)C(O)($R_{3f}$), —S(O)NH($R_{3e}$), —S(O)N($R_{3e}$)($R_{3f}$), —$SO_2$NH($R_{3e}$), —$SO_2$N($R_{3e}$)($R_{3f}$), —NHS(O)($R_{3e}$), —N($R_{3e}$)S(O)($R_{3f}$), —NH$SO_2$($R_{3e}$), and —N($R_{3e}$)$SO_2$($R_{3f}$); $R_{3e}$ and $R_{3f}$ are, for each presence, independently selected from the group consisting of hydrogen and any one of $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl which is optionally substituted by one or more of halogen, hydroxyl, amino, nitro, mercapto, cyano, oxo, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{3e}$ and $R_{3f}$ are linked to the same nitrogen atom, $R_{3e}$ and $R_{3f}$, together with the nitrogen atom linked thereto, form 3- to 10-membered heterocycloalkyl or 5- to 12-membered heteroaryl which is optionally substituted by one or more of halogen, hydroxyl, amino, nitro, mercapto, cyano, oxo, $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

$R_4$ is selected from the group consisting of hydrogen, halogen, nitro, amino, cyano, hydroxyl, carboxyl, mercapto, and any one of $C_{1-6}$ alkyl, $C_{1-6}$ alkoxy, and $C_{1-6}$ alkthio which is optionally substituted by halogen, hydroxyl, or amino;

$R_5$ is selected from the group consisting of hydrogen, halogen, hydroxyl, and any one of $C_{1-6}$ alkyl, $C_{1-6}$ alkoxy, $C_{1-6}$ alkthio, $C_{3-10}$ cycloalkyl, $C_{6-14}$ aryl, 3- to 10-membered heterocycloalkyl, and 5- to 12-membered heteroaryl which is optionally substituted by one or more of halogen, hydroxyl, amino, and cyano;

L is C($R_L$) or N;

$R_L$ is selected from the group consisting of hydrogen, halogen, nitro, amino, cyano, hydroxyl, carboxyl, mercapto, $C_{1-6}$ alkyl, $C_{1-6}$ alkoxy, and $C_{1-6}$ alkthio;

A is

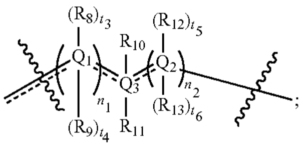

;

wherein ═══ represents a single bond or a double bond; $Q_1$ is linked to W;

$t_1$, $t_2$, $t_3$, $t_4$, $t_5$, and $t_6$ are independently equal to 0 or 1;

$n_1$ and $n_2$ are independently equal to 0, 1, or 2, and $n_1$ and $n_2$ are not simultaneously equal to 0, wherein $n_1$ represents sequentially linked chain of $Q_1$ with $n_1$ repeat units, and $n_2$ represents sequentially linked chain of $Q_2$ with $n_2$ repeat units; two adjacent $Q_1$ are linked by a single bond or a double bond; two adjacent $Q_2$ are linked by a single bond or a double bond;

W, $Q_1$, and $Q_2$ are independently selected from the group consisting of C, O, N, and S;

$Q_3$ is C; when one of the bonds linked to $Q_3$ is a double bond, $R_{10}$ or $R_{11}$ is absent;

$R_6$, $R_7$, $R_8$, $R_9$, $R_{10}$, $R_{11}$, $R_{12}$, and $R_{13}$ are, for each presence, independently selected from the group consisting of hydrogen, halogen, hydroxyl, amino, cyano, nitro, —$R_{6a}$, —$OR_{6a}$, —$SR_{6a}$, —S(O)($R_{6a}$), —$SO_2$($R_{6a}$), —C(O)$R_{6a}$, —C(O)O$R_{6a}$, —OC(O)$R_{6a}$, —NH($R_{6a}$), —N($R_{6a}$)($R_{6b}$), —C(O)NH($R_{6a}$), —C(O)N($R_{6a}$)($R_{6b}$), —NHC(O)($R_{6a}$), —N($R_{6a}$)C(O)($R_{6b}$), —S(O)NH($R_{6a}$), —S(O)N($R_{6a}$)($R_{6b}$), —$SO_2$NH($R_{6a}$), —$SO_2$N($R_{6a}$)($R_{6b}$), —NHS(O)($R_{6a}$), —N($R_{6a}$)S(O)($R_{6b}$), —NH$SO_2$($R_{6a}$), and —N($R_{6a}$)$SO_2$($R_{6b}$); or any two substituents linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with the substituents linked thereto, form $C_{3-10}$ carbocyclyl, 3- to 10-membered heterocyclyl, $C_{6-14}$ aryl, 5- to 12-membered heteroaryl, 4- to 12-membered bridged ring group, 4- to 12-membered heterobridged ring group, monospiro ring group, heteromonospiro ring group, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl, 3- to 10-membered heterocyclyl, $C_{6-14}$ aryl, 5- to 12-membered heteroaryl, monospiro ring group, or heteromonospiro ring group which is optionally substituted by $R_{6c}$;

$R_{6a}$ and $R_{6b}$ are, for each presence, independently selected from the group consisting of hydrogen and any one of $C_{1-6}$ alkyl, $C_{2-6}$ alkenyl, $C_{2-6}$ alkynyl, $C_{1-6}$ alkoxy, $C_{3-10}$ carbocyclyl, 3- to 10-membered heterocyclyl, $C_{6-14}$ aryl, 5- to 12-membered heteroaryl, 4- to 12-membered bridged ring group, 4- to 12-membered heterobridged ring group, monospiro ring group, heteromonospiro ring group, condensed ring group, and heterocondensed ring group which is optionally substituted by $R_{6c}$; or when $R_{6a}$ and $R_{6b}$ are linked to the same nitrogen atom, $R_{6a}$ and $R_{6b}$, together with the nitrogen atom linked thereto, form 3- to 10-membered heterocyclyl or 5- to 12-membered heteroaryl which is optionally substituted by $R_{6c}$;

$R_{6e}$ is, for each presence, independently selected from the group consisting of hydrogen, halogen, hydroxyl, amino, cyano, nitro, azido, oxo, —$R_{6d}$, —$OR_{6d}$, —N($R_{6d}$)$R_{6e}$, —C(O)$R_{6d}$, —C(O)N($R_{6d}$)$R_{6e}$, —N($R_{6d}$)C(O)$R_{6e}$, —C(O)O$R_{6d}$, —OC(O)$R_{6d}$, —S(O)N($R_{6d}$)($R_{6e}$), —$SO_2$N($R_{6d}$)($R_{6e}$), —N($R_{6d}$)S(O)($R_{6e}$), —N($R_{6d}$)$SO_2$($R_{6e}$), ═N—$R_{6d}$, and ═CH—$R_{6d}$; said oxo means that two hydrogens on the same substitution site are replaced by the same oxygen to form a double bond; said ═N—$R_{6d}$ means that two hydrogens on the same substitution site are replaced by the same nitrogen to form a double bond, and said nitrogen is substituted by $R_{6d}$; said ═CH—$R_{6d}$ means that two hydrogens on the same substitution site are replaced by the same carbon to form a double bond, and said carbon is substituted by $R_{6d}$;

$R_{6d}$ and $R_{6e}$ are, for each presence, independently selected from the group consisting of hydrogen, halogen, hydroxyl, amino, nitro, cyano, and an optionally substituted group selected from $C_{1-6}$ alkyl, $C_{2-6}$ alkenyl, $C_{2-6}$ alkynyl, $C_{1-6}$ alkoxy, $C_{3-10}$ carbocyclyl, 3- to 10-membered heterocyclyl, $C_{6-14}$ aryl, 5- to 12-membered heteroaryl, monospiro ring group, heteromonospiro ring group, condensed ring group, and heterocondensed ring group; or when $R_{6d}$ and $R_{6e}$ are linked to the same nitrogen atom, $R_{6d}$ and $R_{6e}$, together with the nitrogen atom linked thereto, form an optionally substituted group selected from 3- to 10-membered heterocyclyl and 5- to 12-membered heteroaryl; said optionally substituted means that hydrogen on a group to be substituted is not substituted or hydrogen on one or more substitution sites of the group to be substituted is independently substituted by $R_{6f}$; $R_{6f}$ is, for each presence, independently selected from the group consisting of hydrogen, halogen, hydroxyl, amino, nitro, mercapto, cyano, oxo, —C(O)$C_{1-6}$ alkyl, —C(O)O—$C_{1-6}$ alkyl, —OC(O)—$C_{1-6}$ alkyl, —NH($C_{1-6}$ alkyl), —N($C_{1-6}$ alkyl)($C_{1-6}$ alkyl), —C(O)NH—$C_{1-6}$ alkyl, —NHC(O)—$C_{1-6}$ alkyl, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said oxo means that two hydrogens on the same substitution site are replaced by the same oxygen to form a double bond;

when the heterocycloalkyl, heteroaryl, heterocyclyl, heteromonospiro ring group, heterocondensed ring group and/or heterobridged ring group is present, the heteroatom thereof is independently selected from the group consisting of O, N, and S, and the number of the heteroatom is 1, 2, 3, or 4.

Preferably, the present disclosure provides a compound or a prodrug, tautomer, optical isomer, geometric isomer, solvate, isotopic derivative, or pharmaceutically acceptable salt thereof, having a structure as represented by formula (I-a):

(I-a)

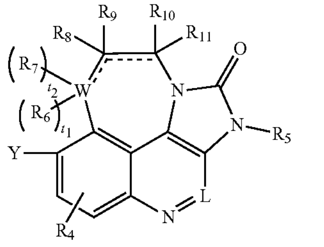

wherein each substituent is as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (I-b):

(I-b)

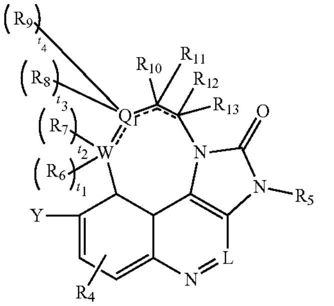

wherein each substituent is as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (I-c):

(I-c)

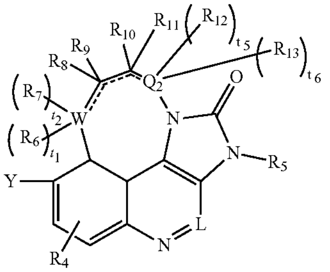

wherein each substituent is as defined in the compound of formula (I') or formula (I).

Preferably, in the compound or the prodrug, tautomer, optical isomer, geometric isomer, solvate, isotopic derivative, or pharmaceutically acceptable salt thereof provided in the present disclosure, $X_1$ is selected from the group consisting of a bond, hydrogen, halogen, hydroxyl, amino, nitro, cyano, —O—, —S—, —C(O)—, —C(O)O—, —OC(O)—, —N($R_{1x}$)C(O)—, —C(O)N($R_{1x}$)—, and —N($R_{1x}$)—; $R_{1x}$ is selected from the group consisting of hydrogen, $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl.

Further preferably, in the compound or the prodrug, tautomer, optical isomer, geometric isomer, solvate, isotopic derivative, or pharmaceutically acceptable salt thereof provided in the present disclosure, $X_1$ is selected from the group consisting of a bond, hydrogen, halogen, hydroxyl, amino, nitro, cyano, —O—, —S—, —C(O)—, —C(O)O—, —OC(O)—, —N($R_{1x}$)C(O)—, —C(O)N($R_{1x}$)—, and —N($R_{1x}$)—; $R_{1x}$ is selected from the group consisting of hydrogen, $C_{1-6}$ alkyl, $C_{3-6}$ cycloalkyl, and 3- to 6-membered heterocycloalkyl.

Further preferably, in the compound or the prodrug, tautomer, optical isomer, geometric isomer, solvate, isotopic derivative, or pharmaceutically acceptable salt thereof provided in the present disclosure, $X_1$ is selected from the group consisting of a bond, hydrogen, halogen, hydroxyl, amino, —O—, —S—, —C(O)—, —C(O)O—, —OC(O)—, —NHC(O)—, —C(O)NH—, —NH—, and —N($CH_3$)—.

Further preferably, in the compound or the prodrug, tautomer, optical isomer, geometric isomer, solvate, isotopic derivative, or pharmaceutically acceptable salt thereof provided in the present disclosure, $X_1$ is selected from the group consisting of a bond, hydrogen, —S—, —NHC(O)—, and —C(O)NH—.

Further preferably, in the compound or the prodrug, tautomer, optical isomer, geometric isomer, solvate, isotopic derivative, or pharmaceutically acceptable salt thereof provided in the present disclosure, $X_1$ is a bond.

Preferably, in the compound or the prodrug, tautomer, optical isomer, geometric isomer, solvate, isotopic derivative, or pharmaceutically acceptable salt thereof provided in the present disclosure, $R_1$ is an optionally substituted 3- to 10-membered heterocyclyl; said optionally substituted represents being optionally substituted by $R_{1a}$.

Further Preferably, in the compound or the prodrug, tautomer, optical isomer, geometric isomer, solvate, isotopic derivative, or pharmaceutically acceptable salt thereof provided in the present disclosure, $R_1$ is an optionally substituted 5- to 8-membered heterocyclyl, the heteroatom thereof is N, and the number of the heteroatom is 1 or 2; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is an optionally substituted dihydropyridinyl; said optionally substituted represents being optionally substituted by $R_{1a}$.

Preferably, in the compound or the prodrug, tautomer, optical isomer, geometric isomer, solvate, isotopic derivative, or pharmaceutically acceptable salt thereof provided in the present disclosure, $R_1$ is absent or selected from the group consisting of a bond, hydrogen, and an optionally substituted group selected from $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of hydrogen and an optionally substituted group selected from $C_{1-6}$ alkyl, $C_{1-6}$ alkoxy, $C_{2-6}$ alkenyl, $C_{2-6}$ alkynyl, $C_{6-14}$ aryl, and 5- to 12-membered heteroaryl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted group selected from $C_{1-6}$ alkyl, $C_{2-6}$ alkynyl, $C_{6-14}$ aryl, and 5- to 12-membered heteroaryl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted group selected from $C_{2-6}$ alkynyl and 5- to 12-membered heteroaryl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted group selected from $C_{2-6}$ alkynyl and 5- to 8-membered heteroaryl, the heteroatom thereof is N, and the number of the heteroatom is 1, 2, or 3; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted $C_{2-6}$ alkynyl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is an optionally substituted 5- to 12-membered heteroaryl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted 5- to 8-membered heteroaryl, the heteroatom thereof is N, and the number of the heteroatom is 1, 2, or 3; said optionally substituted represents being optionally substituted by $R_{1a}$.

Further Preferably, in the compound or the prodrug, tautomer, optical isomer, geometric isomer, solvate, isotopic derivative, or pharmaceutically acceptable salt thereof provided in the present disclosure, $R_1$ is an optionally substituted 5- to 6-membered heteroaryl, the heteroatom thereof is N, and the number of the heteroatom is 1 or 2; said optionally substituted represents being optionally substituted by $R_{1a}$.

Preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted group selected from ethynyl, phenyl, pyridinyl, pyrimidinyl, pyrazinyl, pyrazolyl, imidazolyl, and pyrrolyl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of ethynyl.

Preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted group selected from pyridinyl, pyrimidinyl, pyrazinyl, and pyrazolyl; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is an optionally substituted pyridinyl; said optionally substituted represents being optionally substituted by $R_{1a}$.

Preferably, in the compound or the prodrug, tautomer, optical isomer, geometric isomer, solvate, isotopic derivative, or pharmaceutically acceptable salt thereof provided in the present disclosure, $R_{1a}$ is, for each presence, independently selected from the group consisting of halogen, hydroxyl, amino, oxo, $—R_{1b}$, $—OR_{1b}$, $—SR_{1b}$, $—S(O)R_{1b}$, $—SO_2(R_{1b})$, $—C(O)R_{1b}$, $—C(O)OR_{1b}$, $—OC(O)R_{1b}$, $—NH(R_{1b})$, $—N(R_{1b})(R_{1c})$, $—C(O)NH(R_{1b})$, $—C(O)N(R_{1b})(R_{1c})$, $—NHC(O)(R_{1b})$, $—N(R_{1b})C(O)(R_{1c})$, $—S(O)NH(R_{1b})$, $—S(O)N(R_{1b})(R_{1c})$, $—SO_2NH(R_{1b})$, $—SO_2N(R_{1b})(R_{1c})$, $—NHS(O)(R_{1b})$, $—N(R_{1b})S(O)(R_{1c})$, $—NHSO_2(R_{1b})$, and $—N(R_{1b})SO_2(R_{1c})$; said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_{1a}$ is, for each presence, independently selected from the group consisting of halogen, hydroxyl, amino, oxo, $—R_{1b}$, $—OR_{1b}$, $—SO_2(R_{1b})$, $—C(O)R_{1b}$, $—C(O)OR_{1b}$, $—OC(O)R_{1b}$, $—N(R_{1b})(R_{1c})$, $—C(O)N(R_{1b})(R_{1c})$, $—NHC(O)(R_{1b})$, $—N(R_{1b})C(O)(R_{1c})$, —S(O)NH($R_{1b}$), —S(O)N($R_{1b}$)($R_{1c}$), —$SO_2$NH($R_{1b}$), —$SO_2$N($R_{1b}$)($R_{1c}$), —NHS(O)($R_{1b}$), —N($R_{1b}$)S(O)($R_{1c}$), —$NHSO_2$($R_{1b}$), and —N($R_{1b}$)$SO_2$($R_{1c}$); said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_{1a}$ is, for each presence, independently selected from the group consisting of halogen, hydroxyl, amino, oxo, —$R_{1b}$, —C(O)NH($R_{1c}$), —NHC(O)($R_{1b}$), —N($R_{1b}$)C(O)($R_{1c}$), —S(O)NH($R_{1b}$), —$SO_2$NH($R_{1b}$), —NHS(O)($R_{1b}$), —$NHSO_2$($R_{1b}$), and —N($R_{1b}$)$SO_2$($R_{1c}$); said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_{1a}$ is, for each presence, independently selected from the group consisting of halogen, amino, oxo, —$R_{1b}$, —NHC(O)($R_{1b}$), and —$NHSO_2$($R_{1b}$); said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_{1a}$ is, for each presence, independently selected from the group consisting of —NHC(O)($R_{1b}$) and —$NHSO_2$($R_{1b}$).

Preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of hydrogen and any one of $C_{1-6}$ alkyl, $C_{1-6}$ alkoxy, $C_{2-6}$ alkenyl, $C_{2-6}$ alkynyl, $C_{3-10}$ cycloalkyl, 3- to 10-membered heterocycloalkyl, $C_{6-14}$ aryl, and 5- to 12-membered heteroaryl which is optionally substituted by one or more of halogen, hydroxyl, amino, oxo, $C_{1-6}$ alkyl, $C_{1-6}$ alkoxy, $C_{2-6}$ alkenyl, $C_{2-6}$ alkynyl, $C_{3-8}$ cycloalkyl, 3- to 8-membered heterocycloalkyl, $C_{6-8}$ aryl, and 5- to 8-membered heteroaryl; or when $R_{1b}$ and $R_{1c}$ are linked to the same nitrogen atom, $R_{1b}$ and $R_{1c}$, together with the nitrogen atom linked thereto, form 3- to 10-membered heterocycloalkyl or 5- to 12-membered heteroaryl which is optionally substituted by one or more of halogen, hydroxyl, amino, oxo, $C_{1-6}$ alkyl, $C_{1-6}$ alkoxy, $C_{3-8}$ cycloalkyl, 3- to 8-membered heterocycloalkyl, $C_{6-g}$ aryl, and 5- to 8-membered heteroaryl; said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of hydrogen, $C_{1-6}$ alkyl, $C_{1-6}$ alkoxy, $C_{2-6}$ alkynyl, $C_{3-10}$ cycloalkyl, 3- to 10-membered heterocycloalkyl, $C_{6-14}$ aryl, and 5- to 12-membered heteroaryl; or when $R_{1b}$ and $R_{1c}$ are linked to the same nitrogen atom, $R_{1b}$ and $R_{1c}$, together with the nitrogen atom linked thereto, form 3- to 10-membered heterocycloalkyl.

Further preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of $C_{1-6}$ alkyl, 3- to 8-membered heterocycloalkyl, and $C_{6-8}$ aryl; or when $R_{1b}$ and $R_{1c}$ are linked to the same nitrogen atom, $R_{1b}$ and $R_{1c}$, together with the nitrogen atom linked thereto, form 3- to 8-membered heterocycloalkyl.

Preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of $C_{1-6}$ alkyl, $C_{3-10}$ cycloalkyl, and $C_{6-8}$ aryl; or when $R_{1b}$ and $R_{1c}$ are linked to the same nitrogen atom, $R_{1b}$ and $R_{1c}$, together with the nitrogen atom linked thereto, form 3- to 8-membered heterocycloalkyl.

Further preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of $C_{1-6}$ alkyl, $C_{3-8}$ cycloalkyl, and $C_{6-8}$ aryl.

Further preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of $C_{1-6}$ alkyl, $C_{3-6}$ cycloalkyl, and $C_6$ aryl (i.e., phenyl).

Further preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of $C_{1-6}$ alkyl and $C_{3-6}$ cycloalkyl.

Further preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of $C_{1-4}$ alkyl and $C_{3-4}$ cycloalkyl.

Preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of methyl, ethyl, cyclopropyl, phenyl, and tetrahydropyranyl.

Further preferably, in the compound or the prodrug, tautomer, optical isomer, geometric isomer, solvate, isotopic derivative, or pharmaceutically acceptable salt thereof provided in the present disclosure, $R_{1b}$ and $R_{1c}$ are, for each presence, independently selected from the group consisting of methyl and cyclopropyl.

Preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted pyrazolyl; said optionally substituted represents being optionally substituted by $R_{1a}$; $R_{1a}$ is independently selected from the group consisting of $C_{1-6}$ alkyl and 3- to 8-membered heterocycloalkyl.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted pyrazolyl; said optionally substituted represents being optionally substituted by $R_{1a}$; $R_{1a}$ is independently selected from the group consisting of $C_{1-4}$ alkyl and 6-membered heterocycloalkyl.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of an optionally substituted pyrazolyl; said optionally substituted represents being optionally substituted by $R_{1a}$; $R_{1a}$ is independently selected from the group consisting of methyl, ethyl, and tetrahydropyranyl.

Preferably, in the compound or the prodrug, tautomer, optical isomer, geometric isomer, solvate, isotopic derivative, or pharmaceutically acceptable salt thereof provided in the present disclosure, $R_1$ is an optionally substituted pyridinyl; said optionally substituted represents being optionally substituted by $R_{1a}$; $R_{1a}$ is independently selected from the group consisting of amino, —NHC(O)($R_{1b}$), and —$NHSO_2$($R_{1b}$); $R_{1b}$ is, for each presence, independently selected from the group consisting of $C_{1-6}$ alkyl, $C_{3-6}$ cycloalkyl, and phenyl.

Further preferably, in the compound or the prodrug, tautomer, optical isomer, geometric isomer, solvate, isotopic derivative, or pharmaceutically acceptable salt thereof provided in the present disclosure, $R_1$ is an optionally substituted pyridinyl; said optionally substituted represents being optionally substituted by $R_{1a}$; $R_{1a}$ is independently selected from the group consisting of amino, —NHC(O)($R_{1b}$), and —$NHSO_2$($R_{1b}$); $R_{1b}$ is, for each presence, independently selected from the group consisting of $C_{1-4}$ alkyl, $C_{3-4}$ cycloalkyl, and phenyl.

Preferably, in the compound or the prodrug, tautomer, optical isomer, geometric isomer, solvate, isotopic derivative, or pharmaceutically acceptable salt thereof provided in the present disclosure, $R_1$ is selected from the group consisting of the following optionally substituted groups:

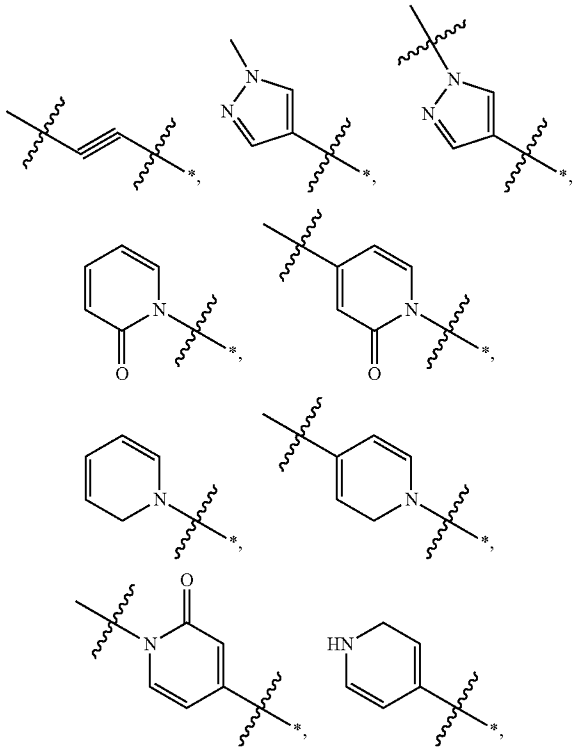

-continued

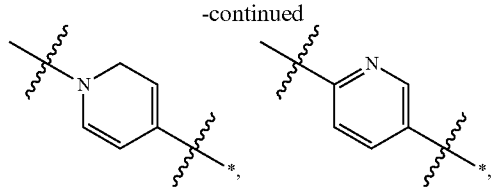

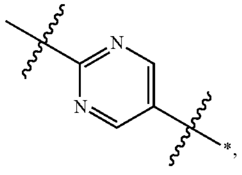

and

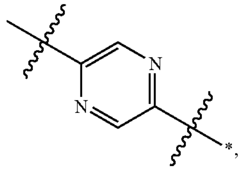

wherein the end with an asterisk "*" is the one linked to $X_1$, and the other end is the one linked to $X_2$; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is an optionally substituted

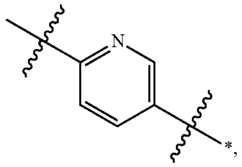

wherein the end with an asterisk "*" is the one linked to $X_1$, and the other end is the one linked to $X_2$; said optionally substituted represents being optionally substituted by $R_{1a}$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of the following groups:

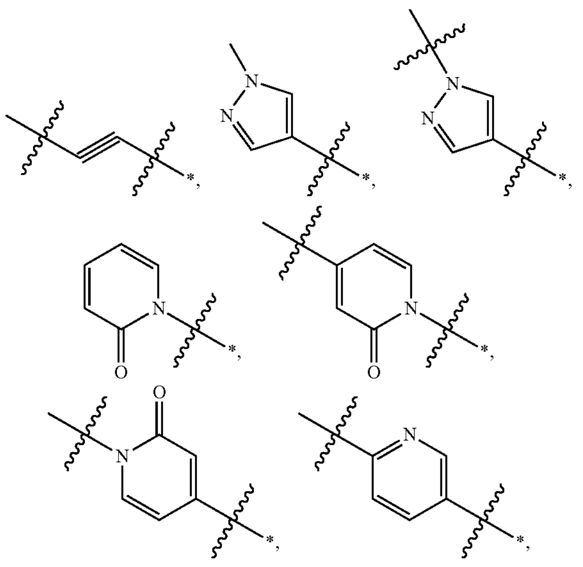

-continued

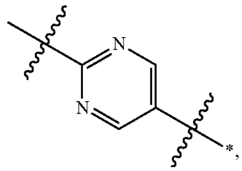
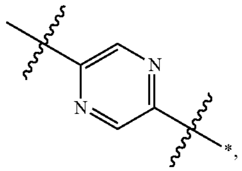
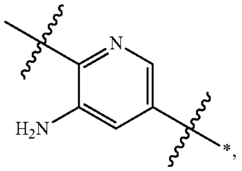
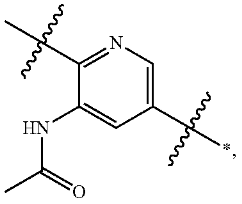
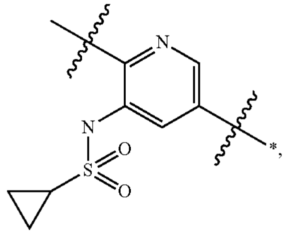
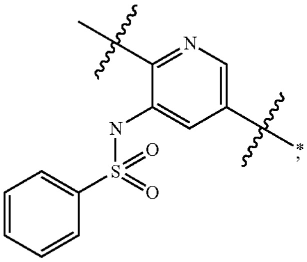
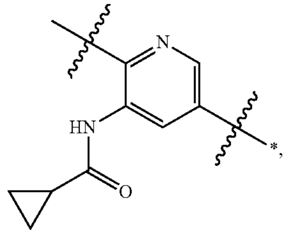
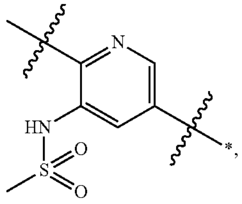
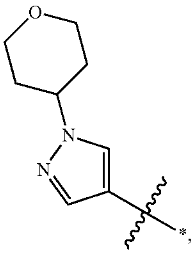
and
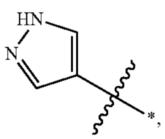

wherein the end with an asterisk "*" is the one linked to $X_1$, and the other end is the one linked to $X_2$.

Further preferably, in the compound or the prodrug, tautomer, optical isomer, geometric isomer, solvate, isotopic derivative, or pharmaceutically acceptable salt thereof provided in the present disclosure, $R_1$ is selected from the group consisting of the following groups:

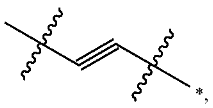
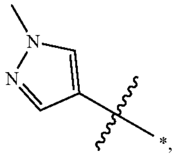
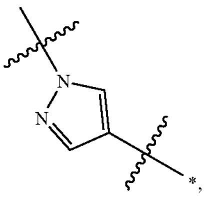
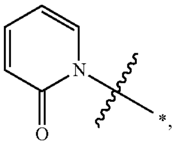
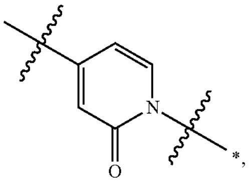
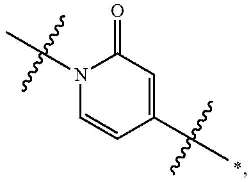
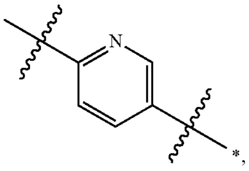
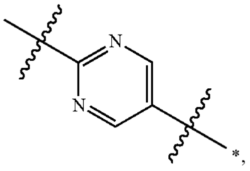
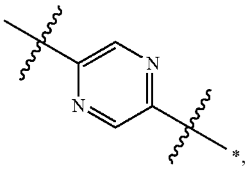
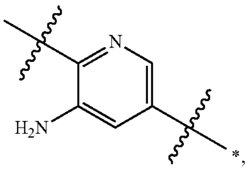
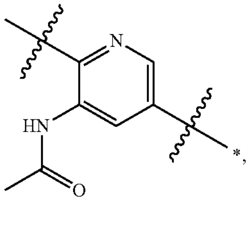
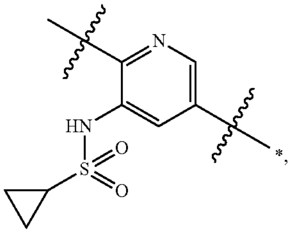
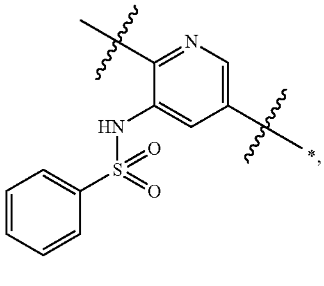
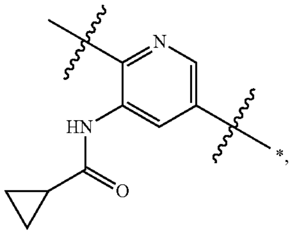
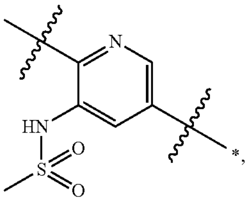

-continued

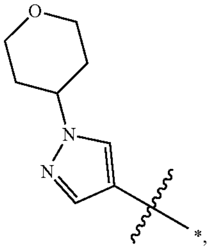

and

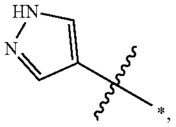

wherein the end with an asterisk “*” is the one linked to $X_1$, and the other end is the one linked to $X_2$.

Preferably, in the compound or the prodrug, tautomer, optical isomer, geometric isomer, solvate, isotopic derivative, or pharmaceutically acceptable salt thereof provided in the present disclosure, $R_1$ is selected from the group consisting of the following groups:

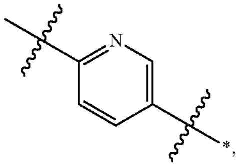

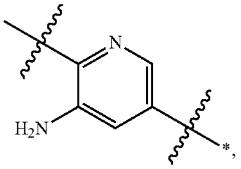

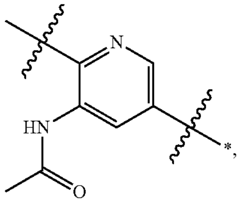

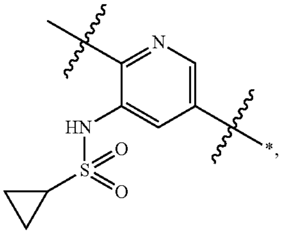

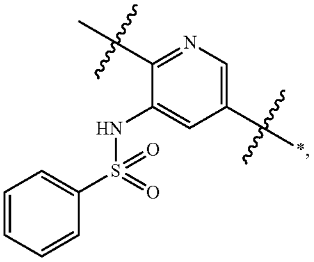

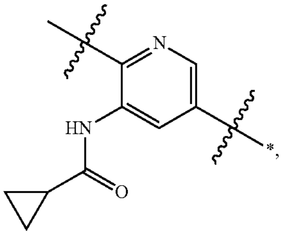

and

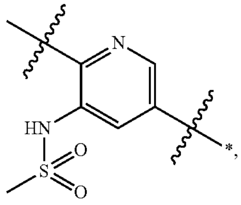

wherein the end with an asterisk “*” is the one linked to $X_1$, and the other end is the one linked to $X_2$.

Further preferably, in the compound or the prodrug, tautomer, optical isomer, geometric isomer, solvate, isotopic derivative, or pharmaceutically acceptable salt thereof provided in the present disclosure, $R_1$ is the following group:

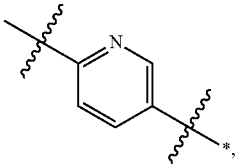

wherein the end with an asterisk “*” is the one linked to $X_1$, and the other end is the one linked to $X_2$.

Preferably, in the compound or the prodrug, tautomer, optical isomer, geometric isomer, solvate, isotopic derivative, or pharmaceutically acceptable salt thereof provided in the present disclosure, $R_1$ is selected from the group consisting of the following groups:

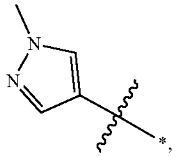

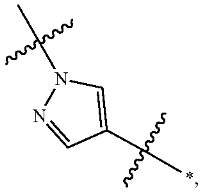

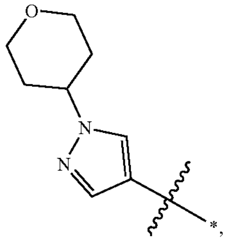

and

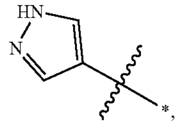

wherein the end with an asterisk “*” is the one linked to $X_1$, and the other end is the one linked to $X_2$.

Further preferably, in the compound or the prodrug, tautomer, optical isomer, geometric isomer, solvate, isotopic derivative, or pharmaceutically acceptable salt thereof provided in the present disclosure, $R_1$ is the following group.

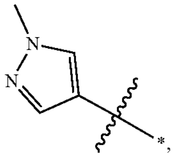 [SMILES: *c1cnn(C)c1]

wherein the end with an asterisk “*” is the one linked to $X_1$.

Preferably, in the compound or the prodrug, tautomer, optical isomer, geometric isomer, solvate, isotopic derivative, or pharmaceutically acceptable salt thereof provided in the present disclosure, $X_2$ is absent or selected from the group consisting of a bond, hydrogen, halogen, hydroxyl, amino, —O—, —S—, —C(O)O—, —OC(O)—, —C(O)N($R_{2x}$)—, —N($R_{2x}$)C(O)—, and —N($R_{2x}$)—; $R_{2x}$ is selected from the group consisting of hydrogen and $C_{1-6}$ alkyl which is optionally substituted by halogen, hydroxyl, or amino.

Further preferably, in the compound or the prodrug, tautomer, optical isomer, geometric isomer, solvate, isotopic derivative, or pharmaceutically acceptable salt thereof provided in the present disclosure, $X_2$ is absent or selected from the group consisting of a bond, hydrogen, halogen, hydroxyl, amino, —O—, —S—, —C(O)O—, —OC(O)—, —C(O)NH—, —NHC(O)—, —NH—, —N($CH_3$)—, and —N($CH_2CH_3$)—.

Further preferably, in the compound or the prodrug, tautomer, optical isomer, geometric isomer, solvate, isotopic derivative, or pharmaceutically acceptable salt thereof provided in the present disclosure, $X_2$ is absent or selected from the group consisting of a bond, —O—, —NH—, and —N($CH_3$)—.

Further preferably, in the compound or the prodrug, tautomer, optical isomer, geometric isomer, solvate, isotopic derivative, or pharmaceutically acceptable salt thereof provided in the present disclosure, $X_2$ is absent or selected from the group consisting of a bond, —O—, and —N($CH_3$)—.

Preferably, in the compound or the prodrug, tautomer, optical isomer, geometric isomer, solvate, isotopic derivative, or pharmaceutically acceptable salt thereof provided in the present disclosure, $X_2$ is selected from the group consisting of a bond, —O—, and —NH—.

Preferably, in the compound or the prodrug, tautomer, optical isomer, geometric isomer, solvate, isotopic derivative, or pharmaceutically acceptable salt thereof provided in the present disclosure, $X_2$ is absent or selected from the group consisting of a bond and —O—.

Further preferably, in the compound or the prodrug, tautomer, optical isomer, geometric isomer, solvate, isotopic derivative, or pharmaceutically acceptable salt thereof provided in the present disclosure, $X_2$ is selected from the group consisting of —O—.

Preferably, in the compound or the prodrug, tautomer, optical isomer, geometric isomer, solvate, isotopic derivative, or pharmaceutically acceptable salt thereof provided in the present disclosure, $R_2$ is absent or selected from the group consisting of a bond, hydrogen, and any one of $C_{1-6}$ alkyl, $C_{1-6}$ alkoxy, $C_{2-6}$ alkenyl, $C_{2-6}$ alkynyl, $C_{3-10}$ cycloalkyl, $C_{6-14}$ aryl, 3- to 10-membered heterocycloalkyl, and 5- to 12-membered heteroaryl which is optionally substituted by one or more of halogen, hydroxyl, amino, oxo, $C_{1-6}$ alkyl, $C_{1-6}$ alkoxy, $C_{2-6}$ alkenyl, $C_{2-6}$ alkynyl, $C_{3-8}$ cycloalkyl, 3- to 8-membered heterocycloalkyl, $C_{6-g}$ aryl, and 5- to 8-membered heteroaryl.

Further preferably, in the compound or the prodrug, tautomer, optical isomer, geometric isomer, solvate, isotopic derivative, or pharmaceutically acceptable salt thereof provided in the present disclosure, $R_2$ is absent or selected from the group consisting of hydrogen, $C_{1-6}$ alkyl, $C_{2-6}$ alkynyl, $C_{3-10}$ cycloalkyl, $C_{6-14}$ aryl, 3- to 10-membered heterocycloalkyl, and 5- to 12-membered heteroaryl.

Further preferably, in the compound or the prodrug, tautomer, optical isomer, geometric isomer, solvate, isotopic derivative, or pharmaceutically acceptable salt thereof provided in the present disclosure, $R_2$ is absent or selected from the group consisting of $C_{1-6}$ alkyl, $C_{2-4}$ alkynyl, and 5- to 6-membered heterocycloalkyl, the heteroatom thereof is N or O, and the number of the heteroatom is 1 or 2.

Further preferably, in the compound or the prodrug, tautomer, optical isomer, geometric isomer, solvate, isotopic derivative, or pharmaceutically acceptable salt thereof provided in the present disclosure, $R_2$ is absent or selected from the group consisting of methyl, ethyl, propyl (n-propyl and isopropyl), butyl (n-butyl, isobutyl, sec-butyl, tert-butyl), ethynyl, piperidinyl, tetrahydropyrrolyl, and tetrahydropyranyl.

Further preferably, in the compound or the prodrug, tautomer, optical isomer, geometric isomer, solvate, isotopic derivative, or pharmaceutically acceptable salt thereof provided in the present disclosure, $R_2$ is n-propyl.

Preferably, in the compound or the prodrug, tautomer, optical isomer, geometric isomer, solvate, isotopic derivative, or pharmaceutically acceptable salt thereof provided in the present disclosure, $R_3$ is absent or selected from the group consisting of hydrogen, halogen, hydroxyl, amino, nitro, mercapto, cyano, oxo, —$R_{3b}$, —$OR_{3b}$, —$SR_{3b}$, —C(O)$R_{3b}$, —C(O)$OR_{3b}$, —OC(O)$R_{3b}$, —N($R_{3b}$)($R_{3c}$), —C(O)N($R_{3b}$)($R_{3c}$), —C(O)NH($R_{3b}$), —NHC(O)($R_{3b}$), —N($R_{3b}$)C(O)($R_{3c}$), —S(O)N($R_{3b}$)($R_{3c}$), —$SO_2$N($R_{3b}$)($R_{3c}$), —N($R_{3b}$)S(O)($R_{3c}$), and —N($R_{3b}$)$SO_2$($R_{3c}$); said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_3$ is absent or selected from the group consisting of hydrogen, halogen, hydroxyl, amino, oxo, —$R_{3b}$, —$OR_{3b}$, —$SR_{3b}$, —C(O)$R_{3b}$, —C(O)$OR_{3b}$, —OC(O)$R_{3b}$, —N($R_{3b}$)($R_{3c}$), —C(O)N($R_{3b}$)($R_{3c}$), —C(O)NH($R_{3b}$), and —NHC(O)($R_{3b}$); said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_3$ is absent or selected from the group consisting of —$R_{3b}$, —$OR_{3b}$, and —N($R_{3b}$)($R_{3c}$).

Further Preferably, in the compound or the prodrug, tautomer, optical isomer, geometric isomer, solvate, isotopic derivative, or pharmaceutically acceptable salt thereof provided in the present disclosure, $R_3$ is —N($R_{3b}$)($R_{3c}$).

Preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently selected from the group consisting of hydrogen and an optionally substituted group selected from $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; or when $R_{3b}$ and $R_{3c}$ are linked to the same nitrogen atom, $R_{3b}$ and $R_{3c}$, together with the nitrogen atom linked thereto, form an optionally substituted group selected from 3- to 10-membered heterocycloalkyl, 4- to 12-membered bicyclic heterocyclyl, and 5- to 12-membered heteroaryl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently selected from the group consisting of hydrogen and an optionally substituted group selected from $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl; or when $R_{3b}$ and $R_{3c}$ are linked to the same nitrogen atom, $R_{3b}$ and $R_{3c}$, together with the nitrogen atom linked thereto, form an optionally substituted group selected from 3- to 10-membered heterocycloalkyl and 5- to 12-membered heteroaryl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently selected from the group consisting of hydrogen and an optionally substituted group selected from $C_{1-6}$ alkyl, $C_{1-6}$ alkoxy, and 3- to 10-membered heterocycloalkyl; or when $R_{3b}$ and $R_{3c}$ are linked to the same nitrogen atom, $R_{3b}$ and $R_{3c}$, together with the nitrogen atom linked thereto, form an optionally substituted 3- to 10-membered heterocycloalkyl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently selected from the group consisting of hydrogen and an optionally substituted group selected from $C_{1-6}$ alkyl, $C_{1-6}$ alkoxy, and 3- to 10-membered heterocycloalkyl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1-6}$ alkyl; said optionally substituted represents being optionally substituted by $R_{3d}$.

Preferably, in the compound or the prodrug, tautomer, optical isomer, geometric isomer, solvate, isotopic derivative, or pharmaceutically acceptable salt thereof provided in the present disclosure, when $R_{3b}$ and $R_{3c}$ are linked to the same nitrogen atom, $R_{3b}$ and $R_{3c}$, together with the nitrogen atom linked thereto, form an optionally substituted 3- to 10-membered heterocycloalkyl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl and 6- to 10-membered bicyclic heterocyclyl, the heteroatom thereof is independently selected from the group consisting of O and N, and the number of the heteroatom is 1, 2, 3, or 4; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_3$ is absent or selected from the group consisting of $C_{1-6}$ alkyl, $C_{1-6}$ alkoxy, and —$N(R_{3b})(R_{3c})$; $R_{3b}$ and $R_{3c}$ are independently an optionally substituted $C_{1-6}$ alkyl; or when $R_{3b}$ and $R_3$, are linked to the same nitrogen atom, $R_{3b}$ and $R_{3c}$, together with the nitrogen atom linked thereto, form an optionally substituted 3- to 10-membered heterocycloalkyl; said optionally substituted represents being optionally substituted by $R_{3d}$.

Preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1-6}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 3- to 10-membered heterocycloalkyl and 4- to 12-membered bicyclic heterocyclyl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1-6}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 4- to 8-membered heterocycloalkyl and 6- to 10-membered bicyclic heterocyclyl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1-4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl and 6- to 10-membered bicyclic heterocyclyl, the heteroatom thereof is independently selected from the group consisting of O and N, and the number of the heteroatom is 1, 2, 3, or 4; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1-4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl, 3-/4-membered heteromonospiro ring group, 4-/3-membered heteromonospiro ring group, 3-/5-membered heteromonospiro ring group, 5-/3-membered heteromonospiro ring group, 3-/6-membered heteromonospiro ring group, 6-/3-membered heteromonospiro ring group, 4-/5-membered heteromonospiro ring group, 5-/4-membered heteromonospiro ring group, 4-/6-membered heteromonospiro ring group, 6-/4-membered heteromonospiro ring group, 4-/4-membered heteromonospiro ring group, 5-/5-membered heteromonospiro ring group, 5-/6-membered heteromonospiro ring group, 6-/5-membered heteromonospiro ring group, 3-/5-membered fused heterocyclyl, 5-/3-membered fused heterocyclyl, 3-/6-membered fused heterocyclyl, 6-/3-membered fused heterocyclyl, 5-/6-membered fused heterocyclyl, and 6-/5-membered fused heterocyclyl, the heteroatom thereof is independently selected from the group consisting of O and N, and the number of the heteroatom is 1, 2, 3, or 4; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1-4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl, 3-/6-membered heteromonospiro ring group, 6-/3-membered heteromonospiro ring group, 4-/6-membered heteromonospiro ring group, 6-/4-membered heteromonospiro ring group, and 4-/4-membered heteromonospiro ring group, the heteroatom thereof is independently selected from the group consisting of O and N, and the number of the heteroatom is 1 or 2; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted methyl; or when $R_{3b}$ and $R_{3c}$ are linked to the same nitrogen atom, $R_{3b}$ and $R_{3c}$, together with the nitrogen atom linked thereto, form an optionally substituted piperidinyl; said optionally substituted represents being optionally substituted by $R_{3d}$.

Preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, halogen, hydroxyl, amino, cyano, —$R_{3e}$, —C(O)$R_{3e}$, —C(O)O$R_{3e}$, —N($R_{3e}$)($R_{3f}$), and —C(O)NH($R_{3e}$); $R_{3e}$ and $R_{3f}$ are, for each presence, independently selected from the group consisting of hydrogen and any one of $C_{1-6}$ alkyl, $C_{1-6}$ alkoxy, $C_{3-10}$ cycloalkyl, 3- to 10-membered heterocycloalkyl, $C_{6-14}$ aryl, and 5- to 12-membered heteroaryl which is optionally substituted by one or more of halogen, hydroxyl, amino, $C_{1-6}$ alkyl, $C_{3-10}$ cycloalkyl, 3- to 10-membered heterocycloalkyl, $C_{6-14}$ aryl, and 5- to 12-membered heteroaryl; or when $R_{3e}$ and $R_{3f}$ are linked to the same nitrogen atom, $R_{3e}$ and $R_{3f}$, together with the nitrogen atom linked thereto, form 3- to 10-membered heterocycloalkyl or 5- to 12-membered heteroaryl which is optionally substituted by one or more of halogen, hydroxyl, amino, $C_{1-6}$ alkyl, $C_{3-10}$ cycloalkyl, 3- to 10-membered heterocycloalkyl, $C_{6-14}$ aryl, and 5- to 12-membered heteroaryl.

Further preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, halogen, hydroxyl, amino, cyano, —$R_{3e}$, —C(O)$R_{3e}$, —C(O)O$R_{3e}$, —N($R_{3e}$)($R_{3f}$), and —C(O)NH($R_{3e}$); $R_{3e}$ and $R_{3f}$ are, for each presence, independently selected from the group consisting of hydrogen and any one of $C_{1-6}$ alkyl, $C_{1-6}$ alkoxy, $C_{3-6}$ cycloalkyl, 3- to 6-membered heterocycloalkyl, $C_6$ aryl, and 5- to 6-membered heteroaryl which is optionally substituted by one or more of halogen, hydroxyl, amino, $C_{1-6}$ alkyl, $C_{3-6}$ cycloalkyl, 3- to 6-membered heterocycloalkyl, $C_6$ aryl, and 5- to 6-membered heteroaryl.

Further preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, halogen, hydroxyl, amino, cyano, —CHO, —CO($C_{1-6}$ alkyl), —COOH, —COO($C_{1-6}$ alkyl), —NH($C_{1-6}$ alkyl), —N($C_{1-6}$ alkyl)($C_{1-6}$ alkyl), —C(O)$NH_2$, $C_{1-6}$ alkyl, $C_{1-6}$ alkoxy, and 3- to 6-membered heterocycloalkyl.

Further preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, hydroxyl, amino, —CHO, —CO($C_{1-6}$ alkyl), —COOH, —COO($C_{1-6}$ alkyl), —NH($C_{1-6}$ alkyl), —N($C_{1-6}$ alkyl)($C_{1-6}$ alkyl), —C(O)$NH_2$, $C_{1-6}$ alkyl, $C_{1-6}$ alkoxy, and 5- to 6-membered heterocycloalkyl.

Preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, fluorine, hydroxyl, amino, cyano, —CHO, —$COCH_3$, —COOH, —$COOCH_3$, —NH($CH_3$), —N($CH_3$)($CH_3$), —C(O)$NH_2$, —$CH_3$, —$CH_2CH_3$, —$CH_2CH_2CH_3$, —$OCH_3$, —$OCH_2CH_3$, —$OCH_2CH_2CH_3$, piperidinyl, piperazinyl, and tetrahydropyrrolyl.

Further preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, fluorine, amino, cyano, —C(O)$NH_2$, —$CH_3$, and piperidinyl.

Preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of halogen, hydroxyl, amino, —$R_{3e}$, and —N($R_{3e}$)($R_{3f}$); $R_{3e}$ and $R_{3f}$ are, for each presence, independently selected from the group consisting of hydrogen and any one of $C_{1-6}$ alkyl, $C_{3-10}$ cycloalkyl, 3- to 10-membered heterocycloalkyl, $C_{6-14}$ aryl, and 5- to 12-membered heteroaryl which is optionally substituted by one or more of halogen, hydroxyl, amino, $C_{1-6}$ alkyl, $C_{3-10}$ cycloalkyl, 3- to 10-membered heterocycloalkyl, $C_{6-14}$ aryl, and 5- to 12-membered heteroaryl; or when $R_{3e}$ and $R_{3f}$ are linked to the same nitrogen atom, $R_{3e}$ and $R_{3f}$, together with the nitrogen atom linked thereto, form 3- to 10-membered heterocycloalkyl or 5- to 12-membered heteroaryl which is optionally substituted by one or more of halogen, hydroxyl, amino, $C_{1-6}$ alkyl, $C_{3-10}$ cycloalkyl, 3- to 10-membered heterocycloalkyl, $C_{6-14}$ aryl, and 5- to 12-membered heteroaryl.

Further preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of —$R_{3e}$ and —N($R_{3e}$)($R_{3f}$); $R_{3e}$ and $R_{3f}$ are, for each presence, independently selected from the group consisting of $C_{1-6}$ alkyl and 3- to 8-membered heterocycloalkyl; or when $R_{3e}$ and $R_{3f}$ are linked to the same nitrogen atom, $R_{3e}$ and $R_{3f}$, together with the nitrogen atom linked thereto, form 3- to 8-membered heterocycloalkyl.

Further preferably, in the compound or the prodrug, tautomer, optical isomer, geometric isomer, solvate, isotopic derivative, or pharmaceutically acceptable salt thereof provided in the present disclosure, $R_{3d}$ is selected from the group consisting of methyl, —N(methyl)(methyl) (i.e., dimethylamino), and piperidinyl.

Preferably, in the compound or the prodrug, tautomer, optical isomer, geometric isomer, solvate, isotopic derivative, or pharmaceutically acceptable salt thereof provided in the present disclosure, $R_3$ is selected from the group consisting of the following optionally substituted groups:

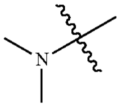 , 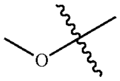 , 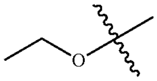 ,

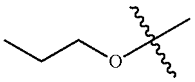 , 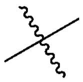 , 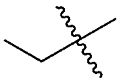 ,

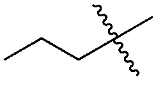 , 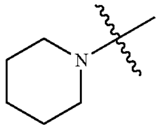 , 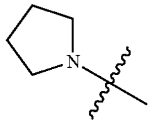 ,

-continued

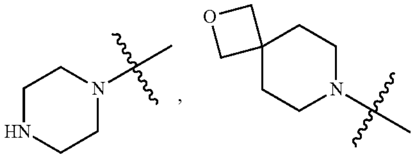,

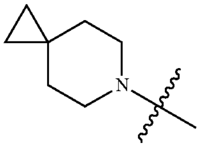, and 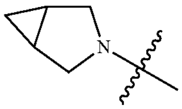, said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_3$ is selected from the group consisting of the following groups:

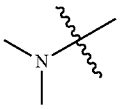, 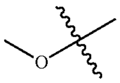, 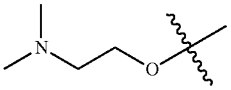,

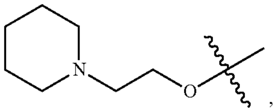, 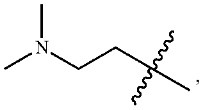,

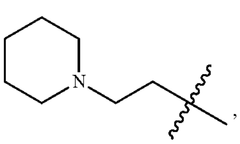, 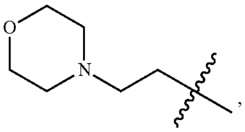,

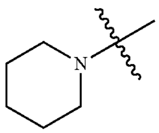, 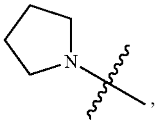, 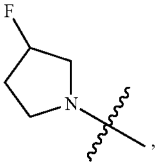,

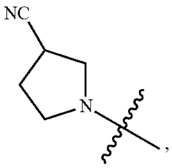, 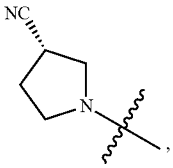, 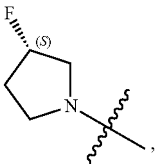,

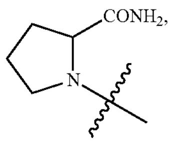, 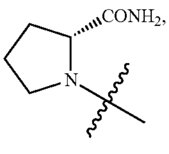, 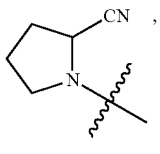,

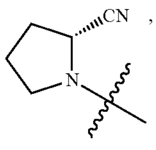, 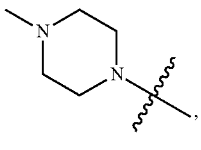, 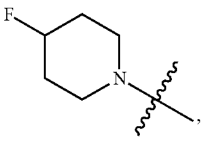,

-continued

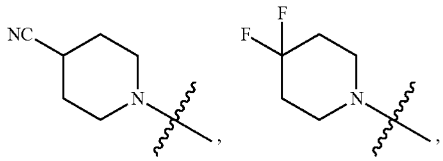,

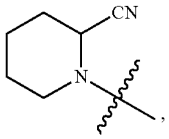, 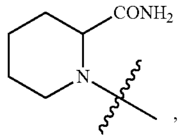, 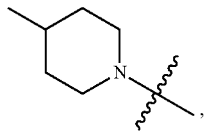,

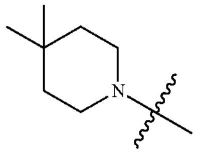, 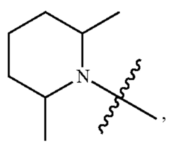, 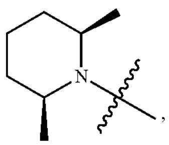,

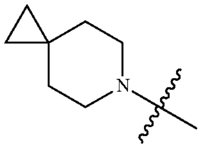, 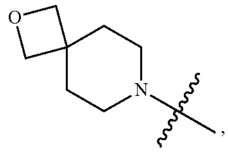,

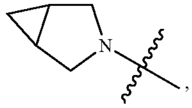, 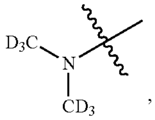, 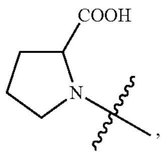,

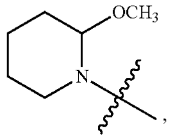, 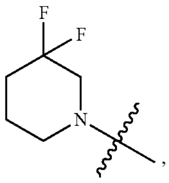, 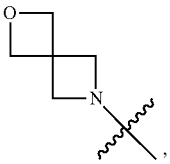, and

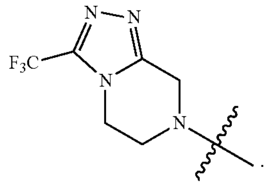.

Further preferably, in the compound or the prodrug, tautomer, optical isomer, geometric isomer, solvate, isotopic derivative, or pharmaceutically acceptable salt thereof provided in the present disclosure, $R_3$ is selected from the group consisting of the following groups:

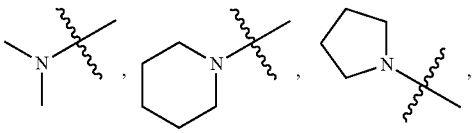,

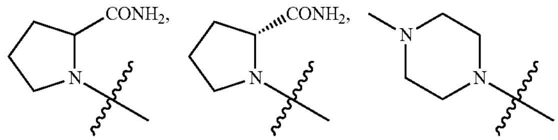,

-continued

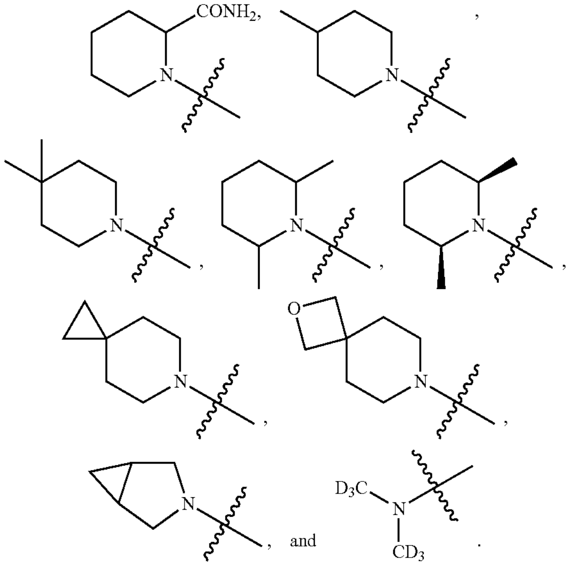

, and .

Preferably, the present disclosure provides a compound or a prodrug, tautomer, optical isomer, geometric isomer, solvate, isotopic derivative, or pharmaceutically acceptable salt thereof, having a structure as represented by formula (II-a):

(II-a)

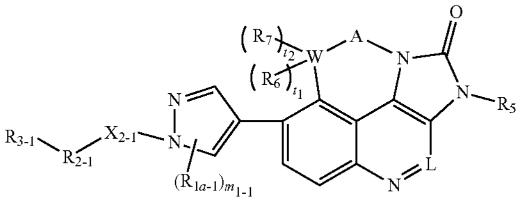

wherein $m_{1-1}$ is selected from the group consisting of 0, 1, and 2, $R_{1a-1}$ is as defined by $R_{1a}$ in the compound of formula (I') or formula (I), $X_{2-1}$ is as defined by $X_2$ in the compound of formula (I') or formula (I), $R_{2-1}$ is as defined by $R_2$ in the compound of formula (I') or formula (I), $R_{3-1}$ is as defined by $R_3$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$a_1$):

(II-$a_1$)

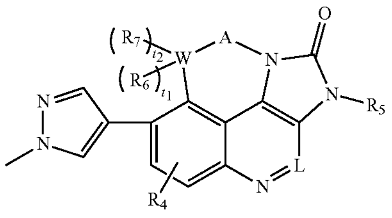

wherein $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$a_2$):

(II-$a_2$)

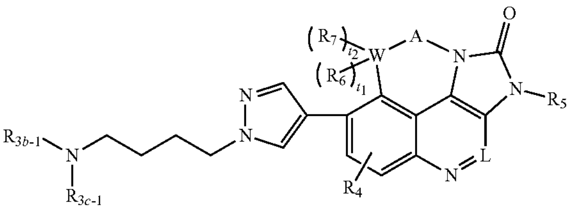

wherein $R_{3b-1}$ is as defined by $R_{3b}$ in the compound of formula (I') or formula (I), $R_{3c-1}$ is as defined by $R_3$, in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-b):

(II-b)

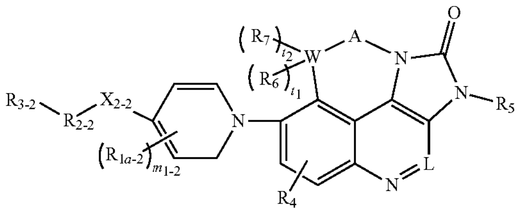

wherein $m_{1-2}$ is selected from the group consisting of 0, 1, 2, and 3, $R_{1a-2}$ is as defined by $R_{1a}$ in the compound of formula (I) or formula (I), $X_{2-2}$ is as defined by $X_2$ in the compound of formula (I) or formula (I), $R_{2-2}$ is as defined by $R_2$ in the compound of formula (I) or formula (I), $R_{3-2}$ is as defined by $R_3$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$b_1$):

(II-$b_1$)

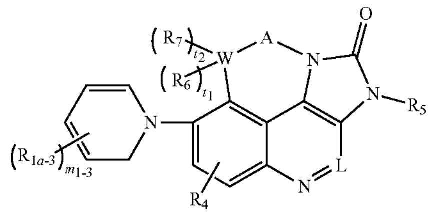

wherein $m_{1-3}$ is selected from the group consisting of 0, 1, 2, and 3, $R_{1a-3}$ is as defined by $R_{1a}$ in the compound of formula (I') or formula (I), and $R_4$, $R_5$, $R_6$, $R_7$, A, W, L, $t_1$, and $t_2$ are as defined in the compound of formula (I) or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-c):

(II-c)

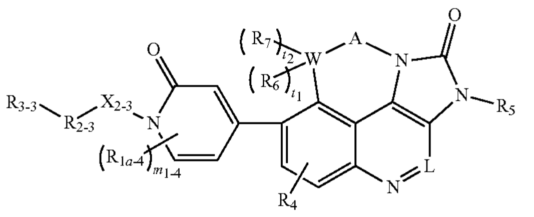

wherein $m_{1-4}$ is selected from the group consisting of 0, 1, 2, and 3, $R_{1a-4}$ is as defined by $R_{1a}$ in the compound of formula (I') or formula (I), $X_{2-3}$ is as defined by $X_2$ in the compound of formula (I') or formula (I), $R_{2-3}$ is as defined by $R_2$ in the compound of formula (I') or formula (I), $R_{3-3}$ is as defined by $R_3$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$c_1$):

(II-$c_1$)

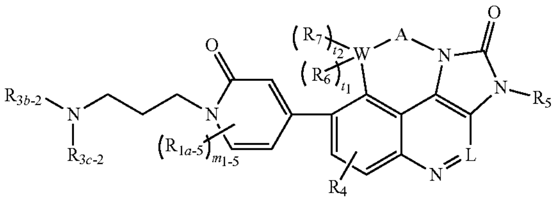

wherein $m_{1-5}$ is selected from the group consisting of 0, 1, 2, and 3, $R_{1a-5}$ is as defined by $R_{1a}$ in the compound of formula (I) or formula (I), $R_{3b-2}$ is as defined by $R_{3b}$ in the compound of formula (I') or formula (I), $R_{3c-2}$ is as defined by $R_{3-1}$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-d):

(II-d)

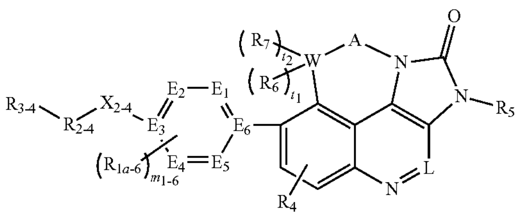

wherein $E_1$, $E_2$, $E_3$, $E_4$, $E_5$, and $E_6$ are independently selected from the group consisting of C and N, $m_{1-6}$ is selected from the group consisting of 0, 1, 2, 3, and 4, $R_{1a-6}$ is as defined by $R_{1a}$ in the compound of formula (I') or formula (I), $X_{2-4}$ is as defined by $X_2$ in the compound of formula (I') or formula (I), $R_{2-4}$ is as defined by $R_2$ in the compound of formula (I') or formula (I), $R_{3-4}$ is as defined by $R_3$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$d_1$):

(II-$d_1$)

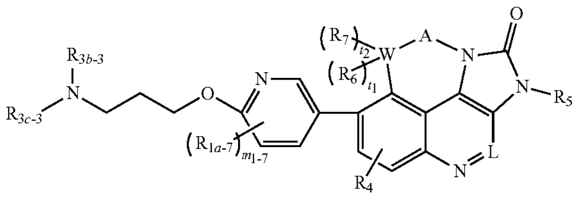

wherein $m_{1-7}$ is selected from the group consisting of 0, 1, 2, and 3, $R_{1a-7}$ is as defined by $R_{1a}$ in the compound of formula (I') or formula (I), $R_{3b-3}$ is as defined by $R_{3b}$ in the compound of formula (I') or formula (I), $R_{3c-3}$ is as defined by $R_3$, in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$d_2$):

(II-$d_2$)

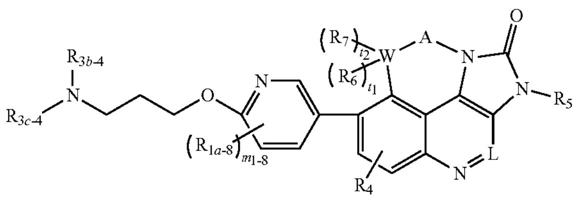

wherein $m_{1-8}$ is selected from the group consisting of 0, 1, and 2, $R_{1a-8}$ is as defined by $R_{1a}$ in the compound of formula (I') or formula (I), $R_{3b-4}$ is as defined by $R_{3b}$ in the compound of formula (I') or formula (I), $R_{3c-4}$ is as defined by $R_3$, in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$d_3$):

(II-d3)

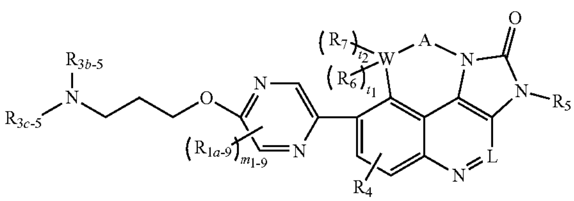

wherein $m_{1-9}$ is selected from the group consisting of 0, 1, and 2, $R_{1a-9}$ is as defined by $R_{1a}$ in the compound of formula (I') or formula (I), $R_{3b-5}$ is as defined by $R_{3b}$ in the compound of formula (I') or formula (I), $R_{3c-5}$ is as defined by $R_3$, in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$d_4$):

(II-d4)

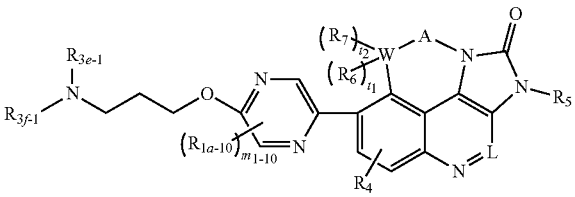

wherein $m_{1-10}$ is selected from the group consisting of 0, 1, 2, and 3, $R_{1a-10}$ is as defined by $R_{1a}$ in the compound of formula (I') or formula (I), $R_{3e-1}$ is as defined by $R_{3e}$ in the compound of formula (I') or formula (I), $R_{3f-1}$ is as defined by $R_{3f}$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$d_5$):

(II-d5)

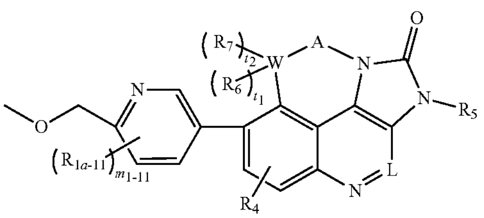

wherein $m_{1-11}$ is selected from the group consisting of 0, 1, 2, and 3, $R_{1a-11}$ is as defined by $R_{1a}$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-$d_6$):

(II-d6)

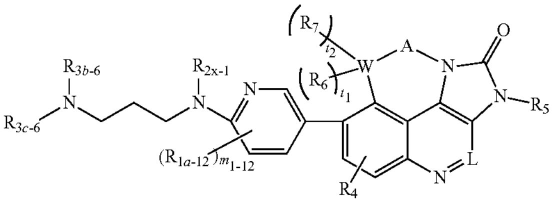

wherein $m_{1-12}$ is selected from the group consisting of 0, 1, 2, and 3, $R_{1a-12}$ is as defined by $R_{1a}$ in the compound of formula (I') or formula (I), $R_{3b-6}$ is as defined by $R_{3b}$ in the compound of formula (I') or formula (I), $R_{3c-6}$ is as defined by $R_{3c}$ in the compound of formula (I') or formula (I), $R_{2x-1}$ is as defined by $R_{2x}$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-e):

(II-e)

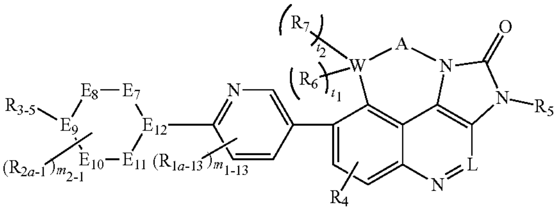

wherein $E_7$, $E_8$, $E_9$, $E_{10}$, $E_{11}$, and $E_{12}$ are independently selected from the group consisting of C and N, $m_{1-13}$ is selected from the group consisting of 0, 1, 2, and 3, $m_{2-1}$ is selected from the group consisting of 0, 1, 2, 3, and 4, $R_{1a-13}$ is as defined by $R_{1a}$ in the compound of formula (I') or formula (I), $R_{2a-1}$ is as defined by $R_{2a}$ in the compound of formula (I') or formula (I), $R_{3-5}$ is as defined by $R_3$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, ageometric isomer, solvate, isotopic derivative, or pharmaceutically acceptable salt thereof, having a structure as represented by formula ($II\text{-}e_1$):

($II\text{-}e_1$)

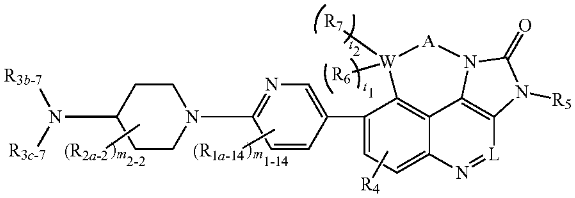

wherein $m_{1\text{-}14}$ is selected from the group consisting of 0, 1, 2, and 3, $m_{2\text{-}2}$ is selected from the group consisting of 0, 1, 2, 3, and 4, $R_{1a\text{-}14}$ is as defined by $R_{1a}$ in the compound of formula (I') or formula (I), $R_{2a\text{-}2}$ is as defined by $R_{2a}$ in the compound of formula (I') or formula (I), $R_{3b\text{-}7}$ is as defined by $R_{3b}$ in the compound of formula (I') or formula (I), $R_{3c\text{-}7}$ is as defined by $R_3$, in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-f):

(II-f)

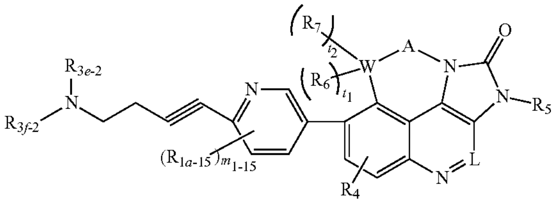

wherein $m_{1\text{-}15}$ is selected from the group consisting of 0, 1, 2, and 3, $R_{1a\text{-}15}$ is as defined by $R_{1a}$ in the compound of formula (I') or formula (I), $R_{3e\text{-}2}$ is as defined by $R_{3e}$ in the compound of formula (I') or formula (I), $R_{3f\text{-}2}$ is as defined by $R_{3f}$ in the compound of formula (I') or formula (I), and $R_4$, $R_5$, $R_6$, $R_7$, A, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (II-g):

(II-g)

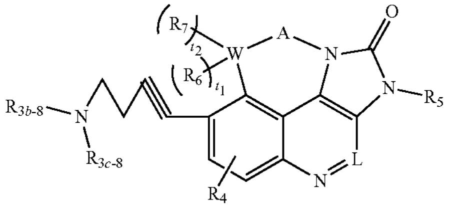

wherein $R_{3b\text{-}8}$ is as defined by $R_{3b}$ in the compound of formula (I') or formula (I), $R_{3c\text{-}8}$ is as defined by $R_3$, in the compound of formula (I) or formula (I), and $R_4$, $R_5$, $R_6$, $R_7$, A, W, L, $t_1$, and $t_2$ are as defined in the compound of formula (I') or formula (I).

Preferably, in the compound or the prodrug, tautomer, optical isomer, geometric isomer, solvate, isotopic derivative, or pharmaceutically acceptable salt thereof provided in the present disclosure, $R_{1a}$ is independently selected from the group consisting of —H, —F, —Cl, —$NH_2$, oxo, —$CH_3$, —$CH_2CH_3$, —$OCH_3$, —$OCH_2CH_3$, —NHC(O)$CH_3$, —C(O)NH$CH_3$,

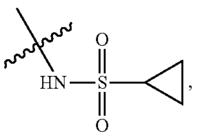,
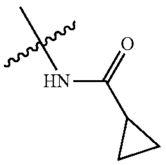,
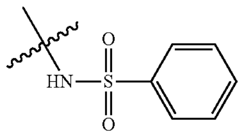, and
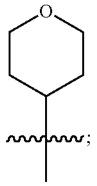;

and said oxo means that two hydrogens on the same substitution site are replaced by the same oxygen to form a double bond.

Further preferably, in the compound or the prodrug, tautomer, optical isomer, geometric isomer, solvate, isotopic derivative, or pharmaceutically acceptable salt thereof provided in the present disclosure, $R_{1a}$ is independently selected from the group consisting of —H, —$NH_2$, oxo, —$CH_3$, —$CH_2CH_3$, —NHC(O)$CH_3$,

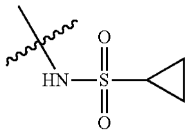,
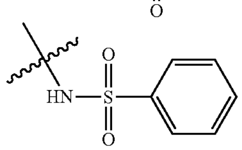, and

-continued

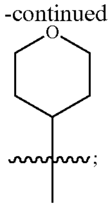;

said oxo means that two hydrogens on the same substitution site are replaced by the same oxygen to form a double bond.

Preferably, in the compound or the prodrug, tautomer, optical isomer, geometric isomer, solvate, isotopic derivative, or pharmaceutically acceptable salt thereof provided in the present disclosure, Y is selected from the group consisting of the following groups:

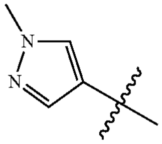,
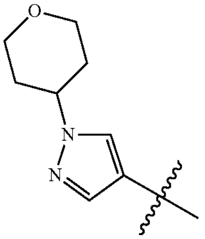,
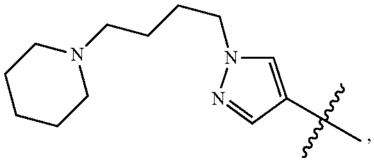,
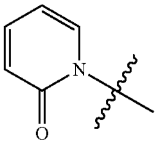,
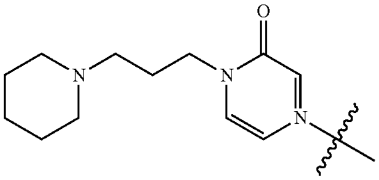,
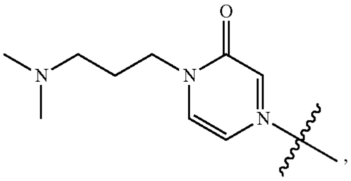,
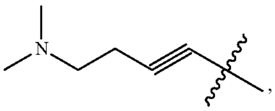,
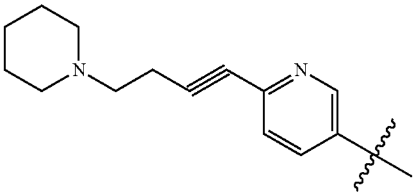,
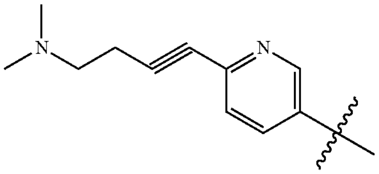, -continued

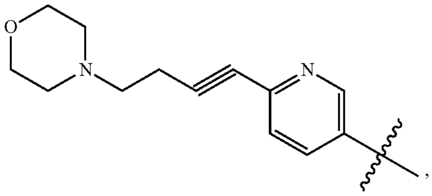,
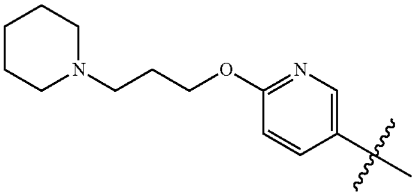,
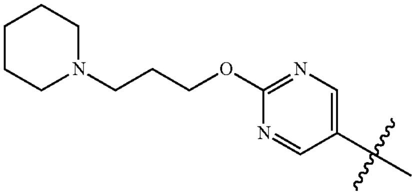,
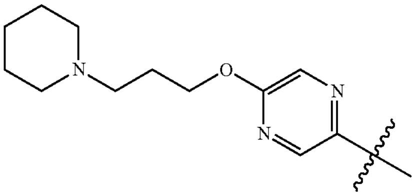,
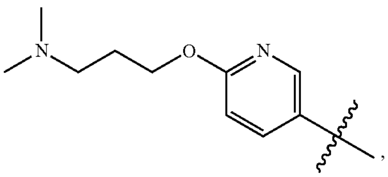,
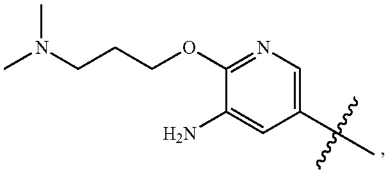,
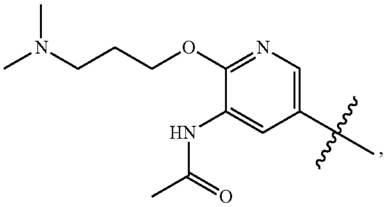,
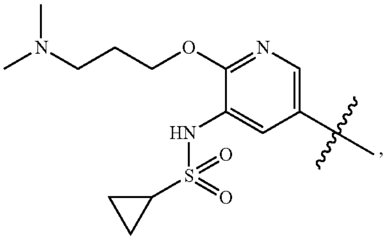, -continued
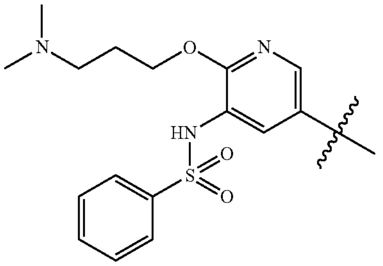
,
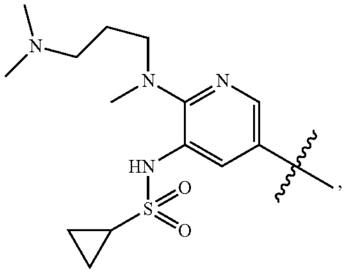
,
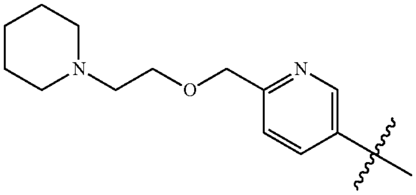
,
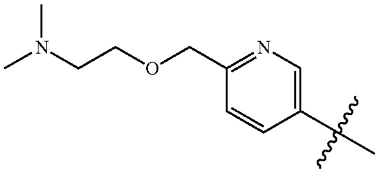
,
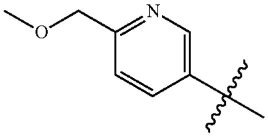
,
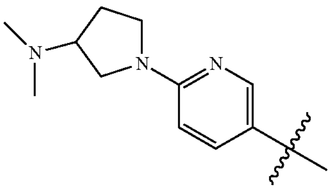
,
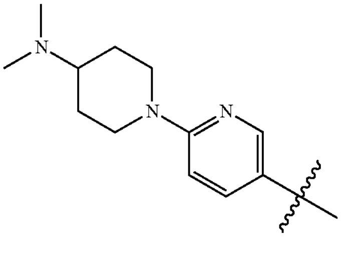
,
-continued
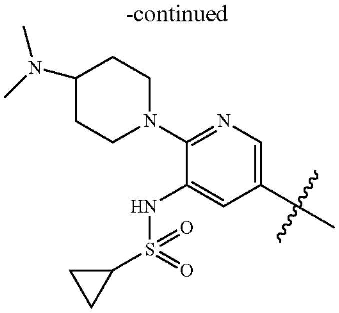
,
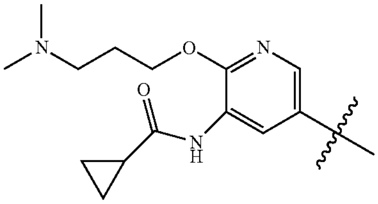
,
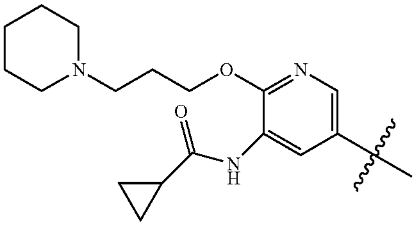
,
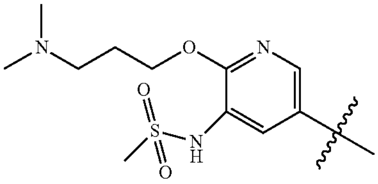
,
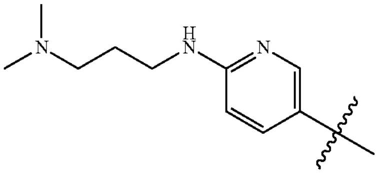
,
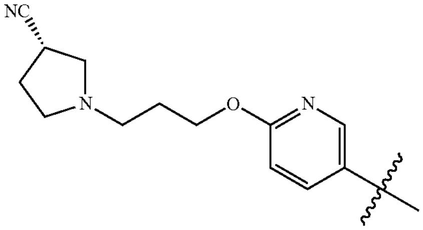
,
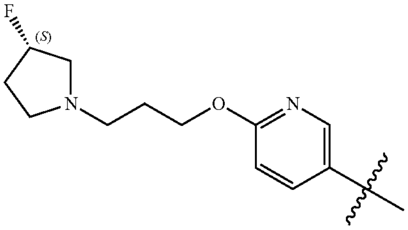
,
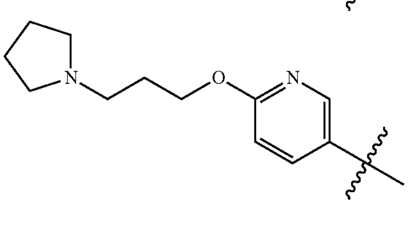
, -continued
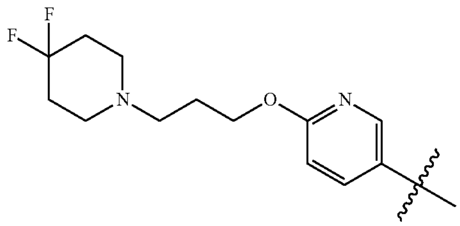
,
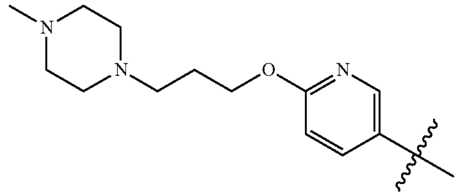
,
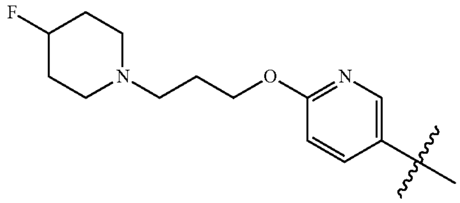
,
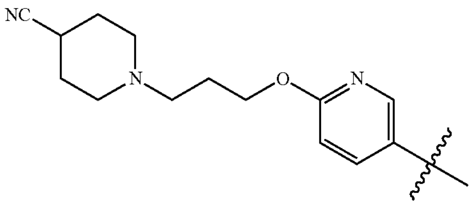
,
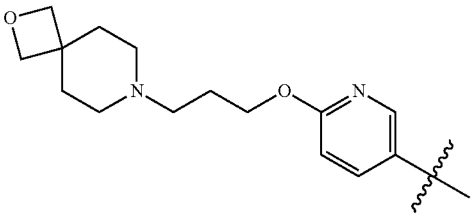
,
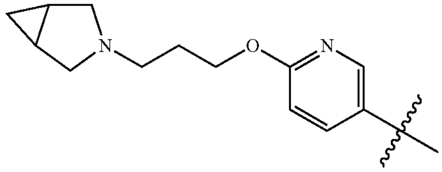
,
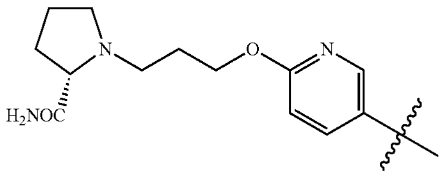
,
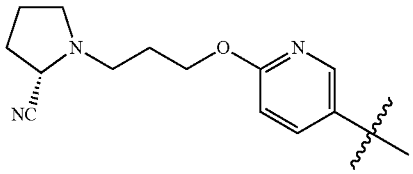
,
-continued
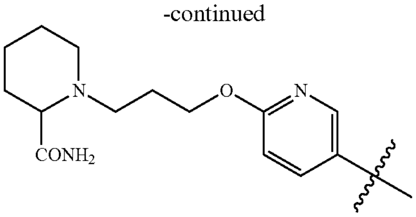
,
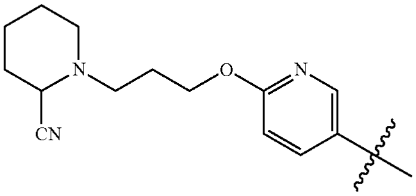
,
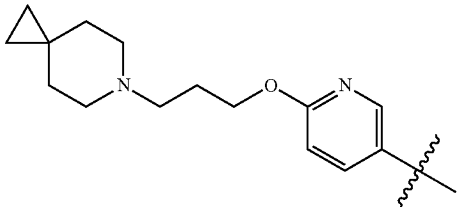
,
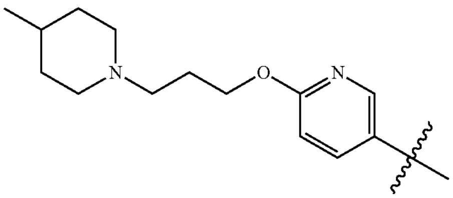
,
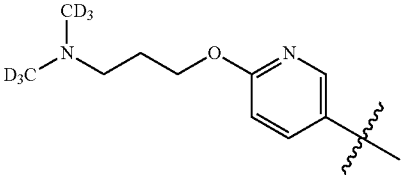
,
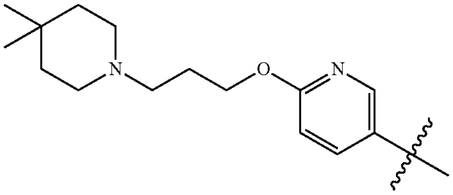
,
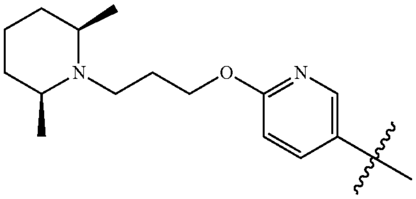
,
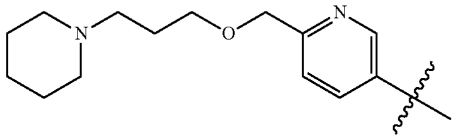
, and
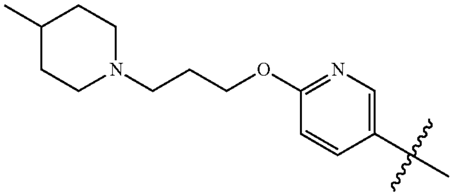

Preferably, in the compound or the prodrug, tautomer, optical isomer, geometric isomer, solvate, isotopic derivative, or pharmaceutically acceptable salt thereof provided in the present disclosure, Y is selected from the group consisting of the following groups:
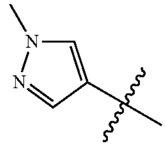,
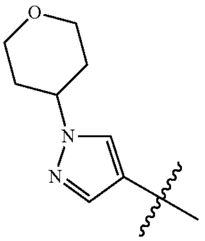,
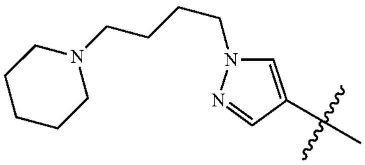,
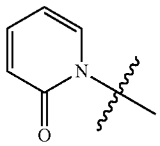,
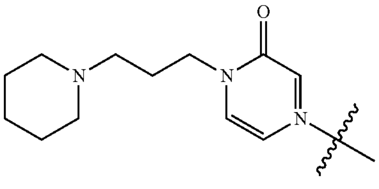,
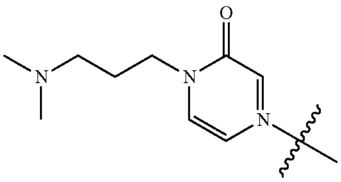,
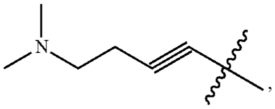,
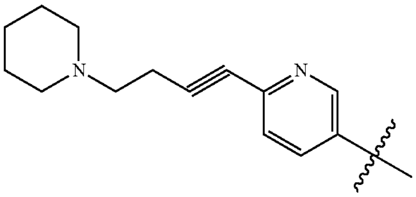,
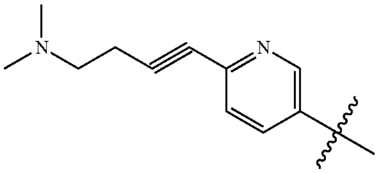,
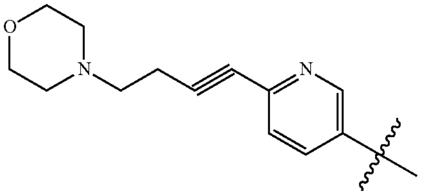,
-continued
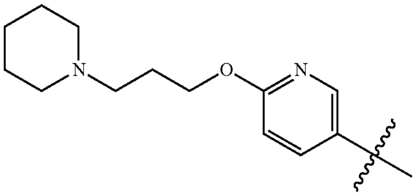,
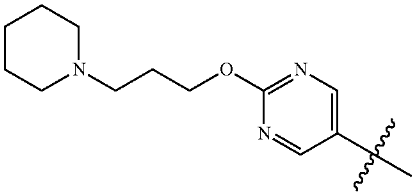,
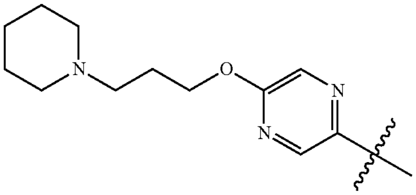,
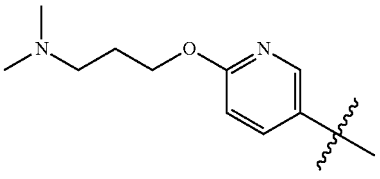,
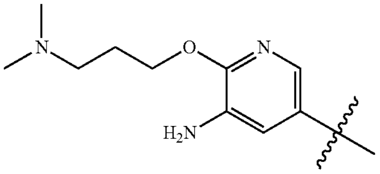,
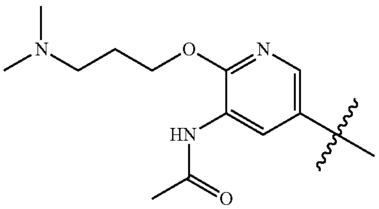,
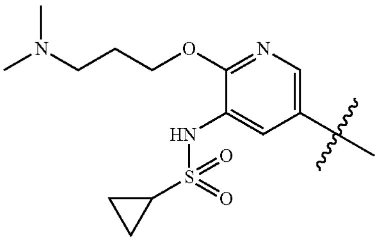,
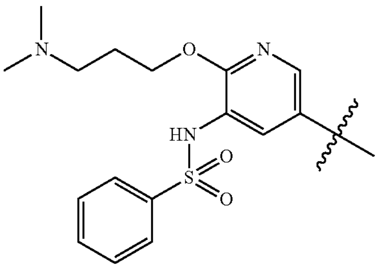, -continued

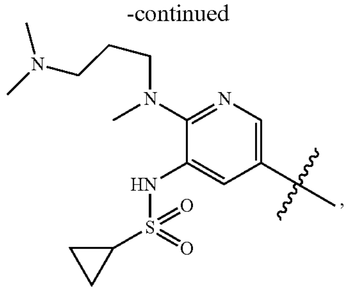

,

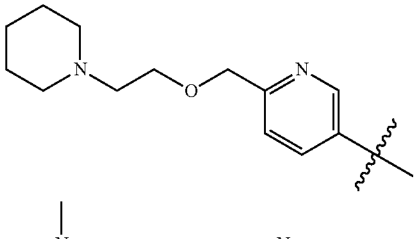

,

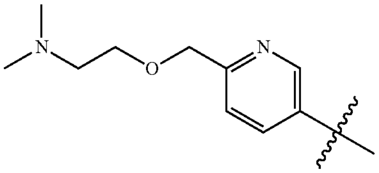

,

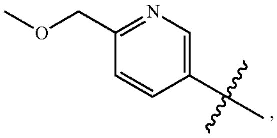

,

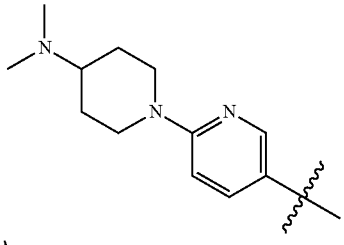

,

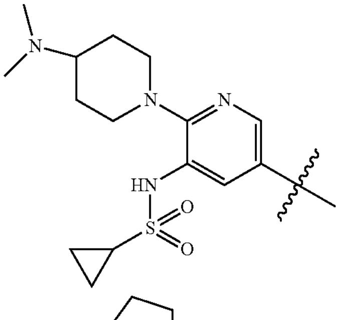

, and

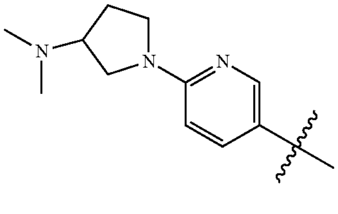

.

Preferably, in the compound or the prodrug, tautomer, optical isomer, geometric isomer, solvate, isotopic derivative, or pharmaceutically acceptable salt thereof provided in the present disclosure, $R_4$ is selected from the group consisting of hydrogen, halogen, amino, and $C_{1-6}$ alkoxy.

Further preferably, in the compound or the prodrug, tautomer, optical isomer, geometric isomer, solvate, isotopic derivative, or pharmaceutically acceptable salt thereof provided in the present disclosure, $R_4$ is selected from the group consisting of hydrogen, halogen, and $C_{1-3}$ alkoxy.

Further preferably, in the compound or the prodrug, tautomer, optical isomer, geometric isomer, solvate, isotopic derivative, or pharmaceutically acceptable salt thereof provided in the present disclosure, $R_4$ is selected from the group consisting of hydrogen, fluorine, and methoxy.

Further preferably, in the compound or the prodrug, tautomer, optical isomer, geometric isomer, solvate, isotopic derivative, or pharmaceutically acceptable salt thereof provided in the present disclosure, $R_4$ is selected from the group consisting of hydrogen and fluorine.

Preferably, in the compound or the prodrug, tautomer, optical isomer, geometric isomer, solvate, isotopic derivative, or pharmaceutically acceptable salt thereof provided in the present disclosure, $R_4$ is selected from the group consisting of methoxy.

Preferably, in the compound or the prodrug, tautomer, optical isomer, geometric isomer, solvate, isotopic derivative, or pharmaceutically acceptable salt thereof provided in the present disclosure, $R_5$ is selected from the group consisting of hydrogen, deuterium and $C_{1-6}$ alkyl which is optionally substituted by one or more deuteriums.

Further preferably, in the compound or the prodrug, tautomer, optical isomer, geometric isomer, solvate, isotopic derivative, or pharmaceutically acceptable salt thereof provided in the present disclosure, $R_5$ is $C_{1-6}$ alkyl.

Further preferably, in the compound or the prodrug, tautomer, optical isomer, geometric isomer, solvate, isotopic derivative, or pharmaceutically acceptable salt thereof provided in the present disclosure, $R_5$ is $C_{1-3}$ alkyl.

Further preferably, in the compound or the prodrug, tautomer, optical isomer, geometric isomer, solvate, isotopic derivative, or pharmaceutically acceptable salt thereof provided in the present disclosure, $R_5$ is methyl.

Preferably, in the compound or the prodrug, tautomer, optical isomer, geometric isomer, solvate, isotopic derivative, or pharmaceutically acceptable salt thereof provided in the present disclosure, L is $C(R_L)$ or N, and $R_L$ is selected from the group consisting of hydrogen, halogen, amino, hydroxyl, $C_{1-6}$ alkyl, and $C_{1-6}$ alkoxy.

Further preferably, in the compound or the prodrug, tautomer, optical isomer, geometric isomer, solvate, isotopic derivative, or pharmaceutically acceptable salt thereof provided in the present disclosure, L is $C(R_L)$, and $R_L$ is selected from the group consisting of hydrogen, halogen, amino, methyl, and methoxy.

Further preferably, in the compound or the prodrug, tautomer, optical isomer, geometric isomer, solvate, isotopic derivative, or pharmaceutically acceptable salt thereof provided in the present disclosure, L is CH.

Preferably, in the compound or the prodrug, tautomer, optical isomer, geometric isomer, solvate, isotopic derivative, or pharmaceutically acceptable salt thereof provided in the present disclosure, L is N.

Preferably, in the compound or the prodrug, tautomer, optical isomer, geometric isomer, solvate, isotopic derivative, or pharmaceutically acceptable salt thereof provided in the present disclosure, W, $Q_1$, and $Q_2$ are independently selected from the group consisting of O, C, S, and N; $Q_3$ is C; wherein $Q_1$ is linked to W.

Further preferably, in the compound or the prodrug, tautomer, optical isomer, geometric isomer, solvate, isotopic derivative, or pharmaceutically acceptable salt thereof provided in the present disclosure, W, $Q_1$, and $Q_2$ are independently selected from the group consisting of O, C, and S; $Q_3$ is C; wherein $Q_1$ is linked to W.

Preferably, in the compound or the prodrug, tautomer, optical isomer, geometric isomer, solvate, isotopic derivative, or pharmaceutically acceptable salt thereof provided in the present disclosure, W is selected from the group consisting of O and N; $Q_1$ is C; $Q_2$ is C; $Q_3$ is C; wherein $Q_1$ is linked to W.

Preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, deuterium, halogen, hydroxyl, amino, cyano, —$R_{6a}$, —$OR_{6a}$, —$SO_2(R_{6a})$, —$C(O)R_{6a}$, —$C(O)OR_{6a}$, —$OC(O)R_{6a}$, —$NH(R_{6a})$, —$N(R_{6a})(R_{6b})$, —$C(O)NH(R_{6a})$, —$C(O)N(R_{6a})(R_{6b})$, —$NHC(O)(R_{6a})$, —$N(R_{6a})C(O)(R_{6b})$, —$SO_2NH(R_{6a})$, —$SO_2N(R_{6a})(R_{6b})$, —$NHSO_2(R_{6a})$, and —$N(R_{6a})SO_2(R_{6b})$; or any two groups linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with the substituents linked thereto, form an $C_{3-10}$ carbocyclyl, 3- to 10-membered heterocyclyl, $C_{6-14}$ aryl, 5- to 12-membered heteroaryl, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl, 3- to 10-membered heterocyclyl, $C_{6-14}$ aryl, 5- to 12-membered heteroaryl, monospiro ring group, or heteromonospiro ring group which is an optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, halogen, hydroxyl, amino, cyano, —$R_{6a}$, —$OR_{6a}$, —$SO_2(R_{6a})$, —$C(O)R_{6a}$, —$C(O)OR_{6a}$, —$OC(O)R_{6a}$, —$NH(R_{6a})$, —$N(R_{6a})(R_{6b})$, —$C(O)NH(R_{6a})$, —$C(O)N(R_{6a})(R_{6b})$, —$NHC(O)(R_{6a})$, —$N(R_{6a})C(O)(R_{6b})$, —$SO_2NH(R_{6a})$, —$SO_2N(R_{6a})(R_{6b})$, —$NHSO_2(R_{6a})$, and —$N(R_{6a})SO_2(R_{6b})$; or any two groups linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with the substituents linked thereto, form $C_{3-10}$ carbocyclyl, 3- to 10-membered heterocyclyl, $C_{6-14}$ aryl, 5- to 12-membered heteroaryl, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl, 3- to 10-membered heterocyclyl, $C_{6-14}$ aryl, 5- to 12-membered heteroaryl, monospiro ring group, or heteromonospiro ring group which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, halogen, hydroxyl, amino, cyano, —$R_{6a}$, —$OR_{6a}$, —$C(O)R_{6a}$, —$C(O)OR_{6a}$, —$OC(O)R_{6a}$, —$NH(R_{6a})$, —$N(R_{6a})(R_{6b})$, —$C(O)NH(R_{6a})$, —$C(O)N(R_{6a})(R_{6b})$, —$NHC(O)(R_{6a})$, and —$N(R_{6a})C(O)(R_{6b})$; or any two groups linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with substituents linked thereto, form $C_{3-10}$ carbocyclyl, 3- to 10-membered heterocyclyl, $C_{6-14}$ aryl, 5- to 12-membered heteroaryl, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl, 3- to 10-membered heterocyclyl, $C_{6-14}$ aryl, or 5- to 12-membered heteroaryl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, halogen, hydroxyl, amino, —$R_{6a}$, —$NH(R_{6a})$, and —$N(R_{6a})(R_{6b})$; or any two groups linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with the substituents linked thereto, form $C_{3-10}$ carbocyclyl, 3- to 10-membered heterocyclyl, $C_{6-14}$ aryl, 5- to 12-membered heteroaryl, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl, 3- to 10-membered heterocyclyl, $C_{6-14}$ aryl, or 5- to 12-membered heteroaryl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, halogen, hydroxyl, amino, —$R_{6a}$, —$NH(R_{6a})$, and —$N(R_{6a})(R_{6b})$; or any two groups linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with substituents linked thereto, form $C_{3-10}$ carbocyclyl, 3- to 10-membered heterocyclyl, $C_{6-14}$ aryl, 5- to 12-membered heteroaryl, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl or 3- to 10-membered heterocyclyl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, halogen, hydroxyl, amino, —$R_{6a}$, —$NH(R_{6a})$, and —$N(R_{6a})(R_{6b})$; or any two groups linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with substituents linked thereto, form $C_{3-10}$ carbocyclyl, 3- to 10-membered heterocyclyl, $C_{6-8}$ aryl, 5- to 10-membered heteroaryl, condensed ring group, or heterocondensed ring group which is optionally substituted by $R_{6c}$; or any one atom among W, each present $Q_1$, each present $Q_2$, and $Q_3$, together with the substituents linked thereto, forms $C_{3-10}$ carbocyclyl or 3- to 10-membered heterocyclyl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, halogen, and —$R_{6a}$; or any two groups linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with substituents linked thereto, form $C_{3-10}$ carbocyclyl, 3- to 10-membered heterocyclyl, $C_{6-g}$ aryl, or 5- to 12-membered heteroaryl which is optionally substituted by $R_{6c}$; or any one atom among W, each present $Q_1$, each present $Q_2$, and $Q_3$, together with the substituents linked thereto, forms $C_{3-10}$ carbocyclyl or 3- to 10-membered heterocyclyl which is optionally substituted by $R_{6c}$.

Preferably, in the compound or the prodrug, tautomer, optical isomer, geometric isomer, solvate, isotopic derivative, or pharmaceutically acceptable salt thereof provided in the present disclosure, any two adjacent atoms among W, each present $Q_1$, each present $Q_2$, and $Q_3$, together with substituents linked thereto, form $C_{3-10}$ carbocyclyl, 3- to 10-membered heterocycloalkyl, $C_{6-8}$ aryl, or 5- to 10-membered heteroaryl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, any two adjacent atoms among W, each present $Q_1$, each present $Q_2$, and $Q_3$, together with the substituents linked thereto, form $C_{3-8}$ cycloalkyl, 3- to 8-membered heterocycloalkyl, $C_{6-8}$ aryl, or 5- to 8-membered heteroaryl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, any two adjacent atoms among W, each present $Q_1$, each present $Q_2$, and $Q_3$, together with the substituents linked thereto, form $C_{5-6}$ cycloalkyl, 5- to 6-membered heterocycloalkyl, $C_6$ aryl, or 5- to 6-membered heteroaryl which is optionally substituted by $R_{6e}$, the heteroatom thereof is selected from the group consisting of O and N, and the number of the heteroatom is 1 or 2.

Preferably, in the compound or the prodrug, tautomer, optical isomer, geometric isomer, solvate, isotopic derivative, or pharmaceutically acceptable salt thereof provided in the present disclosure, any one atom among W, each present $Q_1$, each present $Q_2$, and $Q_3$, together with the substituents linked thereto, forms $C_{3-10}$ cycloalkyl or 3- to 10-membered heterocycloalkyl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, any one atom among W, each present $Q_1$, each present $Q_2$, and $Q_3$, together with the substituents linked thereto, forms $C_{3-6}$ cycloalkyl or 3- to 7-membered heterocycloalkyl which is optionally substituted $R_{6c}$.

Further preferably, in the compound or the prodrug, tautomer, optical isomer, geometric isomer, solvate, isotopic derivative, or pharmaceutically acceptable salt thereof provided in the present disclosure, any one atom among W, each present $Q_1$, each present $Q_2$, and $Q_3$, together with the substituents linked thereto, forms $C_{3-4}$ cycloalkyl or 3- to 6-membered heterocycloalkyl which is optionally substituted by $R_k$e, the heteroatom thereof is selected from the group consisting of O and N, and the number of the heteroatom is 1 or 2.

Further preferably, in the compound or the prodrug, tautomer, optical isomer, geometric isomer, solvate, isotopic derivative, or pharmaceutically acceptable salt thereof provided in the present disclosure, any one atom among W, each present $Q_1$, each present $Q_2$, and $Q_3$, together with the substituents linked thereto, forms $C_{3-4}$ cycloalkyl which is optionally substituted by $R_{6c}$.

Preferably, in the compound or the prodrug, tautomer, optical isomer, geometric isomer, solvate, isotopic derivative, or pharmaceutically acceptable salt thereof provided in the present disclosure, $R_{6a}$ and $R_{6b}$ are, for each presence, independently selected from the group consisting of hydrogen and any one of $C_{1-6}$ alkyl, $C_{1-6}$ alkoxy, $C_{3-10}$ carbocyclyl, 3- to 10-membered heterocyclyl, $C_{6-14}$ aryl, 5- to 12-membered heteroaryl, condensed ring group, and hetero-condensed ring group which is optionally substituted by $R_{6c}$; or when $R_{6a}$ and $R_{6b}$ are linked to a group on the same nitrogen atom, $R_{6a}$ and $R_{6b}$, together with the nitrogen atom linked thereto, form 3- to 10-membered heterocyclyl or 5- to 12-membered heteroaryl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_{6a}$ and $R_{6b}$ are, for each presence, independently selected from the group consisting of hydrogen and any one of $C_{1-6}$ alkyl, $C_{1-6}$ alkoxy, $C_{3-10}$ carbocyclyl, 3- to 10-membered heterocyclyl, $C_{6-8}$ aryl, and 5- to 10-membered heteroaryl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_{6a}$ and $R_{6b}$ are, for each presence, independently selected from the group consisting of hydrogen, deuterium, and any one of $C_{1-6}$ alkyl, $C_{1-6}$ alkoxy, $C_{3-6}$ cycloalkyl, 5- to 6-membered heterocycloalkyl, $C_{6-8}$ aryl, 5- to 6-membered heteroaryl, 9- to 10-membered bicyclic heterocyclyl, and 9- to 10-membered bicyclic heteroaryl which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_{6a}$ and $R_{6b}$ are, for each presence, independently selected from the group consisting of hydrogen and any one of $C_{1-6}$ alkyl and $C_{1-6}$ alkoxy which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_{6a}$ and $R_{6b}$ are, for each presence, independently selected from the group consisting of hydrogen and any one of $C_{1-3}$ alkyl and $C_{1-3}$ alkoxy which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_{6a}$ and $R_{6b}$ are, for each presence, independently selected from the group consisting of hydrogen and any one of methyl, ethyl, n-propyl, isopropyl, methoxy, ethoxy, n-propoxy, and isopropoxy which is optionally substituted by $R_{6c}$.

Further preferably, in the compound or the prodrug, tautomer, optical isomer, geometric isomer, solvate, isotopic derivative, or pharmaceutically acceptable salt thereof provided in the present disclosure, $R_{6a}$ and $R_{6b}$ are, for each presence, independently selected from the group consisting of hydrogen and any one of methyl and ethyl which is optionally substituted by $R_{6c}$.

Preferably, in the compound or the prodrug, tautomer, optical isomer, geometric isomer, solvate, isotopic derivative, or pharmaceutically acceptable salt thereof provided in the present disclosure, $R_{6e}$ is, for each presence, independently selected from the group consisting of hydrogen, deuterium, halogen, hydroxyl, amino, —$R_{6d}$, —$OR_{6d}$, —$N(R_{6d})R_{6e}$, —$C(O)R_{6d}$, —$C(O)N(R_{6d})R_{6e}$, —$N(R_{6d})C(O)R_{6e}$, and —$C(O)OR_{6d}$.

Preferably, in the compound or the prodrug, tautomer, optical isomer, geometric isomer, solvate, isotopic derivative, or pharmaceutically acceptable salt thereof provided in the present disclosure, $R_{6e}$ is, for each presence, independently selected from the group consisting of hydrogen, halogen, hydroxyl, amino, —$R_{6d}$, —$OR_{6d}$, —$N(R_{6d})R_{6e}$, —$C(O)R_{6d}$, —$C(O)N(R_{6d})R_{6e}$, —$N(R_{6d})C(O)R_{6e}$, and —$C(O)OR_{6d}$.

Preferably, in the compound or the prodrug, tautomer, optical isomer, geometric isomer, solvate, isotopic derivative, or pharmaceutically acceptable salt thereof provided in the present disclosure, $R_{6d}$ and $R_{6e}$ are, for each presence, independently selected from the group consisting of hydrogen, halogen, hydroxyl, amino, nitro, cyano, and any one of $C_{1-6}$ alkyl, $C_{2-6}$ alkenyl, $C_{2-6}$ alkynyl, $C_{1-6}$ alkoxy, $C_{3-10}$ carbocyclyl, 3- to 10-membered heterocyclyl, $C_{6-14}$ aryl, 5- to 12-membered heteroaryl, condensed ring group, and heterocondensed ring group which is optionally substituted by halogen, hydroxyl, amino, or $C_{1-6}$ alkyl; or when $R_{6d}$ and $R_{6e}$ are linked to the same nitrogen atom, $R_{6d}$ and $R_{6e}$, together with the nitrogen atom linked thereto, form 3- to 10-membered heterocyclyl or 5- to 12-membered heteroaryl which is optionally substituted by halogen, hydroxyl, amino, or $C_{1-6}$ alkyl.

Further preferably, in the compound or the prodrug, tautomer, optical isomer, geometric isomer, solvate, isotopic derivative, or pharmaceutically acceptable salt thereof provided in the present disclosure, $R_{6d}$ and $R_{6e}$ are, for each presence, independently selected from the group consisting of hydrogen, halogen, hydroxyl, amino, nitro, cyano, $C_{1-6}$ alkyl, $C_{2-6}$ alkenyl, $C_{2-6}$ alkynyl, $C_{1-6}$ alkoxy, $C_{3-10}$ carbocyclyl, 3- to 10-membered heterocyclyl, $C_{6-14}$ aryl, 5- to 12-membered heteroaryl, condensed ring group, and heterocondensed ring group; or when $R_{6a}$ and $R_{6e}$ are linked to the same nitrogen atom, $R_{6d}$ and $R_{6e}$, together with the nitrogen atom linked thereto, form 3- to 10-membered heterocyclyl or 5- to 12-membered heteroaryl.

Further preferably, in the compound or the prodrug, tautomer, optical isomer, geometric isomer, solvate, isotopic derivative, or pharmaceutically acceptable salt thereof provided in the present disclosure, $R_{6d}$ and $R_{6e}$ are, for each presence, independently selected from the group consisting of hydrogen, $C_{1-6}$ alkyl, $C_{1-6}$ alkoxy, $C_{3-10}$ carbocyclyl, 3- to 10-membered heterocyclyl, $C_{6-14}$ aryl, 5- to 12-membered heteroaryl, condensed ring group, and heterocondensed ring group.

Further preferably, in the compound or the prodrug, tautomer, optical isomer, geometric isomer, solvate, isotopic derivative, or pharmaceutically acceptable salt thereof provided in the present disclosure, $R_{6d}$ and $R_{6e}$ are, for each presence, independently selected from the group consisting of hydrogen, $C_{1-6}$ alkyl, $C_{1-6}$ alkoxy, $C_{3-10}$ carbocyclyl, 3- to 10-membered heterocyclyl, $C_{6-8}$ aryl, and 5- to 10-membered heteroaryl.

Preferably, in the compound or the prodrug, tautomer, optical isomer, geometric isomer, solvate, isotopic derivative, or pharmaceutically acceptable salt thereof provided in the present disclosure, $R_6$, is, for each presence, independently selected from the group consisting of hydrogen, fluorine, chlorine, hydroxyl, amino, —$NH(C_{1-6}$ alkyl), —$N(CH_3)(C_{1-6}$ alkyl), —$C(O)(C_{1-6}$ alkyl), —$C(O)NH(C_{1-6}$ alkyl), —$NHC(O)(C_{1-6}$ alkyl), —$C(O)O(C_{1-6}$ alkyl), $C_{1-6}$ alkyl, $C_{1-6}$ alkoxy, $C_{3-10}$ carbocyclyl, 3- to 10-membered heterocyclyl, $C_{6-8}$ aryl, 5- to 10-membered heteroaryl, condensed ring group, and heterocondensed ring group.

Further preferably, in the compound or the prodrug, tautomer, optical isomer, geometric isomer, solvate, isotopic derivative, or pharmaceutically acceptable salt thereof provided in the present disclosure, $R_6$, is, for each presence, independently selected from the group consisting of hydrogen, fluorine, chlorine, hydroxyl, amino, —$NH(C_{1-6}$ alkyl), —$N(CH_3)(C_{1-6}$ alkyl), —$C(O)(C_{1-6}$ alkyl), —$C(O)NH(C_{1-6}$ alkyl), —$NHC(O)(C_{1-6}$ alkyl), —$C(O)O(C_{1-6}$ alkyl), $C_{1-6}$ alkyl, $C_{1-6}$ alkoxy, $C_{3-10}$ carbocyclyl, 3- to 10-membered heterocyclyl, $C_{6-8}$ aryl, and 5- to 10-membered heteroaryl.

Further preferably, in the compound or the prodrug, tautomer, optical isomer, geometric isomer, solvate, isotopic derivative, or pharmaceutically acceptable salt thereof provided in the present disclosure, $R_6$, is, for each presence, independently selected from the group consisting of hydrogen, fluorine, chlorine, hydroxyl, amino, —$NH(C_{1-6}$ alkyl), —$N(CH_3)(C_{1-6}$ alkyl), —$C(O)(C_{1-6}$ alkyl), —$C(O)NH(C_{1-6}$ alkyl), —$NHC(O)(C_{1-6}$ alkyl), —$C(O)O(C_{1-6}$ alkyl), $C_{1-6}$ alkyl, $C_{1-6}$ alkoxy, $C_{3-10}$ carbocyclyl, 3- to 10-membered heterocyclyl, $C_{6-8}$ aryl, and 5- to 10-membered heteroaryl, the heteroatom thereof is selected from the group consisting of N and S, and the number of the heteroatom is 1, 2 or 3.

Further preferably, in the compound or the prodrug, tautomer, optical isomer, geometric isomer, solvate, isotopic derivative, or pharmaceutically acceptable salt thereof provided in the present disclosure, $R_6$, is, for each presence, independently selected from the group consisting of hydrogen, fluorine, chlorine, hydroxyl, amino, —$NH(C_{1-6}$ alkyl), —$N(CH_3)(C_{1-6}$ alkyl), —$C(O)(C_{1-6}$ alkyl), —$C(O)NH(C_{1-6}$ alkyl), —$NHC(O)(C_{1-6}$ alkyl), —$C(O)O(C_{1-6}$ alkyl), $C_{1-6}$ alkyl, $C_{1-6}$ alkoxy, $C_{3-6}$ cycloalkyl, 3- to 6-membered heterocycloalkyl, $C_{6-8}$ aryl, and 5- to 6-membered heteroaryl, the heteroatom thereof is selected from the group consisting of N and S, and the number of the heteroatom is 1, 2 or 3.

Preferably, in the compound or the prodrug, tautomer, optical isomer, geometric isomer, solvate, isotopic derivative, or pharmaceutically acceptable salt thereof provided in the present disclosure, $R_6$, is, for each presence, independently selected from the group consisting of hydrogen, deuterium, halogen, hydroxyl, amino, $C_{1-6}$ alkyl, and $C_{1-6}$ alkoxy.

Further preferably, in the compound or the prodrug, tautomer, optical isomer, geometric isomer, solvate, isotopic derivative, or pharmaceutically acceptable salt thereof provided in the present disclosure, $R_6$, is, for each presence, independently selected from the group consisting of hydrogen, fluorine, chlorine, hydroxyl, amino, methyl, ethyl, n-propyl, isopropyl, methoxy, ethoxy, n-propoxy, and isopropoxy.

Preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen, deuterium, and any one of $C_{1-6}$ alkyl, $C_{1-6}$ alkoxy, $C_{3-6}$ cycloalkyl, 5- to 6-membered heterocycloalkyl, $C_{6-8}$ aryl or 5- to 6-membered heteroaryl, 9- to 10-membered bicyclic heterocyclyl, and 9- to 10-membered bicyclic heteroaryl which is optionally substituted by deuterium, halogen, hydroxyl, amino, $C_{1-6}$ alkyl, $C_{1-6}$ alkoxy, —C(O)($C_{1-6}$ alkyl), —C(O)NH($C_{1-6}$ alkyl), —NHC(O)($C_{1-6}$ alkyl), —C(O)O($C_{1-6}$ alkyl), $C_{3-6}$ cycloalkyl, 5- to 6-membered heterocycloalkyl, phenyl, 5- to 6-membered heteroaryl, 9- to 10-membered bicyclic heterocyclyl, or 9- to 10-membered bicyclic heteroaryl.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen and any one of $C_{1-6}$ alkyl, $C_{1-6}$ alkoxy, $C_{3-6}$ cycloalkyl, 5- to 6-membered heterocycloalkyl, $C_{6-8}$ aryl, and 5- to 6-membered heteroaryl which is optionally substituted by halogen, hydroxyl, amino, $C_{1-6}$ alkyl, $C_{1-6}$ alkoxy, —C(O)($C_{1-6}$ alkyl), —C(O)NH($C_{1-6}$ alkyl), —NHC(O)($C_{1-6}$ alkyl), —C(O)O($C_{1-6}$ alkyl), $C_{3-6}$ cycloalkyl, 5- to 6-membered heterocycloalkyl, phenyl, or 5- to 6-membered heteroaryl.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen and any one of $C_{1-6}$ alkyl and $C_{1-6}$ alkoxy which is optionally substituted by halogen, hydroxyl, amino, $C_{1-6}$ alkyl, $C_{1-6}$ alkoxy, —C(O)($C_{1-6}$ alkyl), —C(O)NH($C_{1-6}$ alkyl), or —NHC(O)($C_{1-6}$ alkyl).

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen and any one of $C_{1-6}$ alkyl and $C_{1-6}$ alkoxy which is optionally substituted by halogen, hydroxyl, amino, $C_{1-6}$ alkyl, or $C_{1-6}$ alkoxy.

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of hydrogen and any one of $C_{1-3}$ alkyl and $C_{1-3}$ alkoxy which is optionally substituted by halogen, hydroxyl, amino, $C_{1-3}$ alkyl, or $C_{1-3}$ alkoxy.

Preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the following groups: —H, —F, —Cl, —OH, —$NH_2$, —$CH_3$, —$CH_2CH_3$, —$CH_2CH_2CH_3$, —$CH(CH_3)CH_3$, —$CH_2CH(CH_3)CH_3$, —$CH_2OH$, —$CH_2CH_2OH$, —$OCH_3$, —$OCH_2CH_3$, —$OCH_2CH_2CH_3$, —$OCH(CH_3)CH_3$, —$CH_2OCH_3$, —$CH_2OCH_2CH_3$, —$CH_2CH_2OCH_3$, —$CH_2CH_2CH_2OCH_3$, —$CH(CH_3)CH_2OCH_3$, —$NHCH_3$, —$N(CH_3)CH_3$, —$CH_2N(CH_3)CH_3$,

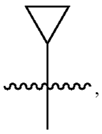, 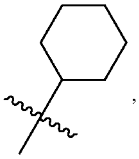, 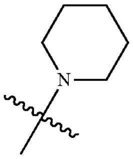, 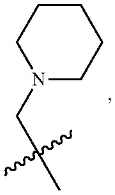,

-continued

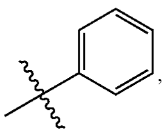, 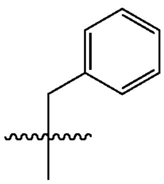, 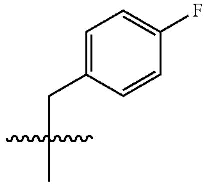,

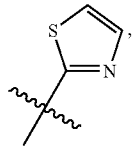, 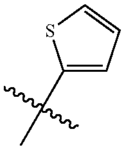, 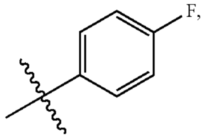,

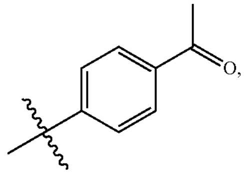, 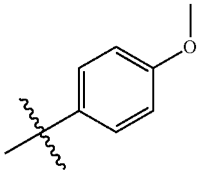,

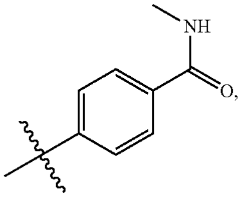, 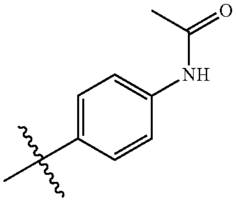,

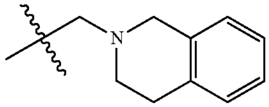, 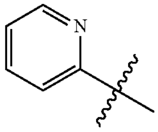,

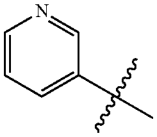, 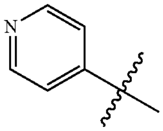, 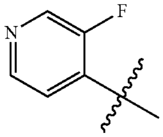,

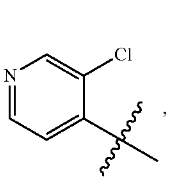, 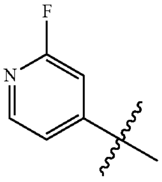, and 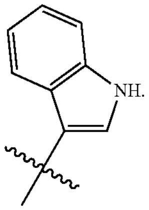

Preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of the following groups: —H, —F, —Cl, —OH, —$NH_2$, —$CH_3$, —$CH_2CH_3$, —$CH_2CH_2CH_3$, —$CH(CH_3)CH_3$, —$CH_2CH(CH_3)CH_3$, —$CH_2OH$, —$CH_2CH_2OH$, —$OCH_3$, —$OCH_2CH_3$, —$OCH_2CH_2CH_3$, —$OCH(CH_3)CH_3$, —$CH_2OCH_3$, —$CH_2OCH_2CH_3$, —$CH_2CH_2OCH_3$, —$NHCH_3$, —$N(CH_3)CH_3$, —$CH_2N(CH_3)CH_3$,

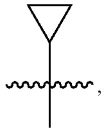, 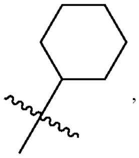, 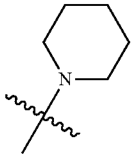, 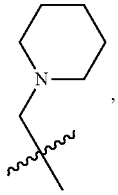,

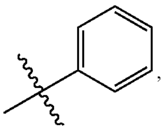, 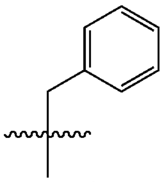, 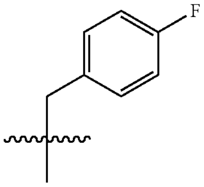,

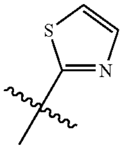, 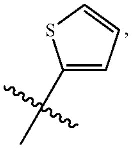, 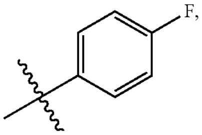

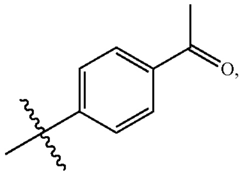 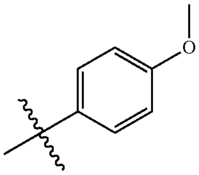,

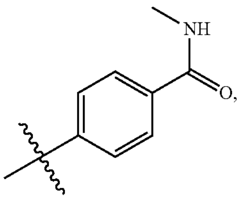 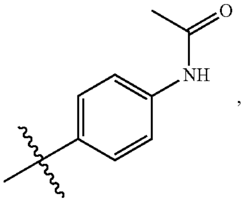,

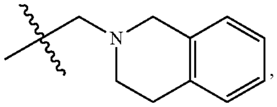, 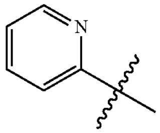,

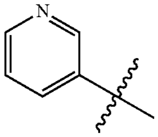, 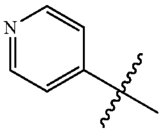, 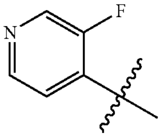,

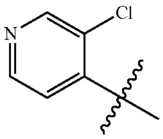, 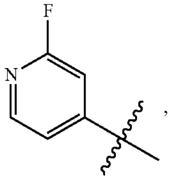, and 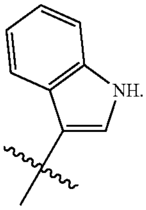

Further preferably, in the compound or the prodrug, tautomer, optical isomer, geometric isomer, solvate, isotopic derivative, or pharmaceutically acceptable salt thereof provided in the present disclosure, $R_6$, $R_7$, $R_8$, $R_9$, $R_{10}$, $R_{11}$, $R_{12}$, and $R_{13}$ are, for each presence, independently selected from the group consisting of the following groups: —H, —F, —Cl, —OH, —$NH_2$, —$CH_3$, —$CH_2CH_3$, —$CH_2CH_2CH_3$, —$CH(CH_3)CH_3$, —$CH_2OCH_3$, —$CH_2CH_2OCH_3$, —$CH_2CH_2CH_2OCH_3$, and —$CH(CH_3)CH_2OCH_3$.

Preferably, in the compound or the prodrug, tautomer, optical isomer, geometric isomer, solvate, isotopic derivative, or pharmaceutically acceptable salt thereof provided in the present disclosure, any two groups linked to the same atom among $R_6$, $R_7$, $R_8$, $R_9$, $R_{10}$, $R_{11}$, $R_{12}$, and $R_{13}$ form =O or =$CH_2$.

Preferably, in the compound or the prodrug, tautomer, optical isomer, geometric isomer, solvate, isotopic derivative, or pharmaceutically acceptable salt thereof provided in the present disclosure, any two adjacent atoms among W, each present $Q_1$, each present $Q_2$, and $Q_3$, together with the substituents linked thereto, form the following groups:

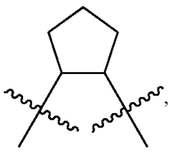, 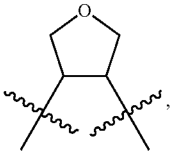, 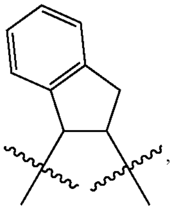,

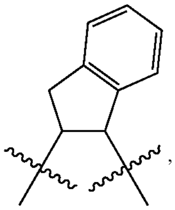, 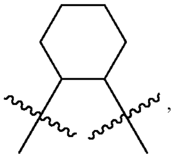, 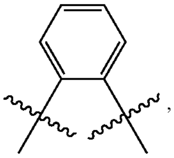,

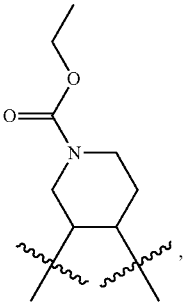, 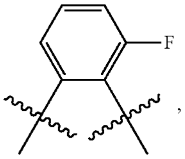, 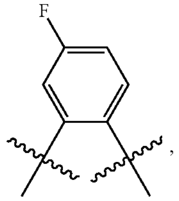,

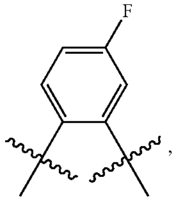, 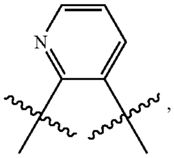, 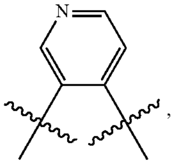,

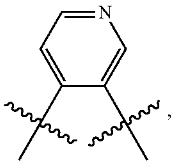, 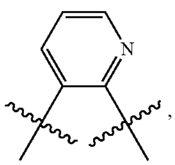, 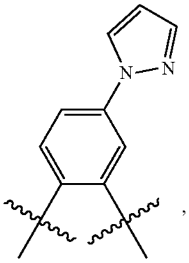,

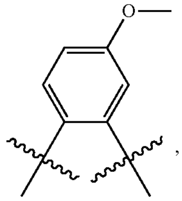, 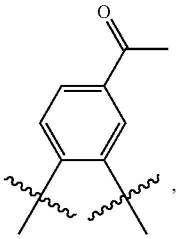,

-continued

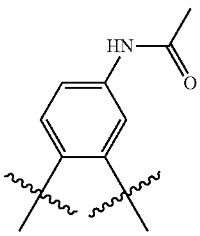
, and
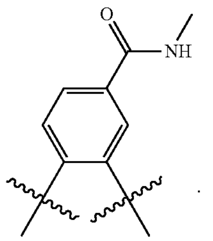
.

Preferably, in the compound or the prodrug, tautomer, optical isomer, geometric isomer, solvate, isotopic derivative, or pharmaceutically acceptable salt thereof provided in the present disclosure, any one atom among W, each present $Q_1$, each present $Q_2$, and $Q_3$, together with the substituents linked thereto, forms the following groups:

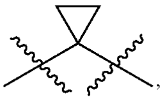
,
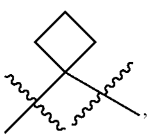
,
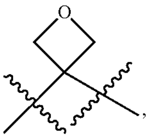
,
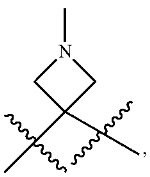
,
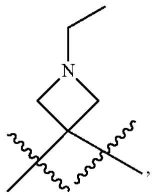
,
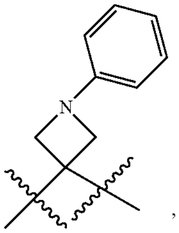
, and
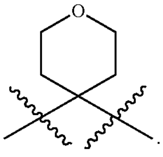
.

Further preferably, in the compound or the prodrug, tautomer, optical isomer, geometric isomer, solvate, isotopic derivative, or pharmaceutically acceptable salt thereof provided in the present disclosure, any one atom among W, each present $Q_1$, each present $Q_2$, and $Q_3$, together with the substituents linked thereto, forms the following groups:

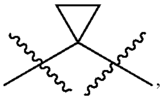
,
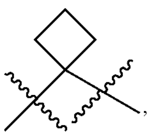
,
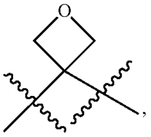
,
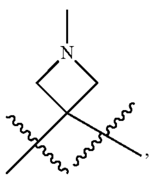
,
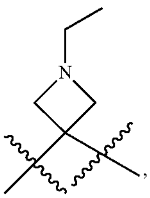
, and

-continued

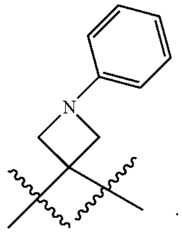
.

Further preferably, in the compound or the prodrug, tautomer, optical isomer, geometric isomer, solvate, isotopic derivative, or pharmaceutically acceptable salt thereof provided in the present disclosure, any one atom among W, each present $Q_1$, each present $Q_2$, and $Q_3$, together with the substituents linked thereto, forms the following groups:

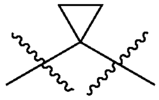
and
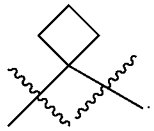
.

Preferably, the present disclosure provides a compound or a prodrug, tautomer, optical isomer, geometric isomer, solvate, isotopic derivative, or pharmaceutically acceptable salt thereof, having a structure as represented by formula (III-a):

(III-a)

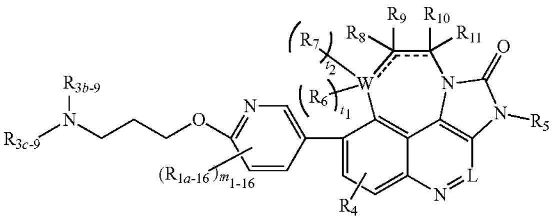

wherein $m_{1-6}$ is selected from the group consisting of 0, 1, 2, and 3, $R_{1a-16}$ is as defined by $R_{1a}$ in the compound of formula (I) or formula (I), $R_{3b-9}$ is as defined by $R_{3b}$ in the compound of formula (I') or formula (I), $R_{3c-9}$ is as defined by $R_3$, in the compound of formula (I') or formula (I), and $R_4$, $R_5$, $R_6$, $R_7$, $R_8$, $R_9$, $R_{10}$, $R_{11}$, W, L, $t_1$, and $t_2$ are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (III-$a_1$):

(III-$a_1$)

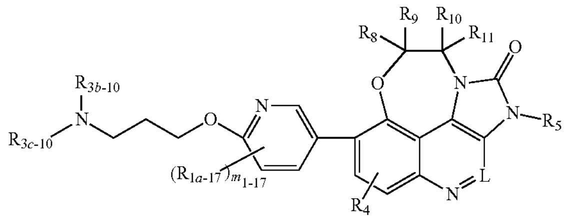

wherein $m_{117}$ is selected from the group consisting of 0, 1, 2, and 3, $R_{1a\text{-}17}$ is as defined by $R_{1a}$ in the compound of formula (I) or formula (I), $R_{3b\text{-}10}$ is as defined by $R_{3b}$ in the compound of formula (I') or formula (I), $R_{3c\text{-}10}$ is as defined by $R_3$, in the compound of formula (I') or formula (I), and $R_4$, $R_5$, $R_8$, $R_9$, $R_{10}$, $R_{11}$, and L are as defined in the compound of formula (I') or formula (I).

Preferably, the present disclosure provides a compound or a prodrug, tautomer, optical isomer, geometric isomer, solvate, isotopic derivative, or pharmaceutically acceptable salt thereof, having a structure as represented by formula (III-$a_2$):

(III-$a_2$)

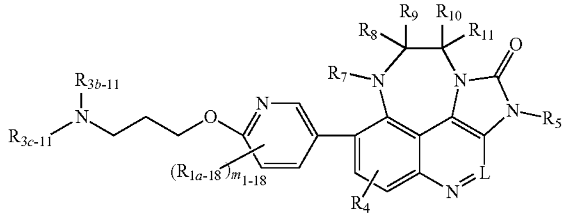

wherein $m_{1\text{-}18}$ is selected from the group consisting of 0, 1, 2, and 3, $R_{1a\text{-}18}$ is as defined by $R_{1a}$ in the compound of formula (I') or formula (I), $R_{3b\text{-}11}$ is as defined by $R_{3b}$ in the compound of formula (I') or formula (I), $R_{3c\text{-}11}$ is as defined by $R_3$, in the compound of formula (I') or formula (I), and $R_4$, $R_5$, $R_7$, $R_8$, $R_9$, $R_{10}$, $R_{11}$, and L are as defined in the compound of formula (I') or formula (I).

Preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1\text{-}6}$ alkyl; or when $R_{3b}$ and $R_{3c}$ are linked to the same nitrogen atom, $R_{3b}$ and $R_{3c}$, together with the nitrogen atom linked thereto, form an optionally substituted 3- to 10-membered heterocycloalkyl; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1\text{-}4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl and 6- to 10-membered bicyclic heterocyclyl, the heteroatom thereof is independently selected from the group consisting of O and N, and the number of the heteroatom is 1, 2, or 3; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted $C_{1\text{-}4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl, 3-/6-membered heteromonospiro ring group, 4-/6-membered heteromonospiro ring group, and 3-/5-membered fused heterocyclyl, the heteroatom thereof is independently selected from the group consisting of O and N, and the number of the heteroatom is 1, 2, or 3; said optionally substituted represents being optionally substituted by $R_{3d}$.

Further preferably, in the compound or the prodrug, tautomer, optical isomer, geometric isomer, solvate, isotopic derivative, or pharmaceutically acceptable salt thereof provided in the present disclosure, $R_{3b}$ and $R_{3c}$ are, for each presence, independently an optionally substituted methyl; or when $R_{3b}$ and $R_{3c}$ are linked to the same nitrogen atom, $R_{3b}$ and $R_{3c}$, together with the nitrogen atom linked thereto, form an optionally substituted group selected from pyrrolidinyl, piperazinyl, piperidinyl, 2-oxa-7-azaspiro[3.5]nonanyl (e.g., 2-oxa-7-azaspiro[3.5]nonan-7-yl), 3-azabicyclo[3.1.0]hexanyl (e.g., 3-azabicyclo[3.1.0]hexan-3-yl), and 6-azaspiro[2.5]octanyl (e.g., 6-azaspiro[2.5]octan-6-yl); said optionally substituted represents being optionally substituted by $R_{3d}$.

Preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, fluorine, hydroxyl, amino, cyano, $—NH(CH_3)$, $—N(CH_3)(CH_3)$, $—C(O)NH_2$, $—CH_3$, $—CH_2CH_3$, and $—CH_2CH_2CH_3$.

Further preferably, in the compound or the prodrug, tautomer, optical isomer, geometric isomer, solvate, isotopic derivative, or pharmaceutically acceptable salt thereof provided in the present disclosure, $R_{3d}$ is, for each presence, independently selected from the group consisting of deuterium, fluorine, cyano, $—C(O)NH_2$, and $—CH_3$.

Further preferably, in the compound or the prodrug, tautomer, optical isomer, geometric isomer, solvate, isotopic derivative, or pharmaceutically acceptable salt thereof provided in the present disclosure, a group formed by $R_{3b}$ and $R_{3c}$ together with the nitrogen atom linked thereto is selected from the group consisting of the following groups:

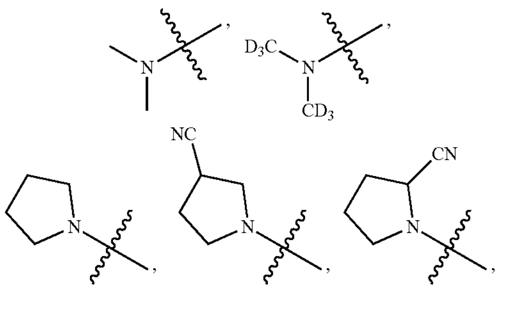

-continued
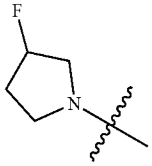, 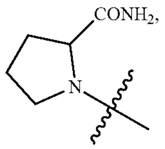
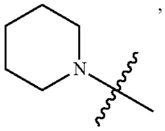, 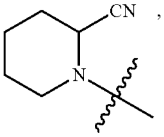, 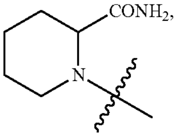
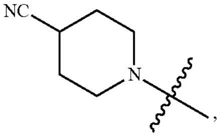 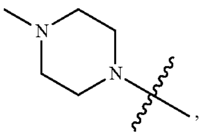
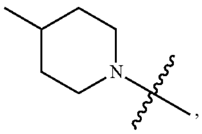 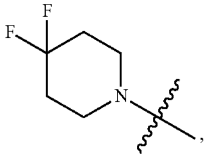
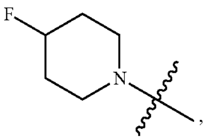 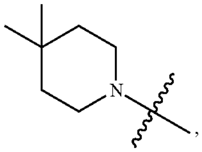
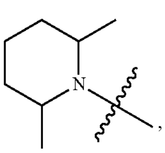 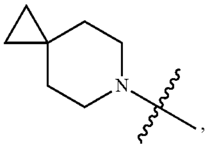
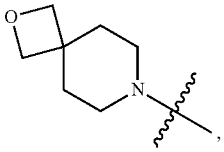, and 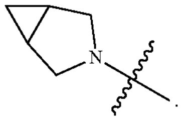.
Preferably, the present disclosure provides a compound as follows or a prodrug, tautomer, optical isomer, geometric isomer, solvate, isotopic derivative, or pharmaceutically acceptable salt thereof.
A-1
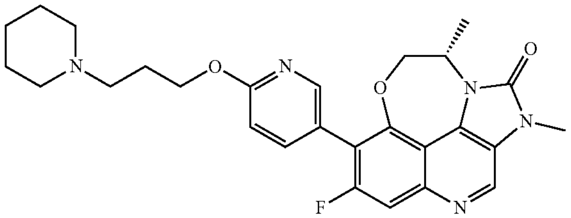
-continued
A-2
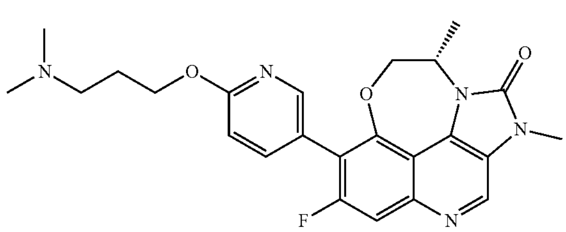
A-3
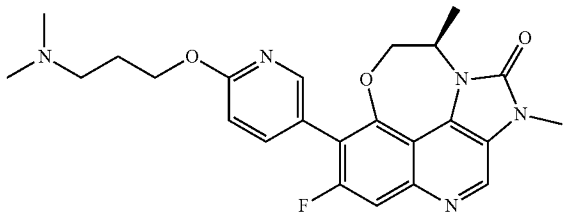
A-4
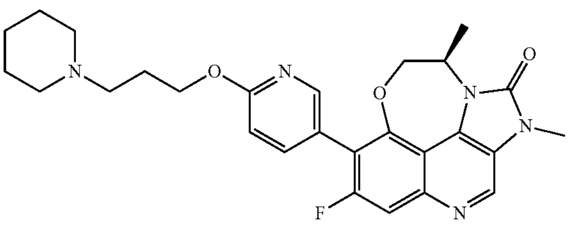
A-5
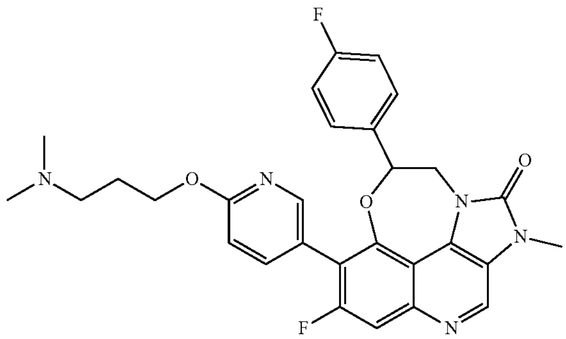
A-6
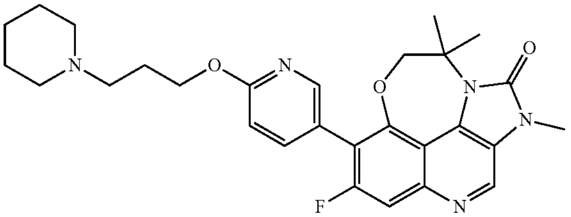
A-7
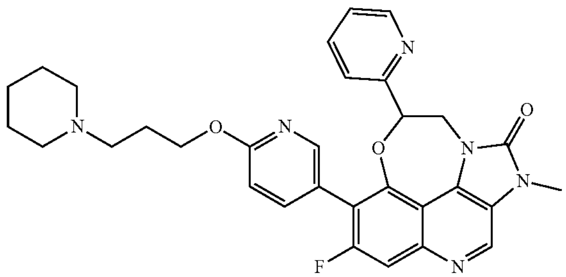

-continued
A-8
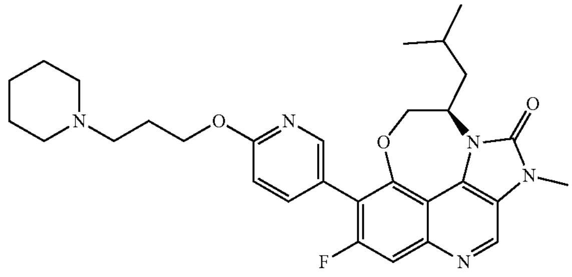
A-9
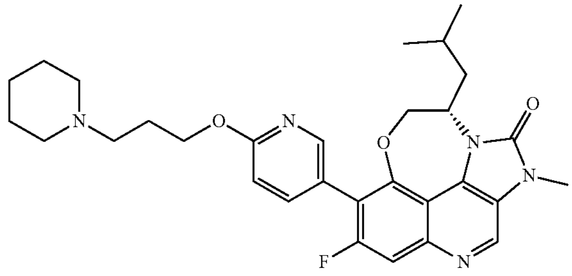
A-10
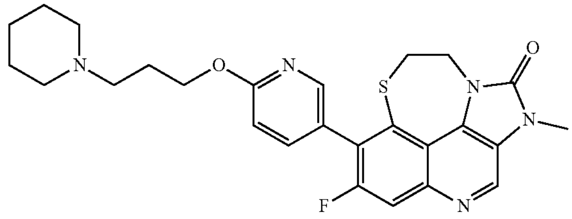
A-11
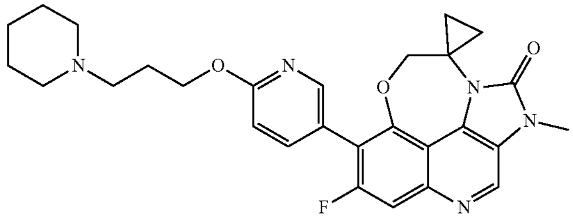
A-12
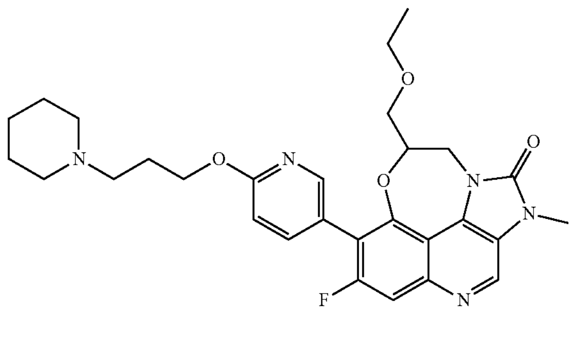
-continued
A-13
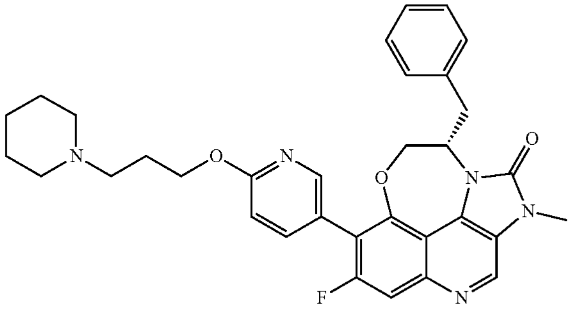
A-14
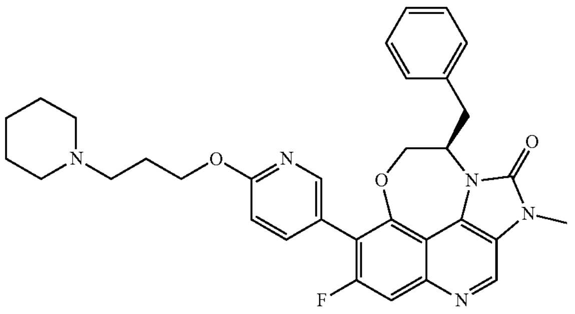
A-15
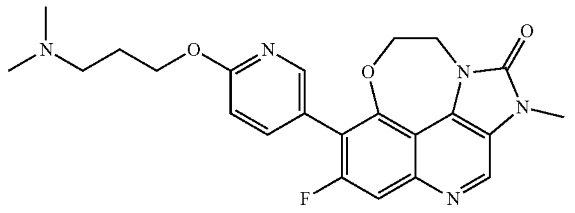
A-16
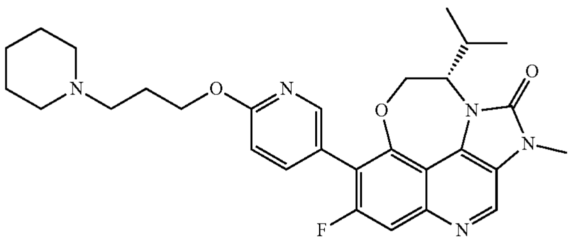
A-17
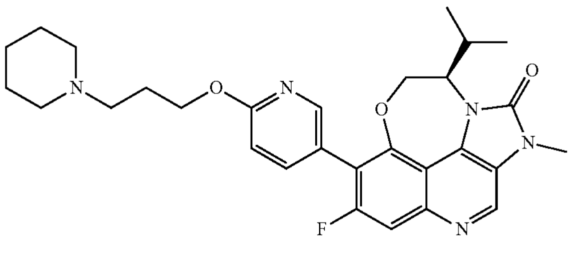

-continued
A-18
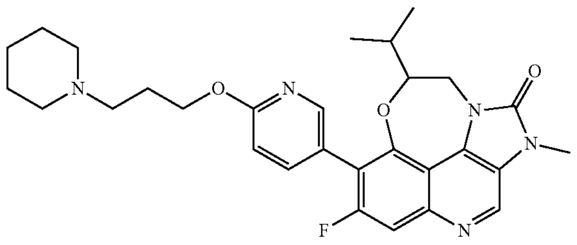
A-19
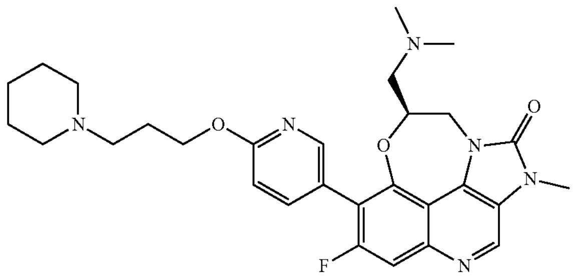
A-20
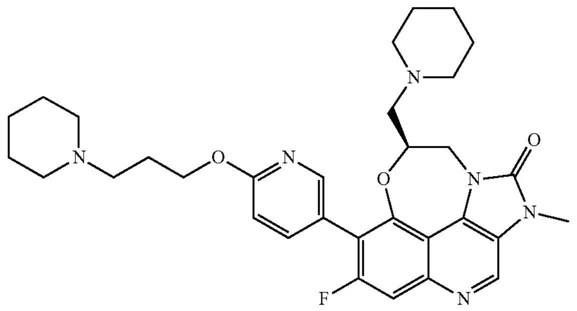
A-21
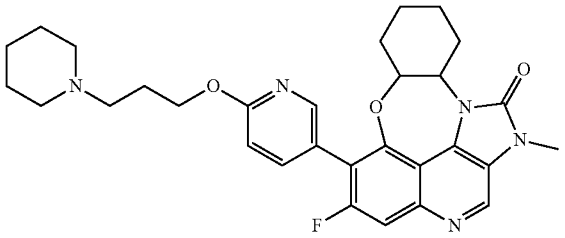
A-22
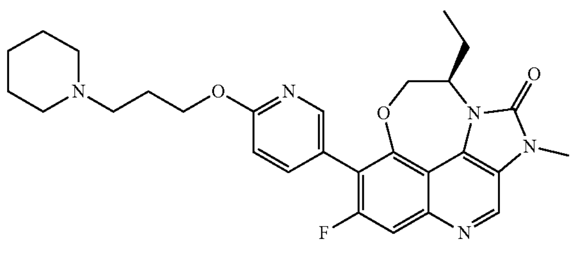
-continued
A-23
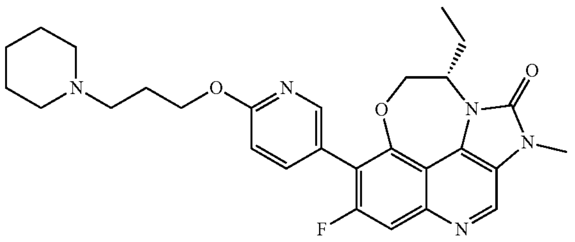
A-24
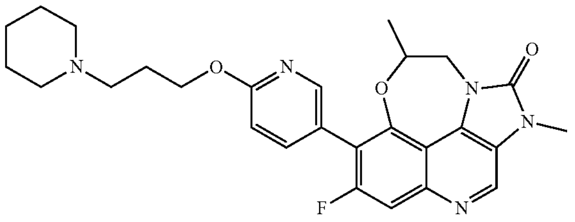
A-25
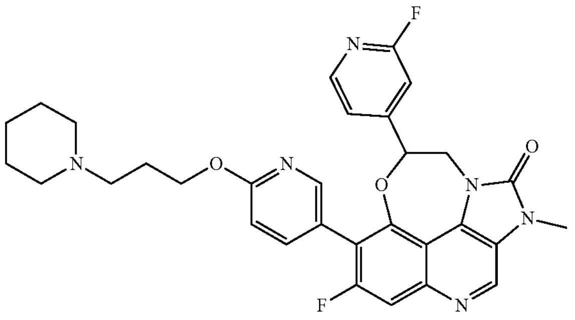
A-26
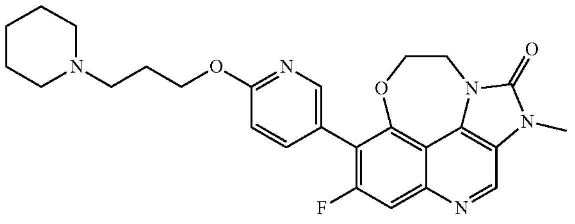
A-27
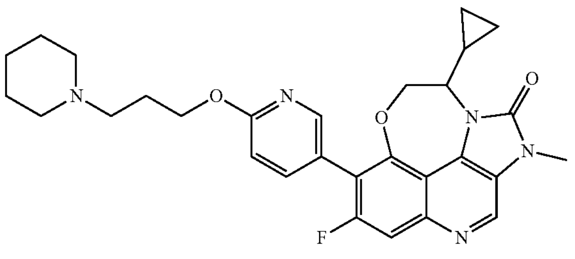
A-28
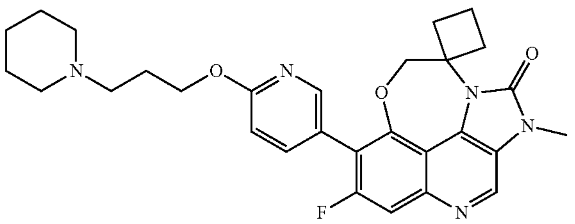

-continued
A-29
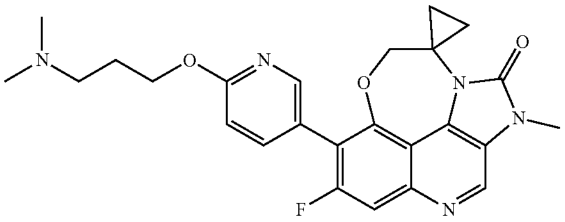
A-30
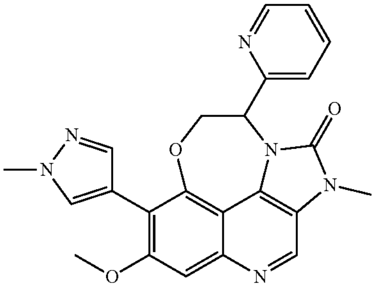
A-31
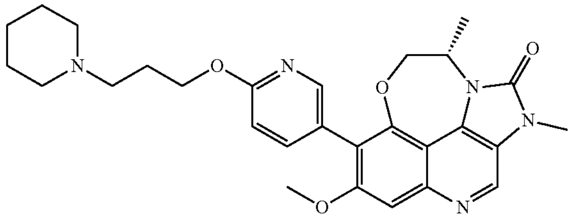
A-32
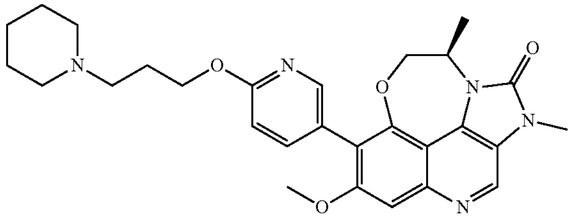
A-33
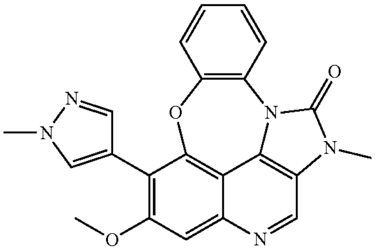
A-34
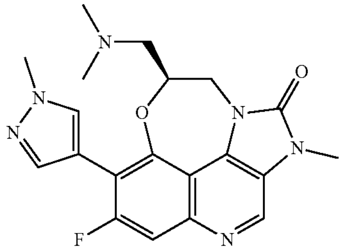
-continued
A-35
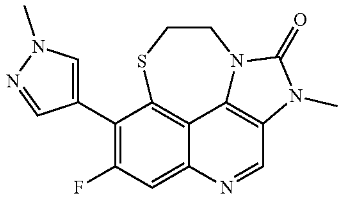
A-36
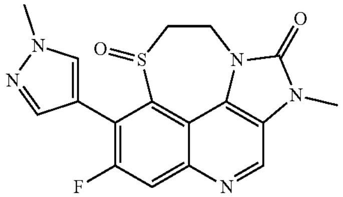
A-37
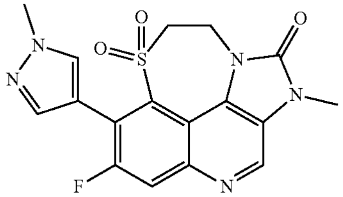
A-38
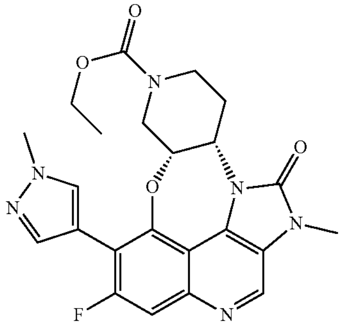
A-39
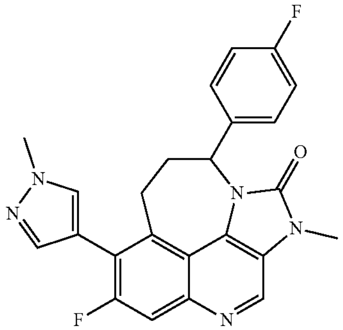
A-40
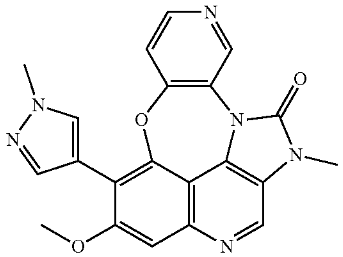

-continued
A-41
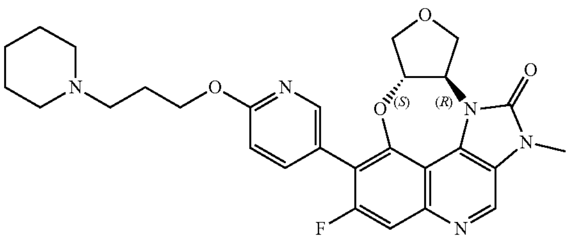
A-42
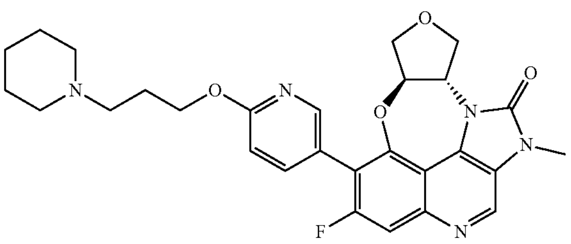
A-43
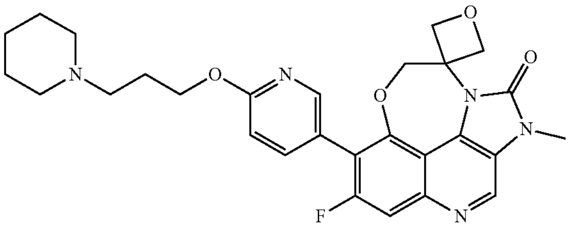
A-44
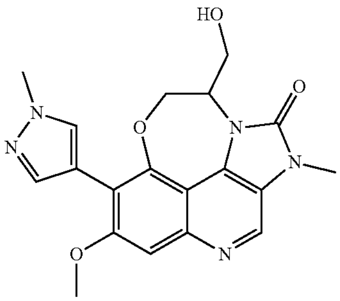
A-45
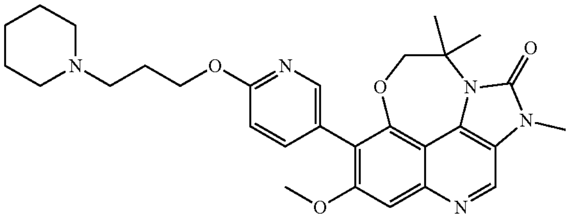
A-46
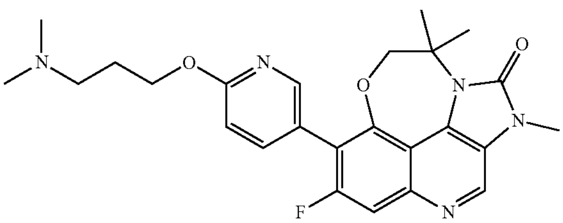
-continued
A-47
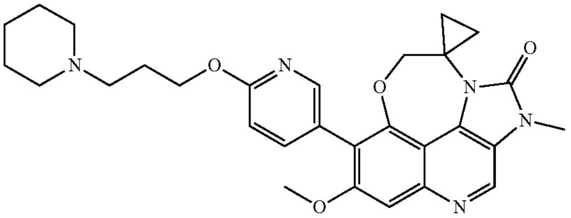
A-48
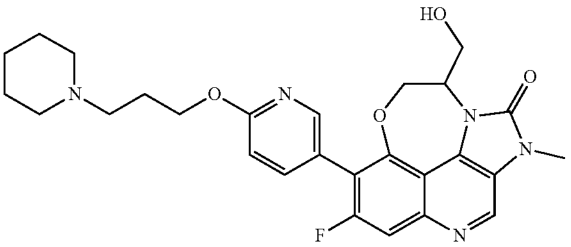
A-49
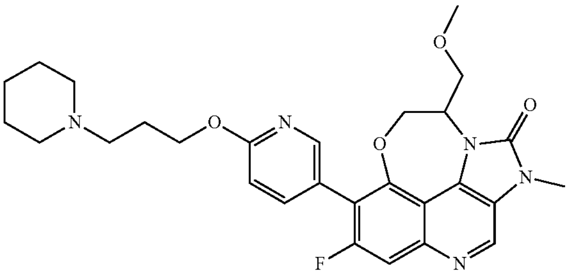
A-50
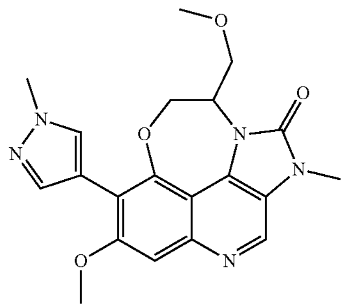
A-51
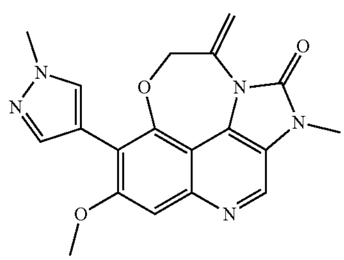

-continued
A-52
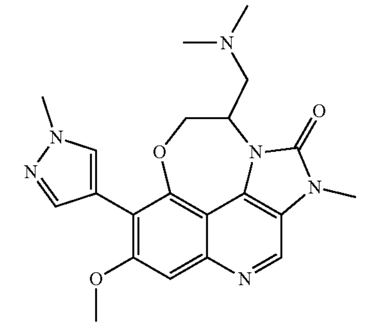
A-53
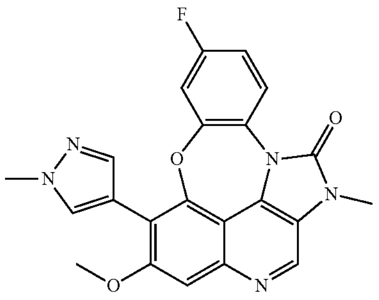
A-54
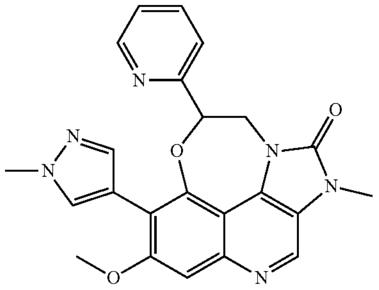
A-55
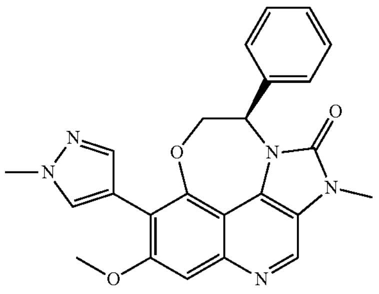
A-56
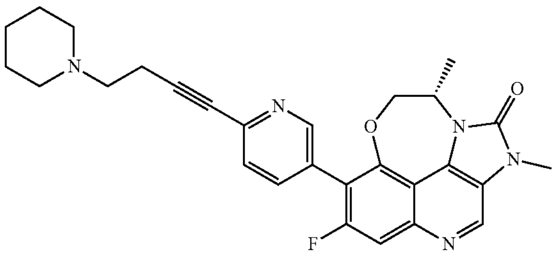
-continued
A-57
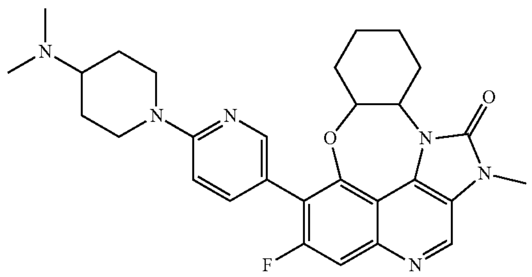
A-58
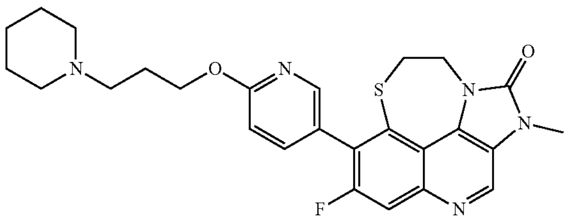
A-59
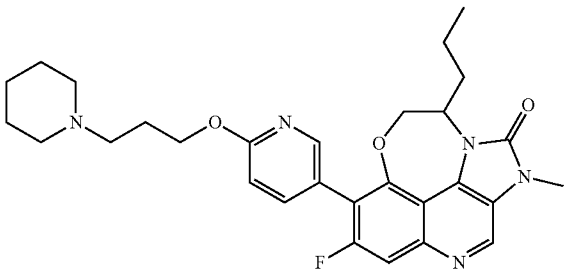
A-60
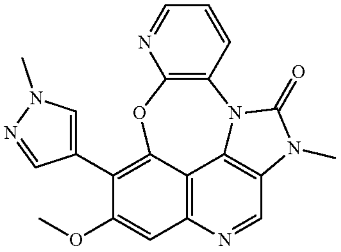
A-61
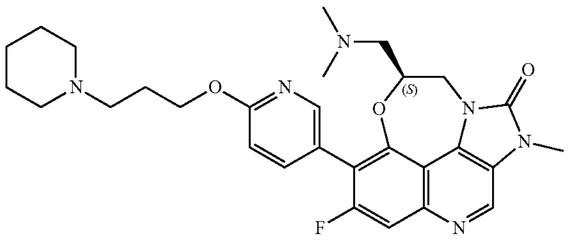
A-62
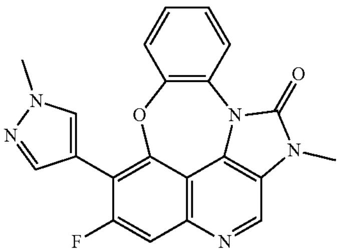

-continued
A-63
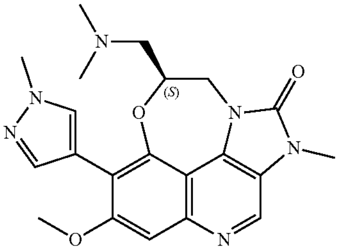
A-64
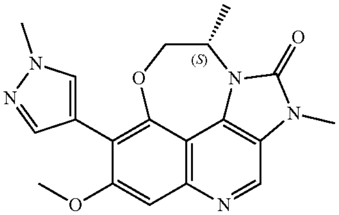
A-65
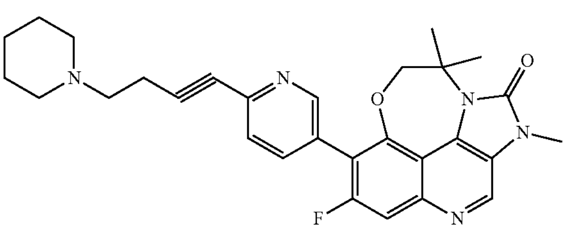
A-66
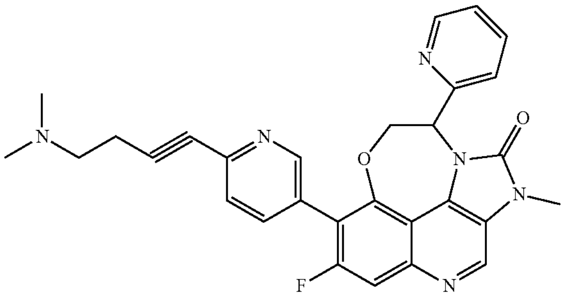
A-67
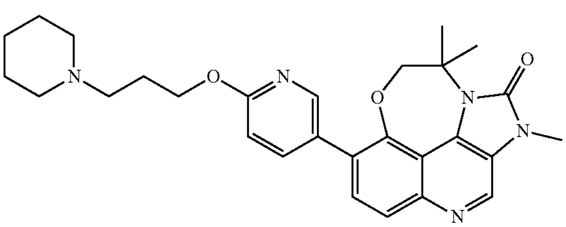
A-68
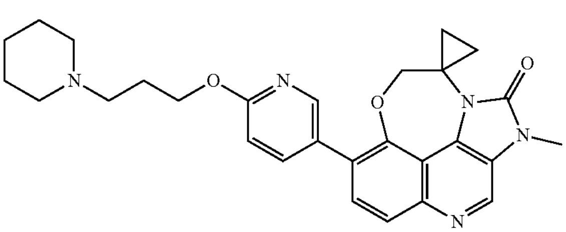
-continued
A-69
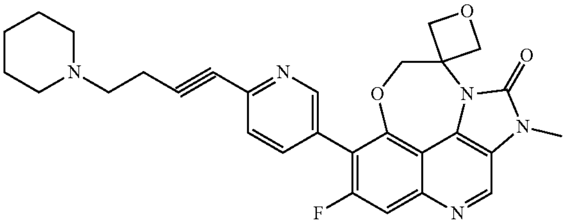
A-70
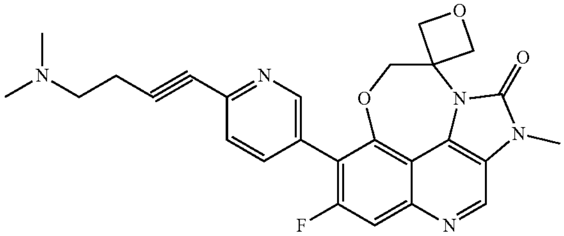
A-71
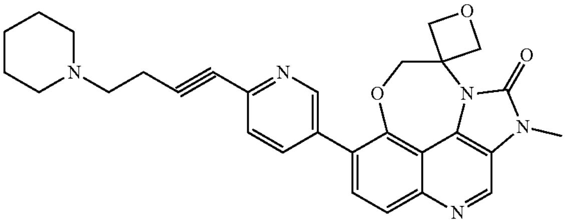
A-72
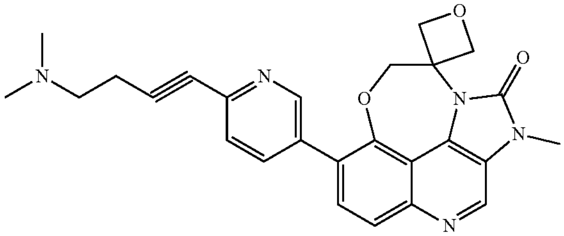
A-73
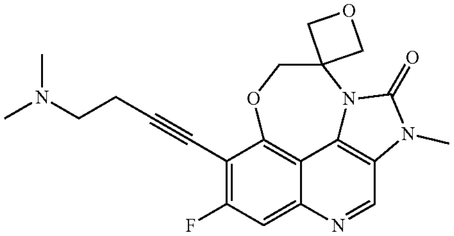
A-74
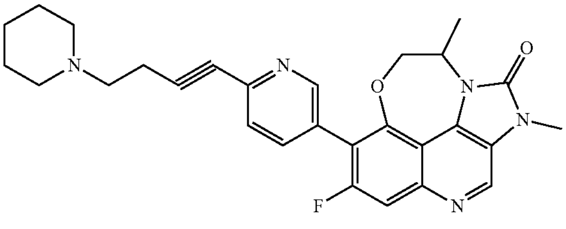

-continued
A-75
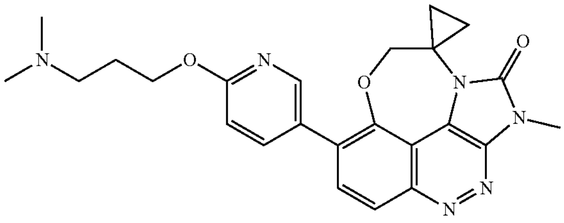
A-76
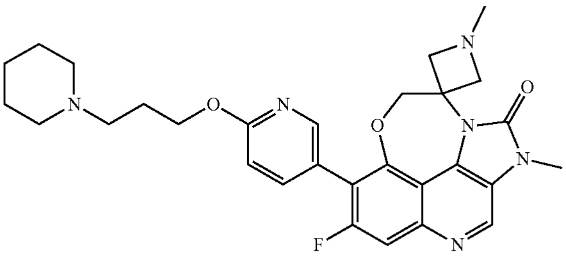
A-77
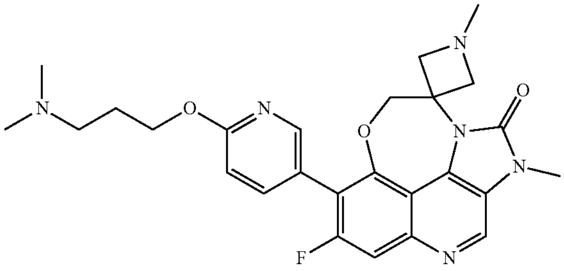
A-78
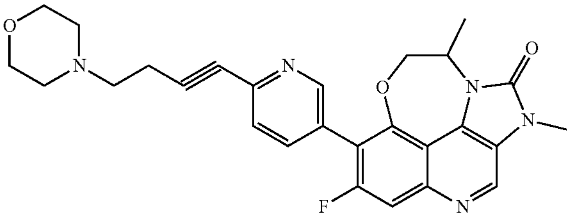
A-79
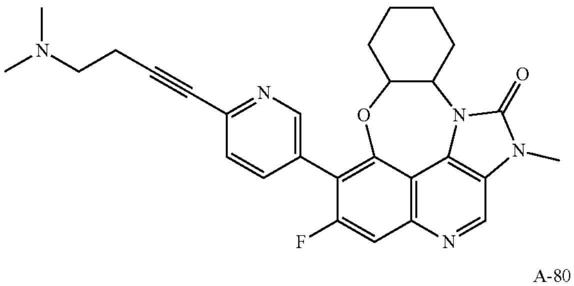
A-80
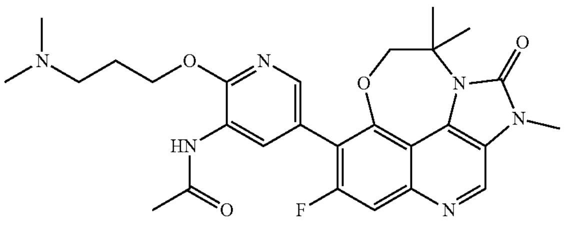
-continued
A-81
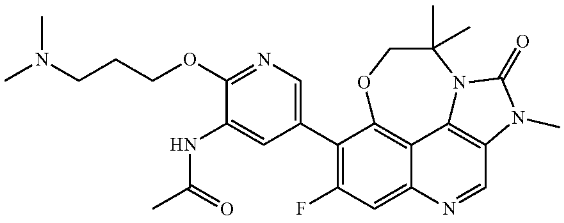
A-82
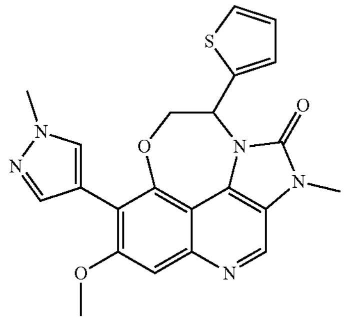
A-83
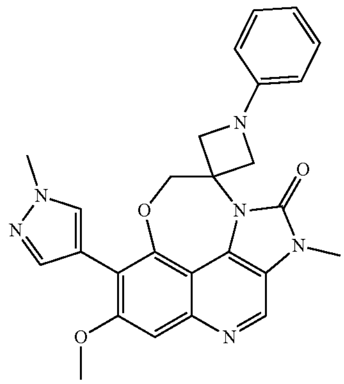
A-84
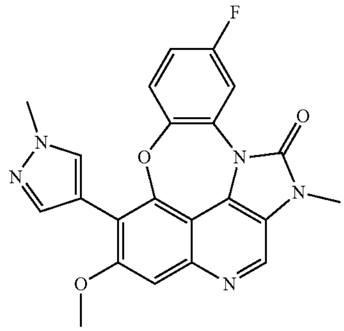

-continued
A-85
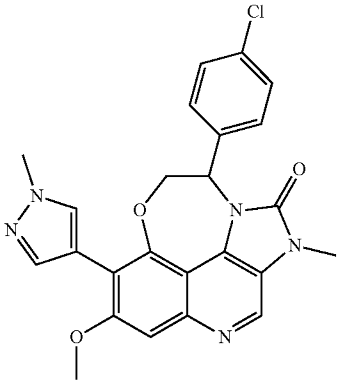
A-86
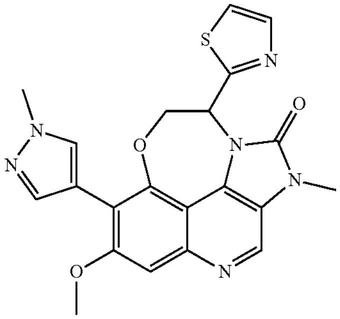
A-87
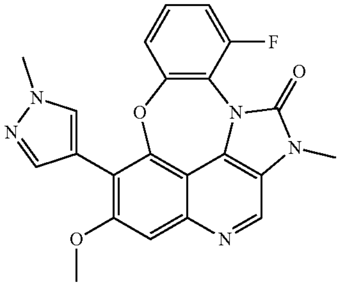
A-88
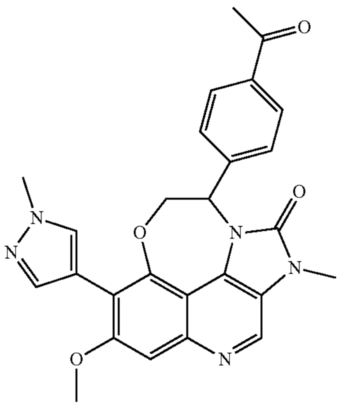
-continued
A-89
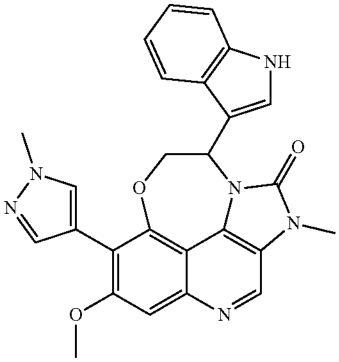
A-90
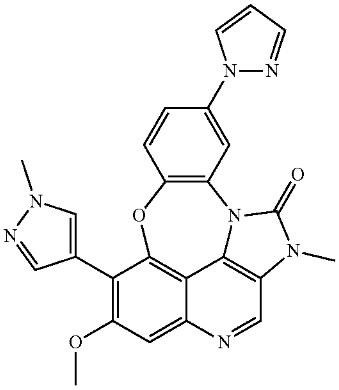
A-91
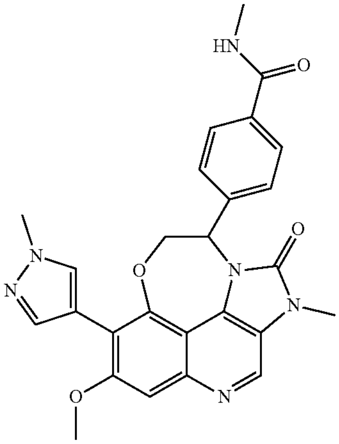
A-92
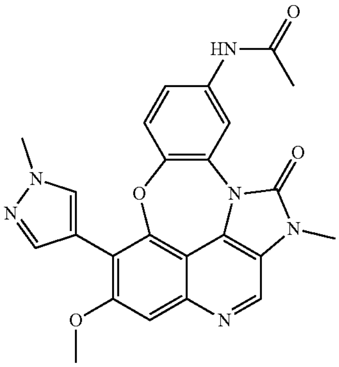

-continued
A-93
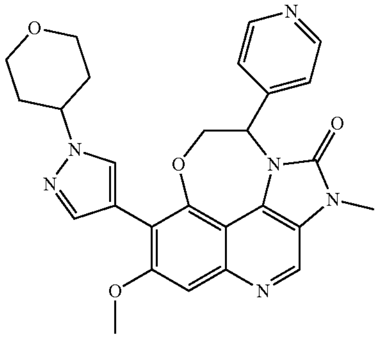
A-94
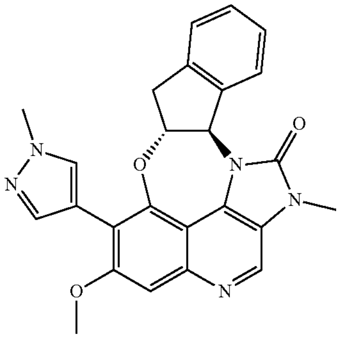
A-95
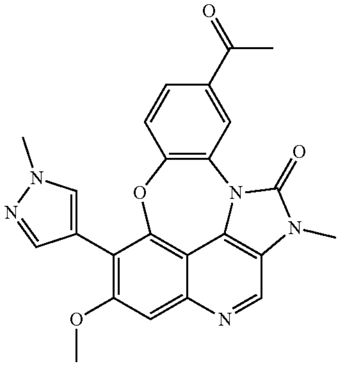
A-96
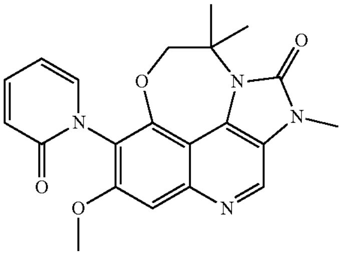
-continued
A-97
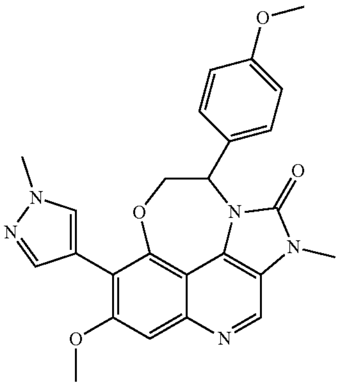
A-98
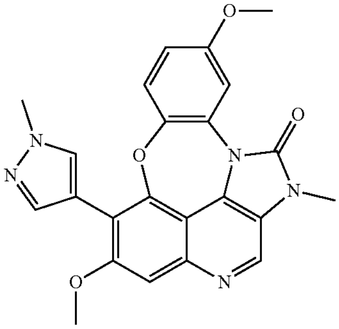
A-99
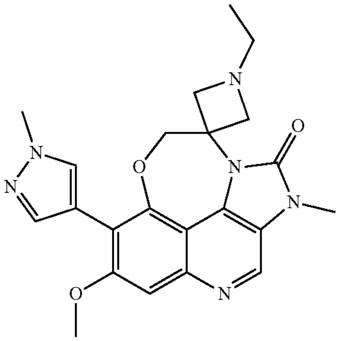
A-100
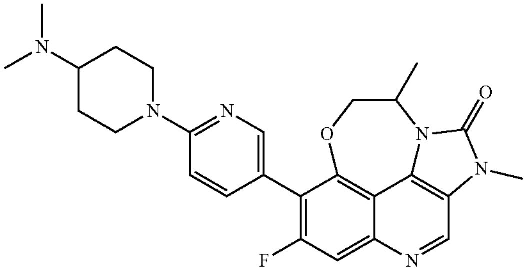

-continued
A-101
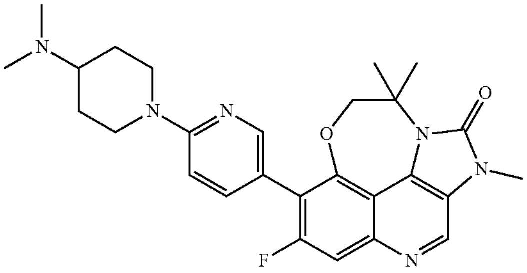
A-102
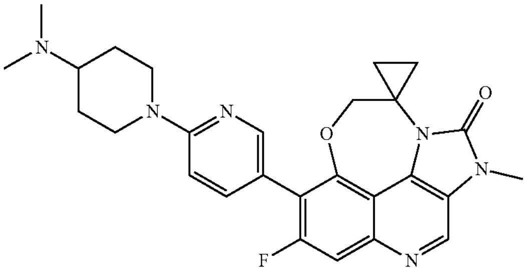
A-103
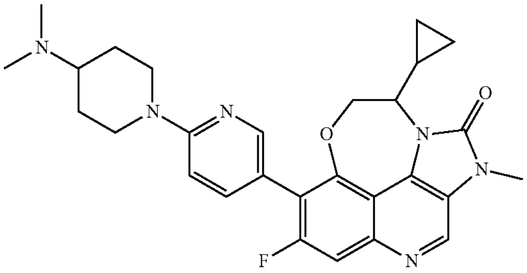
A-104
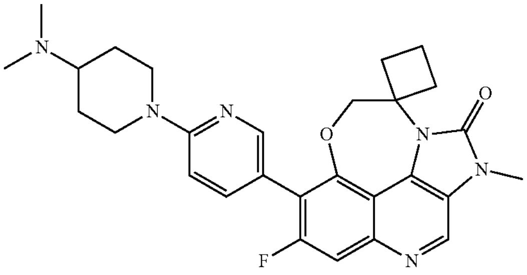
A-105
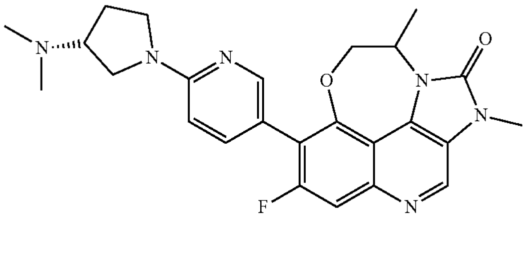
-continued
A-106
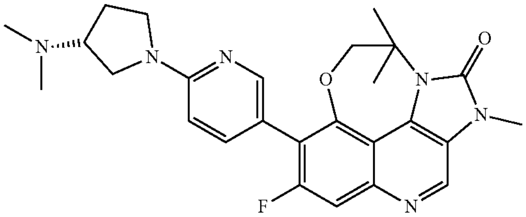
A-107
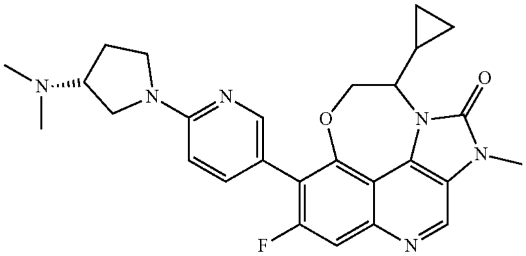
A-108
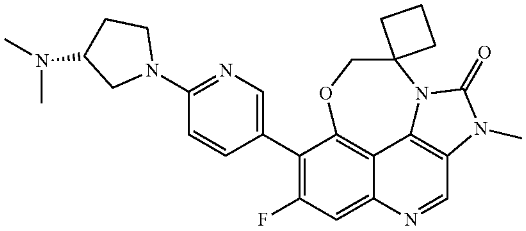
A-109
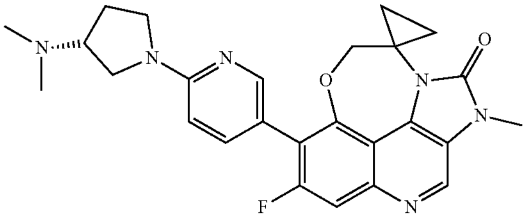
A-110
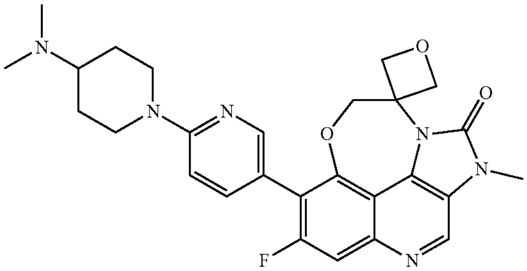
A-111
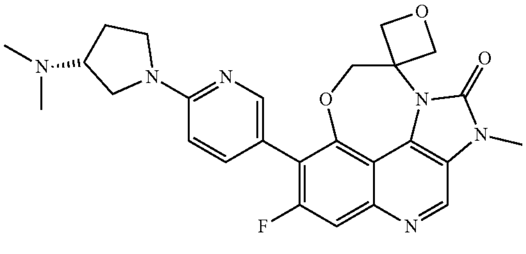

-continued
A-112
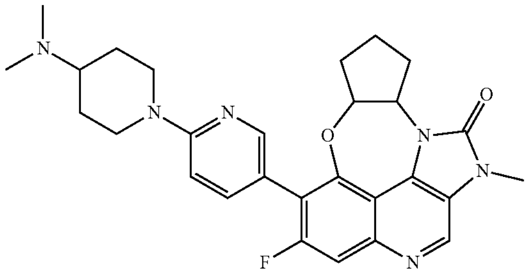
A-113
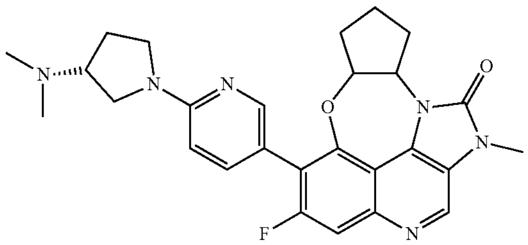
A-114
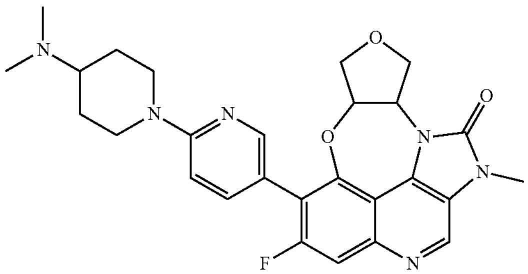
A-115
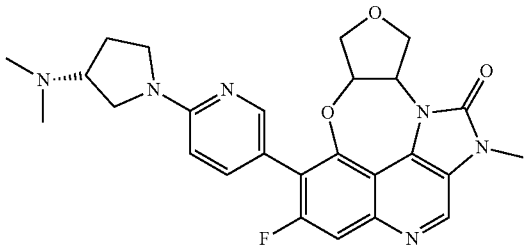
A-116
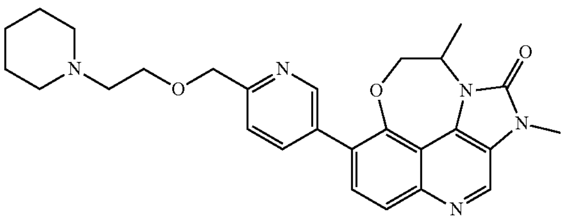
A-117
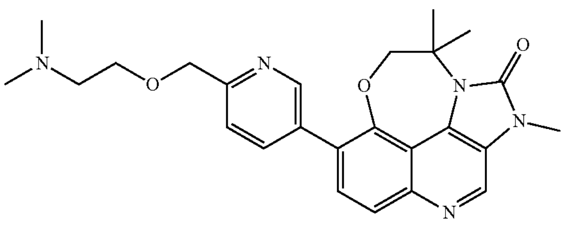
-continued
A-118
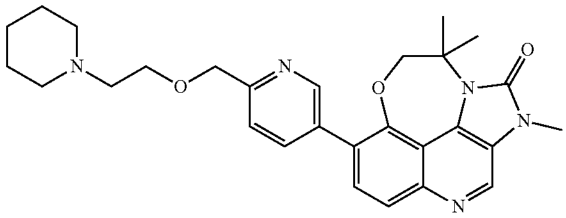
A-119
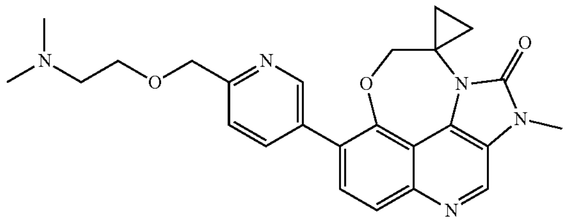
A-120
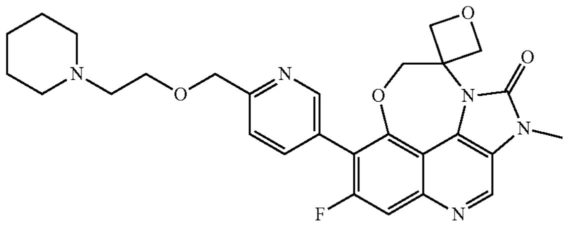
A-121
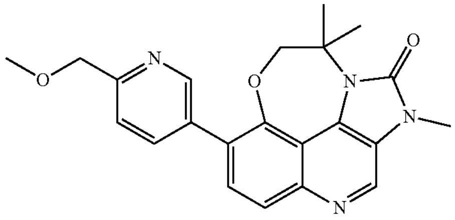
A-122
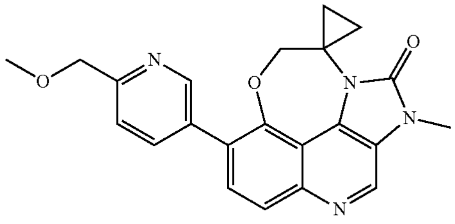
A-123
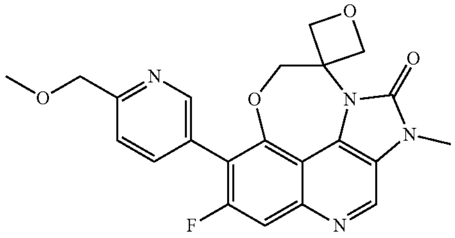

-continued
A-124
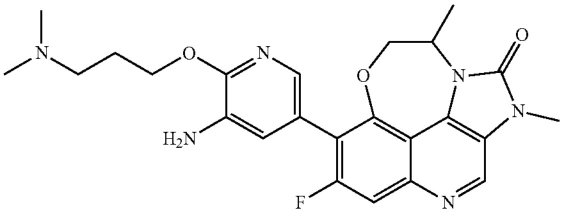
A-125
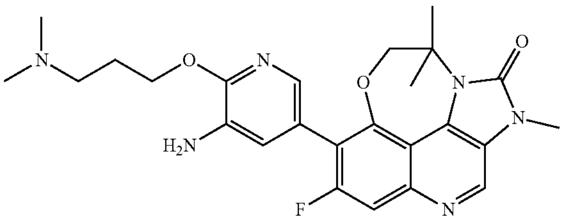
A-126
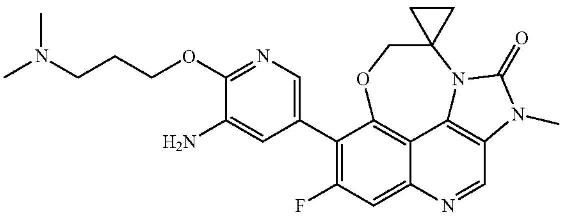
A-127
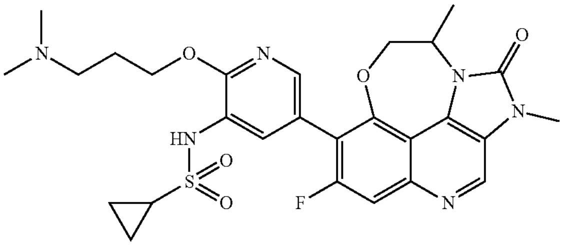
A-128
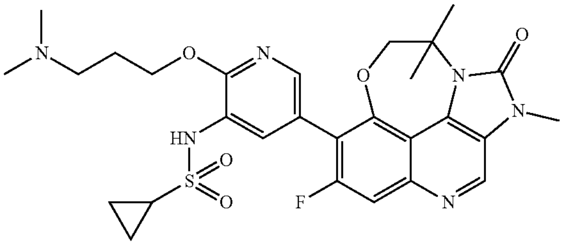
A-129
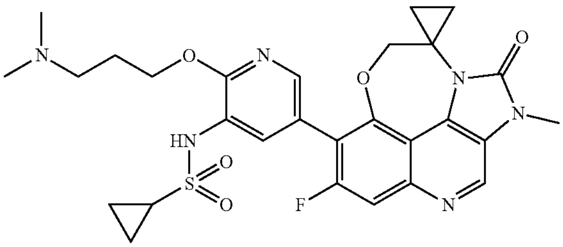
-continued
A-130
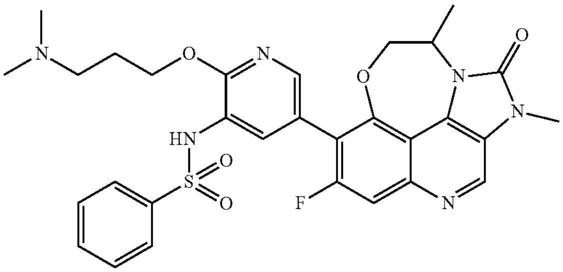
A-131
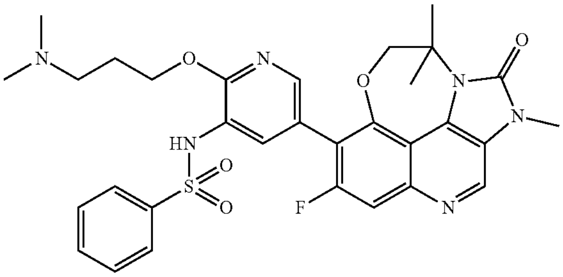
A-132
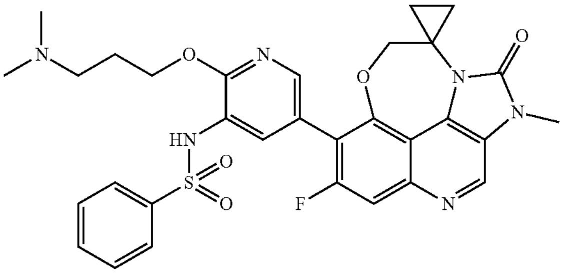
A-133
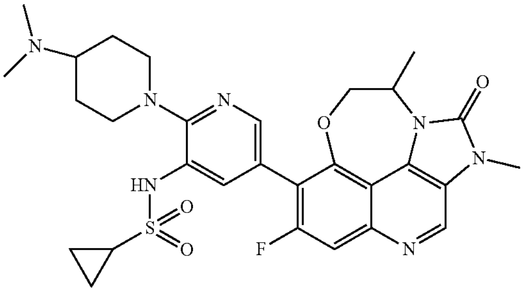
A-134
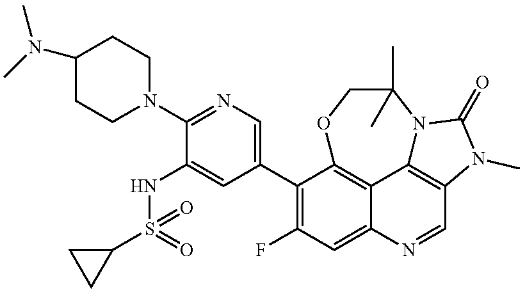

-continued
A-135
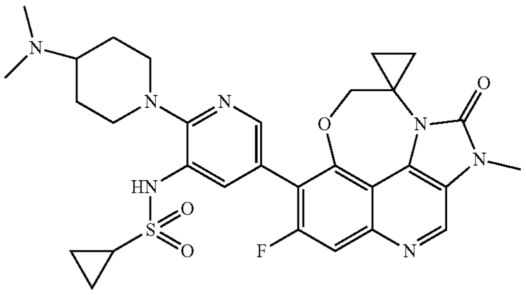
A-136
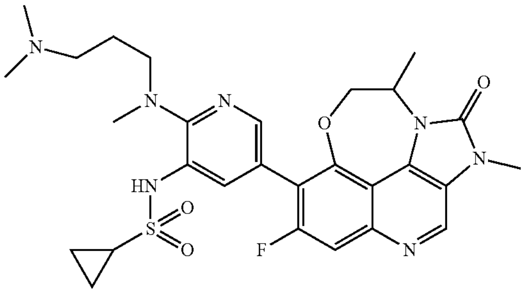
A-137
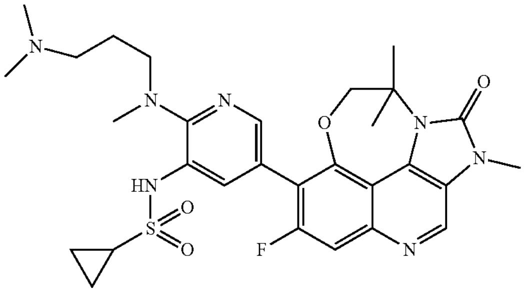
A-138
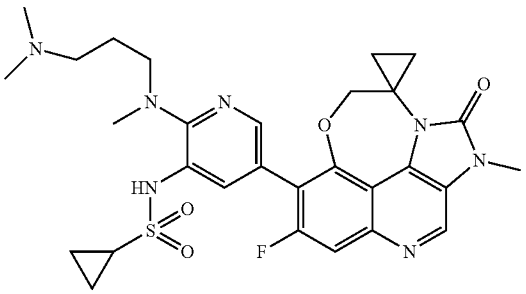
A-139
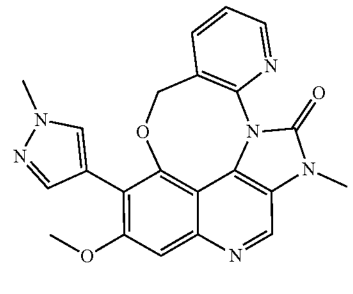
-continued
A-140
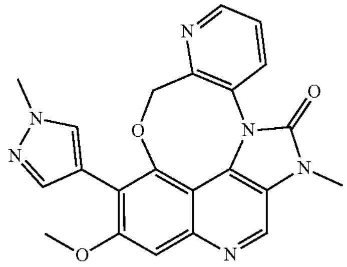
A-141
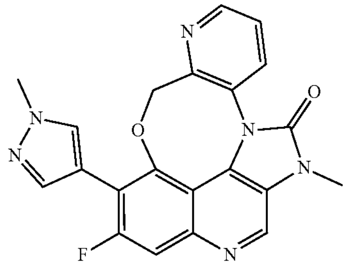
A-142
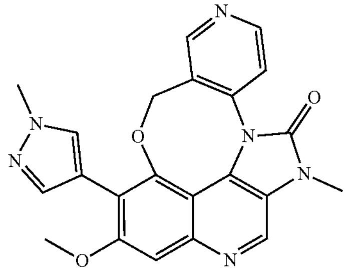
A-143
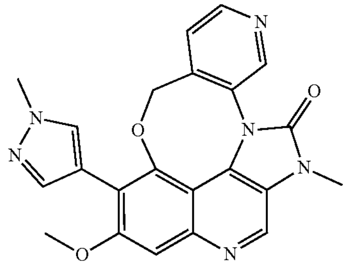
A-144
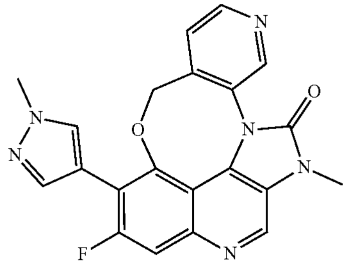
A-145
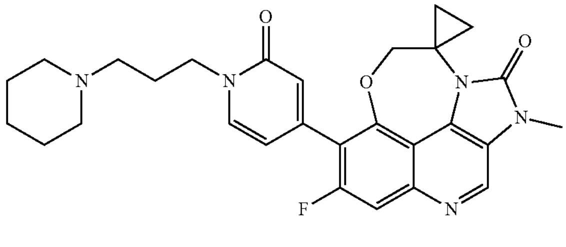

-continued
A-146
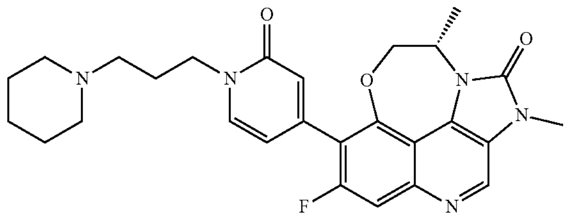
A-147
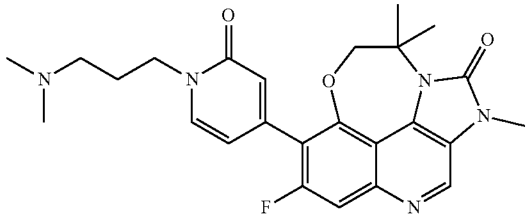
A-148
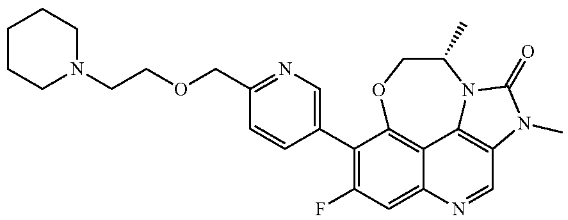
A-149
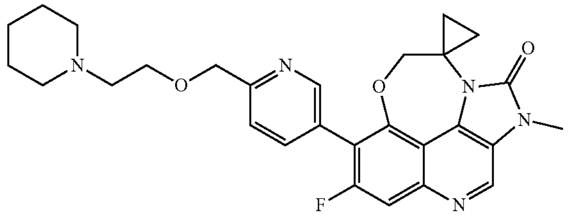
A-150
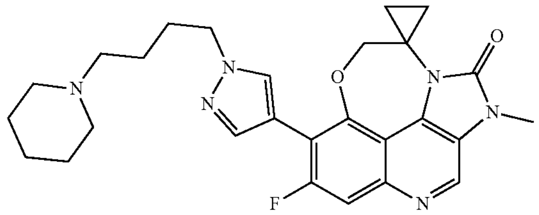
A-151
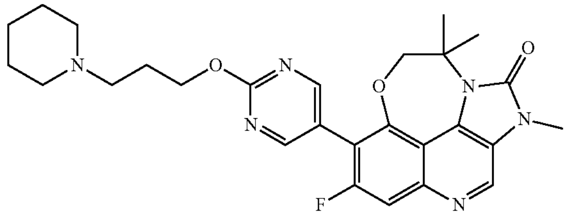
-continued
A-152
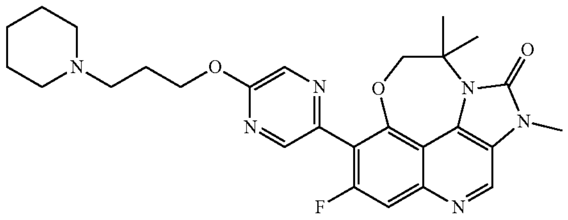
A-153
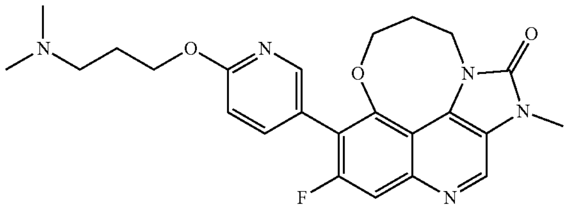
A-154
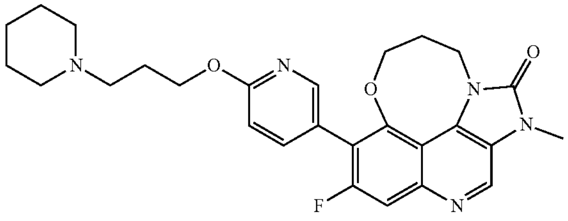
A-155
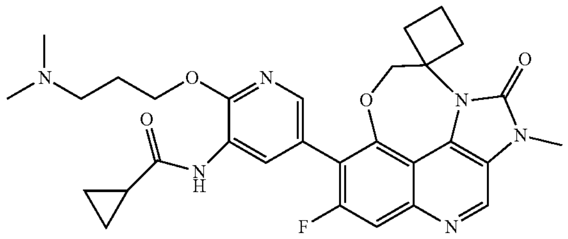
A-156
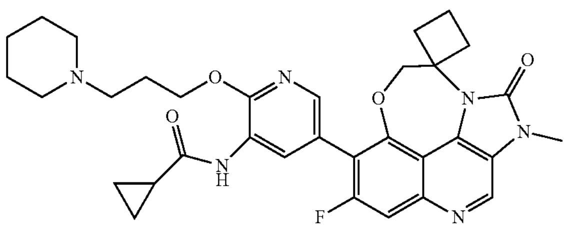
A-157
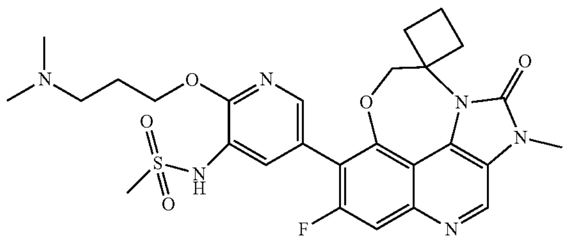

-continued
A-158
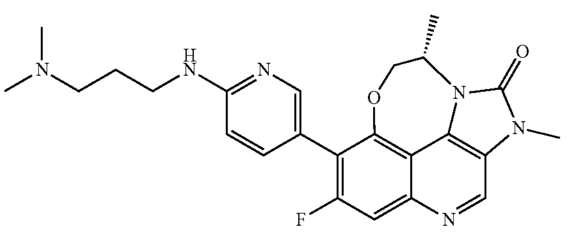
A-159
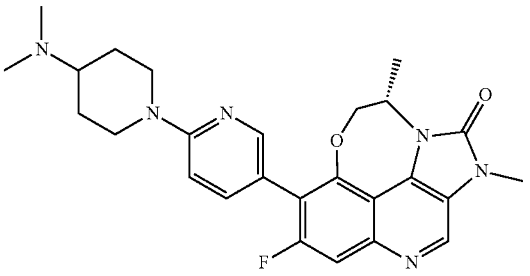
A-160
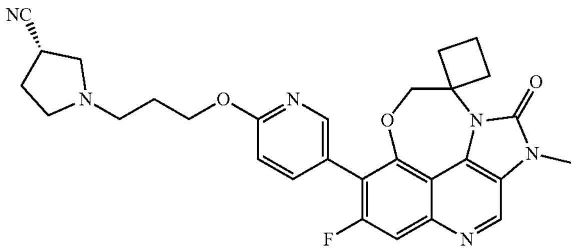
A-161
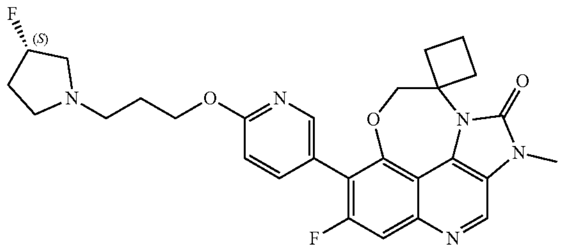
A-162
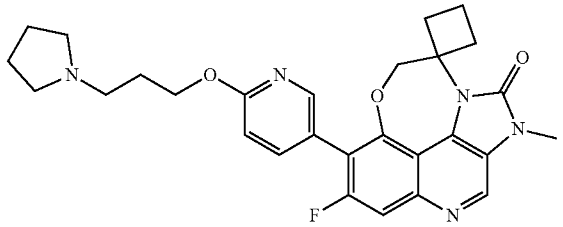
A-163
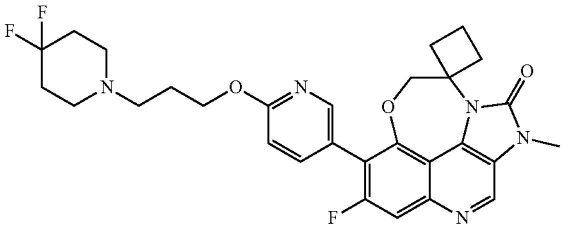
-continued
A-164
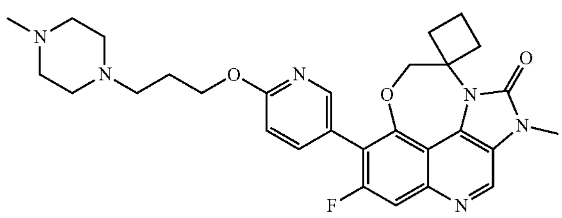
A-165
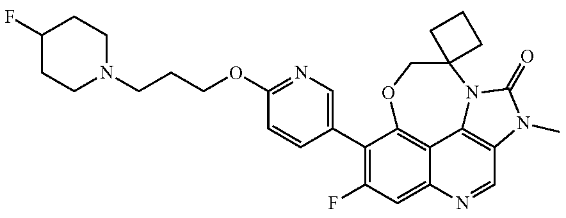
A-166
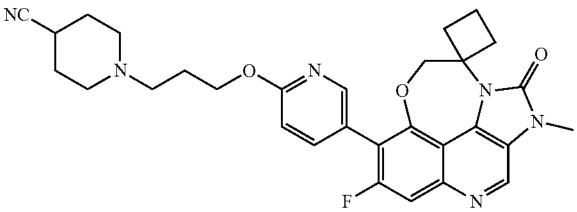
A-167
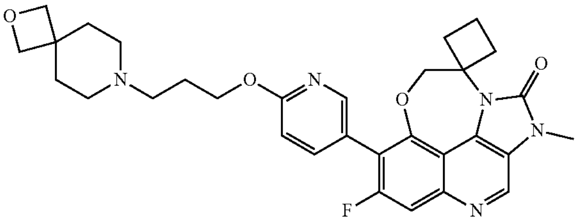
A-168
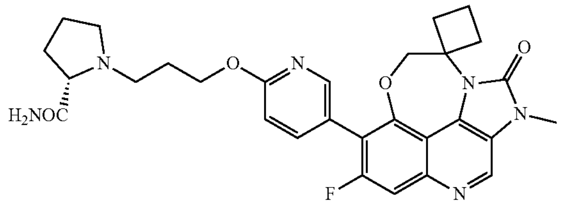
A-169
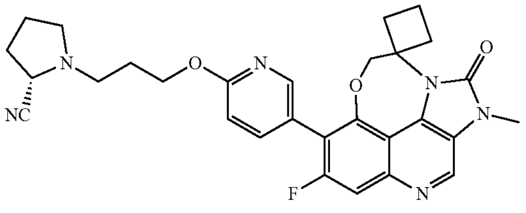

-continued
A-170
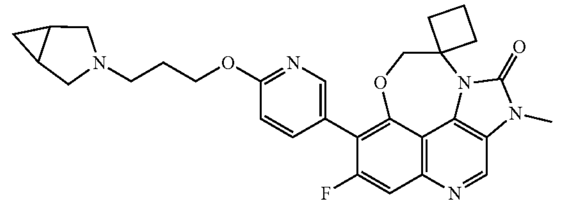
A-171
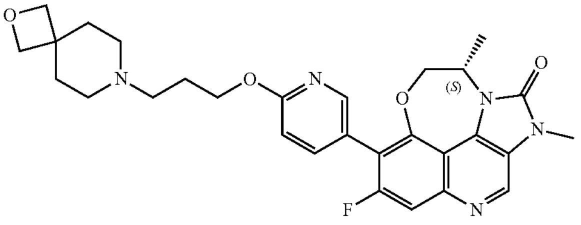
A-172
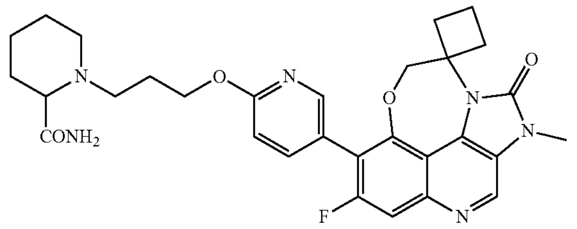
A-173
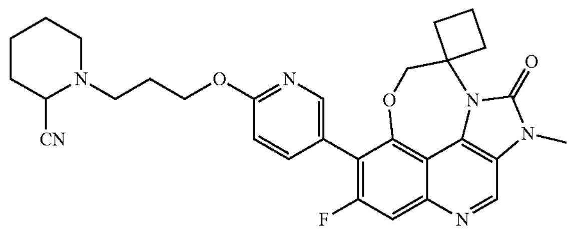
A-174
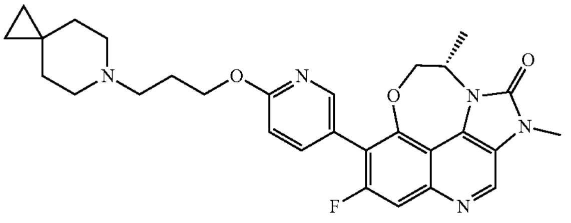
A-175
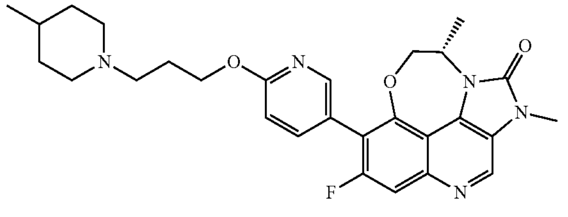
-continued
A-176
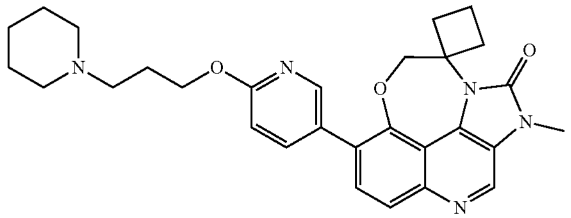
A-177
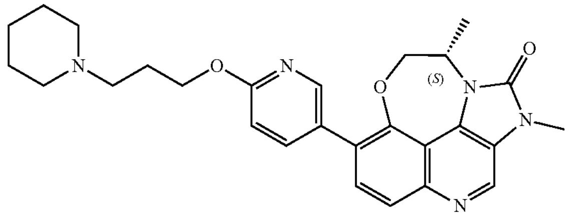
A-178
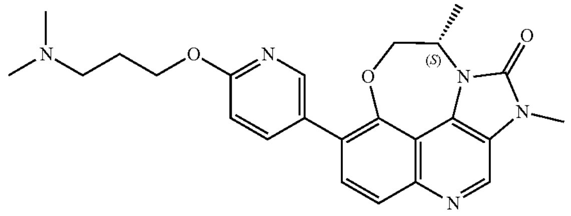
A-179
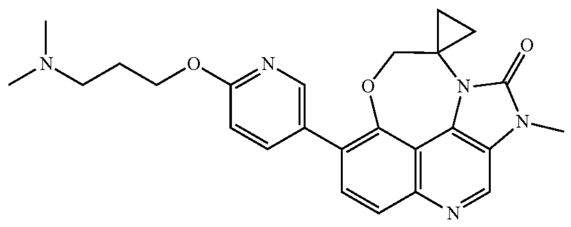
A-180
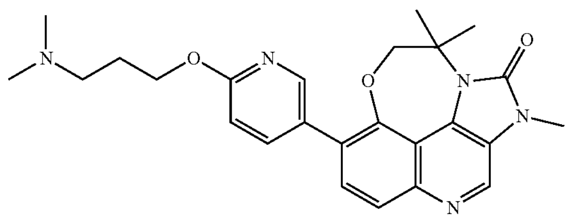
A-181
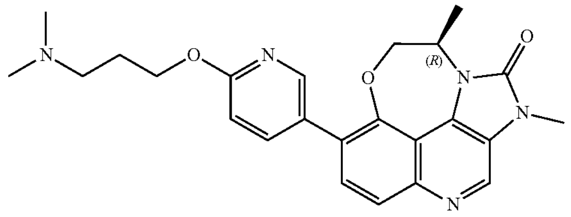

-continued
A-182
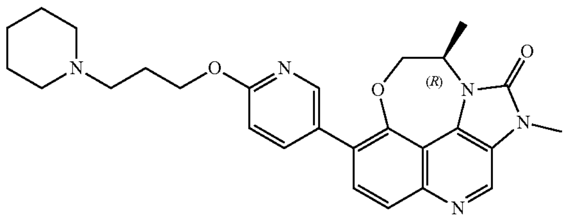
A-183
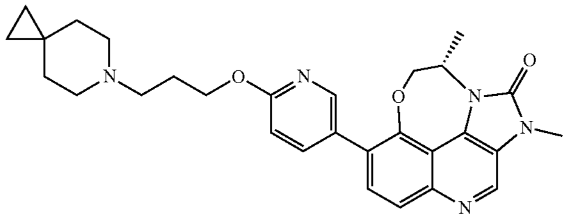
A-184
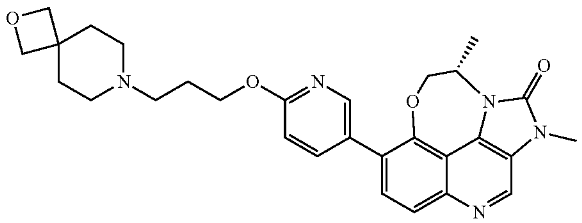
A-185
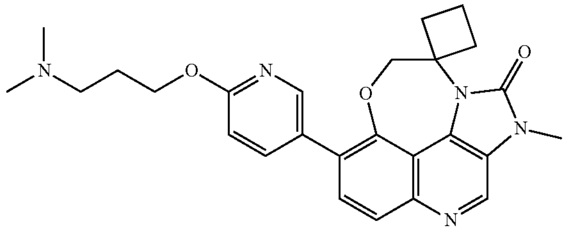
A-186
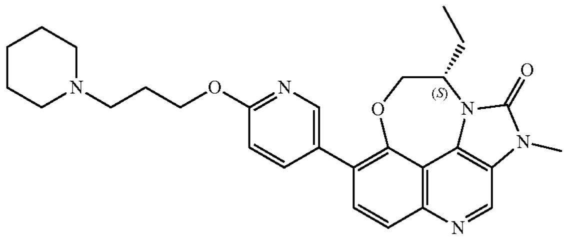
A-187
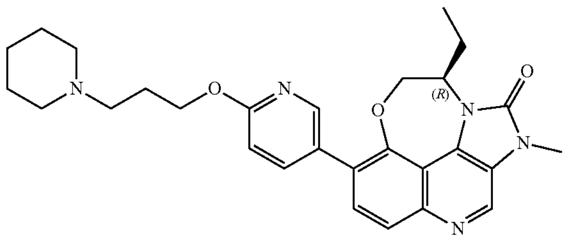
-continued
A-188
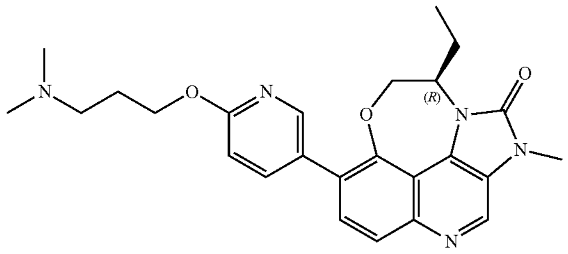
A-189
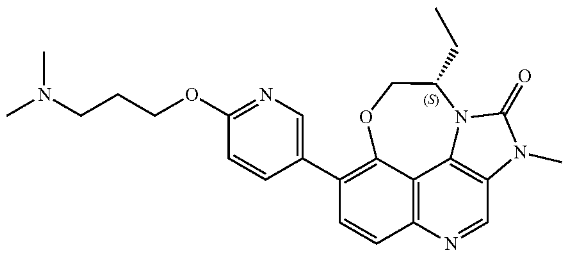
A-190
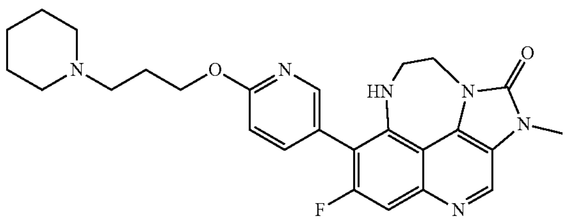
A-191
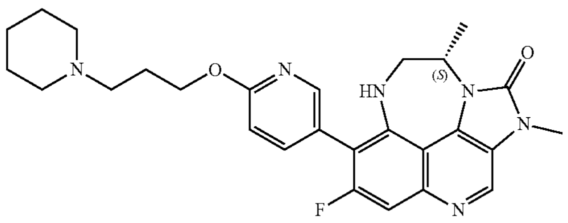
A-192
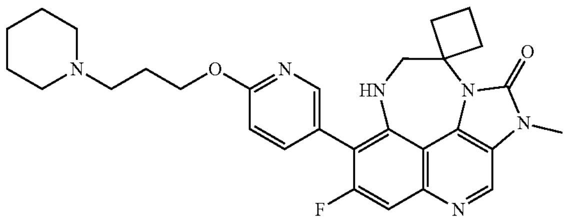
A-193
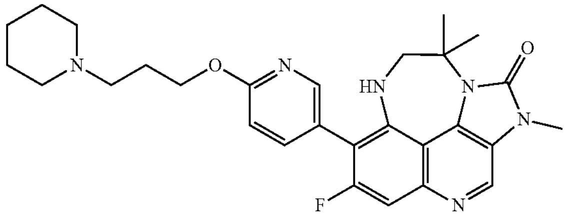

-continued
A-194
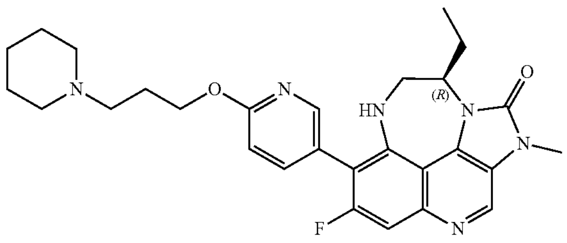
A-195
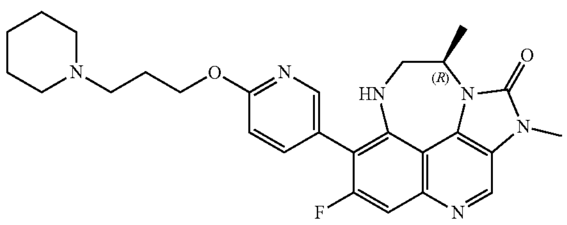
A-196
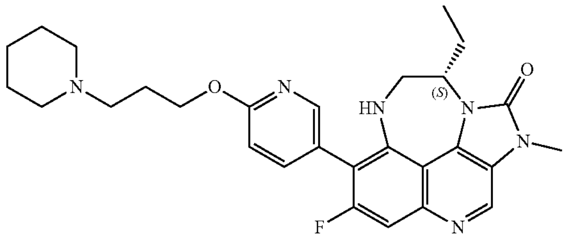
A-197
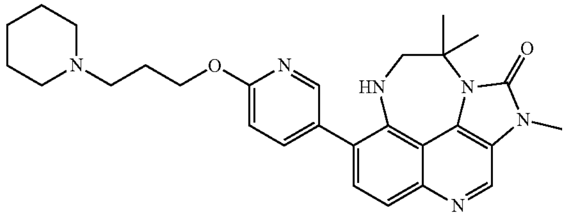
A-198
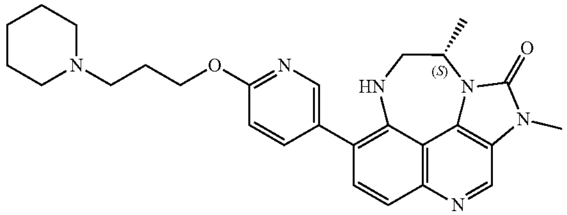
A-199
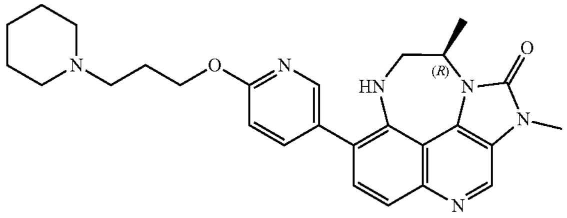
-continued
A-200
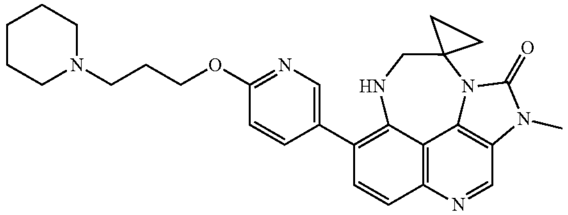
A-201
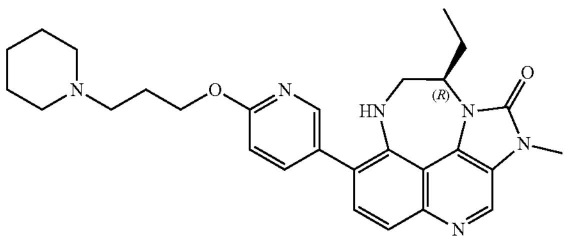
A-202
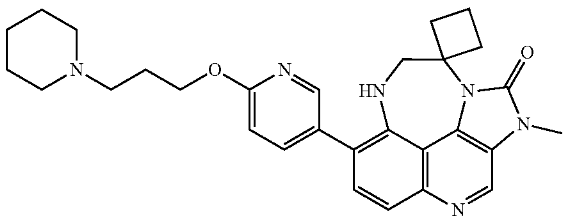
A-203
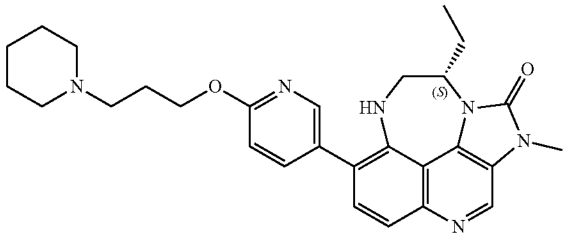
A-204
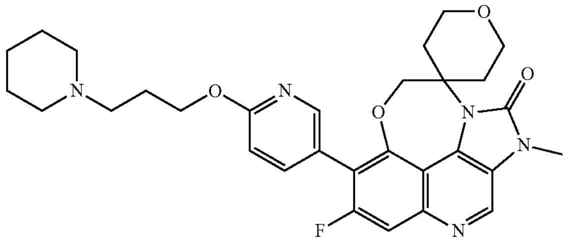
A-205
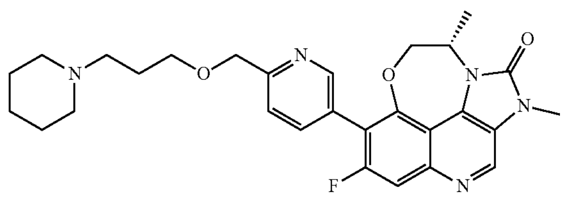

-continued

A-206

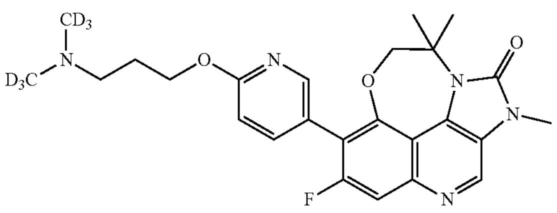

A-207

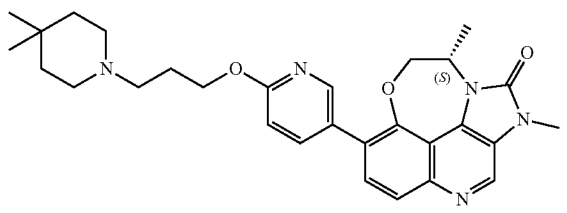

A-208

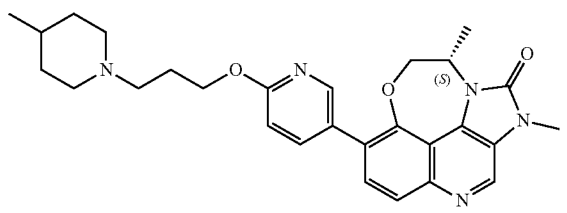

A-209

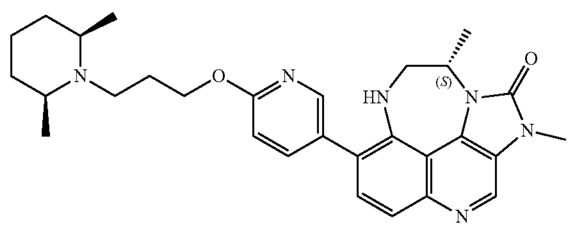

A-210

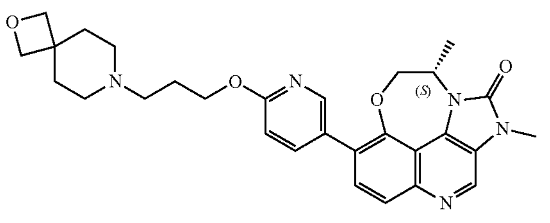

A-211

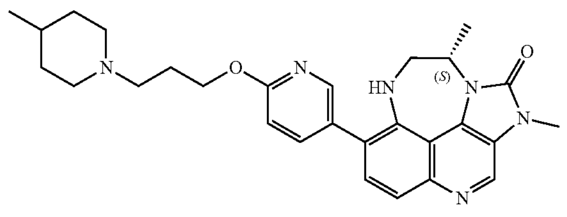

-continued

A-212

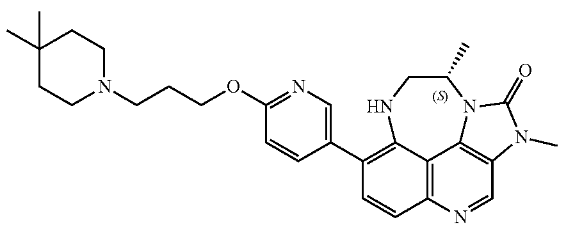

A-190-6

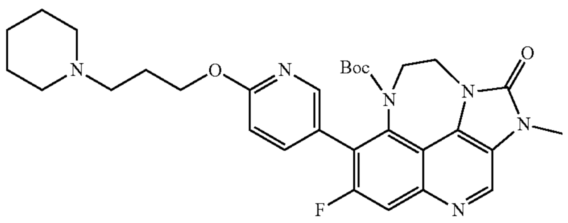

[Synthetic Intermediate and Preparation Method]

With respect to the above compound, the present disclosure also provides an intermediate for preparing the compound of formula (P) or formula (I), having a structure as represented by formula (M-1):

(M-2)

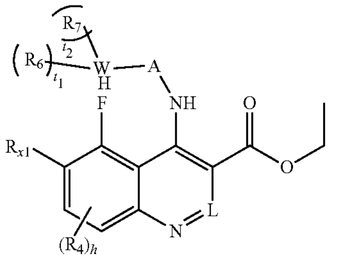

wherein $R_{x1}$ is selected from the group consisting of halogen and hydrogen; and $R_4$, $R_6$, $R_7$, A, W, L, $t_1$, $t_2$, and h are as defined in the compound of formula (I') or formula (I).

With respect to the above compound, the present disclosure also provides an intermediate for preparing the compound of formula (I') or formula (I), having a structure as represented by formula (M-2):

(M-2)

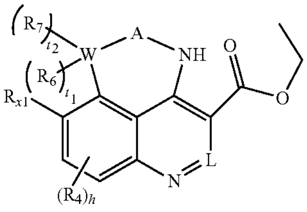

wherein $R_{x1}$ is selected from the group consisting of halogen and hydrogen; and $R_4$, $R_6$, $R_7$, A, W, L, $t_1$, $t_2$, and h are as defined in the compound of formula (I') or formula (I).

With respect to the above compound, the present disclosure also provides an intermediate for preparing the compound of formula (I') or formula (I), having a structure as represented by formula (M-3):

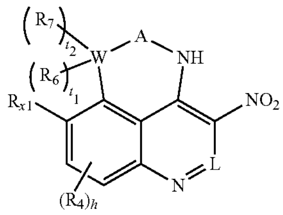

(M-3)

wherein $R_{x1}$ is selected from the group consisting of halogen and hydrogen; and $R_4$, $R_6$, $R_7$, A, W, L, $t_1$, $t_2$, and h are as defined in the compound of formula (I') or formula (I).

With respect to the above compound, the present disclosure also provides an intermediate for preparing the compound of formula (I') or formula (I), having a structure as represented by formula (M-4):

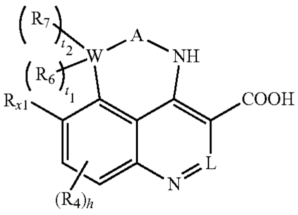

(M-4)

wherein $R_{x2}$ is selected from the group consisting of halogen and hydrogen; and $R_4$, $R_6$, $R_7$, A, W, L, $t_1$, $t_2$, and h are as defined in the compound of formula (I') or formula (I).

With respect to the above compound, the present disclosure also provides an intermediate for preparing the compound of formula (I') or formula (I), having a structure as represented by formula (M-5):

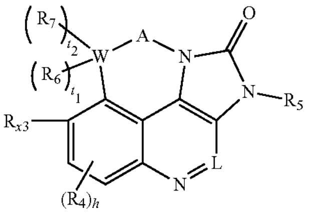

(M-5)

wherein $R_{x3}$ is selected from the group consisting of halogen and hydrogen; and $R_4$, $R_5$, $R_6$, $R_7$, A, W, L, $t_1$, $t_2$, and h are as defined in the compound of formula (I') or formula (I).

With respect to the above compound, the present disclosure also provides an intermediate for preparing the compound of formula (I') or formula (I), having a structure as represented by formula (M-6):

(M-6)

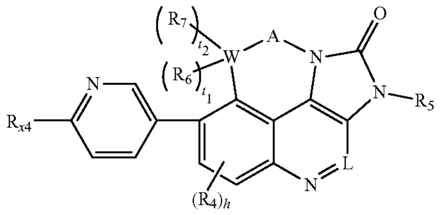

wherein $R_{x4}$ is selected from the group consisting of halogen and hydrogen; and $R_4$, $R_5$, $R_6$, $R_7$, A, W, L, $t_1$, $t_2$, and h are as defined in the compound of formula (I') or formula (I).

Preferably, the present disclosure provides synthetic intermediates as follows for preparing target compounds.

M-1

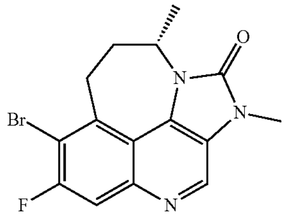

M-2

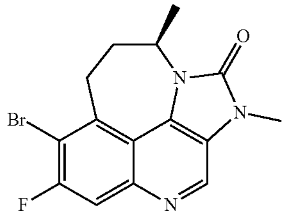

M-3

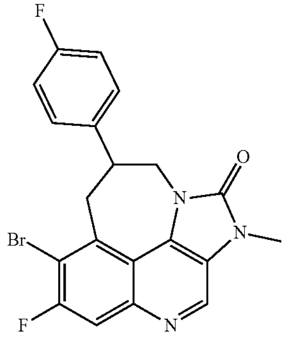

M-4

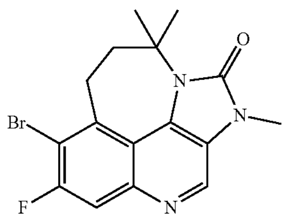

-continued
M-5
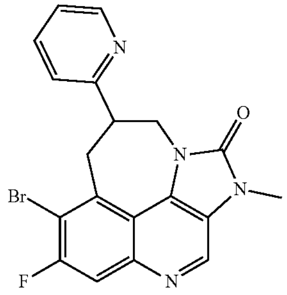
M-6
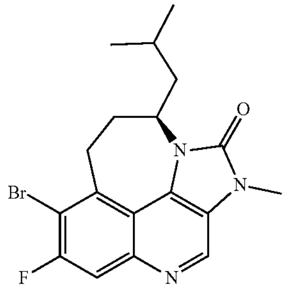
M-7
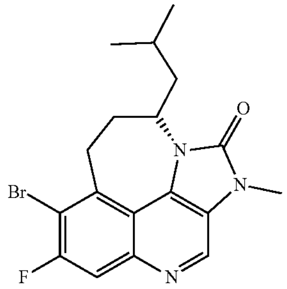
M-8
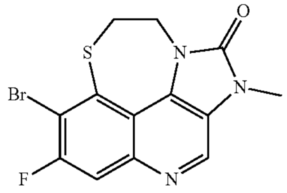
M-9
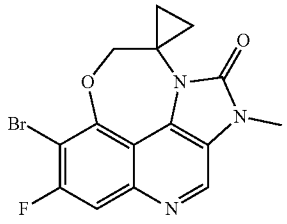
M-10
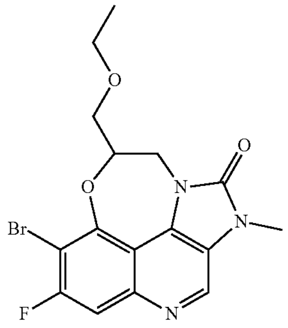
-continued
M-11
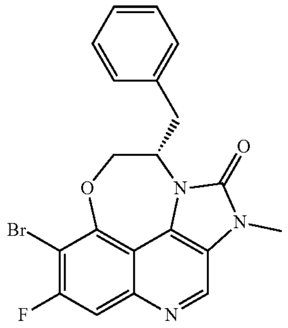
M-12
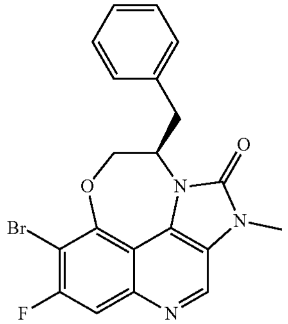
M-13
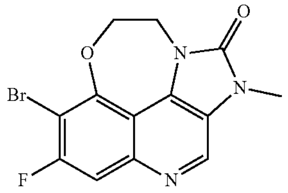
M-14
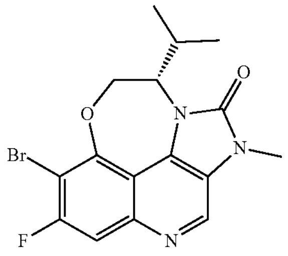
M-15
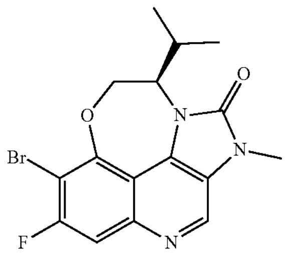
M-16
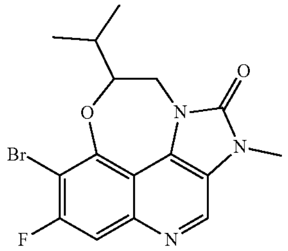

-continued
M-17
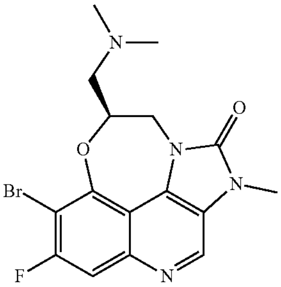
M-18
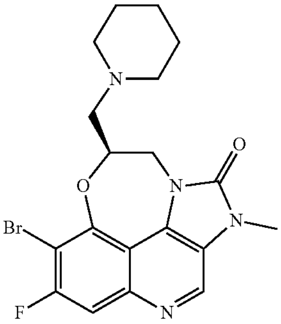
M-19
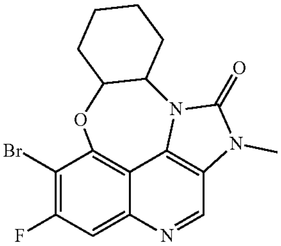
M-20
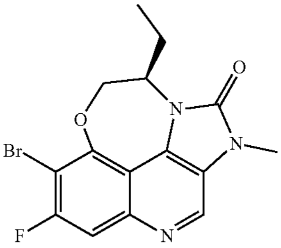
M-21
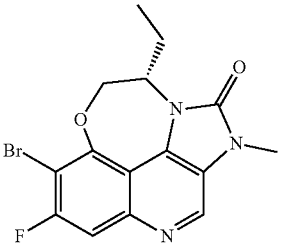
M-22
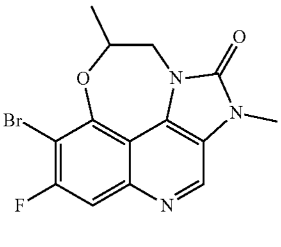
-continued
M-23
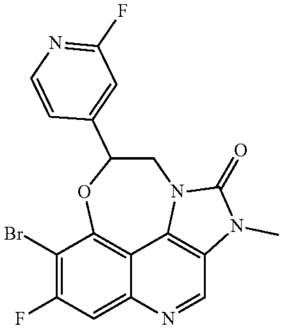
M-24
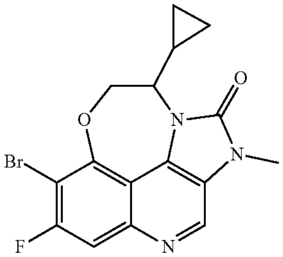
M-25
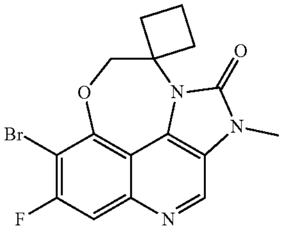
M-26
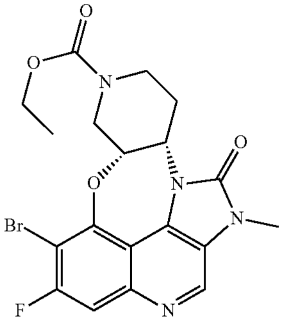
M-27
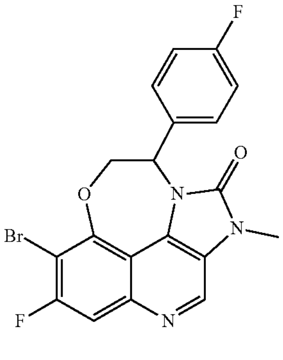

-continued
M-28
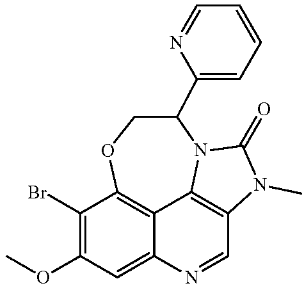
M-29
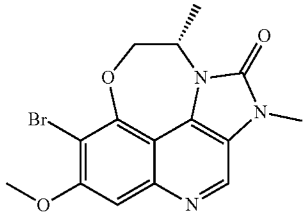
M-30
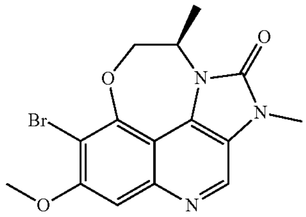
M-31
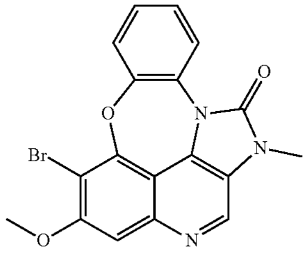
M-32
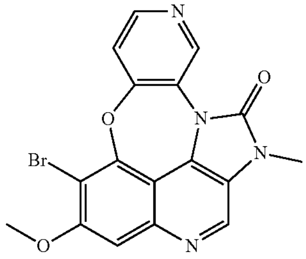
M-33
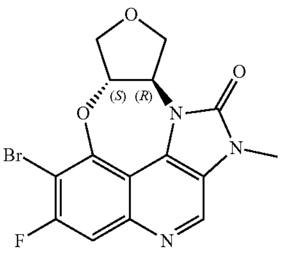
-continued
M-34
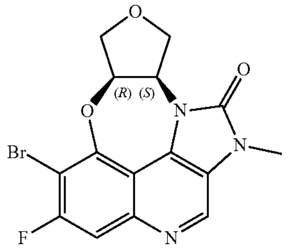
M-35
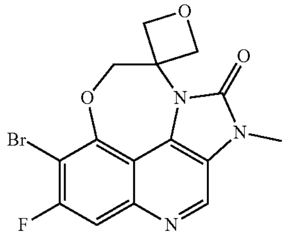
M-36
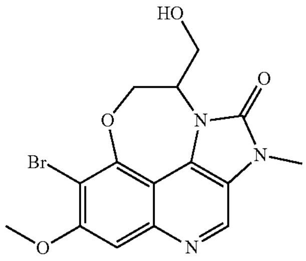
M-37
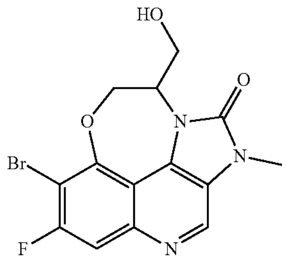
M-38
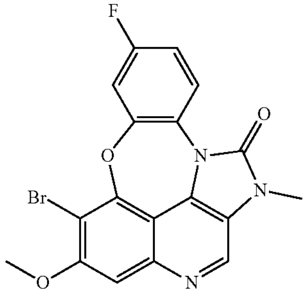
M-39
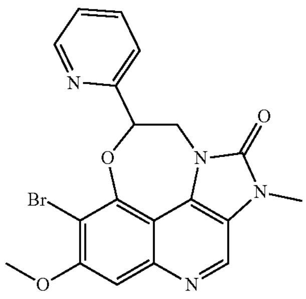

-continued
M-40
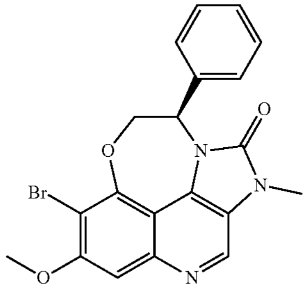
M-1-1
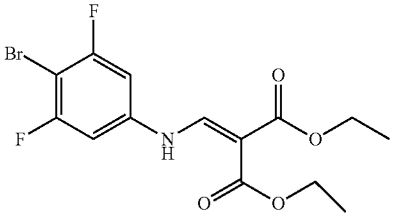
M-1-2
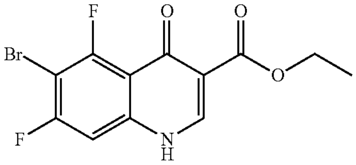
M-1-3
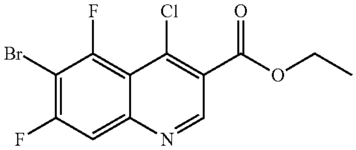
M-1-4
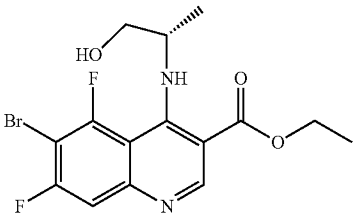
M-1-5
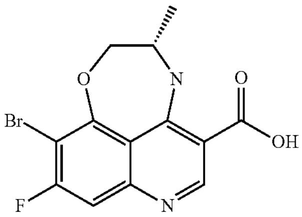
M-1-6
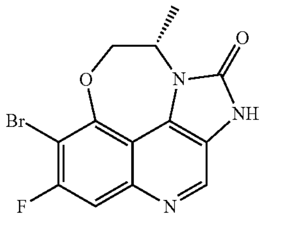
-continued
M-28-1
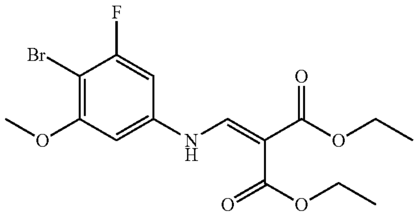
M-28-2
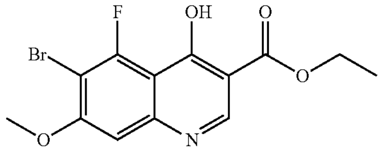
M-28-3
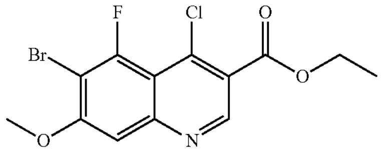
M-28-4
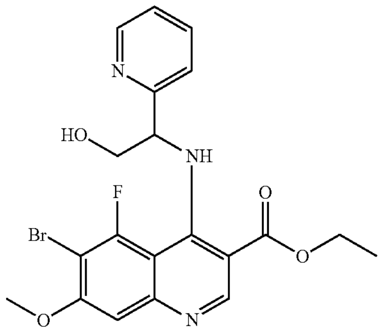
M-28-5
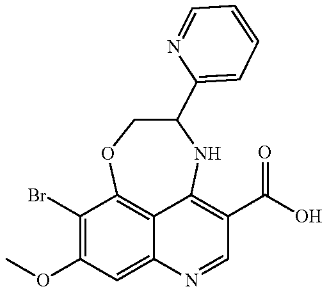
M-28-6
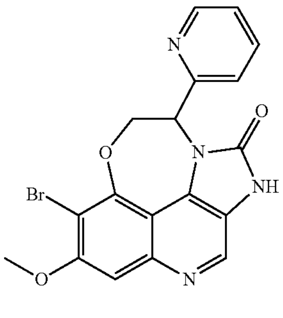

-continued
M-31-1
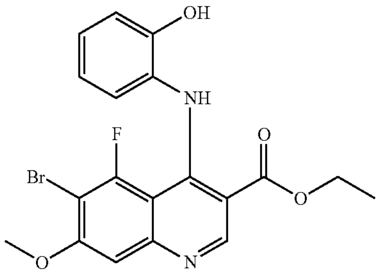
M-31-2
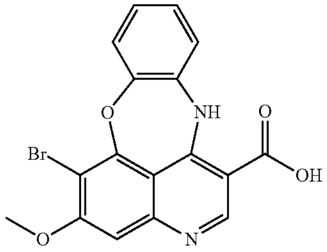
M-31-3
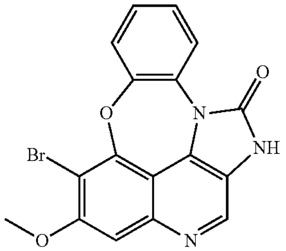
M-31-4
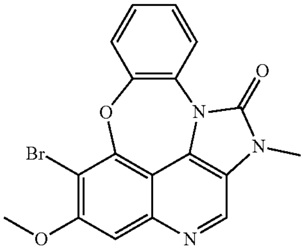
M-48-1
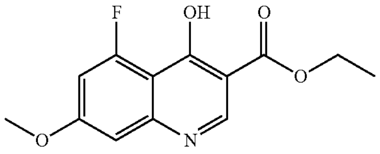
M-41
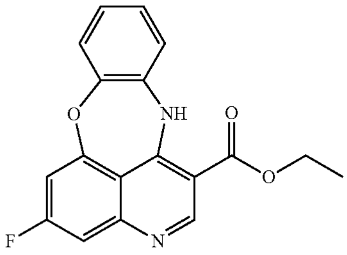
-continued
M-42
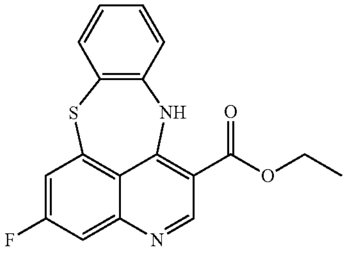
M-43
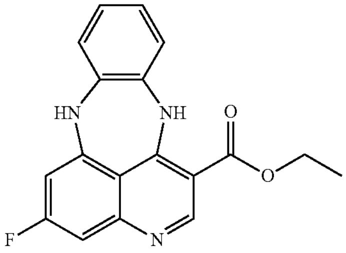
M-44
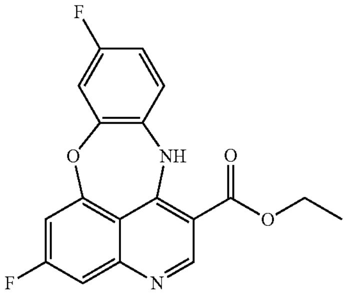
M-45
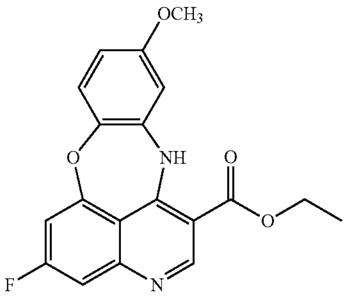
M-46
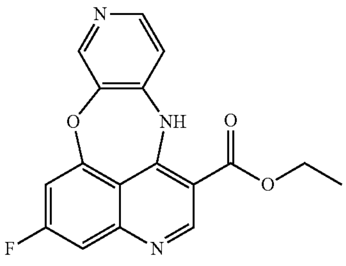
M-47
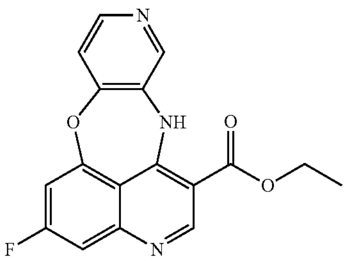

-continued
M-48
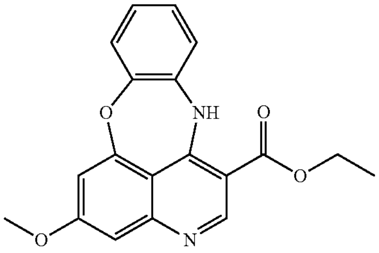
M-49
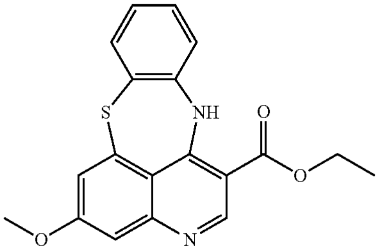
M-50
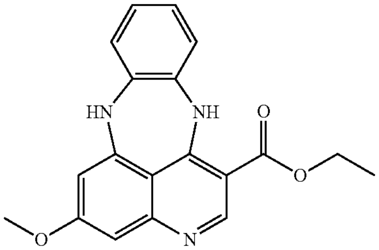
M-51
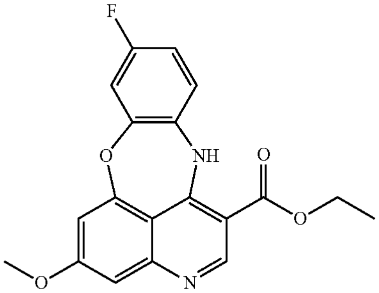
M-52
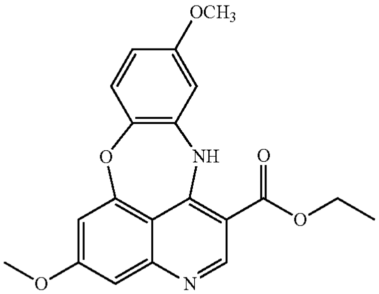
M-53
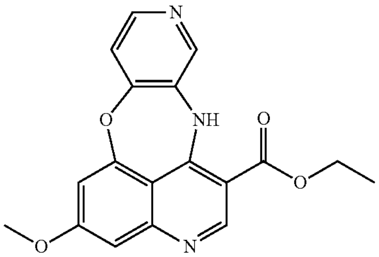
-continued
M-54
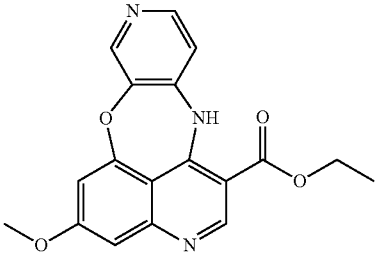
M-55
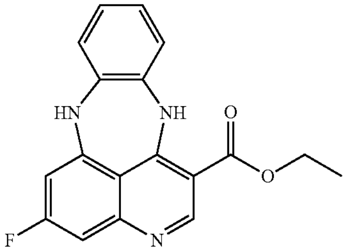
M-56
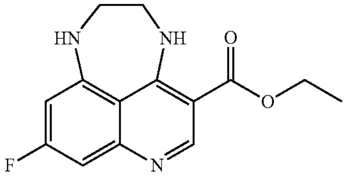
M-57
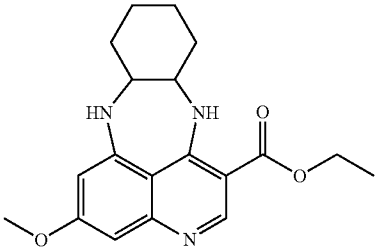
M-58
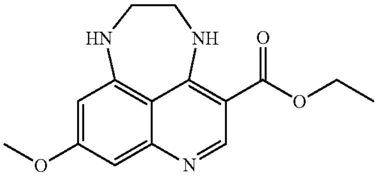
M-59
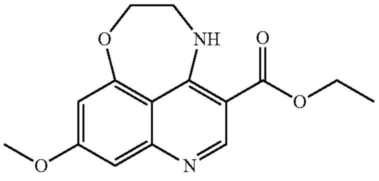

-continued
M-60
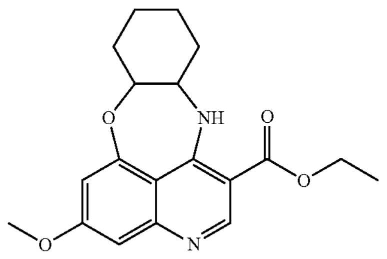
A-1-1
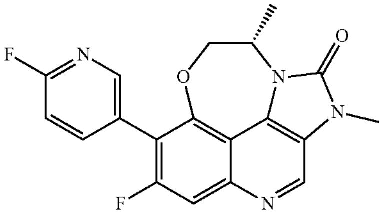
A-3-1
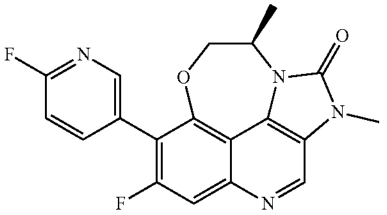
A-5-1
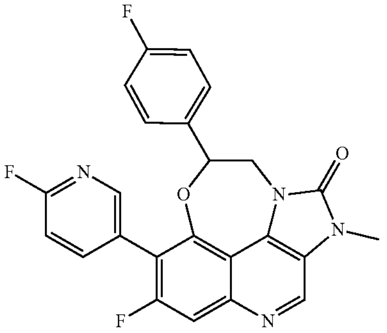
A-6-1
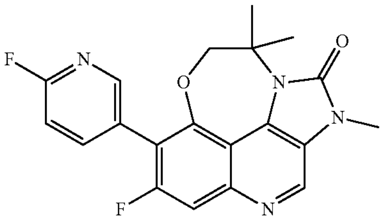
A-7-1
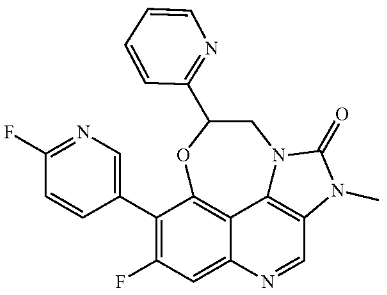
-continued
A-8-1
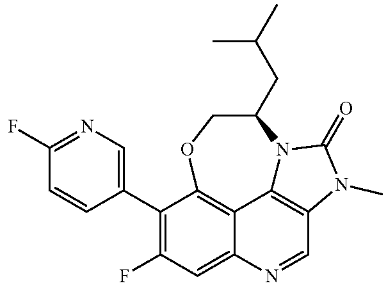
A-9-1
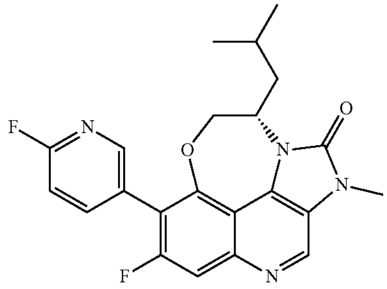
A-10-1
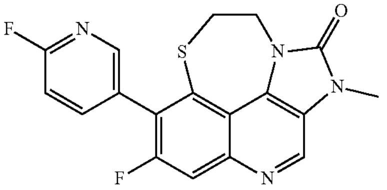
A-11-1
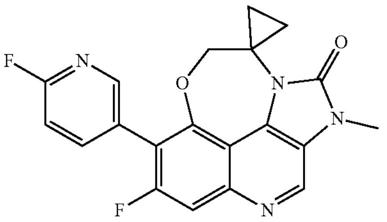
A-12-1
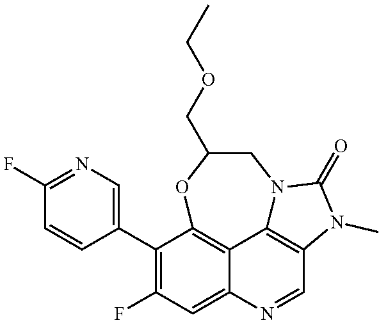

-continued
A-13-1
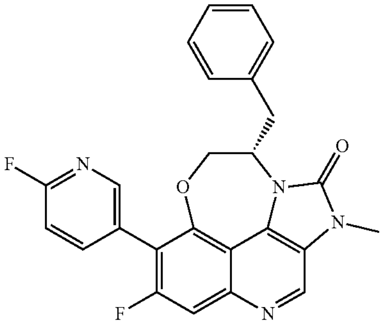
A-14-1
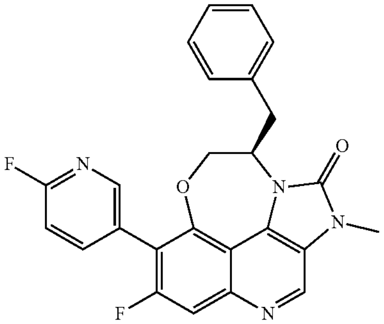
A-15-1
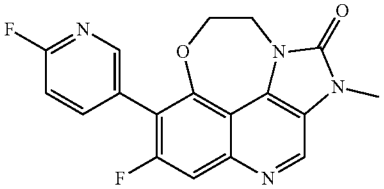
A-16-1
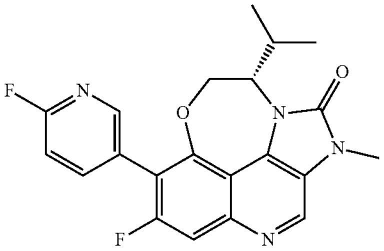
A-17-1
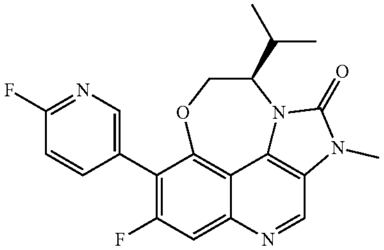
A-18-1
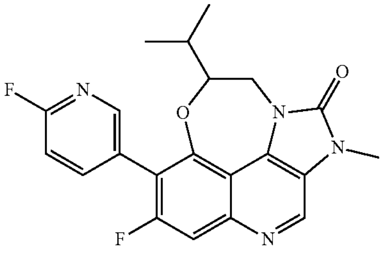
-continued
A-19-1
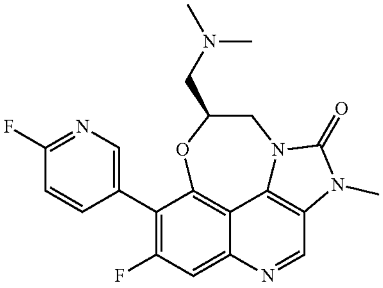
A-20-1
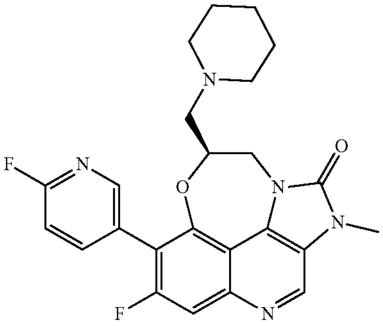
A-21-1
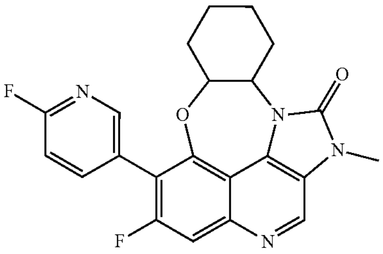
A-22-1
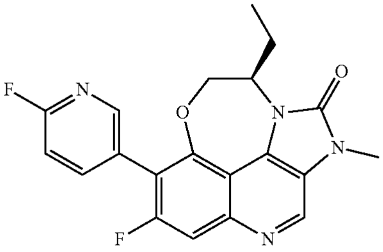
A-23-1
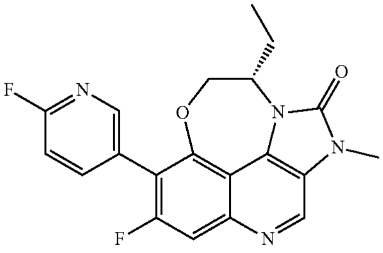
A-24-1
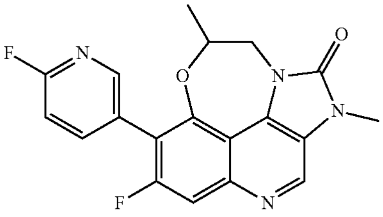

-continued
A-27-1
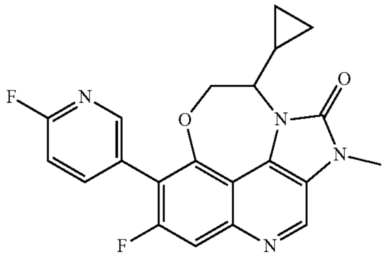
A-28-1
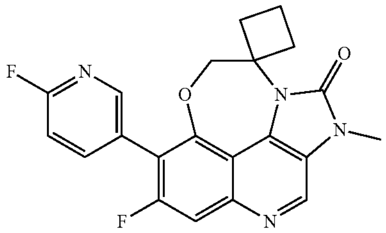
A-31-1
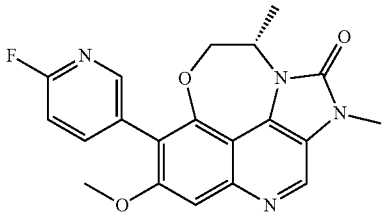
A-32-1
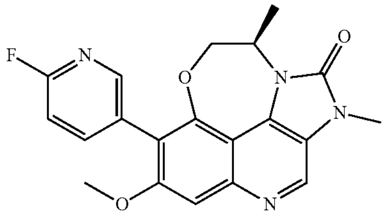
A-41-1
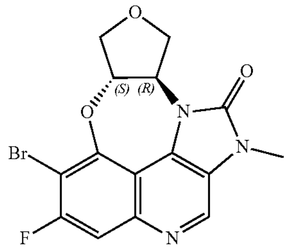
A-41-2
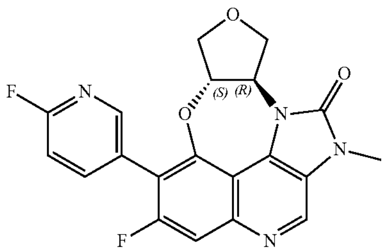
-continued
A-42-1
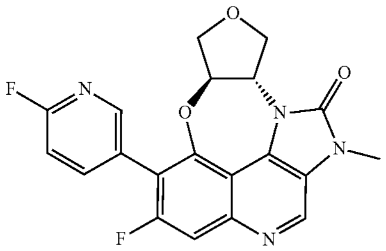
A-43-1
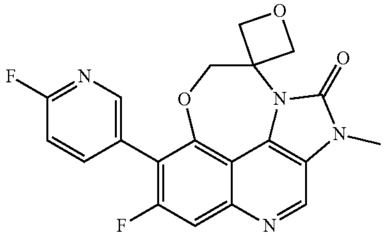
A-49-1
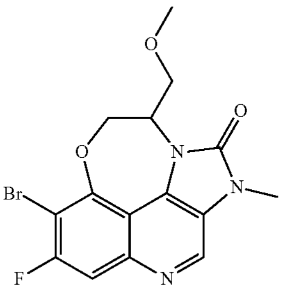
A-52-1
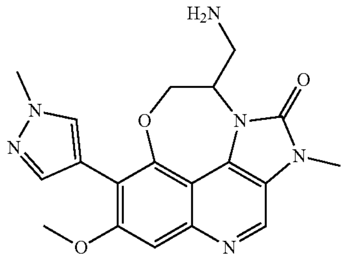
A-56-1
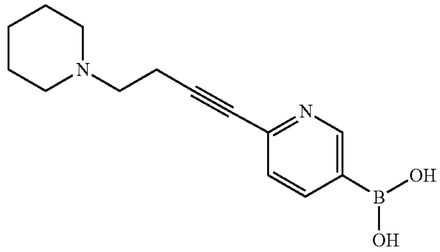
A-67-1
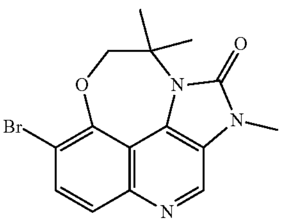

-continued
A-67-2
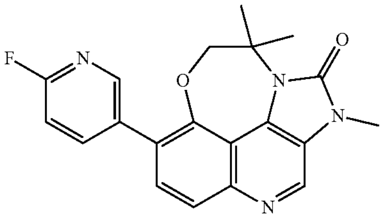
A-146-1
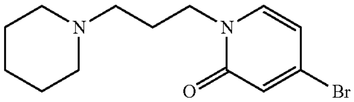
A-146-2
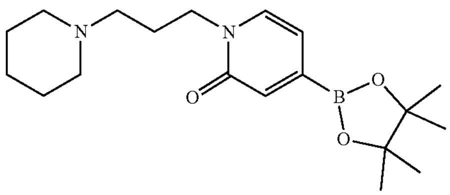
A-148-1
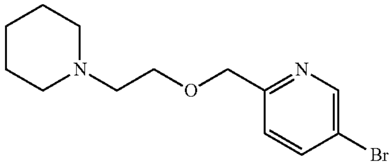
A-148-2
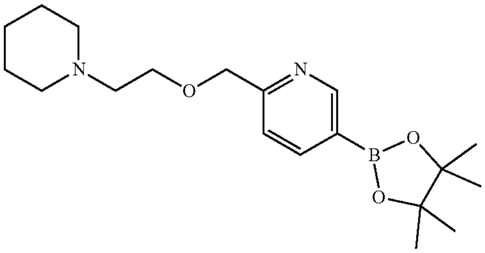
A-155-1
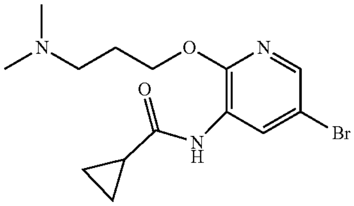
A-155-2
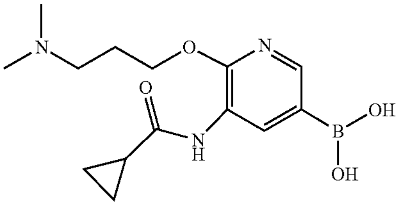
-continued
A-176-1
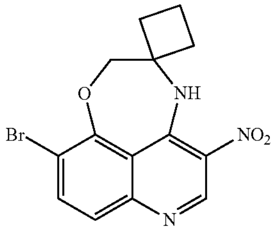
A-176-2
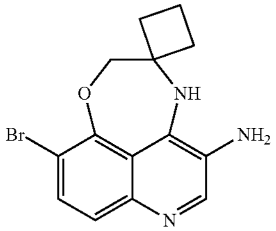
A-176-3
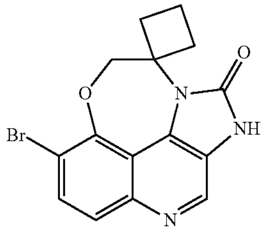
A-176-4
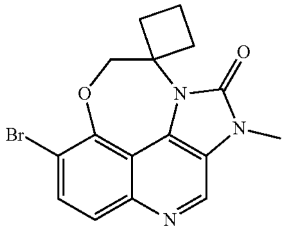
A-181-1
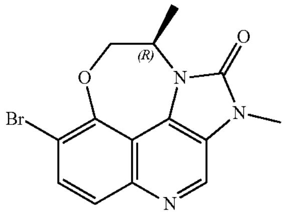
A-181-2
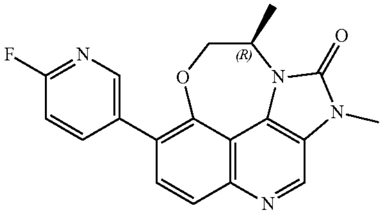
A-183-1
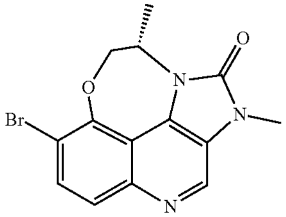

-continued
A-183-2
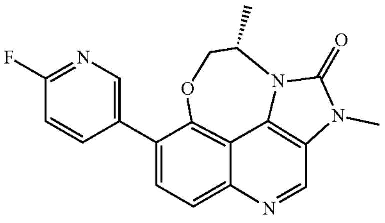
A-190-1
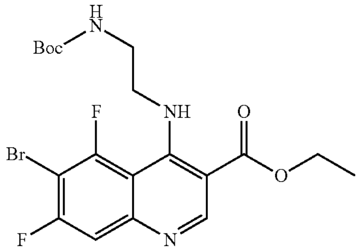
A-190-2
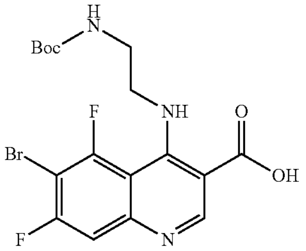
A-190-3
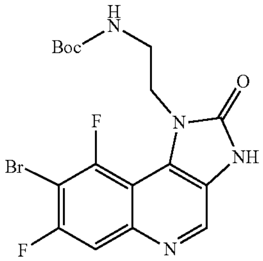
A-190-4
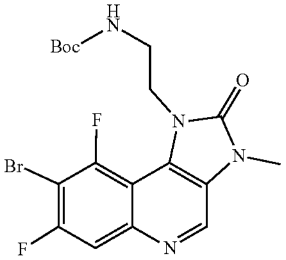
A-190-5
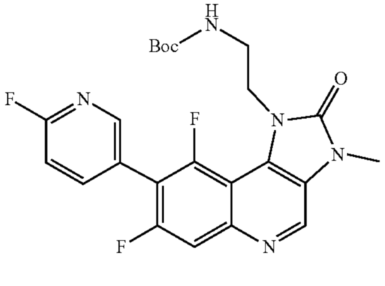
-continued
A-194-1
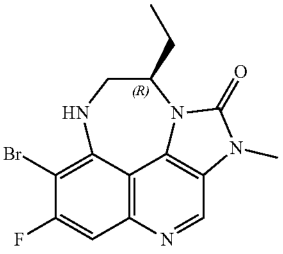
A-197-1
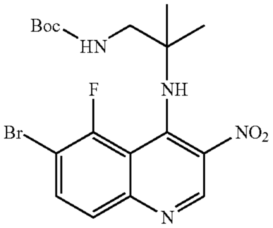
A-197-2
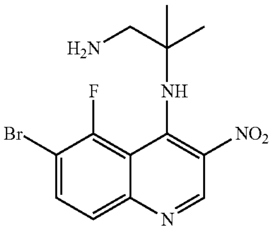
A-197-3
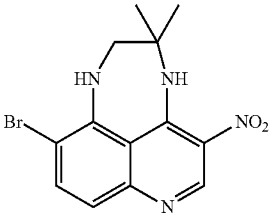
A-197-4
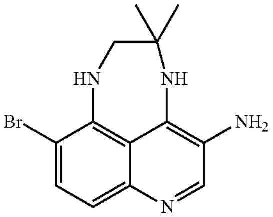
A-197-5
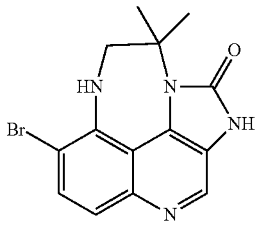

-continued
A-197-6
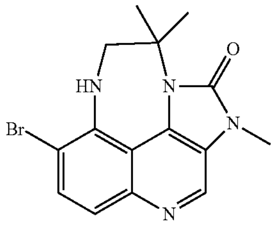
A-200-1
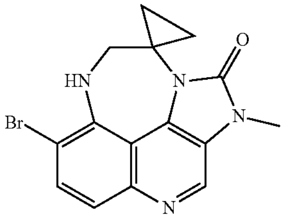
A-201-1
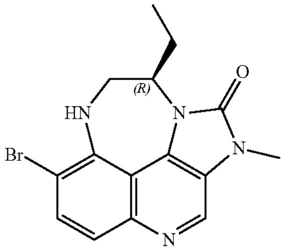
A-204-1
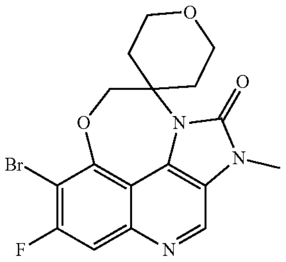
A-204-2
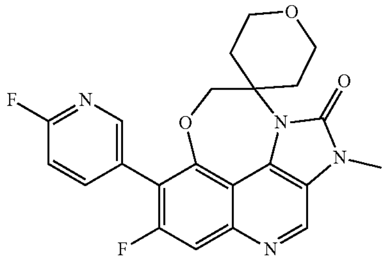
-continued
A-205-1
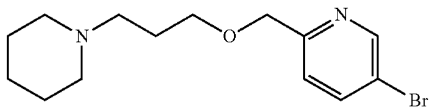
A-205-2
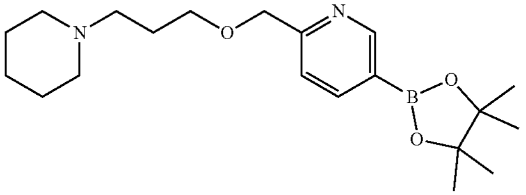
A-211-1
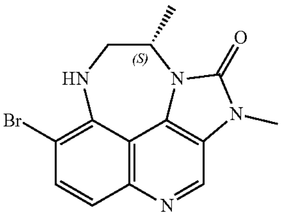
A-211-2
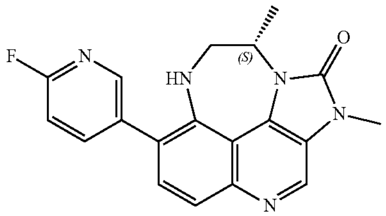
The present disclosure also provides a method for preparing the compound of formula (I') or formula (I), for example, the method shown in synthetic scheme 1, 2, or 3 as described below.
Synthetic Scheme 1:
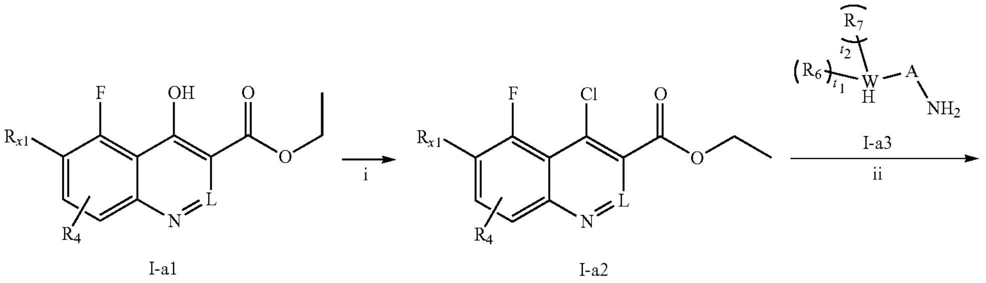

-continued

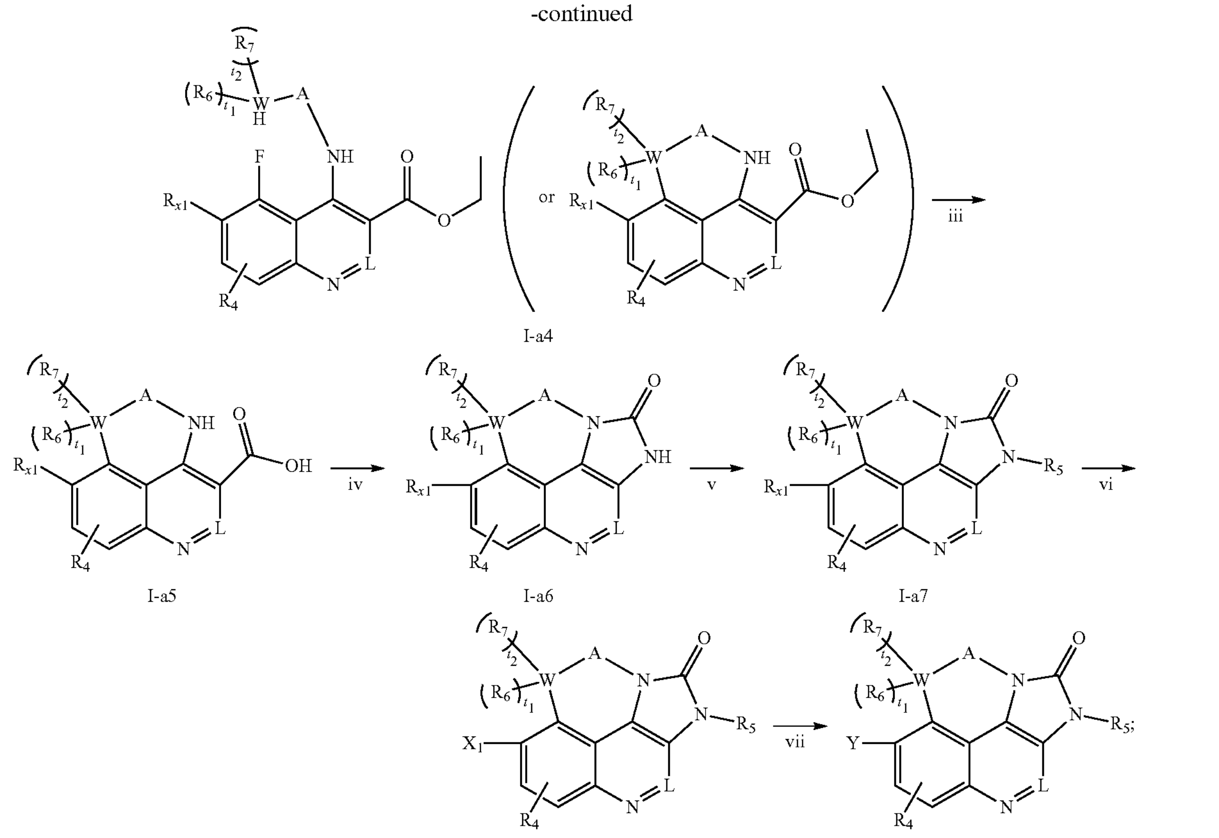

I-a4

I-a5 I-a6 I-a7

I-a8 (I)

wherein i) compound I-a1 is converted to compound I-a2 via chemical conversion (such as a substitution reaction);

for example, compound I-a1, thionyl chloride and the like are used as basic starting materials to obtain compound I-a2;

ii) compound I-a2 is converted to compound I-a4 via chemical conversion (such as a substitution reaction and an optional ring-closing reaction);

for example, the compounds I-a2 and I-a3 are used as basic starting materials and reacted under basic condition to obtain compound I-a4 without or with a new closed ring;

iii) compound I-4a is converted to compound I-a5 via chemical conversion (such as a hydrolysis reaction);

for example, compound I-a4 is reacted under basic condition to obtain compound I-a5;

iv) compound I-a5 is converted to compound I-a6 via chemical conversion (such as a ring-closing reaction);

for example, compound I-a5, diphenyl azidophosphate and the like are used as basic starting materials and reacted under basic condition to obtain compound I-a6;

v) compound I-a6 is converted to compound I-a7 via chemical conversion (such as an alkylation reaction);

for example, compounds I-a6, a halide (such as iodomethane) and the like are used as basic starting materials and reacted under basic condition to obtain compound I-a7;

vi) compound I-a7 is converted to compound I-a8 via chemical conversion (such as a coupling reaction);

for example, compound I-a7, a boric acid derivative and the like are used as basic starting materials and subjected to a coupling reaction to obtain compound I-a8;

vii) compound I-a8 is converted to compound I via chemical conversion (such as a substitution reaction);

for example, compound I-a8 and the like are used as basic starting materials and reacted under basic condition to obtain the compound of general formula I;

Synthetic Scheme 2:

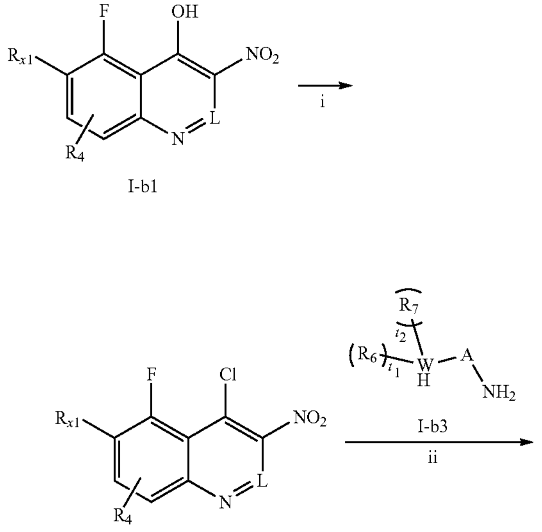

I-b1

I-b3

I-b2

-continued

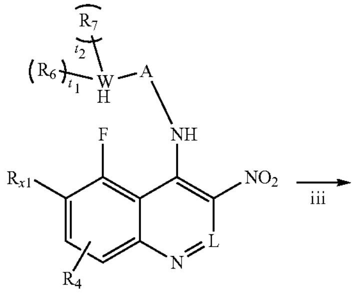

I-b4

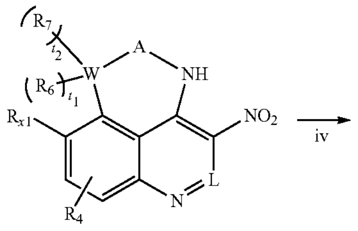

I-b5

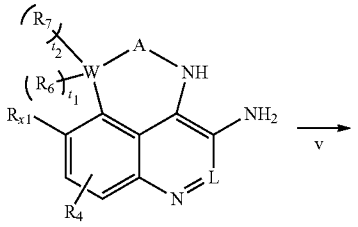

I-b6

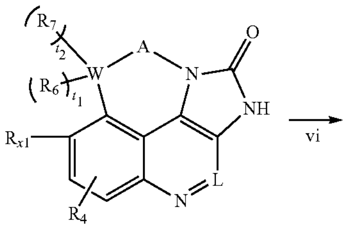

I-b7

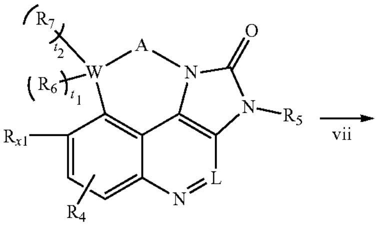

I-b8

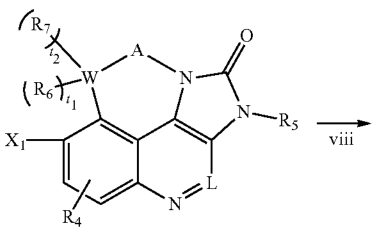

I-b9

-continued

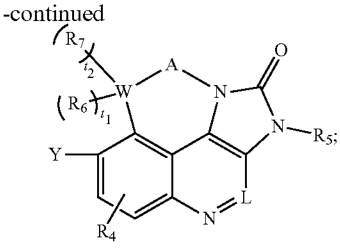

(I)

wherein i) compound I-b1, thionyl chloride and the like are used as basic starting materials to obtain compound I-b2;

ii) compound I-b2 and compound I-b3 are used basic starting materials and reacted under basic condition to obtain compound I-b4;

iii), compound I-b4 is reacted under basic condition to obtain compound I-b5;

iv) compound I-b5, a suitable reducing agent (such as iron powder, zinc powder), ammonium chloride and the like are used as basic starting materials to obtain compound I-b6;

v) compound I-b6, N,N-carbonyl diimidazole (CDI) and the like are used as basic starting materials to obtain compound I-b7;

vi) compounds I-b7, a halide (such as iodomethane) and the like are used as basic starting materials and reacted under basic condition to obtain compound I-b8;

vii) compound I-b8, a boric acid derivative and the like are used as basic starting materials and subjected to a coupling reaction to obtain compound I-b9;

viii) compound I-b9, an amine or alcohol and the like are used as basic starting materials and reacted under basic condition to obtain the compound of general formula I;

Synthetic Scheme 3:

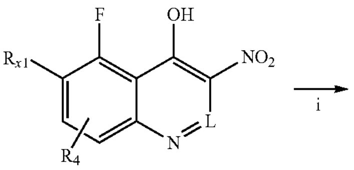

I-b1

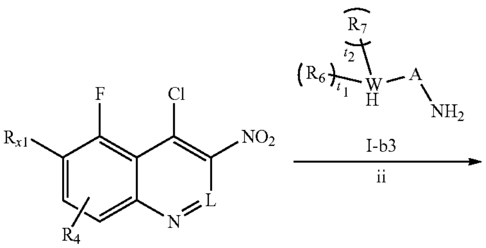

I-b2

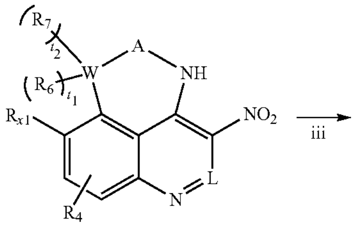

I-b5

-continued

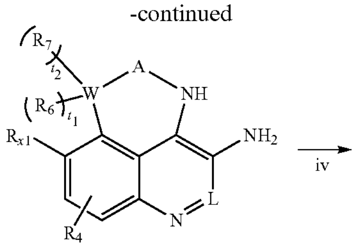

I-b6

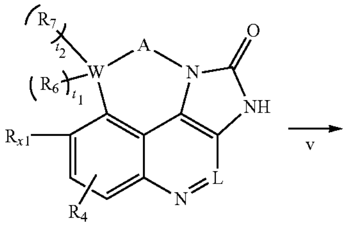

I-b7

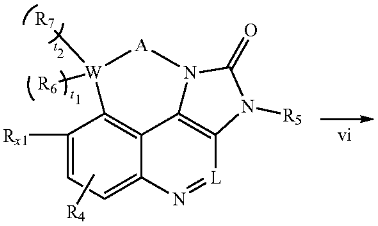

I-b8

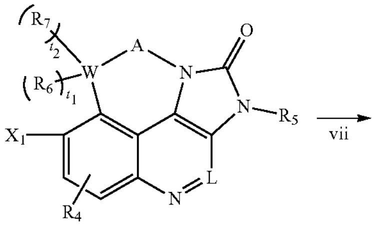

I-b9

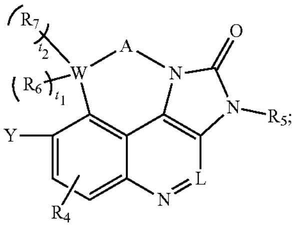

(I)

wherein i) compound 1-b1, thionyl chloride and the like are used as basic starting materials to obtain compound I-b2;

ii) compound I-b2 and compound I-b3 are used as basic starting materials and reacted under basic condition to obtain compound I-b5;

iii) compound I-b5, a suitable reducing agent (such as iron powder, zinc powder), ammonium chloride and the like are used as basic starting materials to obtain compound I-b6;

iv) compound I-b6 and N,N-carbonyl diimidazole (CDI) are used as basic starting materials to obtain compound I-b7;

v) compounds I-b7 and a halide (such as iodomethane) are used as basic starting materials and reacted under basic condition to obtain compound I-b8;

vi) compound I-b8, a boric acid derivative and the like are used as basic starting materials and subjected to a coupling reaction to obtain compound I-b9;

vii) compound I-b9, an amine or alcohol and the like are used as basic starting materials and reacted under basic condition to obtain the compound of general formula I.

Preferably, in the preparation method of the present disclosure, $R_{x1}$ is selected from the group consisting of halogen and hydrogen; and $X_1$, $R_4$, $R_5$, $R_6$, $R_7$, A, W, L, $t_1$, and $t_2$ are as defined in the compound of formula (I') or formula (I).

Preferably, in the preparation method of the present disclosure, the reaction is carried out in an organic solvent.

Further preferably, in the preparation method of the present disclosure, the organic solvent is selected from the group consisting of ethers, halogenated hydrocarbons, alcohols, alkanes, aromatic hydrocarbons, esters, acetonitrile, N,N-dimethyl formamide, and mixtures thereof, preferably, said ethers are selected from the group consisting of tetrahydrofuran, ethyl ether, glycol dimethyl ether, and mixtures thereof, said halogenated hydrocarbons are selected from the group consisting of dichloromethane, chloroform, dichloroethane, tetrachloromethane, and mixtures thereof; said alcohols are selected from the group consisting of methanol, ethanol, n-propanol, isopropanol, and mixtures thereof, said alkanes are selected from the group consisting of petroleum ether, n-hexane, and mixtures thereof, said aromatic hydrocarbons are selected from the group consisting of benzene, toluene, xylene, and mixtures thereof, and said esters are selected from the group consisting of ethyl acetate and the like.

Further preferably, in the preparation method of the present disclosure, the organic solvent is selected from the group consisting of one or more of acetonitrile, N,N-dimethyl formamide, halogenated hydrocarbon, ether, and ethyl acetate; preferably, said halogenated hydrocarbon is dichloroethane.

Preferably, in the preparation method of the present disclosure, the base is selected from the group consisting of one or more of potassium carbonate, sodium carbonate, magnesium carbonate, sodium bicarbonate, cesium carbonate, lithium carbonate, sodium hydroxide, potassium hydroxide, sodium hydride, lithium hydroxide, magnesium hydroxide, cesium hydroxide, triethylamine, diisopropylethylamine, piperidine, pyrrole, pyridine, dimethylpyridine, and dimethylaminopyridine.

[Pharmaceutical Composition]

With respect to the above compound, the present disclosure also provides a pharmaceutical composition, comprising the compound or the prodrug, tautomer, optical isomer, geometric isomer, solvate, isotopic derivative, or pharmaceutically acceptable salt thereof of the present disclosure.

Preferably, the pharmaceutical composition of the present disclosure comprises the compound or the prodrug, tautomer, optical isomer, geometric isomer, solvate, isotopic derivative, or pharmaceutically acceptable salt thereof of the present disclosure, as well as a pharmaceutically acceptable excipient.

[Medical Use]

The present disclosure provides the compound or the prodrug, tautomer, optical isomer, geometric isomer, solvate, isotopic derivative, or pharmaceutically acceptable salt thereof of the present disclosure or the pharmaceutical composition of the present disclosure for use as an ATM kinase inhibitor.

The present disclosure also provides the compound or the prodrug, tautomer, optical isomer, geometric isomer, solvate, isotopic derivative, or pharmaceutically acceptable salt thereof of the present disclosure or the pharmaceutical composition of the present disclosure for use in prevention and/or treatment of a disease and/or disorder which is at least partially mediated by ATM kinase. Preferably, said disease and/or disorder which is at least partially mediated by ATM kinase is a cancer.

Further, the present disclosure also provides the compound or the prodrug, tautomer, optical isomer, geometric isomer, solvate, isotopic derivative, or pharmaceutically acceptable salt thereof of the present disclosure or the pharmaceutical composition of the present disclosure for use in prevention and/or treatment of a cancer. Further, said cancer includes a solid tumor and a hematological tumor. Preferably, said cancer includes breast cancer, non-small cell lung cancer, brain glioma, colon cancer, rectal cancer, malignant glioma, gastric cancer, ovarian cancer, diffuse large B cell lymphoma, chronic lymphocytic leukemia, acute myeloid leukemia, head and neck squamous cell carcinoma, hepatocellular carcinoma, small cell lung cancer, and glioblastoma.

The present disclosure also provides use of the compound or the prodrug, tautomer, optical isomer, geometric isomer, solvate, isotopic derivative, or pharmaceutically acceptable salt thereof of the present disclosure or the pharmaceutical composition of the present disclosure in preparation of an ATM kinase inhibitor.

The present disclosure also provides use of the compound or the prodrug, tautomer, optical isomer, geometric isomer, solvate, isotopic derivative, or pharmaceutically acceptable salt thereof of the present disclosure or the pharmaceutical composition of the present disclosure in preparation of a medicament for preventing and/or treating a disease and/or disorder which is at least partially mediated by ATM kinase. Preferably, said disease and/or disorder which is at least partially mediated by ATM kinase is a cancer.

Further, the present disclosure also provides use of the compound or the prodrug, tautomer, optical isomer, geometric isomer, solvate, isotopic derivative, or pharmaceutically acceptable salt thereof of the present disclosure or the pharmaceutical composition of the present disclosure in preparation of a medicament for preventing and/or treating a cancer. Further, said cancer includes a solid tumor and a hematological tumor. More preferably, said cancer includes breast cancer, non-small cell lung cancer, brain glioma, colon cancer, rectal cancer, malignant glioma, gastric cancer, ovarian cancer, diffuse large B cell lymphoma, chronic lymphocytic leukemia, acute myeloid leukemia, head and neck squamous cell carcinoma, hepatocellular carcinoma, small cell lung cancer, and glioblastoma.

The present disclosure also provides a method for preventing and/or treating a disease and/or disorder which is at least partially mediated by ATM kinase, comprising administering a prophylactically and/or therapeutically effective amount of the compound or the prodrug, tautomer, optical isomer, geometric isomer, solvate, isotopic derivative, or pharmaceutically acceptable salt thereof of the present disclosure or the pharmaceutical composition of the present disclosure to a subject in need thereof; preferably, said disease and/or disorder which is at least partially mediated by ATM kinase is a cancer; more preferably, said cancer includes a solid tumor and a hematological tumor. More preferably, said cancer includes breast cancer, non-small cell lung cancer, brain glioma, colon cancer, rectal cancer, malignant glioma, gastric cancer, ovarian cancer, diffuse large B cell lymphoma, chronic lymphocytic leukemia, acute myeloid leukemia, head and neck squamous cell carcinoma, hepatocellular carcinoma, small cell lung cancer, and glioblastoma.

Further, the present disclosure also provides a method for preventing and/or treating a cancer, comprising administering a prophylactically and/or therapeutically effective amount of the compound or the prodrug, tautomer, optical isomer, geometric isomer, solvate, isotopic derivative, or pharmaceutically acceptable salt thereof of the present disclosure or the pharmaceutical composition of the present disclosure to a subject in need thereof, preferably, said cancer includes a solid tumor and a hematological tumor. More preferably, said cancer includes breast cancer, non-small cell lung cancer, brain glioma, colon cancer, rectal cancer, malignant glioma, gastric cancer, ovarian cancer, diffuse large B cell lymphoma, chronic lymphocytic leukemia, acute myeloid leukemia, head and neck squamous cell carcinoma, hepatocellular carcinoma, small cell lung cancer, and glioblastoma.

Further, in the use or method of the present disclosure, the compound or the prodrug, tautomer, optical isomer, geometric isomer, solvate, isotopic derivative, or pharmaceutically acceptable salt thereof of the present disclosure or the pharmaceutical composition of the present disclosure is administered with at least one additional anti-tumor agent or therapeutic treatment (e.g. radiation therapy). Preferably, said anti-tumor agent is selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738. Preferably, said therapeutic treatment is selected from radiation therapy.

Further, in the use or method of the present disclosure, the compound or the prodrug, tautomer, optical isomer, geometric isomer, solvate, isotopic derivative, or pharmaceutically acceptable salt thereof of the present disclosure or the pharmaceutical composition of the present disclosure is administered with radiation therapy simultaneously, separately, or sequentially.

The present disclosure provides a drug combination (or a drug combination composition, a drug complex composition), comprising the compound or the prodrug, tautomer, optical isomer, geometric isomer, solvate, isotopic derivative, or pharmaceutically acceptable salt thereof of the present disclosure or the pharmaceutical composition of the present disclosure, as well as at least one additional anti-tumor agent. Preferably, said anti-tumor agent is selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738.

[Term Definitions]

The terms "optional", "arbitrary", "optionally", and "arbitrarily" mean that an event or a situation described subsequently may, but not necessarily, occurs and such description includes the case in which the event or the situation occurs and the case in which the event or the situation does not occur.

Accordingly, the term "optionally substituted" means that a certain group may either be not substituted or may be substituted on its substitution site(s) by one or more substituents existing independently from one another. When the group is substituted, hydrogen on one or more substitution sites of the group to be substituted is independently substituted by a substituent; said substituent may be independently selected from the group consisting of deuterium, halogen, hydroxyl, amino, nitro, mercapto, cyano, oxo, —C(O)$C_{1-6}$ alkyl, —C(O)O—$C_{1-6}$ alkyl, —OC(O)—$C_{1-6}$ alkyl, —NH($C_{1-6}$ alkyl), —N($C_{1-6}$ alkyl)($C_{1-6}$ alkyl), —C(O)NH—$C_{1-6}$ alkyl, —NHC(O)—$C_{1-6}$ alkyl, $C_{1-6}$ alkyl, $C_{1-6}$ alkoxy, $C_{3-10}$ cycloalkyl, $C_{2-6}$ alkenyl, $C_{2-6}$ alkynyl, 3- to 10-membered heterocycloalkyl, $C_{6-14}$ aryl, and 5- to 12-membered heteroaryl; said oxo means that two hydrogens on the same substitutional site are replaced by the same oxygen to form a double bond.

Unless otherwise specified, the term "bond" refers to a chemical bond, including (but not limited to) a covalent bond (e.g., a carbon-carbon single bond, a carbon-nitrogen single bond, a carbon-oxygen single bond, a carbon-sulfur single bond, a carbon-carbon double bond, a carbon-nitrogen double bond, a carbon-oxygen double bond, a carbon-sulfur double bond, a carbon-carbon triple bond, a carbon-nitrogen triple bond, etc.), an ionic bond, a coordinate bond, etc.; in the compound of the present disclosure, a bond between parent nucleus and substituent or a bond between different substituents is substantially a covalent bond.

Unless otherwise specified, the term "carboxyl" refers to "—C(O)OH" group.

Unless otherwise specified, the term "hydroxyl" refers to "—OH" group.

Unless otherwise specified, the term "mercapto" refers to "—SH" group.

Unless otherwise specified, the term "amino" refers to "—$NH_2$" group. In some embodiments, the amino group also includes a group formed by substitution of one or two hydrogen atoms thereof with alkyl (e.g., —NH($C_{1-6}$ alkyl), —N($C_{1-6}$ alkyl)$_2$, etc.).

Unless otherwise specified, the term "nitro" refers to the "—$NO_2$" group.

Unless otherwise specified, the term "cyano" refers to the "—CN" group.

The term "oxo" means that two hydrogens at the same substitution site are replaced by the same oxygen to form a double bond (i.e., "═O").

Unless otherwise specified, the term "alkyl" refers to a linear or branched, saturated, and monovalent aliphatic hydrocarbon group, which may contain 1 to 20 carbon atoms, preferably contain 1 to 10 carbon atoms, further preferably contain 1 to 8 carbon atoms, more preferably contain 1 to 6 carbon atoms (i.e., $C_{1-6}$ alkyl). For example, "$C_{1-6}$ alkyl" means that such group is an alkyl, and the number of carbon atoms in the carbon chain thereof is between 1 and 6 (specifically, 1, 2, 3, 4, 5, or 6). Exemplary examples of alkyl include, but are not limited to, methyl, ethyl, n-propyl, isopropyl, n-butyl, isobutyl, tert-butyl, sec-butyl, n-amyl, neopentyl, 1,1-dimethylpropyl, 1,2-dimethylpropyl, 2,2-dimethylpropyl, 1-ethylpropyl, 2-methylbutyl, 3-methylbutyl, n-hexyl, n-heptyl, n-octyl, etc.

Unless otherwise specified, the term "alkoxy" refers to —O-alkyl, wherein the alkyl is as defined above, which may contain 1 to 20 carbon atoms, preferably contain 1 to 10 carbon atoms, further preferably contain 1 to 8 carbon atoms, more preferably contain 1 to 6 carbon atoms (i.e., $C_{1-6}$ alkoxy). For example, "$C_{1-6}$ alkoxy" means that such group is an alkoxy, and the number of carbon atoms in the carbon chain thereof is between 1 and 6 (specifically, 1, 2, 3, 4, 5, or 6). Exemplary examples of alkoxy include, but are not limited to, methoxy, ethoxy, propoxy, isopropoxy, butoxy, 1-methylpropoxy, 2-methylpropoxy, tert-butoxy, pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, etc.

Unless otherwise specified, the term "halogen" or "halogenated" refers to fluorine (F), chlorine (Cl), bromine (Br), or iodine (I).

Unless otherwise specified, the term "haloalkyl" refers to a group formed by substitution of one, two, more, or all hydrogen atoms of the alkyl as defined above with halogen. Exemplary examples of haloalkyl include, but are not limited to, —$CCl_3$, —$CF_3$, —$CHCl_2$, —$CH_2Cl$, —$CH_2Br$, —$CH_2I$, —$CH_2CF_3$, —$CF_2CF_3$, etc.

Unless otherwise specified, the term "alkenyl" refers to a linear or branched, monovalent aliphatic hydrocarbon group containing one or more (for example, 1, 2, 3, or 4) carbon-carbon double bonds, which may contain 2 to 20 carbon atoms, preferably contain 2 to 10 carbon atoms, further preferably contain 2 to 8 carbon atoms, more preferably contain 2 to 6 carbon atoms (i.e., $C_{2-6}$ alkyl). For example, "$C_{2-6}$ alkenyl" means that such group is an alkenyl, and the number of carbon atoms in the carbon chain thereof is between 2 and 6 (specifically, 2, 3, 4, 5, or 6). Exemplary examples of alkenyl include, but are not limited to, vinyl, n-propenyl, n-butenyl, n-pentenyl, etc.

Unless otherwise specified, the term "alkynyl" refers to a linear or branched, monovalent aliphatic hydrocarbon group containing one or more (for example, 1, 2, 3, or 4) carbon-carbon triple bonds, which may contain 2 to 20 carbon atoms, preferably contain 2 to 10 carbon atoms, further preferably contain 2 to 8 carbon atoms, more preferably contain 2 to 6 carbon atoms (i.e., $C_{2-6}$ alkynyl). For example, "$C_{2-6}$ alkynyl" means that such group is an alkynyl, and the number of carbon atoms in the carbon chain thereof is between 2 and 6 (specifically, 2, 3, 4, 5, or 6). Exemplary examples of alkynyl include, but are not limited to, ethynyl, n-propynyl, n-butynyl, n-pentynyl, etc.

Unless otherwise specified, the term "carbocyclyl" or "carbocycle" refers to a monocyclic or polycyclic, saturated or partially unsaturated, monovalent non-aromatic hydrocarbon group, which may contain 3 to 14 ring carbon atoms (i.e., $C_{3-14}$ carbocyclyl), preferably contain 3 to 12 ring carbon atoms (i.e., $C_{3-12}$ carbocyclyl), further preferably contain 4 to 12 ring carbon atoms (i.e., $C_{4-12}$ carbocyclyl) or 3 to 10 ring carbon atoms (i.e., $C_{3-10}$ carbocyclyl). In some embodiments, the carbocyclyl group has 3 to 8 ring carbon atoms ("$C_{3-8}$ carbocyclyl"). Exemplary examples of $C_{3-6}$ carbocyclyl include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), etc. Exemplary examples of $C_{3-8}$ carbocyclyl include, but are not limited to, $C_{3-6}$ carbocyclyl as described above as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), etc. Exemplary examples of $C_{3-10}$ carbocyclyl include, but are not limited to, $C_{3-8}$ carbocyclyl as described above as well as cyclononyl ($C_9$), cyclononenyl ($C_9$), cyclodecyl ($C_{10}$), cyclodecenyl ($C_{10}$), octahydro-1H-indenyl ($C_9$), decahydronaphthyl ($C_{10}$), spiro[4.5]decyl ($C_{10}$), etc. The carbocyclyl may either be a monocyclic ("monocyclic carbocyclyl") ring system or a condensed (condensed ring group), bridged (bridged ring group), or spiro (spiro ring group) ring system, such as a bicyclic system ("bicyclic carbocyclyl"), and may be saturated or partially unsaturated. In some embodiments, the carbocyclyl further includes a ring system in which the carbocyclyl as defined above is fused with one or more aryl/heteroaryl groups, wherein the fusion positions are on the carbocyclyl ring; or, in some embodiments, a ring system in which the carbocyclyl as defined above is fused with one or more carbocyclyls as defined above, wherein the fusion positions are on any one of the carbocyclyl rings. In the above cases, the number of ring atoms of such carbocyclyl ring system is the number of ring carbon atoms of the fused ring system. In some embodiments, the carbocyclyl is optionally substituted, i.e., unsubstituted ("unsubstituted carbocyclyl") or substituted by one or more substituents ("substituted carbocyclyl"). In some embodiments, such carbocyclyl is an unsubstituted $C_{3-10}$ carbocyclyl. In some embodiments, such carbocyclyl is a substituted $C_{3-10}$ carbocyclyl.

Unless otherwise specified, the term "cycloalkyl" refers to a monocyclic, saturated, monovalent aliphatic hydrocarbon group, which may contain 3 to 12 carbon atoms (i.e., $C_{3-12}$ cycloalkyl), preferably contain 3 to 10 carbon atoms (i.e., $C_{3-10}$ cycloalkyl), further preferably contain 3 to 7 carbon atoms (i.e., $C_{3-7}$ cycloalkyl), 4-6 carbon atoms (i.e., $C_{4-6}$ cycloalkyl), or 5 to 6 carbon atoms (i.e., $C_{5-6}$ cycloalkyl). For example, "$C_{3-10}$ cycloalkyl" means that such group is a cycloalkyl, and the number of carbon atoms in the carbon ring thereof is between 3 and 10 (specifically, 3, 4, 5, 6, 7, 8, 9, or 10). Exemplary examples of cycloalkyl include, but are not limited to, cyclopropyl cyclobutyl, cyclopentyl, cyclohexyl, methylcyclopropyl, 2-ethylcyclopentyl, dimethylcyclobutyl, etc.

Unless otherwise specified, the term "heterocyclyl" or "heterocycle" refers to a monocyclic or polycyclic, saturated or partially unsaturated, monovalent non-aromatic group having ring carbon atom(s) and 1 to 4 ring heteroatoms, which may contain 3 to 20 ring atoms, wherein one, two, three, or more ring atoms are selected from the group consisting of N, O, and S, the remaining ring atoms are C, preferably contain 3 to 12 ring atoms (i.e., 3- to 12-membered heterocyclyl), further preferably contain 3 to 10 ring atoms (i.e., 3- to 10-membered heterocyclyl), 3 to 8 ring atoms (i.e., 3- to 8-membered heterocyclyl), 3 to 6 ring atoms (i.e., 3- to 6-membered heterocyclyl), 4 to 6 ring atoms (i.e., 4- to 6-membered heterocyclyl), or 5 to 6 ring atoms (i.e., 5- to 6-membered heterocyclyl), with the number of the heteroatom of 1 to 4, preferably 1 to 3 (i.e., 1, 2, or 3). Exemplary examples of monocyclic heterocyclyl include, but are not limited to, pyrrolidinyl, imidazolidinyl, tetrahydrofuranyl, dihydropyrrolyl, piperidinyl, piperazinyl, pyranyl, etc. Polycyclic heterocycly includes fused, spiro, condensed, and bridged heterocyclic groups. The heterocyclyl may either be a monocyclic ("monocyclic heterocyclyl") ring system or a condensed (condensed heterocyclyl or heterocondensed ring group), fused (heterofused ring group or fused heterocyclyl), bridged (heterobridged ring group or bridged heterocyclyl), or spiro (heterospiro ring group or spiro heterocyclyl) ring system, such as a bicyclic system ("bicyclic heterocyclyl"), and may be saturated or partially unsaturated. A bicyclic heterocyclyl may contain one or more heteroatoms in one or both rings. In some embodiments, the heterocyclyl further includes a ring system in which the heterocyclyl as defined above is fused with one or more carbocyclyl groups, wherein the fusion positions are on the carbocyclyl or heterocyclyl ring; or, in some embodiments, the heterocyclyl further includes a ring system in which the heterocyclyl as defined above is fused with one or more aryl/heteroaryl groups as defined above, wherein the fusion positions are on the aryl/heteroaryl or heterocyclyl ring; or, in some embodiments, a ring system in which the heterocyclyl as defined above is fused with one or more heterocyclyls as defined above, wherein the fusion positions are on any one of the heterocyclyl rings. In the above cases, the number of ring atoms of such heterocyclyl ring system is the number of ring atoms of the fused ring system. In some embodiments, the heterocyclyl is optionally substituted, i.e., unsubstituted ("unsubstituted heterocyclyl") or substituted by one or more substituents ("substituted heterocyclyl"). Exemplary examples of 3-membered heterocyclyl containing one heteroatom include, but are not limited to, aziridinyl, oxiranyl, and thiorenyl. Exemplary examples of 4-membered heterocyclyl containing one heteroatom include, but are not limited to, azetidinyl, oxetanyl, and thietanyl. Exemplary examples of 5-membered heterocyclyl containing one heteroatom include, but are not limited to, tetrahydrofuranyl, dihydrofuranyl, tetrahydrothiophenyl, dihydrothiophenyl, pyrrolidinyl, dihydropyrrolyl, and 2,5-dioxopyrrolidinyl. Exemplary examples of 5-membered heterocyclyl containing two heteroatoms include, but are not limited to, dioxolanyl, oxathiolanyl, dithiolanyl, and 2-oxooxazolidinyl. Exemplary examples of 5-membered heterocyclyl containing three heteroatoms include, but are not limited to, triazolinyl, oxadiazolinyl, and thiadiazolinyl. Exemplary examples of 6-membered heterocyclyl containing one heteroatom include, but are not limited to, piperidinyl, tetrahydropyranyl, dihydropyridinyl, and thianyl. Exemplary examples of 6-membered heterocyclyl containing two heteroatoms include, but are not limited to, piperazinyl, morpholinyl, dithianyl, and dioxanyl. Exemplary examples of 6-membered heterocyclyl containing three heteroatoms include, but are not limited to, triazinanyl, oxadiazinanyl, thiadiazinanyl, oxathiazinanyl, and dioxazinanyl. Exemplary examples of 7-membered heterocyclyl containing one heteroatom include, but are not limited to, azepanyl, oxepanyl, and thiepanyl. Exemplary examples of 8-membered heterocyclyl containing one heteroatom include, but are not limited to, azecanyl, oxecanyl, and thiecanyl. Exemplary examples of 5-membered heterocyclyl fused with one $C_6$ aryl ring (also referred to herein as 5,6-bicyclic heterocyclyl) include, but are not limited to, indolinyl, isoindolinyl, dihydrobenzofuranyl, dihydrobenzothienyl, benzoxazolinonyl, etc. Exemplary examples of 6-membered heterocyclyl fused with one $C_6$ aryl ring (also referred to herein as 6,6-bicyclic heterocyclyl) include, but are not limited to, tetrahydroquinolinyl, tetrahydroisoquinolinyl, etc.

Unless otherwise specified, the term "heterocycloalkyl" refers to a monocyclic, saturated "heterocyclyl" or "heterocycle" as defined above, which may contain 3 to 20 ring atoms (i.e., 3- to 20-membered heterocyclyl), wherein one, two, three, or more ring atoms are selected from the group consisting of N, O, and S, the remaining ring atoms are C, preferably contain 3 to 12 ring atoms (i.e., 3- to 12-membered heterocycloalkyl), further preferably contain 3 to 10 ring atoms (i.e., 3- to 10-membered heterocycloalkyl), 3 to 8 ring atoms (i.e., 3- to 8-membered heterocycloalkyl), 4 to 7 ring atoms (i.e., 4- to 7-membered heterocycloalkyl), 5 to 10 ring atoms (i.e., 5- to 10-membered "heterocycloalkyl), or 5 to 6 ring atoms (i.e., 5- to 6-membered heterocycloalkyl), with the number of the heteroatom of 1 to 4, preferably 1 to 3 (1, 2, or 3). In some embodiments, the heterocycloalkyl is optionally substituted, for example, unsubstituted ("unsubstituted heterocycloalkyl") or substituted by one or more substituents ("substituted heterocycloalkyl"). Exemplary examples of "heterocycloalkyl" have been given in the above description of "heterocyclyl" or "heterocycle", which still include, but are not limited to, aziridinyl, oxiranyl, thiorenyl, azetidinyl, oxetanyl, thietanyl, tetrahydrofuranyl, tetrahydropyranyl, piperidinyl, piperazinyl, morpholinyl, thiomorpholinyl, oxathianyl, oxazolidinyl, dioxanyl, dithianyl, thiazolidinyl, pyrrolidinyl, pyrazolidinyl, imidazolidinyl, etc.

Unless otherwise specified, the term "fused ring" refers to a non-aromatic, saturated or partially unsaturated ring system formed by two or more rings sharing two adjacent atoms with one another, including fused carbocyclyl and fused heterocyclyl, wherein the ring atoms of the fused heterocyclyl contain one or more heteroatoms independently selected from the group consisting of oxygen, nitrogen, and sulfur.

Unless otherwise specified, the term "monospiro ring group" refers to a saturated, monovalent aliphatic hydrocarbon group containing only one spiro carbon atom, which may contain 6 to 14 ring carbon atoms, preferably contain 7 to 10 ring carbon atoms. The monospiro ring group includes 3-/5-membered, 4-/4-membered, 4-/5-membered, 4-/6-membered, 5-/5-membered, and 5-/6-membered monospiro ring groups, in which the spiro atom is counted separately in the number of ring atoms of each ring. Exemplary examples of monospiro ring group include, but are not limited to,

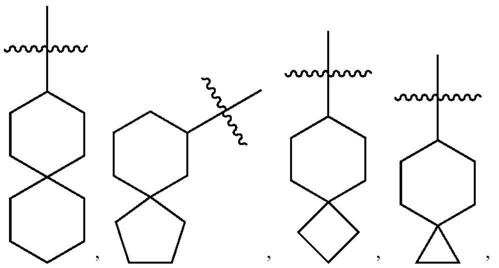
,
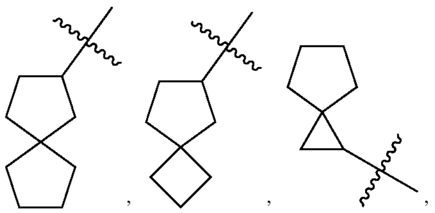
,
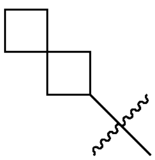
, etc.

Unless otherwise specified, the term "heteromonospiro ring group" refers to a saturated, monovalent aliphatic hydrocarbon group containing only one spiro carbon atom, which may contain 6 to 14 ring atoms, preferably contain 7 to 10 ring atoms, including 1 to 4 ring heteroatoms thereof, preferably including 1 to 3 (i.e., 1, 2, or 3) ring heteroatoms thereof, and the heteroatoms thereof are independently selected from the group consisting of N, O, and S. The heteromonospiro ring group includes 3-/5-membered, 4-/4-membered, 4-/5-membered, 4-/6-membered, 5-/5-membered, and 5-/6-membered heteromonospiro ring groups, in which the spiro atom is counted separately in the number of ring atoms of each ring. Exemplary examples of heteromonospiro ring group include, but are not limited to,

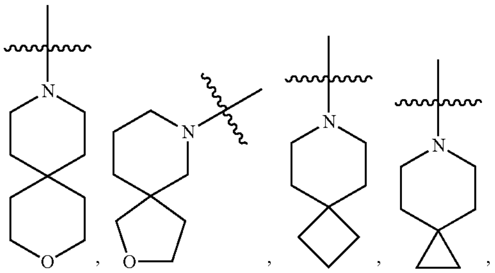
,
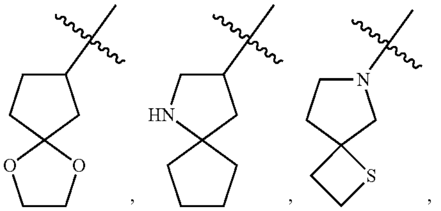
,
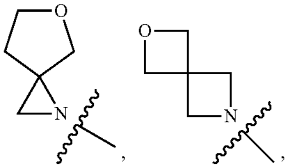
, etc.

Unless otherwise specified, the term "bridged ring group" refers to a polycyclic, monovalent aliphatic hydrocarbon group in which any two rings share two non-adjacent ring carbon atoms, which may contain 5 to 20 ring carbon atoms, preferably contain 6 to 14 ring carbon atoms, more preferably contain 7 to 10 ring carbon atoms, and may contain one or more double bonds, but none of the rings has a fully conjugated π-electron system. The bridged ring group includes bicyclic, tricyclic, tetracyclic, or polycyclic bridged ring group, preferably bicyclic, tricyclic, or tetracyclic bridged ring group, more preferably bicyclic or tricyclic bridged ring group. Exemplary examples of bridged ring group include, but are not limited to,

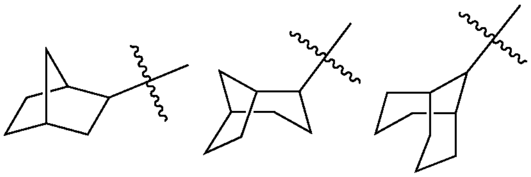

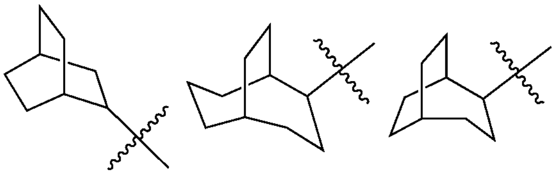

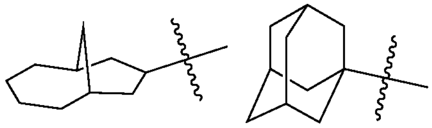
.

Unless otherwise specified, the term "heterobridged ring group" refers to a polycyclic, monovalent aliphatic hydrocarbon group in which any two rings share two non-adjacent ring atoms, which may contain 5 to 14 ring atoms, preferably contain 6 to 14 ring atoms, more preferably contain 7 to 10 ring atoms, including 1 to 4 ring heteroatoms thereof, preferably including 1 to 3 (i.e., 1, 2, or 3) ring heteroatoms thereof, and the heteroatoms thereof are independently selected from the group consisting of N, O, and S, and may contain one or more double bonds, but none of the rings has a fully conjugated π-electron system. The heterobridged ring group includes bicyclic, tricyclic, tetracyclic, or polycyclic heterobridged ring group, preferably bicyclic, tricyclic, or tetracyclic heterobridged ring group, more preferably bicyclic or tricyclic heterobridged ring group. Exemplary examples of heterobridged ring group include, but are not limited to,

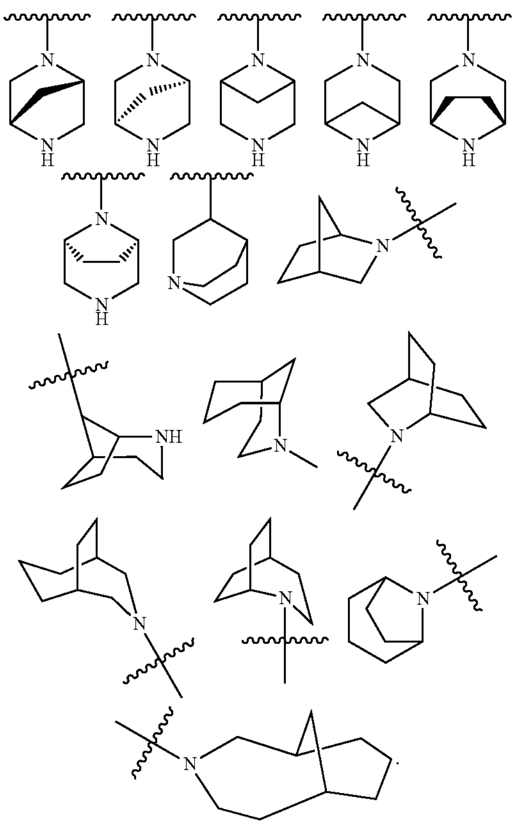

Unless otherwise specified, the terms "aryl" or "aromatic ring group" refers to a monocyclic or polycyclic monovalent aromatic hydrocarbon group, which may contain 6 to 16 ring carbon atoms (i.e., $C_{6-16}$ aryl), 6 to 14 ring carbon atoms (i.e., $C_{6-14}$ aryl), 6 to 12 ring carbon atoms (i.e., $C_{6-12}$ aryl), or 6 to 10 ring carbon atoms (i.e., $C_{6-10}$ aryl). In some embodiments, the term "aryl" may be used interchangeably with the term "aromatic ring". Exemplary examples of aryl include, but are not limited to, phenyl, naphthyl, anthracenyl, phenanthryl, pyrenyl, etc.

Unless otherwise specified, the term "heteroaryl" or "heteroaromatic ring group" refers to a monocyclic or polycyclic, monovalent aromatic group, which may contain 5 to 14 ring atoms (i.e., 5- to 14-membered heteroaryl), 5 to 10 ring atoms (i.e., 5- to 10-membered heteroaryl), 5 to 8 ring atoms (i.e., 5- to 8-membered heteroaryl), or 5 to 6 ring atoms (i.e., 5- to 6-membered heteroaryl), wherein one, two, three, or more ring atoms are heteroatoms independently selected from the group consisting of O, N, and S, and the remaining ring atoms are C. In some embodiments, the term "heteroaryl" may be used interchangeably with the term "heteroaromatic ring". Exemplary examples of heteroaryl include, but are not limited to, furanyl, thienyl, oxazolyl, thiazolyl, isoxazolyl, oxdiazolyl, thiadiazolyl, pyrrolyl, pyrazolyl, imidazolyl, triazolyl, tetrazolyl, pyridinyl, pyrimidinyl, pyrazinyl, pyridazinyl, thiodiazolyl, triazinyl, phthalazinyl, quinolinyl, isoquinolinyl, pteridinyl, purinyl, indolyl, isoindolyl, indazolyl, benzofuranyl, benzothiophenyl, benzopyridinyl, benzopyrimidinyl, benzopyrazinyl, benzimidazolyl, benzophthalazinyl, pyrrolo[2,3-b]pyridinyl, imidazolo[1,2-a]pyridinyl, pyrazolo[1,5-a]pyridinyl, pyrazolo[1,5-a]pyrimidinyl, imidazolo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridinyl, etc.

Unless otherwise specified, the term "pharmaceutically acceptable salt" or "officinal salt" refers to a salt that is suitable for contact with mammalian (especially human) tissues within the scope of reasonable medical judgment without excessive toxicity, irritation, allergic response, etc., and is commensurate with a reasonable benefit/risk ratio, for example, the pharmaceutically acceptable salts of amines, carboxylic acids, and other types of compounds are well known in the art. Said salt may be prepared in-situ during the final separation and purification of the compound of the present disclosure, alternatively, said salt may be prepared individually by reacting a free base or free acid with a suitable reagent.

Unless otherwise specified, the term "isotopic derivative" means that the compound of the present disclosure may exist in an isotopically traced or enriched form, and contains one or more atoms whose atomic weight or mass number is different from that of the atom with the greatest natural abundance. The isotope may be a radioactive or non-radioactive isotope. The isotopes commonly used as isotope labels include, but are not limited to, hydrogen isotopes: $^{2}H$ and $^{3}H$; carbon isotopes: $^{13}C$ and $^{14}C$; chlorine isotopes: $^{35}Cl$ and $^{37}Cl$; fluorine isotope: $^{18}F$; iodine isotopes: $^{123}I$ and $^{125}I$; nitrogen isotopes: $^{13}N$ and $^{15}N$; oxygen isotopes: $^{15}O$, $^{17}O$, and $^{18}O$; and sulfur isotopes: $^{35}S$. These isotopically labelled compounds can be used to study the distribution of medicinal molecules in tissues. Especially, $^{2}H$ and $^{13}C$ are more widely used because they are easy to label and convenient to detect.

Unless otherwise specified, the terms "solvate" refers to a physical association of the compound of the present disclosure with one or more solvent molecules (whether organic or inorganic). The physical association is hydrogen bond mediated association. In certain instances, for example, when one or more solvent molecules are incorporated into the crystal lattice of a crystalline solid, the solvate may be isolated. The solvent molecules in the solvate may exist in regular and/or irregular arrangements. The solvate may contain stoichiometric or non-stoichiometric solvent molecules. The "solvate" encompasses both solution-phase and isolatable solvates. Exemplary examples of solvate include, but are not limited to, hydrate, ethanolate, methanolate, and isopropanolate. Solvation methods are well known in the art.

Unless otherwise specified, the term "optical isomer" refers to an isomer with similar physical and chemical properties, identical linking sequence of atoms in molecule, but different optical activity.

Unless otherwise specified, the term "geometrical isomer" (in particular "cis/trans isomer") refers to an isomer containing a carbon-carbon or carbon-nitrogen double bond existing in E or Z configuration, wherein the term "E" means that the substituent with a higher priority lies on the opposite side of the carbon-carbon or carbon-nitrogen double bond, and the term "Z" means that the substituent with a higher priority lies on the same side of the carbon-carbon or carbon-nitrogen double bond, and the priority can be determined by Cahn-Ingold-Prelog sequence rules. The compound of the present disclosure may also exist in the form of a mixture of "E" and "Z" isomers.

Unless otherwise specified, the term "tautomer" refers to an isomer with different energy, which may be converted between one another through a low energy barrier. If tautomerism is possible (such as in a solution), the chemical equilibrium of the tautomers may be achieved. For example, proton tautomers (also known as proton transfer tautomers) include tautomers that are mutually converted by proton transfer, such as keto-enol tautomerism and imine-enamine tautomerism. Valence tautomer includes the tautomers that are mutually converted by recombination of bonding electrons.

Unless otherwise specified, the structural formulas described herein include all isomeric forms (e.g., enantiomeric, diastereomeric, geometrical isomeric (e.g., conformational isomeric), tautomeric, etc.). For example, the isomers having an asymmetric center of R or S configuration, the isomers having a double bond of (Z) or (E) configuration, and the conformational isomers of those of (Z) or (E) configuration. Thus, an individual stereoisomer of the compound of the present disclosure or a mixture thereof with its enantiomer, diastereomer, or geometrical isomer (such as conformational isomer) will fall within the scope of the present disclosure.

Unless otherwise specified, the term "prodrug" refers to a drug that is converted into its parent drug in vivo. The prodrug is usually useful, which may improve some certain and undesirable physical or biological properties. The physical properties usually refer to related solubility (excessive or insufficient solubility in lipid or water) or stability, while problematic biological properties include overquick metabolism or poor bioavailability, which may itself be related to physical and chemical properties. For example, they can be bioavailable by oral administration, while the parent drugs cannot. Compared with the parent drug, the solubility of the prodrug in a pharmaceutical composition is also improved. An exemplary example of prodrug may be, but not limited to, any compound of the present disclosure, which is administered as an ester ("prodrug") to facilitate transport through cell membranes, and subsequently hydrolyzed to a carboxylic acid (i.e. active entity), wherein the water solubility thereof is detrimental to the transport but beneficial once it gets into the cell. Another exemplary example of the prodrug may be a short peptide (polyamino acid) attached to a carboxyl group, wherein the peptide is metabolized to release the active moiety.

[Beneficial Effects]

The present disclosure provides an ATM kinase inhibitor with a novel structure, a preparation method therefor, and use thereof in the field of medicines. In particular, the compound of the present disclosure is useful in treating cancer. Enzymatic assay results show that the compound of the present disclosure has good selectivity to ATM as a target and is capable of significantly inhibiting ATM kinase activity. In addition, the present disclosure adopts a specific synthesis method, which is simple in process and convenient in operation. Thus, it is beneficial to large-scale industrial production and application.

DETAILED DESCRIPTION

The present disclosure will be further described in connection with the specific examples below. It should be understood that these embodiments are merely intended to illustrate the present disclosure and not to limit the scope of the present disclosure.

The experimental methods without specific conditions in the following examples usually follow the conventional conditions or the conditions suggested by the manufacturers. In addition, any method and material similar to or equal to the content as described herein can be applied to the method of the present disclosure.

Unless otherwise specified, scientific and technical terms used in the following examples have meanings familiar to those skilled in the art. Abbreviations used in the preparation examples, examples, and elsewhere in the context have the meanings as follows.

DCM dichloromethane
TEA triethylamine
DIEA/N,N-diisopropylethylamine
DIPEA
DMF N,N-dimethylformamide
EtOAc ethyl acetate
h hour
mL milliliter
HATU 2-(7-azobenzotriazol-1-yl)-N,N,N',N'-tetramethyluronium
hexafluorophosphate
MeOH methanol
TFA trifluoroacetic acid
DMSO-$d_6$ dimethyl sulfoxide-$d_6$

INTERMEDIATE PREPARATION EXAMPLE

Intermediate Preparation Example 1: Preparation of (S)-7-bromo-6-fluoro-2,10-dimethyl-9,10-dihydro-8-oxa-2,4,10a-triazanaphtho[2,1,8-cde]azulen-1(2H)-one (M-1)

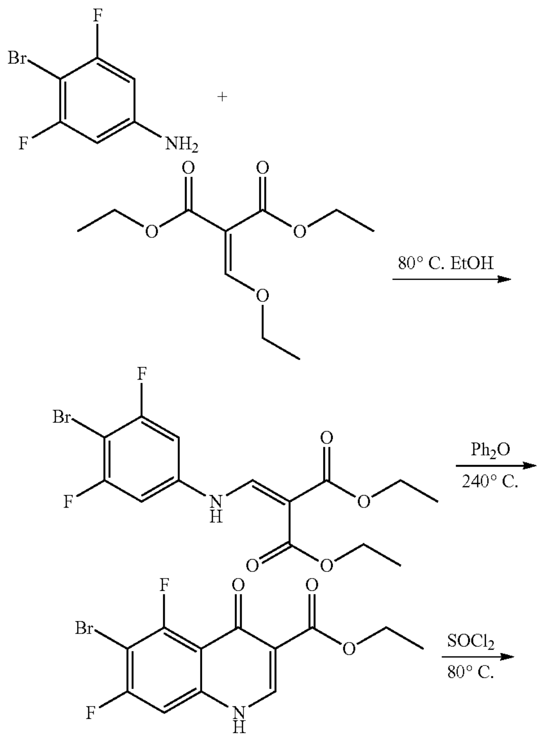

-continued

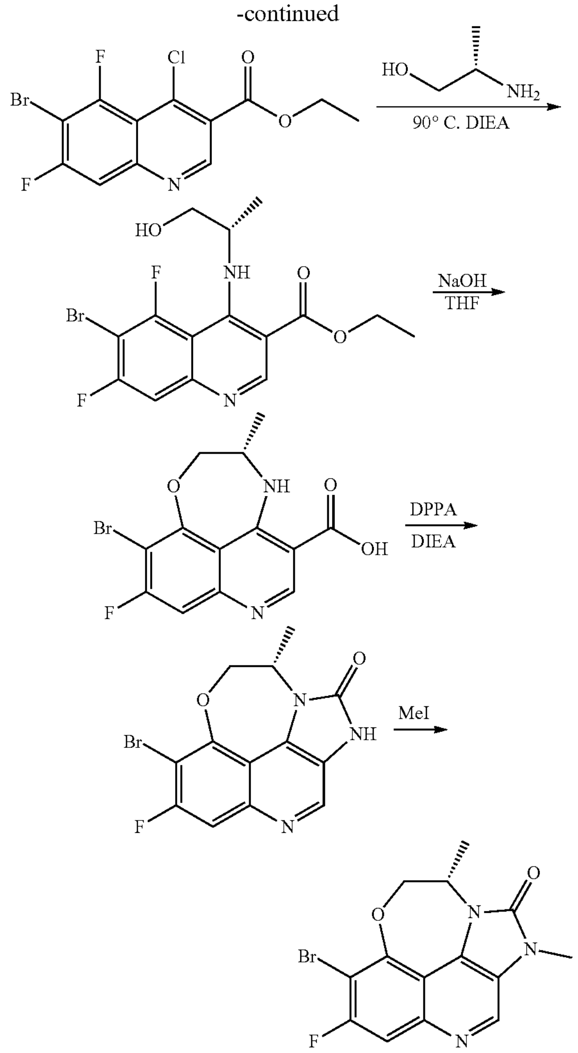

M-1

Step 1: Synthesis of diethyl 2-(((4-bromo-3,5-difluorophenyl)amino)methylene)malonate 4-bromo-3,5-difluoroaniline (5.00 g, 24 mmol), diethyl 2-(ethoxymethylene)malonate (7.80 g, 36 mmol), and anhydrous ethanol (50 mL) were added to a 250 mL reaction bottle. The reaction solution was heated to reflux for 8 h. When the reaction was completed as detected by thin-layer chromatography (TLC), the reaction solution was cooled down to 10° C. to precipitate a white solid, and then the solid was collected by suction filtration, rinsed with n-hexane, and dried to afford diethyl 2-(((4-bromo-3,5-difluorophenyl)amino)methylene)malonate (7.3 g, 80.3% yield). ESI-MS (m/z): 378.01/380.01 $[M+H]^+$; $^1H$ NMR (600 MHz, DMSO-$d_6$) δ: 1.236-1.269 (m, 6H), 4.137 (q, 2H), 4.216 (q, 2H), 7.483-7.506 (t, 2H), 8.308 (d, 1H), 10.613 (d, 1H).

Step 2: Synthesis of ethyl 6-bromo-5,7-difluoro-4-hydroxyquinoline-3-carboxylate Diphenyl ether (80 mL) was added to a 250 mL reaction bottle and heated up to 240° C., followed by adding diethyl 2-(((4-bromo-3,5-difluorophenyl)amino)methylene)malonate (7.30 g, 19.3 mmol) in batches. The reaction solution was reacted for 1 h at 240° C. When the reaction was completed as detected by TLC, the reaction solution was cooled down to 25° C. to precipitate a crystalline solid, the mixture was diluted with ether (80 mL), and the solid was collected by suction filtration, rinsed with n-hexane, and dried to afford ethyl 6-bromo-5,7-difluoro-4-hydroxyquinoline-3-carboxylate (5.50 g, 85.8% yield). ESI-MS (m/z): 331.97/333.96 $[M+H]^+$; $^1H$ NMR (600 MHz, DMSO-$d_6$) δ: 1.271 (t, 3H), 4.208 (q, 2H), 7.402 (d, 1H), 8.528 (s, 1H), 12.404 (s, 1H).

Step 3: Synthesis of ethyl 6-bromo-4-chloro-5,7-difluoroquinoline-3-carboxylate

Thionyl chloride (20 mL) and ethyl 6-bromo-5,7-difluoro-4-hydroxyquinoline-3-carboxylate (1.40 g, 4.2 mmol) were added to a 100 mL reaction bottle. The reaction solution was reacted for 3 h at 80° C. When the reaction was completed as detected by TLC, the reaction solution was cooled down and concentrated to dryness to afford a crude product of ethyl 6-bromo-4-chloro-5,7-difluoroquinoline-3-carboxylate (1.48 g, 100% yield). ESI-MS (m/z): 351.93 $[M+H]^+$.

Step 4: Synthesis of ethyl (S)-6-bromo-5,7-difluoro-4-((1-hydroxypropan-2-yl)amino)quinoline-3-carboxylate DMF (20 mL), ethyl 6-bromo-4-chloro-5,7-difluoroquinoline-3-carboxylate (1.48 g, 4.2 mmol), L-aminopropanol (0.47 g, 6.3 mmol), and DIEA (1.09 g, 8.4 mmol) were successively added to a 100 mL reaction bottle. The reaction solution was heated up to 90° C. to react for 3 h. When the reaction was completed as detected by TLC, the reaction solution was cooled down to room temperature followed by adding water to precipitate a solid, and then the solid was collected by suction filtration, rinsed with water, and dried to afford ethyl (S)-6-bromo-5,7-difluoro-4-((1-hydroxypropan-2-yl)amino)quinoline-3-carboxylate (1.2 g, 73.4% yield). ESI-MS (m/z): 389.02/391.02 $[M+H]^+$; $^1H$ NMR (600 MHz, $CDCl_3$) δ: 1.429 (t, 3H), 1.555 (d, 3H), 4.292-4.356 (m, 2H), 4.420 (q, 2H), 4.638 (d, 1H), 8.010 (s, 1H), 9.048 (s, 1H), 11.557 (s, 1H).

Step 5: Synthesis of (S)-10-bromo-9-fluoro-3-methyl-3,4-dihydro-2H-[1,4]oxazepino[5,6,7-de]quinoline-5-carboxylic acid Tetreahydrofuran (THF) (10 mL), ethyl (S)-6-bromo-5,7-difluoro-4-((1-hydroxypropan-2-yl)amino)quinoline-3-carboxylate (1.20 g, 3.08 mmol), water (5 mL) and sodium hydroxide (0.37 g, 9.24 mmol) were successively added to a 100 mL reaction bottle. The reaction solution was heated up to 60° C. to react for 3 h. When the reaction was completed as detected by TLC, the reaction solution was cooled down to room temperature followed by adjusting pH to 5 with 1N hydrochloric acid to precipitate a solid, and then the solid was collected by suction filtration, rinsed with water and dried to afford (S)-10-bromo-9-difluoro-3-methyl-3,4-dihydro-2H-[1,4]oxazepino[5,6,7-de]quinoline-5-carboxylic acid (0.8 g, 76.1% yield). ESI-MS (m/z): 340.99/342.98 $[M+H]^+$.

Step 6: Synthesis of (S)-7-bromo-6-fluoro-10-methyl-9,10-dihydro-8-oxa-2,4,10a-triazanaphtho[2,1,8-cde]azulen-1(2H)-one DMF (15 mL), (S)-10-bromo-9-fluoro-3-methyl-3,4-dihydro-2H-[1,4]oxazepino[5,6,7-de]quinoline-5-carboxylic acid (0.8 g, 2.35 mmol), DIEA (0.46 g, 3.53 mmol), and diphenyl azidophosphate (0.78 g, 2.82 mmol) were successively added to a 100 mL reaction bottle. The reaction solution was heated up to 60° C. to react for 3 h. When the reaction was completed as detected by TLC, the reaction solution was cooled down to room temperature followed by adding water to precipitate a solid, and then the solid was collected by suction filtration, rinsed with water, and dried to afford (S)-7-bromo-6-fluoro-10-methyl-9,10-dihydro-8-oxa-2,4,10a-triazanaphtho[2,1,8-cde]azulen-1(2H)-one (0.7 g, 88.1% yield). ESI-MS (m/z): 337.99/339.98 $[M+H]^+$; $^1H$ NMR (600 MHz, DMSO-$d_6$) δ: 1.443 (d, 3H), 4.593-4.616 (m, 2H), 4.803-4.829 (m, 1H), 7.594 (d, 1H), 8.678 (s, 1H), 11.681 (s, 1H).

Step 7: Synthesis of (S)-7-bromo-6-fluoro-2,10-dimethyl-9,10-dihydro-8-oxa-2,4,10a-triazanaphtho[2,1,8-cde]azulen-1(2H)-one (M-1)

DMF (15 mL) and (S)-7-bromo-6-fluoro-10-methyl-9,10-dihydro-8-oxa-2,4,10a-triazanaphtho[2,1,8-cde]azulen-1(2H)-one (0.7 g, 2.07 mmol) were successively added to a 100 mL reaction bottle and cooled down to 0° C. followed by adding NaH (0.124 g, 3.11 mmol), the reaction was conducted at this temperature for 0.5 h, then iodomethane (0.441 g, 3.11 mmol) was added and the reaction was continued overnight at room temperature. When the reaction was completed as detected by TLC, the reaction solution was added with water to precipitate a solid, and then the solid was collected by suction filtration, rinsed with water, and dried to afford (S)-7-bromo-6-fluoro-2,10-methyl-9,10-dihydro-8-oxa-2,4,10a-triazanaphtho[2,1,8-cde]azulen-1(2H)-one (0.62 g, 85.1% yield). ESI-MS (m/z): 352.00/354.00 $[M+H]^+$; $^1H$ NMR (600 MHz, DMSO-$d_6$) δ: 1.451 (d, 3H), 3.536 (s, 3H), 4.590-4.612 (m, 1H), 4.651-4.665 (m, 1H), 4.814-4.841 (m, 1H), 7.635 (d, 1H), 8.925 (s, 1H).

Intermediate Preparation Example 2: Preparation of (R)-7-bromo-6-fluoro-2,10-dimethyl-9,10-dihydro-8-oxa-2,4,10a-triazanaphtho[2,1,8-cde]azulen-1(2H)-one (M-2)

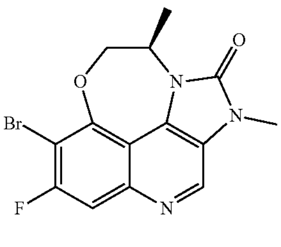 [SMILES: C[C@@H]1COc2c(Br)c(F)cc3ncc4c(c23)n1c(=O)n4C]

The synthesis method was the same as that of intermediate preparation example 1, except that D-aminopropanol was used instead of L-aminopropanol to afford (R)-7-bromo-6-fluoro-2,10-dimethyl-9,10-dihydro-8-oxa-2,4,10a-triazanaphtho[2,1,8-cde]azulen-1(2H)-one with a yield of 75.4%. ESI-MS (m/z): 352.20/354.19 $[M+H]^+$.

Intermediate Preparation Example 3: Preparation of 7-bromo-6-fluoro-9-(4-fluorophenyl)-2-methyl-9,10-dihydro-8-oxa-2,4,10a-triazanaphtho[2,1,8-cde]azulen-1(2H)-one (M-3)

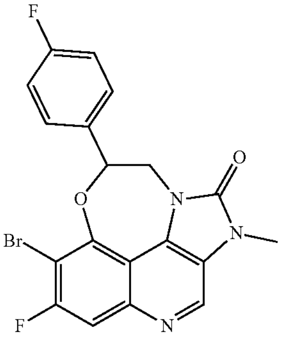 [SMILES: Cn1c(=O)n2c3c4c(c(Br)c(F)cc4ncc31)OC(c1ccc(F)cc1)C2]

The synthesis method was the same as that of intermediate preparation example 1, except that 2-amino-1-(4-fluorophenyl)ethanol was used instead of L-aminopropanol to afford 7-bromo-6-fluoro-9-(4-fluorophenyl)-2-methyl-9,10-dihydro-8-oxa-2,4,10a-triazanaphtho[2,1,8-cde]azulen-1(2H)-one with a yield of 82.4%. ESI-MS (m/z): 432.01/434.01 $[M+H]^+$.

Intermediate Preparation Example 4: Preparation of 7-bromo-6-fluoro-2,10,10-trimethyl-9,10-dihydro-8-oxa-2,4,10a-triazanaphtho[2,1,8-cde]azulen-1(2H)-one (M-4)

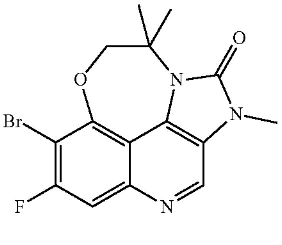 [SMILES: Cn1c(=O)n2c3c4c(c(Br)c(F)cc4ncc31)OCC2(C)C]

The synthesis method was the same as that of intermediate preparation example 1, except that 2-amino-2-methylpropanol was used instead of L-aminopropanol to afford 7-bromo-6-fluoro-2,10,10-trimethyl-9,10-dihydro-8-oxa-2,4,10a-triazanaphtho[2,1,8-cde]azulen-1(2H)-one with a yield of 82.4%. ESI-MS (m/z): 366.01/368.01 $[M+H]^+$.

Intermediate Preparation Example 5: Preparation of 7-bromo-6-fluoro-2-methyl-9-(pyridin-2-yl)-9,10-dihydro-8-oxa-2,4,10a-triazanaphtho[2,1,8-cde]azulen-1(2H)-one (M-5)

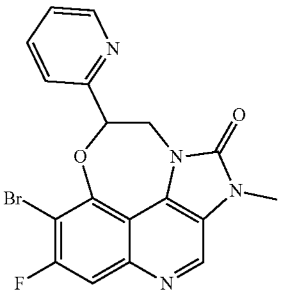 [SMILES: Cn1c(=O)n2c3c4c(c(Br)c(F)cc4ncc31)OC(c1ccccn1)C2]

The synthesis method was the same as that of intermediate preparation example 1, except that 2-amino-1-(pyridin-2-yl)ethanol was used instead of L-aminopropanol to afford 7-bromo-6-fluoro-2-methyl-9-(pyridin-2-yl)-9,10-dihydro-8-oxa-2,4,10a-triazanaphtho[2,1,8-cde]azulen-1(2H)-one. ESI-MS (m/z): 415.01/417.01 $[M+H]^+$.

Intermediate Preparation Example 6: Preparation of (R)-7-bromo-6-fluoro-10-isobutyl-2-methyl-9,10-dihydro-8-oxa-2,4,10a-triazanaphtho[2,1,8-cde]azulen-1(2H)-one (M-6)

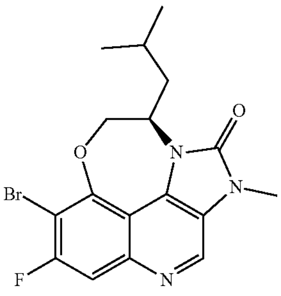 [SMILES: CC(C)C[C@@H]1COc2c(Br)c(F)cc3ncc4c(c23)n1c(=O)n4C]

The synthesis method was the same as that of intermediate preparation example 1, except that D-leucinol was used instead of L-aminopropanol to afford (R)-7-bromo-6-fluoro-10-isobutyl-2-methyl-9,10-dihydro-8-oxa-2,4,10a-triazanaphtho[2,1,8-cde]azulen-1(2H)-one with a yield of 30.9%. ESI-MS (m/z): 394.05/396.05 $[M+H]^+$.

Intermediate Preparation Example 7: Preparation of (S)-7-bromo-6-fluoro-10-isobutyl-2-methyl-9,10-dihydro-8-oxo-2,4,10a-triazanaphtho[2,1,8-cde]azulen-1(2H)-one (M-7)

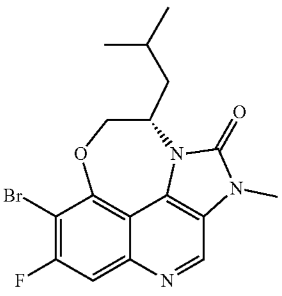 [SMILES: CC(C)C[C@H]1COc2c(Br)c(F)cc3ncc4c(c23)n1c(=O)n4C]

The synthesis method was the same as that of intermediate preparation example 1, except that L-leucinol was used instead of L-aminopropanol to afford (S)-7-bromo-6-fluoro-10-isobutyl-2-methyl-9,10-dihydro-8-oxo-2,4,10a-triazanaphtho[2,1,8-cde]azulen-1(2H)-one with a yield of 51.0%. ESI-MS (m/z): 393.92/395.87 $[M+H]^+$.

Intermediate Preparation Example 8: Preparation of 7-bromo-6-fluoro-2-methyl-9,10-dihydro-8-thia-2,4,10a-triazanaphtho[2,1,8-cde]azulen-1(2H)-one (M-8)

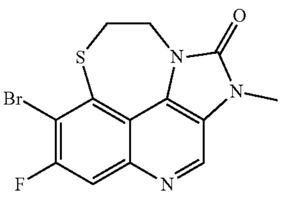 [SMILES: Cn1c(=O)n2c3c4c(c(Br)c(F)cc4ncc31)SCC2]

The synthesis method was the same as that of preparation example 1, except that mercaptoethylamine was used instead of L-aminopropanol to afford 7-bromo-6-fluoro-2-methyl-9,10-dihydro-8-thia-2,4,10a-triazanaphtho[2,1,8-cde]azulen-1(2H)-one with a yield of 82.1%. ESI-MS (m/z): 353.96/355.97 $[M+H]^+$.

Intermediate Preparation Example 9: Preparation of 7-bromo-6-fluoro-2-methyl-2,9-dihydro-1H-spiro[8-oxa-2,4,10a-triazanaphtho[2,1,8-cde]azulene-10,1-cyclopropan]-1-one (M-9)

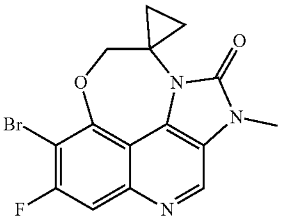 [SMILES: Cn1c(=O)n2c3c4c(c(Br)c(F)cc4ncc31)OCC21CC1]

The synthesis method was the same as that of intermediate preparation example 1, except that (1-aminocyclopropyl)

methanol was used instead of L-aminopropanol to afford 7-bromo-6-fluoro-2-methyl-2,9-dihydro-1H-spiro[8-oxa-2,4,10a-triazanaphtho[2,1,8-cde]azulene-10,1-cyclopropan]-1-one with a yield of 43.7%. ESI-MS (m/z): 364.01/366.01 $[M+H]^+$.

Intermediate Preparation Example 10: Preparation of 7-bromo-9-(ethoxymethyl)-6-fluoro-2-methyl-9,10-dihydro-8-oxa-2,4,10a-triazanaphtho[2,1,8-cde]azulen-1(2H)-one (M-10)

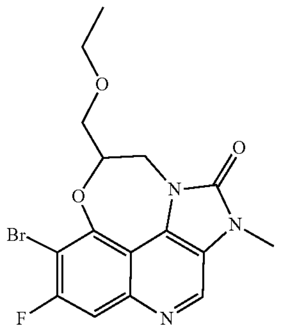 [SMILES: CCOCC1Cn2c(=O)n(C)c3cnc4cc(F)c(Br)c(c4c32)O1]

The synthesis method was the same as that of preparation example 1, except that 1-amino-3-ethoxypropan-2-ol was used instead of L-aminopropanol to afford 7-bromo-9-(ethoxymethyl)-6-fluoro-2-methyl-9,10-dihydro-8-oxa-2,4,10a-triazanaphtho[2,1,8-cde]azulen-1(2H)-one with a yield of 49.3%. ESI-MS (m/z): 396.03/398.03 $[M+H]^+$.

Intermediate Preparation Example 11: Preparation of (S)-10-benzyl-7-bromo-6-fluoro-2-methyl-9,10-dihydro-8-oxa-2,4,10a-triazanaphtho[2,1,8-cde]azulen-1(2H)-one (M-11)

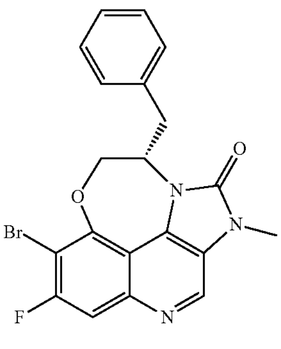 [SMILES: Cn1c(=O)n2c3c4c(c(Br)c(F)cc4ncc31)OC[C@@H]2Cc1ccccc1]

The synthesis method was the same as that of preparation example 1, except that (S)-2-amino-3-phenylpropan-1-ol was used instead of L-aminopropanol to afford (S)-10-benzyl-7-bromo-6-fluoro-2-methyl-9,10-dihydro-8-oxa-2,4,10a-triazanaphtho[2,1,8-cde]azulen-1(2H)-one with a yield of 53.2%. ESI-MS (m/z): 428.03/430.03 $[M+H]^+$.

Intermediate Preparation Example 12: Preparation of (R)-10-benzyl-7-bromo-6-fluoro-2-methyl-9,10-dihydro-8-oxa-2,4,10a-triazanaphtho[2,1,8-cde]azulen-1(2H)-one (M-12)

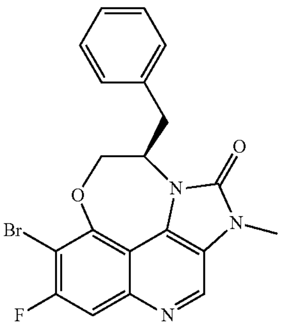 [SMILES: Cn1c(=O)n2c3c4c(c(Br)c(F)cc4ncc31)OC[C@H]2Cc1ccccc1]

The synthesis method was the same as that of preparation example 1, except that (R)-2-amino-3-phenylpropan-1-ol was used instead of L-aminopropanol to afford (R)-10-benzyl-7-bromo-6-fluoro-2-methyl-9,10-dihydro-8-oxa-2,4,10a-triazanaphtho[2,1,8-cde]azulen-1(2H)-one with a yield of 32.6%. ESI-MS (m/z): 428.03/430.03 $[M+H]^+$.

Intermediate Preparation Example 13: Preparation of 7-bromo-6-fluoro-2-methyl-9,10-dihydro-8-oxa-2,4,10a-triazanaphtho[2,1,8-cde]azulen-1(2H)-one (M-13)

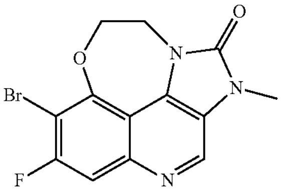 [SMILES: Cn1c(=O)n2c3c4c(c(Br)c(F)cc4ncc31)OCC2]

The synthesis method was the same as that of intermediate preparation example 1, except that 2-aminoethanol was used instead of L-aminopropanol to afford 7-bromo-6-fluoro-2-methyl-9,10-dihydro-8-oxa-2,4,10a-triazanaphtho[2,1,8-cde]azulen-1(2H)-one with a yield of 40.7%. ESI-MS (m/z): 337.99/339.99 $[M+H]^+$.

Intermediate Preparation Example 14: Preparation of (S)-7-bromo-6-fluoro-10-isopropyl-2-methyl-9,10-dihydro-8-oxa-2,4,10a-triazanaphtho[2,1,8-cde]azulen-1(2H)-one (M-14)

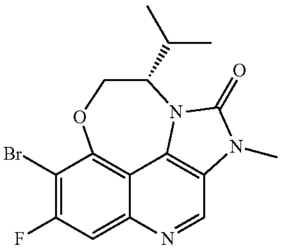 [SMILES: CC(C)[C@H]1COc2c(Br)c(F)cc3ncc4c(c23)n1c(=O)n4C]

The synthesis method was the same as that of intermediate preparation example 1, except that L-valinol was used instead of L-aminopropanol to afford (S)-7-bromo-6-fluoro-10-isopropyl-2-methyl-9,10-dihydro-8-oxa-2,4,10a-triazanaphtho[2,1,8-cde]azulen-1(2H)-one with a yield of 52.3%. ESI-MS (m/z): 380.03/382.03 $[M+H]^+$.

Intermediate Preparation Example 15: Preparation of (R)-7-bromo-6-fluoro-10-isopropyl-2-methyl-9,10-dihydro-8-oxa-2,4,10a-triazanaphtho[2,1,8-cde]azulen-1(2H)-one (M-15)

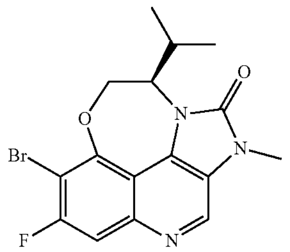 [SMILES: CC(C)[C@@H]1COc2c(Br)c(F)cc3ncc4c(c23)n1c(=O)n4C]

The synthesis method was the same as that of intermediate preparation example 1, except that D-valinol was used instead of L-aminopropanol to afford (R)-7-bromo-6-fluoro-10-isopropyl-2-methyl-9,10-dihydro-8-oxa-2,4,10a-triazanaphtho[2,1,8-cde]azulen-1(2H)-one with a yield of 59.3%. ESI-MS (m/z): 380.03/382.03 $[M+H]^+$.

Intermediate Preparation Example 16: Preparation of 7-bromo-6-fluoro-9-isopropyl-2-methyl-9,10-dihydro-8-oxa-2,4,10a-triazanaphtho[2,1,8-cde]azulen-1(2H)-one (M-16)

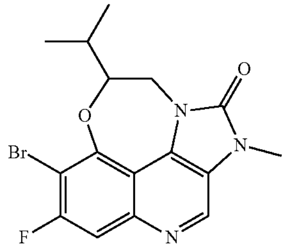 [SMILES: CC(C)C1Cn2c(=O)n(C)c3cnc4cc(F)c(Br)c(c4c32)O1]

The synthesis method was the same as that of intermediate preparation example 1, except that 1-amino-3-methylbutan-2-ol was used instead of L-aminopropanol to afford 7-bromo-6-fluoro-9-isopropyl-2-methyl-9,10-dihydro-8-oxa-2,4,10a-triazanaphtho[2,1,8-cde]azulen-1(2H)-one with a yield of 30.6%. ESI-MS (m/z): 380.03/382.03 $[M+H]^+$.

Intermediate Preparation Example 17: Preparation of (S)-7-bromo-9-((dimethylamino)methyl)-6-fluoro-2-methyl-9,10-dihydro-8-oxa-2,4,10a-triazanaphtho[2,1,8-cde]azulen-1(2H)-one (M-17)

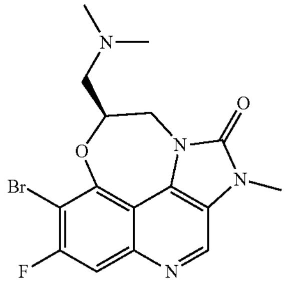 [SMILES: CN(C)C[C@H]1Cn2c(=O)n(C)c3cnc4cc(F)c(Br)c(c4c32)O1]

The synthesis method was the same as that of preparation example 1, except that (R)-1-amino-3-(dimethylamino)propan-2-ol was used instead of L-aminopropanol to afford (S)-7-bromo-9-((dimethylamino)methyl)-6-fluoro-2-methyl-9,10-dihydro-8-oxa-2,4,10a-triazanaphtho[2,1,8-cde]azulen-1(2H)-one with a yield of 75.5%. ESI-MS (m/z): 395.04/397.04 $[M+H]^+$.

Intermediate Preparation Example 18: Preparation of (S)-7-bromo-6-fluoro-2-methyl-9-(piperidin-1-ylmethyl)-9,10-dihydro-8-oxa-2,4,10a-triazanaphtho[2,1,8-cde]azulen-1(2H)-one (M-18)

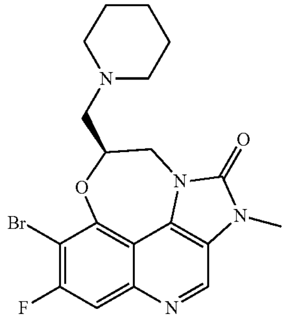 [SMILES: Cn1c(=O)n2c3c4c(c(Br)c(F)cc4ncc31)O[C@@H](CN1CCCCC1)C2]

The synthesis method was the same as that of intermediate preparation example 1, except that (R)-1-amino-3-(piperidin-1-yl)propan-2-ol was used instead of L-aminopropanol to afford (S)-7-bromo-6-fluoro-2-methyl-9-(piperidin-1-ylmethyl)-9,10-dihydro-8-oxa-2,4,10a-triazanaphtho[2,1,8-cde]azulen-1(2H)-one with a yield of 72.1%. ESI-MS (m/z): 435.08/437.08 $[M+H]^+$.

Intermediate Preparation Example 19: Preparation of 5-bromo-4-fluoro-12-methyl-6a,7,8,9,10,10a-hexahydro-6-oxa-2,10b,12-triazacyclopenta[gh]pleiaden-11(12H)-one (M-19)

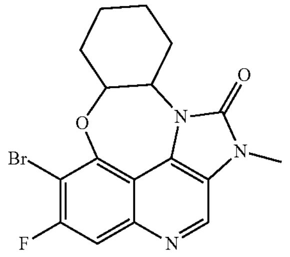 [SMILES: Cn1c(=O)n2c3c4c(c(Br)c(F)cc4ncc31)OC1CCCCC12]

The synthesis method was the same as that of preparation example 1, except that 2-aminocyclohexanol was used instead of L-aminopropanol to afford 5-bromo-4-fluoro-12-methyl-6a,7,8,9,10,10a-hexahydro-6-oxa-2,10b,12-triazacyclopenta[gh]pleiaden-11(12H)-one with a yield of 68.5%. ESI-MS (m/z): 392.03/394.03 $[M+H]^+$.

Intermediate Preparation Example 20: Preparation of (R)-7-bromo-10-ethyl-6-fluoro-2-methyl-9,10-dihydro-8-oxa-2,4,10a-triazanaphtho[2,1,8-cde]azulen-1(2H)-one (M-20)

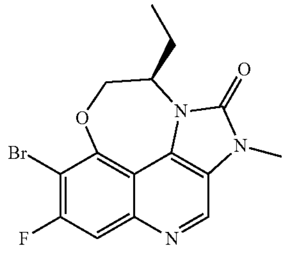 [SMILES: CC[C@@H]1COc2c(Br)c(F)cc3ncc4c(c23)n1c(=O)n4C]

The synthesis method was the same as that of intermediate preparation example 1, except that (R)-2-aminobutan-1-ol was used instead of L-aminopropanol to afford (R)-7-bromo-10-ethyl-6-fluoro-2-methyl-9,10-dihydro-8-oxa-2,4,10a-triazanaphtho[2,1,8-cde]azulen-1(2H)-one with a yield of 71.5%. ESI-MS (m/z): 366.02/368.02 $[M+H]^+$.

Intermediate Preparation Example 21: Preparation of (S)-7-bromo-10-ethyl-6-fluoro-2-methyl-9,10-dihydro-8-oxa-2,4,10a-triazanaphtho[2,1,8-cde]azulen-1(2H)-one (M-21)

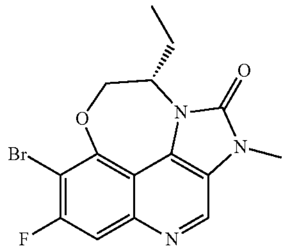 [SMILES: CC[C@H]1COc2c(Br)c(F)cc3ncc4c(c23)n1c(=O)n4C]

The synthesis method was the same as that of intermediate preparation example 1, except that (S)-2-aminobutan-1-ol was used instead of L-aminopropanol to afford (S)-7-bromo-10-ethyl-6-fluoro-2-methyl-9,10-dihydro-8-oxa-2,4,10a-triazanaphtho[2,1,8-cde]azulen-1(2H)-one with a yield of 68.5%. ESI-MS (m/z): 366.02/368.02 $[M+H]^+$.

Intermediate Preparation Example 22: Preparation of 7-bromo-6-fluoro-2,9-dimethyl-9,10-dihydro-8-oxa-2,4,10a-triazanaphtho[2,1,8-cde]azulen-1(2H)-one (M-22)

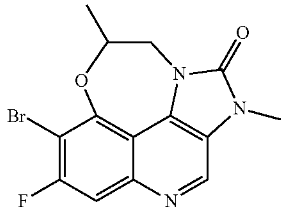 [SMILES: CC1COc2c(Br)c(F)cc3ncc4c(c23)n(c(=O)n4C)C1]

The synthesis method was the same as that of intermediate preparation example 1, except that 1-aminopropan-2-ol was used instead of L-aminopropanol to afford 7-bromo-6-fluoro-2,9-dimethyl-9,10-dihydro-8-oxa-2,4,10a-triazanaphtho[2,1,8-cde]azulen-1(2H)-one with a yield of 82.4%. ESI-MS (m/z): 352.00/354.00 $[M+H]^+$.

Intermediate Preparation Example 23: Preparation of 7-bromo-6-fluoro-9-(2-fluoropyridin-4-yl)-2-methyl-9,10-dihydro-8-oxa-2,4,10a-triazanaphtho[2,1,8-cde]azulen-1(2H)-one (M-23)

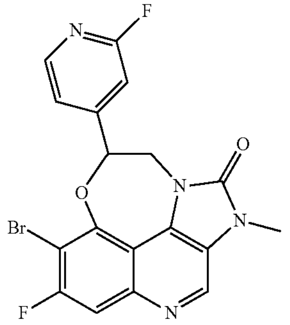 [SMILES: Cn1c(=O)n2c3c4c(c(Br)c(F)cc4ncc31)OCC(c1ccnc(F)c1)C2]

The synthesis method was the same as that of intermediate preparation example 1, except that 2-amino-1-(2-fluoropyridin-4-yl)ethanol was used instead of L-aminopropanol to afford 7-bromo-6-fluoro-9-(2-fluoropyridin-4-yl)-2-methyl-9,10-dihydro-8-oxa-2,4,10a-triazanaphtho[2,1,8-cde]azulen-1(2H)-one with a yield of 32.5%. ESI-MS (m/z): 433.00/435.00 $[M+H]^+$.

Intermediate Preparation Example 24: Preparation of 7-bromo-10-cyclopropyl-6-fluoro-2-methyl-9,10-dihydro-8-oxa-2,4,10a-triazanaphtho[2,1,8-cde]azulen-1(2H)-one (M-24)

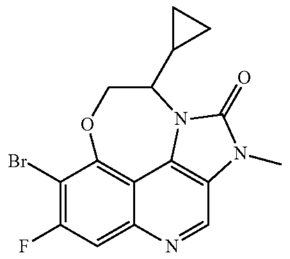 [SMILES: Cn1c(=O)n2c3c4c(c(Br)c(F)cc4ncc31)OCC2C1CC1]

The synthesis method was the same as that of intermediate preparation example 1, except that 2-amino-2-cyclopropylethanol was used instead of L-aminopropanol to afford 7-bromo-10-cyclopropyl-6-fluoro-2-methyl-9,10-dihydro-8-oxa-2,4,10a-triazanaphtho[2,1,8-cde]azulen-1(2H)-one with a yield of 28.4%. ESI-MS (m/z): 378.02/380.02 $[M+H]^+$.

Intermediate Preparation Example 25: Preparation of 7-bromo-6-fluoro-2-methyl-2,9-dihydro-1H-spiro[8-oxa-2,4,10a-triazanaphtho[2,1,8-cde]azulene-10,1'-cyclobutan]-1-one (M-25)

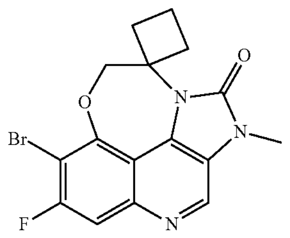 [SMILES: Cn1c(=O)n2c3c4c(c(Br)c(F)cc4ncc31)OCC21CCC1]

The synthesis method was the same as that of intermediate preparation example 1, except that (1-aminocyclobutyl)methanol was used instead of L-aminopropanol to afford 7-bromo-6-fluoro-2-methyl-2,9-dihydro-1H-spiro[8-oxa-2,4,10a-triazanaphtho[2,1,8-cde]azulene-10,1'-cyclobutan]-1-one with a yield of 37.5%. ESI-MS (m/z): 377.93/379.95 $[M+H]^+$.

Intermediate Preparation Example 26: Preparation of ethyl (6aR,10aS)-5-bromo-4-fluoro-12-methyl-11-oxo-6a,7,10,10a,11,12-hexahydro-6-oxa-2,8,10b,12-tetraazacyclopentadiene-8(9H)-carboxylate (M-26)

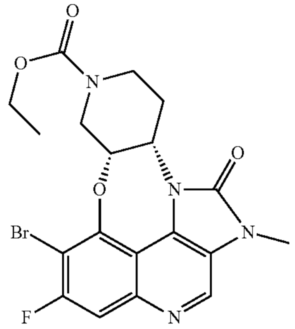 [SMILES: CCOC(=O)N1CC[C@H]2[C@@H](C1)Oc1c(Br)c(F)cc3ncc4c(c13)n2c(=O)n4C]

The synthesis method was the same as that of intermediate preparation example 1, except that ethyl (3S,4R)-4-amino-3-hydroxypiperidin-1-carboxylate was used instead of L-aminopropanol to afford ethyl (6aR,10aS)-5-bromo-4-fluoro-12-methyl-11-oxo-6a,7,10,10a,11,12-hexahydro-6-oxa-2,8,10b,12-tetraazacyclopentadiene-8(9H)-carboxylate with a yield of 37.5%. ESI-MS (m/z): 464.93/466.95 $[M+H]^+$.

Intermediate Preparation Example 27: Preparation of 7-bromo-6-fluoro-10-(4-fluorophenyl)-2-methyl-9,10-dihydro-8-oxa-2,4,10a-triazanaphtho[2,1,8-cde]azulen-1(2H)-one (M-27)

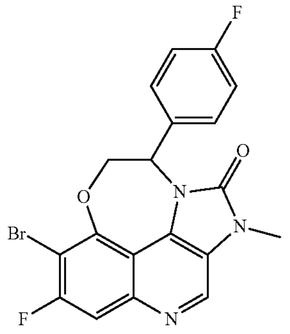 [SMILES: Cn1c(=O)n2c3c4c(c(Br)c(F)cc4ncc31)OCC2c1ccc(F)cc1]

The synthesis method was the same as that of intermediate preparation example 1, except that 2-amino-2-(4-fluorophenyl)ethanol was used instead of L-aminopropanol to afford 7-bromo-6-fluoro-10-(4-fluorophenyl)-2-methyl-9,10-dihydro-8-oxa-2,4,10a-triazanaphtho[2,1,8-cde]azulen-1(2H)-one (100 mg, 32% yield). ESI-MS (m/z): 432.21/434.25 $[M+H]^+$.

Intermediate Preparation Example 28: Preparation of 7-bromo-6-methoxy-2-methyl-10-(pyridin-2-yl)-9,10-dihydro-8-oxa-2,4,10a-triazanaphtho[2,1,8-cde]azulen-1(2H)-one (M-28)

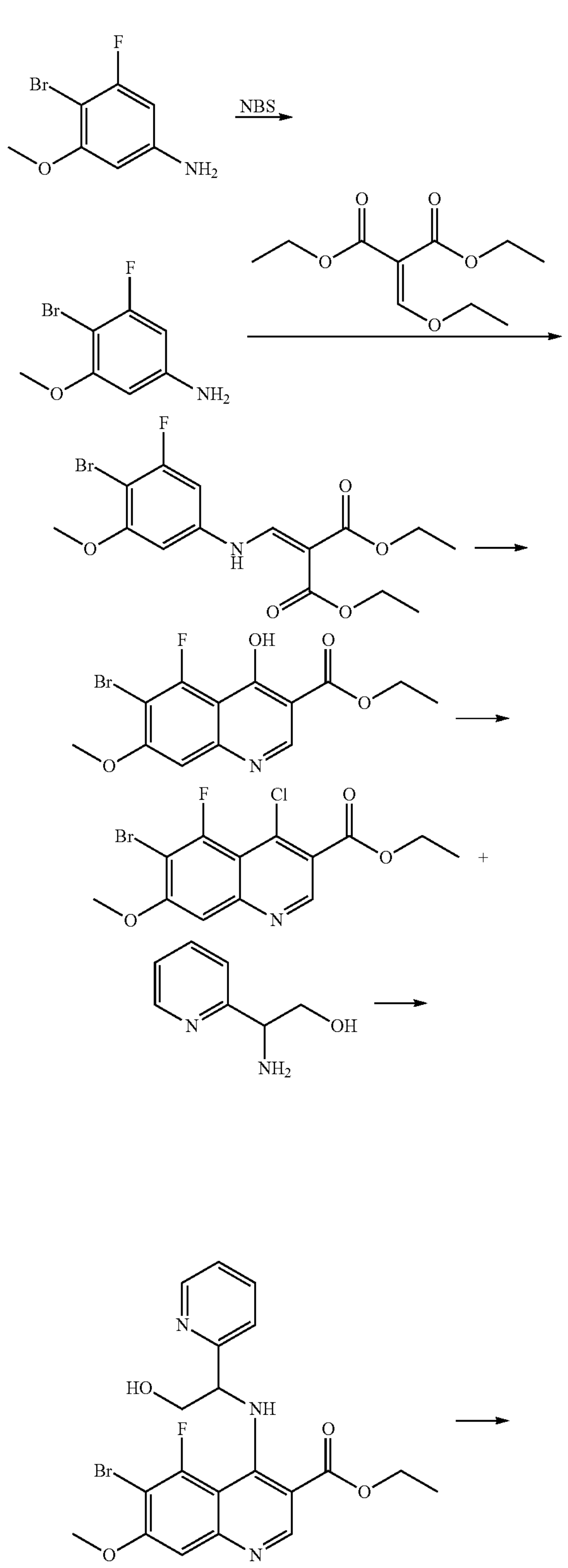

-continued

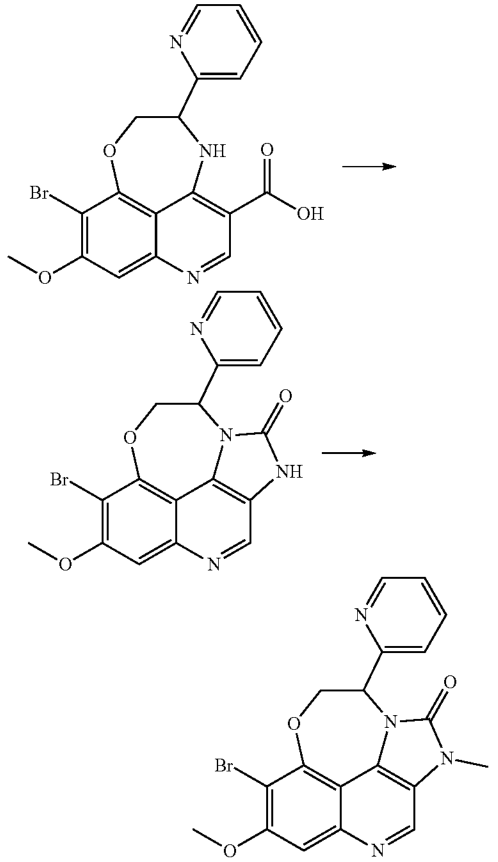

Step 1: Synthesis of 4-bromo-3-fluoro-5-methoxyaniline 3-fluoro-5-methoxyaniline (4.1 g, 29.1 mmol) and DMF (50 mL) were successively added to a 250 mL reaction bottle, followed by adding N-bromosuccinimide (NBS) (5.2 g, 29.1 mmol) in batches at room temperature, and the reaction solution was reacted at room temperature for 1 h. After the reaction solution was cooled down, 100 mL of water and 100 mL of ethyl acetate were added into the reaction solution, the target product was extracted into the organic phase, and the organic phase was separated and concentrated to dryness, and then the residue was purified by column chromatography (PE:EA=10:1-2:1) to afford 4-bromo-3-fluoro-5-methoxyaniline (4.90 g). ESI-MS (m/z): 219.98/222.01 $[M+H]^+$.

Step 2: Synthesis of diethyl 2-(((4-bromo-3-fluoro-5-methoxyphenyl)amino)methylene)malonate 4-bromo-3-fluoro-5-methoxyaniline (4.8 g, 21.8 mmol), diethyl 2-(ethoxymethylene)malonate (7.0 g, 32.4 mmol), and 50 mL of anhydrous ethanol were successively added to a 250 mL reaction bottle. The reaction solution was heated to reflux and reacted for 6 h, then cooled down to room temperature and added with 100 mL of n-hexane at room temperature, and then the reaction mixture was filtrated to afford diethyl 2-(((4-bromo-3-fluoro-5-methoxyphenyl)amino)methylene)malonate (5.9 g). ESI-MS (m/z): 390.20/392.18 $[M+H]^+$.

Step 3: Synthesis of ethyl 6-bromo-5-fluoro-4-hydroxy-7-methoxyquinoline-3-carboxylate 40 mL of diphenyl ether was added to a 250 mL reaction bottle and heated up to 240° C., followed by adding diethyl 2-(((4-bromo-3-fluoro-5-methoxyphenyl)amino)methylene) malonate (5.9 g, 15.1 mmol) in batches. The reaction solution was reacted at this temperature for 1 h, then cooled down to room temperature and added with 100 mL of n-hexane at room temperature, and then the reaction mixture was filtrated to afford ethyl 6-bromo-5-fluoro-4-hydroxy-7-methoxyquinoline-3-carboxylate (4.6 g). ESI-MS (m/z): 344.14/346.18 $[M+H]^+$.

Step 4: Synthesis of ethyl 6-bromo-4-chloro-5-fluoro-7-methoxyquinoline-3-carboxylate Ethyl 6-bromo-5-fluoro-4-hydroxy-7-methoxyquinolin-3-carboxylate (800 mg, 2.32 mmol) and thionyl chloride (10 mL) were added to a 100 mL reaction bottle, and added dropwise with DMF (two drops). After refluxing for 4 h, the reaction was completed, and the concentration under reduced pressure was carried out to dryness to afford ethyl 6-bromo-4-chloro-5-fluoro-7-methoxyquinoline-3-carboxylate (840 mg). ESI-MS (m/z): 361.91/363.99 $[M+H]^+$.

Step 5: Synthesis of ethyl 6-bromo-5-fluoro-4-((2-hydroxy-1-(pyridin-2-yl)ethyl)amino)-7-methoxyquinoline-3-carboxylate Ethyl 6-bromo-4-chloro-5-fluoro-7-methoxyquinoline-3-carboxylate (840 mg, 2.32 mmol), DMF (10 mL), DIPEA (1500 mg, 11.6 mmol), and 2-amino-2-(pyridin-2-yl)ethanol (600 mg, 2.84 mmol) were successively added to a 100 mL reaction bottle. The reaction solution was heated up to 90° C. to react for 2 h. When the reaction was completed as detected by TLC, the reaction solution was cooled down to room temperature, added with water, and then filtrated, and the filter cake was dried to afford ethyl 6-bromo-5-fluoro-4-((2-hydroxy-1-(pyridin-2-yl)ethyl)amino)-7-methoxyquinoline-3-carboxylate (1.1 g). ESI-MS (m/z): 464.29/466.30 $[M+H]^+$.

Step 6: Synthesis of 10-bromo-9-methoxy-3-(pyridin-2-yl)-3,4-dihydro-2H-[1,4]oxazepino[5,6,7-de] quinoline-5-carboxylic acid Ethyl 6-bromo-5-fluoro-4-((2-hydroxy-1-(pyridin-2-yl) ethyl)amino)-7-methoxyquinoline-3-carboxylate (1100 mg, 2.37 mmol), THF (10 mL), water (5 mL), and sodium hydroxide (520 mg, 13.0 mmol) were added to a 100 mL reaction bottle. The reaction solution was heated up to 60° C. to react for 8 h. When the reaction was completed, THF was removed under reduced pressure, the pH value was adjusted to 3 with 6N hydrochloric acid, and filtration was carried out to afford 10-bromo-9-methoxy-3-(pyridin-2-yl)-3,4-dihydro-2H-[1,4]oxazepino[5,6,7-de]quinoline-5-carboxylic acid (0.3 g). ESI-MS (m/z): 416.19/418.20 $[M+H]^+$.

Step 7: Synthesis of 7-bromo-6-methoxy-10-(pyridin-2-yl)-9,10-dihydro-8-oxa-2,4,10a-triazanaphtho [2,1,8-cde]azulen-1(2H)-one 10-bromo-9-methoxy-3-(pyridin-2-yl)-3,4-dihydro-2H-[1,4]oxazepino[5,6,7-de]quinoline-5-carboxylic acid (300 mg, 0.72 mmol), DMF (10 mL), triethylamine (150 mg, 1.48 mmol), and DPPA (300 mg, 1.09 mmol) were successively added to a 100 mL reaction bottle. The reaction solution was heated up to 90° C. to react for 2 h. When the reaction was completed as detected by TLC, the reaction solution was cooled down to room temperature followed by adding water to precipitate a solid, and then the solid was filtrated to afford 7-bromo-6-methoxy-10-(pyridin-2-yl)-9,10-dihydro-8-oxa-2,4,10a-triazanaphtho[2,1,8-cde]azulen-1(2H)-one (0.3 g). ESI-MS (m/z): 412.19/414.23 $[M+H]^+$.

Step 8: Synthesis of 7-bromo-6-methoxy-2-methyl-10-(pyridin-2-yl)-9,10-dihydro-8-oxa-2,4,10a-triazanaphtho[2,1,8-cde]azulen-1(2H)-one 7-bromo-6-methoxy-10-(pyridin-2-yl)-9,10-dihydro-8-oxa-2,4,10a-triazanaphtho[2,1,8-cde]azulen-1(2H)-one (300 mg, 0.72 mmol), cesium carbonate (474 mg, 1.45 mmol), and DMF (10 mL) were successively added to a reaction bottle, followed by adding iodomethane (155 mg, 1.10 mmol) at room temperature, and the reaction solution was reacted for 1.5 h at room temperature. When the reaction was completed as detected by TLC, the reaction solution was cooled down to room temperature followed by adding water to precipitate a solid, and the solid was filtrated to afford 7-bromo-6-methoxy-2-methyl-10-(pyridin-2-yl)-9,10-dihydro-8-oxa-2,4,10a-triazanaphtho[2,1,8-cde]azulen-1 (2H)-one (0.2 g) with a yield of 64.5%. ESI-MS (m/z): 427.03/429.03 $[M+H]^+$.

Intermediate Preparation Example 29: Preparation of (S)-7-bromo-6-methoxy-2,10-dimethyl-9,10-dihydro-8-oxa-2,4,10a-triazanaphtho[2,1,8-cde]azulen-1(2H)-one (M-29)

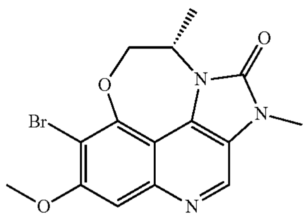

The synthesis method was the same as that of intermediate preparation example 1, except that 4-bromo-3-fluoro-5-methoxyaniline was used instead of 4-bromo-3,5-difluoroaniline to afford (S)-7-bromo-6-methoxy-2,10-dimethyl-9,10-dihydro-8-oxa-2,4,10a-triazanaphtho[2,1,8-cde]azulen-1 (2H)-one with a yield of 82.4%. ESI-MS (m/z): 364.02/366.02 $[M+H]^+$.

Intermediate Preparation Example 30: Preparation of (R)-7-bromo-6-methoxy-2,10-dimethyl-9,10-dihydro-8-oxa-2,4,10a-triazanaphtho[2,1,8-cde]azulen-1(2H)-one (M-30)

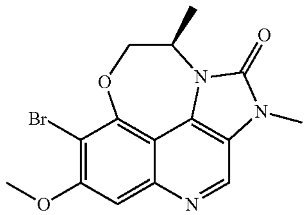

The synthesis method was the same as that of intermediate preparation example 1, except that 4-bromo-3-fluoro-5-methoxyaniline was used instead of 4-bromo-3,5-difluoroaniline, and (R)-2-aminopropan-1-ol was used instead of (S)-2-aminopropan-1-ol, to afford (R)-7-bromo-6-methoxy-2,10-dimethyl-9,10-dihydro-8-oxa-2,4,10a-triazanaphtho[2,1,8-cde]azulen-1(2H)-one with a yield of 82.4%. ESI-MS (m/z): 364.02/366.02 $[M+H]^+$.

Intermediate Preparation Example 31: Preparation of 5-bromo-4-methoxy-12-methyl-6-oxa-2,10b,12-triazacyclopenta[gh]pleiaden-11(12H)-one (M-31)

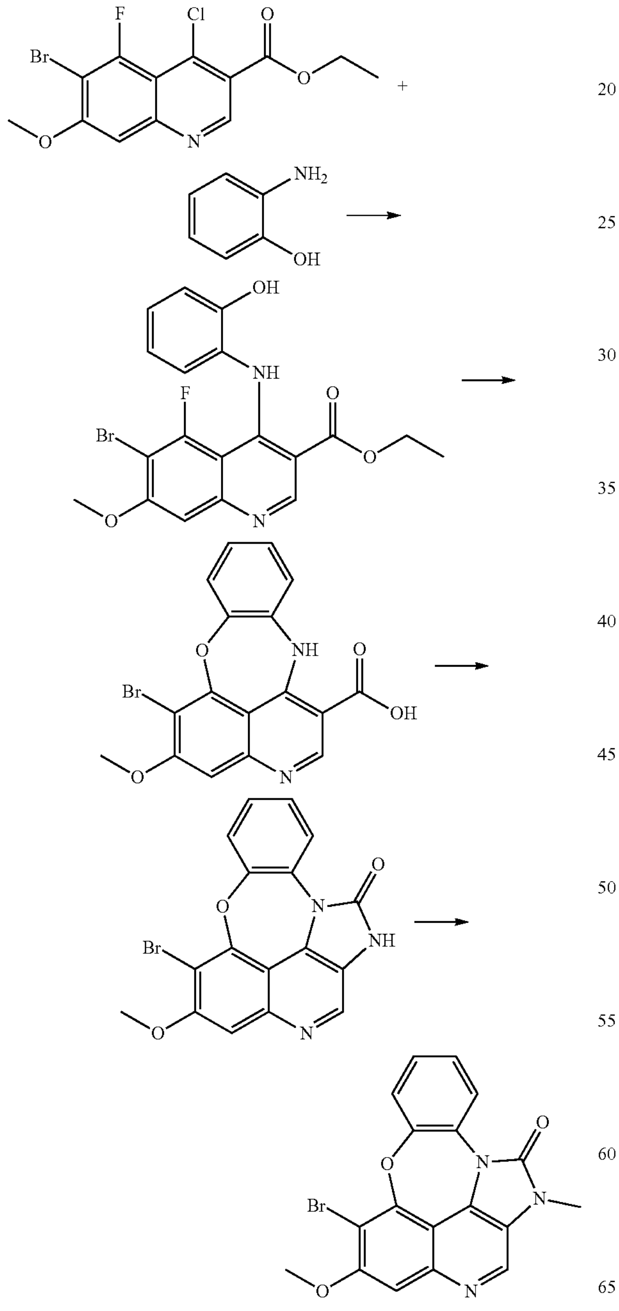

Step 1: Synthesis of ethyl 6-bromo-5-fluoro-4-((2-hydroxyphenyl)amino)-7-methoxyquinoline-3-carboxylate Ethyl 6-bromo-4-chloro-5-fluoro-7-methoxyquinoline-3-carboxylate (840 mg, 2.32 mmol), 2-aminophenol (280 mg, 2.57 mmol), and glacial acetic acid (10 mL) were successively added to a 100 mL reaction bottle. The reaction solution was heated up to 60° C. to react for 1 h. When the reaction was completed as detected by TLC, the reaction solution was cooled down to room temperature and added with water and ethyl acetate. Then the organic phase was separated, washed twice with saturated sodium bicarbonate, and concentrated to dryness under reduced pressure to afford ethyl 6-bromo-5-fluoro-4-((2-hydroxyphenyl)amino)-7-methoxyquinoline-3-carboxylate (1.0 g).

Step 2: Synthesis of 6-bromo-5-methoxy-12H-benzo[2,3][1,4]oxazepino[5,6,7-de]quinoline-1-carboxylic acid Ethyl 6-bromo-5-fluoro-4-((2-hydroxyphenyl)amino)-7-methoxyquinoline-3-carboxylate (1000 mg, 2.30 mmol), THF (10 mL), water (5 mL), and sodium hydroxide (460 mg, 11.5 mmol) were added to a 100 mL reaction bottle. The reaction solution was heated up to 60° C. to react for 8 h. After the reaction was completed, THF was removed under reduced pressure, the pH value was adjusted to 3 with 6N hydrochloric acid, and filtration was carried out to afford 6-bromo-5-methoxy-12H-benzo[2,3][1,4]oxazepino[5,6,7-de]quinoline-1-carboxylic acid (0.86 g).

Step 3: Synthesis of 5-bromo-4-methoxy-6-oxa-2,10b,12-triazacyclopenta[gh]pleiaden-11(12H)-one 6-bromo-5-methoxy-12H-benzo[2,3][1,4]oxazepino [5,6,7-de]quinoline-1-carboxylic acid (860 mg, 2.22 mmol), DMF (10 ml), triethylamine (450 mg, 4.45 mmol), and DPPA (917 mg, 3.33 mmol) were successively added to a 100 mL reaction bottle. The reaction solution was heated up to 90° C. to react for 2 h. When the reaction was completed as detected by TLC, the reaction solution was cooled down to room temperature followed by adding water to precipitate a solid, and then the solid was filtrated to afford 5-bromo-4-methoxy-6-oxa-2,10b,12-triazacyclopenta[gh]pleiaden-11(12H)-one (0.84 g).

Step 4: Synthesis of 5-bromo-4-methoxy-12-methyl-6-oxa-2,10b,12-triazacyclopenta[gh]pleiaden-11(12H)-one 5-bromo-4-methoxy-6-oxa-2,10b,12-triazacyclopenta [gh]pleiaden-11(12H)-one (840 mg, 2.19 mmol), cesium carbonate (1420 mg, 4.36 mmol), and DMF (10 ml) were successively added to a reaction bottle, followed by adding iodomethane (466 mg, 3.28 mmol) dropwise at room temperature, then the reaction solution was reacted for 1.5 h at room temperature. When the reaction was completed as detected by TLC, the reaction solution was added with water to precipitate a solid, and then the solid was filtrated to afford 5-bromo-4-methoxy-12-methyl-6-oxa-2,10b,12-triazacyclopenta[gh]pleiaden-11(12H)-one (0.76 g, 87.3% yield). ESI-MS (m/z): 398.01/400.01 $[M+H]^+$.

Intermediate Preparation Example 32: Preparation of 5-bromo-4-methoxy-12-methyl-6-oxa-2,9,10b,12-tetraazacyclopenta[gh]pleiaden-11(12H)-one (M-32)

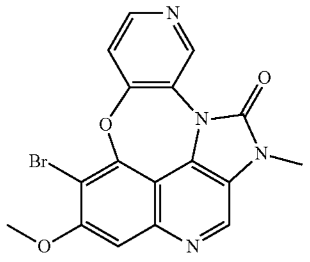

The synthesis method was the same as that of intermediate preparation example 31, except that 3-amino-4-hydroxypyridine was used instead of 2-aminophenol to afford 5-bromo-4-methoxy-12-methyl-6-oxa-2,9,10b,12-tetraazacyclopenta[gh]pleiaden-11(12H)-one with a yield of 27.3%. ESI-MS (m/z): 398.99/400.96 $[M+H]^+$.

Intermediate Preparation Example 33: Preparation of (6aS,9aR)-5-(6-bromopyridin-3-yl)-4-fluoro-11-methyl-6a,7,9,9a-tetrahydro-6,8-dioxa-2,9b,11-triazacyclopenta[h]naphtho[2,1,8-cde]azulen-10(11H)-one (M-33)

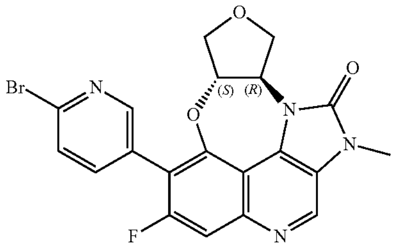

The synthesis method was the same as that of intermediate preparation example 1, except that (3 S,4R)-4-aminotetrahydrofuran-3-ol was used instead of L-aminopropanol to afford (6aS,9aR)-5-(6-bromopyridin-3-yl)-4-fluoro-11-methyl-6a,7,9,9a-tetrahydro-6,8-dioxa-2,9b,11-triazacyclopenta[h]naphtho[2,1,8-cde]azulen-10(11H)-one with a yield of 60.3%. ESI-MS (m/z): 379.94/381.95 $[M+H]^+$.

Intermediate Preparation Example 34: Preparation of (6aR,9aS)-5-bromo-4-fluoro-11-methyl-6a,7,9,9a-tetrahydro-6,8-dioxa-2,9b,11-triazacyclopenta[h]naphtho[2,1,8-cde]azulen-10(11H)-one (M-34)

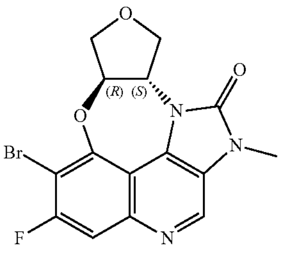

The synthesis method was the same as that of intermediate preparation example 1, except that (3R,4S)-4-aminotetrahydrofuran-3-ol was used instead of L-aminopropanol to afford (6aR,9aS)-5-bromo-4-fluoro-11-methyl-6a,7,9,9a-tetrahydro-6,8-dioxa-2,9b,11-triazacyclopenta[h]naphtho[2,1,8-cde]azulen-10(11H)-one with a yield of 82.4%. ESI-MS (m/z): 380.00/382.00 $[M+H]^+$.

Intermediate Preparation Example 35: Preparation of 7-bromo-6-fluoro-2-methyl-2,9-dihydro-1H-spiro [8-oxa-2,4,10a-triazanaphtho[2,1,8-cde]azulene-10, 3'-oxetan]-1-one (M-35)

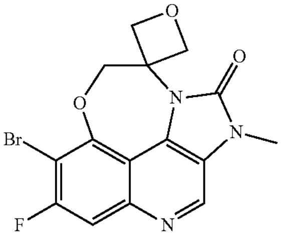 [SMILES: Cn1c(=O)n2c3c4c(c(Br)c(F)cc4ncc31)OCC21COC1]

The synthesis method was the same as that of intermediate preparation example 1, except that 3-amino-3-(hydroxymethyl)oxetane was used instead of L-aminopropanol to afford 7-bromo-6-fluoro-2-methyl-2,9-dihydro-1H-spiro [8-oxa-2,4,10a-triazanaphtho[2,1,8-cde]azulene-10,3'-oxetan]-1-one with a yield of 32.1%. ESI-MS (m/z): 380.00/381.99 $[M+H]^+$.

Intermediate Preparation Example 36: Preparation of 7-bromo-6-methoxy-10-(hydroxymethyl)-2-methyl-9,10-dihydro-8-oxa-2,4,10a-triazanaphtho[2,1,8-cde]azulen-1(2H)-one (M-36)

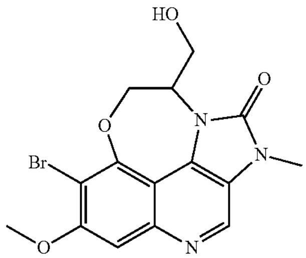

The synthesis method was the same as that of intermediate preparation example 31, except that 2-aminopropane-1,3-diol was used instead of 2-aminophenol to afford 7-bromo-6-methoxy-10-(hydroxymethyl)-2-methyl-9,10-dihydro-8-oxa-2,4,10a-triazanaphtho[2,1,8-cde]azulen-1 (2H)-one with a yield of 28.0%. ESI-MS (m/z): 380.02/382.02 $[M+H]^+$.

Intermediate Preparation Example 37: Preparation of 7-bromo-6-fluoro-10-(hydroxymethyl)-2-methyl-9,10-dihydro-8-oxa-2,4,10a-triazanaphtho[2,1,8-cde]azulen-1(2H)-one (M-37)

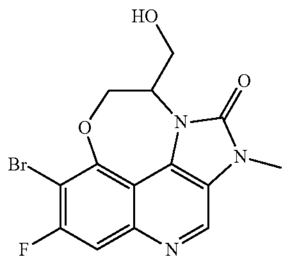 [SMILES: Cn1c(=O)n2c3c4c(c(Br)c(F)cc4ncc31)OCC2CO]

The synthesis method was the same as that of intermediate preparation example 1, except that 2-aminopropane-1,3-diol was used instead of L-aminopropanol to afford 7-bromo-6-fluoro-10-(hydroxymethyl)-2-methyl-9,10-dihydro-8-oxa-2,4,10a-triazanaphtho[2,1,8-cde]azulen-1(2H)-one with a yield of 74.2%. ESI-MS (m/z): 367.96/370.02 $[M+H]^+$.

Intermediate Preparation Example 38: Preparation of 5-bromo-8-fluoro-4-methoxy-12-methyl-6-oxa-2,10b,12-triazacyclopenta[gh]pleiaden-11(12H)-one (M-38)

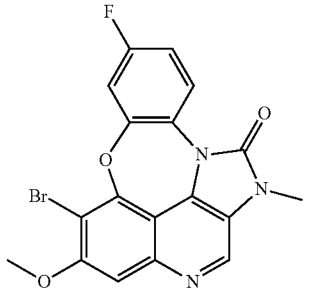

The synthesis method was the same as that of intermediate preparation example 31, except that 2-amino-5-fluorophenol was used instead of 2-aminophenol to afford 5-bromo-8-fluoro-4-methoxy-12-methyl-6-oxa-2,10b,12-triazacyclopenta[gh]pleiaden-11(12H)-one with a yield of 74.5%. ESI-MS (m/z): 416.20/418.20 $[M+H]^+$.

Intermediate Preparation Example 39: Preparation of 7-bromo-6-methoxy-2-methyl-9-(pyridin-2-yl)-9,10-dihydro-8-oxa-2,4,10a-triazanaphtho[2,1,8-cde]azulen-1(2H)-one (M-39)

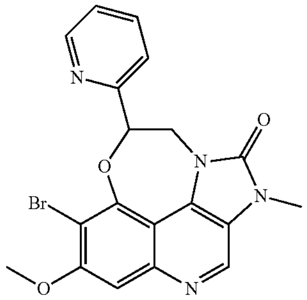

The synthesis method was the same as that of intermediate preparation example 28, except that 2-amino-1-(pyridin-2-yl)ethanol was used instead of 2-amino-2-(pyridin-2-yl)ethanol to afford 7-bromo-6-methoxy-2-methyl-9-(pyridin-2-yl)-9,10-dihydro-8-oxa-2,4,10a-triazanaphtho[2,1,8-cde]azulen-1(2H)-one with a yield of 63.8%. ESI-MS (m/z): 427.03/429.03 $[M+H]^+$.

Intermediate Preparation Example 40: Preparation of (R)-7-bromo-6-methoxy-2-methyl-10-phenyl-9,10-dihydro-8-oxa-2,4,10a-triazanaphtho[2,1,8-cde]azulen-1(2H)-one (M-40)

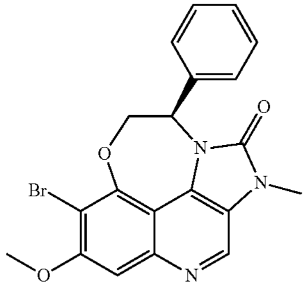

The synthesis method was the same as that of intermediate preparation example 28, except that (R)-2-amino-2-phenylethanol was used instead of 2-amino-2-(pyridin-2-yl)ethanol to afford (R)-7-bromo-6-methoxy-2-methyl-10-phenyl-9,10-dihydro-8-oxa-2,4,10a-triazanaphtho[2,1,8-cde]azulen-1(2H)-one with a yield of 67.2%. ESI-MS (m/z): 426.04/428.04 $[M+H]^+$.

Intermediate Preparation Example 41: Preparation of ethyl 5-fluoro-12H-benzo[2,3][1,4]oxazepino[5,6,7-de]quinoline-1-carboxylate (M-41)

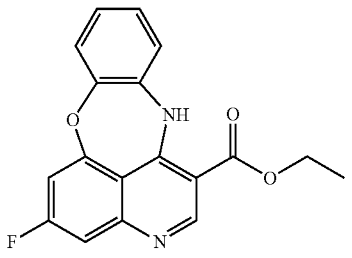 [SMILES: CCOC(=O)c1cnc2cc(F)cc3c2c1Nc1ccccc1O3]

Ethyl 4-chloro-5,7-difluoroquinoline-3-carboxylate (0.20 mmol), o-aminophenol (0.24 mmol), DIPEA (0.4 mmol), and DMF (20 mL) were successively added to a 100 mL round-bottomed flask, and the reaction mixture was stirred at 90° C. for 2 h. When no starting material was found as detected by TLC, the reaction solution was no longer heated, but cooled down to room temperature, then added with water and ethyl acetate. The target product was extracted into the organic phase, and the organic phase was separated and concentrated under reduced pressure, the resultant crude product was purified by column chromatography to afford ethyl 5-fluoro-12H-benzo[2,3][1,4]oxazepino[5,6,7-de]quinoline-1-carboxylate with a yield of 83.7%. $^1$H NMR (600 MHz, $CDCl_3$) δ 11.590 (s, 1H), 9.130 (s, 1H), 7.388 (d, J=10.2 Hz, 1H), 7.238-7.250 (m, 1H), 7.105-7.126 (m, 2H), 7.025-7.061 (m, 2H), 4.470 (q, J=6.6 Hz, 2H), 1.470 (t, J=6.6 Hz, 3H); $^{13}$C NMR (150 MHz, $CDCl_3$) δ 168.78, 165.44, 163.76, 156.80 (d, J=13.5 Hz), 153.05 (d, J=13.5 Hz), 152.54, 151.39, 148.82, 133.76, 125.85, 125.54, 121.70, 110.35 (d, J=19.5 Hz), 107.28 (d, J=27 Hz), 102.71, 61.51, 14.39; HR-MS (ESI): calculated for $C_{18}H_{14}FN_2O_3$ $[M+H]^+$: 325.1734, found: 325.1732.

Intermediate Preparation Example 42: Preparation of ethyl 5-fluoro-12H-benzo[2,3][1,4]thiazepino[5,6,7-de]quinoline-1-carboxylate (M-42)

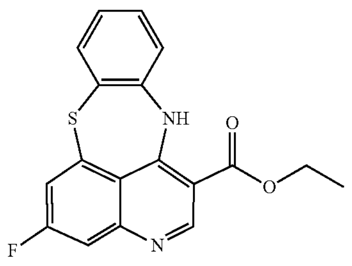 [SMILES: CCOC(=O)c1cnc2cc(F)cc3c2c1Nc1ccccc1S3]

The synthesis method was the same as that of intermediate preparation example 41 to afford ethyl 5-fluoro-12H-benzo[2,3][1,4]thiazepino[5,6,7-de]quinoline-1-carboxylate with a yield of 81.6%. $^1$H NMR (600 MHz, $CDCl_3$) δ 11.885 (s, 1H), 9.181 (s, 1H), 7.549 (d, J=7.2 Hz, 1H), 7.500 (d, J=7.8 Hz, 1H), 7.429-7.442 (m, 1H), 7.295-7.320 (m, 1H), 7.134-7.167 (m, 2H), 4.495 (q, J=7.2 Hz, 2H), 1.484 (t, J=6.6 Hz, 3H); $^{13}$C NMR (150 MHz, $CDCl_3$) δ 168.99, 164.33, 162.63, 154.39, 154.00 (d, J=13.5 Hz), 152.55, 144.81, 135.75 (d, J=9.0 Hz), 131.88, 129.85, 128.59, 126.04, 123.62, 119.35 (d, J=24 Hz), 113.95 (d, J=21 Hz), 104.93, 61.71, 14.41; HR-MS (ESI) calculated for $C_{18}H_{14}FN_2O_2S$ $[M+H]^+$: 341.0957, found: 341.0959.

Intermediate Preparation Example 43: Preparation of ethyl 5-fluoro-7,12-dihydrobenzo[2,3][1,4]diazepino[5,6,7-de]quinoline-1-carboxylate (M-43)

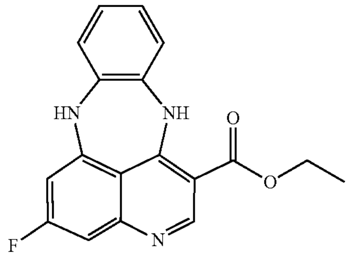 [SMILES: CCOC(=O)c1cnc2cc(F)cc3c2c1Nc1ccccc1N3]

The synthesis method was the same as that of intermediate preparation example 41 to afford ethyl 5-fluoro-7,12-dihydrobenzo[2,3][1,4]diazepino[5,6,7-de]quinoline-1-carboxylate with a yield of 86.4%. $^1$H NMR (600 MHz, $CD_3OD+CF_3COOH$) δ 9.040 (s, 1H), 7.021-7.035 (m, 1H), 6.958-6.976 (m, 1H), 6.875-6.900 (m, 1H), 6.793-6.806 (m, 2H), 6.757-6.778 (m, 1H), 4.496 (q, J=7.2 Hz, 2H), 1.474 (t, J=7.2 Hz, 3H); $^{13}$C NMR (150 MHz, $CD_3OD+CF_3COOH$) δ 168.10, 156.01, 145.60, 135.97, 124.63, 123.84, 120.84, 118.89, 117.00, 115.12, 113.23, 106.01 (d, J=25.5 Hz), 104.73, 102.73, 99.08 (d, J=25.5 Hz), 64.20, 55.61, 14.30; HR-MS (ESI) calculated for $C_{18}H_{15}FN_3O_2$ $[M+H]^+$: 324.1171, found: 324.1173.

Intermediate Preparation Example 44: Preparation of ethyl 5,9-difluoro-12H-benzo[2,3][1,4]oxazepino[5,6,7-de]quinoline-1-carboxylate (M-44)

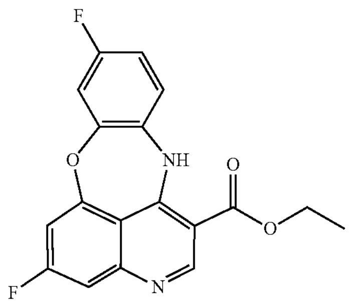 [SMILES: CCOC(=O)c1cnc2cc(F)cc3c2c1Nc1ccc(F)cc1O3]

The synthesis method was the same as that of intermediate preparation example 41 to afford ethyl 5,9-difluoro-12H-benzo[2,3][1,4]oxazepino[5,6,7-de]quinoline-1-carboxylate with a yield of 80.3%. $^1$H NMR (600 MHz, $CDCl_3$) δ 11.585 (s, 1H), 9.161 (s, 1H), 7.439 (d, J=8.4 Hz, 1H), 7.022-7.060 (m, 3H), 6.888-6.899 (m, 1H), 4.476 (q, J=7.2 Hz, 2H), 1.475 (t, J=7.2 Hz, 3H); $^{13}$C NMR (150 MHz, $CDCl_3$) δ 168.84, 165.48, 163.67, 160.62, 158.98, 156.30 (d, J=15 Hz), 156.05, 152.63, 151.25, 130.27, 122.36 (d, J=9 Hz), 112.90 (d, J=25.5 Hz), 110.76 (d, J=19.5 Hz), 109.35 (d, J=24 Hz), 107.48 (d, J=25.5 Hz), 102.77, 61.65, 14.43; HR-MS (ESI) calculated for $C_{18}H_{13}F_2N_2O_3$ $[M+H]^+$: 343.2013, found: 343.2011.

Intermediate Preparation Example 45: Preparation of ethyl 5-fluoro-10-methoxy-12H-benzo[2,3][1,4]oxazepino[5,6,7-de]quinoline-1-carboxylate (M-45)

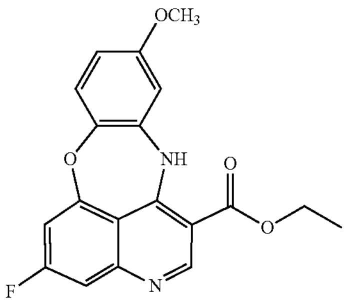 [SMILES: CCOC(=O)c1cnc2cc(F)cc3c2c1Nc1cc(OC)ccc1O3]

The synthesis method was the same as that of intermediate preparation example 41 to afford ethyl 5-fluoro-10-methoxy-12H-benzo[2,3][1,4]oxazepino[5,6,7-de]quinoline-1-carboxylate with a yield of 85.6%. $^1$H NMR (600 MHz, $CDCl_3$) δ 11.542 (s, 1H), 9.124 (s, 1H), 7.370-7.390 (m, 1H), 7.136 (d, J=9.0 Hz, 1H), 6.987-7.006 (m, 1H), 6.215-6.634 (m, 1H), 6.536 (m, 1H), 4.462 (q, J=7.2 Hz, 2H), 3.768 (s, 3H), 1.467 (t, J=7.2 Hz, 3H); $^{13}$C NMR (150 MHz, $CDCl_3$) δ 168.82, 165.52, 163.84, 157.39, 157.20 (d, J=13.5 Hz), 152.50 (d, J=13.5 Hz), 152.42, 151.62, 142.84, 134.35, 122.24, 111.14, 110.51 (d, J=3 Hz), 110.14 (d, J=21 Hz), 107.10 (d, J=25.5 Hz), 106.39, 102.70, 61.56, 55.93, 14.40; HR-MS (ESI) calculated for $C_{19}H_{16}FN_2O_4$ $[M+H]^+$: 355.0978, found: 355.0980.

Intermediate Preparation Example 46: Preparation of ethyl 5-fluoro-12H-pyrido[3',4':2,3][1,4]oxazepino[5,6,7-de]quinoline-1-carboxylate (M-46)

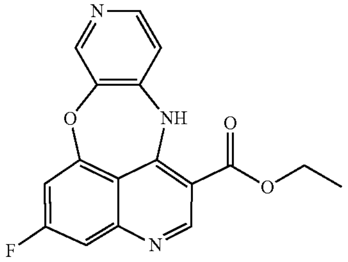 [SMILES: CCOC(=O)c1cnc2cc(F)cc3c2c1Nc1ccncc1O3]

The synthesis method was the same as that of intermediate preparation example 41 to afford ethyl 5-fluoro-12H-pyrido[3',4':2,3][1,4]oxazepino[5,6,7-de]quinoline-1-carboxylate with a yield of 95.8%. $^1$H NMR (600 MHz, $CD_3OD$) δ 9.425 (s, 1H), 8.932 (s, 1H), 8.585 (d, J=4.8 Hz, 1H), 7.636-7.736 (m, 3H), 4.619 (q, J=6.6 Hz, 2H), 1.528 (t, J=6.6 Hz, 3H); $^{13}$C NMR (150 MHz, $CD_3OD+CF_3COOH$) δ 168.23, 166.68, 156.40 (d, J=15 Hz), 152.15, 150.11, 145.83 (d, J=18 Hz), 142.15, 139.35, 119.32, 117.80, 116.99, 115.89, 111.65 (d, J=28.5 Hz), 110.61, 106.95, 64.53, 14.31; HR-MS (ESI) calculated for $C_{17}H_{13}FN_3O_3$ $[M+H]^+$: 326.0832, found: 326.0830.

Intermediate Preparation Example 47: Preparation of ethyl 5-fluoro-12H-pyrido[4',3':2,3][1,4]oxazepino[5,6,7-de]quinoline-1-carboxylate (M-47)

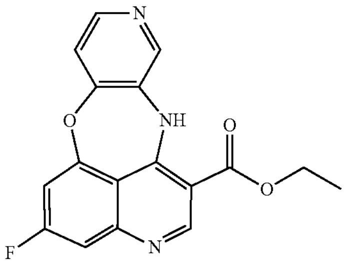 [SMILES: CCOC(=O)c1cnc2cc(F)cc3c2c1Nc1cnccc1O3]

The synthesis method was the same as that of intermediate preparation example 41 to afford ethyl 5-fluoro-12H-pyrido[4',3':2,3][1,4]oxazepino[5,6,7-de]quinoline-1-carboxylate with a yield of 94.5%. $^1$H NMR (600 MHz, $CF_3COOH+CDCl_3$) δ 13.144 (s, 1H), 9.406 (s, 1H), 8.799 (s, 1H), 8.588 (d, J=4.2 Hz, 1H), 7.927 (d, J=7.8 Hz, 1H), 7.584 (d, J=5.4 Hz, 1H), 7.422 (d, J=7.8 Hz, 1H), 4.571 (q, J=7.2 Hz, 2H), 1.485 (t, J=7.2 Hz, 3H); $^{13}$C NMR (150 MHz, $CF_3COOH+CDCl_3$) δ 167.84, 166.63, 166.09, 156.08, 154.78 (d, J=13.5 Hz), 153.43, 146.80, 144.71, 140.78, 129.00, 118.64, 116.56, 117.69 (d, J=27 Hz), 107.99, 106.15 (d, J=24 Hz), 104.00, 64.24, 13.93; HR-MS (ESI) calculated for $C_{17}H_{13}FN_3O_3$ $[M+H]^+$: 326.1438, found: 326.1440.

Intermediate Preparation Example 48: Preparation of ethyl 5-methoxy-12H-benzo[2,3][1,4]oxazepino[5,6,7-de]quinoline-1-carboxylate (M-48)

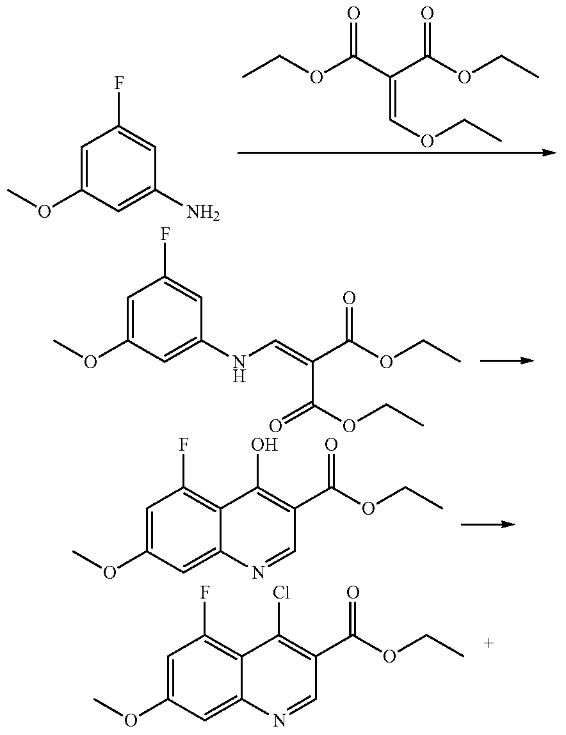

-continued

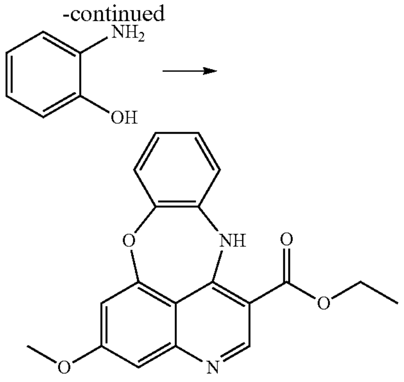

Step 1: Synthesis of diethyl 2-(((3-fluoro-5-methoxyphenyl)amino)methylene)malonate 3-fluoro-5-methoxyaniline (1.41 g, 0.01 mol), diethyl 2-(ethoxymethylene)malonate (2.16 g, 0.01 mol), and 25 mL of anhydrous ethanol were successively added to a 100 mL reaction bottle, and the reaction solution was heated to reflux and reacted for 6 h and then cooled down to room temperature, the solvent was removed by rotary evaporation to afford diethyl 2-(((3-fluoro-5-methoxyphenyl)amino)methylene)malonate as a colorless and transparent liquid (2.76 g, 88.7% yield). HR-MS (ESI) calculated for $C_{15}H_{19}FNO_5$ $[M+H]^+$: 312.0755, found: 312.0756; $^1H$ NMR (600 MHz, $CDCl_3$) δ: 10.841-10.862 (m, 1H), 8.322-8.344 (m, 1H), 6.304-6.395 (m, 3H), 4.165-4.239 (m, 4H), 3.716-3.726 (m, 3H), 1.243-1.316 (m, 6H).

Step 2: Synthesis of ethyl 5-fluoro-7-methoxy-4-oxo-1,4-difluoroquinoline-3-carboxylate 40 mL of diphenyl ether was added to a 100 mL reaction bottle and heated up to 240° C., followed by adding diethyl 2-(((3-fluoro-5-methoxyphenyl)amino)methylene)malonate (3.11 g, 0.01 mol), the reaction solution was maintained at the temperature to react for 1 h and then cooled down to room temperature, followed by adding 100 mL of n-hexane at room temperature, and then filtrated to afford ethyl 5-fluoro-7-methoxy-4-oxo-1,4-difluoroquinoline-3-carboxylate (2.24 g, 84.4% yield) as a white solid, HR-MS (ESI) calculated for $C_{13}H_{12}FNO_4$ $[M+H]^+$: 266.1326, found: 266.1328; $^1H$ NMR (600 MHz, DMSO-$d_6$) δ: 12.071 (s, 1H), 8.396 (s, 1H), 6.833-6.844 (m, 1H), 6.758-6.780 (m, 1H), 4.155-4.201 (m, 2H), 3.853 (s, 3H), 1.244-1.286 (m, 3H).

Step 3: Synthesis of ethyl 4-chloro-5-fluoro-7-methoxyquinoline-3-carboxylate Ethyl 5-fluoro-7-methoxy-4-oxo-1,4-difluoroquinoline-3-carboxylate (1.30 g, 4.90 mmol) and thionyl chloride (10 mL) were added to a 50 mL reaction bottle, and added dropwise with DMF (two drops), after refluxing for 4 h, the reaction was completed. The reaction mixture was concentrated to dryness under reduced pressure to afford ethyl 4-chloro-5-fluoro-7-methoxyquinoline-3-carboxylate (1.21 g, 87.1% yield) as a yellow solid. HR-MS (ESI) calculated for $C_{13}H_{12}ClFNO_3$ $[M+H]^+$: 283.1184, found: 283.1186; $^1H$ NMR (600 MHz, $CDCl_3$) δ: 9.152 (s, 1H), 7.785 (m, 1H), 6.955-6.976 (m, 1H), 4.522 (q, J=7.2 Hz, 2H), 4.025 (s, 3H), 1.444 (t, J=7.2 Hz, 3H).

Step 4: Synthesis of ethyl of 5-methoxy-12H-benzo[2,3][1,4]oxazepino[5,6,7-de]quinoline-1-carboxylate Ethyl 4-chloro-5-fluoro-7-methoxyquinoline-3-carboxylate (0.20 mmol), o-aminophenol (0.24 mmol), DIPEA (0.4 mmol), and DMF (20 mL) were successively added to a 100 mL round-bottomed flask, and the reaction mixture was stirred at 90° C. for 2 h. When no starting material was found as detected by TLC, the reaction solution was no longer heated, but cooled down to room temperature and then added with water and ethyl acetate. The target product was extracted into the organic phase, and the organic phase was separated and concentrated under reduced pressure, and the resultant crude product was purified by column chromatography to afford ethyl 5-methoxy-12H-benzo[2,3][1,4]oxazepino[5,6,7-de]quinoline-1-carboxylate with a yield of 75.0%. $^1H$ NMR (600 MHz, $CDCl_3$) δ 11.535 (s, 1H), 9.122 (s, 1H), 7.276-7.290 (m, 1H), 7.081-7.169 (m, 4H), 6.937-6.941 (m, 1H), 4.483 (q, J=7.2 Hz, 2H), 3.959 (s, 3H), 1.494 (t, J=7.2 Hz, 3H); $^{13}C$ NMR (150 MHz, $CDCl_3$) δ 168.99, 163.05, 156.11, 153.64, 152.18, 151.32, 149.00, 134.20, 125.58, 125.24, 121.79, 121.61, 108.68, 107.97, 105.52, 101.94, 61.27, 55.91, 14.46; HR-MS (ESI) calculated for $C_{19}H_{14}N_2O_4$ $[M+H]^+$: 337.1074, found: 337.1076.

Intermediate Preparation Example 49: Preparation of ethyl 5-methoxy-12H-benzo[2,3][1,4]thiazepino[5,6,7-de]quinoline-1-carboxylate (M-49)

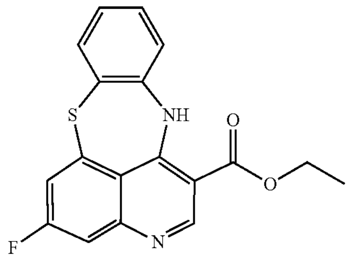 [SMILES: CCOC(=O)c1cnc2cc(F)cc3c2c1Nc1ccccc1S3]

The synthesis method was the same as that of intermediate preparation example 48 to afford ethyl 5-methoxy-12H-benzo[2,3][1,4]thiazepino[5,6,7-de]quinoline-1-carboxylate with a yield of 64.0%. $^1H$ NMR (600 MHz, DMSO-$d_6$) δ 11.565 (s, 1H), 9.051 (s, 1H), 7.611 (d, J=7.2 Hz, 1H), 7.399-7.422 (m, 1H), 7.338 (d, J=3.0 Hz, 2H), 7.279 (d, J=3.0 Hz, 1H), 7.197-7.242 (m, 2H), 4.454 (q, J=7.2 Hz, 2H), 3.909 (s, 3H), 1.417 (t, J=7.2 Hz, 3H); $^{13}C$ NMR (150 MHz, $CDCl_3$) δ 169.10, 161.96, 154.33, 154.13, 151.90, 145.07, 134.17, 131.88, 129.59, 128.77, 125.74, 123.49, 121.56, 116.46, 108.45, 104.12, 61.50, 55.87, 14.45; HR-MS (ESI) calculated for $C_{19}H_{17}N_2O_3S$ $[M+H]^+$: 353.1283, found: 353.1284.

Intermediate Preparation Example 50: Preparation of ethyl 5-methoxy-7,12-dihydrobenzo[2,3][1,4]diazepino[5,6,7-de]quinoline-1-carboxylate (M-50)

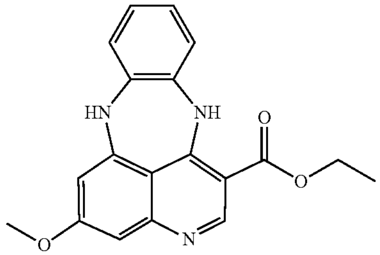 [SMILES: CCOC(=O)c1cnc2cc(OC)cc3c2c1Nc1ccccc1N3]

The synthesis method was the same as that of intermediate preparation example 48 to afford ethyl 5-methoxy-7,12-dihydrobenzo[2,3][1,4]diazepino[5,6,7-de]quinoline-1-carboxylate with a yield of 79.0%. $^1H$ NMR (600 MHz, $CDCl_3$) δ 11.641 (s, 1H), 9.109 (s, 1H), 6.899-6.963 (m, 4H), 6.772-6.785 (m, 1H), 6.406-6.409 (m, 1H), 6.085 (s, 1H), 4.431 (q, J=7.2 Hz, 2H), 3.878 (s, 3H), 1.452 (t, J=7.2 Hz, 3H); $^{13}C$ NMR (150 MHz, $CDCl_3$) δ 169.20, 162.68, 153.63, 152.28, 151.58, 144.79, 135.46, 131.39, 124.64, 122.84, 121.62, 119.15, 105.33, 104.62, 102.77, 101.68, 61.20, 55.61, 14.41; HR-MS (ESI) calculated for $C_{19}H_{18}N_3O_3$ $[M+H]^+$: 336.0512, found: 336.0513.

Intermediate Preparation Example 51: Preparation of ethyl 9-fluoro-5-methoxy-12H-benzo[2,3][1,4]oxazepino[5,6,7-de]quinoline-1-carboxylate (M-51)

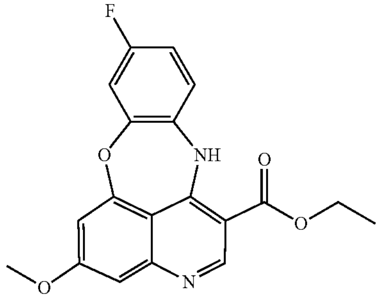 [SMILES: CCOC(=O)c1cnc2cc(OC)cc3c2c1Nc1ccc(F)cc1O3]

The synthesis method was the same as that of intermediate preparation example 48 to afford ethyl 9-fluoro-5-methoxy-12H-benzo[2,3][1,4]oxazepino[5,6,7-de]quinoline-1-carboxylate with a yield of 56.3%. $^1H$ NMR (600 MHz, $CDCl_3$) δ 11.481 (s, 1H), 9.102 (s, 1H), 7.169-7.173 (m, 1H), 7.002-7.035 (m, 2H), 6.902-6.906 (m, 1H), 6.839-6.871 (m, 1H), 4.458 (q, J=6.6 Hz, 2H), 3.942 (s, 3H), 1.468 (t, J=6.6 Hz, 3H); $^{13}C$ NMR (150 MHz, $CDCl_3$) δ 168.99, 163.07, 160.43, 158.80, 155.60, 152.13, 151.12, 149.48 (d, J=10.5 Hz), 130.61, 122.18 (d, J=10.5 Hz), 112.53 (d, J=22.5 Hz), 109.34 (d, J=24 Hz), 108.85, 107.73, 105.75, 101.97, 61.38, 56.00, 14.43; HR-MS (ESI) calculated for $C_{19}H_{16}FN_2O_4$ $[M+H]^+$: 355.1337, found: 355.1338.

Intermediate Preparation Example 52: Preparation of ethyl 5,10-dimethoxy-12H-benzo[2,3][1,4]oxazepino[5,6,7-de]quinoline-1-carboxylate (M-52)

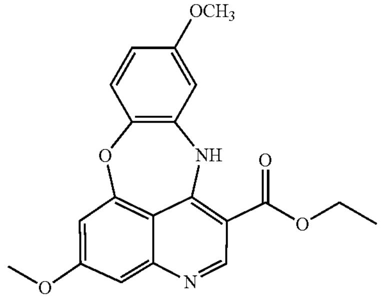 [SMILES: CCOC(=O)c1cnc2cc(OC)cc3c2c1Nc1cc(OC)ccc1O3]

The synthesis method was the same as that of intermediate preparation example 48 to afford ethyl 5,10-dimethoxy-12H-benzo[2,3][1,4]oxazepino[5,6,7-de]quinoline-1-carboxylate with a yield of 59.4%. $^1H$ NMR (600 MHz, DMSO-$d_6$) δ 10.955 (s, 1H), 9.766 (s, 1H), 8.894 (s, 1H), 8.582 (s, 1H), 8.321 (s, 1H), 7.165 (m, 1H), 6.194-6.199 (m, 1H), 4.435 (q, J=7.2 Hz, 2H), 3.939 (s, 3H), 3.737 (s, 3H), 1.408 (t, J=7.2 Hz, 3H); $^{13}C$ NMR (150 MHz, $CDCl_3$) δ 168.98, 163.32, 157.24, 156.53, 153.29, 151.88, 151.63, 143.03, 134.70, 122.35, 111.01, 108.57, 108.09, 106.30, 105.11, 101.93, 61.38, 55.96, 14.46; HR-MS (ESI) calculated for $C_{20}H_{18}N_2O_5$ $[M+H]^+$: 367.1534, found: 367.1535.

Intermediate Preparation Example 53: Preparation of ethyl 5-methoxy-12H-pyrido[4',3':2,3][1,4]oxazepino[5,6,7-de]quinoline-1-carboxylate (M-53)

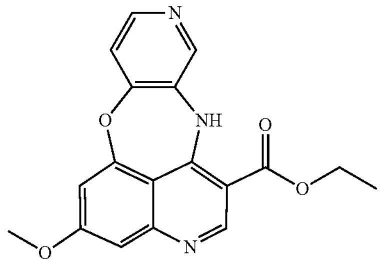 [SMILES: CCOC(=O)c1cnc2cc(OC)cc3c2c1Nc1cnccc1O3]

The synthesis method was the same as that of intermediate preparation example 48 to afford ethyl 5-methoxy-12H-pyrido[4',3':2,3][1,4]oxazepino[5,6,7-de]quinoline-1-carboxylate with a yield of 81.2%. $^1H$ NMR (600 MHz, DMSO-$d_6$) δ 11.456 (s, 1H), 9.058 (s, 1H), 8.493 (s, 1H), 8.350 (d, J=5.4 Hz, 1H), 7.442 (d, J=5.4 Hz, 1H), 7.265 (d, J=2.4 Hz, 1H), 7.161 (d, J=2.4 Hz, 1H), 4.464 (q, J=7.2 Hz, 2H), 3.962 (s, 3H), 1.427 (t, J=7.2 Hz, 3H); $^{13}C$ NMR (150 MHz, $CDCl_3$) δ 175.53, 158.63, 163.25, 153.84, 152.10, 151.08, 150.34, 145.88, 142.68, 130.14, 116.44, 109.87, 106.14, 105.17, 102.37, 61.81, 56.12, 14.34; HR-MS (ESI) calculated for $C_{18}H_{16}N_3O_4$ $[M+H]^+$: 338.1382, found: 338.1382.

Intermediate Preparation Example 54: Preparation of ethyl 5-methoxy-12H-pyrido[3',4':2,3][1,4]oxazepino[5,6,7-de]quinoline-1-carboxylate (M-54)

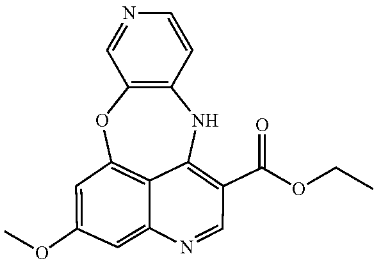 [SMILES: CCOC(=O)c1cnc2cc(OC)cc3c2c1Nc1ccncc1O3]

The synthesis method was the same as that of preparation example 48 to afford ethyl 5-methoxy-12H-pyrido[3',4':2,3][1,4]oxazepino[5,6,7-de]quinoline-1-carboxylate with a yield of 89.4%. $^1$H NMR (600 MHz, $CDCl_3$) δ 11.831 (s, 1H), 9.145 (s, 1H), 8.508 (s, 1H), 8.273 (s, 1H), 7.182 (m, 1H), 6.948-6.988 (m, 2H), 4.471 (q, J=7.2 Hz, 2H), 3.946 (s, 3H), 1.473 (t, J=7.2 Hz, 3H); $^{13}$C NMR (150 MHz, $CDCl_3$) δ 168.99, 163.10, 154.94, 153.65, 151.98, 149.68, 146.62, 144.38, 143.81, 140.10, 115.09, 109.56, 107.02, 106.06, 102.75, 61.74, 56.02, 14.40; HR-MS (ESI) calculated for $C_{18}H_{16}N_3O_4$ $[M+H]^+$: 338.1438, found: 338.1440.

Intermediate Preparation Example 55: Preparation of ethyl 5-fluoro-7,7a,8,9,10,11,11a,12-octahydrobenzo[2,3][1,4]diazepino[5,6,7-de]quinoline-1-carboxylate (M-55)

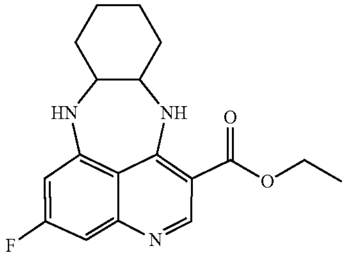 [SMILES: CCOC(=O)c1cnc2cc(F)cc3c2c1NC1CCCCC1N3]

The synthesis method was the same as that of intermediate preparation example 41 to afford ethyl 5-fluoro-7,7a,8,9,10,11,11a,12-octahydrobenzo[2,3][1,4]diazepino[5,6,7-de]quinoline-1-carboxylate with a yield of 95.7%. $^1$H NMR (600 MHz, $CDCl_3$) δ 10.086 (s, 1H), 8.911 (s, 1H), 6.860-6.880 (m, 1H), 6.215-6.236 (m, 1H), 4.485 (s, 1H), 4.422 (q, J=7.2 Hz, 2H), 3.228-3.267 (m, 1H), 3.099-3.139 (m, 1H), 2.189-2.212 (m, 1H), 2.036-2.057 (m, 1H), 1.807-1.814 (m, 2H), 1.296-1.528 (m, 7H); $^{13}$C NMR (150 MHz, $CDCl_3$) δ 169.38, 165.53, 163.38, 156.22, 154.47 (d, J=15 Hz), 152.68, 149.54 (d, J=13.5 Hz), 105.52, 103.58 (d, J=21 Hz), 99.35, 99.20, 99.03, 60.50 (d, J=15 Hz), 59.35, 32.89, 32.39, 23.79 (d, J=6 Hz), 14.47; HR-MS (ESI) calculated for $C_{18}H_{20}FN_3O_2$ $[M+H]^+$: 330.1237, found: 330.1238.

Intermediate Preparation Example 56: Preparation of ethyl 5-fluoro-7,7a,8,9,10,11,11a,12-octahydrobenzo[2,3][1,4]diazepino[5,6,7-de]quinoline-1-carboxylate (M-56)

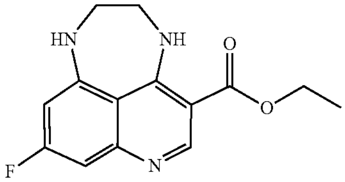 [SMILES: CCOC(=O)c1cnc2cc(F)cc3c2c1NCCN3]

The synthesis method was the same as that of intermediate preparation example 41 to afford ethyl 5-fluoro-7,7a,8,9,10,11,11a,12-octahydrobenzo[2,3][1,4]diazepino[5,6,7-de]quinoline-1-carboxylate with a yield of 96.4%. $^1$H NMR (600 MHz, $CDCl_3$) δ 10.637 (s, 1H), 8.923 (s, 1H), 6.909-6.928 (m, 1H), 6.300-6.321 (m, 1H), 5.383 (s, 1H), 4.349 (q, J=6.6 Hz, 2H), 3.708-3.722 (m, 2H), 3.584-3.596 (m, 2H), 1.401 (t, J=6.6 Hz, 3H); $^{13}$C NMR (150 MHz, $CDCl_3$) δ 169.81, 169.25, 165.82, 164.05, 157.74, 151.56, 104.78, 102.76, 99.41 (d, J=21 Hz), 99.17, 60.95, 47.47, 46.83, 14.47; HR-MS (ESI) calculated for $C_{14}H_{15}FN_3O_2$ $[M+H]^+$: 276.0974, found: 276.0973.

Intermediate Preparation Example 57: Preparation of ethyl 5-methoxy-7,7a,8,9,10,11,11a,12-octahydrobenzo[2,3][1,4]diazepino[5,6,7-de]quinoline-1-carboxylate (M-57)

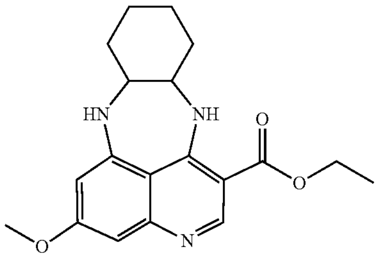 [SMILES: CCOC(=O)c1cnc2cc(OC)cc3c2c1NC1CCCCC1N3]

The synthesis method was the same as that of intermediate preparation example 48 to afford ethyl 5-methoxy-7,7a,8,9,10,11,11a,12-octahydrobenzo[2,3][1,4]diazepino[5,6,7-de]quinoline-1-carboxylate with a yield of 95.4%. $^1$H NMR (600 MHz, $CDCl_3$) δ 10.333 (s, 1H), 8.825 (s, 1H), 6.827-6.830 (m, 1H), 6.209-6.212 (m, 1H), 4.782 (s, 1H), 4.321 (q, J=7.2 Hz, 2H), 3.816 (s, 3H), 3.294-3.335 (m, 1H), 3.287-3.127 (m, 1H), 2.211-2.234 (m, 1H), 2.139-2.160 (m, 1H), 1.821-1.836 (m, 2H), 1.315-1.528 (m, 7H); $^{13}$C NMR (150 MHz, $CDCl_3$) δ 168.69, 163.32, 156.43, 149.30, 149.02, 102.72, 100.86, 98.63, 97.86, 61.10, 61.05, 58.72, 55.68, 32.70, 32.40, 29.83, 23.82, 23.73, 14.46; HR-MS (ESI) calculated for $C_{19}H_{24}N_3O_3$ $[M+H]^+$: 342.2013, found: 342.2011.

Intermediate Preparation Example 58: Preparation of ethyl 9-methoxy-4,5,6,7-tetrahydro-[1,4]diazepino[5,6,7-de]quinoline-3-carboxylate (M-58)

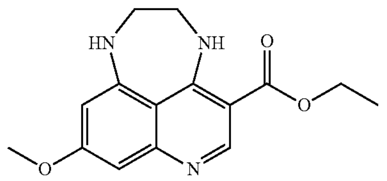 [SMILES: CCOC(=O)c1cnc2cc(OC)cc3c2c1NCCN3]

The synthesis method was the same as that of preparation example 48 to afford ethyl 9-methoxy-4,5,6,7-tetrahydro-[1,4]diazepino[5,6,7-de]quinoline-3-carboxylate with a yield of 97.1%. $^1$H NMR (600 MHz, DMSO-$d_6$) δ 10.219 (s, 1H), 8.664 (s, 1H), 7.182 (s, 1H), 6.487-6.492 (m, 1H), 6.261-6.265 (m, 1H), 4.461 (q, J=7.2 Hz, 2H), 3.771 (s, 3H), 3.610-3.627 (m, 2H), 3.374-3.390 (m, 2H), 1.314 (t, J=7.2 Hz, 3H); $^{13}$C NMR (150 MHz, DMSO-$d_6$) δ 168.38, 161.84, 156.80, 154.00, 151.06, 150.82, 101.75, 99.14, 98.06, 97.11, 59.93, 54.97, 47.07, 45.79, 14.31; HR-MS (ESI) calculated for $C_{15}H_{18}N_3O_3$ $[M+H]^+$: 288.0876, found: 276.0878.

EXAMPLES

Example 1: (S)-6-fluoro-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-1)

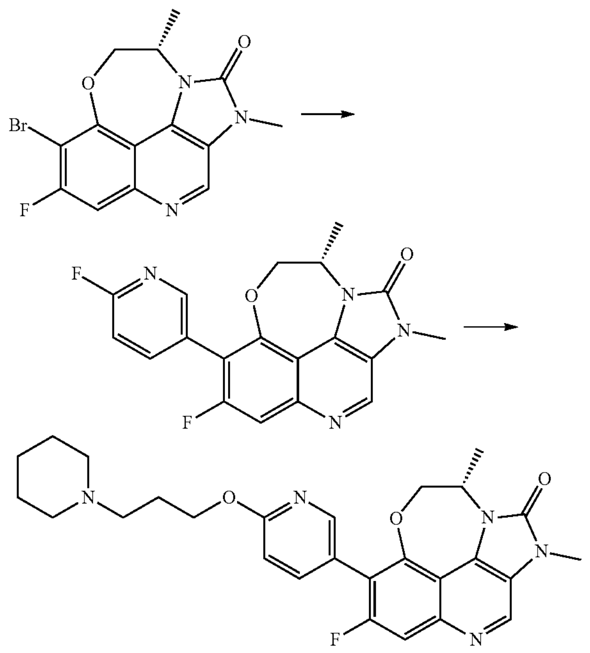

Step 1: Synthesis of (S)-6-fluoro-7-(6-fluoropyridin-3-yl)-2,10-dimethyl-9,10-dihydro-8-oxa-2,4,10a-triazanaphtho[2,1,8-cde]azulen-1(2H)-one 1,4-dioxane (15 mL), (S)-7-bromo-6-fluoro-2,10-dimethyl-9,10-dihydro-8-oxa-2,4,10a-triazanaphtho[2,1,8-cde]azulen-1(2H)-one (0.62 g, 1.76 mmol), (6-fluoropyridine-3-yl)boronic acid (0.315 g, 2.11 mmol), potassium carbonate (0.607 g, 4.4 mmol), water (1.5 mL), and tetrakis(triphenylphosphine)palladium (0.203 g, 0.18 mmol) were successively added to a 100 mL reaction bottle. The reaction solution was heated up to 90° C. under nitrogen protection and reacted for 2.5 h. When the reaction was completed as detected by TLC, the reaction solution was concentrated to dryness, and then the residue was purified by column chromatography (DCM:MeOH=60:1) to afford (S)-6-fluoro-7-(6-fluoropyridin-3-yl)-2,10-dimethyl-9,10-dihydro-8-oxa-2,4,10a-triazanaphtho[2,1,8-cde]azulen-1(2H)-one (0.43 g, 66.3% yield). ESI-MS (m/z): 369.11 $[M+H]^+$; $^1$H NMR (600 MHz, $CD_3OD$) δ: 1.541 (d, 3H), 3.632 (s, 3H), 4.525-4.660 (m, 2H), 4.707-4.739 (m, 1H), 7.213-7.231 (m, 1H), 7.565 (d, 1H), 8.105 (t, 1H), 8.343 (s, 1H), 8.837 (s, 1H).

Step 2: Preparation of (S)-6-fluoro-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one THF (4 mL) and 3-(piperidin-1-yl)propan-1-ol (115 mg, 0.8 mmol) were added to a 100 mL reaction bottle and cooled down to 0° C., followed by adding NaH (56 mg, 1.4 mmol) and the reaction was conducted at this temperature for 0.5 h, then (S)-6-fluoro-7-(6-fluoropyridin-3-yl)-2,10-dimethyl-9,10-dihydro-8-oxa-2,4,10a-triazanaphtho[2,1,8-cde]azulen-1(2H)-one (147 mg, 0.4 mmol) was added, and the reaction was continued at room temperature overnight. When the reaction was completed as detected by TLC, the reaction solution was quenched with water and concentrated to dryness, and then the residue was purified by column chromatography (DCM:MeOH=20:1-15:1) to afford (S)-6-fluoro-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (63 mg, 32% yield). ESI-MS (m/z): 492.23 $[M+H]^+$; $^1$H NMR (600 MHz, $CD_3OD$) δ: 1.495-1.533 (m, 5H), 1.620-1.657 (m, 4H), 2.027-2.053 (m, 2H), 2.507-2.577 (m, 6H), 3.610 (s, 3H), 4.373 (t, J=6.0 Hz, 2H), 4.467-4.612 (m, 2H), 4.630-4.701 (m, 1H), 6.899 (d, J=8.4 Hz, 1H), 7.480 (d, J=10.8 Hz, 1H), 7.794 (d, J=8.4 Hz, 1H), 8.209 (s, 1H), 8.767 (s, 1H).

Example 2: (S)-7-(6-(3-(dimethylamino)propoxy)pyridin-3-yl)-6-fluoro-2,10-dimethyl-9,10-dihydro-8-oxa-2,4,10a-triazanaphtho[2,1,8-cde]azulen-1(2H)-one (A-2)

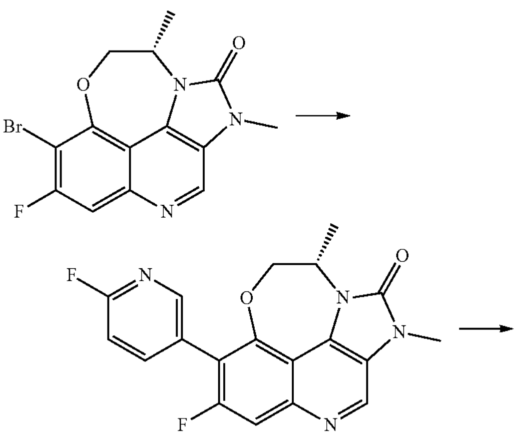

-continued

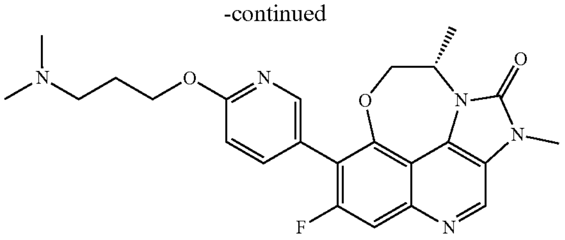

The synthesis method was the same as that of example 1, except that 3-(dimethylamino)propan-1-ol was used instead of 3-(piperidin-1-yl)propan-1-ol to afford (S)-7-(6-(3-(dimethylamino)propoxy)pyridin-3-yl)-6-fluoro-2,10-dimethyl-9,10-dihydro-8-oxa-2,4,10a-triazanaphtho[2,1,8-cde]azulen-1(2H)-one (30 mg, 32.0% yield). ESI-MS (m/z): 452.20 $[M+H]^+$; $^1H$ NMR (600 MHz, $CD_3OD$) δ: 1.526 (d, J=7.2 Hz, 3H), 2.040-2.066 (m, 2H), 2.390 (s, 6H), 2.662 (t, J=7.8 Hz, 2H), 3.610 (s, 3H), 4.398 (t, J=6.0 Hz, 2H), 4.467-4.632 (m, 2H), 4.689-4.702 (m, 1H), 6.912 (d, J=8.4 Hz, 1H), 7.476 (d, J=11.4 Hz, 1H), 7.800 (d, J=9.0 Hz, 1H), 8.215 (s, 1H), 8.765 (s, 1H).

Example 3: (R)-7-(6-(3-(dimethylamino)propoxy)pyridin-3-yl)-6-fluoro-2,10-dimethyl-9,10-dihydro-8-oxa-2,4,10a-triazanaphtho[2,1,8-cde]azulen-1(2H)-one (A-3)

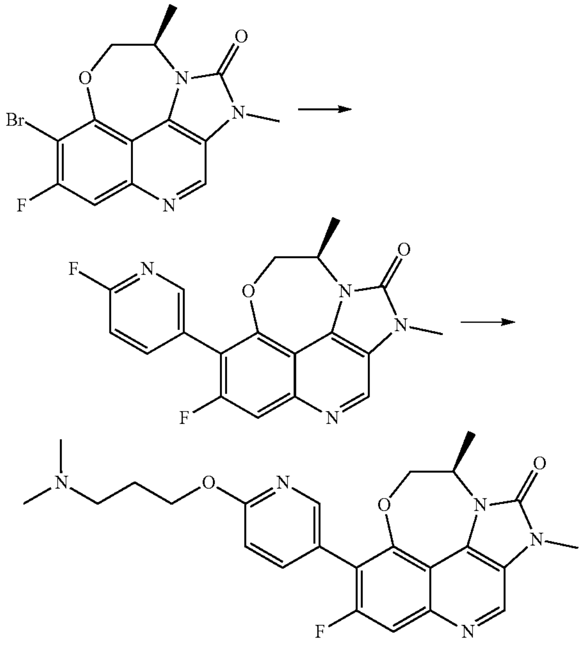

Except starting materials were changed, the synthesis method was the same as that of example 1 to afford (R)-7-(6-(3-(dimethylamino)propoxy)pyridin-3-yl)-6-fluoro-2,10-dimethyl-9,10-dihydro-8-oxa-2,4,10a-triazanaphtho[2,1,8-cde]azulen-1(2H)-one (25 mg, 27.1% yield). ESI-MS (m/z): 452.20 $[M+H]^+$; $^1H$ NMR (600 MHz, $CD_3OD$) δ: 1.536 (d, J=7.2 Hz, 3H), 2.001-2.048 (m, 2H), 2.310 (s, 6H), 2.565 (t, J=7.8 Hz, 2H), 3.620 (s, 3H), 4.388 (t, J=6.0 Hz, 2H), 4.484-4.641 (m, 2H), 4.698-4.712 (m, 1H), 6.915 (d, J=9.0 Hz, 1H), 7.509 (d, J=11.4 Hz, 1H), 7.803-7.818 (m, 1H), 8.226 (s, 1H), 8.792 (s, 1H).

Example 4: (R)-6-fluoro-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-4)

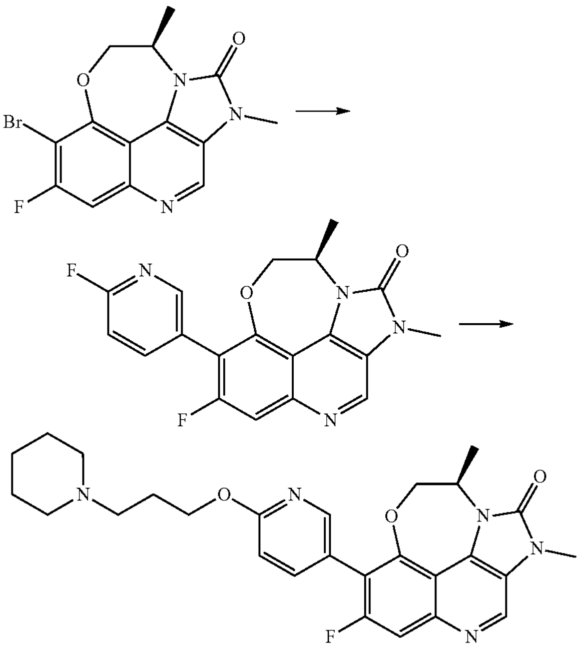

Except starting materials were changed, the synthesis method was the same as that of example 1 to afford (R)-6-fluoro-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (63 mg, 32% yield). ESI-MS (m/z): 492.20 $[M+H]^+$; $^1H$ NMR (600 MHz, $CDCl_3$) δ: 1.577-1.588 (m, 4H), 1.590-2.100 (m, 6H), 2.211-3.199 (m, 7H), 3.629 (s, 3H), 4.366-4.388 (m, 1H), 4.465 (t, J=6.0 Hz, 2H), 4.582-4.608 (m, 1H), 4.735-4.749 (m, 1H), 6.848 (d, J=8.4 Hz, 1H), 7.607 (d, J=10.8 Hz, 1H), 7.732-7.746 (m, 1H), 8.291 (s, 1H), 8.691 (s, 1H).

Example 5: 7-(6-(3-(dimethylamino)propoxy)pyridin-3-yl)-6-fluoro-9-(4-fluorophenyl)-2-methyl-9,10-dihydro-8-oxa-2,4,10a-triazanaphtho[2,1,8-cde]azulen-1(2H)-one (A-5)

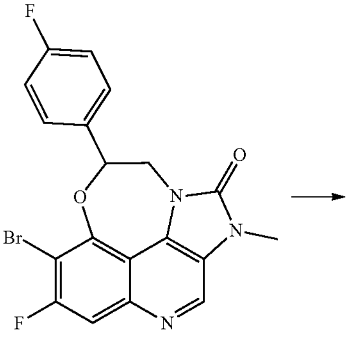

-continued

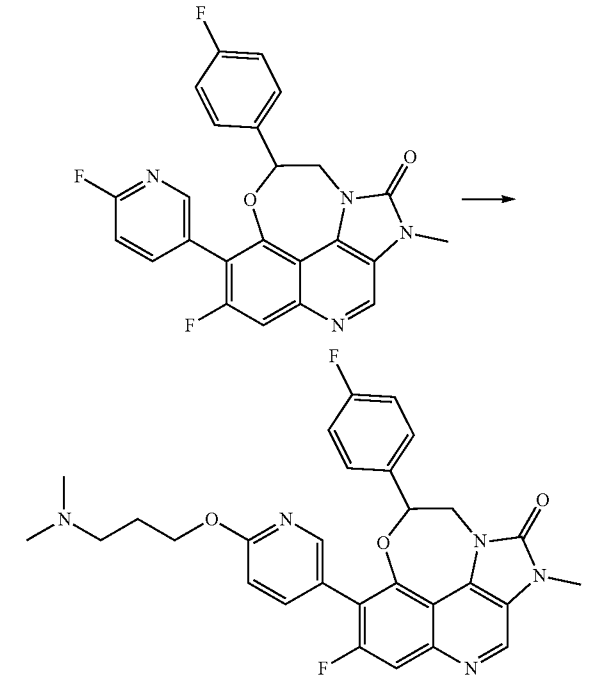

Except starting materials were changed, the synthesis method was the same as that of example 1 to afford 7-(6-(3-(dimethylamino)propoxy)pyridin-3-yl)-6-fluoro-9-(4-fluorophenyl)-2-methyl-9,10-dihydro-8-oxa-2,4,10a-triazanaphtho[2,1,8-cde]azulen-1(2H)-one (15 mg, 13.0% yield). ESI-MS (m/z): 532.21 $[M+H]^+$; $^1H$ NMR (600 MHz, DMSO-$d_6$) δ: 1.230-1.236 (m, 2H), 1.937 (t, J=6.6 Hz, 2H), 2.349 (s, 6H), 2.610-2.618 (m, 2H), 3.533 (s, 3H), 4.220-4.242 (m, 1H), 4.315 (t, J=6.0 Hz, 2H), 6.864 (d, J=8.4 Hz, 1H), 6.871-7.180 (m, 3H), 7.501-7.522 (m, 2H), 7.800-7.814 (m, 1H), 8.234 (s, 1H), 8.788 (s, 1H).

Example 6: 6-fluoro-2,10,10-trimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-6)

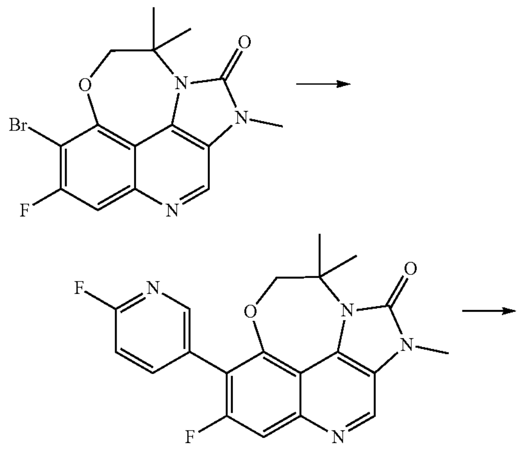

-continued

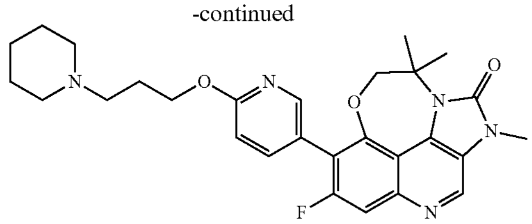

Except starting materials were changed, the synthesis method was the same as that of example 1 to afford 6-fluoro-2,10,10-trimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (70 mg, 33.2% yield). ESI-MS (m/z): 506.25 $[M+H]^+$; $^1H$ NMR (600 MHz, DMSO-$d_6$) δ: 1.383 (s, 2H), 1.482-1.518 (m, 4H), 1.639 (s, 6H), 1.883-1.928 (m, 2H), 2.348-2.405 (m, 4H), 2.498-2.510 (m, 2H), 3.503 (s, 3H), 4.335 (t, J=6.6 Hz, 2H), 4.441 (s, 2H), 6.937-6.952 (m, 1H), 7.560 (d, J=10.8 Hz, 1H), 7.824-7.844 (m, 1H), 8.276 (s, 1H), 8.899 (s, 1H).

Example 7: 6-fluoro-2-methyl-7-(6-(3-(piperidin-1-yl)propoxy)pyridin-3-yl)-9-(pyridin-2-yl)-9,10-dihydro-8-oxa-2,4,10a-triazanaphtho[2,1,8-cde]azulen-1(2H)-one (A-7)

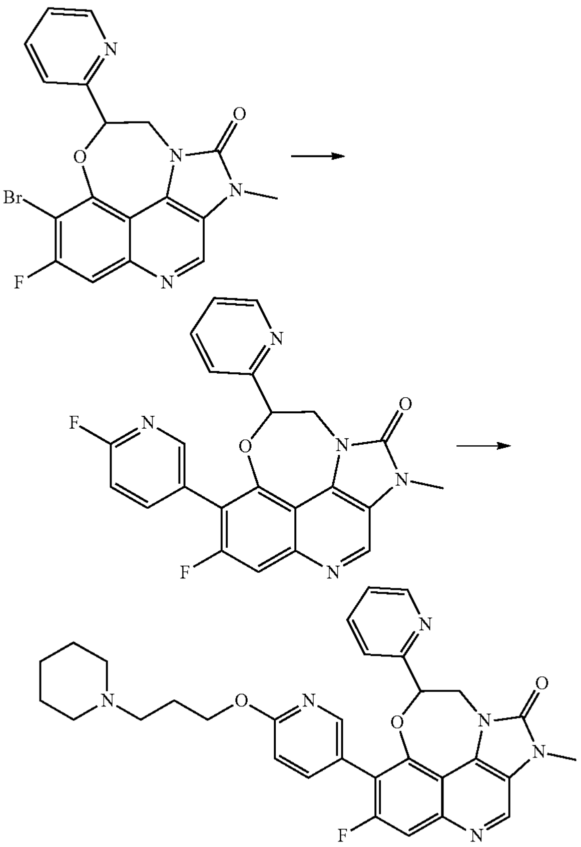

Except starting materials were changed, the synthesis method was the same as that of example 1 to afford 6-fluoro-2-methyl-7-(6-(3-(piperidin-1-yl)propoxy)pyridin-3-yl)-9-(pyridin-2-yl)-9,10-dihydro-8-oxa-2,4,10a-triazanaphtho[2,1,8-cde]azulen-1(2H)-one (63 mg, 32.0% yield).

ESI-MS (m/z): 555.2 $[M+H]^+$; $^1H$ NMR (600 MHz, DMSO) δ: 1.439 (brs, 2H), 1.382-1.579 (m, 4H), 1.970-1.997 (m, 2H), 2.487-2.500 (m, 2H), 2.520-2.750 (m, 4H), 3.581 (s, 3H), 4.228-4.239 (m, 1H), 4.332 (d, J=6.6 Hz, 2H), 4.887 (d, J=13.8 Hz, 1H), 5.858 (d, J=9.6 Hz, 1H), 6.855 (d, J=9.0 Hz, 1H), 7.177 (d, J=8.4 Hz, 1H), 7.370-7.391 (m, 1H), 7.663 (d, J=10.8 Hz, 1H), 7.733 (d, J=7.2 Hz, 1H), 7.711-7.752 (m, 1H), 7.818 (d, J=8.4 Hz, 1H), 8.242 (s, 1H), 8.600 (d, J=4.2 Hz, 1H), 8.963 (s, 1H).

Example 8: (R)-6-fluoro-10-isobutyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-8)

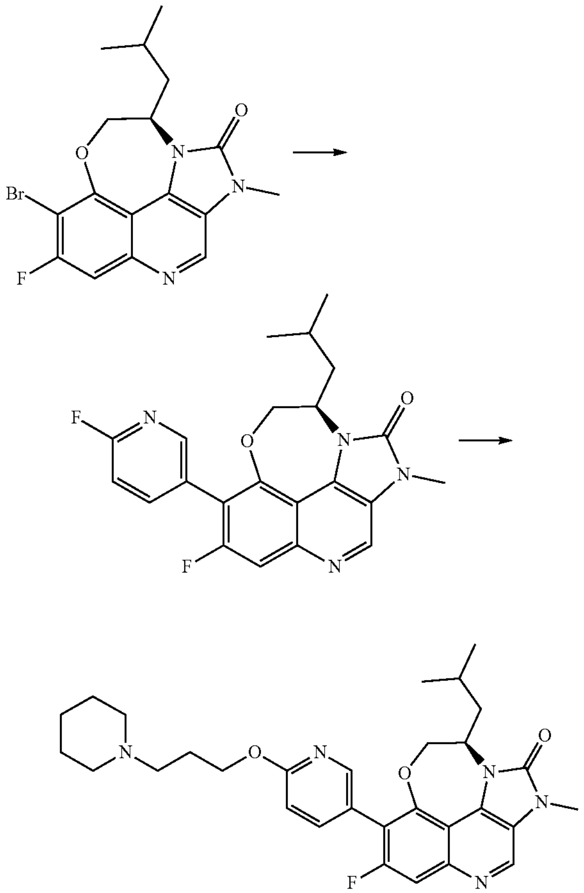

Except starting materials were changed, the synthesis method was the same as that of example 1 to afford (R)-6-fluoro-10-isobutyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (53 mg, 45.3% yield). ESI-MS (m/z): 534.28 $[M+H]^+$; $^1H$ NMR (600 MHz, DMSO-$d_6$) δ: 0.980 (s, 3H), 1.239 (s, 3H), 1.395 (s, 2H), 1.515 (s, 4H), 1.567-1.616 (m, 1H), 1.695-1.762 (m, 2H), 1.921 (s, 2H), 2.287-2.492 (m, 6H), 3.550 (s, 3H), 4.344 (t, J=6.6 Hz, 2H), 4.516 (d, J=13.2 Hz, 1H), 4.595-4.701 (m, 1H), 4.722 (d, J=3.0 Hz, 1H), 6.948 (d, J=8.4 Hz, 1H), 7.594 (d, J=10.8 Hz, 1H), 7.837 (d, J=8.4 Hz, 1H), 8.278 (s, 1H), 8.913 (s, 1H).

Example 9: (S)-6-fluoro-10-isobutyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-9)

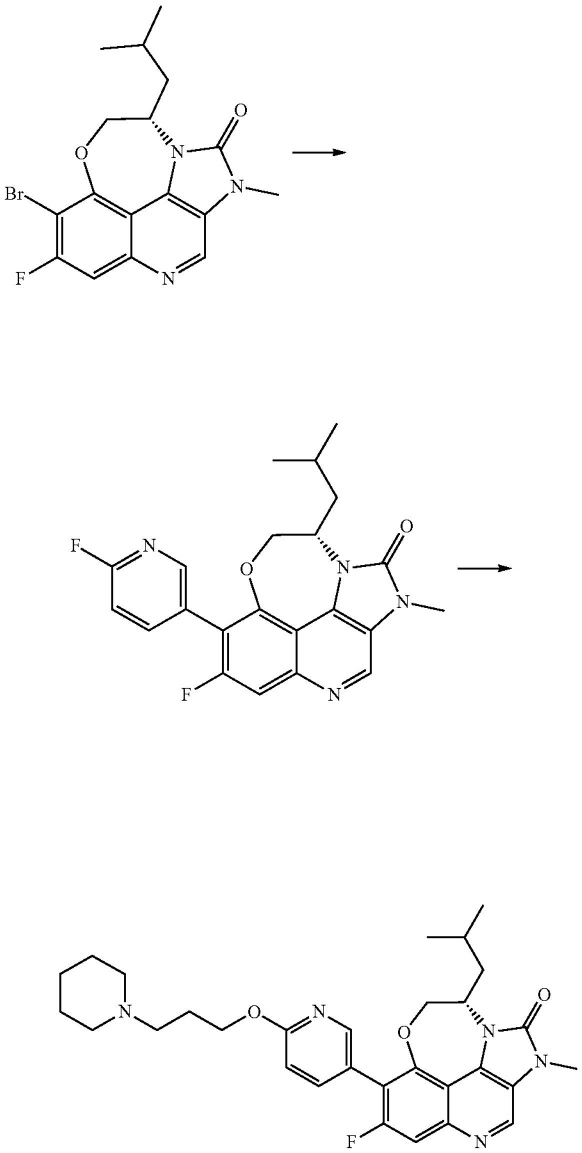

Except starting materials were changed, the synthesis method was the same as that of example 1 to afford (S)-6-fluoro-10-isobutyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (60 mg, 46.0% yield). ESI-MS (m/z): 534.28 $[M+H]^+$; $^1H$ NMR (600 MHz, DMSO-$d_6$) δ: 0.920-0.930 (d, J=6.0 Hz, 3H), 0.970-0.980 (d, J=6.0 Hz, 3H), 1.400-1.402 (m, 2H), 1.518-1.600 (m, 6H), 1.706-1.741 (m, 1H), 1.918-1.924 (m, 2H), 2.345-2.392 (m, 6H), 3.550 (s, 3H), 4.334-4.356 (t, J=6.6 Hz, J=6.6 Hz, 2H), 4.505-4.527 (d, J=13.2 Hz, 1H), 4.606-4.615 (d, J=5.4 Hz, 1H), 4.697-4.724 (m, 1H), 6.941-6.956 (d, J=9.0 Hz, 1H), 7.586-7.604 (d, J=10.8 Hz, 1H), 7.830-7.845 (d, J=9.0 Hz, 1H), 8.279 (s, 1H), 8.914 (s, 1H).

Example 10: 6-fluoro-2-methyl-7-(6-(3-(piperidin-1-yl)propoxy)pyridin-3-yl)-9,10-dihydro-8-thia-2,4,10a-triazanaphtho[2,1,8-cde]azulen-1(2H)-one (A-10)

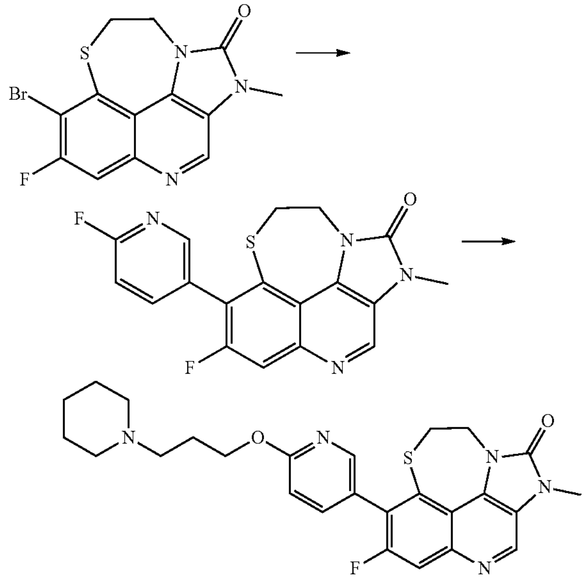

Except starting materials were changed, the synthesis method was the same as that of example 1 to afford 6-fluoro-2-methyl-7-(6-(3-(piperidin-1-yl)propoxy)pyridin-3-yl)-9,10-dihydro-8-thia-2,4,10a-triazanaphtho[2,1,8-cde] azulen-1(2H)-one (90 mg, 45.2% yield). ESI-MS (m/z): 494.12 $[M+H]^+$; $^1H$ NMR (600 MHz, DMSO-$d_6$) δ: 1.424-1.425 (m, 3H), 1.560-1.562 (m, 5H), 1.910-1.980 (m, 2H), 2.420-2.421 (m, 2H), 2.631-2.632 (m, 2H), 3.350-3.353 (m, 2H), 3.565 (s, 3H), 4.297-4.366 (m, 4H), 6.952-6.966 (d, J=8.4 Hz, 1H), 7.719-7.774 (m, 2H), 8.126-8.130 (d, J=8.4 Hz, 1H), 8.996 (s, 1H).

Example 11: 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1-cyclopropan]-1-one (A-11)

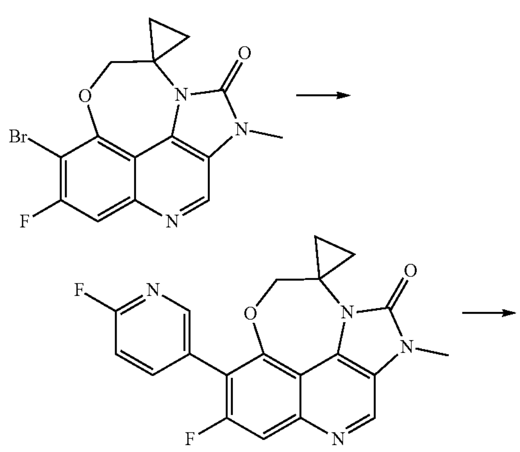

-continued

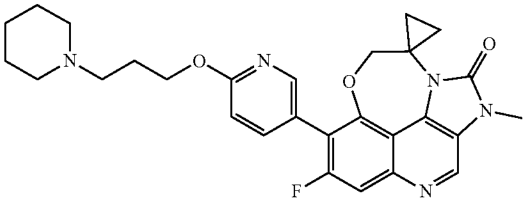

Except starting materials were changed, the synthesis method was the same as that of example 1 to afford 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1-cyclopropan]-1-one (50 mg, 21.2% yield). ESI-MS (m/z): 504.23 $[M+H]^+$; $^1H$ NMR (600 MHz, DMSO-$d_6$) δ: 1.062-1.064 (m, 2H), 1.425-1.557 (m, 2H), 1.557-1.574 (m, 4H), 1.915-2.207 (m, 4H), 2.508-2.587 (m, 5H), 3.90-3.475 (m, 4H), 4.33-4.354 (t, J=6.6 Hz, 2H), 4.464 (s, 2H), 6.939 (d, J=8.4 Hz, 1H), 7.594 (d, J=10.8 Hz, 1H), 7.812 (m 1H), 8.254 (s, 1H), 8.896 (s, 1H).

Example 12: 9-(ethoxymethyl)-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-12)

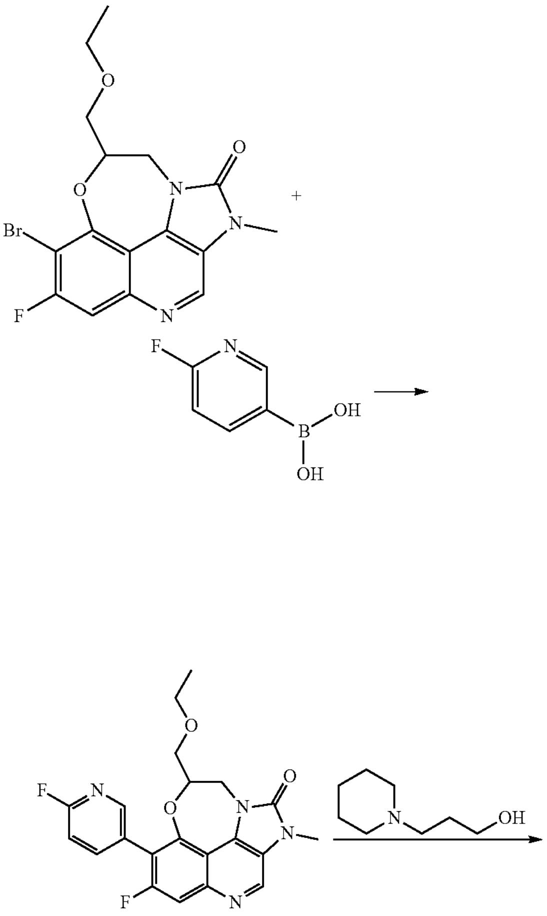

-continued

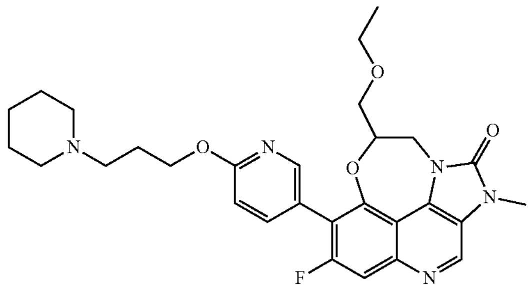

Except starting materials were changed, the synthesis method was the same as that of example 1 to afford 9-(ethoxymethyl)-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (86 mg, 51.0% yield). ESI-MS (m/z): 536.26 $[M+H]^+$; $^1H$ NMR (600 MHz, $CD_3OD$) δ: 1.110-1.134 (m, 3H), 1.594 (s, 2H), 1.744-1.762 (m, 4H), 2.145-1.172 (m, 2H), 2.870-2.918 (m, 6H), 3.423-3.489 (m, 2H), 3.612-3.720 (m, 5H), 3.987-4.026 (m, 1H), 4.419-4.439 (m, 2H), 4.545 (d, J=13.8 Hz, 1H), 4.657 (d, J=9.6 Hz, 1H), 6.921 (d, J=8.4 Hz, 1H), 7.513 (d, J=10.8 Hz, 1H), 7.884 (dd, $J_1$=1.2 Hz, $J_2$=8.4 Hz, 1H), 8.285 (s, 1H), 8.788 (s, 1H).

Example 13: (S)-10-benzyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-13)

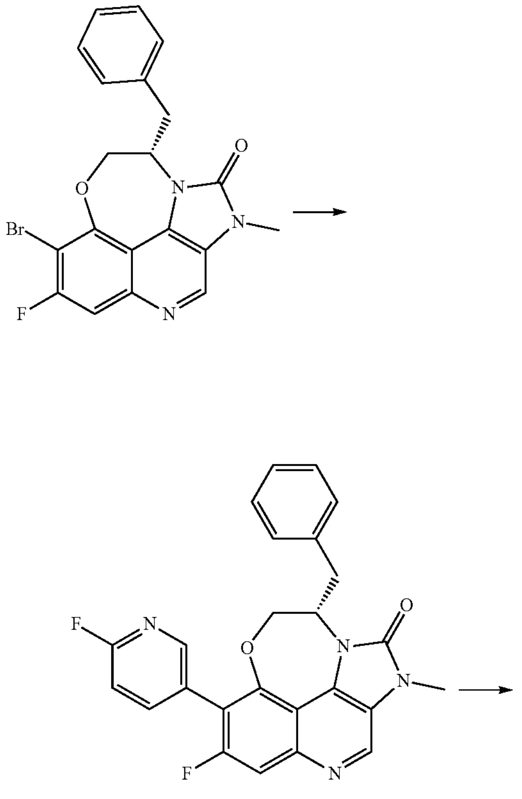

-continued

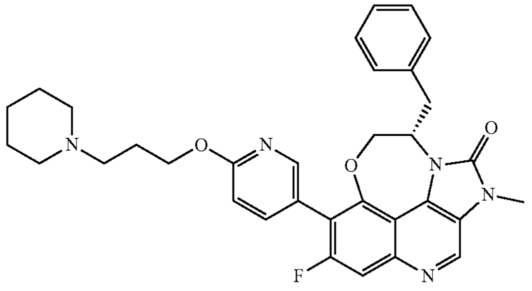

Except starting materials were changed, the synthesis method was the same as that of example 1 to afford (S)-10-benzyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (30 mg, 20.2% yield). ESI-MS (m/z): 568.26 $[M+H]^+$; $^1H$NMR (600 MHz, DMSO-$d_6$) δ: 1.463-1.624 (m, 6H), 2.055-2.103 (m, 2H), 2.695-2.713 (m, 4H), 3.104-3.190 (m, 4H), 3.569 (s, 3H), 4.297-4.440 (m, 4H), 4.692-4.714 (m, 1H), 6.985 (d, J=8.4 Hz, 1H), 7.246-7.349 (m, 5H), 7.626 (d, J=11.4 Hz, 1H), 7.928 (d, J=8.4 Hz, 1H), 8.343 (s, 1H), 8.952 (s, 1H).

Example 14: (R)-10-benzyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-14)

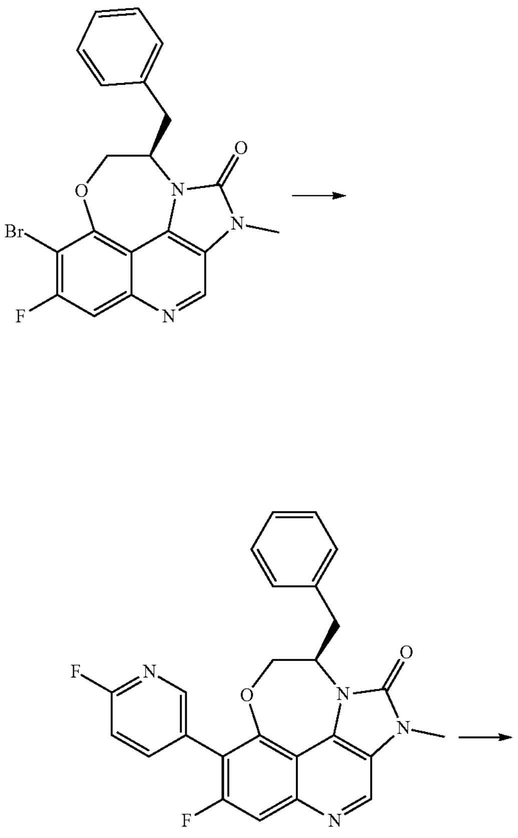

-continued

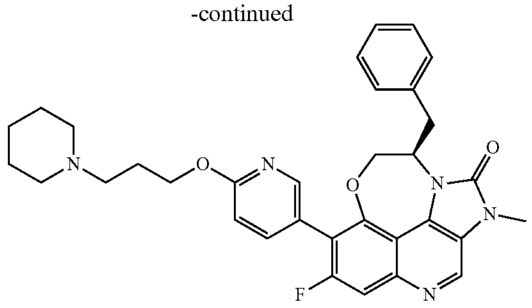

Except starting materials were changed, the synthesis method was the same as that of example 1 to afford (R)-10-benzyl-6-fluoro-2-methyl-7-(6-(3-(piperidin-1-yl) propoxy)pyridin-3-yl)-9,10-dihydro-8-oxa-2,4,10a-triazanaphtho[2,1,8-cde]azulen-1(2H)-one (53 mg, 41.5% yield). ESI-MS (m/z): 568.26 $[M+H]^+$; $^1H$ NMR (600 MHz, DMSO-$d_6$) δ: 1.463-1.624 (m, 6H), 2.055-2.103 (m, 2H), 2.695-2.713 (m, 4H), 3.104-3.190 (m, 4H), 3.569 (s, 3H), 4.297-4.440 (m, 4H), 4.692-4.714 (m, 1H), 6.976-6.990 (d, J=8.4 Hz, 1H), 7.246-7.349 (m, 5H), 7.616-7.635 (d, J=11.4 Hz, 1H), 7.921-7.935 (d, J=8.4 Hz, 1H), 8.343 (s, 1H), 8.952 (s, 1H).

Example 15: 7-(6-(3-dimethylamino-propoxy)-pyridin-3-yl)-6-fluoro-2-methyl-9,10-dihydro-8-oxa-2,4,10a-triazanaphtho[2,1,8-cde]azulen-1(2H)-one (A-15)

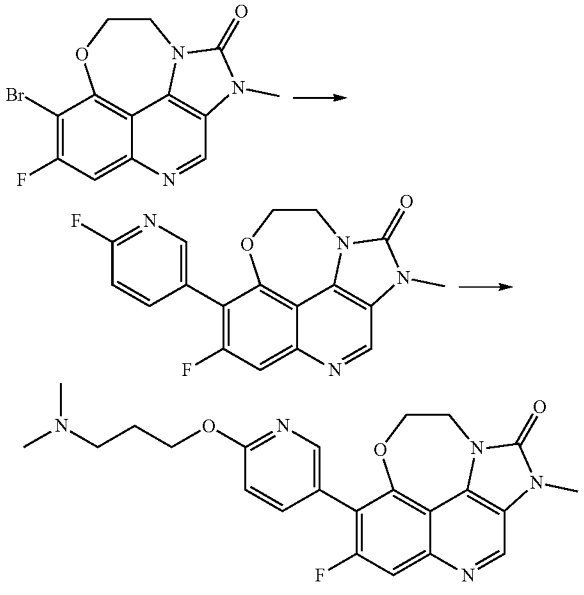

Except starting materials were changed, the synthesis method was the same as that of example 1 to afford 7-(6-(3-dimethylamino-propoxy)-pyridin-3-yl)-6-fluoro-2-methyl-9,10-dihydro-8-oxa-2,4,10a-triazanaphtho[2,1,8-cde]azulen-1(2H)-one (15 mg, 48.2% yield). ESI-MS (m/z): 438.42 $[M+H]^+$; $^1H$ NMR (600 MHz, $CD_3OD$) δ: 2.076-2.102 (m, 2H), 2.467 (s, 6H), 2.747-2.773 (m, 2H), 3.624 (s, 3H), 4.325-4.330 (m, 2H), 4.407-4.427 (m, 2H), 4.608-4.620 (m, 2H), 6.939 (d, J=8.4 Hz, 1H), 7.534 (d, J=16.8 Hz, 1H), 7.832 (d, J=14.4 Hz, 1H), 8.236 (s, 1H), 8.807 (s, 1H).

Example 16: (S)-6-fluoro-10-isopropyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-16)

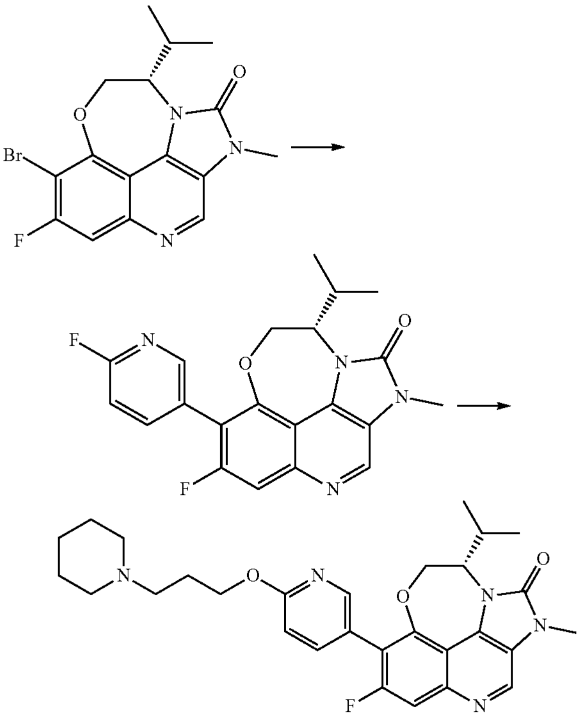

Except starting materials were changed, the synthesis method was the same as that of example 1 to afford (S)-6-fluoro-10-isopropyl-2-methyl-7-(6-(3-(piperidin-1-yl) propoxy)pyridin-3-yl)-9,10-dihydro-8-oxa-2,4,10a-triazanaphtho[2,1,8-cde]azulen-1(2H)-one (50 mg, 24% yield). ESI-MS (m/z): 520.26 $[M+H]^+$; $^1H$ NMR (600 MHz, DMSO-$d_6$) δ: 0.933 (d, J=7.2 Hz, 3H), 1.013 (d, J=6.6 Hz, 3H), 1.400-1.537 (m, 6H), 1.922-1.954 (m, 2H), 2.221-2.258 (m, 1H), 2.433-2.514 (m, 6H), 3.558 (s, 3H), 4.282-4.351 (m, 3H), 4.445-4.468 (m, 1H), 4.828-4.856 (m, 1H), 6.935 (d, J=8.4 Hz, 1H), 7.566 (d, J=10.8 Hz, 1H), 7.828-7.813 (m, 1H), 8.260 (s, 1H), 8.909 (s, 1H).

Example 17: (R)-6-fluoro-10-isopropyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-17)

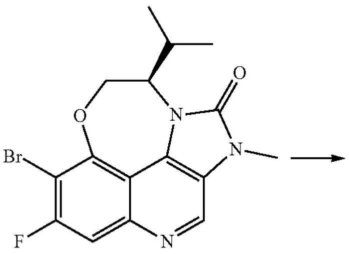

-continued

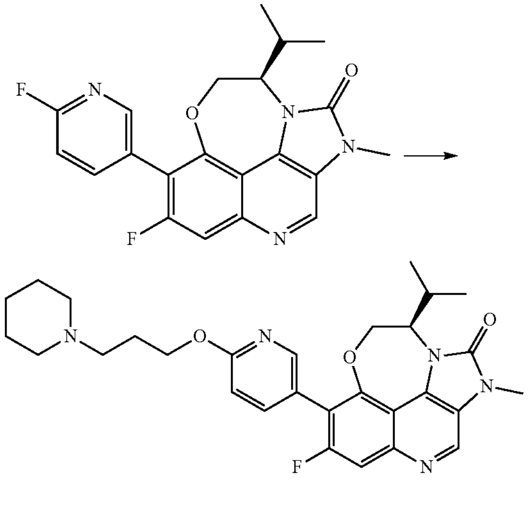

Except starting materials were changed, the synthesis method was the same as that of example 1 to afford (R)-6-fluoro-10-isopropyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (45 mg, 24% yield). ESI-MS (m/z): 520.26 $[M+H]^+$; $^1H$ NMR (600 MHz, DMSO-$d_6$) δ: 0.947 (d, J=6.6 Hz, 3H), 1.022 (d, J=6.6 Hz, 3H), 1.415-1.544 (m, 6H), 1.933-1.963 (m, 2H), 2.240-2.261 (m, 1H), 2.449-2.529 (m, 6H), 3.560 (s, 3H), 4.296-4.365 (m, 3H), 4.459-4.482 (m, 1H), 4.839-4.867 (m, 1H), 6.949 (d, J=8.4 Hz, 1H), 7.579 (d, J=10.8 Hz, 1H), 7.840-7.825 (m, 1H), 8.271 (s, 1H), 8.920 (s, 1H).

Example 18: 6-fluoro-9-isopropyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-18)

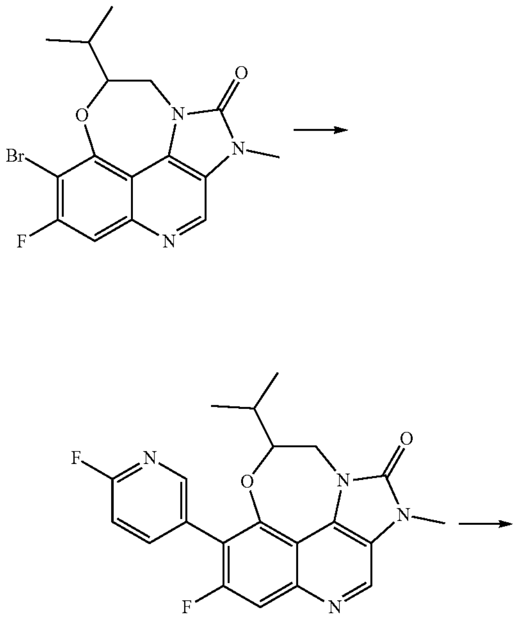

-continued

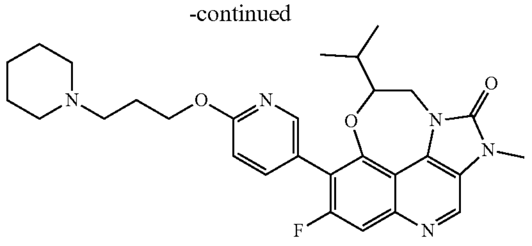

Except starting materials were changed, the synthesis method was the same as that of example 1 to afford 6-fluoro-9-isopropyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (58 mg, 44.3% yield). ESI-MS (m/z): 519.26 $[M+H]^+$; $^1H$ NMR (600 MHz, DMSO) S: 0.635 (d, J=7.2 Hz, 3H), 0.798 (d, J=6.6 Hz, 3H), 1.305-1.892 (m, 6H), 1.909-1.962 (m, 1H), 2.012-2.198 (m, 2H), 2.753-2.965 (m, 2H), 3.137-3.326 (m, 4H), 3.547 (s, 3H), 3.994-4.032 (m, 1H), 4.290-4.378 (m, 4H), 6.961 (d, J=8.4 Hz, 1H), 7.590 (d, J=10.8 Hz, 1H), 7.852-7.840 (m, 1H), 8.267 (s, 1H), 8.921 (s, 1H).

Example 19: (S)-9-((dimethylamino)methyl)-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-19)

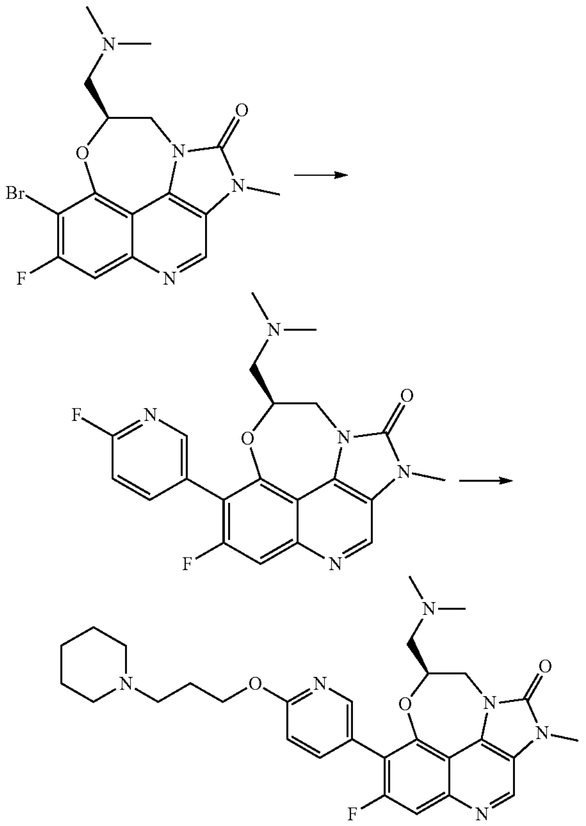

Except starting materials were changed, the synthesis method was the same as that of example 1 to afford (S)-9-((dimethylamino)methyl)-6-fluoro-2-methyl-7-(6-(3-(piperidin-1-yl)propoxy)pyridin-3-yl)-9,10-dihydro-8-oxa- 2,4,10a-triazanaphtho[2,1,8-cde]azulen-1(2H)-one (100 mg, 55.0% yield). ESI-MS (m/z): 535.28 $[M+H]^+$; $^1H$ NMR (600 MHz, DMSO-$d_6$) δ: 1.600 (s, 2H), 1.746-1.763 (m, 4H), 2.149-2.193 (m, 8H), 2.650-2.671 (m, 2H), 2.813-2.864 (m, 6H), 3.648 (s, 3H), 4.016-4.055 (q, 1H), 4.448 (t, J=6.0 Hz, 2H), 4.660 (d, J=13.2 Hz, 2H), 6.960 (d, J=9.0 Hz, 1H), 7.550 (d, J=10.8 Hz, 1H), 7.797 (d, J=8.4 Hz, 1H), 8.290 (s, 1H), 8.833 (s, 1H).

Example 20: (S)-6-fluoro-2-methyl-7-(6-(3-(piperidin-1-yl)propoxy)pyridin-3-yl)-9-(piperidin-1-ylmethyl)-9,10-dihydro-8-oxa-2,4,10a-triazanaphtho[2,1,8-cde]azulen-1(2H)-one (A-20)

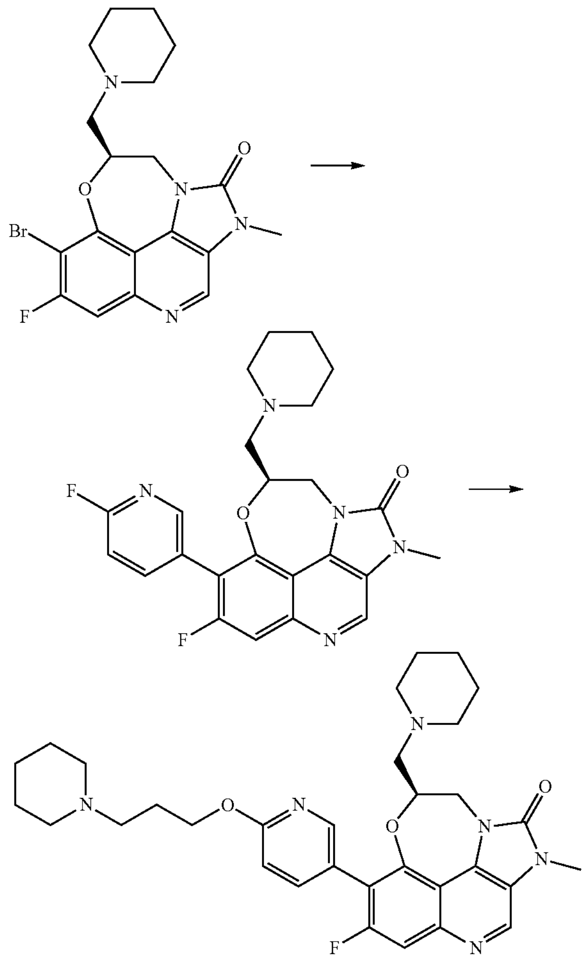

Except starting materials were changed, the synthesis method was the same as that of example 1 to afford (S)-6-fluoro-2-methyl-7-(6-(3-(piperidin-1-yl)propoxy) pyridin-3-yl)-9-(piperidin-1-ylmethyl)-9,10-dihydro-8-oxa-2,4,10a-triazanaphtho[2,1,8-cde]azulen-1(2H)-one (150 mg, 29.6% yield). ESI-MS (m/z): 575.31 $[M+H]^+$; $^1H$ NMR (600 MHz, DMSO-$d_6$) δ: 1.396 (s, 2H), 1.478-1.515 (m, 4H), 1.550 (s, 2H), 1.678-1.716 (m, 4H), 2.092-2.119 (m, 2H), 2.329 (s, 4H), 2.607-2.700 (m, 8H), 3.627 (s, 3H), 3.973-4.013 (m, 1H), 4.415-4.587 (m, 2H), 4.611-4.915 (m, 2H), 6.942 (d, J=9.0 Hz, 1H), 7.521 (d, J=10.8 Hz, 1H), 7.902-7.921 (m, 1H), 8.318 (s, 1H), 8.785 (s, 1H).

Example 21: 4-fluoro-12-methyl-5-(6-(3-(piperidin-1-yl)propoxy)pyridin-3-yl)-6a,7,8,9,10,10a-hexahydro-6-oxa-2,10b,12-triazacyclopenta[gh]pleiaden-11(12H)-one (A-21)

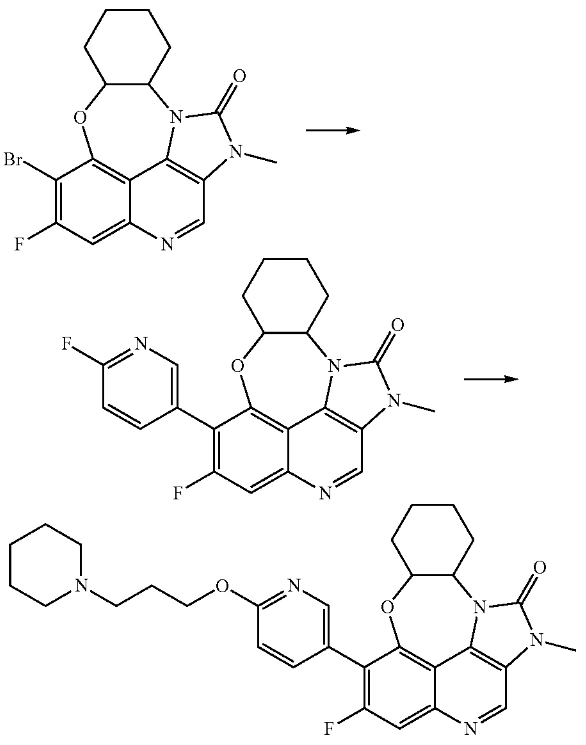

Except starting materials were changed, the synthesis method was the same as that of example 1 to afford 4-fluoro-12-methyl-5-(6-(3-(piperidin-1-yl)propoxy)pyridin-3-yl)-6a,7,8,9,10,10a-hexahydro-6-oxa-2,10b,12-triazacyclopenta[gh]pleiaden-11(12H)-one (200 mg, 38.5% yield). ESI-MS (m/z): 532.26 $[M+H]^+$; $^1H$ NMR (600 MHz, DMSO-$d_6$) δ: 1.635-1.693 (m, 4H), 1.788-1.830 (m, 7H), 2.120 (d, J=12.0 Hz, 1H), 2.179-2.225 (m, 2H), 2.954-2.999 (m, 7H), 3.593 (s, 3H), 3.691 (d, J=13.2 Hz, 1H), 4.305-4.339 (m, 2H), 4.456-4.476 (m, 2H), 6.961 (d, J=8.4 Hz, 1H), 7.517 (d, J=10.8 Hz, 1H), 7.852-7.869 (m, 1H), 8.271 (s, 1H), 8.794 (s, 1H).

Example 22: (R)-10-ethyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-22)

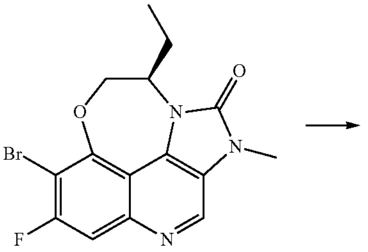

-continued

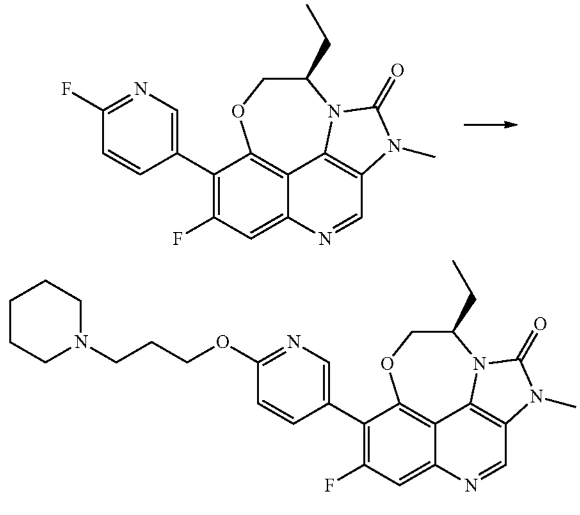

Except starting materials were changed, the synthesis method was the same as that of example 1 to afford (R)-10-ethyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (150 mg, 14.3% yield). ESI-MS (m/z): 506.25 $[M+H]^+$; $^1H$ NMR (600 MHz, DMSO-$d_6$) δ: 1.099-1.111 (m, 3H), 1.560 (s, 2H), 1.693-1.730 (m, 4H), 1.942-1.979 (m, 2H), 2.091-2.138 (m, 2H), 2.682-2.749 (m, 6H), 3.640 (s, 3H), 4.410-4.460 (m, 3H), 4.510-4.525 (m, 1H), 4.815-4.842 (m, 1H), 6.938 (d, J=8.4 Hz, 1H), 7.505 (d, J=10.8 Hz, 1H), 7.825 (d, J=8.4 Hz, 1H), 8.238 (s, 1H), 8.802 (s, 1H).

Example 23: (S)-10-ethyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-23)

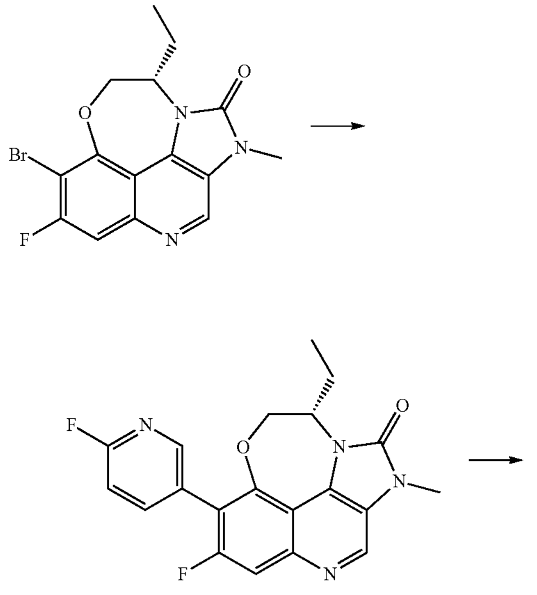

-continued

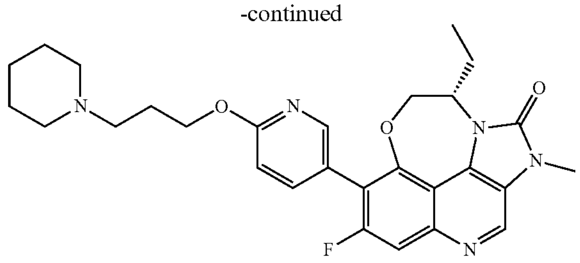

Except starting materials were changed, the synthesis method was the same as that of example 1 to afford (S)-10-ethyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (180 mg, 42.6% yield). ESI-MS (m/z): 506.25 $[M+H]^+$; $^1H$ NMR (600 MHz, DMSO-$d_6$) δ: 1.099-1.111 (m, 3H), 1.533 (s, 2H), 1.663-1.701 (m, 4H), 1.932-1.969 (m, 2H), 2.065-2.112 (m, 2H), 2.643-2.712 (m, 6H), 3.625 (s, 3H), 4.390-4.441 (m, 2H), 4.442 (d, J=13.2 Hz, 1H), 4.484-4.512 (m, 1H), 4.798-4.825 (m, 1H), 6.922 (d, J=8.4 Hz, 1H), 7.512 (d, J=10.8 Hz, 1H), 7.807-7.824 (m, 1H), 8.229 (s, 1H), 8.802 (s, 1H).

Example 24: 6-fluoro-2,9-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-24)

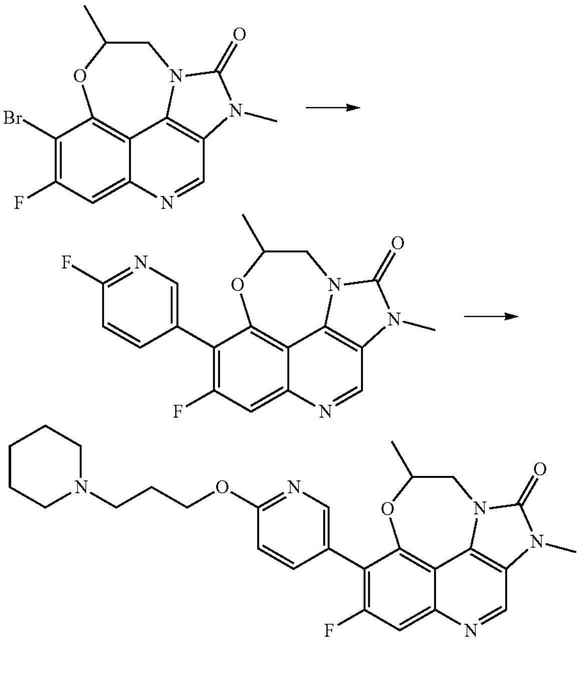

Except starting materials were changed, the synthesis method was the same as that of example 1 to afford 6-fluoro-2,9-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (68 mg, 33.2% yield). ESI-MS (m/z): 491.23 $[M+H]^+$; $^1H$ NMR (600 MHz, $CD_3OD$) δ: 1.448 (d, J=5.4 Hz, 3H), 1.537 (m, 2H), 1.663-1.701 (m, 4H), 2.067-2.114 (m, 2H), 2.579-2.654 (m, 6H), 3.620 (s, 3H), 3.932-3.971 (m, 1H), 4.405-4.432 (m, 3H), 4.677-4.702 (m, 1H), 6.942 (d, J=8.4 Hz, 1H), 7.504 (d, J=10.8 Hz, 1H), 7.831-7.849 (m, 1H), 8.245 (s, 1H), 8.777 (s, 1H), 1.448 (d, 3H), 1.537 (m, 2H), 1.663-1.701 (m, 4H), 2.067-2.114 (m, 2H), 2.579-2.654 (m, 6H), 3.620 (s, 3H), 3.932-3.971 (m, 1H), 4.405-4.432 (m, 3H), 4.677-4.702 (m, 1H), 6.942 (d, 1H), 7.504 (d, 1H), 7.831-7.849 (m, 1H), 8.245 (s, 1H), 8.777 (s, 1H).

Example 25: 6-fluoro-9-(2-fluoropyridin-4-yl)-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-25)

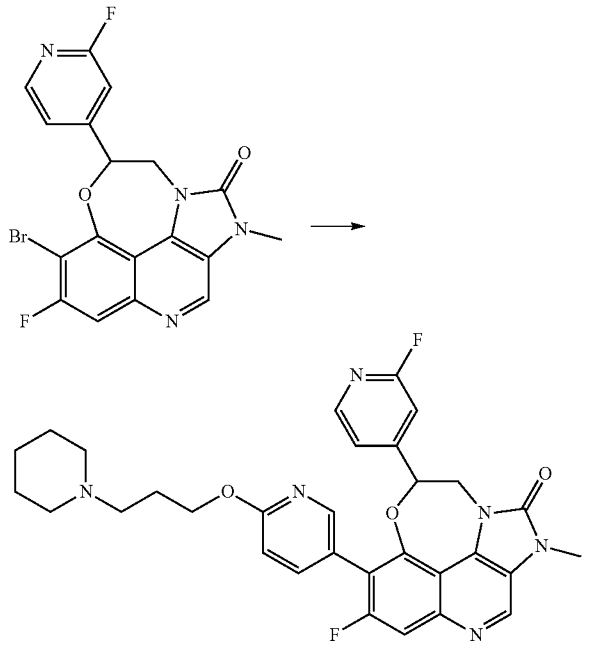

Except starting materials were changed, the synthesis method was the same as that of example 1 to afford 6-fluoro-9-(2-fluoropyridin-4-yl)-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (85 mg, 26.8% yield). ESI-MS (m/z): 573.23 $[M+H]^+$; $^1H$ NMR (600 MHz, MeOD) δ 1.530-1.687 (m, 6H), 2.025-2.089 (m, 2H), 2.649-2.675 (m, 6H), 3.645 (s, 3H), 4.187-4.227 (m, 1H), 4.365 (t, J=6.6 Hz, 2H), 4.646-4.669 (m, 1H), 5.808-5.824 (m, 1H), 6.781 (d, J=7.8 Hz, 1H), 6.974 (s, 1H), 7.305 (d, J=4.8 Hz, 1H), 7.597 (d, J=10.8 Hz, 1H), 7.751 (d, J=8.4 Hz, 1H), 8.161-8.199 (m, 2H), 8.860 (s, 1H).

Example 26: 6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-26)

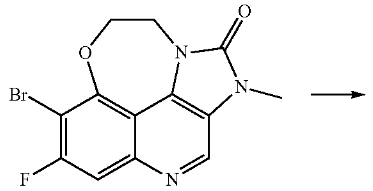

-continued

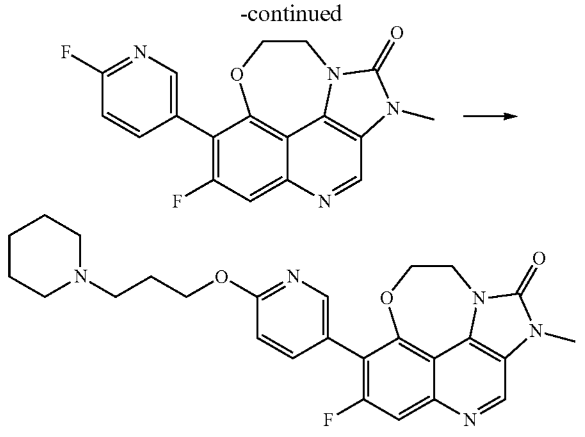

Except starting materials were changed, the synthesis method was the same as that of example 1 to afford 6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (25 mg, 1900 yield). ESI-MS (m/z): 478.22 $[M+H]^+$; $^1H$ NMR (600 MHz, DMSO-$d_6$) δ: 1.356-1.450 (m, 2H), 1.514-1.532 (m, 4H), 1.916-1.939 (m, 2H), 2.406-2.461 (m, 6H), 3.540 (s, 3H), 4.204-4.212 (m, 2H), 4.331-4.353 (t, J=6.6 Hz, 2H), 4.607-4.619 (t, J=3.6 Hz, 2H), 6.943 (d, J=8.4 Hz, 1H), 7.585 (d, J=10.8 Hz, 1H), 7.821 (d, J=8.4 Hz, 1H), 8.257 (s, 1H), 8.903 (s, 1H).

Example 27: 10-cyclopropyl-6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-27)

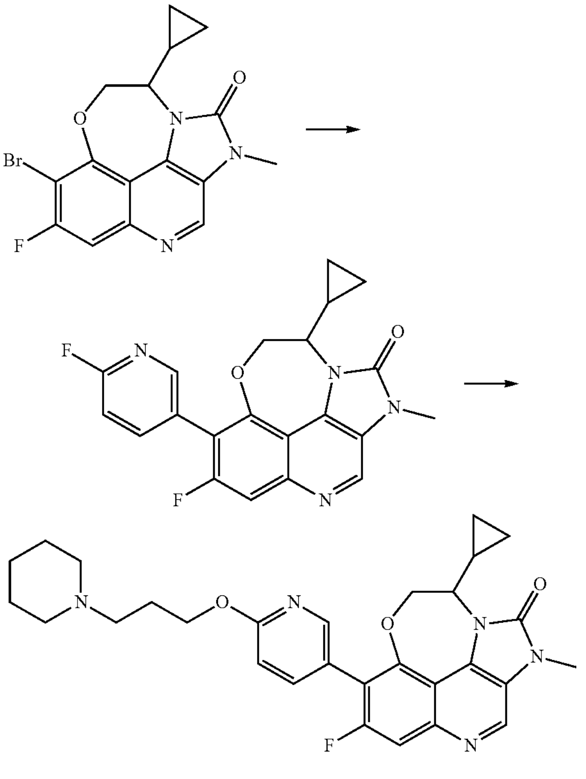

Except starting materials were changed, the synthesis method was the same as that of example 1 to afford 10-cyclopropyl-6-fluoro-2-methyl-7-(6-(3-(piperidin-1-yl) propoxy)pyridin-3-yl)-9,10-dihydro-8-oxa-2,4,10a-triazanaphtho[2,1,8-cde]azulen-1(2H)-one (40 mg, 39.0% yield). ESI-MS (m/z): 518.25 $[M+H]^+$; $^1H$ NMR (600 MHz, DMSO-$d_6$) δ 0.495-0.535 (m, 3H), 0.863-0.901 (m, 1H), 1.281-1.358 (m, 1H), 1.388-1.490 (m, 2H), 1.501-1.592 (m, 4H), 1.901-1.992 (m, 2H), 2.385-2.502 (m, 6H), 3.550 (s, 3H), 3.924-3.943 (m, 1H), 4.336-4.358 (t, J=6.6 Hz, 2H), 4.535-4.557 (d, J=13.2 Hz, 1H), 4.698-4.725 (m, 1H), 6.945-6.960 (m, 1H), 7.586-7.605 (d, J=11.4 Hz, 1H), 7.838-7.854 (m, 1H), 8.285 (s, 1H), 8.913 (s, 1H).

Example 28: 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclobutan]-1-one (A-28)

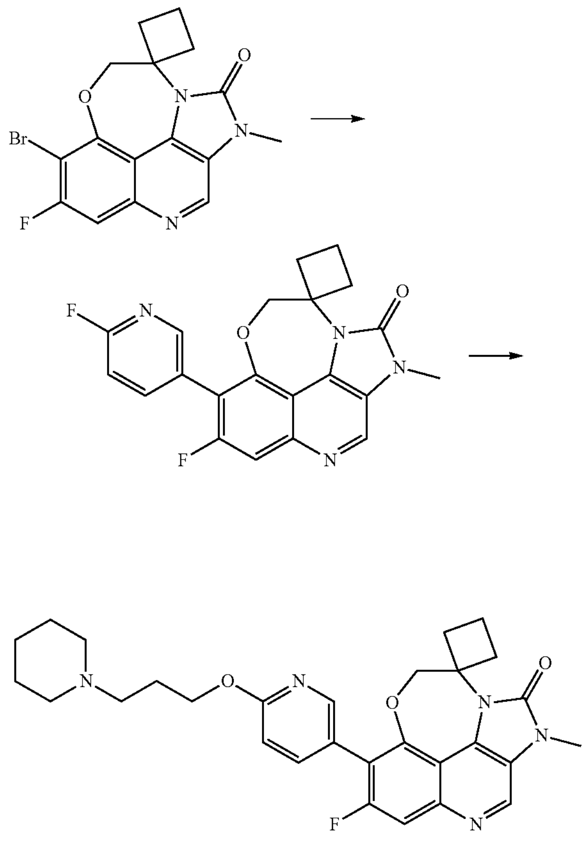

Except starting materials were changed, the synthesis method was the same as that of example 1 to afford 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclobutan]-1-one (70 mg, 44.2% yield). ESI-MS (m/z): 518.25 $[M+H]^+$; $^1H$ NMR (600 MHz, DMSO-$d_6$) δ: 1.410-1.541 (m, 8H), 1.910-1.964 (m, 6H), 2.466-2.508 (m, 6H), 3.524 (s, 3H), 4.344-4.365 (t, J=6.6 Hz, 2H), 4.647 (m, 2H), 6.953-6.967 (d, J=8.4 Hz, 1H), 7.577-7.595 (d, J=10.8 Hz, 1H), 7.839-7.853 (d, J=8.4 Hz, 1H), 8.286 (s, 1H), 8.900 (s, 1H).

Example 29: 7-(6-(3-(dimethylamino)propoxy)pyridin-3-yl)-6-fluoro-2-methyl-2,9-dihydro-1H-spiro[8-oxa-2,4,10a-triazanaphtho[2,1,8-cde]azulene-10,1'-cyclopropan]-1-one (A-29)

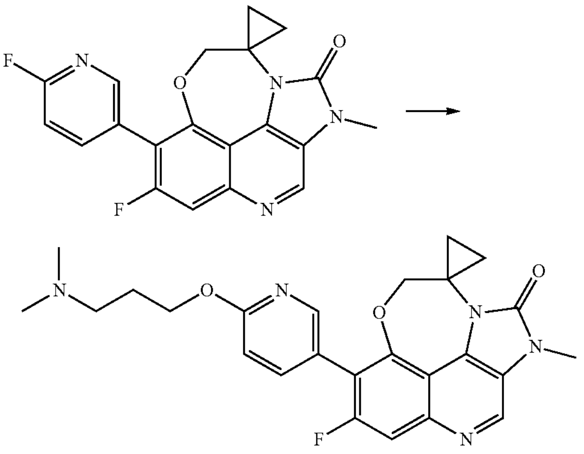

Except starting materials were changed, the synthesis method was the same as that of example 1 to afford 7-(6-(3-(dimethylamino)propoxy)pyridin-3-yl)-6-fluoro-2-methyl-2,9-dihydro-1H-spiro[8-oxa-2,4,10a-triazanaphtho[2,1,8-cde]azulene-10,1'-cyclopropan]-1-one (47 mg, 39.1% yield). ESI-MS (m/z): 464.20 $[M+H]^+$; $^1H$ NMR (600 MHz, DMSO-$d_6$) δ: 1.058-1.061 (m, 2H), 1.962-2.194 (m, 4H), 2.383 (s, 6H), 2.660-2.663 (m, 2H), 3.478 (s, 3H), 4.338-4.359 (t, J=6.6 Hz, 2H), 4.468 (m, 2H), 6.927-6.941 (d, J=8.4 Hz, 1H), 7.599-7.618 (d, J=11.4 Hz, 1H), 7.817-7.832 (d, J=9.0 Hz, 1H), 8.256 (s, 1H), 8.916 (s, 1H).

Example 30: 6-methoxy-2-methyl-7-(1-methyl-1H-pyrazol-4-yl)-10-(pyridin-2-yl)-9,10-dihydro-8-oxa-2,4,10a-triazanaphtho[2,1,8-cde]azulen-1(2H)-one (A-30)

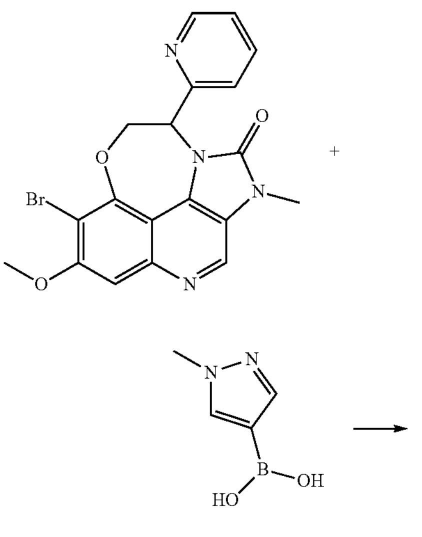

-continued

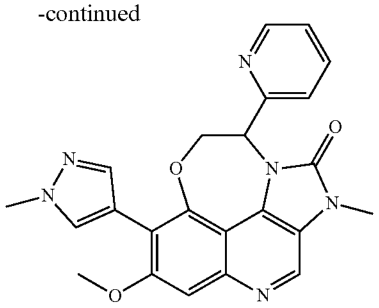

7-bromo-6-methoxy-2-methyl-10-(pyridin-2-yl)-9,10-dihydro-8-oxa-2,4,10a-trazanaphtho[2,1,8-cde]azulen-1(2H)-one (200 mg, 0.47 mmol), cesium carbonate (382 mg, 1.17 mmol), (1-methyl-1H-pyrazol-4-yl)boronic acid (90 mg, 0.71 mmol), tetrakis(triphenylphosphine)palladium (55 mg, 0.05 mmol), and 1,4-dioxane (20 mL) were successively added to a 100 mL reaction bottle. The reaction solution was heated up to 120° C. under $N_2$ protection to react for 4 h. The reaction solution was cooled down to room temperature, concentrated to dryness, and then the residue was purified by column chromatography (DCM:MeOH=40:1-30:1) to afford 6-methoxy-2-methyl-7-(1-methyl-1H-pyrazol-4-yl)-10-(pyridin-2-yl)-9,10-dihydro-8-oxa-2,4,10a-triazanaphtho[2,1,8-cde]azulen-1(2H)-one (80 mg, 40.1% yield). ESI-MS (m/z): 429.16 $[M+H]^+$; $^1H$ NMR (600 MHz, DMSO-$d_6$) δ: 3.525 (s, 3H), 3.943-3.967 (m, 6H), 4.867-4.916 (m, 2H), 5.206 (m, 1H), 7.039 (s, 1H), 7.233-7.255 (m, 1H), 7.533 (d, J=8.4 Hz, 1H), 7.755-7.783 (m, 1H), 8.234 (s, 1H), 8.274 (d, J=3.6 Hz, 1H), 8.372 (s, 1H), 8.669 (s, 1H).

Example 31: (S)-6-methoxy-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-31)

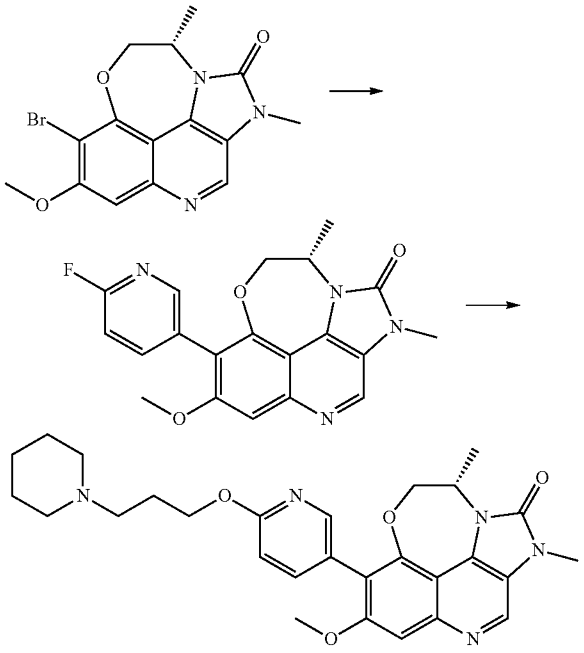

Except starting materials were changed, the synthesis method was the same as that of example 1 to afford (S)-6-methoxy-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (68 mg, 33.2% yield). ESI-MS (m/z): 504.25 $[M+H]^+$; $^1H$ NMR (600 MHz, $CD_3OD$) δ: 1.543 (d, J=6.6 Hz, 3H), 1.573-1.626 (m, 2H), 1.781 (m, 4H), 2.170-2.196 (m, 2H), 2.945 (brs, 6H), 3.637 (s, 3H), 3.925 (s, 3H), 4.436 (t, J=6.0 Hz, 2H), 4.465-4.571 (m, 2H), 4.685-4.699 (m, 1H), 6.916 (d, J=9.0 Hz, 1H), 7.308 (s, 1H), 7.749-7.767 (m, 1H), 8.152-8.156 (m, 1H), 8.743 (s, 1H).

Example 32: (R)-6-methoxy-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-32)

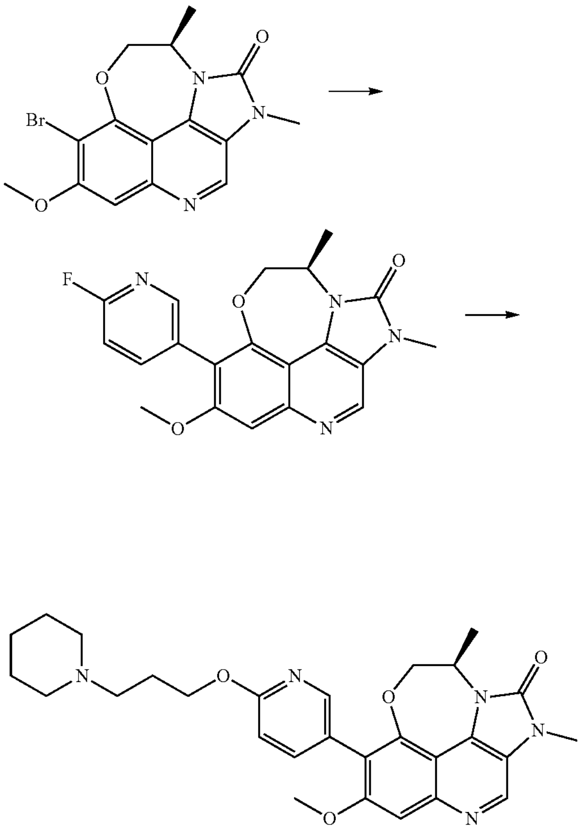

Except starting materials were changed, the synthesis method was the same as that of example 1 to afford (R)-6-methoxy-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (68 mg, 33.2% yield). ESI-MS (m/z): 504.25 $[M+H]^+$; $^1H$ NMR (600 MHz, $CD_3OD$) δ: 1.509 (d, J=6.6 Hz, 3H), 1.597 (brs, 2H), 1.739-1.776 (m, 4H), 2.134-2.181 (m, 2H), 2.881-2.938 (m, 6H), 3.604 (s, 3H), 3.893 (s, 3H), 4.407 (t, J=6.0 Hz, 2H), 4.426-4.538 (m, 2H), 4.651-4.665 (m, 1H), 6.878-6.893 (m, 1H), 7.268 (s, 1H), 7.717-7.735 (m, 1H), 8.119-8.123 (m, 1H), 8.703 (s, 1H).

Example 33: 4-methoxy-12-methyl-5-(1-methyl-1H-pyrazol-4-yl)-6-oxa-2,10b,12-triazacyclopenta[gh]pleiaden-11(12H)-one (A-33)

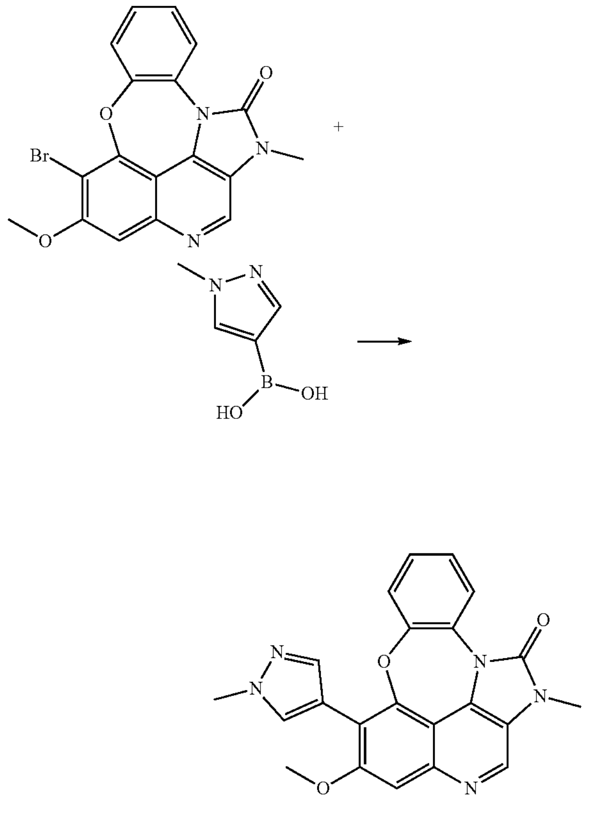

Except starting materials were changed, the synthesis method was the same as that of example 30 to afford 4-methoxy-12-methyl-5-(1-methyl-1H-pyrazol-4-yl)-6-oxa-2,10b,12-triazacyclopenta[gh]pleiaden-11(12H)-one (120 mg, 31.5% yield). ESI-MS (m/z): 400.41 $[M+H]^+$; $^1H$ NMR (600 MHz, DMSO-$d_6$) δ: 3.585 (s, 3H), 3.970-3.998 (m, 6H), 7.192-7.208 (m, 1H), 7.271-7.299 (m, 1H), 7.316-7.344 (m, 2H), 8.005 (s, 1H), 8.251 (s, 1H), 8.414-8.431 (m, 1H), 8.866 (s, 1H).

Example 34: (S)-9-(dimethylamino)methyl)-6-fluoro-2-methyl-7-(1-methyl-1H-pyrazol-4-yl)-9,10-dihydro-8-oxa-2,4,10a-triazanaphtho[2,1,8-cde]azulen-1(2H)-one (A-34)

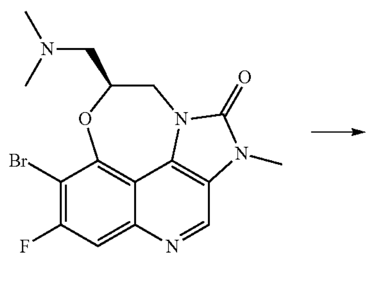

-continued

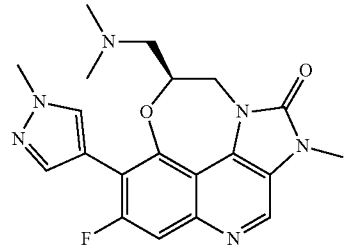

Except starting materials were changed, the synthesis method was the same as that of example 30 to afford (S)-9-(dimethylamino)methyl)-6-fluoro-2-methyl-7-(1-methyl-1H-pyrazol-4-yl)-9,10-dihydro-8-oxa-2,4,10a-triazanaphtho[2,1,8-cde]azulen-1(2H)-one (60 mg, 50% yield). ESI-MS (m/z): 397.17 $[M+H]^+$; $^1H$ NMR (600 MHz, $CD_3OD$) δ: 2.235 (s, 6H), 2.729-2.801 (m, 2H), 3.533 (s, 3H), 3.935 (s, 4H), 4.523-4.546 (m, 1H), 4.779-4.787 (m, 1H), 7.555 (d, J=13.2 Hz, 1H), 7.996 (d, J=2.4 Hz, 1H), 8.488 (s, 1H), 8.851 (s, 1H).

Example 35: 6-fluoro-2-methyl-7-(1-methyl-1H-pyrazol-4-yl)-9,10-dihydro-8-thia-2,4,10a-triazanaphtho[2,1,8-cde]azulen-1(2H)-one (A-35)

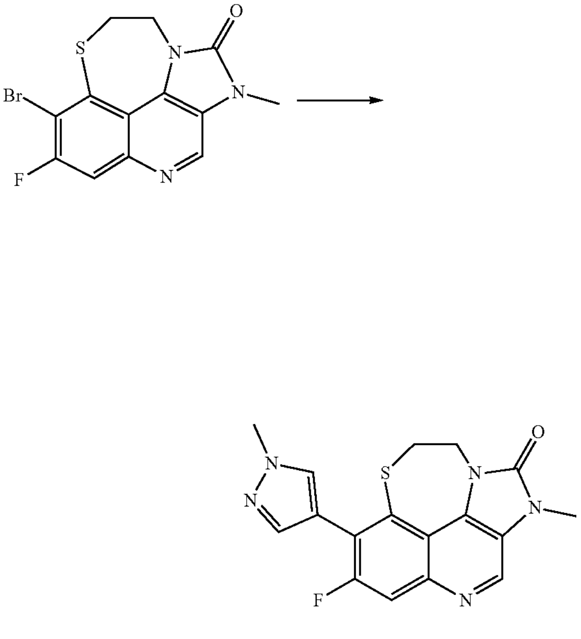

Except starting materials were changed, the synthesis method was the same as that of example 30 to afford 6-fluoro-2-methyl-7-(1-methyl-1H-pyrazol-4-yl)-9,10-dihydro-8-thia-2,4,10a-triazanaphtho[2,1,8-cde]azulen-1(2H)-one (0.15 g, 50% yield). ESI-MS (m/z): 356.23 $[M+H]^+$; $^1H$ NMR (600 MHz, DMSO-$d_6$) δ: 3.362 (t, J=4.8 Hz, 2H), 3.561 (s, 3H), 3.954 (s, 3H), 4.347 (t, J=4.8 Hz, 2H), 7.589 (s, 1H), 7.708 (d, J=10.2 Hz, 1H), 7.948 (s, 1H), 8.952 (s, 1H).

Example 36: 6-fluoro-2-methyl-7-(1-methyl-1H-pyrazol-4-yl)-9,10-dihydro-8-thia-2,4,10a-triazanaphtho[2,1,8-cde]azulen-1(2H)-one 8-oxide (A-36)

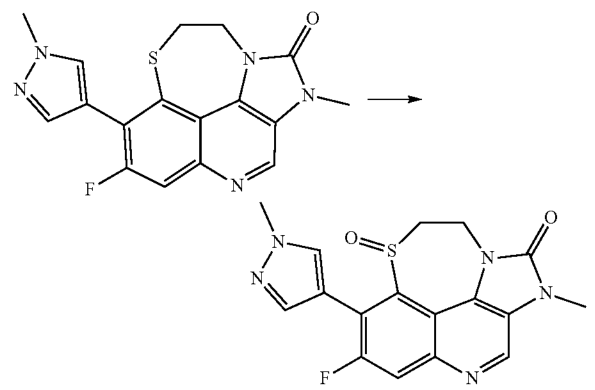

6-fluoro-2-methyl-7-(1-methyl-1H-pyrazol-4-yl)-9,10-dihydro-8-thia-2,4,10a-triazinaphthalo[2,1,8-cde]azulen-1 (2H)-one (0.05 g, 0.14 mmol) was dissolved in dichloromethane (20 mL), and followed by adding m-chloroperoxybenzoic acid (0.03 g, 0.17 mmol) into the vessel of reaction mixture in an ice bath, and the system was stirred for 1 h in the ice bath. A small amount of starting material was found as detected by TLC. The reaction solution was washed with a saturated aqueous solution of sodium thiosulfate (10 mL×2) and a saturated aqueous solution of sodium chloride (10 mL×2), then dried with anhydrous sodium sulfate, concentrated under reduced pressure to remove the solvent, and the residue was purified by column chromatography (DCM:MeOH=50:1-25:1) to afford final product 6-fluoro-2-methyl-7-(1-methyl-1H-pyrazol-4-yl)-9,10-dihydro-8-thia-2,4,10a-triazanaphtho[2,1,8-cde] azulen-1(2H)-one 8-oxide (0.04 g, 77% yield). ESI-MS (m/z): 372.23 $[M+H]^+$; $^1H$ NMR (600 MHz, DMSO-$d_6$) δ: 3.651 (m, 3H), 3.842-3.793 (m, 1H), 3.994 (s, 3H), 4.053-4.022 (m, 1H), 4.541-4.530 (m, 1H), 4.567-4.552 (m, 1H), 7.751 (s, 1H), 8.104 (d, J=10.8 Hz, 1H), 8.153 (s, 1H), 9.048 (s, 1H).

Example 37: 6-fluoro-2-methyl-7-(1-methyl-1H-pyrazol-4-yl)-9,10-dihydro-8-thia-2,4,10a-triazanaphtho[2,1,8-cde]azulen-1(2H)-one 8,8-dioxide (A-37)

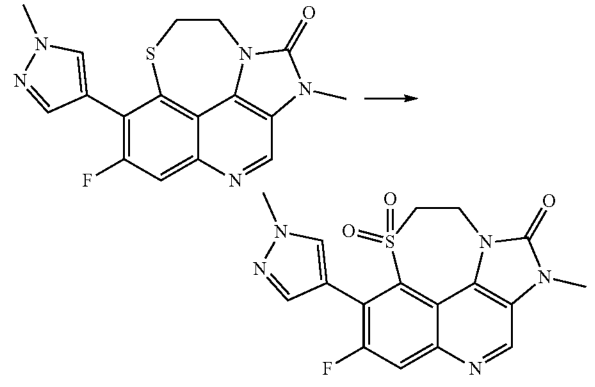

6-fluoro-2-methyl-7-(1-methyl-1H-pyrazol-4-yl)-9,10-dihydro-8-thia-2,4,10a-triazinaphthalo [2,1,8-cde]azulen-1 (2H)-one (0.05 g, 0.14 mmol) was dissolved in dichloromethane (20 mL), and followed by adding m-chloroperoxybenzoic acid (0.05 g, 0.28 mmol) into the vessel of reaction mixture in an ice bath, and the system was stirred for 24 h at room temperature. No starting material was found as detected by TLC. The reaction solution was washed with a saturated aqueous solution of sodium thiosulfate (10 mL×2) and a saturated aqueous solution of sodium chloride (10 mL×2), then dried with anhydrous sodium sulfate, concentrated under reduced pressure to remove the solvent, and the residue was purified by column chromatography (DCM:MeOH=50:1-30:1) to afford 6-fluoro-2-methyl-7-(1-methyl-1H-pyrazol-4-yl)-9,10-dihydro-8-thia-2,4,10a-triazanaphtho[2,1,8-cde]azulen-1 (2H)-one 8,8-dioxide (0.015 g, 27.3% yield). ESI-MS (m/z): 388.34 $[M+H]^+$; $^1H$ NMR (600 MHz, DMSO-$d_6$) δ: 3.590 (s, 3H), 3.941 (s, 3H), 4.202 (t, J=4.8 Hz, 2H), 4.423 (t, J=4.8 Hz, 2H), 7.634 (s, 1H), 7.974 (s, 1H), 8.193 (d, J=10.2 Hz, 1H), 9.112 (s, 1H).

Example 38: Ethyl (6aR,10aS)-4-fluoro-12-methyl-5-(1-methyl-1H-pyrazol-4-yl)-11-oxo-6a,7,10,10a,11,12-hexahydro-6-oxa-2,8,10b,12-tetraazacyclopentadiene-8(9H)-carboxylate (A-38)

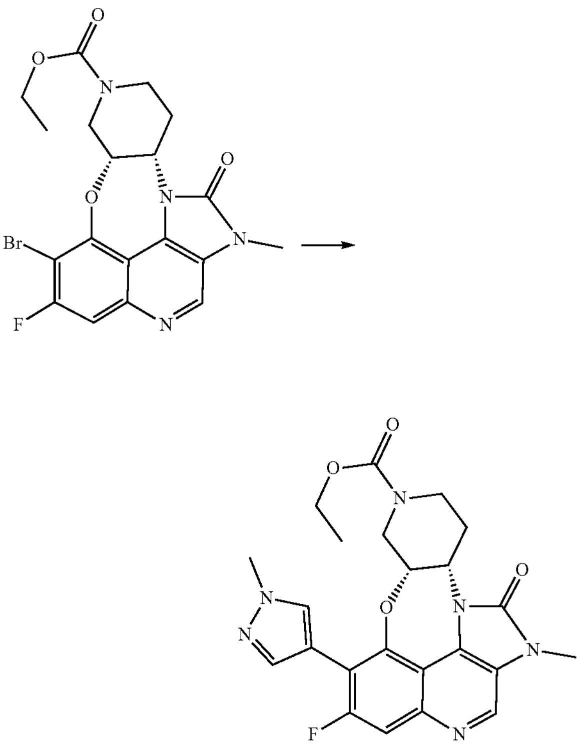

Except starting materials were changed, the synthesis method was the same as that of example 30 to afford ethyl (6aR,10aS)-4-fluoro-12-methyl-5-(1-methyl-1H-pyrazol-4-yl)-11-oxo-6a,7,10,10a,11,12-hexahydro-6-oxa-2,8,10b,12-tetraazacyclopentadiene-8(9H)-carboxylate (0.10 g, 59% yield). ESI-MS (m/z): 467.2 $[M+H]^+$.

Example 39: 6-fluoro-10-(4-fluorophenyl)-2-methyl-7-(1-methyl-1H-pyrazol-4-yl)-9,10-dihydro-8-oxa-2,4,10a-triazanaphtho[2,1,8-cde]azulen-1(2H)-one (A-39)

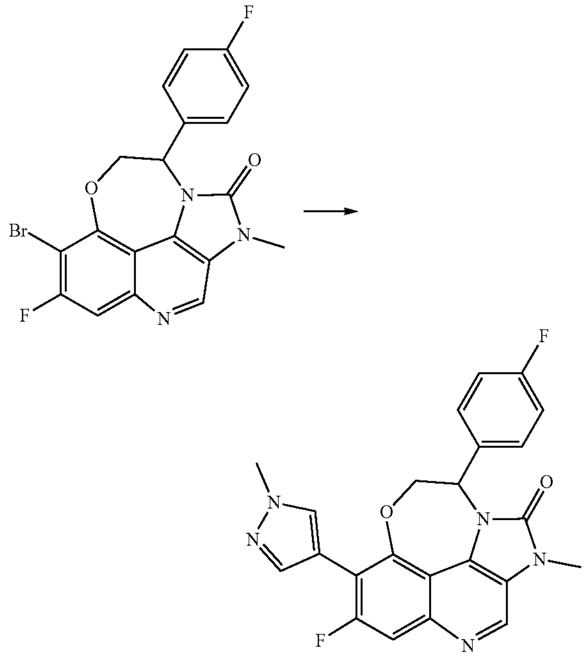

Except starting materials were changed, the synthesis method was the same as that of example 30 to afford 6-fluoro-10-(4-fluorophenyl)-2-methyl-7-(1-methyl-1H-pyrazol-4-yl)-9,10-dihydro-8-oxa-2,4,10a-triazanaphtho[2,1,8-cde]azulen-1(2H)-one (0.05 g, 50% yield). ESI-MS (m/z): 434.2 $[M+H]^+$; $^1H$ NMR (600 MHz, DMSO-$d_6$) δ: 3.561 (s, 3H), 3.882 (s, 3H), 4.833 (d, J=13.2 Hz, 1H), 5.134 (d, J=13.2 Hz, 1H), 5.820 (s, 1H), 7.171-7.141 (m, 2H), 7.282-7.262 (m, 2H), 7.603 (d, J=12.6 Hz, 1H), 7.774 (s, 1H), 8.070 (s, 1H), 8.941 (s, 1H).

Example 40: 4-methoxy-12-methyl-5-(1-methyl-1H-pyrazol-4-yl)-6-oxa-2,9,10b,12-tetraazacyclopenta[gh]pleiaden-11(12H)-one (A-40)

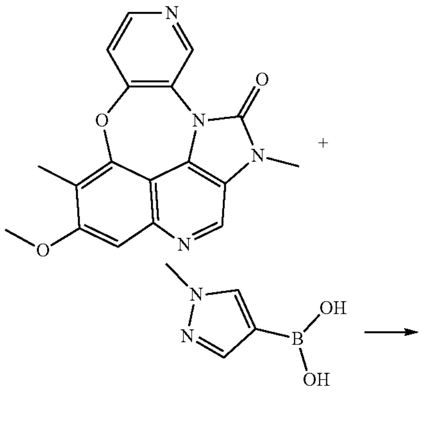

-continued

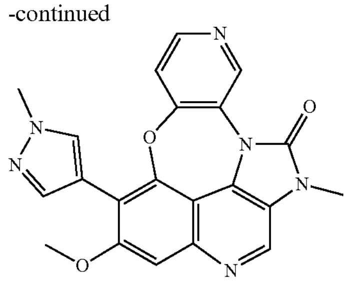

Except starting materials were changed, the synthesis method was the same as that of example 30 to afford 4-methoxy-12-methyl-5-(1-methyl-1H-pyrazol-4-yl)-6-oxa-2,9,10b,12-tetraazacyclopenta[gh]pleiaden-11(12H)-one (12 mg, 30% yield). ESI-MS (m/z): 401.11 $[M+H]^+$; $^1H$ NMR (600 MHz, $CD_3OD$) δ: 3.597 (s, 3H), 3.973 (s, 3H), 4.001 (s, 3H), 7.261 (d, J=5.4 Hz, 1H), 7.399 (s, 1H), 7.953 (s, 1H), 8.230 (s, 1H), 8.455 (d, J=5.4 Hz, 1H), 8.923 (s, 1H), 9.714 (s, 1H).

Example 41: (6aS,9aR)-4-fluoro-11-methyl-5-(6-(3-(piperidin-1-yl)propoxy)pyridin-3-yl)-6a,7,9,9a-tetrahydro-6,8-dioxa-2,9b,11-triazacyclopenta[h]naphtho[2,1,8-cde]azulen-10(11H)-one (A-41)

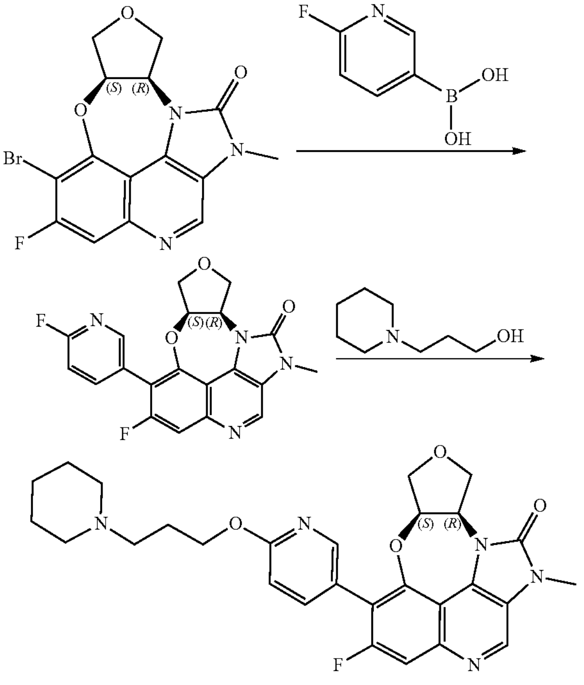

Except starting materials were changed, the synthesis method was the same as that of example 1 to afford (6aS,9aR)-4-fluoro-11-methyl-5-(6-(3-(piperidin-1-yl)propoxy)pyridin-3-yl)-6a,7,9,9a-tetrahydro-6,8-dioxa-2,9b,11-triazacyclopenta[h]naphtho[2,1,8-cde]azulen-10(11H)-one (40 mg, 33.6% yield). ESI-MS (m/z): 520.19 $[M+H]^+$; $^1H$ NMR (600 MHz, DMSO-$d_6$) δ: 1.590 (s, 2H), 1.749 (t, J=10.8 Hz, 4H), 2.136-2.172 (m, 2H), 2.855-2.913 (m, 6H), 3.563 (s, 3H), 3.791 (t, J=16.8 Hz, 1H), 4.144 (t, J=19.8 Hz, 1H), 4.209 (t, J=16.8 Hz, 1H), 4.420 (t, J=12.0 Hz, 2H), 4.628-4.671 (m, 1H), 4.879 (s, 1H), 5.194 (dd, J=1=8.4 Hz, $J_2$=16.2 Hz, 1H), 6.915 (d, J=8.4 Hz, 1H), 7.545 (d, J=10.8 Hz, 1H), 7.804 (d, J=7.8 Hz, 1H), 8.210 (s, 1H), 8.791 (s, 1H).

Example 42: (6aR,9aS)-4-fluoro-11-methyl-5-(6-(3-(piperidin-1-yl)propoxy)pyridin-3-yl)-6a,7,9,9a-tetrahydro-6,8-dioxa-2,9b,11-triazacyclopenta[h]naphtho[2,1,8-cde]azulen-10(11H)-one (A-42)

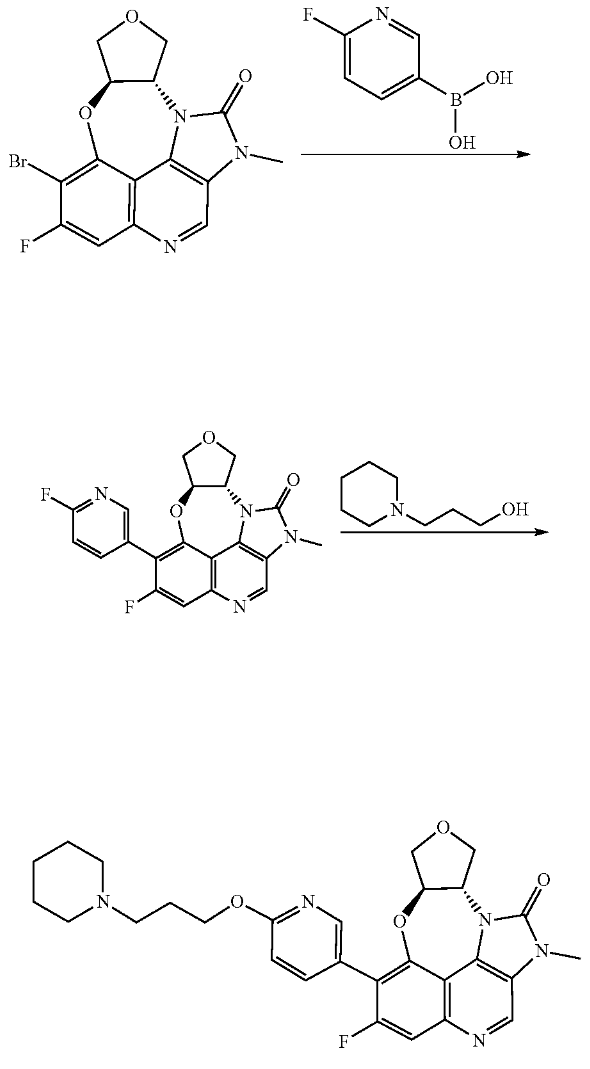

Except starting materials were changed, the synthesis method was the same as that of example 1 to afford (6aR,9aS)-4-fluoro-11-methyl-5-(6-(3-(piperidin-1-yl)propoxy)pyridin-3-yl)-6a,7,9,9a-tetrahydro-6,8-dioxa-2,9b,11-triazacyclopenta[h]naphtho[2,1,8-cde]azulen-10(11H)-one. ESI-MS (m/z): 520.23 $[M+H]^+$; $^1H$ NMR (600 MHz, $CD_3OD$) δ: 1.550 (brs, 2H), 1.674-1.711 (m, 4H), 2.071-2.118 (m, 2H), 2.679-2.743 (m, 6H), 3.581 (s, 3H), 3.807 (t, J=8.4 Hz, 1H), 4.148-4.180 (m, 1H), 4.218 (t, J=8.4 Hz, 1H), 4.397 (t, J=6.0 Hz, 2H), 4.678-4.722 (m, 1H), 4.910-4.937 (m, 1H), 5.230 (q, J=8.4 Hz, 1H), 6.908 (d, J=8.4 Hz, 1H), 7.572 (d, J=13.2 Hz, 1H), 7.801 (d, J=8.4 Hz, 1H), 8.206 (s, 1H), 8.824 (s, 1H).

Example 43: 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,3'-oxetan]-1-one (A-43)

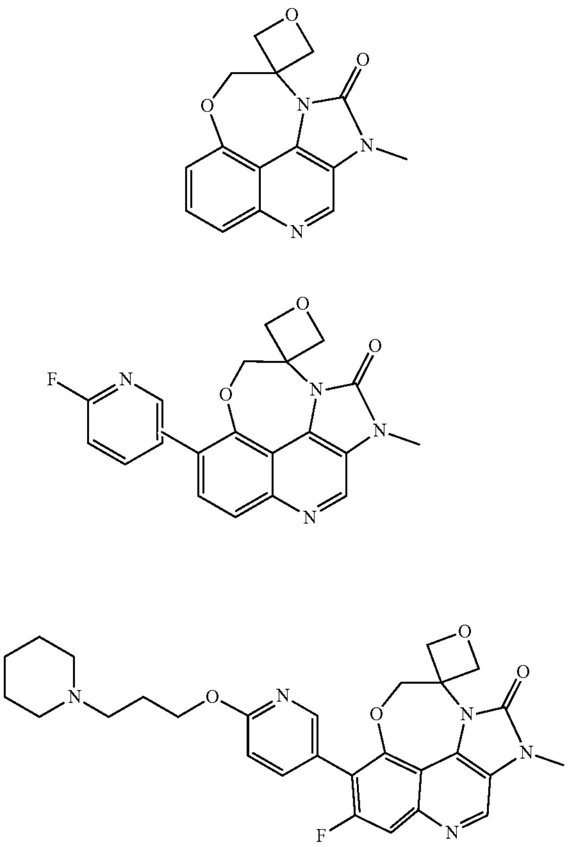

Except starting materials were changed, the synthesis method was the same as that of example 1 to afford 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,3'-oxetan]-1-one (74 mg, 40.4% yield). ESI-MS (m/z): 520.23 $[M+H]^+$; $^1H$ NMR (600 MHz, DMSO-$d_6$) δ: 1.380-1.405 (m, 2H), 1.500-1.589 (m, 4H), 1.947-1.956 (m, 2H), 2.465-2.737 (m, 6H), 3.557 (s, 3H), 4.348-4.370 (t, J=6.6 Hz, 2H), 4.348-4.500 (m, 2H), 4.875-4.960 (m, 2H), 5.424-5.592 (m, 2H), 6.958-6.972 (d, J=8.4 Hz, 1H), 7.621-7.639 (d, J=10.8 Hz, 1H), 7.860-7.874 (d, J=8.4 Hz, 1H), 8.298 (s, 1H), 8.952 (s, 1H).

Example 44: 6-methoxy-10-(hydroxymethyl)-2-methyl-7-(1-methyl-1H-pyrazol-4-yl)-9,10-dihydro-8-oxa-2,4,10a-triazanaphtho[2,1,8-cde]azulen-1(2H)-one (A-44)

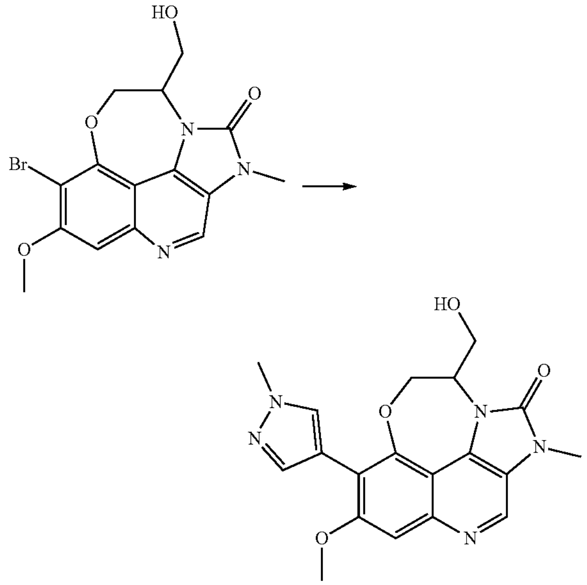

Except starting materials were changed, the synthesis method was the same as that of example 30 to afford 6-methoxy-10-hydroxymethyl-2-methyl-7-(1-methyl-1H-pyrazol-4-yl)-9,10-dihydro-8-oxa-2,4,10a-triazanaphtho[2,1,8-cde]azulen-1(2H)-one (180 mg, 90.2% yield). ESI-MS (m/z): 370.1 $[M+H]^+$; $^1H$ NMR (600 MHz, DMSO) δ: 3.332 (s, 3H), 3.718-3.740 (m, 2H), 3.916 (s, 3H), 3.945 (s, 3H), 4.373-4.415 (m, 1H), 4.993-5.019 (m, 1H), 5.326-5.345 (m, 1H), 7.229 (s, 1H), 7.924 (s, 1H), 8.125 (s, 1H), 8.729 (s, 1H).

Example 45: 6-methoxy-2,10,10-trimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-45)

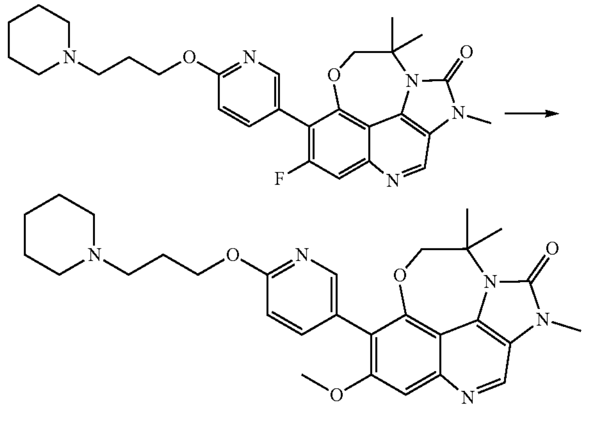

DMF (10 mL) and methanol (8 mg, 0.24 mmol) were added to a 100 mL reaction bottle and cooled down to 0° C., followed by adding NaH (60%, 15 mg, 0.36 mmol), and the reaction was conducted at this temperature for 0.5 h. Then 6-fluoro-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (60 mg, 0.12 mmol) was added, and the reaction was conducted at 65° C. for 24 h. When the reaction was completed as detected by TLC, water was added into the reaction solution to quench the reaction, and then the reaction mixture was concentrated to dryness. The residue was purified by column chromatography (DCM:MeOH=20:1-15:1) to afford 6-methoxy-2,10,10-trimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (36 mg, 58.2% yield). ESI-MS (m/z): 518.27 $[M+H]^+$; $^1H$ NMR (600 MHz, DMSO-$d_6$) δ: 1.370-1.405 (m, 2H), 1.490-1.520 (m, 4H), 1.609 (s, 6H), 1.862-1.910 (m, 2H), 2.356-2.410 (m, 6H), 3.474 (s, 3H), 3.383 (s, 3H), 4.300-4.339 (m, 4H), 6.871 (d, J=8.4 Hz, 1H), 7.269 (s, 1H), 7.688-7.706 (m, 1H), 8.138 (d, J=1.8 Hz, 1H), 8.784 (s, 1H).

Example 46: 7-(6-(3-(dimethylamino)propoxy)pyridin-3-yl)-6-fluoro-2,10,10-trimethyl-9,10-dihydro-8-oxa-2,4,10a-triazanaphtho[2,1,8-cde]azulen-1(2H)-one (A-46)

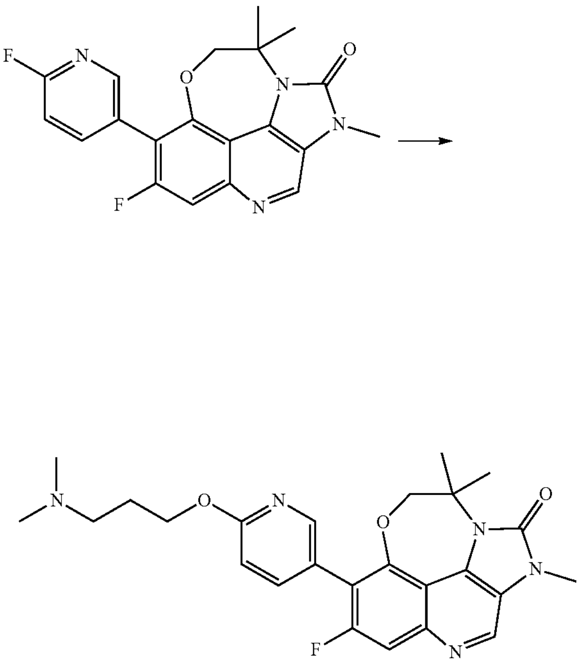

The synthesis method was the same as that of example 1, except that 3-(dimethylamino)propan-1-ol was used instead of 3-(piperidin-1-yl)propan-1-ol to afford 7-(6-(3-(dimethylamino)propoxy)pyridin-3-yl)-6-fluoro-2,10,10-trimethyl-9,10-dihydro-8-oxa-2,4,10a-triazanaphtho[2,1,8-cde]azulen-1(2H)-one (40 mg, 41.5% yield). ESI-MS (m/z): 466.22 $[M+H]^+$; $^1H$ NMR (600 MHz, DMSO-$d_6$) δ: 1.639 (s, 6H), 1.874-1.898 (m, 2H), 2.156 (s, 6H), 2.366 (t, J=7.2 Hz, 2H), 3.504 (s, 3H), 4.340 (t, J=6.6 Hz, 2H), 4.443 (s, 2H), 6.948 (d, J=8.4 Hz, 1H), 7.598 (d, J=11.4 Hz, 1H), 7.827-7.843 (m, 1H), 8.276 (s, 1H), 8.901 (s, 1H).

Example 47: 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclopropan]-1-one (A-47)

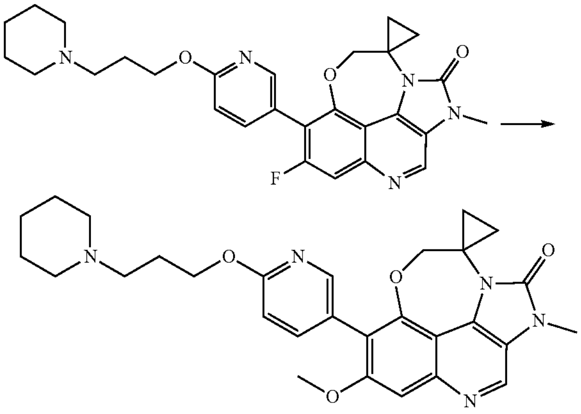

Except starting materials were changed, the synthesis method was the same as that of example 45 to afford 6-fluoro-2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclopropan]-1-one (25 mg, 49.2% yield). ESI-MS (m/z): 504.22 $[M+H]^+$; $^1H$ NMR (600 MHz, DMSO-$d_6$) δ: 0.999-1.050 (m, 2H), 1.130-1.283 (m, 2H), 1.400-1.596 (m, 2H), 1.604-1.710 (m, 4H), 2.067-2.174 (m, 4H), 2.508-2.873 (m, 4H), 3.451 (s, 3H), 3.836 (s, 3H), 4.327-4.348 (m, 4H), 6.860 (d, J=8.4 Hz, 1H), 7.294 (s, 1H), 7.680-7.697 (m, 1H), 8.115 (d, J=1.8 Hz, 1H), 8.803 (s, 1H).

Example 48: 6-fluoro-10-(hydroxymethyl)-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-48)

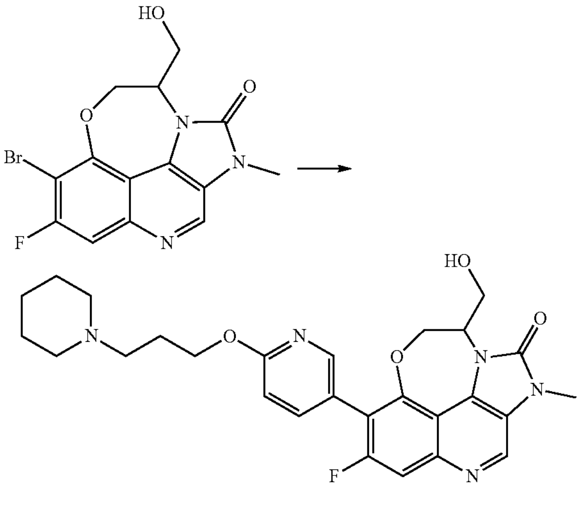

Except starting materials were changed, the synthesis method was the same as that of example 1 to afford 6-fluoro-10-(hydroxymethyl)-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (0.10 g, 48.3% yield). ESI-MS (m/z): 508.21 $[M+H]^+$; $^1H$ NMR (600 MHz, DMSO-$d_6$) δ: 1.427-1.568 (m, 6H), 1.984-1.985 (m, 2H), 2.500-2.506 (m, 6H), 3.547 (s, 3H), 3.630-3.721 (m, 2H), 4.350-4.371 (t, J=6.6 Hz, 2H), 4.438-4.444 (m, 1H), 4.505-4.527 (m, 1H), 4.820-4.846 (m, 1H), 5.268-5.287 (t, J=11.4 Hz, 1H), 6.947-6.962 (d, J=9.0 Hz, 1H), 7.590-7.609 (d, J=11.4 Hz, 1H), 7.844-7.858 (d, J=8.4 Hz, 1H), 8.288 (s, 1H), 8.918 (s, 1H).

Example 49: 6-fluoro-10-(methoxymethyl)-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-49)

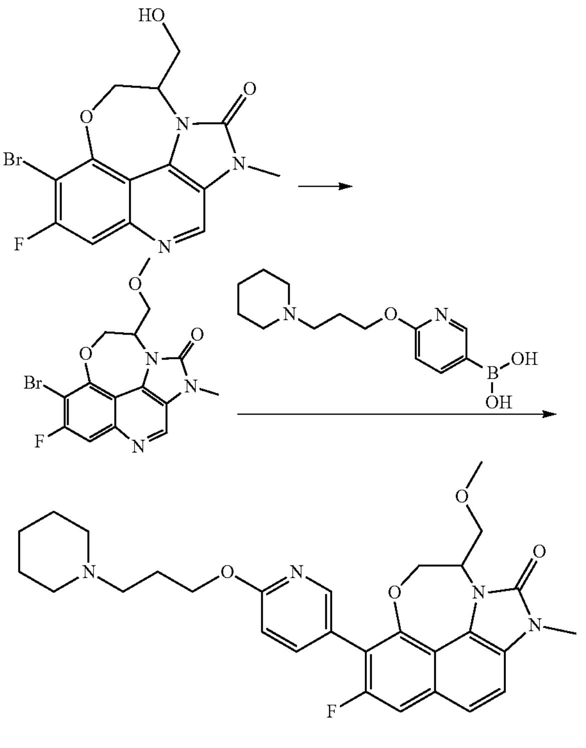

Step 1: Synthesis of 7-bromo-6-fluoro-10-(methoxymethyl)-2-methyl-9,10-dihydro-8-oxa-2,4,10a-triazanaphtho[2,1,8-cde]azulen-1(2H)-one THF (10 mL) and 7-bromo-6-fluoro-10-(hydroxymethyl)-2-methyl-9,10-dihydro-8-oxa-2,4,10a-triazanaphtho[2,1,8-cde]azulen-1(2H)-one (0.10 g, 0.27 mmol) were successively added to a 100 mL reaction bottle, cooled down to 0° C. followed by adding NaH (0.03 g, 0.82 mmol), and the reaction was conducted at this temperature for 0.5 h. Then iodomethane (0.08 g, 0.54 mmol) was added, and the reaction was rewarmed to room temperature and reacted for 5 h. When the reaction was completed as detected by TLC, water was added into the reaction solution to quench the reaction, and then the reaction mixture was concentrated to dryness. The residue was purified by column chromatography (DCM:MeOH=50:1-25:1) to afford 7-bromo-6-fluoro-10-(methoxymethyl)-2-methyl-9,10-dihydro-8-oxa-2,4,10a-triazanaphtho[2,1,8-cde]azulen-1(2H)-one (30 mg, 29.4% yield). ESI-M (m/z): 381.95 $[M+H]^+$.

Step 2: Synthesis of 6-fluoro-10-(methoxymethyl)-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one 1,4-dioxane (15 mL), 7-bromo-6-fluoro-10-(methoxymethyl)-2-methyl-9,10-dihydro-8-oxa-2,4,10a-triazanaphtho[2,1,8-cde]azulen-1(2H)-one (0.03 g, 0.08 mmol), (6-(3-(piperidin-1-yl)propoxy)pyridin-3-yl)boronic acid (0.03 g, 0.12 mmol), cesium carbonate (0.05 g, 0.16 mmol), water (1.5 mL), and tetrakis(triphenylphosphine)palladium (0.02 g, 0.02 mmol) were successively added to a 100 mL reaction bottle. The reaction solution was heated to 90° C. under nitrogen protection to react for 2.5 h. When the reaction was completed as detected by TLC, the reaction solution was concentrated to dryness, and then the residue was purified by column chromatography (DCM:MeOH=50:1-10:1) to afford 6-fluoro-10-(methoxymethyl)-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (0.16 g, 39.2% yield). ESI-MS (m/z): 522.15 $[M+H]^+$; $^1H$ NMR (600 MHz, DMSO-$d_6$) δ: 1.400-1.528 (m, 6H), 1.926-1.947 (m, 2H), 2.434-2.497 (m, 6H), 3.307 (s, 3H), 3.570 (s, 3H), 3.578-3.713 (m, 2H), 4.330-4.351 (t, J=6.6 Hz, 2H), 4.526-4.548 (m, 1H), 4.647-4.734 (m, 1H), 4.752-4.757 (m, 1H), 6.939-6.953 (d, J=8.4 Hz, 1H), 7.593-7.612 (d, J=11.4 Hz, 1H), 7.826-7.840 (d, J=8.4 Hz, 1H), 8.272 (s, 1H), 8.920 (s, 1H).

Example 50: 6-methoxy-10-(methoxymethyl)-2-methyl-7-(1-methyl-1H-pyrazol-4-yl)-9,10-dihydro-8-oxa-2,4,10a-triazanaphtho[2,1,8-cde]azulen-1(2H)-one (A-50)

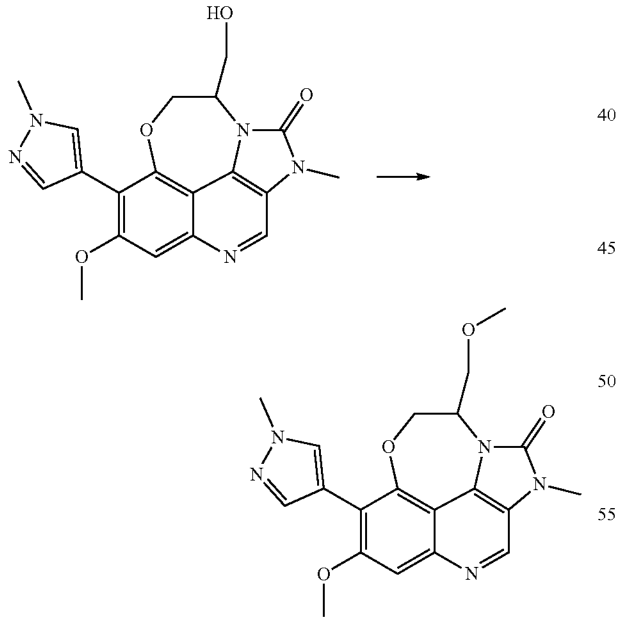

Anhydrous tetrahydrofuran (10 mL) and 10-(hydroxymethyl)-6-methoxy-2-methyl-7-(1-methyl-1H-pyrrole-4-yl)-9,10-dihydro-8-oxa-2,4,10a-triazanaphtho[2,1,8-cde]azulen-1(2H)-one (50 mg, 0.13 mmol) were added to a 50 mL reaction bottle, then sodium hydride (25 mg, 0.65 mmol) was added into the vessel of the reaction mixture in an ice bath, and then the reaction mixture was stirred in an ice bath for 30 min followed by adding iodomethane (22 mg, 0.15 mmol). The reaction was conducted under nitrogen protection at room temperature for 2 h. When the reaction was completed as detected by TLC, the reaction solution was concentrated to dryness, and then the residue was purified by column chromatography (DCM:MeOH=30:1) to afford 6-methoxy-10-(methoxymethyl)-2-methyl-7-(1-methyl-1H-pyrazol-4-yl)-9,10-dihydro-8-oxa-2,4,10a-triazanaphtho[2,1,8-cde]azulen-1(2H)-one (20 mg, 40.4% yield). ESI-MS (m/z): 396.16 $[M+H]^+$; $^1H$ NMR (600 MHz, DMSO-$d_6$) δ: 3.336 (s, 3H), 3.501 (s, 3H), 3.608-3.633 (m, 1H), 3.733-3.764 (m, 1H), 3.915 (s, 3H), 3.941 (s, 3H), 4.409-4.431 (m, 1H), 4.614-4.636 (m, 1H), 4.904-4.926 (m, 1H), 7.233 (s, 1H), 7.780 (s, 1H), 8.089 (s, 1H), 8.734 (s, 1H).

Example 51: 6-methoxy-2-methyl-7-(1-methyl-1H-pyrazol-4-yl)-10-methylene-9,10-dihydro-8-oxa-2,4,10a-triazanaphtho[2,1,8-cde]azulen-1(2H)-one (A-51)

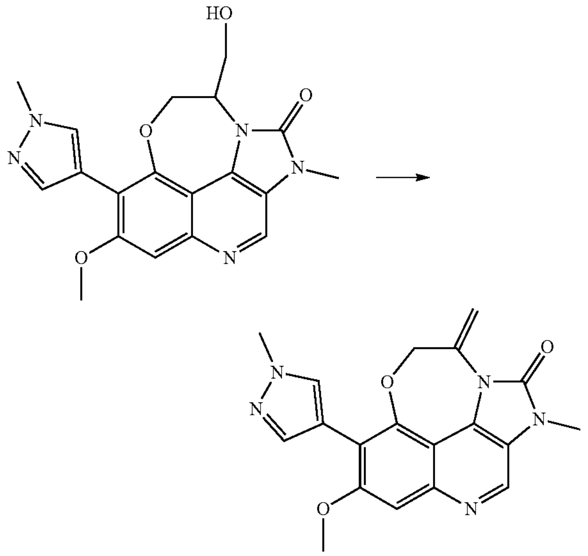

Anhydrous tetrahydrofuran (2 mL) and 10-(hydroxymethyl)-6-methoxy-2-methyl-7-(1-methyl-1H-pyrrole-4-yl)-9,10-dihydro-8-oxa-2,4,10a-triazanaphtho[2,1,8-cde]azulen-1(2H)-one (20 mg, 0.05 mmol) were added to a 50 mL reaction bottle, followed by DMF (1 mL), then sodium hydride (25 mg, 0.65 mmol) was added into the reaction bottle in an ice bath, and then the reaction solution was stirred in an ice bath for 30 min followed by adding p-toluenesulfonyl chloride (15 mg, 0.08 mmol). The reaction was conducted under nitrogen protection at room temperature for 2 h. When the reaction was completed as detected by TLC, the reaction solution was concentrated to dryness, and then the residue was purified by column chromatography (DCM:MeOH=30:1) to afford 6-methoxy-2-methyl-7-(1-methyl-1H-pyrazol-4-yl)-10-methylene-9,10-dihydro-8-oxa-2,4,10a-triazanaphtho[2,1,8-cde]azulen-1(2H)-one (10 mg, 48.2% yield). ESI-MS (m/z): 364.13 $[M+H]^+$; $^1H$ NMR (600 MHz, DMSO-$d_6$) δ: 3.352 (s, 3H), 3.915 (s, 3H), 3.962 (s, 3H), 4.954 (s, 2H), 5.396 (s, 1H), 6.182 (s, 1H), 7.283 (s, 1H), 7.925 (s, 1H), 8.157 (s, 1H), 8.835 (s, 1H).

Example 52: 10-((dimethylamino)methyl)-6-methoxy-2-methyl-7-(1-methyl-1H-pyrazol-4-yl)-9,10-dihydro-8-oxa-2,4,10a-triazanaphtho[2,1,8-cde]azulen-1(2H)-one (A-52)

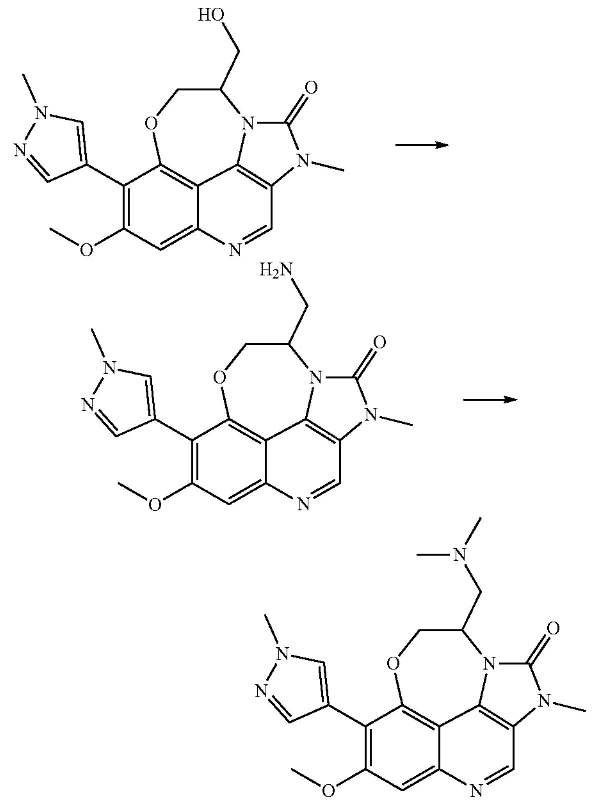

Step 1: Synthesis of 10-(aminomethyl)-6-methoxy-2-methyl-7-(1-methyl-1H-pyrazol-4-yl)-9,10-dihydro-8-oxa-2,4,10a-triazanaphtho[2,1,8-cde]azulen-1(2H)-one Anhydrous N,N-dimethyl formamide (2 mL), 6-methoxy-10-(hydroxymethyl)-2-methyl-7-(1-methyl-1H-pyrrole-4-yl)-9,10-dihydro-8-oxa-2,4,10a-triazanaphtho[2,1,8-cde]azulen-1(2H)-one (50 mg, 0.13 mmol), triphenylphosphine (138 mg, 0.524 mmol), and phthaldiamide (29 mg, 0.19 mmol) were successively added to a 50 mL reaction bottle, diisopropyl azodicarboxylate (106 mg, 0.524 mmol) was added under nitrogen protection, and then the reaction was conducted under nitrogen protection at room temperature for 2 h. When the reaction was completed as detected by TLC, the reaction solution was added with 50 mL of water and extracted with 30 mL of dichloromethane for 4 times, the organic phases were combined, dried with anhydrous sodium sulfate, and concentrated to dryness for instant use in the next step. To the residue, methanol (15 mL) and hydrazine hydrate (2 mL) were added, and the reaction was conducted under nitrogen protection at room temperature for 2 h, and completed as detected by TLC. The reaction solution was concentrated under reduced pressure to remove methanol, and then extracted with 30 mL of dichloromethane for 4 times, the organic phases were combined, dried with anhydrous sodium sulfate, and then purified by column chromatography (DCM:MeOH=20:1) to afford 10-(aminomethyl)-6-methoxy-2-methyl-7-(1-methyl-1H-pyrazol-4-yl)-9,10-dihydro-8-oxa-2,4,10a-triazanaphtho[2,1,8-cde]azulen-1(2H)-one (29 mg, 58.1% yield). ESI-MS (m/z): 381.16 $[M+H]^+$.

Step 2: Synthesis of 10-((dimethylamino)methyl)-6-methoxy-2-methyl-7-(1-methyl-1H-pyrazol-4-yl)-9,10-dihydro-8-oxa-2,4,10a-triazanaphtho[2,1,8-cde]azulen-1(2H)-one Anhydrous methanol (6 mL) and 10-(aminomethyl)-6-methoxy-2-methyl-7-(1-methyl-1H-pyrazol-4-yl)-9,10-dihydro-8-oxa-2,4,10a-triazanaphtho[2,1,8-cde]azulen-1(2H)-one (29 mg, 0.08 mmol) were added to a 50 mL reaction bottle, followed by adding an aqueous solution of formaldehyde (2 mL) and acetic acid (10 μL), and then the reaction solution was stirred at room temperature for 30 min, followed by adding sodium triacetoxyborohydride (49 mg, 0.23 mmol). The reaction was rewarmed to room temperature and reacted for 12 h. When the reaction was completed as detected by TLC, the reaction solution was concentrated to dryness, and then the residue was purified by column chromatography (DCM:MeOH=15:1) to afford 10-((dimethylamino)methyl)-6-methoxy-2-methyl-7-(1-methyl-1H-pyrazol-4-yl)-9,10-dihydro-8-oxa-2,4,10a-triazanaphtho[2,1,8-cde]azulen-1(2H)-one (7 mg, 27.3% yield). ESI-MS (m/z): 409.19 $[M+H]^+$; $^1H$ NMR (600 MHz, $CDCl_3$) δ: 2.503 (s, 6H), 2.694-2.712 (d, J=10.8 Hz, 1H), 3.121 (s, 1H), 3.594 (s, 3H), 4.007 (s, 3H), 4.019 (s, 3H), 4.269-4.290 (d, J=12.6 Hz, 1H), 4.646-4.659 (d, J=7.8 Hz, 1H), 5.166-5.187 (d, J=12.6 Hz, 1H), 7.265 (s, 1H), 7.310 (s, 1H), 8.102 (s, 1H), 8.555 (s, 1H).

Example 53: 8-fluoro-4-methoxy-12-methyl-5-(1-methyl-1H-pyrazol-4-yl)-6-oxa-2,10b,12-triazanaphtho[gh]pleiaden-11(12H)-one (A-53)

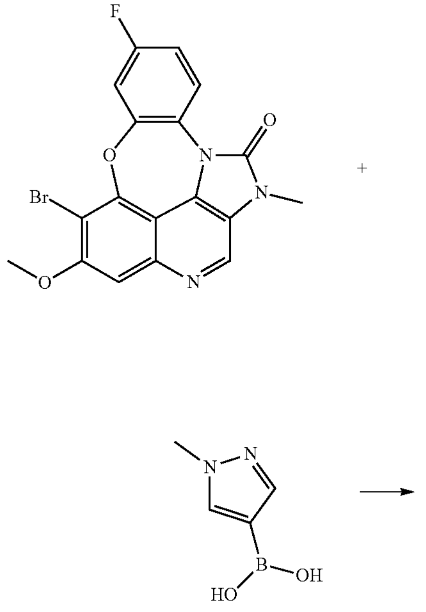

-continued

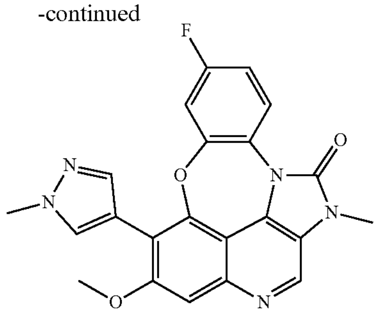

Except starting materials were changed, the synthesis method was the same as that of example 30 to afford 8-fluoro-4-methoxy-12-methyl-5-(1-methyl-1H-pyrazol-4-yl)-6-oxa-2,10b,12-triazanaphtho[gh]pleiaden-11(12H)-one (200 mg, 66.6% yield). ESI-MS (m/z): 418.12 $[M+H]^+$; $^1H$ NMR (600 MHz, DMSO-$d_6$) δ: 3.577 (s, 3H), 3.967-3.998 (m, 6H), 6.934-6.943 (m, 1H), 7.253 (s, 1H), 7.349 (s, 1H), 7.972 (s, 1H), 8.235 (s, 1H), 8.475 (s, 1H), 8.872 (s, 1H).

Example 54: 6-methoxy-2-methyl-7-(1-methyl-1H-pyrazol-4-yl)-9-(pyridin-2-yl)-9,10-dihydro-8-oxa-2,4,10a-triazanaphtho[2,1,8-cde]azulen-1(2H)-one (A-54)

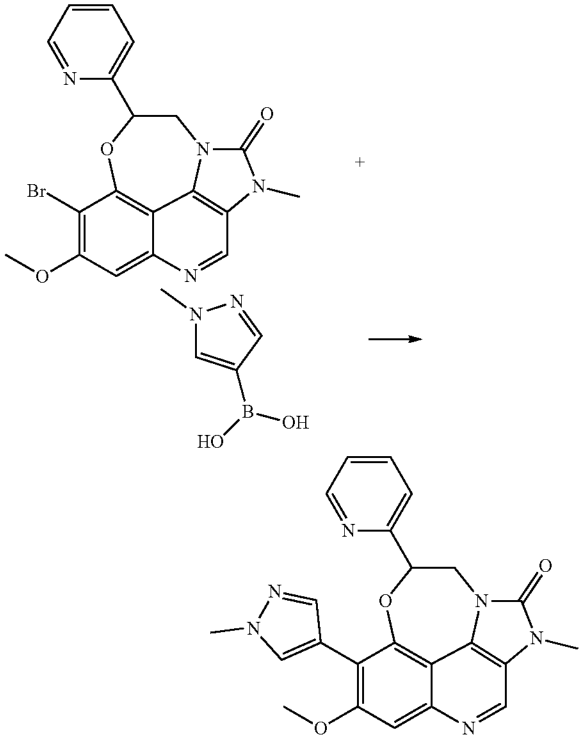

Except starting materials were changed, the synthesis method was the same as that of example 30 to afford 6-methoxy-2-methyl-7-(1-methyl-1H-pyrazol-4-yl)-9-(pyridin-2-yl)-9,10-dihydro-8-oxa-2,4,10a-triazanaphtho[2,1,8-cde]azulen-1(2H)-one (230 mg, 63.9% yield). ESI-MS (m/z); 429.16 $[M+H]^+$; $^1H$ NMR (600 MHz, DMSO-$d_6$) δ: 3.523 (s, 3H), 3.773 (s, 3H), 3.937 (s, 3H), 4.369-4.406 (m, 1H), 4.674-4.698 (m, 1H), 5.734 (d, J=9.0 Hz, 1H), 7.259 (s, 1H), 7.435-7.446 (m, 2H), 7.662 (s, 1H), 7.849-7.906 (m, 2H), 8.653 (s, 1H), 8.763 (s, 1H).

Example 55: (R)-6-methoxy-2-methyl-7-(1-methyl-1H-pyrazol-4-yl)-10-phenyl-9,10-dihydro-8-oxa-2,4,10a-triazanaphtho[2,1,8-cde]azulen-1(2H)-one (A-55)

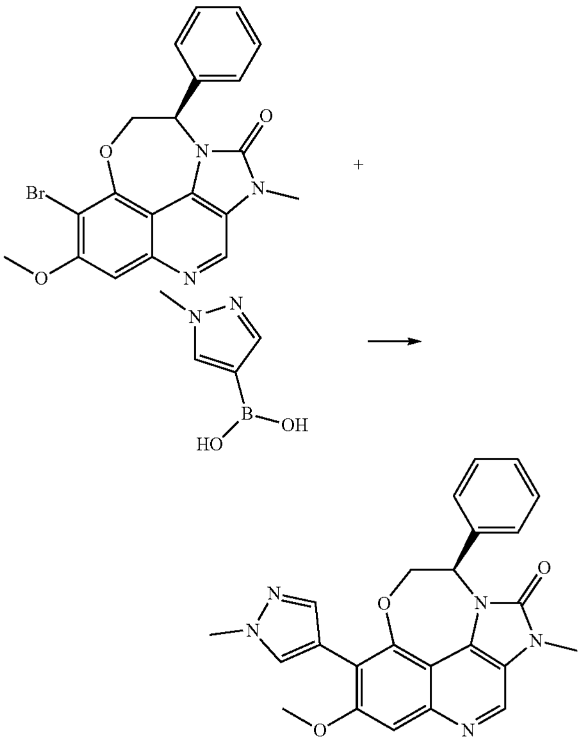

Except starting materials were changed, the synthesis method was the same as that of example 30 to afford (R)-6-methoxy-2-methyl-7-(1-methyl-1H-pyrazol-4-yl)-10-phenyl-9,10-dihydro-8-oxa-2,4,10a-triazanaphtho[2,1,8-cde]azulen-1(2H)-one (130 mg, 43.3% yield). ESI-MS (m/z); 428.16 $[M+H]^+$; $^1H$ NMR (600 MHz, DMSO-$d_6$) δ: 3.522 (s, 3H), 3.830 (s, 3H), 3.939 (s, 3H), 4.747-4.769 (m, 1H), 5.008-5.034 (m, 1H), 5.746 (s, 1H), 7.174-7.187 (m, 2H), 7.261-7.275 (m, 2H), 7.296-7.321 (m, 2H), 7.689 (s, 1H), 7.945 (s, 1H), 8.821 (s, 1H).

Example 56: (S)-6-fluoro-2,10-dimethyl-7-(6-(4-(piperidin-1-yl)but-1-yn-1-yl)pyridin-3-yl)-9,10-dihydro-8-oxa-2,4,10a-triazanaphtho[2,1,8-cde]azulen-1(2H)-one (A-56)

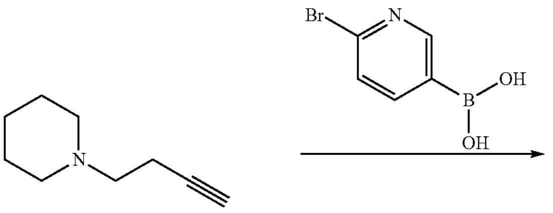

-continued

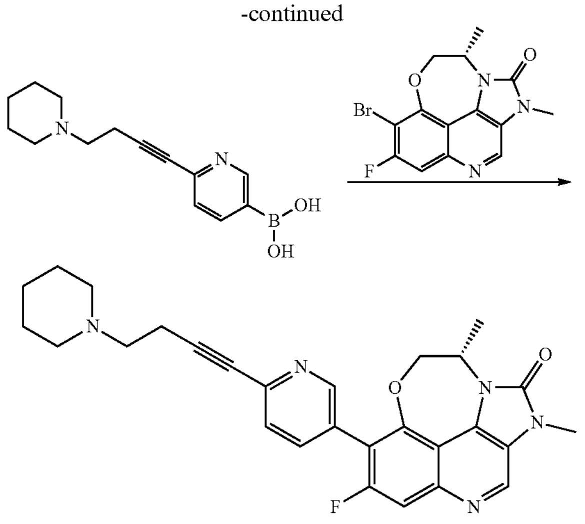

Step 1: Synthesis of (6-(4-(piperidin-1-yl)but-1-yn-1-yl)pyridin-3-yl)boronic acid Acetonitrile (20 mL), 1-(but-3-yn-1-yl)piperidine (1.37 g, 10.0 mmol), (2-bromopyridine-5-yl)boronic acid (2.01 g, 10.0 mmol), tetrakis(triphenylphosphine)palladium (0.40 g, 0.35 mmol), cuprous iodide (0.07 g, 0.35 mmol), and triethylamine (2 mL) were successively added to a 50 mL reaction bottle. The reaction was conducted under nitrogen protection at room temperature for 6 h. When the reaction was completed as detected by TLC, the reaction solution was concentrated to dryness, and then the residue was subject to column chromatography (DCM:MeOH=30:1) to afford (6-(4-(piperidin-1-yl)but-1-yn-1-yl)pyridin-3-yl)boronic acid (1.26 g, 61.1% yield). ESI-MS (m/z): 259.15 $[M+H]^+$.

Step 2: Synthesis of (S)-6-fluoro-2,10-dimethyl-7-(6-(4-(piperidin-1-yl)but-1-yn-1-yl)pyridin-3-yl)-9,10-dihydro-8-oxa-2,4,10a-triazanaphtho[2,1,8-cde]azulen-1(2H)-one 1,4-dioxane (10 mL), (S)-7-bromo-6-fluoro-2,10-dimethyl-9,10-dihydro-8-oxa-2,4,10a-triazanaphtho[2,1,8-cde]azulen-1(2H)-one (170 mg, 0.48 mmol), (6-(4-(piperidin-1-yl) but-1-yn-1-yl)pyridin-3-yl)boronic acid, potassium carbonate (132 mg, 0.96 mmol), water (1 mL), and tetrakis (triphenylphosphine)palladium (55 mg, 0.048 mmol) were successively added to a 50 mL reaction bottle. The reaction solution was heated up to 90° C. under nitrogen protection to react for 3 h. When the reaction was completed as detected by TLC, the reaction solution was concentrated to dryness, and then the residue was purified by column chromatography (DCM:MeOH=20:1-10:1) to afford (S)-6-fluoro-2,10-dimethyl-7-(6-(4-(piperidin-1-yl)but-1-yn-1-yl) pyridin-3-yl)-9,10-dihydro-8-oxa-2,4,10a-triazanaphtho[2,1,8-cde]azulen-1(2H)-one (35 mg, 15% yield). ESI-MS (m/z): 486.22 $[M+H]^+$; $^1H$ NMR (600 MHz, $CD_3OD$) δ: 1.532-1.543 (m, 6H), 1.722 (s, 4H), 2.775 (s, 2H), 2.812-2.836 (m, 2H), 2.931 (s, 2H), 3.632 (s, 4H), 4.531-4.553 (m, 1H), 4.639-4.661 (m, 1H), 4.722-4.731 (m, 1H), 7.569 (d, J=11.4 Hz, 1H), 7.630 (d, J=8.4 Hz, 1H), 7.981 (d, J=7.8 Hz, 1H), 8.622 (s, 1H), 8.842 (s, 1H).

Example 57: 5-(6-(4-(dimethylamino)piperidin-1-yl) pyridin-3-yl)-4-fluoro-12-methyl-6a,7,8,9,10,10a-hexahydro-6-oxa-2,10b,12-triazacyclopenta[gh]pleiaden-11(12H)-one (A-57)

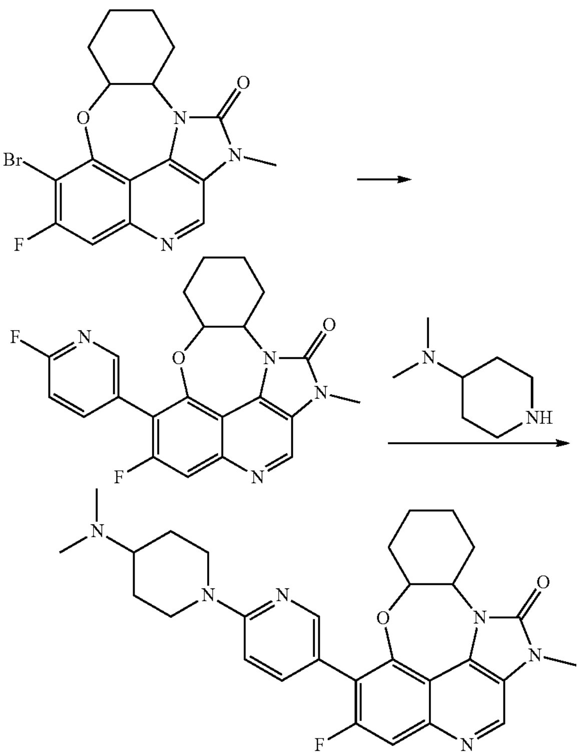

Step 1: Synthesis of 4-fluoro-5-(6-fluoropyridin-3-yl)-12-methyl-6a,7,8,9,10,10a-hexahydro-6-oxa-2,10b,12-triazacyclopenta[gh]azulen-11(12H)-one 1,4-dioxane (15 mL), 5-bromo-4-fluoro-12-methyl-6a,7,8,9,10,10a-hexahydro-6-oxa-2,10b,12-triazacyclopenta[gh]pleiaden-11(12H)-one (0.69 g, 1.76 mmol), (6-fluoropyridine-3-yl)boronic acid (0.315 g, 2.23 mmol), potassium carbonate (0.607 g, 4.4 mmol), water (1.5 mL), and tetrakis (triphenylphosphine)palladium (0.203 g, 0.18 mmol) were successively added to a 100 mL reaction bottle. The reaction solution was heated up to 90° C. under nitrogen protection to react for 2.5 h. When the reaction was completed as detected by TLC, the reaction solution was concentrated to dryness, and then the residue was purified by column chromatography (DCM:MeOH=60:1) to afford 4-fluoro-5-(6-fluoropyridin-3-yl)-12-methyl-6a,7,8,9,10,10a-hexahydro-6-oxa-2,10b,12-triazacyclopenta[gh]azulene-11 (12H)-one (0.35 g, 48.7% yield). ESI-MS (m/z): 409.31 $[M+H]^+$.

Step 2: Synthesis of 5-(6-(4-(dimethylamino)piperidin-1-yl)pyridin-3-yl)-4-fluoro-12-methyl-6a,7,8,9,10,10a-hexahydro-6-oxa-2,10b,12-triazacyclopenta[gh]pleiaden-11(12H)-one (A-57)

DMSO (10 mL), DIPEA (3 mL), 4-fluoro-5-(6-fluoropyridin-3-yl)-12-methyl-6a,7,8,9,10,10a-hexahydro-6-oxa-2,10b,12-triazacyclopenta[gh]azulen-11(12H)-one (170 mg, 0.417 mmol) and N,N-dimethylpiperidin-4-amine hydrochloride (167 mg, 0.834 mmol) were successively added to a 100 mL reaction bottle. The reaction solution was heated up to 150° C. to react for 12 h, then cooled down to room temperature and washed with ethyl acetate and a saturated saline solution for 2 to 3 times, and then the organic phase was dried and concentrated to afford a crude product. The crude product was purified by column chromatography (DCM:MeOH=30:1-6:1) to afford 5-(6-(4-(dimethylamino) piperidin-1-yl)pyridin-3-yl)-4-fluoro-12-methyl-6a,7,8,9,10,10a-hexahydro-6-oxa-2,10b,12-triazacyclopenta[gh]pleiaden-11(12H)-one (30 mg, 13.9% yield). ESI-MS (m/z): 517.24 $[M+H]^+$; $^1H$ NMR (600 MHz, DMSO-$d_6$) δ: 1.280-1.353 (m, 2H), 1.412-1.466 (m, 2H), 1.533-1.641 (m, 1H), 1.656-1.667 (m, 1H), 1.713-1.728 (m, 1H), 1.915 (d, 2H), 2.098 (d, 1H), 2.357 (s, 6H), 2.615-2.636 (m, 1H), 2.860 (t, J=12.6 Hz, 2H), 3.491 (s, 3H), 3.554-3.576 (m, 2H), 4.218-4.259 (m, 1H), 4.373-4.391 (m, 3H), 6.973 (d, J=9.0 Hz, 1H), 7.543 (d, J=10.8 Hz, 1H), 7.647 (d, J=8.4 Hz, 1H), 8.197 (s, 1H), 8.856 (s, 1H).

Example 58: (S)-6-fluoro-2,10-dimethyl-7-(2-oxo-1-(3-(piperidin-1-yl)propyl)-1,2-dihydropyridin-4-yl)-9,10-dihydro-8-oxa-2,4,10a-triazanaphtho[2,1,8-cde] azulen-1(2H)-one (A-146)

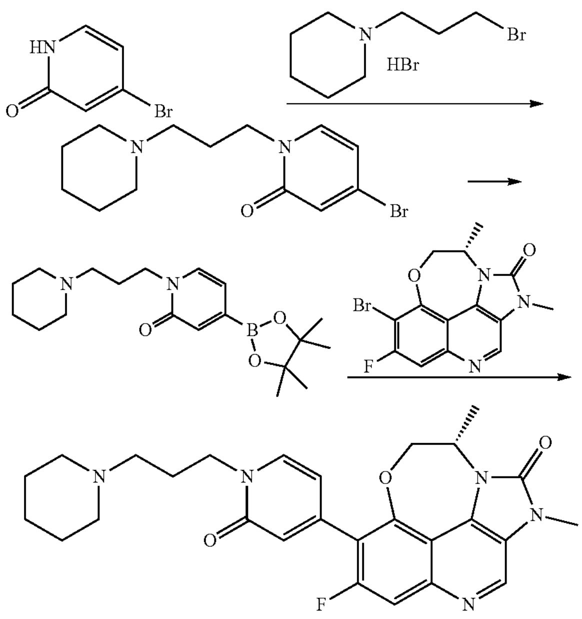

Step 1: Synthesis of 4-bromo-1-(3-(piperidin-1-yl) propyl)pyridin-2(1H)-one

Acetonitrile (30 mL), 1-(3-bromopropyl)piperidine hydrobromide (1.81 g, 6.32 mmol), 4-bromo-2-hydroxypyridine (1.0 g, 5.75 mmol), and potassium carbonate (1.98 g, 14.37 mmol) were successively added to a 100 mL reaction bottle and heated to reflux for 5 h. When the reaction was completed as detected by TLC, the reaction solution was concentrated to dryness, and then the residue was purified by column chromatography (DCM:MeOH=20:1-15:1) to afford 4-bromo-1-(3-(piperidin-1-yl)propyl)pyridin-2(1H)-one (1.24 g, 72.0% yield). ESI-M (m/z): 299.07/301.07 $[M+H]^+$.

Step 2: Synthesis of 1-(3-(piperidin-1-yl)propyl)-4-(4,4,5,5-tetramethyl-1,3,2-dioxaborolan-2-yl)pyridin-2(1H)-one 1,4-dioxane (25 mL), 4-bromo-1-(3-(piperidin-1-yl)propyl)pyridin-2(1H)-one (1.24 g, 4.14 mmol), bis(pinacolato) diboron (2.10 g, 8.28 mmol), potassium acetate (1.22 g, 12.42 mmol), and [1,1'-bis(diphenylphosphino)ferrocene] palladium dichloride (0.30 g, 0.41 mmol) were successively added to a 100 mL reaction bottle. The reaction solution was heated up to 90° C. under nitrogen protection to react for 3 h. When the reaction was completed as detected by TLC, the reaction solution was concentrated to dryness, and then the residue was purified by column chromatography (DCM: MeOH=20:1-15:1) to afford 1-(3-(piperidin-1-yl)propyl)-4-(4,4,5,5-tetramethyl-1,3,2-dioxaborolan-2-yl)pyridin-2 (1H)-one (1.13 g, 79% yield).

Step 3: Synthesis of (S)-6-fluoro-2,10-dimethyl-7-(2-oxo-1-(3-piperidin-1-yl)propyl)-1,2-dihydropyridin-4-yl)-9,10-dihydro-8-oxa-2,4,10a-triazanaphtho [2,1,8-cde]azulen-1(2H)-one 1,4-dioxane (5 mL), 1-(3-(piperidin-1-yl)propyl)-4-(4,4,5,5-tetramethyl-1,3,2-dioxaborolan-2-yl)pyridin-2(1H)-one (156 mg, 0.45 mmol), (S)-7-bromo-6-fluoro-2,10-dimethyl-9,10-dihydro-8-oxa-2,4,10a-triazanaphtho[2,1,8-cde]azulen-1(2H)-one (106 mg, 0.3 mmol), potassium carbonate (83 mg, 0.6 mmol), water (0.5 mL), and tetrakis(triphenylphosphine)palladium (35 mg, 0.03 mmol) were successively added to a 50 mL reaction bottle. The reaction solution was heated up to 90° C. under nitrogen protection to react for 3 h. When the reaction was completed as detected by TLC, the reaction solution was concentrated to dryness, and then the residue was purified by column chromatography (DCM: MeOH=20:1-10:1) to afford (S)-6-fluoro-2,10-dimethyl-7-(2-oxo-1-(3-piperidin-1-yl)propyl)-1,2-dihydropyridin-4-yl)-9,10-dihydro-8-oxa-2,4,10a-triazanaphtho[2,1,8-cde] azulen-1(2H)-one (25 mg, 17% yield). ESI-M (m/z): 492.23 $[M+H]^+$; $^1H$ NMR (600 MHz, $CD_3OD$) δ: 1.561-1.572 (m, 5H), 1.707-1.726 (m, 4H), 2.100-2.148 (m, 2H), 2.665 (brs, 6H), 3.657 (s, 3H), 4.146 (t, J=7.2 Hz, 2H), 4.559-4.580 (m, 1H), 4.689-4.715 (m, 1H), 4.745-4.779 (m, 1H), 6.582 (d, J=6.6 Hz, 1H), 6.727 (s, 1H), 7.560 (d, J=11.4 Hz, 1H), 7.795 (d, J=6.6 Hz, 1H), 8.868 (s, 1H).

Example 59: (S)-6-fluoro-2,10-dimethyl-7-(6-((2-(piperidin-1-yl)ethoxy)methyl)pyridin-3-yl)-9,10-dihydro-8-oxa-2,4,10a-triazanaphtho[2,1,8-cde]azulen-1(2H)-one (A-148)

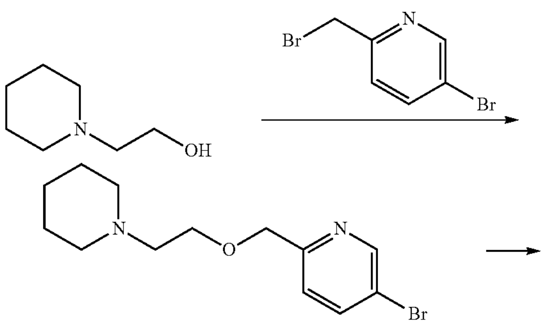

-continued

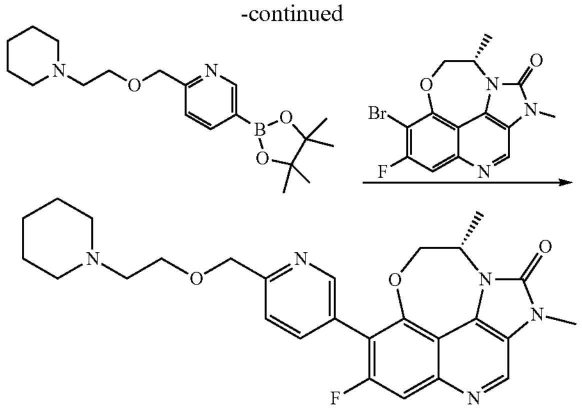

Step 1: Synthesis of 5-bromo-2-((2-(piperidin-1-yl) ethoxy)methyl)pyridine

THF (30 mL) and N-hydroxyethylpiperidine (1.0 g, 7.74 mmol) were successively added to a 100 mL reaction bottle, and cooled down to 0° C., followed by adding NaH (0.62 g, 15.48 mmol), the reaction was conducted at this temperature for 0.5 h, then 5-bromo-2-(bromomethyl)pyridine (1.94 g, 7.74 mmol) was added, and the reaction was rewarmed to room temperature and reacted for 5 h. When the reaction was completed as detected by TLC, water was added into the reaction solution to quench the reaction, and concentrated to dryness, and then the residue was purified by column chromatography (DCM:MeOH=20:1-15:1) to afford 5-bromo-2-((2-(piperidin-1-yl)ethoxy)methyl)pyridine (1.97 g, 85.0% yield). ESI-MS (m/z): 299.07/301.07 $[M+H]^+$.

Step 2: Synthesis of 2-((2-(piperidin-1-yl)ethoxy) methyl)-5-(4,4,5,5-tetramethyl-1,3,2-dioxaborolan-2-yl)pyridine 1,4-dioxane (25 mL), 5-bromo-2-((2-(piperidin-1-yl) ethoxy)methyl)pyridine (1.97 g, 6.58 mmol), bis(pinacolato) diboron (3.34 g, 13.16 mmol), potassium acetate (1.61 g, 16.45 mmol), and [1,1'-bis(diphenylphosphino)ferrocene] palladium dichloride (0.48 g, 0.66 mmol) were successively added to a 100 mL reaction bottle. The reaction solution was heated up to 90° C. under nitrogen protection to react for 3 h. When the reaction was completed as detected by TLC, the reaction solution was concentrated to dryness to afford a crude product of 2-((2-(piperidin-1-yl)ethoxy)methyl)-5-(4,4,5,5-tetramethyl-1,3,2-dioxaborolan-2-yl)pyridine for instant use in the next step.

Step 3: Synthesis of (S)-6-fluoro-2,10-dimethyl-7-(6-((2-(piperidin-1-yl)ethoxy)methyl)pyridin-3-yl)-9,10-dihydro-8-oxa-2,4,10a-triazanaphtho[2,1,8-cde] azulen-1(2H)-one 1,4-dioxane (5 mL), 2-((2-(piperidin-1-yl)ethoxy) methyl)-5-(4,4,5,5-tetramethyl-1,3,2-dioxaborolan-2-yl) pyridine (156 mg, 0.45 mmol), (S)-7-bromo-6-fluoro-2,10-dimethyl-9,10-dihydro-8-oxa-2,4,10a-triazanaphtho[2,1,8-cde]azulen-1(2H)-one (106 mg, 0.3 mmol), potassium carbonate (83 mg, 0.6 mmol), water (0.5 mL), and tetrakis (triphenylphosphine)palladium (35 mg, 0.03 mmol) were successively added to a 50 mL reaction bottle. The reaction solution was heated up to 90° C. under nitrogen protection and reacted for 3 h. When the reaction was completed as detected by TLC, the reaction solution was concentrated to dryness, and then the residue was purified by column chromatography (DCM:MeOH=20:1-10:1) to afford (S)-6-fluoro-2,10-dimethyl-7-(6-((2-(piperidin-1-yl)ethoxy) methyl)pyridin-3-yl)-9,10-dihydro-8-oxa-2,4,10a-triazanaphtho[2,1,8-cde]azulen-1(2H)-one (25 mg, 17% yield). ESI-MS (m/z): 492.23 $[M+H]^+$; $^1H$ NMR (600 MHz, $CD_3OD$) δ: 1.463-1.624 (m, 5H), 1.693-1.711 (m, 4H), 2.748 (brs, 4H), 2.881 (brs, 2H), 3.622 (s, 3H), 3.835 (t, J=5.4 Hz, 2H), 4.520-4.542 (m, 1H), 4.613-4.634 (m, 1H), 4.711-4.726 (m, 3H), 7.533 (d, J=11.4 Hz, 1H), 7.676 (d, J=8.4 Hz, 1H), 8.004 (d, J=8.4 Hz, 1H), 8.630 (s, 1H), 8.811 (s, 1H).

Example 60: N-(2-(3-(dimethylamino)propoxy)-5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',4a1'(7a'),6'-pentanen-7'-yl) pyridin-3-yl)cyclopropanecarboxamide (A-155)

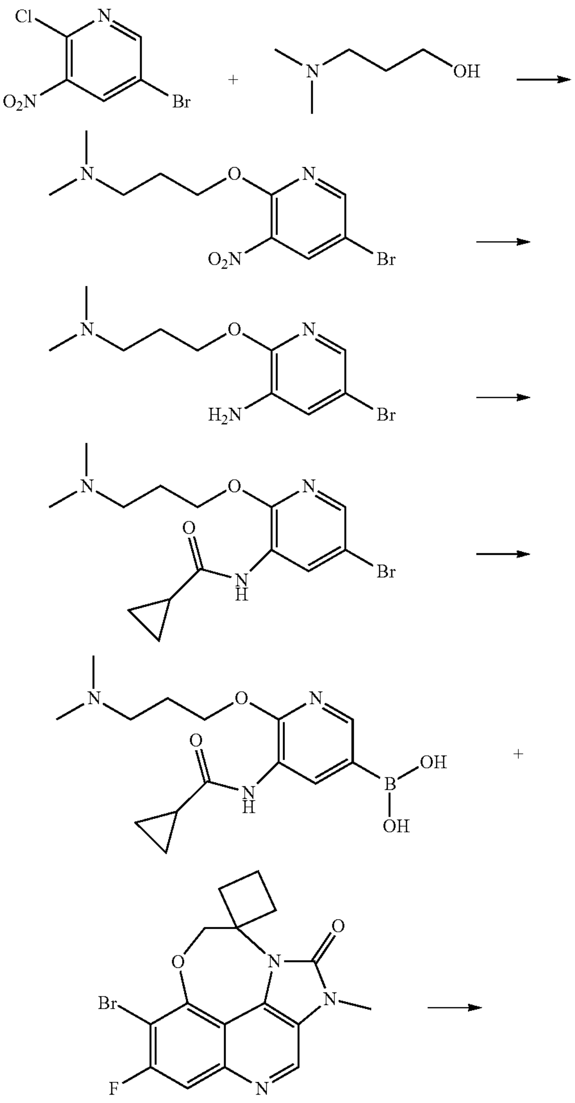

-continued

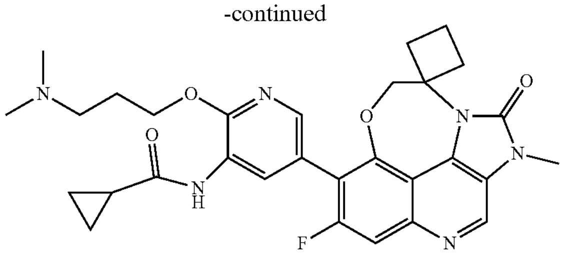

Step 1: Synthesis of 3-((5-bromo-3-nitropyridin-2-yl)oxy)-N,N-dimethylpropane-1-amine Anhydrous THF (4 mL) and 3-(dimethylamino)propan-1-ol (1.7 g, 16.4 mmol) were successively added to a 250 mL reaction bottle, and cooled down to 0° C., followed by adding NaH (0.66 g, 16.4 mmol), and the reaction solution was rewarmed to room temperature with stirring for 0.5 h. The reaction solution was cooled down under $N_2$ protection, and a solution of 5-bromo-2-chloro-3-nitropyridine (3 g, 12.6 mmol) in THF (30 mL) was added dropwise at −5° C., and then the reaction solution was rewarmed to room temperature to react for 3 h. When the reaction was completed as shown by LC-MS, a saturated ammonium chloride solution was added to quench the reaction, then water was added to dilute the reaction solution, followed by adding ethyl acetate, stirring, and separating the phases, and the organic phase was concentrated to dryness under reduced pressure, and then the residue was purified by column chromatography (DCM:MeOH=40:1-10:1) to afford 3-((5-bromo-3-nitropyridin-2-yl)oxy)-N,N-dimethylpropane-1-amine (2.1 g, 54.5% yield). ESI-MS (m/z): 304.02/306.02 $[M+H]^+$.

Step 2: Synthesis of 5-bromo-2-(3-(dimethylamino)propoxy)pyridine-3-amine

AcOH (50 mL), 3-((5-bromo-3-nitropyridin-2-yl)oxy)-N,N-dimethylpropane-1-amine (2.1 g, 6.9 mmol), and iron powder (2.0 g, 35.7 mmol) were added to a 250 mL reaction bottle and reacted at room temperature for 2 h. When the reaction was completed as detected by LC-MS, THF (50 mL) and DCM (100 mL) were added, then the reaction solution was filtered, the filter cake was washed with DCM, the filtrate was concentrated to dryness under reduced pressure, and then the residue was purified by column chromatography (DCM:MeOH=80:1-5:1) to afford 5-bromo-2-(3-(dimethylamino)propoxy)pyridine-3-amine (1.4 g, 73.7% yield). ESI-MS (m/z): 274.05/276.02 $[M+H]^+$.

Step 3: Synthesis of N-(5-bromo-2-(3-(dimethylamino)propoxy)pyridin-3-yl)cyclopropanecarboxamide DCM (20 mL), 5-bromo-2-(3-(dimethylamino)propoxy)pyridin-3-amine (0.50 g, 1.8 mmol), and TEA (0.46 g, 4.5 mmol) were successively added to a 100 mL reaction bottle, and cooled down to 0° C., followed by adding cyclopropanecarbonyl chloride (0.25 g, 2.4 mol) dropwise at this temperature. After addition, the reaction was rewarmed to room temperature and reacted for 2 h. When the reaction was completed as shown by LC-MS, water was added to quench the reaction, the reaction solution was subjected to phase separation, then the organic phase was concentrated to dryness under reduced pressure, and then the residue was purified by column chromatography (DCM:MeOH=30:1-10:1) to afford N-(5-bromo-2-(3-(dimethylamino)propoxy)pyridin-3-yl)cyclopropanecarboxamide (0.5 g, 80.6% yield). ESI-MS (m/z): 342.07/344.07 $[M+H]^+$.

Step 4: Synthesis of N-(2-(3-(dimethylamino)propoxy)-5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',4a1'(7a'),6'-pentanen-7'-yl)pyridin-3-yl)cyclopropanecarboxamide DMF (20 mL), N-(5-bromo-2-(3-(dimethylamino)propoxy)pyridin-3-yl)cyclopropanecarboxamide (0.5 g, 1.5 mmol), bis(pinacolato)diboron (0.76 g, 3.0 mmol), $PdCl_2$(dppf) (0.11 g, 0.15 mmol), and potassium acetate (0.37 g, 3.8 mmol) were successively added to a 100 mL reaction bottle and reacted for 4 h under nitrogen protection at 90° C. Then the reaction solution was cooled down, and 7-bromo-6-fluoro-2-methyl-2,9-dihydro-1H-spiro[8-oxa-2,4,10a-triazanaphtho[2,1,8-cde]azulene-10,1'-cyclobutan]-1-one (0.57 g, 1.5 mmol), potassium carbonate (0.62 g, 4.5 mmol), water (1 mL), and tetra (triphenylphosphine)palladium (0.17 g, 0.15 mmol) were added. The reaction solution was heated up to 90° C. under nitrogen protection to react for 4 h. The reaction solution was concentrated to dryness, and then the residue was purified by column chromatography (DCM:MeOH=20:1-5:1) to afford N-(2-(3-(dimethylamino)propoxy)-5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',4a1'(7a'),6'-pentanen-7'-yl)pyridin-3-yl)cyclopropanecarboxamide (35 mg, 4.3% yield). ESI-MS (m/z): 561.25 $[M+H]^+$; $^1H$ NMR (600 MHz, $CD_3OD$) δ: 0.907-0.987 (m, 6H), 1.318-1.329 (m, 5H), 1.942-1.957 (m, 1H), 1.995-2.009 (m, 1H), 2.102-2.137 (m, 3H), 2.367 (s, 6H), 2.626-2.651 (m, 2H), 3.589 (s, 3H), 4.540-4.561 (m, 2H), 7.491 (d, J=10.8 Hz, 1H), 7.973 (s, 1H), 8.484 (s, 1H), 8.769 (s, 1H).

Example 61: N-(5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',4a1'(7a'),6'-pentanen-7'-yl)-2-(3-(piperidin-1-yl)propoxy)pyridin-3-yl)cyclopropanecarboxamide (A-156)

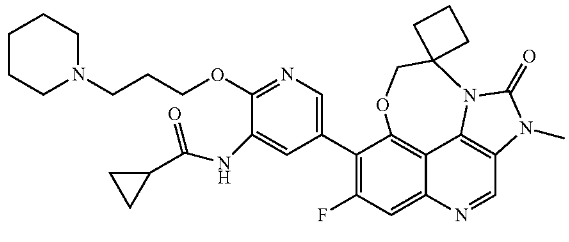 [SMILES: Cn1c(=O)n2c3c4c(c(-c5cnc(OCCCN6CCCCC6)c(NC(=O)C6CC6)c5)c(F)cc4ncc31)OCC21CCC1]

Except starting materials were changed, the synthesis method was the same as that of example 60 to afford N-(5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',4a1'(7a'),6'-pentanen-7'-yl)-2-(3-(piperidin-1-yl)propoxy)pyridin-3-yl)cyclopropanecarboxamide (40 mg, 35.5% yield). ESI-MS (m/z): 601.29 $[M+H]^+$; $^1H$ NMR (600 MHz, $CD_3OD$) δ: 0.897-0.985 (m, 6H), 1.273-1.295 (m, 5H), 1.629-1.639 (m, 2H), 1.648-1.666 (m, 1H), 1.891-1.995 (m, 1H), 2.000-2.007 (m, 1H), 2.014-2.139 (m, 4H), 2.533-2.579 (m, 4H), 2.592-2.604 (m, 2H), 3.582 (s, 3H), 4.518-4.528 (m, 2H), 4.539-4.604 (m, 2H), 7.468 (d, J=10.8 Hz, 1H), 7.958 (s, 1H), 8.487 (s, 1H), 8.749 (s, 1H).

Example 62: N-(2-(3-(dimethylamino)propoxy)-5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',4a1'(7a'),6'-pentanen-7'-yl)pyridin-3-yl)methanesulfonamide (A-157)

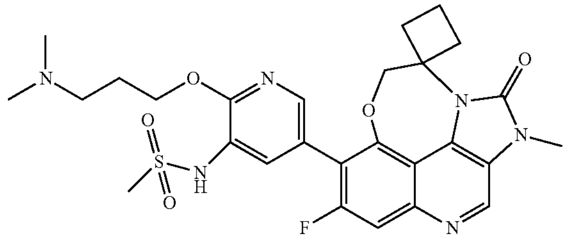

Except starting materials were changed, the synthesis method was the same as that of example 60 to afford N-(2-(3-(dimethylamino)propoxy)-5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',4a1'(7a'),6'-pentanen-7'-yl)pyridin-3-yl)methanesulfonamide (28 mg, 25.2% yield). ESI-MS (m/z): 571.21 $[M+H]^+$; $^1H$ NMR (600 MHz, $CD_3OD$) δ: 0.885-0.908 (m, 2H), 1.284 (s, 3H), 1.912-1.930 (m, 1H), 2.069-2.087 (m, 1H), 2.132-2.154 (m, 2H), 2.542 (s, 6H), 2.831-2.854 (m, 2H), 3.020 (s, 3H), 3.585 (s, 3H), 4.502-4.522 (m, 2H), 4.462 (s, 2H), 7.496 (d, J=10.8 Hz, 1H), 7.870 (s, 1H), 7.946 (s, 1H), 8.764 (s, 1H).

Example 63: (S)-7-(6-((3-(dimethylamino)propyl)amino)pyridin-3-yl)-6-fluoro-2,10-dimethyl-9,10-dihydro-8-oxa-2,4,10a-triazanaphtho[2,1,8-cde]azulen-1(2H)-one (A-158)

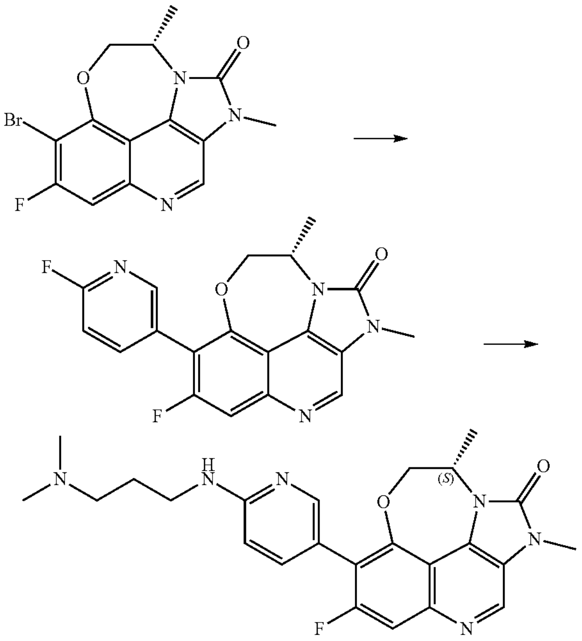

The synthesis method was the same as that of example 57 except that the starting material in step 1 was changed to (S)-7-bromo-6-fluoro-2,10-dimethyl-9,10-dihydro-8-oxa-2,4,10a-triazanaphtho[2,1,8-cde]azulen-1(2H)-one, and N,N-dimethyl-1,3-diaminopropane was used instead of N,N-dimethylpiperidin-4-amine hydrochloride in step 2, to afford (S)-7-(6-((3-(dimethylamino)propyl)amino)pyridin-3-yl)-6-fluoro-2,10-dimethyl-9,10-dihydro-8-oxa-2,4,10a-triazanaphtho[2,1,8-cde]azulen-1(2H)-one (88 mg, 47.5% yield). ESI-MS (m/z): 451.22 $[M+H]^+$; $^1H$ NMR (600 MHz, $CD_3OD$) δ: 1.549 (d, J=6.6 Hz, 3H), 2.004 (m, 2H), 2.777 (s, 6H), 3.028 (t, J=6.6 Hz, 2H), 3.488 (t, J=6.0 Hz, 2H), 3.627 (s, 3H), 4.501 (d, J=13.2 Hz, 1H), 4.641 (m, 1H), 4.717 (m, 2H), 6.700 (d, J=8.4 Hz, 1H), 7.515 (d, J=11.4 Hz, 1H), 7.617 (d, J=9.0 Hz, 1H), 8.143 (s, 1H), 8.802 (s, 1H).

Example 64: (S)-7-(6-(4-(dimethylamino)piperidin-1-yl)pyridin-3-yl)-6-fluoro-2,10-dimethyl-9,10-dihydro-8-oxa-2,4,10a-triazanaphtho[2,1,8-cde]azulen-1(2H)-one (A-159)

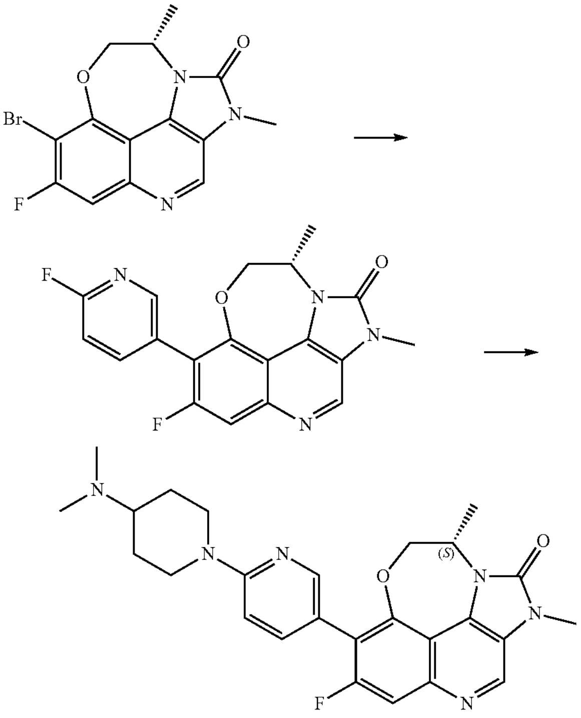

The synthesis method was the same as that of example 57 except that the starting material in step 1 was changed to (S)-7-bromo-6-fluoro-2,10-dimethyl-9,10-dihydro-8-oxa-2,4,10a-triazanaphtho[2,1,8-cde]azulen-1(2H)-one, to afford (S)-7-(6-(4-(dimethylamino)piperidin-1-yl)pyridin-3-yl)-6-fluoro-2,10-dimethyl-9,10-dihydro-8-oxa-2,4,10a-triazanaphtho[2,1,8-cde]azulen-1(2H)-one (31 mg, 16.7% yield). ESI-MS (m/z): 477.23 $[M+H]^+$; $^1H$ NMR (600 MHz, $CD_3OD$) δ: 1.538 (d, J=6.6 Hz, 3H), 1.619-1.666 (m, 2H), 2.091 (d, J=12.6H, 2H), 2.609 (s, 6H), 2.966 (m, 3H), 3.616 (s, 3H), 4.465-4.532 (m, 3H), 4.611-4.637 (m, 1H), 4.699 (d, J=5.4 Hz, 1H), 6.977 (d, J=9.0 Hz, 1H), 7.484 (d, J=11.4 Hz, 1H), 7.697 (d, J=9.0 Hz, 1H), 8.216 (s, 1H), 8.771 (s, 1H).

Example 65: (S)-1-(3-((5-(6-fluoro-2-methyl-1-oxo-2,9-dihydro-1H-spiro[8-oxa-2,4,10a-triazanaphtho[2,1,8-cde]azulene-10,1'-cyclopropan]-7-yl)pyridin-2-yl)oxy)propyl)pyrrolidine-3-carbonitrile (A-160)

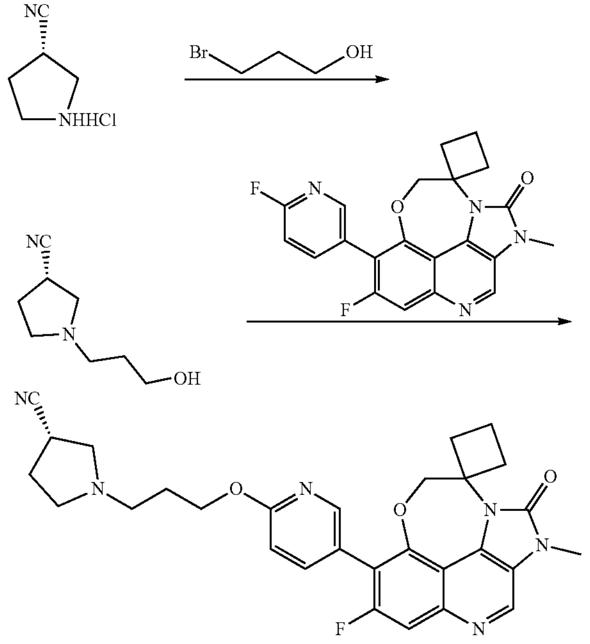

Step 1: Synthesis of (S)-1-(3-hydroxypropyl)pyrrolidine-3-carbonitrile (S)-3-cyanopyrrolidine hydrochloride (0.95 g, 7.13 mmol), acetonitrile (20 mL), potassium carbonate (3.94 g, 28.54 mmol), and 3-bromopropan-1-ol (1.19 g, 8.56 mmol) were added to a 100 mL reaction bottle. The reaction solution was heated up to 80° C. to react for 5 h. When the reaction was completed as detected by TLC, the reaction solution was cooled down to room temperature and subjected to suction filtration, the filtrate was concentrated to dryness, and then the residue was purified by column chromatography (DCM:MeOH=50:1-20:1) to afford (S)-1-(3-hydroxypropyl)pyrrolidine-3-carbonitrile (0.62 g, 56.4% yield). ESI-MS (m/z): 155.11 $[M+H]^+$.

Step 2: Synthesis of (S)-1-(3-((5-(6-fluoro-2-methyl-1-oxo-2,9-dihydro-1H-spiro[8-oxa-2,4,10a-triazanaphtho[2,1,8-cde]azulene-10,1'-cyclopropan]-7-yl)pyridin-2-yl)oxy)propyl)pyrrolidine-3-carbonitrile Anhydrous THF (4 mL) and (S)-1-(3-hydroxypropyl) pyrrolidine-3-carbonitrile (78 mg, 0.51 mmol) were added to a 50 mL reaction bottle and cooled down to 0° C., followed by adding NaH (35 mg, 0.89 mmol) in batches. After 0.5 h of reaction at room temperature, 6-fluoro-7-(6-fluoropyridin-3-yl)-2-methyl-2,9-dihydro-1H-spiro[8-oxa-2,4,10a-triazanaphtho[2,1,8-cde]azulene-10,1'-cyclobutan]-1-one (100 mg, 0.25 mmol) was added, and the reaction was continued at room temperature overnight. When the reaction was completed as detected by TLC, the reaction solution was concentrated to dryness and the residue was purified by column chromatography (DCM:MeOH=20:1-10:1) to afford a crude product. The crude product was further purified by preparative thin-layer chromatography to afford (S)-1-(3-((5-(6-fluoro-2-methyl-1-oxo-2,9-dihydro-1H-spiro[8-oxa-2,4,10a-triazanaphtho[2,1,8-cde]azulene-10,1'-cyclopropan]-7-yl)pyridin-2-yl)oxy)propyl)pyrrolidine-3-carbonitrile (23 mg, 17.4%). ESI-MS (m/z): 529.23 $[M+H]^+$; $^1H$ NMR (600 MHz, $CD_3OD$) δ: 0.886-0.909 (m, 2H), 1.288-1.320 (m, 2H), 1.929-1.948 (m, 1H), 2.031-2.099 (m, 4H), 2.295-2.311 (m, 1H), 2.655-2.950 (m, 6H), 3.195-3.306 (m, 1H), 3.599 (s, 3H), 4.426 (t, J=6.0 Hz, 2H), 4.840 (brs, 2H), 6.938 (d, J=8.4 Hz, 1H), 7.515 (d, J=10.8 Hz, 1H), 7.833 (d, J=8.4 Hz, 1H), 8.252 (s, 1H), 8.787 (s, 1H).

Example 66: (S)-6-fluoro-7-(6-(3-(3-fluoropyrrolidin-1-yl)propoxy)pyridin-3-yl)-2-methyl-2,9-dihydro-1H-spiro[8-oxa-2,4,10a-triazanaphtho[2,1,8-cde]azulene-10,1'-cyclobutan]-1-one (A-161)

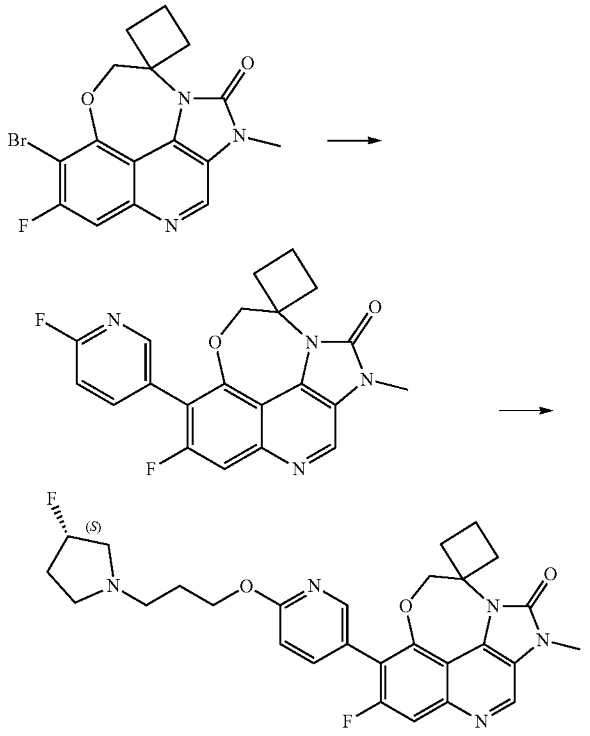

Except starting materials were changed, the synthesis method was the same as that of example 65 to afford (S)-6-fluoro-7-(6-(3-(3-fluoropyrrolidin-1-yl)propoxy)pyridin-3-yl)-2-methyl-2,9-dihydro-1H-spiro[8-oxa-2,4,10a-triazanaphtho[2,1,8-cde]azulene-10,1'-cyclobutan]-1-one (30 mg, 29.2% yield). ESI-MS (m/z): 522.22 $[M+H]^+$; $^1H$ NMR (600 MHz, $CD_3OD$) δ: 0.693 (m, 1H), 1.444-1.457 (m, 1H), 1.703-1.727 (m, 1H), 1.923-1.955 (m, 2H), 2.010-2.078 (m, 4H), 2.198-2.255 (m, 1H), 2.482-2.495 (m, 1H), 2.704-2.755 (m, 3H), 2.955-3.306 (m, 2H), 3.588 (s, 3H), 4.271-4.293 (m, 1H), 4.402-4.423 (m, 2H), 4.892 (s, 2H), 6.929 (d, J=8.4 Hz, 1H), 7.481 (d, J=10.8 Hz, 1H), 7.823 (d, J=8.4 Hz, 1H), 8.240 (s, 1H), 8.760 (s, 1H).

Example 67: 6-fluoro-2-methyl-7-(6-(3-(pyrrolidin-1-yl)propoxy)pyridin-3-yl)-2,9-dihydro-1H-spiro[8-oxa-2,4,10a-triazanaphtho[2,1,8-cde]azulene-10,1'-cyclobutan]-1-one (A-162)

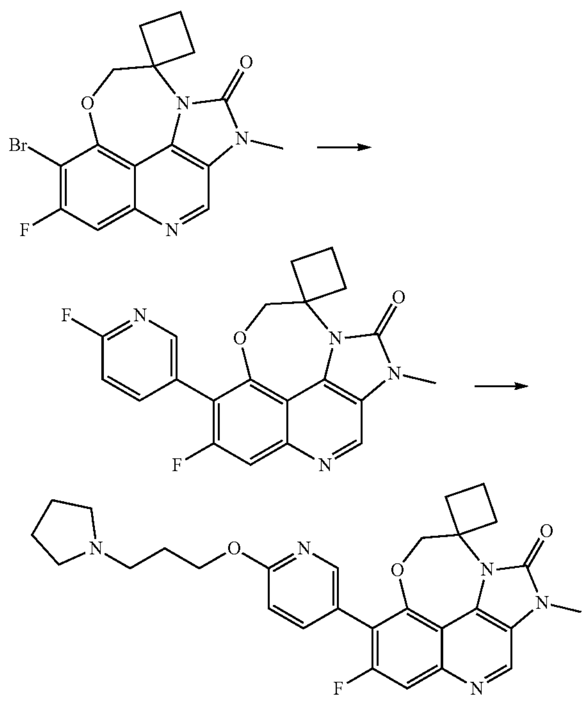

Except starting materials were changed, the synthesis method was the same as that of example 65 to afford 6-fluoro-2-methyl-7-(6-(3-(pyrrolidin-1-yl)propoxy)pyridin-3-yl)-2,9-dihydro-1H-spiro[8-oxa-2,4,10a-triazanaphtho[2,1,8-cde]azulene-10,1'-cyclobutan]-1-one (28 mg, 27.9% yield). ESI-MS (m/z): 504.23 $[M+H]^+$; $^1H$ NMR (600 MHz, $CD_3OD$) δ: 0.885-0.905 (m, 2H), 1.285 (s, 2H), 1.834-1.854 (m, 4H), 1.913-1.948 (m, 1H), 2.049-2.096 (m, 3H), 2.638 (s, 4H), 2.710-2.736 (m, 2H), 3.575 (s, 3H), 4.396-4.417 (m, 2H), 4.571 (s, 2H), 6.918 (d, J=8.4 Hz, 1H), 7.455 (d, J=10.8 Hz, 1H), 7.807 (d, J=8.4 Hz, 1H), 8.227 (s, 1H), 8.728 (s, 1H).

Example 68: 7'-(6-(3-(4,4-difluoropiperidin-1-yl) propoxy)pyridin-3-yl)-6'-fluoro-2'-methyl-9'-H-8'-oxa-2',4',10a'-triazaspiro[cyclobutane-1,10'-naphtho [2,1,8-cde]azulen]-2a',3',4a',5',7'-pentaen-1'(2'H)-one (A-163)

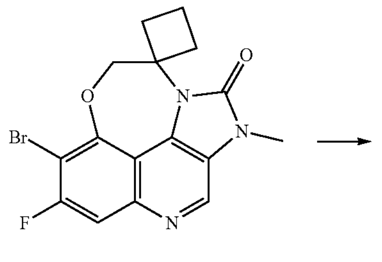

-continued

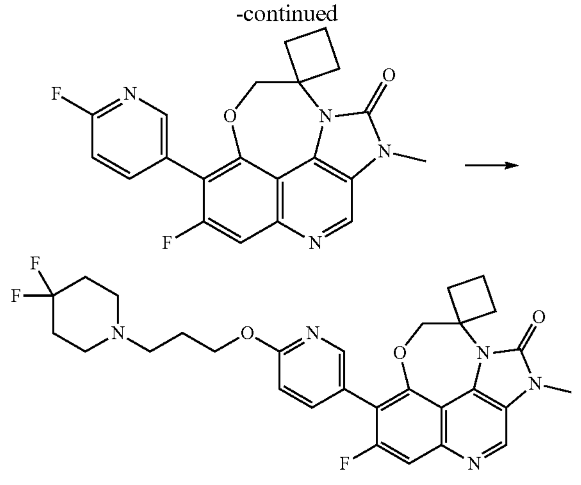

Except starting materials were changed, the synthesis method was the same as that of example 65 to afford 7'-(6-(3-(4,4-difluoropiperidin-1-yl)propoxy)pyridin-3-yl)-6'-fluoro-2'-methyl-9'-H-8'-oxa-2',4',10a'-triazaspiro[cyclobutane-1,10'-naphtho[2,1,8-cde]azulen]-2a',3',4a',5',7'-pentaen-1'(2'H)-one (48 mg, 20.1% yield). ESI-MS (m/z): 554.23 $[M+H]^+$; $^1H$ NMR (600 MHz, $CD_3OD$) δ: 0.897 (t, J=7.2 Hz, 2H), 1.288 (m, 2H), 1.925-1.988 (m, 2H), 1.998-2.091 (m, 6H), 2.649 (t, J=7.2 Hz, 6H), 3.596 (s, 3H), 4.419 (t, J=6.6 Hz, 2H), 4.605 (brs, 2H), 6.932 (d, J=8.4 Hz, 1H), 7.505 (d, J=11.4 Hz, 1H), 7.822-7.837 (m, 1H), 8.247 (s, 1H), 8.778 (s, 1H).

Example 69: 6'-fluoro-2'-methyl-7'-(6-(3-(4-methylpiperazin-1-yl)propoxy)pyridin-3-yl)-9'-H-8'-oxa-2',4',10a'-triazaspiro[cyclobutane-1,10'-naphtho[2,1,8-cde]azulen]-2a',3',4a',5',7'-pentaen-1'(2'H)-one (A-164)

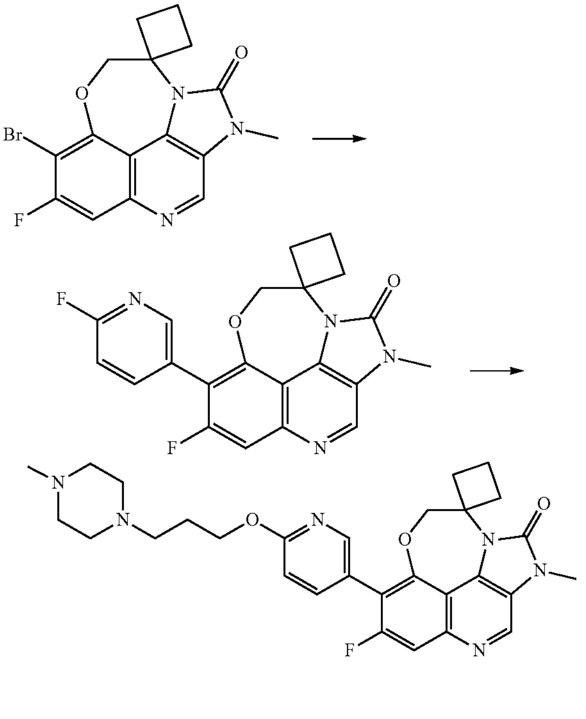

Except starting materials were changed, the synthesis method was the same as that of example 65 to afford 6'-fluoro-2'-methyl-7'-(6-(3-(4-methylpiperazin-1-yl)propoxy)pyridin-3-yl)-9'-H-8'-oxa-2',4',10a'-triazaspiro[cyclobutane-1,10'-naphtho[2,1,8-cde]azulen]-2a',3',4a',5',7'-pentaen-1'(2'H)-one (38 mg, 19.7% yield). ESI-MS (m/z): 533.26 $[M+H]^+$; $^1H$ NMR (600 MHz, $CD_3OD$) δ: 0.897 (t, J=6.6H, 2H), 1.288 (m, 2H), 1.907-1.957 (m, 2H), 2.023-2.090 (m, 3H), 2.336 (s, 3H), 2.564-2.632 (m, 9H), 3.591 (s, 3H), 4.410 (t, J=6.0 Hz, 2H), 4.595 (brs, 2H), 6.925 (d, J=8.4 Hz, 1H), 7.490 (d, J=10.8 Hz, 1H), 7.822 (d, J=8.4 Hz, 1H), 8.240 (s, 1H), 8.763 (s, 1H).

Example 70: 6'-fluoro-7'-(6-(3-(4-fluoropiperidin-1-yl)propoxy)pyridin-3-yl)-2'-methyl-9'-H-8'-oxa-2',4',10a'-triazaspiro[cyclobutane-1,10'-naphtho[2,1,8-cde]azulen]-2a',3',4a',5',7'-pentaen-1'(2'H)-one (A-165)

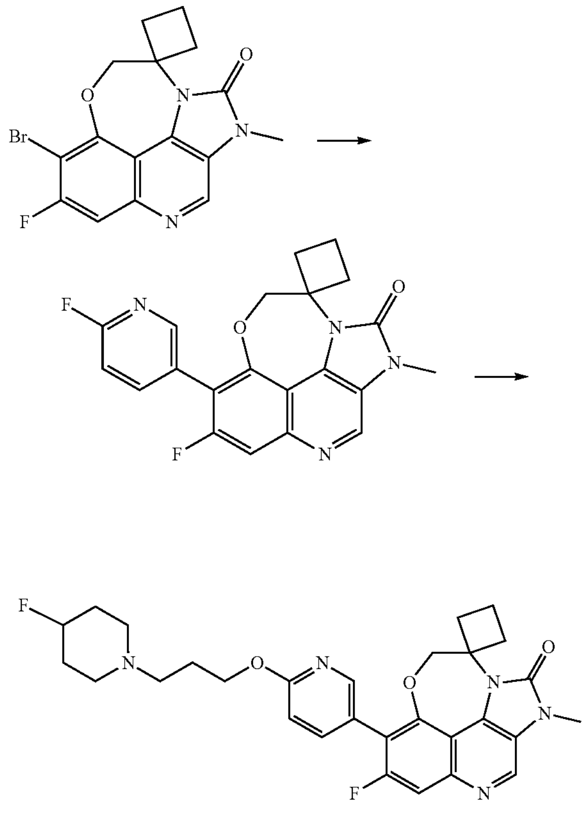

Except starting materials were changed, the synthesis method was the same as that of example 65 to afford 6'-fluoro-7'-(6-(3-(4-fluoropiperidin-1-yl)propoxy)pyridin-3-yl)-2'-methyl-9'-H-8'-oxa-2',4',10a'-triazaspiro[cyclobutane-1,10'-naphtho[2,1,8-cde]azulen]-2a',3',4a',5',7'-pentaen-1'(2'H)-one (23 mg, 16.3% yield). ESI-MS (m/z): 536.24 $[M+H]^+$; $^1H$ NMR (600 MHz, $CD_3OD$) δ: 1.850-1.855 (m, 4H), 1.908-1.942 (m, 4H), 2.032-2.068 (m, 5H), 2.501 (s, 2H), 2.591-2.671 (m, 4H), 3.569 (s, 3H), 4.396 (t, J=6.0 Hz, 2H), 4.562 (brs, 1H), 4.633 (s, 1H), 6.907 (d, J=8.4 Hz, 1H), 7.430 (d, J=10.8 Hz, 1H), 7.796 (d, J=8.4 Hz, 1H), 8.216 (s, 1H), 8.705 (s, 1H).

Example 71: 1-(3-((5-(6'-fluoro-2'-methyl-1'-oxo-1',2'-dihydro-9'-H-8'-oxa-2',4',10a'-triazaspiro[cyclobutane-1,10'-naphtho[2,1,8-cde]azulen]-2a',3',4a',5',7'-pentanen-7'-yl)pyridin-2-yl)oxy)propyl)piperidin-4-carbonitrile (A-166)

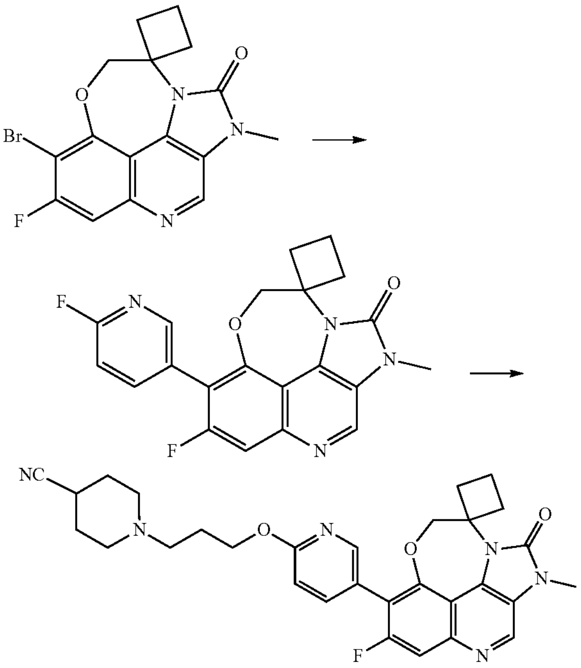

Except starting materials were changed, the synthesis method was the same as that of example 65 to afford 1-(3-((5-(6'-fluoro-2'-methyl-1'-oxo-1',2'-dihydro-9'-H-8'-oxa-2',4',10a'-triazaspiro[cyclobutane-1,10'-naphtho[2,1,8-cde]azulen]-2a',3',4a',5',7'-pentanen-7'-yl)pyridin-2-yl)oxy)propyl)piperidin-4-carbonitrile (41 mg, 22.6% yield). ESI-MS (m/z): 543.24 $[M+H]^+$; $^1H$ NMR (600 MHz, $CD_3OD$) δ: 0.886-2.056 (m, 12H), 2.446 (d, J=14.4 Hz, 2H), 2.599 (s, 2H), 2.618 (d, J=7.2 Hz, 2H), 2.832 (s, 1H), 3.599 (s, 3H), 4.407 (t, J=6.6 Hz, 2H), 4.609 (brs, 2H), 6.933 (d, J=8.4 Hz, 1H), 7.513 (d, J=10.8 Hz, 1H), 7.833 (d, J=8.4 Hz, 1H), 8.251 (s, 1H), 8.787 (s, 1H).

Example 72: 7'-(6-(3-(2-oxa-7-azaspiro[3.5]nonan-7-yl)propoxy)pyridin-3-yl)-6'-fluoro-2'-methyl-9'H-8'-oxa-2',4',10a'-triazaspiro[cyclobutane-1,10'-naphtho[2,1,8-cde]azulen]-2a',3',4a',5',7'-pentaen-1'(2'H)-one (A-167)

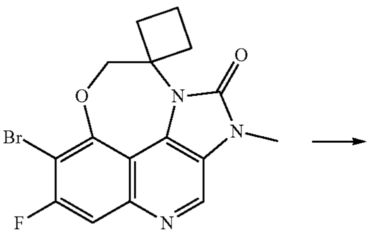

-continued

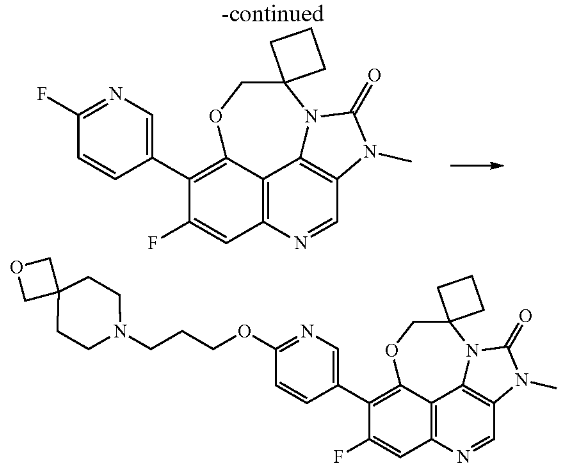

Except starting materials were changed, the synthesis method was the same as that of example 65 to afford 7'-(6-(3-(2-oxa-7-azaspiro[3.5]nonan-7-yl)propoxy)pyridin-3-yl)-6'-fluoro-2'-methyl-9'H-8'-oxa-2',4',10a'-triazaspiro [cyclobutane-1,10'-naphtho[2,1,8-cde]azulen]-2a',3',4a',5',7'-pentaen-1'(2'H)-one (64 mg, 32.5% yield). ESI-MS (m/z): 560.26 [M+H]$^+$; $^1$H NMR (600 MHz, $CD_3OD$) δ: 0.851-2.068 (m, 12H), 2.471 (s, 3H), 2.572 (t, J=7.8 Hz, 3H), 3.554 (s, 3H), 4.379 (t, J=6.6 Hz, 2H), 4.424 (s, 4H), 4.532 (s, 2H), 6.891 (d, J=8.4 Hz, 1H), 7.394 (d, J=10.8 Hz, 1H), 7.782 (d, J=8.4 Hz, 1H), 8.200 (s, 1H), 8.671 (s, 1H).

Example 73: (S)-1-(3-((5-(6'-fluoro-2'-methyl-1'-oxo-1',2'-dihydro-9'H-8'-oxa-2',4',10a'-triazaspiro [cyclobutane-1,10'-naphtho[2,1,8-cde]azulen]-2a',3',4a',5',7'-pentanen-7'-yl)pyridin-2-yl)oxy)propyl) pyrrolidine-2-carboxamide (A-168)

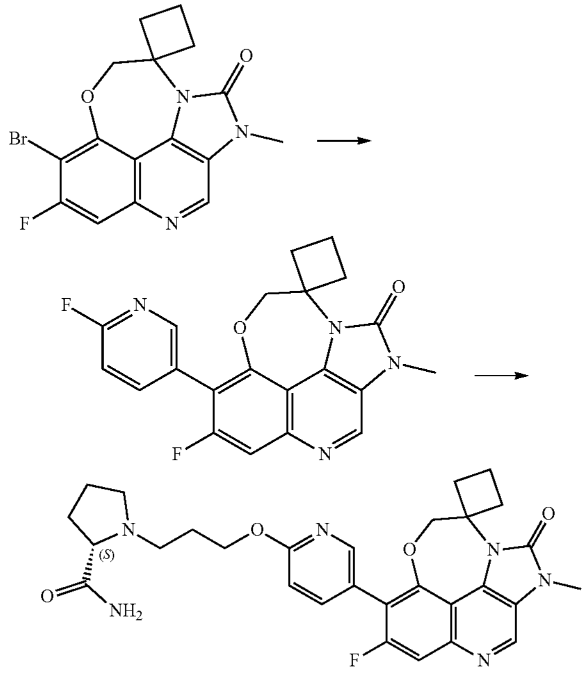

Except starting materials were changed, the synthesis method was the same as that of example 65 to afford (S)-1-(3-((5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',5',7'-pentanen-7'-yl)pyridin-2-yl) oxy)propyl)pyrrolidine-2-carboxamide (22 mg, 22.1% yield). ESI-MS (m/z): 547.24 [M+H]$^+$; $^1$H NMR (600 MHz, $CD_3OD$) δ: 0.897-0.909 (m, 2H), 1.287 (s, 3H), 1.843 (s, 3H), 1.895-1.975 (m, 1H), 2.024-2.107 (m, 3H), 2.209 (s, 1H), 2.381 (s, 1H), 2.626 (s, 1H), 2.908-3.007 (m, 2H), 3.596 (s, 3H), 4.420-4.499 (m, 2H), 4.597 (s, 2H), 6.934 (d, J=8.4 Hz, 1H), 7.504 (d, J=10.8 Hz, 1H), 7.833 (d, J=8.4 Hz, 1H), 8.250 (s, 1H), 8.780 (s, 1H).

Example 74: (S)-1-(3-((5-(6'-fluoro-2'-methyl-1'-oxo-1',2'-dihydro-9'H-8'-oxa-2',4',10a'-triazaspiro [cyclobutane-1,10'-naphtho[2,1,8-cde]azulen]-2a',3',4a',5',7'-pentanen-7'-yl)pyridin-2-yl)oxy)propyl) pyrrolidine-2-carbonitrile (A-169)

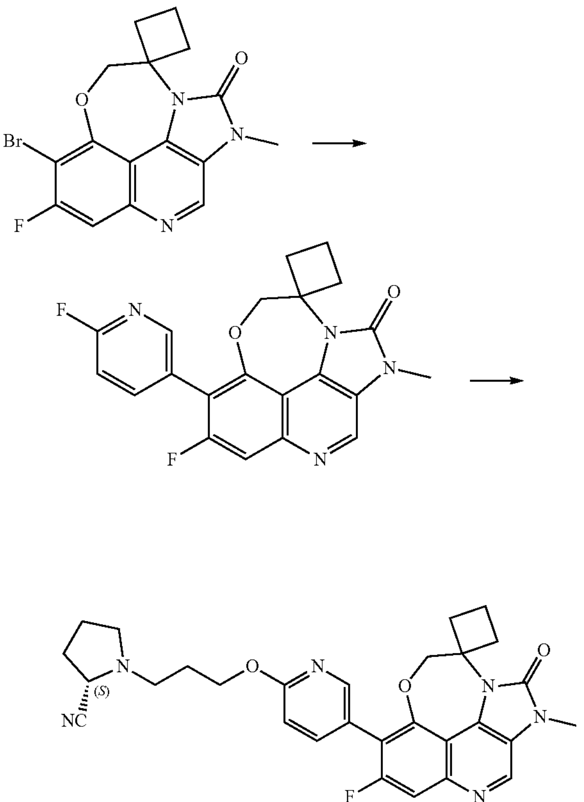

Except starting materials were changed, the synthesis method was the same as that of example 65 to afford (S)-1-(3-((5-(6'-fluoro-2'-methyl-1'-oxo-1',2'-dihydro-9'H-8'-oxa-2',4',10a'-triazaspiro[cyclobutane-1,10'-naphtho[2,1,8-cde]azulen]-2a',3',4a',5',7'-pentanen-7'-yl)pyridin-2-yl) oxy)propyl)pyrrolidine-2-carboxamide (15 mg, 18.6% yield). ESI-MS (m/z): 529.23 [M+H]$^+$; $^1$H NMR (600 MHz, $CD_3OD$) δ: 0.885-0.908 (m, 2H), 1.926-1.953 (m, 4H), 2.055-2.088 (m, 4H), 2.219-2.245 (m, 1H), 2.622-2.649 (m, 1H), 2.773-2.793 (m, 1H), 2.805-2.937 (m, 2H), 3.595 (s, 5H), 3.935-3.953 (m, 2H), 4.424-4.499 (m, 2H), 6.941 (d, J=8.4 Hz, 1H), 7.501 (d, J=10.8 Hz, 1H), 7.830 (d, J=8.4 Hz, 1H), 8.247 (s, 1H), 8.777 (s, 1H).

Example 75: 7'-(6-(3-(3-azabicyclo[3.1.0]hexan-3-yl)propoxy)pyridin-3-yl)-6'-fluoro-2'-methyl-9'H-8'-oxa-2',4',10a'-triazaspiro[cyclobutane-1,10'-naphtho[2,1,8-cde]azulen]-2a',3',4a',5',7'-pentaen-1'(2'H)-one (A-170)

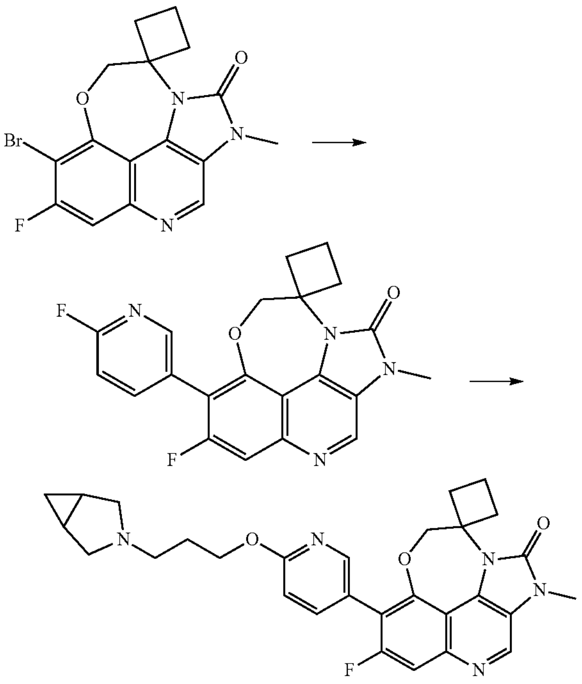

Except starting materials were changed, the synthesis method was the same as that of example 65 to afford 7'-(6-(3-(3-azabicyclo[3.1.0]hexan-3-yl)propoxy)pyridin-3-yl)-6'-fluoro-2'-methyl-9'H-8'-oxa-2',4',10a'-triazaspiro[cyclobutane-1,10'-naphtho[2,1,8-cde]azulen]-2a',3',4a',5',7'-pentaen-1'(2'H)-one (75 mg, 38.8% yield). ESI-MS (m/z): 516.23 [M+H]$^+$; $^1$H NMR (600 MHz, $CD_3OD$) δ: 0.451-0.485 (m, 1H), 0.665-0.686 (m, 1H), 0.896 (t, J=6.6 Hz, 1H), 1.276 (s, 1H), 1.486 (t, J=3.6 Hz, 2H), 1.900-2.100 (m, 4H), 2.555 (d, J=9.0 Hz, 2H), 2.734 (t, J=7.8 Hz, 2H), 3.134 (d, J=9.0 Hz, 2H), 3.581 (s, 3H), 4.367-4.580 (m, 2H), 4.866 (s, 2H), 6.911 (d, J=9.0 Hz, 1H), 7.460 (d, J=11.4 Hz, 1H), 7.802-7.818 (m, 1H), 8.226 (s, 1H), 8.737 (s, 1H).

Example 76: (S)-7-(6-(3-(2-oxa-7-azaspiro[3.5]nonan-7-yl)propoxy)pyridin-3-yl)-6-fluoro-2,10-dimethyl-9,10-dihydro-8-oxa-2,4,10a-triazanaphtho[2,1,8-cde]azulen-1(2H)-one (A-171)

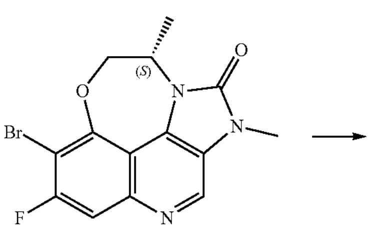

-continued

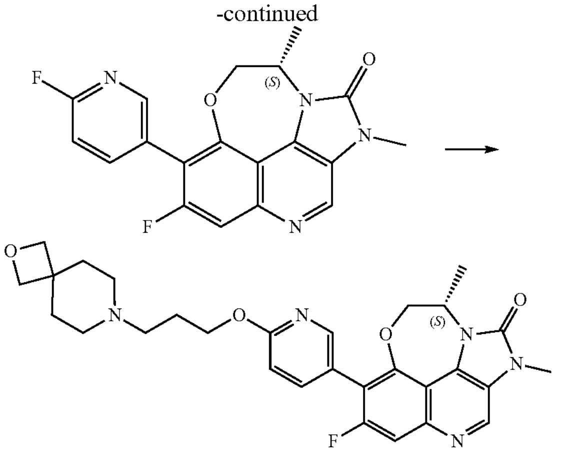

Except starting materials were changed, the synthesis method was the same as that of example 65 to afford (S)-7-(6-(3-(2-oxa-7-azaspiro[3.5]nonan-7-yl)propoxy)pyridin-3-yl)-6-fluoro-2,10-dimethyl-9,10-dihydro-8-oxa-2,4,10a-triazanaphtho[2,1,8-cde]azulen-1(2H)-one (79 mg, 37.8% yield). ESI-MS (m/z): 534.24 [M+H]$^+$; $^1$H NMR (600 MHz, $CD_3OD$) δ: 1.540 (d, J=6.6 Hz, 3H), 1.919 (s, 4H), 2.035 (t, J=7.8 Hz, 2H), 2.453 (s, 3H), 2.557 (t, J=7.8 Hz, 3H), 3,624 (s, 3H), 4.383 (t, J=6.6 Hz, 2H), 4.430 (s, 4H), 4.501 (d, J=13.2 Hz, 1H), 4.617 (d, J=2.4 Hz, 1H), 4.637-4.714 (m, 1H), 6.908 (d, J=8.4 Hz, 1H), 7.522 (d, J=10.8 Hz, 1H), 7.812 (d, J=8.4 Hz, 1H), 8.227 (s, 1H), 8.802 (s, 1H).

Example 77: 1-(3-((5-(6-fluoro-2-methyl-1-oxo-2,9-dihydro-1H-spiro[8-oxa-2,4,10a-triazanaphtho[2,1,8-cde]azulene-10,1'-cyclopropan]-7-yl)pyridin-2-yl)oxy)propyl)piperidine-2-carboxamide (A-172)

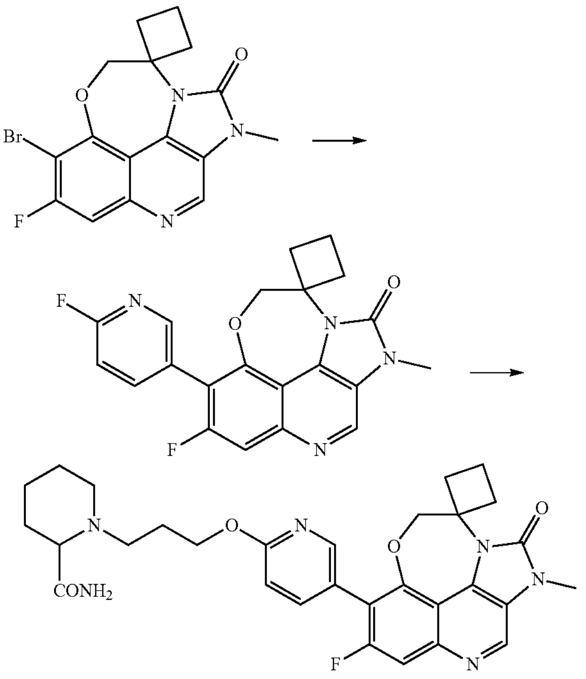

Except starting materials were changed, the synthesis method was the same as that of example 65 to afford 1-(3-((5-(6-fluoro-2-methyl-1-oxo-2,9-dihydro-1H-spiro[8-oxa-2,4,10a-triazanaphtho[2,1,8-cde]azulene-10,1'-cyclopropan]-7-yl)pyridin-2-yl)oxy)propyl)piperidine-2-carboxamide (20 mg, 26.5% yield). ESI-MS (m/z): 561.25 $[M+H]^+$; $^1H$ NMR (600 MHz, DMSO-$d_6$) δ: 0.848-0.871 (m, 2H), 1.223-1.274 (m, 3H), 1.445-1.494 (m, 2H), 1.515-1.576 (m, 1H), 1.644-1.677 (m, 2H), 1.917-1.969 (m, 5H), 2.226-2.247 (m, 1H), 2.499-2.505 (m, 1H), 2.578-2.600 (m, 1H), 3.071-3.090 (m, 1H), 3.525 (s, 3H), 4.039-4.327 (m, 1H), 4.382-4.399 (m, 1H), 4.651 (s, 2H), 6.946 (d, J=8.4 Hz, 1H), 6.979 (s, 1H), 7.075 (s, 1H), 7.590 (d, J=10.8 Hz, 1H), 7.838 (d, J=8.4 Hz, 1H), 8.284 (s, 1H), 8.906 (s, 1H).

Example 78: 1-(3-((5-(6-fluoro-2-methyl-1-oxo-2,9-dihydro-1H-spiro[8-oxa-2,4,10a-triazanaphtho[2,1,8-cde]azulene-10,1'-cyclopropan]-7-yl)pyridin-2-yl)oxy)propyl)piperidine-2-carbonitrile (A-173)

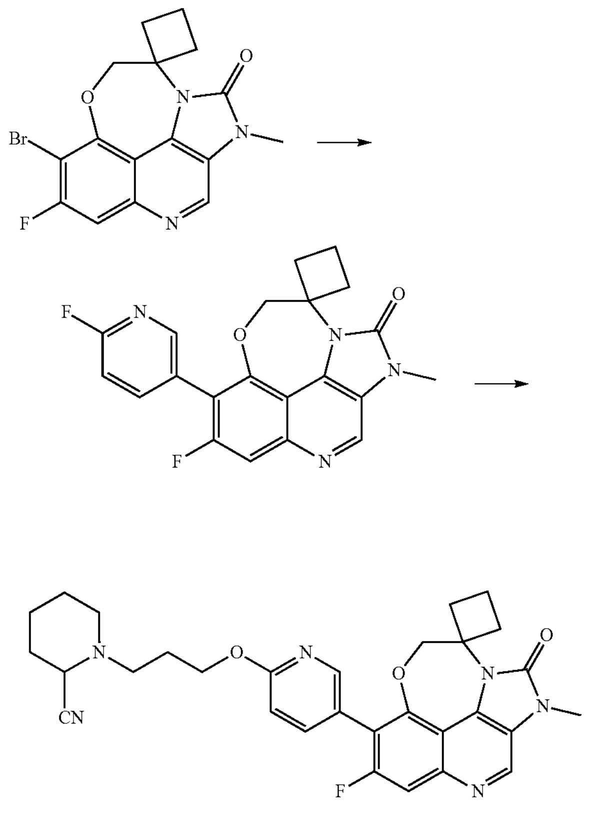

Except starting materials were changed, the synthesis method was the same as that of example 65 to afford 1-(3-((5-(6-fluoro-2-methyl-1-oxo-2,9-dihydro-1H-spiro[8-oxa-2,4,10a-triazanaphtho[2,1,8-cde]azulene-10,1'-cyclopropan]-7-yl)pyridin-2-yl)oxy)propyl)piperidine-2-carbonitrile (25 mg, 27.1% yield). ESI-MS (m/z): 543.24 $[M+H]^+$; $^1H$ NMR (600 MHz, DMSO-$d_6$) δ: 0.848-0.860 (m, 1H), 1.244-1.261 (m, 2H), 1.351-1.461 (m, 2H), 1.604-1.732 (m, 3H), 1.815-1.837 (m, 1H), 1.917-1.962 (m, 4H), 2.142-2.185 (m, 1H), 2.499-2.563 (m, 2H), 2.808-2.828 (m, 1H), 3.526 (s, 3H), 4.203 (s, 1H), 4.346-4.367 (m, 2H), 4.650 (s, 2H), 6.963 (d, J=8.4 Hz, 1H), 7.591 (d, J=10.8 Hz, 1H), 7.848 (d, J=8.4 Hz, 1H), 8.287 (s, 1H), 8.907 (s, 1H).

Example 79: (S)-7-(6-(3-(6-azaspiro[2.5]octan-6-yl)propoxy)pyridin-3-yl)-6-fluoro-2,10-dimethyl-9,10-dihydro-8-oxa-2,4,10a-triazanaphtho[2,1,8-cde]azulen-1(2H)-one (A-174)

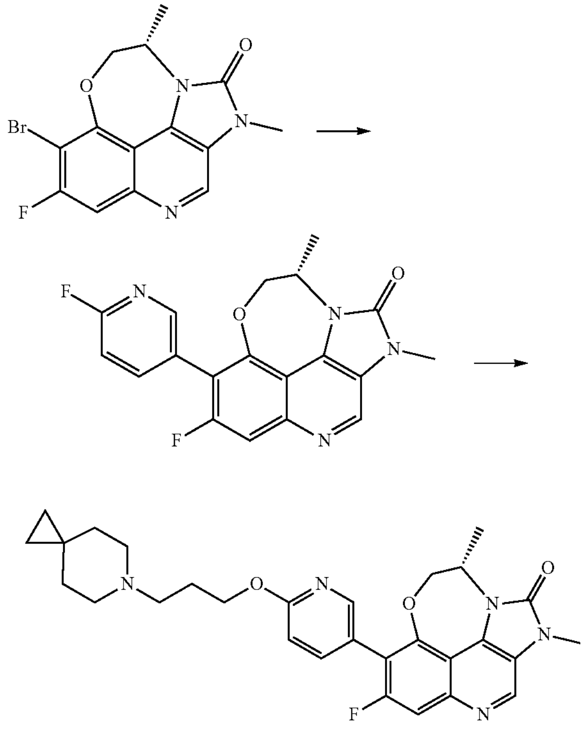

Except starting materials were changed, the synthesis method was the same as that of example 65 to afford (S)-7-(6-(3-(6-azaspiro[2.5]octan-6-yl)propoxy)pyridin-3-yl)-6-fluoro-2,10-dimethyl-9,10-dihydro-8-oxa-2,4,10a-triazanaphtho[2,1,8-cde]azulen-1(2H)-one (45 mg, 30.6% yield). ESI-MS (m/z): 518.25 $[M+H]^+$; $^1H$ NMR (600 MHz, $CD_3OD$) δ: 0.357 (s, 4H), 1.535-1.561 (m, 7H), 2.095-2.142 (m, 2H), 2.740-2.773 (m, 6H), 3.627 (s, 3H), 4.410-4.430 (m, 2H), 4.496-4.518 (m, 1H), 4.616-4.642 (m, 1H), 4.705-4.717 (m, 1H), 6.929 (d, J=8.4 Hz, 1H), 7.528 (d, J=10.8 Hz, 1H), 7.826 (d, J=8.4 Hz, 1H), 8.242 (s, 1H), 8.809 (s, 1H).

Example 80: (S)-6-fluoro-2,10-dimethyl-7-(6-(3-(4-methylpiperidin-1-yl)propoxy)pyridin-3-yl)-9,10-dihydro-8-oxa-2,4,10a-triazanaphtho[2,1,8-cde]azulen-1(2H)-one (A-175)

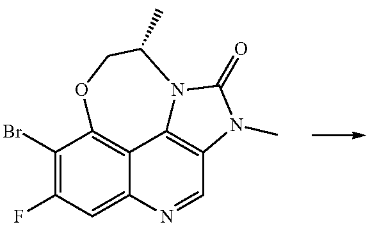

-continued

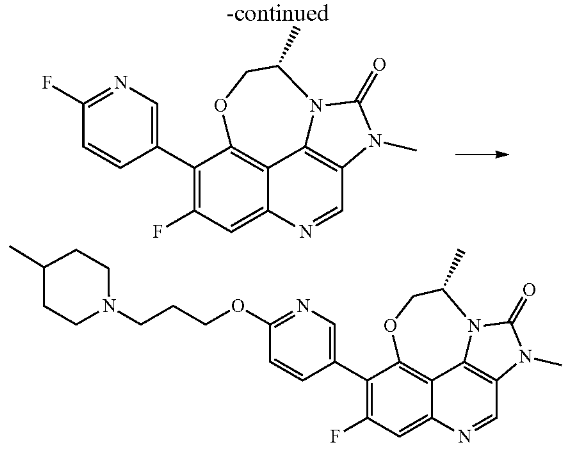

Except starting materials were changed, the synthesis method was the same as that of example 65 except that 3-(4-methylpiperidin-1-yl)propan-1-ol was used instead of 3-(piperidin-1-yl)propan-1-ol, to afford (S)-6-fluoro-2,10-dimethyl-7-(6-(3-(4-methylpiperidin-1-yl)propoxy)pyridin-3-yl)-9,10-dihydro-8-oxa-2,4,10a-triazanaphtho[2,1,8-cde]azulen-1(2H)-one (50 mg, 29.8% yield). ESI-MS (m/z): 506.25 $[M+H]^+$; $^1H$ NMR (600 MHz, $CD_3OD$) δ: 0.885-0.908 (m, 3H), 1.350-1.394 (m, 2H), 1.531-1.565 (m, 4H), 1.792-1.815 (m, 2H), 2.138-2.164 (m, 2H), 2.458-2.496 (m, 2H), 2.904-2.916 (m, 2H), 3.242-3.309 (m, 2H), 3.625 (s, 3H), 4.402-4.440 (m, 2H), 4.494-4.516 (m, 1H), 4.609-4.635 (m, 1H), 4.704-4.717 (m, 1H), 6.931 (d, J=8.4 Hz, 1H), 7.522 (d, J=10.8 Hz, 1H), 7.830 (d, J=8.4 Hz, 1H), 8.243 (s, 1H), 8.807 (s, 1H).

Example 81: 2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclobutan]-1-one (A-176)

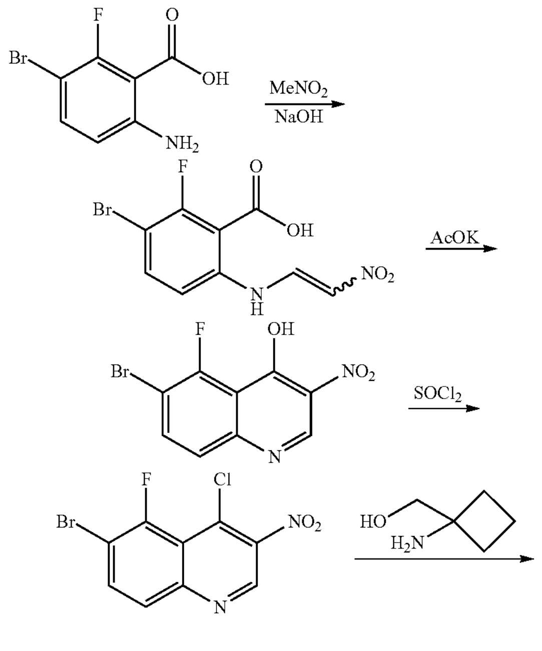

-continued

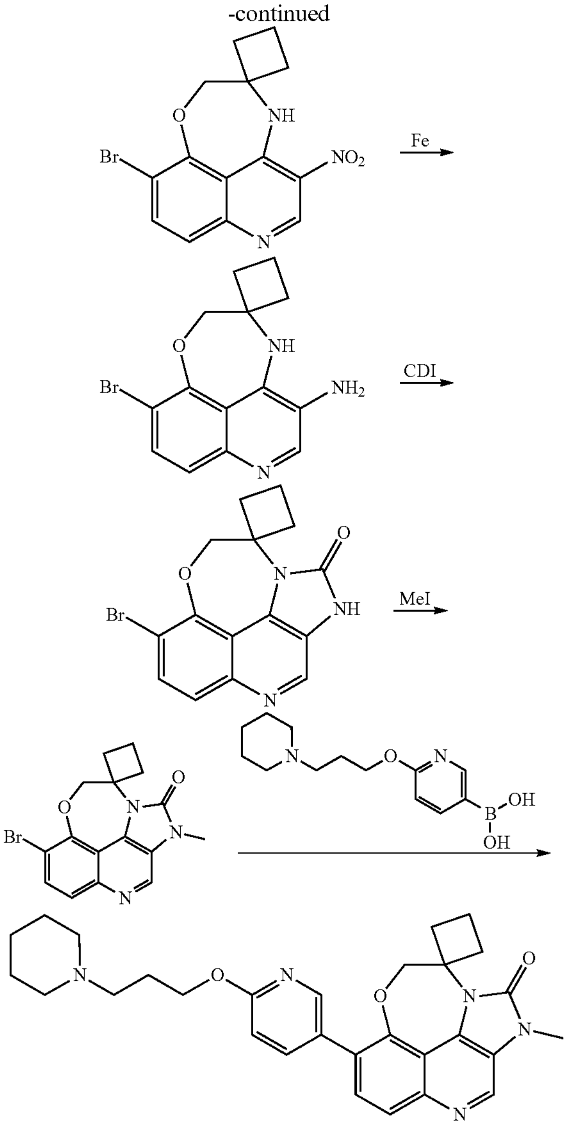

Step 1: Synthesis of 3-bromo-2-fluoro-6-((2-nitrovinyl)amino)benzoic acid

Sodium hydroxide (6.4 g, 160 mmol) and water (30 mL) were added to a 100 mL reaction bottle. Nitromethane (3.66 g, 60 mmol) was added dropwise to the reaction bottle at 25° C. to 30° C., after addition, the reaction solution was heated up to 45° C. to react for 5 min, and then cooled down to room temperature, and poured into a mixture of ice (14.5 g) and concentrated hydrochloric acid (14.5 mL) to afford a solution of nitroacetaldoxime. To a 500 mL reaction bottle, 6-amino-3-bromo-2-fluorobenzoic acid (4.68 g, 20 mmol), concentrated hydrochloric acid (23 mL), and water (132 mL) were successively added as a reaction solution, and the resultant nitroacetaldoxime solution as mentioned above was added dropwise to the reaction solution at room temperature, after addition, the reaction was continued at room temperature overnight. When the reaction was completed, the reaction solution was subjected to suction filtration. The filter cake was rinsed with water and dried to afford 3-bromo-2-fluoro-6-((2-nitrovinyl)amino)benzoic acid (5.08 g, 83.1% yield). ESI-MS (m/z): 304.95/306.95 $[M+H]^+$.

Step 2: Synthesis of 6-bromo-5-fluoro-3-nitroquinoline-4-ol

Acetic anhydride (100 mL) and 3-bromo-2-fluoro-6-((2-nitrovinyl)amino)benzoic acid (4.88 g, 16 mmol) were added to a 250 mL reaction bottle, and the reaction solution was heated up to 70° C. until the starting materials were completely dissoluted, and then cooled down to 40° C., followed by adding potassium acetate (1.88 g, 19.2 mmol). The reaction solution was reacted for 1.5 h at 90° C. When the reaction was completed as detected by TLC, the reaction solution was cooled down to room temperature, added with water (18 mL), stirred for 2 h, and then filtrated, the filter cake was rinsed with acetic acid and n-hexane respectively, and dried to afford 6-bromo-5-fluoro-3-nitroquinoline-4-ol (2.4 g, 51.0% yield). ESI-MS (m/z): 286.94/288.94 $[M+H]^+$.

Step 3: Synthesis of 6-bromo-4-chloro-5-fluoro-3-nitroquinoline

Thionyl chloride (6 mL) and 6-bromo-5-fluoro-3-nitroquinoline-4-ol (430 mg, 1.5 mmol) were added to a 50 mL reaction bottle. The reaction solution was reacted for 3 h at 80° C. When the reaction was completed as detected by TLC, the reaction solution was cooled down and concentrated to dryness to afford a crude product of 6-bromo-4-chloro-5-fluoro-3-nitroquinoline (457 mg, 100% yield). ESI-MS (m/z): 306.90 $[M+H]^+$.

Step 4: Synthesis of 10-bromo-5-nitro-2,4-dihydrospiro[[1,4]oxazepino[5,6,7-de]quinoline-3,1'-cyclobutane]

DMF (5 mL), 6-bromo-4-chloro-5-fluoro-3-nitroquinoline (457 mg, 1.5 mmol), (1-aminocyclobutyl)methanol (228 mg, 2.25 mmol), and DIEA (580 mg, 45 mmol) were successively added to a 50 mL reaction bottle. The reaction solution was heated up to 90° C. to react for 3 h. When the reaction was completed as detected by TLC, the reaction solution was cooled down to room temperature, followed by adding water to precipitate a solid, and then the solid was collected by suction filtration, rinsed with water and dried to afford 10-bromo-5-nitro-2,4-dihydrospiro[[1,4]oxazepino[5,6,7-de]quinoline-3,1'-cyclobutane] (420 mg, 80.0% yield). ESI-MS (m/z): 350.01/352.0 $[M+H]^+$.

Step 5: Synthesis of 10-bromo-2,4-dihydrospiro[[1,4]oxazepino[5,6,7-de]quinoline-3,1'-cyclobutane]-5-amine Ethanol (10 mL), 10-bromo-5-nitro-2,4-dihydrospiro[[1,4]oxazepino[5,6,7-de]quinoline-3,1'-cyclobutane] (420 mg, 1.2 mmol), water (3 mL), iron powder (257 mg, 4.8 mmol), and ammonium chloride (268 mg, 4.8 mmol) were successively added to a 50 mL reaction bottle. The reaction solution was heated up to 80° C. to react for 3 h. When the reaction was completed as detected by TLC, the reaction solution was cooled down to room temperature and concentrated to dryness, and then purified by column chromatography (DCM:MeOH=15:1-10:1) to afford 10-bromo-2,4-dihydrospiro[[1,4]oxazepino[5,6,7-de]quinoline-3,1'-cyclobutane]-5-amine (382 mg, 100% yield). ESI-MS (m/z): 320.03/322.03 $[M+H]^+$.

Step 6: Synthesis of 7-bromo-2,9-dihydro-1H-spiro[8-oxa-2,4,10a-triazanaphtho[2,1,8-cde]azulene-10,1'-cyclopropan]-1-one DMF (8 mL), 10-bromo-2,4-dihydrospiro[[1,4]oxazepino[5,6,7-de]quinoline-3,1'-cyclobutane]-5-amine (382 mg, 1.2 mmol), DIEA (310 mg, 2.4 mmol), and carbonyl diimidazole (CDI) (292 mg, 1.8 mmol) were successively added to a 50 mL reaction bottle. The reaction solution was heated up to 80° C. to react for 8 h. When the reaction was completed as detected by TLC, the reaction solution was cooled down to room temperature, followed by adding water to precipitate a solid, and then the solid was collected by suction filtration, rinsed with water and dried to afford 7-bromo-2,9-dihydro-1H-spiro[8-oxa-2,4,10a-triazanaphtho[2,1,8-cde]azulene-10,1'-cyclopropan]-1-one (345 mg, 83.3% yield). ESI-MS (m/z): 346.01/348.01 $[M+H]^+$.

Step 7: Synthesis of 7-bromo-2-methyl-2,9-dihydro-1H-spiro[8-oxa-2,4,10a-triazanaphtho[2,1,8-cde]azulene-10,1'-cyclopropan]-1-one DMF (5 mL), 7-bromo-2,9-dihydro-1H-spiro[8-oxa-2,4,10a-triazanaphtho[2,1,8-cde]azulene-10,1'-cyclopropane]-1-one (345 mg, 1.0 mmol), cesium carbonate (652 mg, 2.0 mmol), and iodomethane (213 mg, 1.5 mmol) were successively added to a 50 mL reaction bottle, and then reacted at room temperature for 1 h. When the reaction was completed as detected by TLC, the reaction solution was added with water and extracted with ethyl acetate, the organic phase was washed with water, dried and concentrated to dryness, and then purified by column chromatography (DCM:MeOH=70:1-60:1) to afford 7-bromo-2-methyl-2,9-dihydro-1H-spiro[8-oxa-2,4,10a-triazanaphtho[2,1,8-cde]azulene-10,1'-cyclopropan]-1-one (90 mg, 25.0% yield). ESI-MS (m/z): 360.03/362.02 $[M+H]^+$.

Step 8: Synthesis of 2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclobutan]-1-one 1,4-dioxane (4 mL), 7-bromo-2-methyl-2,9-dihydro-1H-spiro[8-oxa-2,4,10a-triazanaphtho[2,1,8-cde]azulene-10,1'-cyclopropan]-1-one (90 mg, 0.25 mmol), (6-(3-(piperidin-1-yl)propoxy)pyridin-3-yl)boronic acid (132 mg, 0.50 mmol), potassium carbonate (104 mg, 0.75 mmol), water (1 mL), and tetrakis(triphenylphosphine)palladium (29 mg, 0.025 mmol) were successively added to a 50 mL reaction bottle. The reaction solution was heated up to 90° C. under nitrogen protection to react for 4 h. When the reaction was completed as detected by TLC, the reaction solution was concentrated to dryness and the residue was purified by column chromatography (DCM:MeOH=20:1-10:1) to afford a crude product, and then the crude product was further purified by high-pressure preparative liquid chromatography to afford 2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclobutan]-1-one (42 mg, 33.6% yield). ESI-MS (m/z): 500.26 $[M+H]^+$; $^1H$ NMR (600 MHz, $CD_3OD$) δ: 1.513 (brs, 2H), 1.640-1.678 (m, 4H), 1.931-1.990 (m, 1H), 2.054-2.080 (m, 3H), 2.559-2.632 (m, 6H), 3.615 (s, 3H), 4.393 (t, J=6.0 Hz, 2H), 4.625 (brs, 2H), 6.923 (d, J=8.4 Hz, 1H), 7.652 (d, J=9.0 Hz, 1H), 7.819 (d, J=9.0 Hz, 1H), 7.972-7.990 (m, 1H), 8.387 (d, J=2.4 Hz, 1H), 8.784 (s, 1H).

Example 82: (S)-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-177)

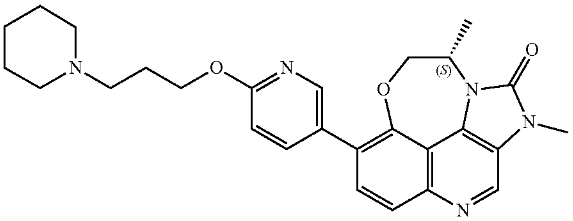

Except starting materials were changed, the synthesis method was the same as that of example 81 to afford (S)-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (25 mg, 27.1% yield). ESI-MS (m/z): 474.43 $[M+H]^+$; $^1$H NMR (600 MHz, $CD_3OD$) δ: 1.561 (brs, 2H), 1.615 (d, J=6.6 Hz, 3H), 1.692-1.720 (m, 4H), 2.101-2.127 (m, 2H), 2.670-2.722 (m, 6H), 3.672 (s, 3H), 4.424 (t, J=6.0 Hz, 2H), 4.516-4.699 (m, 2H), 4.747-4.758 (m, 1H), 6.940 (d, J=8.4 Hz, 1H), 7.700 (d, J=9.0 Hz, 1H), 7.867 (d, J=8.4 Hz, 1H), 7.988-8.006 (m, 1H), 8.402 (d, J=1.8 Hz, 1H), 8.838 (s, 1H).

Example 83: (S)-7-(6-(3-(dimethylamino)propoxy)pyridin-3-yl)-2,10-dimethyl-9,10-dihydro-8-oxa-2,4,10a-triazanaphtho[2,1,8-cde]azulen-1(2H)-one (A-178)

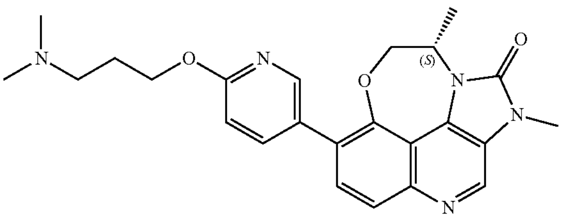

Except starting materials were changed, the synthesis method was the same as that of example 81 to afford (S)-7-(6-(3-(dimethylamino)propoxy)pyridin-3-yl)-2,10-dimethyl-9,10-dihydro-8-oxa-2,4,10a-triazanaphtho[2,1,8-cde]azulen-1(2H)-one (25 mg, 27.1% yield). ESI-MS (m/z): 434.21 $[M+H]^+$; $^1$H NMR (600 MHz, $CD_3OD$) δ: 1.587 (d, J=7.2 Hz, 3H), 2.048-2.074 (m, 2H), 2.408 (s, 6H), 2.675-2.688 (m, 2H), 3.644 (s, 3H), 4.401 (t, J=6.0 Hz, 2H), 4.487-4.675 (m, 2H), 4.718-4.732 (m, 1H), 6.916 (d, J=9.0 Hz, 1H), 7.672 (d, J=9.0 Hz, 1H), 7.869 (d, J=9.0 Hz, 1H), 7.961-7.979 (m, 1H), 8.375 (d, J=2.4 Hz, 1H), 8.809 (s, 1H).

Example 84: 2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclopropan]-1-one (A-68)

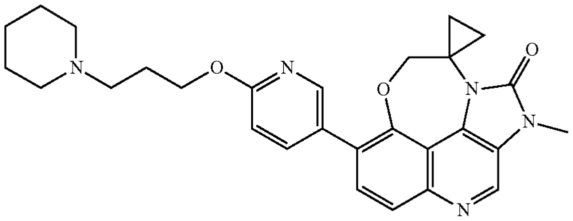 [SMILES: Cn1c(=O)n2c3c4c(c(-c5ccc(OCCCN6CCCCC6)nc5)ccc4ncc31)OCC21CC1]

Except starting materials were changed, the synthesis method was the same as that of example 81 to afford 2-methyl-7-(6-(3-(piperidin-1-yl)propoxy)pyridin-3-yl)-2,9-dihydro-1H-spiro[8-oxa-2,4,10a-triazanaphtho[2,1,8-cde]azulene-10,1'-cyclopropan]-1-one (25 mg, 27.1% yield). ESI-MS (m/z): 486.47 $[M+H]^+$; $^1$H NMR (600 MHz, $CD_3OD$) δ: 1.126 (brs, 2H), 1.524 (brs, 2H), 1.662-1.681 (m, 4H), 2.056-2.083 (m, 2H), 2.347 (brs, 2H), 2.614-2.663 (m, 6H), 3.564 (s, 3H), 4.378 (t, J=6.0 Hz, 2H), 4.414 (brs, 2H), 6.886 (d, J=8.4 Hz, 1H), 7.754 (d, J=8.4 Hz, 1H), 7.837 (d, J=8.4 Hz, 1H), 7.937-7.955 (m, 1H), 8.345 (d, J=1.8 Hz, 1H), 8.784 (s, 1H).

Example 85: 7-(6-(3-(dimethylamino)propoxy)pyridin-3-yl)-2-methyl-2,9-dihydro-1H-spiro[8-oxa-2,4,10a-triazanaphtho[2,1,8-cde]azulene-10,1'-cyclopropan]-1-one (A-179)

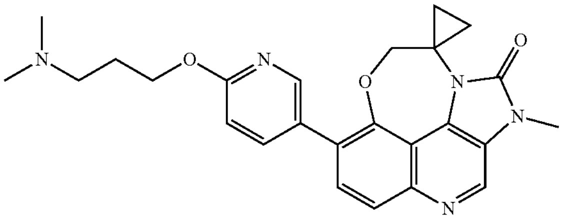

Except starting materials were changed, the synthesis method was the same as that of example 81 to afford 7-(6-(3-(dimethylamino)propoxy)pyridin-3-yl)-2-methyl-2,9-dihydro-1H-spiro[8-oxa-2,4,10a-triazanaphtho[2,1,8-cde]azulene-10,1'-cyclopropan]-1-one (25 mg, 27.1% yield). ESI-MS (m/z): 456.44 $[M+H]^+$; $^1$H NMR (600 MHz, $CD_3OD$) δ: 1.124 (brs, 2H), 2.045-2.071 (m, 2H), 2.342 (brs, 2H), 2.419 (s, 6H), 2.698 (t, J=7.2 Hz, 2H), 3.563 (s, 3H), 4.379-4.412 (m, 4H), 6.893 (d, J=8.4 Hz, 1H), 7.652 (d, J=9.0 Hz, 1H), 7.834 (d, J=9.0 Hz, 1H), 7.940-7.958 (m, 1H), 8.348 (d, J=2.4 Hz, 1H), 8.781 (s, 1H).

Example 86: 2,10,10-trimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-67)

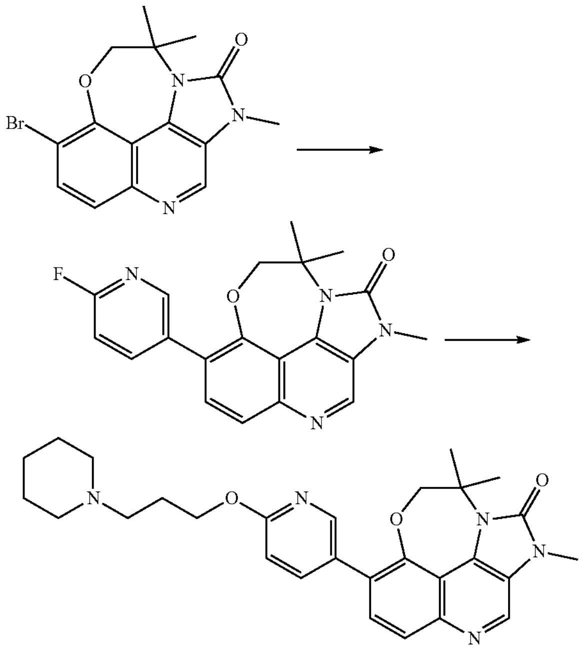

Except starting materials were changed, the synthesis method was the same as that of example 81 to afford 2,10,10-trimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (90 mg, 38.3% yield). ESI-MS (m/z): 488.26 $[M+H]^+$; $^1H$ NMR (600 MHz, $CD_3OD$) δ: 1.591 (s, 2H), 1.750 (s, 10H), 2.136-2.162 (m, 2H), 2.859-2.916 (m, 6H), 3.581 (s, 3H), 4.374-4.423 (m, 4H), 6.903 (d, J=9.0 Hz, 1H), 7.615 (d, J=8.4 Hz, 1H), 7.796 (d, J=9.0 Hz, 1H), 7.938-7.956 (m, 1H), 8.354 (s, 1H), 8.754 (s, 1H).

Example 87: 7-(6-(3-(dimethylamino)propoxy)pyridin-3-yl)-2,10,10-trimethyl-9,10-dihydro-8-oxa-2,4,10a-triazanaphtho[2,1,8-cde]azulen-1(2H)-one (A-180)

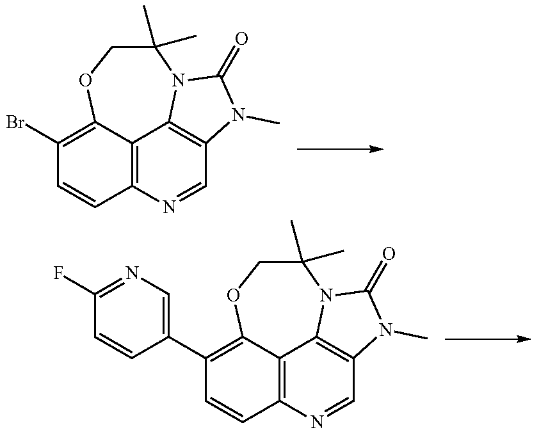

-continued

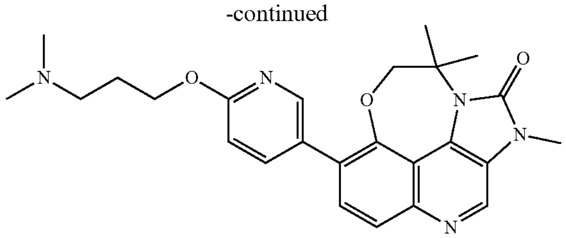

Except starting materials were changed, the synthesis method was the same as that of example 81 to afford 7-(6-(3-(dimethylamino)propoxy)pyridin-3-yl)-2,10,10-trimethyl-9,10-dihydro-8-oxa-2,4,10a-triazanaphtho[2,1,8-cde]azulen-1(2H)-one (72 mg, 36.7% yield). ESI-MS (m/z): 448.23 $[M+H]^+$; $^1H$ NMR (600 MHz, $CD_3OD$) δ: 1.758 (s, 6H), 2.048-2.095 (m, 2H), 2.443 (s, 6H), 2.728 (t, J=7.8 Hz, 2H), 3.586 (s, 3H), 4.387-4.411 (m, 4H), 6.908 (d, J=8.4 Hz, 1H), 7.635 (d, J=9.0 Hz, 1H), 7.812 (d, J=8.4 Hz, 1H), 7.946-7.964 (m, 1H), 8.363 (d, J=2.4 Hz, 1H), 8.766 (s, 1H).

Example 88: (R)-7-(6-(3-(dimethylamino)propoxy)pyridin-3-yl)-2,10-dimethyl-9,10-dihydro-8-oxa-2,4,10a-triazanaphtho[2,1,8-cde]azulen-1(2H)-one (A-181)

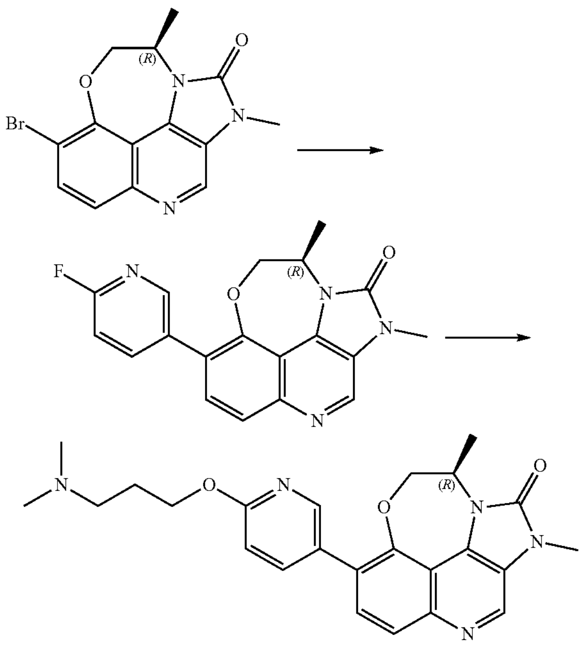

Except starting materials were changed, the synthesis method was the same as that of example 81 to afford (R)-7-(6-(3-(dimethylamino)propoxy)pyridin-3-yl)-2,10-dimethyl-9,10-dihydro-8-oxa-2,4,10a-triazanaphtho[2,1,8-cde]azulen-1(2H)-one (158 mg, 42.5% yield). ESI-MS (m/z): 434.21 $[M+H]^+$; $^1H$ NMR (600 MHz, $CD_3OD$) δ: 1.567-1.578 (m, 3H), 2.178-2.224 (m, 2H), 2.760 (s, 6H), 3.122 (t, J=7.8 Hz, 2H), 3.634 (s, 3H), 4.444-4.489 (m, 3H), 4.632-4.658 (m, 1H), 4.706-4.717 (m, 1H), 6.935 (d, J=9.0 Hz, 1H), 7.647 (d, J=8.4 Hz, 1H), 7.816 (d, J=9.0 Hz, 1H), 7.962-7.980 (m, 1H), 8.375 (d, J=2.4 Hz, 1H), 8.790 (s, 1H).

Example 89: (R)-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-182)

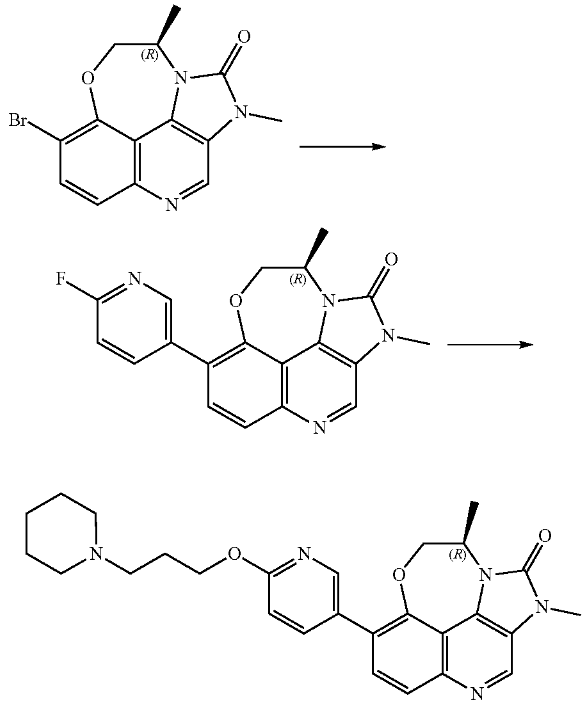

Except starting materials were changed, the synthesis method was the same as that of example 81 to afford (R)-2,10-dimethyl-7-(6-(3-(piperidin-1-yl)propoxy)pyridin-3-yl)-9,10-dihydro-8-oxa-2,4,10a-triazanaphtho[2,1,8-cde]azulen-1(2H)-one (78 mg, 29.1% yield). ESI-MS (m/z): 474.24 $[M+H]^+$; $^1$H NMR (600 MHz, $CD_3OD$) δ: 1.574-1.585 (m, 5H), 1.707-1.724 (m, 4H), 2.103-2.127 (m, 2H), 2.746-2.801 (m, 6H), 3.637 (s, 3H), 4.405 (t, J=6.0 Hz, 2H), 4.473-4.495 (m, 1H), 4.643-4.665 (m, 1H), 4.712-4.723 (m, 1H), 6.909 (d, J=8.4 Hz, 1H), 7.656 (d, J=8.4 Hz, 1H), 7.824 (d, J=8.4 Hz, 1H), 7.952-7.970 (m, 1H), 8.368 (s, 1H), 8.796 (s, 1H).

Example 90: (S)-7-(6-(3-(6-azaspiro[2.5]octan-6-yl)propoxy)pyridin-3-yl)-2,10-dimethyl-9,10-dihydro-8-oxa-2,4,10a-triazanaphtho[2,1,8-cde]azulen-1(2H)-one (A-183)

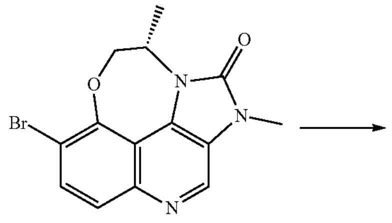

-continued

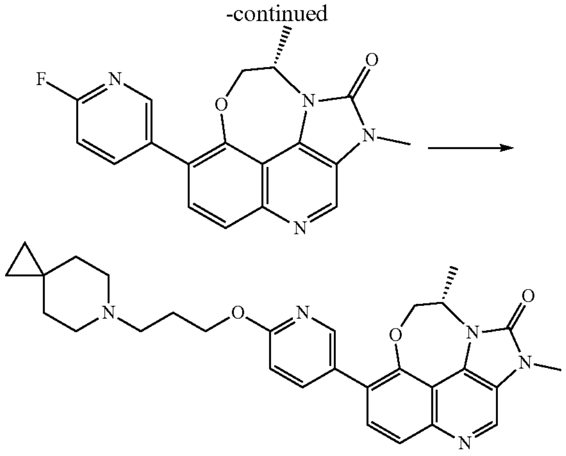

Except starting materials were changed, the synthesis method the same as that of example 81 to afford (S)-7-(6-(3-(6-azaspiro[2.5]octan-6-yl)propoxy)pyridin-3-yl)-2,10-dimethyl-9,10-dihydro-8-oxa-2,4,10a-triazanaphtho[2,1,8-cde]azulen-1(2H)-one (45 mg, 30.6% yield). ESI-MS (m/z): 500.26 $[M+H]^+$; $^1$H NMR (600 MHz, $CD_3OD$) δ: 0.402 (s, 4H), 1.579-1.590 (m, 7H), 2.155-2.179 (m, 2H), 2.921 (s, 6H), 3.643 (s, 3H), 4.423-4.443 (m, 2H), 4.486-4.507 (m, 1H), 4.647-4.669 (m, 1H), 4.718-4.729 (m, 1H), 6.918 (d, J=8.4 Hz, 1H), 7.667 (d, J=8.4 Hz, 1H), 7.836 (d, J=8.4 Hz, 1H), 7.966-7.984 (m, 1H), 8.382 (s, 1H), 8.808 (s, 1H).

Example 91: (S)-7-(6-(3-(2-oxa-7-azaspiro[3.5]nonan-7-yl)propoxy)pyridin-3-yl)-2,10-dimethyl-9,10-dihydro-8-oxa-2,4,10a-triazanaphtho[2,1,8-cde]azulen-1(2H)-one (A-184)

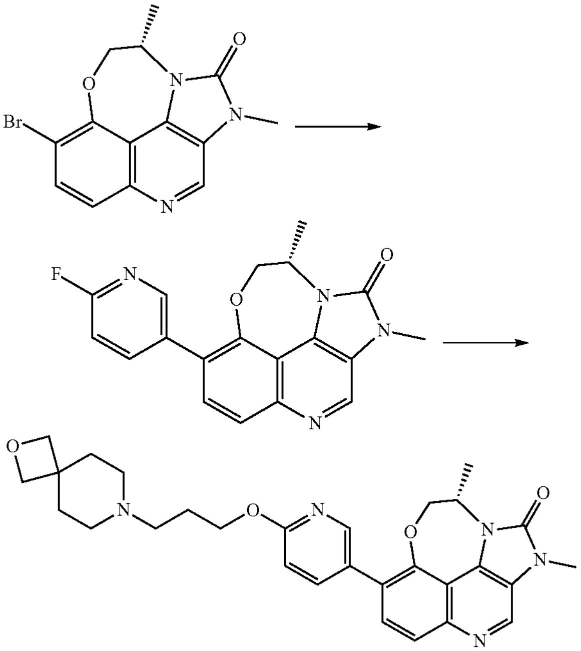

Except starting materials were changed, the synthesis method was the same as that of example 81 to afford (S)-7-(6-(3-(2-oxa-7-azaspiro[3.5]nonan-7-yl)propoxy)

pyridin-3-yl)-2,10-dimethyl-9,10-dihydro-8-oxa-2,4,10a-triazanaphtho[2,1,8-cde]azulen-1(2H)-one (48 mg, 30.8% yield). ESI-MS (m/z): 516.25 $[M+H]^+$; $^1H$ NMR (600 MHz, $CD_3OD$) δ: 1.581-1.592 (m, 3H), 1.960 (s, 4H), 2.060-2.084 (m, 2H), 2.593-2.676 (m, 6H), 3.644 (s, 3H), 4.383-4.509 (m, 7H), 4.646-4.851 (m, 2H), 6.905 (d, J=8.4 Hz, 1H), 7.668 (d, J=8.4 Hz, 1H), 7.838 (d, J=8.4 Hz, 1H), 7.957-7.975 (m, 1H), 8.368-8.371 (m, 1H), 8.810 (s, 1H).

Example 92: 7-(6-(3-(dimethylamino)propoxy)pyridin-3-yl)-2-methyl-2,9-dihydro-1H-spiro[8-oxa-2,4,10a-triazanaphtho[2,1,8-cde]azulene-10,1'-cyclobutan]-1-one (A-185)

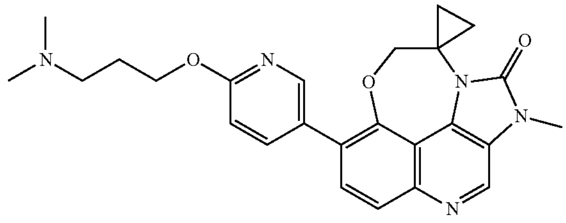

Except starting materials were changed, the synthesis method was the same as that of example 81 to afford 7-(6-(3-(dimethylamino)propoxy)pyridin-3-yl)-2-methyl-2,9-dihydro-1H-spiro[8-oxa-2,4,10a-triazanaphtho[2,1,8-cde]azulene-10,1'-cyclobutan]-1-one (75.8% yield). ESI-MS (m/z): 460.23 $[M+H]^+$; $^1H$ NMR (600 MHz, $CD_3OD$) δ: 1.311 (brs, 1H), 1.962-2.141 (m, 5H), 2.423 (s, 6H), 2.698 (t, J=7.8 Hz, 2H), 3.638 (s, 3H), 4.433 (t, J=6.6 Hz, 2H), 4.638 (brs, 2H), 6.954 (d, J=8.4 Hz, 1H), 7.670 (d, J=9.0 Hz, 1H), 7.837 (d, J=9.0 Hz, 1H), 7.997-8.016 (m, 1H), 8.413 (d, J=2.4 Hz, 1H), 8.800 (s, 1H).

Example 93: (S)-10-ethyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-186)

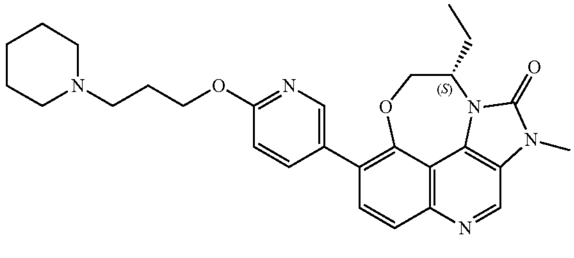

Except starting materials were changed, the synthesis method was the same as that of example 81 to afford (S)-10-ethyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (65.6% yield). ESI-MS (m/z): 488.26 $[M+H]^+$; $^1H$ NMR (600 MHz, $CD_3OD$) δ: 1.122 (t, J=7.2 Hz, 3H), 1.535 (brs, 2H), 1.666-1.703 (m, 4H), 1.994-2.030 (m, 2H), 2064-2.101 (m, 2H), 2.648-2.705 (m, 6H), 3.643 (s, 3H), 4.396 (t, J=6.0 Hz, 2H), 4.420-4.443 (m, 1H), 4.499-4.513 (m, 1H), 4.836-4.853 (m, 1H), 6.905-6.920 (m, 1H), 7.662 (d, J=9.0 Hz, 1H), 7.828 (d, J=9.0 Hz, 1H), 7.950-7.969 (m, 1H), 8.370 (d, J=1.8 Hz, 1H), 8.805 (s, 1H).

Example 94: (R)-10-ethyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (A-187)

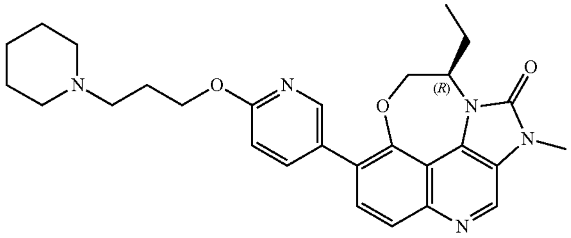

Except starting materials were changed, the synthesis method was the same as that of example 81 to afford (R)-10-ethyl-2-methyl-7-(6-(3-(piperidin-1-yl)propoxy)pyridin-3-yl)-9,10-dihydro-8-oxa-2,4,10a-triazanaphtho[2,1,8-cde]azulen-1(2H)-one (85 mg, 35.5% yield). ESI-MS (m/z): 488.26 $[M+H]^+$; $^1H$ NMR (600 MHz, $CD_3OD$) δ: 1.117-1.129 (m, 3H), 1.551 (s, 2H), 1.685-1.723 (m, 4H), 1.985-2.019 (m, 2H), 2.102-2.118 (m, 2H), 2.711-2.777 (m, 6H), 3.638 (s, 3H), 4.389-4.429 (m, 3H), 4.485-4.515 (m, 1H), 4.828-4.833 (m, 1H), 6.909 (d, J=8.4 Hz, 1H), 7.649 (d, J=8.4 Hz, 1H), 7.815 (d, J=8.4 Hz, 1H), 7.943-7.961 (m, 1H), 8.362-8.366 (m, 1H), 8.793 (s, 1H).

Example 95: (R)-7-(6-(3-(dimethylamino)propoxy)pyridin-3-yl)-10-ethyl-2-methyl-9,10-dihydro-8-oxa-2,4,10a-triazanaphtho[2,1,8-cde]azulen-1(2H)-one (A-188)

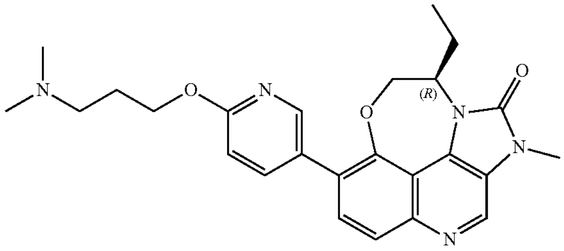

Except starting materials were changed, the synthesis method was the same as that of example 81 to afford (R)-7-(6-(3-(dimethylamino)propoxy)pyridin-3-yl)-10-ethyl-2-methyl-9,10-dihydro-8-oxa-2,4,10a-triazanaphtho[2,1,8-cde]azulen-1(2H)-one (67 mg, 33.2% yield). ESI-MS (m/z): 448.23 $[M+H]^+$; $^1H$ NMR (600 MHz, $CD_3OD$) δ: 1.104-1.129 (m, 3H), 1.984-2.067 (m, 4H), 2.397 (s, 6H), 2.660-2.685 (m, 2H), 3.636 (s, 3H), 4.384-4.426 (m, 3H), 4.488-4.512 (m, 1H), 4.829-4.833 (m, 1H), 6.909 (d, J=8.4 Hz, 1H), 7.648 (d, J=8.4 Hz, 1H), 7.812 (d, J=8.4 Hz, 1H), 7.939-7.957 (m, 1H), 8.359-8.363 (m, 1H), 8.789 (s, 1H).

Example 96: (S)-7-(6-(3-(dimethylamino)propoxy)pyridin-3-yl)-10-ethyl-2-methyl-9,10-dihydro-8-oxa-2,4,10a-triazanaphtho[2,1,8-cde]azulen-1(2H)-one (A-189)

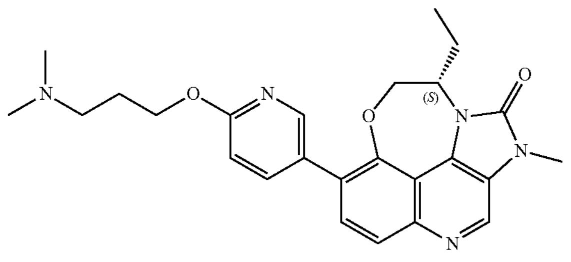

Except starting materials were changed, the synthesis method was the same as that of example 81 to afford (S)-7-(6-(3-(dimethylamino)propoxy)pyridin-3-yl)-10-ethyl-2-methyl-9,10-dihydro-8-oxa-2,4,10a-triazanaphtho[2,1,8-cde]azulen-1(2H)-one (58.7% yield). ESI-MS (m/z): 448.23 $[M+H]^+$; $^1H$ NMR (600 MHz, $CD_3OD$) δ: 1.124 (t, J=7.2 Hz, 3H), 1.979-2.009 (m, 2H), 2.071-2.118 (m, 2H), 2.476 (s, 6H), 2.761 (t, J=7.2 Hz, 2H), 3.642 (s, 3H), 4.383-4.426 (m, 3H), 4.495 (t, J=6.6 Hz, 1H), 4.483-4.856 (m, 1H), 6.917 (d, J=8.4 Hz, 1H), 7.633 (d, J=8.4 Hz, 1H), 7.796 (d, J=8.4 Hz, 1H), 7.935-7.953 (m, 1H), 8.358 (d, J=1.8 Hz, 1H), 8.770 (s, 1H).

Example 97: 6-fluoro-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-190)

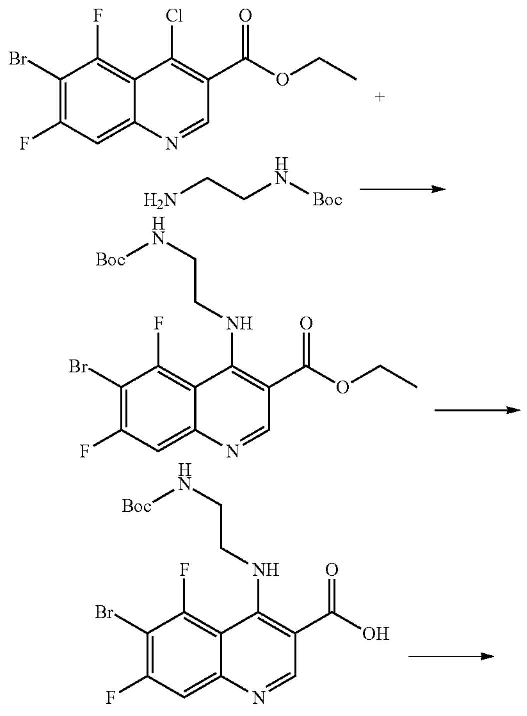

-continued

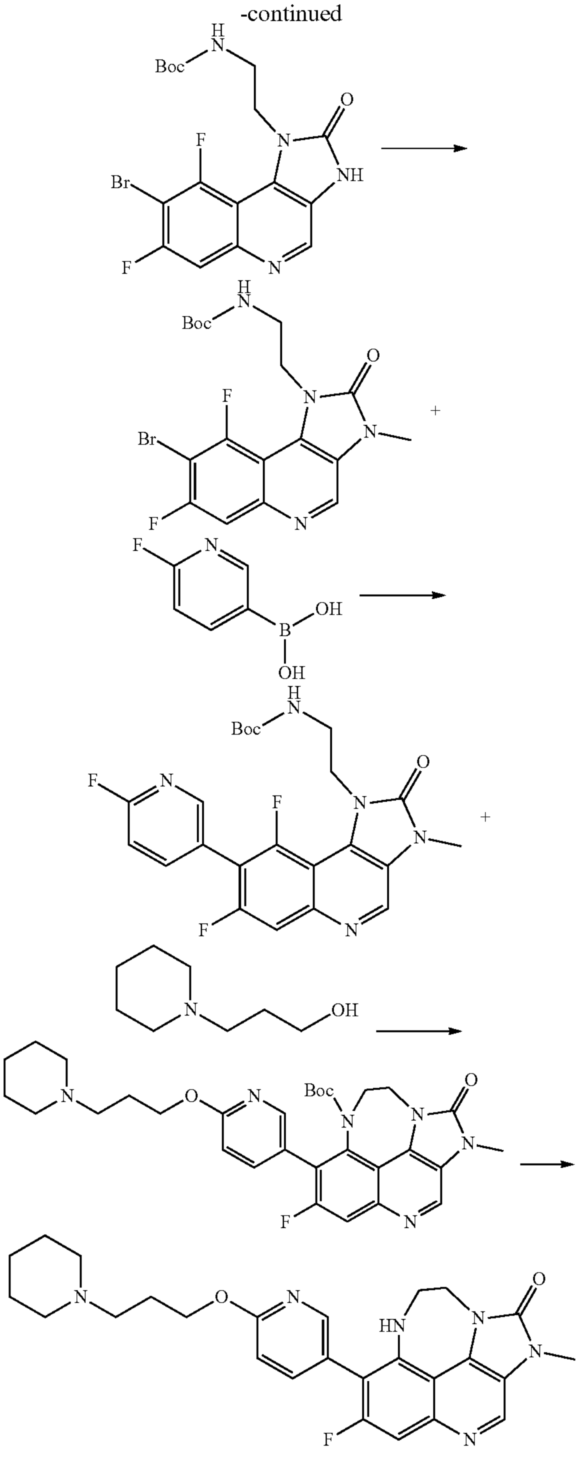

Step 1: Synthesis of ethyl 6-bromo-4-((2-((tert-butoxycarbonyl)amino)ethyl)amino)-5,7-difluoroquinoline-3-carboxylate DMF (20 mL), ethyl 6-bromo-4-chloro-5,7-difluoroquinoline-3-carboxylate (1.48 g, 4.2 mmol), N-Boc-ethane-1,2-diamine (0.94 g, 6.3 mmol), and DIEA (1.09 g, 8.4 mmol) were successively added to a 100 mL reaction bottle. The reaction solution was heated up to 90° C. to react for 3 h. When the reaction was completed as detected by TLC, the reaction solution was cooled down to room temperature, followed by adding water to precipitate a solid, and then the solid was collected by suction filtration, rinsed with water and dried to afford ethyl 6-bromo-4-((2-((tert-butoxycarbonyl)amino)ethyl)amino)-5,7-difluoroquinoline-3-carboxylate (2.0 g, 100% yield). ESI-MS (m/z): 474.08/476.08 $[M+H]^+$.

Step 2: Synthesis of 6-bromo-4-((2-((tert-butoxycarbonyl)amino)ethyl)amino)-5,7-difluoroquinoline-3-carboxylic acid THF (10 mL), ethyl 6-bromo-4-((2-((tert-butoxycarbonyl)amino)ethyl)amino)-5,7-difluoroquinoline-3-carboxylate (2.00 g, 4.2 mmol), water (5 mL), and sodium hydroxide (0.84 g, 21.0 mmol) were successively added to a 100 mL reaction bottle. The reaction solution was heated up to 60° C. to react for 3 h. When the reaction was completed as detected by TLC, the reaction solution was cooled down to room temperature, followed by adjusting the pH value to 5 with 1N hydrochloric acid to precipitate a solid, and then the solid was collected by suction filtration, rinsed with water and dried to afford 6-bromo-4-((2-((tert-butoxycarbonyl)amino)ethyl)amino)-5,7-difluoroquinoline-3-carboxylic acid (1.5 g, 79.8% yield). ESI-MS (m/z): 446.04/448.04 $[M+H]^+$.

Step 3: Synthesis of tert-butyl (2-(8-bromo-7,9-difluoro-2-oxo-2,3-dihydro-1H-imidazo[4,5-c]quinolin-1-yl)ethyl)carbamate DMF (15 mL), 6-bromo-4-((2-((tert-butoxycarbonyl)amino)ethyl)amino)-5,7-difluoroquinoline-3-carboxylic acid (1.5 g, 3.36 mmol), DIEA (0.87 g, 6.73 mmol), and diphenyl azidophosphate (1.40 g, 5.04 mmol) were successively added to a 100 mL reaction bottle. The reaction solution was heated up to 60° C. to react for 3 h. When the reaction was completed as detected by TLC, the reaction solution was cooled down to room temperature, followed by adding water to precipitate a solid, and then the solid was collected by suction filtration, rinsed with water and dried to afford tert-butyl (2-(8-bromo-7,9-difluoro-2-oxo-2,3-dihydro-1H-imidazo[4,5-c]quinolin-1-yl)ethyl)carbamate (1.2 g, 80.5% yield). ESI-MS (m/z): 443.05/445.05 $[M+H]^+$.

Step 4: Synthesis of tert-butyl (2-(8-bromo-7,9-difluoro-3-methyl-2-oxo-2,3-dihydro-1H-imidazo[4,5-c]quinolin-1-yl)ethyl)carbamate Anhydrous THF (15 mL), tert-butyl (2-(8-bromo-7,9-difluoro-2-oxo-2,3-dihydro-1H-imidazo[4,5-c]quinolin-1-yl)ethyl)carbamate (1.2 g, 2.70 mmol), and cesium carbonate (0.164 g, 4.11 mmol) were successively added to a 100 mL reaction bottle, then iodomethane (0.58 g, 4.11 mmol) was added at room temperature, and the reaction was continued at room temperature for 2 h. When the reaction was completed as detected by TLC, the reaction solution was added with water to precipitate a solid, and then the solid was collected by suction filtration, rinsed with water and dried to afford tert-butyl (2-(8-bromo-7,9-difluoro-3-methyl-2-oxo-2,3-dihydro-1H-imidazo[4,5-c]quinolin-1-yl)ethyl)carbamate (0.90 g, 72.6% yield). ESI-MS (m/z): 457.06/459.06 $[M+H]^+$.

Step 5: Synthesis of tert-butyl (2-(7,9-difluoro-8-(6-fluoropyridin-3-yl)-3-methyl-2-oxo-2,3-dihydro-1H-imidazo[4,5-c]quinolin-1-yl)ethyl)carbamate 1,4-dioxane (15 mL), tert-butyl (2-(8-bromo-7,9-difluoro-3-methyl-2-oxo-2,3-dihydro-1H-imidazo[4,5-c]quinolin-1-yl)ethyl)carbamate (0.80 g, 1.76 mmol), (6-fluoropyridine-3-yl)boronic acid (0.315 g, 2.11 mmol), potassium carbonate (0.607 g, 4.4 mmol), water (1.5 mL), and tetrakis(triphenylphosphine)palladium (0.203 g, 0.18 mmol) were successively added to a 100 mL reaction bottle. The reaction solution was heated up to 90° C. under nitrogen protection to react for 2.5 h. When the reaction was completed as detected by TLC, the reaction solution was concentrated to dryness, and then the residue was purified by column chromatography (DCM:MeOH=60:1) to afford tert-butyl (2-(7,9-difluoro-8-(6-fluoropyridin-3-yl)-3-methyl-2-oxo-2,3-dihydro-1H-imidazo[4,5-c]quinolin-1-yl)ethyl)carbamate (0.63 g, 76.0% yield). ESI-MS (m/z): 474.17 $[M+H]^+$.

Step 6: Synthesis of tert-butyl 6-fluoro-2-methyl-1-oxo-7-(6-(3-(piperidin-1-yl)propoxy)pyridin-3-yl)-9,10-dihydro-1H-2,4,8,10a-tetraazanaphtho[2,1,8-cde]azulene-8(2H)-carboxylate THF (4 mL) and 3-(piperidin-1-yl)propan-1-ol (115 mg, 0.8 mmol) were added to a 100 mL reaction bottle and cooled down to 0° C., followed by adding NaH (56 mg, 1.4 mmol) and the reaction was conducted at this temperature for 0.5 h, then tert-butyl (2-(7,9-difluoro-8-(6-fluoropyridin-3-yl)-3-methyl-2-oxo-2,3-dihydro-1H-imidazo[4,5-c]quinolin-1-yl)ethyl)carbamate (190 mg, 0.4 mmol) was added, and the reaction was continued at room temperature overnight. When the reaction was completed as detected by TLC, water was added into the reaction solution to quench the reaction. The reaction mixture was concentrated to dryness, and then the residue was purified by column chromatography (DCM:MeOH=20:1-15:1) to afford tert-butyl 6-fluoro-2-methyl-1-oxo-7-(6-(3-(piperidin-1-yl)propoxy)pyridin-3-yl)-9,10-dihydro-1H-2,4,8,10a-tetraazanaphtho[2,1,8-cde]azulene-8(2H)-carboxylate (100 mg, 43.3% yield). ESI-MS (m/z): 577.29 $[M+H]^+$.

Step 7: Synthesis of 6-fluoro-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-155)

DCM (20 mL) and tert-butyl 6-fluoro-2-methyl-1-oxo-7-(6-(3-(piperidin-1-yl)propoxy)pyridin-3-yl)-9,10-dihydro-1H-2,4,8,10a-tetraazanaphtho[2,1,8-cde]azulene-8(2H)-carboxylate (100 mg, 0.17 mmol) were successively added to a 100 mL reaction bottle, followed by the addition of trifluoroacetic acid (4 mL) at room temperature, and the reaction was continued at room temperature for 2 h. When the reaction was completed as detected by TLC, the reaction solution was concentrated to dryness, and then the residue was purified by column chromatography (DCM:MeOH=20:1-5:1) to afford 6-fluoro-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (40 mg, 48.2% yield). ESI-MS (m/z): 477.23 $[M+H]^+$; $^1H$ NMR (600 MHz, $CD_3OD$) δ: 1.570 (s, 2H), 1.715-1.734 (m, 4H), 2.116-2.142 (m, 2H), 2.775-2.882 (m, 6H), 3.593 (s, 6H), 4.086 (s, 2H), 4.425 (s, 2H), 6.980 (d, J=8.4 Hz, 1H), 7.512 (d, J=9.6 Hz, 1H), 7.693-7.711 (m, 1H), 8.126-8.129 (m, 1H), 8.689 (s, 1H).

Example 98: (S)-6-fluoro-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-191)

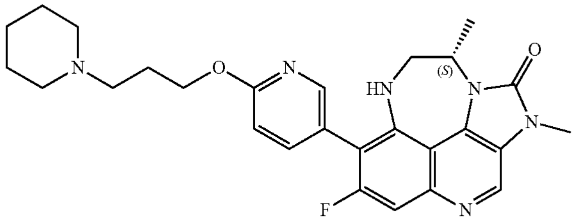

Except starting materials were changed, the synthesis method was the same as that of example 97 to afford (S)-6-fluoro-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (25 mg, 26.8% yield). ESI-MS (m/z): 491.25 $[M+H]^+$; $^1H$ NMR (600 MHz, $CD_3OD$) δ: 1.395-1.408 (m, 3H), 1.510 (s, 2H), 1.639-1.676 (m, 4H), 2.043-2.090 (m, 2H) 2.556-2.632 (m, 6H), 3.461-3.485 (m, 1H), 3.604 (s, 3H), 3.646-3.690 (m, 1H), 4.391-4.412 (m, 2H), 4.601-4.616 (m, 1H), 5.768 (s, 1H), 6.977 (d, J=8.4 Hz, 1H), 7.157 (d, J=10.8 Hz, 1H), 7.696-7.714 (m, 1H), 8.131-8.135 (m, 1H), 8.696 (s, 1H).

Example 99: 6-fluoro-2-methyl-7-(6-(3-(piperidin-1-yl)propoxy)pyridin-3-yl)-8,9-dihydrospiro[2,4,8,10a-tetraazanaphtho[2,1,8-cde]azulene-10,1'-cyclobutan]-1(2H)-one (A-192)

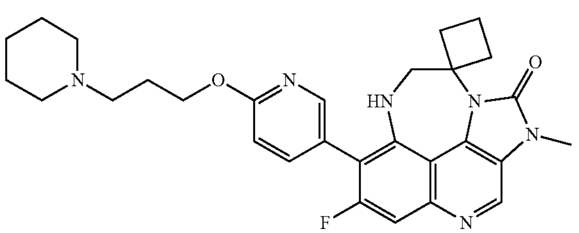 [SMILES: Cn1c(=O)n2c3c4c(c(-c5ccc(OCCCN6CCCCC6)nc5)c(F)cc4ncc31)NCC21CCC1]

Except starting materials were changed, the synthesis method was the same as that of example 97 to afford 6-fluoro-2-methyl-7-(6-(3-(piperidin-1-yl)propoxy)pyridin-3-yl)-8,9-dihydrospiro[2,4,8,10a-tetraazanaphtho[2,1,8-cde]azulene-10,1'-cyclobutan]-1(2H)-one (25 mg, 26.8% yield). ESI-MS (m/z): 517.26 $[M+H]^+$; $^1H$ NMR (600 MHz, $CD_3OD$) δ: 1.535 (brs, 2H), 1.672-1.709 (m, 5H), 0.798-1.817 (m, 1H), 2.008-2.115 (m, 3H), 2.350 (brs, 1H), 2.662-2.721 (m, 7H), 3.549 (s, 3H), 3.720-4.150 (m, 2H), 4.300 (t, J=6.0 Hz, 1H), 4.406 (t, J=6.0 Hz, 2H), 6.972 (d, J=8.4 Hz, 1H), 7.126 (d, J=10.2 Hz, 1H), 7.661-7.703 (m, 1H), 8.086-8.124 (m, 1H), 8.628 (s, 1H).

Example 100: 6-fluoro-2,10,10-trimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-193)

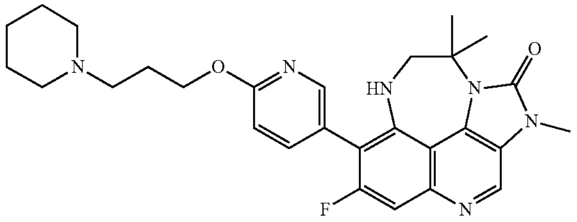 [SMILES: Cn1c(=O)n2c3c4c(c(-c5ccc(OCCCN6CCCCC6)nc5)c(F)cc4ncc31)NCC2(C)C]

Except starting materials were changed, the synthesis method was the same as that of example 97 to afford 6-fluoro-2,10,10-trimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (75 mg, 35.5% yield). ESI-MS (m/z): 505.26 $[M+H]^+$; $^1H$ NMR (600 MHz, $CD_3OD$) δ: 1.500 (s, 2H), 1.642-1.676 (m, 10H), 2.008-2.073 (m, 2H), 2.511-2.582 (m, 6H), 3.304-3.309 (m, 2H), 3.546 (s, 3H), 4.392-4.402 (m, 2H), 6.967 (d, J=8.4 Hz, 1H), 7.165 (d, J=10.8 Hz, 1H), 7.688-7.705 (m, 1H), 8.124 (s, 1H), 8.673 (s, 1H).

Example 101: (R)-10-ethyl-6-fluoro-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-194)

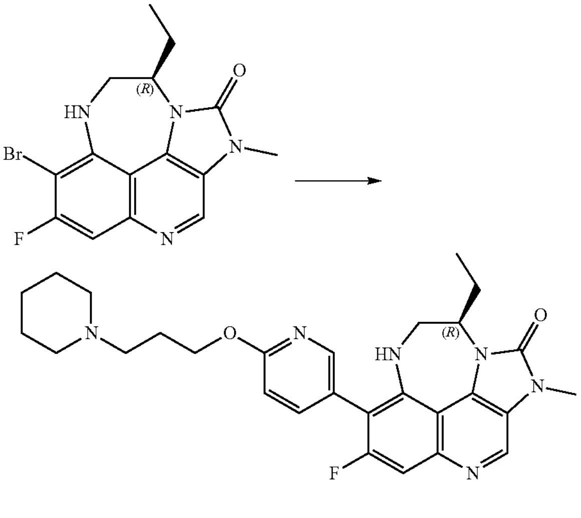

Except starting materials were changed, the synthesis method was the same as that of example 97 to afford (R)-10-ethyl-6-fluoro-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (45 mg, 19.7% yield). ESI-MS (m/z): 505.26 $[M+H]^+$; $^1H$ NMR (600 MHz, $CD_3OD$) δ: 0.993-1.018 (m, 3H), 1.529 (s, 2H), 1.658 (s, 4H), 1.667-1.878 (m, 2H), 2.061-2.108 (m, 2H), 2.622-2.674 (m, 6H), 3.369-3.394 (m, 1H), 3.603 (s, 3H), 3.836-3.867 (m, 1H), 4.291-4.419 (m, 3H), 6.978 (d, J=8.4 Hz, 1H), 7.136 (d, J=10.8 Hz, 1H), 7.687-7.704 (m, 1H), 8.127 (s, 1H), 8,686 (s, 1H).

Example 102: (R)-6-fluoro-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-195)

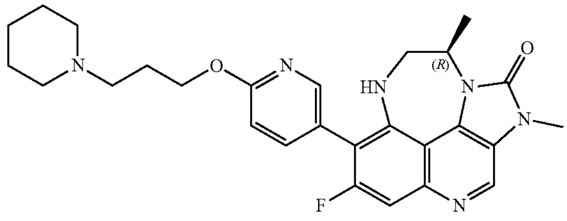

Except starting materials were changed, the synthesis method was the same as that of example 97 to afford (R)-6-fluoro-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (70 mg, 34.5% yield). ESI-MS (m/z): 491.25 $[M+H]^+$; $^1H$ NMR (600 MHz, $CD_3OD$) δ: 1.407-1.418 (m, 3H), 1.501 (s, 2H), 1.625-1.662 (m, 4H), 2.026-2.073 (m, 2H), 2.541-2.584 (m, 6H), 3.448-3.473 (m, 1H), 3.598 (s, 3H), 3.648-3.686 (m, 1H), 4.381-4.402 (m, 2H), 4.592-4.607 (m, 1H), 6.970 (d, J=8.4 Hz, 1H), 7.145 (d, J=9.6 Hz, 1H), 7.688-7.706 (m, 1H), 8.125-8.128 (m, 1H), 8.683 (s, 1H).

Example 103: (S)-10-ethyl-6-fluoro-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-196)

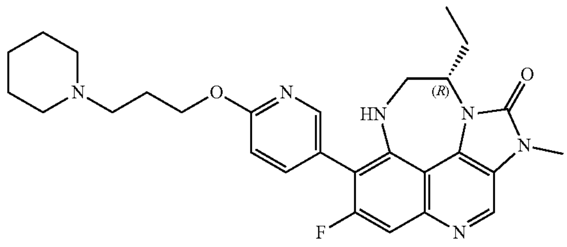

Except starting materials were changed, the synthesis method was the same as that of example 97 to afford (S)-10-ethyl-6-fluoro-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (41.4% yield). ESI-MS (m/z): 505.60 $[M+H]^+$; $^1H$ NMR (600 MHz, $CD_3OD$) δ: 1.033 (t, J=7.2 Hz, 3H), 1.567 (brs, 2H), 1.716-1.734 (m, 4H), 1.819-1.917 (m, 2H), 2.101-2.148 (m, 2H), 2.684-2.738 (m, 6H), 3.399-3.423 (m, 1H), 3.632 (s, 3H), 3.864-3.895 (m, 1H), 4.393-4.452 (m, 3H), 7.008 (d, J=8.4 Hz, 1H), 7.765 (d, J=10.8 Hz, 1H), 7.718-7.735 (m, 1H), 8.155 (d, J=1.8 Hz, 1H), 8.717 (s, 1H).

Example 104: 2,10,10-trimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-197)

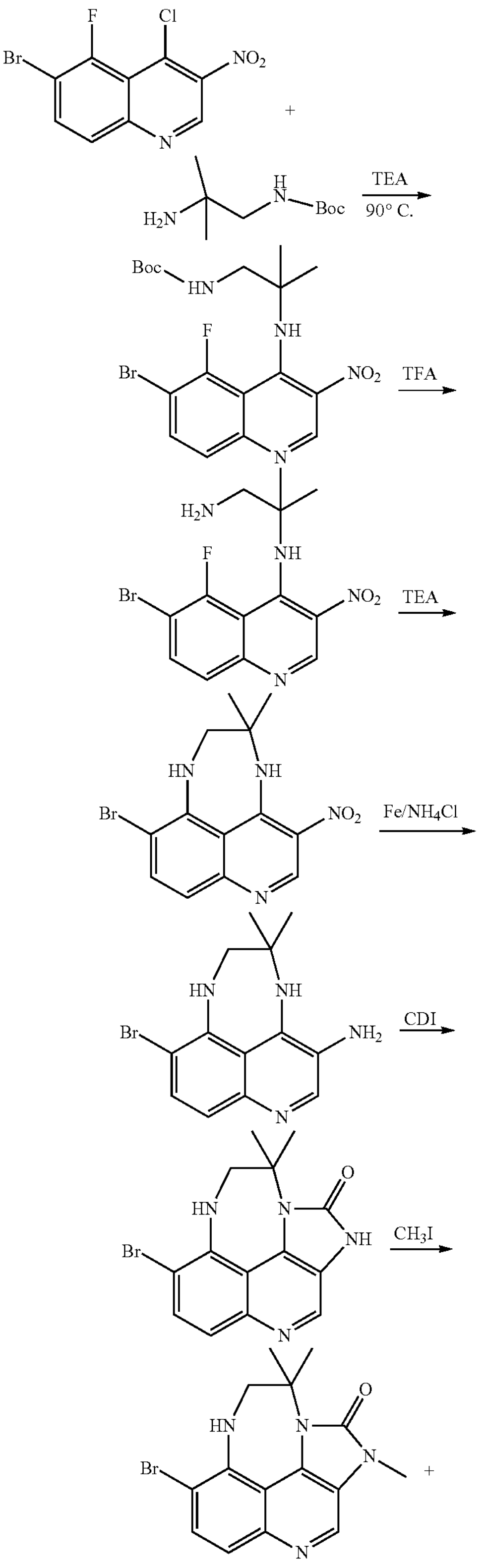

-continued

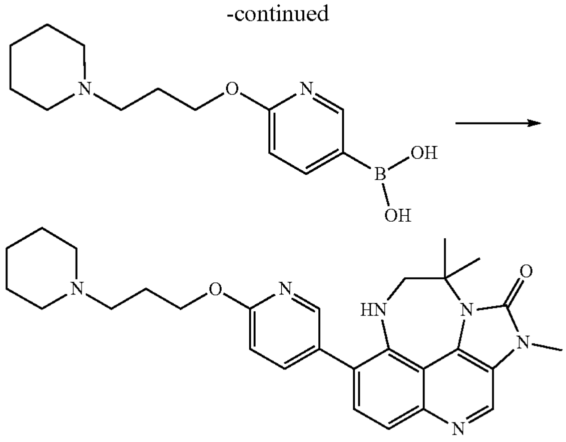

Step 1: tert-butyl (2-((6-bromo-5-fluoro-3-nitroquinolin-4-yl)amino)-2-methylpropyl)carbamate DMF (10 mL), 6-bromo-4-chloro-5-fluoro-3-nitroquinoline (0.58 g, 1.91 mmol), 2-methyl-2-amino-N-tert-butoxycarbonylpropan-1-amine (0.47 g, 2.50 mmol), and TEA (0.97 g, 9.58 mmol) were successively added to a 100 mL reaction bottle. The reaction solution was heated up to 90° C. to react for 3 h. When the reaction was completed as detected by TLC, the reaction solution was cooled down to room temperature, added with water without precipitation, and extracted with ethyl acetate for three times, the combined organic phase was washed with water once, concentrated to dryness, and the residue was purified by column chromatography (n-hexane:ethyl acetate=4:1-2:1) to afford tert-butyl (2-((6-bromo-5-fluoro-3-nitroquinolin-4-yl)amino)-2-methylpropyl)carbamate (0.61 g, 70.1% yield). ESI-MS (m/z): 457.06/459.02 $[M+H]^+$.

Step 2: $N^2$-(6-bromo-5-fluoro-3-nitroquinolin-4-yl)-2-methylpropane-1,2-diamine DCM (10 mL) and tert-butyl (2-((6-bromo-5-fluoro-3-nitroquinolin-4-yl)amino)-2-methylpropyl)carbamate (0.61 g, 1.34 mmol) were successively added to a 100 mL reaction bottle, then trifluoroacetic acid (5 mL) was added at room temperature, and the reaction was continued at room temperature for 2 h. When the reaction was completed as detected by TLC, the reaction solution was concentrated to dryness to afford $N^2$-(6-bromo-5-fluoro-3-nitroquinolin-4-yl)-2-methylpropane-1,2-diamine. ESI-MS (m/z): 357.08/359.08 $[M+H]^+$. The intermediate was ready for instant use in the next step without treatment.

Step 3: 8-bromo-5,5-dimethyl-3-nitro-4,5,6,7-tetrahydro-[1,4]diazepino[5,6,7-de]quinoline DMF (10 mL), $N^2$-(6-bromo-5-fluoro-3-nitroquinolin-4-yl)-2-methylpropane-1,2-diamine (crude) and TEA (8 mL) were successively added to a 100 mL reaction bottle, the pH value of reaction solution was detected as 12, and then the reaction solution was heated up to 90° C. to react for 2 h. When the reaction was completed as detected by TLC, the reaction solution was cooled down to room temperature, added with 50 mL of water, and subjected to suction filtration. The solid was collected, rinsed with water, and dried to afford 8-bromo-5,5-dimethyl-3-nitro-4,5,6,7-tetrahydro-[1,4]diazepino[5,6,7-de]quinoline (0.36 g, 80% yield). ESI-MS (m/z): 336.88/338.88 $[M+H]^+$; $^1H$ NMR (600 MHz, $CD_3OD$) δ: 1.470 (s, 6H), 3.524 (s, 2H), 7.115 (d, J=9.0 Hz, 1H), 7.866 (d, J=8.4 Hz, 1H), 9.104 (s, 1H).

Step 4: 8-bromo-5,5-dimethyl-4,5,6,7-tetrahydro-[1,4]diazepino[5,6,7-de]quinolin-3-amine Ethanol (10 mL), water (5 mL), 8-bromo-5,5-dimethyl-3-nitro-4,5,6,7-tetrahydro-[1,4]diazepino[5,6,7-de]quinoline (0.36 g, 1.07 mmol), iron powder (0.36 g, 6.43 mmol), and $NH_4Cl$ (0.34 g, 6.35 mmol) were successively added to a 100 mL reaction bottle and heated up to 80° C. to react for 3 h. When the reaction was completed as detected by TLC, the reaction solution was subjected to hot filtration, the solid was rinsed with ethanol, and the filtrate was concentrated to dryness and then the residue was purified by column chromatography (DCM:MeOH=30:1-10:1) to afford 8-bromo-5,5-dimethyl-4,5,6,7-tetrahydro-[1,4]diazepino[5,6,7-de]quinolin-3-amine (0.33 g, 100% yield). ESI-MS (m/z): 306.92/308.88 $[M+H]^+$; $^1H$ NMR (600 MHz, $CD_3OD$) δ: 1.446 (s, 6H), 3.580 (s, 2H), 6.891 (d, J=9.0 Hz, 1H), 7.759 (d, J=9.0 Hz, 1H), 7.896 (s, 1H).

Step 5: 7-bromo-10,10-dimethyl-2,8,9,10-tetrahydro-1H-2,4,8,10a-tetraazanaphtho[2,1,8-cde]azulen-1(2H)-one DMF (10 mL), 8-bromo-5,5-dimethyl-4,5,6,7-tetrahydro-[1,4]diazepino[5,6,7-de]quinolin-3-amine (0.33 g, 1.07 mmol), CDI (0.43 g, 2.65 mmol), and TEA (0.32 g, 3.16 mmol) were successively added to a 100 mL reaction bottle. The reaction solution was heated up to 80° C. to react for 3 h. When the reaction was completed as detected by TLC, the reaction solution was cooled down to temperature, added with water and ethyl acetate for phase separation, and the organic phase was concentrated to dryness and then the residue was purified by column chromatography (DCM:MeOH=50:1-20:1) to afford 7-bromo-10,10-dimethyl-2,8,9,10-tetrahydro-1H-2,4,8,10a-tetraazanaphtho[2,1,8-cde]azulen-1(2H)-one (0.31 g, 87.3% yield). ESI-MS (m/z): 332.94/334.92 $[M+H]^+$; $^1H$ NMR (600 MHz, $CD_3OD$) δ: 1.415 (s, 6H), 4.048 (s, 2H), 5.319 (s, 1H), 7.353 (d, J=9.0 Hz, 1H), 7.681-7.704 (m, 1H), 8.609 (s, 1H).

Step 6: 7-bromo-2,10,10-trimethyl-2,8,9,10-tetrahydro-1H-2,4,8,10a-tetraazanaphtho[2,1,8-cde]azulen-1(2H)-one Anhydrous DMF (15 mL), 7-bromo-10,10-dimethyl-2,8,9,10-tetrahydro-1H-2,4,8,10a-tetraazanaphtho[2,1,8-cde]azulen-1(2H)-one (0.31 g, 0.93 mmol), and cesium carbonate (0.58 g, 1.78 mmol) were successively added to a 100 mL reaction bottle, then iodomethane (0.19 g, 1.34 mmol) was added at room temperature, and the reaction was rewarmed to room temperature for 1 h. When the reaction was completed as detected by TLC, the reaction solution was added with water (50 mL) to precipitate a solid, and then the solid was subjected to suction filtration, collected, rinsed with water, and dried to afford 7-bromo-2,10,10-trimethyl-2,8,9,10-tetrahydro-1H-2,4,8,10a-tetraazanaphtho[2,1,8-cde]azulen-1(2H)-one (0.20 g, 62.5% yield). ESI-MS (m/z): 346.95/348.96 $[M+H]^+$; $^1H$ NMR (600 MHz, $CD_3OD$) δ: 1.418 (s, 6H), 3.640 (s, 3H), 4.068 (s, 2H), 5.319 (s, 1H), 7.376 (d, J=9.0 Hz, 1H), 7.713 (d, J=9.0 Hz, 1H), 8.757 (s, 1H).

Step 7: 2,10,10-trimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-197)

1,4-dioxane (15 mL), 7-bromo-2,10,10-trimethyl-2,8,9,10-tetrahydro-1H-2,4,8,10a-tetraazanaphtho[2,1,8-cde]azulen-1(2H)-one (0.20 g, 0.58 mmol), (6-(3-(piperidin-1-yl)propoxy)pyridin-3-yl)boronic acid (0.23 g, 0.87 mmol), potassium carbonate (0.16 g, 1.16 mmol), water (1.5 mL), and tetrakis(triphenylphosphine)palladium (0.07 g, 0.06 mmol) were successively added to a 100 mL reaction bottle. The reaction solution was heated up to 90° C. under nitrogen protection to react for 2.5 h. When the reaction was completed as detected by TLC, the reaction solution was added with water and ethyl acetate for phase separation, the organic phase was concentrated to dryness and then purified by column chromatography (DCM:MeOH=30:1-10:1) to afford a crude product (120 mg), and then the crude product was purified by pre-HPLC to afford 2,10,10-trimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (100 mg, 35.6% yield). ESI-MS (m/z): 487.27 $[M+H]^+$; $^1H$ NMR (600 MHz, $CD_3OD$) δ: 1.284-1.305 (m, 6H), 1.519 (s, 2H), 1.655-1.674 (m, 4H), 2.049-2.096 (m, 2H), 2.577-2.636 (m, 6H), 3.632 (s, 3H), 4.008 (s, 2H), 4.404 (t, J=6.0 Hz, 2H), 4,732 (s, 1H), 6.974 (d, J=9.0 Hz, 1H), 7.384 (d, J=8.4 Hz, 1H), 7.551 (d, J=8.4 Hz, 1H), 7.763-7.781 (m, 1H), 8.184 (d, J=2.4 Hz, 1H), 8.752 (s, 1H).

Example 105: (S)-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-198)

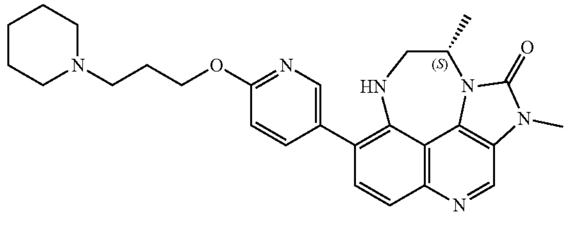

Except starting materials were changed, the synthesis method was the same as that of example 104 to afford (S)-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (55 mg, 32.5% yield). ESI-MS (m/z): 473.26 $[M+H]^+$; $^1H$ NMR (600 MHz, $CD_3OD$) δ: 1.451-1.461 (m, 3H), 1.516 (s, 2H), 1.643-1.681 (m, 4H), 2.039-2.086 (m, 2H), 2.573-2.639 (m, 6H), 3.455-3.480 (m, 1H), 3.615 (s, 3H), 3.640-3.684 (m, 1H), 4.375-4.396 (m, 2H), 4.589 (s, 1H), 5.618-5.631 (m, 1H), 6.943 (d, J=8.4 Hz, 1H), 7.339 (d, J=8.4 Hz, 1H), 7.493 (d, J=8.4 Hz, 1H), 7.769-7.787 (m, 1H), 8.200-8.203 (m, 1H), 8.701 (s, 1H).

Example 106: (R)-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-199)

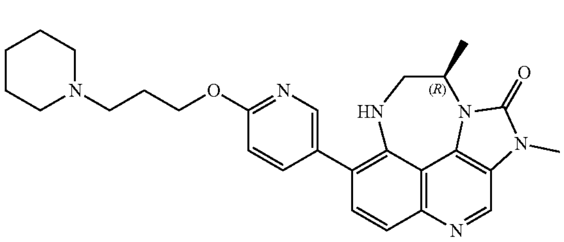

Except starting materials were changed, the synthesis method was the same as that of example 104 to afford (R)-2,10-dimethyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (50 mg, 30.5% yield). ESI-MS (m/z): 473.26 $[M+H]^+$; $^1H$ NMR (600 MHz, $CD_3OD$) δ: 1.444-1.455 (m, 3H), 1.525 (s, 2H), 1.655-1.692 (m, 4H), 2.046-2.093 (m, 2H), 2.614-2.675 (m, 6H), 3.439-3.463 (m, 1H), 3.609 (s, 3H), 3.634-3.677 (m, 1H), 4.373-4.394 (m, 2H), 4.586 (s, 1H), 5.617-5.629 (m, 1H), 6.938 (d, J=8.4 Hz, 1H), 7.328 (d, J=8.4 Hz, 1H), 7.485 (d, J=8.4 Hz, 1H), 7.763-7.781 (m, 1H), 8.195-8.198 (m, 1H), 8.688 (s, 1H).

Example 107: 2'-methyl-7'-(6-(3-(piperidin-1-yl)propoxy)pyridin-3-yl)-8',9'-dihydro-2',4',8',10a'-tetraazaspiro[cyclobutane-1,10'-naphtho[2,1,8-cde]azulen]-2a',3',4a',5',7'-pentaen-1'(2'H)-one (A-200)

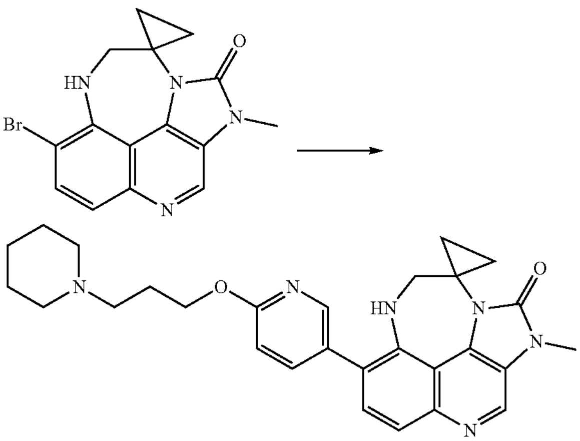

Except starting materials were changed, the synthesis method was the same as that of example 104 to afford 2'-methyl-7'-(6-(3-(piperidin-1-yl)propoxy)pyridin-3-yl)-8',9'-dihydro-2',4',8',10a'-tetraazaspiro[cyclobutane-1,10'-naphtho[2,1,8-cde]azulen]-2a',3',4a',5',7'-pentaen-1'(2'H)-one (81 mg, 35.4% yield). ESI-MS (m/z): 485.26 [M+H]; $^1$HNMR (600 MHz, $CD_3OD$) δ: 0.896-0.936 (m, 4H), 1.528 (s, 2H), 1.652-1.690 (m, 4H), 2.043-2.080 (m, 2H), 2.538-2.606 (m, 6H), 3.640 (s, 3H), 4.057 (brs, 2H), 4.396 (t, J=6.0 Hz, 2H), 6.941 (d, J=8.4 Hz, 1H), 7.532 (d, J=8.4 Hz, 1H), 7.573 (d, J=9.0 Hz, 1H), 7.651-7.669 (m, 1H), 8.090 (d, J=2.4 Hz, 1H), 8.758 (s, 1H).

Example 108: (R)-10-ethyl-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-201)

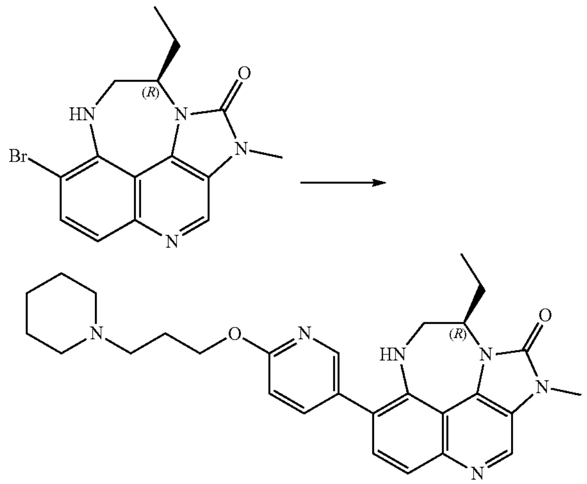

Except starting materials were changed, the synthesis method was the same as that of example 104 to afford (R)-10-ethyl-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (128 mg, 42.1% yield). ESI-MS (m/z): 487.27 $[M+H]^+$; $^1H$ NMR (600 MHz, $CD_3OD$) δ: 1.017-1.042 (m, 3H), 1.512 (s, 2H), 1.634-1.672 (m, 4H), 1.826-1.860 (m, 1H), 1.933-1.948 (m, 1H), 2.034-2.081 (m, 2H), 2.543-2.611 (m, 6H), 3.299-3.395 (m, 1H), 3.620 (s, 3H), 3.841-3.872 (m, 1H), 4.362-4.392 (m, 3H), 5.694-5.706 (m, 1H), 6.948 (d, J=8.4 Hz, 1H), 7.333 (d, J=9.0 Hz, 1H), 7.478 (d, J=8.4 Hz, 1H), 7.766-7.785 (m, 1H), 8.196 (s, 1H), 8.707 (s, 1H).

Example 109: 2-methyl-7-(6-(3-(piperidin-1-yl)propoxy)pyridin-3-yl)-8,9-dihydrospiro[2,4,8,10a-tetraazanaphtho[2,1,8-cde]azulene-10,1'-cyclobutan]-1(2H)-one (A-202)

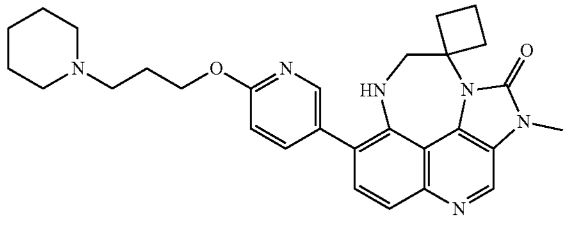

Except starting materials were changed, the synthesis method was the same as that of example 104 to afford 2-methyl-7-(6-(3-(piperidin-1-yl)propoxy)pyridin-3-yl)-8,9-dihydrospiro[2,4,8,10a-tetraazanaphtho[2,1,8-cde]azulene-10,1'-cyclobutan]-1(2H)-one (54.2% yield). ESI-MS (m/z): 499.27 $[M+H]^+$; $^1H$ NMR (600 MHz, $CD_3OD$) δ: 1.509 (brs, 1H), 1.647-1.664 (m, 4H), 1.918-2.064 (m, 8H), 2.547-2.621 (m, 6H), 3.608 (s, 3H), 4.160 (s, 2H), 4.406 (t, J=6.0 Hz, 2H), 6.987 (d, J=8.4 Hz, 1H), 7.375 (d, J=8.4 Hz, 1H), 7.525 (d, J=8.4 Hz, 1H), 7.817 (d, J=6.6 Hz, 1H), 8.237 (s, 1H), 8.686 (s, 1H).

Example 110: (S)-10-ethyl-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (A-203)

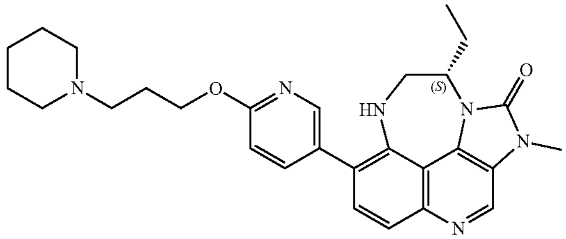

Except starting materials were changed, the synthesis method was the same as that of example 104 to afford (S)-10-ethyl-2-methyl-7-(6-(3-(piperidin-1-yl)propoxy)pyridin-3-yl)-2,8,9,10-tetrahydro-1H-2,4,8,10a-tetraazanaphtho[2,1,8-cde]azulen-1(2H)-one (37.6% yield). ESI-MS (m/z): 487.27 $[M+H]^+$; $^1H$ NMR (600 MHz, $CD_3OD$) δ: 1.024 (t, J=7.2 Hz, 3H), 1.528 (brs, 2H), 1.666-1.693 (m, 4H), 1.814-1.934 (m, 2H), 2.050-2.097 (m, 2H), 2.624-2.683 (m, 6H), 3.350-3.374 (m, 1H), 3.612 (s, 3H), 3.832-3.863 (m, 1H), 4.340-4.392 (m, 3H), 6.943 (d, J=8.4 Hz, 1H), 7.319 (d, J=8.4 Hz, 1H), 7.467 (d, J=8.4 Hz, 1H), 7.760-7.778 (m, 1H), 8.194 (d, J=2.4 Hz, 1H), 8.692 (s, 1H).

Example 111: 6-fluoro-2-methyl-7-(6-(3-(piperidin-1-yl)propoxy)pyridin-3-yl)-2',3',5',6'-tetrahydro-9H-8-oxa-2,4,10a-triazaspiro[naphtho[2,1,8-cde]azulene-10,4'-pyran]-2a,3,4a,5,7-pentaen-1(2H)-one (A-204)

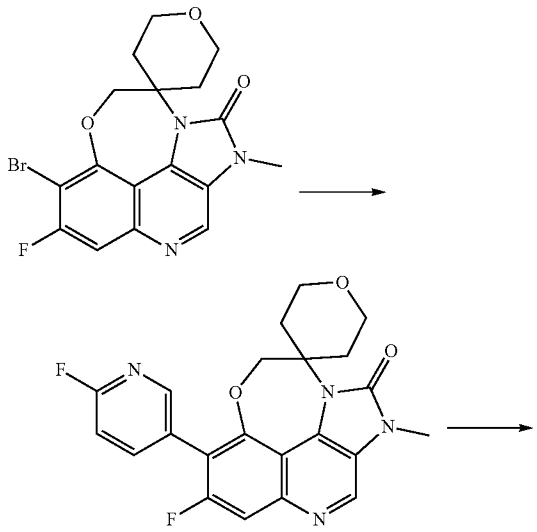

-continued

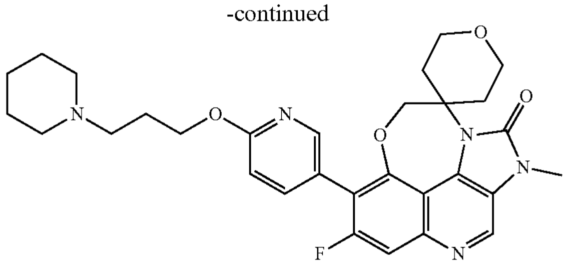

The synthesis method is the same as that of example 1 except that the starting material in step 1 was changed to 7-bromo-6-fluoro-2-methyl-2',3',5',6'-tetrahydro-9H-8-oxa-2,4,10a-triazaspiro[naphtho[2,1,8-cde]azulene-10,4'-pyran]-2a,3,4a,5,7-pentaen-1(2H)-one (the starting material was synthesized in the same way as that in intermediate preparation example 1, i.e., (4-aminotetrahydro-2H-pyran-4-yl)methanol was used instead of L-aminopropanol) to afford 6-fluoro-2-methyl-7-(6-(3-(piperidin-1-yl)propoxy)pyridin-3-yl)-2',3',5',6'-tetrahydro-9H-8-oxa-2,4,10a-triazaspiro[naphtho[2,1,8-cde]azulene-10,4'-pyran]-2a,3,4a,5,7-pentaen-1(2H)-one (46 mg, 33.5% yield). ESI-MS (m/z): 548.26 $[M+H]^+$; $^1H$ NMR (600 MHz, $CD_3OD$) δ: 0.897 (t, J=6.6 Hz, 2H), 1.285 (m, 2H), 1.595 (m, 2H), 1.753 (t, J=5.4 Hz, 4H), 2.136-2.182 (m, 2H), 2.876-2.911 (m, 6H), 3.580 (s, 3H), 3.673-3.711 (m, 2H), 3.952-3.980 (m, 4H), 4.439 (t, J=6.6 Hz, 2H), 6.943 (d, J=8.4 Hz, 1H), 7.539 (d, J=10.8 Hz, 1H), 7.845 (d, J=8.4 Hz, 1H), 8.261 (s, 1H), 8.811 (s, 1H).

Example 112: (S)-6-fluoro-2,10-dimethyl-7-(6-((3-(piperidin-1-yl)propoxy)methyl)pyridin-3-yl)-9,10-dihydro-8-oxa-2,4,10a-triazanaphtho[2,1,8-cde]azulen-1(2H)-one (A-205)

Step 1: Synthesis of 5-bromo-2-((3-(piperidin-1-yl)propoxy)methyl)pyridine

THF (30 mL) and N-hydroxypropylpiperidine (1.11 g, 7.74 mmol) were successively added to a 100 mL reaction bottle and cooled down to 0° C., followed by adding NaH (0.62 g, 15.48 mmol), and the reaction was conducted at this temperature for 0.5 h, then 5-bromo-2-(bromomethyl)pyridine (1.94 g, 7.74 mmol) was added and the reaction was rewarmed to room temperature and reacted for 5 h. When the reaction was completed as detected by TLC, water was added into the reaction solution to quench the reaction, and the reaction mixture was concentrated to dryness, and then the residue was purified by column chromatography (DCM: MeOH=20:1-15:1) to afford 5-bromo-2-((3-(piperidin-1-yl)propoxy)methyl)pyridine (2.06 g, 85.0% yield). ESI-MS (m/z): 313.08/315.08 $[M+H]^+$.

Step 2: Synthesis of 2-((3-(piperidin-1-yl)propoxy)methyl)-5-(4,4,5,5-tetramethyl-1,3,2-dioxaborolan-2-yl)pyridine 1,4-dioxane (25 mL), 5-bromo-2-((2-(piperidin-1-yl)propoxy)methyl)pyridine (2.06 g, 6.58 mmol), bis(pinacolato)diboron (3.34 g, 13.16 mmol), potassium acetate (1.61 g, 16.45 mmol), and [1,1'-bis(diphenylphosphino)ferrocene] palladium dichloride (0.48 g, 0.66 mmol) were successively added to a 100 mL reaction bottle. The reaction solution was heated up to 90° C. under nitrogen protection to react for 3 h. When the reaction was completed as detected by TLC, the reaction solution was concentrated to dryness to afford a crude product 2-((3-(piperidin-1-yl)propoxy)methyl)-5-(4,4,5,5-tetramethyl-1,3,2-dioxaborolan-2-yl)pyridine for instant use in the next step. ESI-MS (m/z): 361.26 $[M+H]^+$.

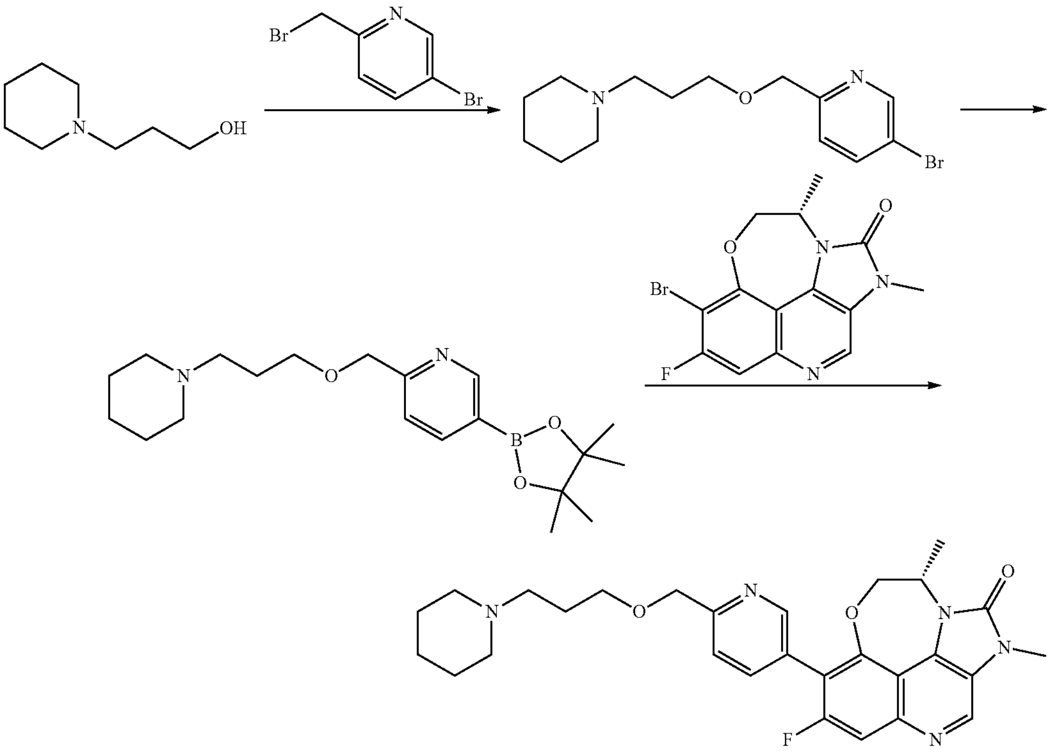

Step 3: Synthesis of (S)-6-fluoro-2,10-dimethyl-7-(6-((3-(piperidin-1-yl)propoxy)methyl)pyridin-3-yl)-9,10-dihydro-8-oxa-2,4,10a-triazanaphtho[2,1,8-cde]azulen-1(2H)-one 1,4-dioxane (5 mL), 2-((3-(piperidin-1-yl)propoxy)methyl)-5-(4,4,5,5-tetramethyl-1,3,2-dioxaborolan-2-yl)pyridine (162 mg, 0.45 mmol), (S)-7-bromo-6-fluoro-2,10-dimethyl-9,10-dihydro-8-oxa-2,4,10a-triazanaphtho[2,1,8-cde]azulen-1(2H)-one (106 mg, 0.3 mmol), potassium carbonate (83 mg, 0.6 mmol), water (0.5 mL), and tetrakis(triphenylphosphine)palladium (35 mg, 0.03 mmol) were successively added to a 50 mL reaction bottle. The reaction solution was heated up to 90° C. under nitrogen protection to react for 3 h. When the reaction was completed as detected by TLC, the reaction solution was concentrated to dryness, and the residue was purified by column chromatography (DCM:MeOH=20:1-10:1) to afford (S)-6-fluoro-2,10-dimethyl-7-(6-((3-(piperidin-1-yl)propoxy)methyl)pyridin-3-yl)-9,10-dihydro-8-oxa-2,4,10a-triazanaphtho[2,1,8-cde]azulen-1(2H)-one (26 mg, 17% yield). ESI-MS (m/z): 506.25 $[M+H]^+$.

Example 113: 7-(6-(3-(bis(methyl-$d_3$)amino)propoxy)pyridin-3-yl)-6-fluoro-2,10,10-trimethyl-9,10-dihydro-8-oxa-2,4,10a-triazanaphtho[2,1,8-cde]azulen-1(2H)-one (A-206)

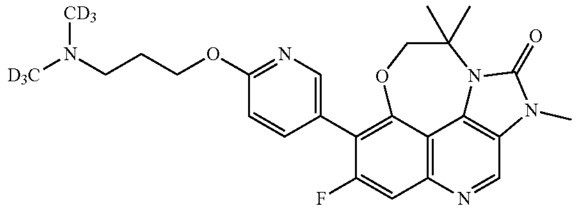 [SMILES: [2H]C([2H])([2H])N(CCCOc1ccc(-c2c(F)cc3ncc4c5c3c2OCC(C)(C)n5c(=O)n4C)cn1)C([2H])([2H])[2H]]

Except starting materials were changed, the synthesis method was the same as that of example 1 to afford 7-(6-(3-(bis(methyl-$d_3$)amino)propoxy)pyridin-3-yl)-6-fluoro-2,10,10-trimethyl-9,10-dihydro-8-oxa-2,4,10a-triazanaphtho[2,1,8-cde]azulen-1(2H)-one (70 mg, 34.2% yield). ESI-MS (m/z): 472.26 $[M+H]^+$; $^1H$ NMR (600 MHz, $CD_3OD$) δ: 1.735 (s, 6H), 2.116-2.162 (m, 2H), 2.919-2.945 (m, 2H), 3.575 (s, 3H), 4.393 (s, 2H), 4.426-4.446 (m, 2H), 6.943 (d, J=8.4 Hz, 1H), 7.512 (d, J=10.8 Hz, 1H), 7.837 (d, J=8.4 Hz, 1H), 8.249 (s, 1H), 8.787 (s, 1H).

Example 114: (S)-7-(6-(3-(4,4-dimethylpiperidin-1-yl)propoxy)pyridin-3-yl)-2,10-dimethyl-9,10-dihydro-8-oxa-2,4,10a-triazanaphtho[2,1,8-cde]azulen-1(2H)-one (A-207)

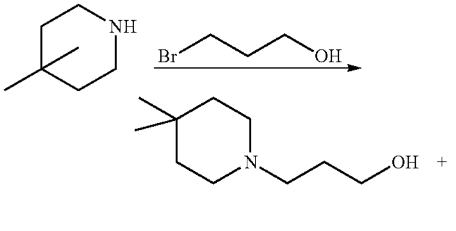

-continued

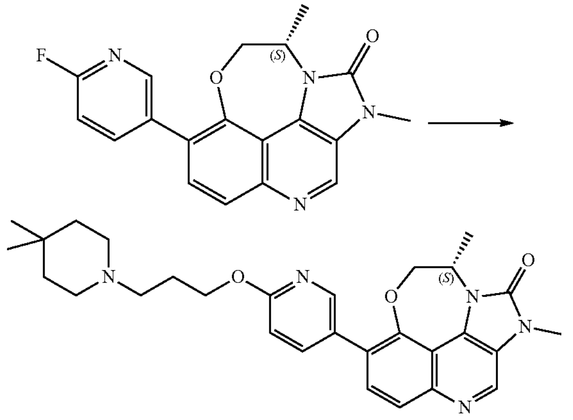

Step 1: Synthesis of 3-(4,4-dimethylpiperidin-1-yl)propanol 4,4-dimethylpiperidine (0.81 g, 7.13 mmol), acetonitrile (20 mL), potassium carbonate (3.94 g, 28.54 mmol), and 3-bromopropan-1-ol (1.19 g, 8.56 mmol) were added to a 100 mL reaction bottle. The reaction solution was heated up to 80° C. to react for 5 h, when the reaction was completed as detected by TLC, the reaction solution was cooled down to room temperature and subjected to suction filtration, and the filtrate was concentrated to dryness and the residue was purified by column chromatography (DCM:MeOH=50:1-20:1) to afford 3-(4,4-dimethylpiperidin-1-yl)propanol (0.56 g, 46.0% yield). ESI-MS (m/z): 172.10 $[M+H]^+$.

Step 2: Synthesis of (S)-7-(6-(3-(4,4-dimethylpiperidin-1-yl)propoxy)pyridin-3-yl)-2,10-dimethyl-9,10-dihydro-8-oxa-2,4,10a-triazanaphtho[2,1,8-cde]azulen-1(2H)-one Anhydrous THF (4 mL) and 3-(4,4-dimethylpiperidin-1-yl)propanol (87 mg, 0.51 mmol) were added to a 50 mL reaction bottle and cooled down to 0° C., followed by adding NaH (35 mg, 0.89 mmol) in batches. After 0.5 h of reaction at room temperature, (S)-7-(6-fluoropyridin-3-yl)-2,10-methyl-9,10-dihydro-8-oxa-2,4,10a-triazanaphtho[2,1,8-cde]azulen-1(2H)-one (87 mg, 0.25 mmol) was added, and the reaction was continued at room temperature overnight. When the reaction was completed as detected by TLC, the reaction solution was concentrated to dryness and the residue was purified by column chromatography (DCM:MeOH=20:1-10:1) to afford a crude product, and the crude product was further purified by preparative thin-layer liquid chromatography to afford (S)-7-(6-(3-(4,4-dimethylpiperidin-1-yl)propoxy)pyridin-3-yl)-2,10-dimethyl-9,10-dihydro-8-oxa-2,4,10a-triazanaphtho[2,1,8-cde]azulen-1(2H)-one (33 mg, 26.3% yield). ESI-MS (m/z): 502.27 $[M+H]^+$; $^1H$ NMR (600 MHz, $CD_3OD$) δ: 1.061 (s, 6H), 1.583 (d, J=7.2 Hz, 3H), 1.630-1.649 (m, 4H), 2.207-2.253 (m, 2H), 3.128-3.178 (m, 6H), 3.644 (s, 3H), 4.451-4.512 (m, 3H), 4.637-4.663 (m, 1H), 4.720-4.731 (m, 1H), 6.933 (d, J=9.0 Hz, 1H), 7.665 (d, J=9.0 Hz, 1H), 7.839 (d, J=8.4 Hz, 1H), 7.977-7.995 (m, 1H), 8.389 (d, J=2.4 Hz, 1H), 8.814 (s, 1H).

Example 115: (S)-2,10-dimethyl-7-(6-(3-(4-methylpiperidin-1-yl)propoxy)pyridin-3-yl)-9,10-dihydro-8-oxa-2,4,10a-triazanaphtho[2,1,8-cde]azulen-1(2H)-one (A-208)

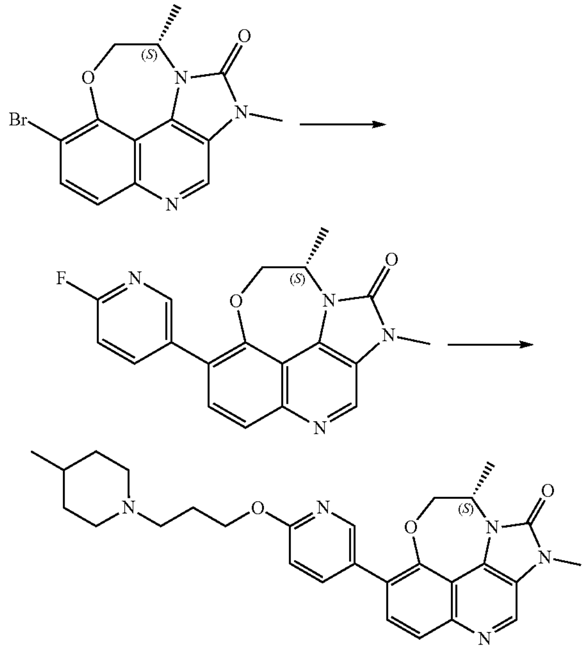

Except starting materials were changed, the synthesis method was the same as that of example 114 to afford (S)-2,10-dimethyl-7-(6-(3-(4-methylpiperidin-1-yl)propoxy)pyridin-3-yl)-9,10-dihydro-8-oxa-2,4,10a-triazanaphtho[2,1,8-cde]azulen-1(2H)-one (55 mg, 37.7% yield). ESI-MS (m/z): 488.26 $[M+H]^+$; $^1H$ NMR (600 MHz, $CD_3OD$) δ: 0.862-0.908 (m, 2H), 0.997-1.008 (m, 3H), 1.348-1.417 (m, 2H), 1.578-1.606 (m, 3H), 1.829-1.851 (m, 2H), 2.163-2.189 (m, 2H), 2.598 (brs, 2H), 2.994 (brs, 2H), 3.303-3.308 (m, 1H), 3.643 (s, 3H), 4.425-4.445 (m, 2H), 4.487-4.509 (m, 1H), 4.640-4.666 (m, 1H), 4.720-4.731 (m, 1H), 6.923 (d, J=8.4 Hz, 1H), 7.665 (d, J=9.0 Hz, 1H), 7.838 (d, J=9.0 Hz, 1H), 7.969-7.987 (m, 1H), 8.382 (d, J=2.4 Hz, 1H), 8.811 (s, 1H).

Example 116: (S)-2,10-dimethyl-7-(6-(3-(4-methylpiperidin-1-yl)propoxy)pyridin-3-yl)-2,8,9,10-tetrahydro-1H-2,4,8,10a-tetraazanaphtho[2,1,8-cde]azulen-1(2H)-one (A-211)

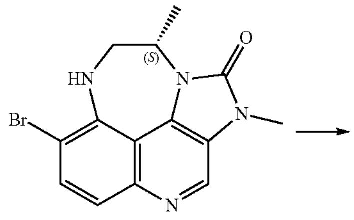

-continued

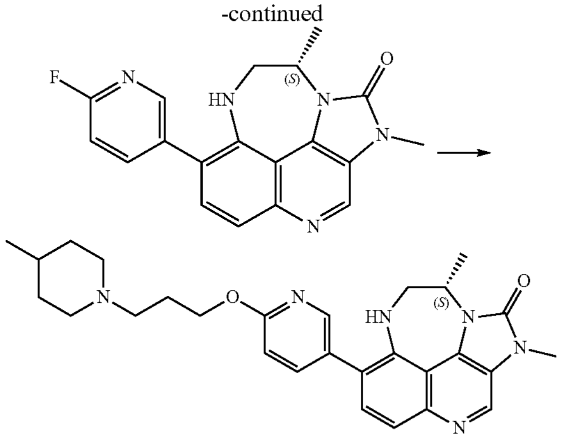

Except starting materials were changed, the synthesis method was the same as that of example 104 to afford (S)-2,10-dimethyl-7-(6-(3-(4-methylpiperidin-1-yl)propoxy)pyridin-3-yl)-2,8,9,10-tetrahydro-1H-2,4,8,10a-tetraazanaphtho[2,1,8-cde]azulen-1(2H)-one (26 mg, 38.3% yield). ESI-MS (m/z): 486.27 $[M+H]^+$; $^1H$ NMR (600 MHz, $CD_3OD$) δ: 0.911-0.922 (m, 2H), 0.984-0.994 (s, 3H), 1.475-1.485 (m, 4H), 1.733-1.755 (m, 2H), 2.083-2.108 (m, 2H), 2.186-2.224 (m, 2H), 2.681-2.706 (m, 2H), 3.082-3.100 (m, 2H), 3.466-3.490 (m, 1H), 3.639-3.692 (m, 4H), 4.402-4.617 (m, 2H), 4.887 (s, 1H), 6.967 (d, J=8.4 Hz, 1H), 7.359 (d, J=8.4 Hz, 1H), 7.516 (d, J=9.6 Hz, 1H), 7.803 (d, J=8.4 Hz, 1H), 8.227 (s, 1H), 8.720 (s, 1H).

Example 117: (S)-7-(6-(3-(4,4-dimethylpiperidin-1-yl)propoxy)pyridin-3-yl)-2,10-dimethyl-2,8,9,10-tetrahydro-1H-2,4,8,10a-tetraazanaphtho[2,1,8-cde]azulen-1(2H)-one (A-212)

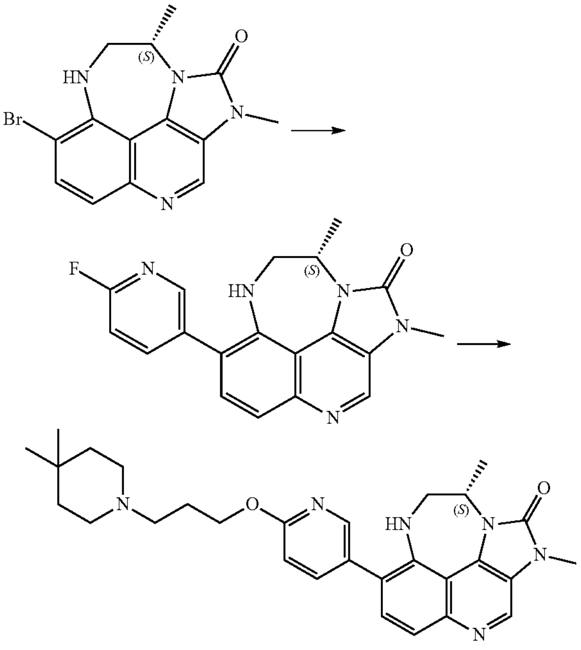

Except starting materials were changed, the synthesis method was the same as that of example 104 to afford (S)-7-(6-(3-(4,4-dimethylpiperidin-1-yl)propoxy)pyridin-3-yl)-2,10-dimethyl-2,8,9,10-tetrahydro-1H-2,4,8,10a-tetraazanaphtho[2,1,8-cde]azulen-1(2H)-one (38 mg, 35.4% yield). ESI-MS (m/z): 500.29 $[M+H]^+$; $^1H$ NMR (600 MHz, DMSO-$d_6$) δ: 0.904 (s, 6H), 1.337-1.346 (m, 8H), 1.909-1.931 (m, 2H), 2.369-2.515 (m, 6H), 3.534 (s, 3H), 3.636-3.667 (m, 1H), 4.331-4.351 (m, 2H), 4.503 (s, 1H), 5.846 (d, J=7.2 Hz, 1H), 6.943 (d, J=8.4 Hz, 1H), 7.262 (d, J=8.4 Hz, 1H), 7.420 (d, J=8.4 Hz, 1H), 7.780 (d, J=7.2 Hz, 1H), 8.230 (s, 1H), 8.785 (s, 1H).

[Experimental Example]

The activity tests and data of the compounds of the present disclosure are as follows.

1 Test on ATM Inhibitory Activity and Enzymatic Selectivity of the Compounds of the Present Disclosure 1.1 Experimental Materials

| Reagent | Supplier | Article Number |
|---|---|---|
| PI3Kα (p110α/p85α) | Invitrogen | PV4788 |
| PI3Kβ (p110β) | Eurofins | 14-603M |
| PI3Kδ (p110δ/p85δ) | Invitrogen | PV6542 |
| PI3Kγ (pp110gamma) | Invitrogen | PR8641C |
| mTOR | Millipore | 14-770 |
| DNA-PK | Promege | V4106 |
| ATR | Eurofins | 14-953 |
| ATM | Millipore | 14-933 |
| Wortmannin | Selleckchem | S2758 |
| ATP | Sigma | A7699-1G |
| PI103 | TOCRIS | 2930 |
| AZ20 | MCE | HY-15557 |
| Staurosporine | Selleckchem | S1421 |
| 5-FAM-AK-17 | GL | 524315 |
| Ulight-4E-BP1 (Thr37/46) Peptide [1] | PE | TRF0128-M |
| Eu-anti-P-4E-BP1 (Thr37/46) [2] | PE | TRF0216-M |
| ADP-Glo Kinase Assay | Promege | V9102 |
| DMSO | Sigma | D2650 |
| EDTA | Sigma | E5134 |
| EGTA | Sigma | E3889-25G |
| 96-well plate | Corning | 3365 |
| 384-well plate | Corning | 3573 |
| 384-well plate | Corning | 4512 |

Note:
[1] Ulight-4E-BP1 (Thr37/46) Peptide: Ulight-labeled peptide chain of eukaryotic translation initiation factor 4E-binding protein 1 (Thr37/46).
[2] EU-anti-P-4E-BP1 (Thr37/46): EU-labeled anti-phosphorylation 4E-BP1 (Thr37/46) antibody.

1.2 Determination of the Inhibitory Activities of Compounds on ATM: Caliper Mobility Shift Assay for ATM Experimental Procedures (1) Preparation of 1× kinase basal buffer and reaction termination solution 1) 1× kinase basal buffer 50 mM HEPES, pH 7.5

0.0015% Brij-35 (polyoxyethylene lauryl ether)

100 mM $Na_3VO_4$

5 M NaCl

1 M $MgCl_2$

1 M $MnCl_2$

2) Reaction termination solution 100 mM HEPES, pH 7.5

0.015% Brij-35

0.2% Coating Reagent #3

50 mM EDTA (2) Preparation of test compound

1) Dissolution and dilution of compound: a compound was dissolved into DMSO to yield a 10 mM or 5 mM stock solution. To a 96-well plate, 98 μL of DMSO and 2 μL of the 10 mM stock solution were added and mixed evenly so that the concentration of the solution was 200 μM. To another 96-well plate, 45 μL of DMSO and 5 μL of the 200 μM solution were added to yield a 20 μM working solution.

2) The working solution of the compound was sequentially diluted in the 96-well plate by the way of taking 10 μL of a solution at a higher concentration to 30 μL of DMSO to yield a mixed solution at a lower concentration and transferring the mixed solution to the next well, and so on, in order to set up 10 concentration gradients.

3) 100 μL of DMSO was added to the blank well and served as a blank control without compound or enzyme.

4) Preparation of intermediate sample plate: 40 μL of each of the solutions with gradient concentrations prepared in the 96-well plate was taken and transferred to a new 384-well plate as an intermediate sample plate.

(3) Preparation of test plate 100 nL of the compound solution was taken from each well of the intermediate sample plate to a 384-well plate as a test plate.

(4) Kinase reaction

1) The kinase was dissolved in the 1× kinase basal buffer to yield a 2× enzyme solution.

2) 10 μL of the 2× enzyme solution was taken to the 384-well test plate.

3) The 384-well test plate was incubated at room temperature for 10 min.

4) FAM-labeled polypeptide substrate and ATP were dissolved in the 1× kinase basal buffer to yield a 2× substrate peptide solution.

5) 10 μL of the 2× substrate peptide solution was taken to each well of the 384-well test plate, respectively.

6) Progress and termination of enzymatic reaction: the test plate, to which the enzyme solution and the substrate peptide solution were added, was incubated at 37° C. for a while, and then 35 μL of the reaction termination solution was added to terminate the reaction.

(5) Reading of the reaction wells (6) Calculation of inhibitory rates by means of curve fitting to the read values % inhibitory rate=(max−conversion)/(max−min)*100; wherein "max" represents the read value of the total reaction well with DMSO but no compound; "min" represents the read value of the blank control well; "conversion" represents the read value of the test well.

Based on the inhibitory rates of the compound at different concentrations, $IC_{50}$ was calculated according to the formula: $Y=Bottom+(Top-Bottom)/(1+(IC_{50}/X)\hat{}HillSlope)$.

1.3 Determination of the Inhibitory Activities of Compounds on PI3Kα, PI3Kβ, PI3Kγ, and PI3Kδ Kinase: ADP-Glo Kinase Assay Experimental procedures (1) Preparation of 1× kinase buffer 50 mM HEPES, pH 7.5

3 mM $MgCl_2$ 1 mM EGTA 100 mM NaCl 0.03% CHAPS 2 mM DTT (2) Preparation of test compound 1) Dissolution and dilution of compound:

The compound was dissolved in DMSO to yield a stock solution. Before the assay, the stock solution of the compound was diluted with DMSO in a 384-well plate to yield a 100× solution at a concentration that is 100 times a target concentration for assay.

50 μL of DMSO was added, respectively, into two blank wells in the same 384 well plate, corresponding to the total reaction control without compound and the blank control without enzyme.

2) Preparation of test plate: 50 nL of the compound solution in each of the above wells was taken to a test plate.

(3) Kinase reaction

1) PI3Kα, PI3Kβ, PI3Kγ, and PI3Kδ kinases were dissolved, respectively, in 1× kinase buffer to yield a 2× enzyme solution at a concentration that is twice the final concentration. 2.5 μL of the 2× enzyme solution was taken to each well of the test plate. The blank control without enzyme was added with 2.5 μL of the 1× kinase buffer instead of the enzyme solution. The test plate was shaken for mixing evenly.

2) PIP2 substrate and ATP were dissolved in the 1× kinase buffer to yield a 2× substrate solution that is twice the final concentration. 2.5 μL of the 2× substrate solution was taken to each well of the test plate. The test plate was shaken for mixing evenly.

3) Kinase reaction

Each well of the test plate was covered and incubated at room temperature for 1 h.

(4) Kinase detection

1) The ADP-Glo reagent was equilibrated at room temperature.

2) 5 μL of ADP-Glo reagent was added to each well of the test plate to terminate the reaction.

3) The plate was centrifuged for a short time to mix evenly, shaken gently, and equilibrated for 120 min.

4) 10 μL of kinase detection reagent was added to each well, with shaking for 1 min, after equilibrating for 30 min, fluorescence detection was performed.

(5) Reading of the reaction wells (6) Calculation of inhibitory rates by means of curve fitting to the read values % inhibitory rate=(max−sample RLU)/(max−min)*100; wherein "max" represents the RLU of the total reaction well with DMSO but no compound; "min" represents the RLU of the blank control well without enzyme and compound.

Based on the inhibitory rates of the compound at different concentrations, $IC_{50}$ was calculated according to the formula: $Y=Bottom+(Top-Bottom)/(1+(IC_{50}/X)^{HillSlope})$.

1.4 Determination of the Inhibitory Activities of Compounds on DNA-PK Kinase: ADP-Glo Kinase Assay Experimental Procedures (1) Preparation of 1× kinase buffer 40 mM Tris, pH 7.5

0.0055% Brij-35

20 mM $MgCl_2$ 0.05 mM DTT (2) Preparation of test compound

1) The compound was dissolved in DMSO to yield a stock solution. Before the assay, the stock solution of the compound was diluted with DMSO to yield a 100× solution at a concentration that is 100 times a target concentration for assay. If the target concentration was 10 μM, the stock solution should be diluted to yield a 1 mM solution at this step.

2) 100 μL of DMSO was added, respectively, into two blank wells in the same 96 well plate, corresponding to the total reaction control without compound and the blank control without enzyme.

3) Preparation of test plate: 50 nL of the compound solution in each of the above wells was taken to a 384-well plate as a test plate.

(3) Kinase reaction

1) DNA-PK kinase was dissolved in 1× kinase buffer to yield a 2× enzyme solution that is twice the final concentration. 2.5 μL of the 2× enzyme solution was taken to each well of the test plate. The blank control without enzyme was added with 2.5 μL of the 1× kinase buffer instead of the enzyme solution. The test plate was shaken for mixing evenly.

2) The substrate and ATP were dissolved in the 1× kinase buffer to yield a 2× substrate solution that is twice the final concentration. 2.5 μL of the 2× substrate solution was taken to each well of the test plate. The test plate was shaken for mixing evenly.

3) Kinase reaction

Each well of the test plate was covered and incubated at room temperature for 3 h.

(4) Kinase detection

1) The ADP-Glo reagent was equilibrated at room temperature.

2) 5 μL of ADP-Glo reagent was added to each well of the test plate to terminate the reaction.

3) The plate was centrifuged for a short time to mix evenly, shaken gently, and equilibrated for 120 min.

4) 10 μL of kinase detection reagent was added to each well, with shaking for 1 min, after equilibrating for 30 min, fluorescence detection was performed.

(5) Reading of the reaction wells (6) Calculation of inhibitory rates by means of curve fitting to the read values.

% inhibitory rate=(max−sample RLU)/(max−min)*100; wherein "max" represents the RLU of the total reaction well with DMSO but no compound; "min" represents the RLU of the blank control well without enzyme and compound.

Based on the inhibitory rates of the compound at different concentrations, $IC_{50}$ was calculated according to the formula: $Y=Bottom+(Top-Bottom)/(1+(IC_{50}/X)^{HillSlope})$.

1.5 the Inhibitory Activities of Compounds on mTOR Kinase: LanceUltra Kinase Assay Experimental Procedures (1) Preparation of 1× kinase buffer 50 mM HEPES, pH 7.5

1 mM EGTA 0.01% Tween-20

(2) Preparation of test compound

1) The compound was dissolved in DMSO to yield a stock solution. Before the assay, the stock solution of the compound was diluted with DMSO to yield a 100× solution at a concentration that is 100 times a target concentration for assay. If the target concentration was 10 μM, the stock solution should be diluted to yield a 1 mM solution at this step.

2) 100 μL of DMSO was added, respectively, into two blank wells in the same 96 well plate, corresponding to the total reaction control without compound and the blank control without enzyme.

3) Preparation of intermediate sample plate: 4 μL of the 100× solution was added into a new 96-well plate, then 96 μL of the 1× kinase buffer was added, and the plate was shaken for 10 min for mixing evenly to serve as an intermediate sample plate.

4) Preparation of test plate: 2.5 nL of the compound solution was taken from each well of the intermediate sample plate to a 384-well plate.

(3) Kinase reaction

1) The mTOR kinase was dissolved in the 1× kinase buffer to yield a 4× enzyme solution at a concentration that is 4 times the final concentration. 2.5 μL of the 2× enzyme solution was taken to each well of the test plate. The blank control without enzyme was added with 2.5 μL of the 1× kinase buffer instead of the enzyme solution. The test plate was shaken for mixing evenly.

2) ULight-4E-BP1 polypeptide substrate and ATP were dissolved in the 1× kinase buffer to yield a 2× substrate solution at a concentration that is twice the final concentration. 5 μL of the 2× substrate solution was taken to each well of the test plate. The test plate was shaken for mixing evenly.

3) Kinase reaction:

Each well of the test plate was covered and incubated at room temperature for 30 min.

(4) Kinase detection

1) The kinase quench buffer (EDTA) and Eu-anti-phospho-4E-BP1 antibody were formulated into a detection buffer at a concentration that is twice the final concentration. 10 μL of the detection buffer was added to each well of the test plate.

2) The plate was centrifuged for a short time to mix evenly, shaken gently, and equilibrated at room temperature for 60 min.

(5) Reading of the reaction wells (6) Calculation of inhibitory rates by means of curve fitting to the read values.

% inhibitory rate=(max−sample fluorescence value)/(max−min)*100; wherein "max" represents the fluorescence value of the total reaction well with DMSO but no compound; "min" represents the fluorescence value of the blank control well without enzyme and compound.

Based on the inhibitory rates of the compound at different concentrations, $IC_{50}$ was calculated according to the formula: $Y=Bottom+(Top-Bottom)/(1+(IC_{50}/X)$ ^HillSlope).

1.6 Determination of the Inhibitory Activity of Compounds on ATR: Caliper Mobility Shift Assay for ATR Experimental Procedures (1) Preparation of 1× kinase buffer and reaction termination solution 1) 1× kinase buffer 50 mM HEPES, pH 7.5

0.0015% Brij-35

1 M $MnCl_2$

2) Reaction termination solution 100 mM HEPES, pH 7.5

0.015% Brij-35

0.2% Coating Reagent #3

50 mM EDTA (2) Preparation of test compound

1) The compound was dissolved in DMSO to yield a stock solution. Before the assay, to a 96-well plate, 30 μL of a 10 mM stock solution was taken and added with 60 μL of DMSO. The solution was sequentially diluted by the way of taking 30 μL of a solution at a higher concentration to 60 μL of DMSO to yield a mixed solution at a lower concentration and transferring the mixed solution to the next well, and so on, and 10 concentration gradients were set up.

2) 100 μL of DMSO was added, respectively, into two blank wells in the same 96 well plate, corresponding to the total reaction control without compound and the blank control without enzyme.

3) Preparation of intermediate sample plate: 40 μL of the solution in each well of the above 96-well plate was taken and transferred to a new 384-well plate as an intermediate sample plate.

(3) Preparation of test plate 60 nL of the solution in each well of the intermediate sample plate was taken to a test plate.

(4) Kinase reaction

1) ATR kinase was dissolved in the 1× kinase buffer to yield a 2× enzyme solution at a concentration that is twice the final concentration. 10 μL of the 2× enzyme solution was taken to each well of the test plate and incubated at room temperature for 10 min.

2) FAM-labeled polypeptide substrate and ATP were dissolved in the 1× kinase buffer to yield a 2× substrate solution at a concentration that is twice the final concentration. 10 L of the 2× substrate solution was taken to each well of the test plate.

3) Kinase reaction:

After incubation at 28° C. for a certain time, 30 μL of the reaction termination solution was added to terminate the enzymatic reaction.

(5) Reading of the reaction wells (6) Calculation of inhibitory rates by means of curve fitting to the read values.

% inhibitory rate=(max−sample value)/(max−min)*100; wherein "max" represents the value of the total reaction well with DMSO but no compound; "min" represents the value of the blank control well without enzyme and compound.

Based on the inhibitory rates of the compound at different concentrations, $IC_{50}$ was calculated according to the formula: $Y=Bottom+(Top-Bottom)/(1+(IC_{50}/X)$ ^HillSlope).

2 Results of the Test on ATM Inhibitory Activity of the Compounds of the Present Disclosure

| Compound No. | $IC_{50}$ (nM) | Compound No. | $IC_{50}$ (nM) | Compound No. | $IC_{50}$ (nM) |
|---|---|---|---|---|---|
| A-1 | 0.79 | A-159 | 0.92 | A-186 | 0.38 |
| A-4 | 0.90 | A-160 | 0.43 | A-187 | 0.22 |
| A-6 | 0.37 | A-161 | 0.32 | A-188 | 0.40 |
| A-9 | 0.20 | A-162 | 0.36 | A-189 | 0.38 |
| A-11 | 0.54 | A-164 | 0.59 | A-191 | 0.69 |
| A-13 | 0.40 | A-165 | 0.37 | A-192 | 0.53 |
| A-14 | 0.42 | A-166 | 0.21 | A-193 | 0.65 |
| A-21 | 0.45 | A-167 | 0.33 | A-194 | 0.45 |
| A-22 | 0.52 | A-170 | 0.70 | A-195 | 0.41 |
| A-23 | 0.42 | A-171 | 0.42 | A-196 | 0.51 |
| A-27 | 0.28 | A-176 | 0.17 | A-197 | 0.59 |
| A-28 | 0.28 | A-177 | 0.25 | A-198 | 0.44 |
| A-30 | 0.27 | A-178 | 0.25 | A-199 | 0.92 |
| A-32 | 0.94 | A-179 | 0.37 | A-201 | 0.61 |
| A-33 | 0.08 | A-180 | 0.26 | A-202 | 0.23 |
| A-46 | 0.52 | A-181 | 0.72 | A-203 | 0.54 |
| A-49 | 0.86 | A-182 | 0.46 | A-204 | 0.78 |
| A-67 | 0.26 | A-183 | 0.23 | A-207 | 0.44 |
| A-68 | 0.37 | A-184 | 0.25 | A-208 | 0.29 |
| A-154 | 0.71 | A-185 | 0.25 | AZD1390 | 0.20 |
| A-211 | 0.33 | A-212 | 0.37 | | |

Note:
as positive control drug, AZD1390 is the compound in Example 2 of patent applicaiton CN 201680052951.0.

The in vitro enzymatic assay results show that the compound of the present disclosure is a strong inhibitor of ATM kinase. The $IC_{50}$ of the inhibitory activity of each compound of the present disclosure on ATM kinase was less than 1 nM; the $IC_{50}$ of some of compounds such as A-33 is 0.08 nM, and the inhibitory effect thereof on ATM kinase is higher than that of AZD1390.

3 Results of the Test on Enzymatic Selectivity of the Compounds of the Present Disclosure

| Compound | $IC_{50}$ of kinase inhibitory activity (nM) | | | | | | | |
|---|---|---|---|---|---|---|---|---|
| No. | ATR | mTOR | DNA-PK | PI3K α | PI3K β | PI3K γ | PI3K δ | ATM |
| A-21 | >10000 | >10000 | 2226.0 | >10000 | >10000 | >10000 | >10000 | 0.45 |
| A-22 | >10000 | 1275 | 852.2 | 6279.2 | >10000 | >10000 | >10000 | 0.52 |

At the level of in vitro enzymatic assay, the kinase inhibitory activities of the compounds of the present disclosure on an ATM-related family were determined. The results show that, as compared to the $IC_{50}$ of the inhibitory activity on ATM kinase, the $IC_{50}$s of the inhibitory activities of the compound of the present disclosure on ATR, mTOR, DNA-PK, PI3Kα, PI3Kβ, PI3Kγ, and PI3Kδ kinases range from several hundred nM to more than 10000 nM, which shows extremely weak or no inhibitory activity, indicating that the compound of the present disclosure is a selective inhibitor of ATM kinase.

4 Inhibition on Intracellular ATM-Phosphorylated KAP1 Level by the Compounds of the Present Disclosure: ICW Assay 4.1 Experimental Materials and Instruments Cell: Human breast cancer cell line MCF7

Materials and reagents:

| Reagent | Supplier | Article Number |
|---|---|---|
| DMEM | Gibco | 10569-010 |
| FBS | Gibco | 10099-141 |
| Penicillin-Streptomycin | Gibco | 15140-122 |
| Odyssey Blocking Buffer | LI-COR | 927-70001 |
| anti-phospho-KAP1(S824) | Bethyl Laboratories | A300-767A |
| DRAQ5 | CST | 4048L |
| IRDye 800CW Goat anti-Rabbit IgG (H + L) | LI-COR | 926-32211 |
| DMSO | Solarbio | D8371-50 |

| Consumable and Instrument | Supplier | Article Number or Model Number |
|---|---|---|
| 384-Well Polypropylene microplate, Clear, Flat Bottom | Labcyte | PP-0200 |
| Poly-D-Lysine Black/Clear Microtest (TM) Tissue-Culture Treated Polystyrene, 384-well plate | Corning | 356663 |
| Plate shaker | Thermo | 4625-1 CECN/THZ Q |
| Centrifuge | Eppendorf | 5810R |
| I-DOT One | Dispendix | 0027 |
| Odyssey | Li-COR | CLX |
| Vortex | IKA | MS3 digital |

4.2 Experimental Procedures (1) Cell inoculation

MCF7 cells were inoculated on a 384-well plate, 10000 cells/well (25 μL/well), and cultured overnight at 37° C. with 5% $CO_2$.

(2) Activity detection

1) The compound was formulated into a 100 mM solution with DMSO and then sequentially diluted with a gradient of 1:3 to yield a total of 10 concentration gradients, wherein the maximum concentration was 100 μM.

2) 25 nL of each of the compound solutions with gradient concentrations prepared in step 1) was added to each well of the cell plate (Corning #356663) by using I-DOT One, resulting in a final concentration of 100 nM (maximum dose).

3) The cell plate containing compound was incubated at 37° C. with 5% $CO_2$ for 2 h. After 2 h, the cell plate was irradiated with a dose of 10 Gy, and then further incubated for 1 h.

4) 25 μL of 8% paraformaldehyde was added to each well, followed by incubating at room temperature for 20 min.

5) The 8% paraformaldehyde was discarded, followed by adding 0.1% TrintonX-100 and incubating at room temperature for 30 min.

6) Odessey blocking buffer was added at 50 μL/well, followed by incubating at room temperature for 1.5 h.

7) The Odessey blocking buffer was discarded, and then a primary antibody (Phospho-KAP1, 1:2000 dilution) was added, followed by incubating overnight at 4° C.

8) The primary antibody was removed, followed by washing with PBS+0.1% Tween 20 for 5 times.

9) DNA dye DRAQ5 coated with a second antibody (IRDye 800CW Goat anti-Rabbit, 1:4000 dilution) was added, followed by incubating at room temperature for 1 h.

10) The second antibody was removed, followed by washing with PBS+0.1% Tween 20 for 5 times.

11) PBS+0.1% Tween 20 was sucked off with Odyssey.

(3) Data analysis 1) the relative ratio of Channel 800/Channel 700 for each well was detected.

2) % of KAP1 phosphorylation was calculated according to the following formula:

% of KAP1 phosphorylation=[(Ratiocmpd−(Ratio)Positive)/((Ratio)Vehicle−(Ratio)Positive]*100

(Ratio)Positive: the mean value of the test values of each positive control well in the test cell plate;

(Ratio)Vehicle: the mean value of the test values of each negative control well in the test cell plate.

3) the $IC_{50}$ of each compound was calculated and the dose-effect curve was plotted: % of KAP1 phosphorylation and log of compound's concentration were fit by using Graphpad 8.0 so as to calculate the $IC_{50}$.

$$Y = \text{Bottom}+(\text{Top}-\text{Bottom})/(1+10\verb|^|((\text{Log}IC_{50}-X)*HillSlope))$$

X: log of compound's concentration

Y: % of KAP1 phosphorylation 4.3 the Inhibitory Activities of Compounds on Intracellular ATM-Phosphorylated KAP1 Level

| Compound No. | pKAP1 $IC_{50}$ (nM) | Compound No. | pKAP1 $IC_{50}$ (nM) |
|---|---|---|---|
| AZD1390 | 0.45 | A-203 | 0.83 |
| A-198 | 0.64 | A-183 | 0.22 |
| A-193 | 1.75 | A-184 | 0.33 |
| A-68 | 0.90 | A-199 | 0.78 |
| A-177 | 0.61 | A-192 | 1.44 |
| A-211 | 0.33 | A-212 | 0.37 |

At the cellular level, the compounds have inhibitory effects on ATM KAP phosphorylation. Among those, the inhibitory effects of A-183, A-184, A-211, and A-212 are higher than that of AZD1390 as positive control.

5 Test of the Inhibitory Activities of the Compounds of the Present Disclosure Combined with Radiotherapy on LN18 Cell Proliferation 5.1 Experimental Materials and Instruments Cell: Human glioblastoma cell line LN-18

Experimental Materials and Reagents:

| Reagent | Supplier | Article Number |
|---|---|---|
| Dulbecco's Modified Eagle Medium (D-MEM) | invitrogen | 11965-092 |
| Fetal Bovine Serum | Gibco | 10099141 |
| Cell titre glo | Promega | G7573 |
| DMSO | Sigma | D8418 |

Consumables and Instruments:

| Consumable and Instrument | Supplier | Article Number or Model Number |
|---|---|---|
| V96 MicroWell Plates | Nunc | 249944 |
| CulturPlate-96 (White) | PerkinElmer | 6005680 |
| Deep Well Plates | Axygen | P-DW-11-C-S |
| 50 mL Centrifuge Tube | BD-Falcon | 352098 |
| 15 mL Centrifuge Tube | BD-Falcon | 352097 |
| 5 mL Serological pipet | BD-Falcon | 357543 |
| 10 mL Serological pipet | BD-Falcon | 357551 |
| 25 mL Serological pipet | BD-Falcon | 357525 |
| Sample grooves | Corning | 4870 |
| 25 cm2 Flask | Corning | 430639 |
| 75 cm2 Flask | Corning | 430641 |
| 225 cm2 Flask | Corning | 431082 |
| Plate shaker | QILINBEIER | QB-9002 |
| Centrifuge | Eppendorf | 5810R |
| X-Ray | PRECISION | X-RAD 225 |
| Multiplate reader | PerkinElmer | EnVision 2105 |

5.2 Experimental Procedures (1) Cell inoculation

1) The cell culture fluid was preheated at 37° C.

2) A complete culture medium of LN18 cells was prepared, at a ratio of DMEM medium:FBS=95:5 (V/V).

3) Cells were digested with trypsin, collected to serve as a cell suspension, and counted, the cell suspension was then added into a 96-well plate at 1500 cells/well and 100 μL of cell fluid/well, and three parallel wells were set.

4) After inoculated in the plate, the cells were cultured overnight under the condition of 37° C. and 5% $CO_2$.

(2) Compound addition and incubation

1) AZD1390 and tested compounds, respectively, were sequentially diluted 5 times with DMSO, starting from the concentration of 10 mM and yielding the concentrations of 10, 2, 0.4, 0.08, 0.016, 0.0032, 0.00064, 0.000128, and 0.0000256 mM in turn. The compound solutions at the above concentrations were diluted 5000 times with the complete culture medium. The final 2× concentrations were in order 2000, 400, 80, 16, 3.2, 0.64, 0.128, 0.0256, and 0.00512 nM. The vehicle control was 0.02% DMSO culture fluid.

2) A complete culture medium containing 100 μL of the compound solution was added to each well, and the final concentrations of the compounds in the wells were in order 1000, 200, 40, 8, 1.6, 0.32, 0.064, 0.0128, and 0.00256 nM. The 0.01% DMSO culture fluid was contained in the vehicle control well. After incubated with compound for 1 h, the cells were irradiated at a dose of 1 Gy.

3) After irradiation, the plate was put into an incubator and incubated under the condition of 37° C. and 5% $CO_2$ for 6 days. Then detection was performed by adopting CTG assay (100 μL of liquid from each well was sucked out and discarded, and 50 μL of CTG reagent was added to each well, and incubated at room temperature for 30 min, and the luminescence intensity was detected).

(3) Data analysis

1) The Luminescence signal (RLU) of each well was detected.

2) Proliferation inhibitory activity was calculated according to the formula: % inhibitory activity=RLUtreatment/RLUAvg(Vehicle)*100.

5.3 the Inhibitory Activities of Compounds of the Present Disclosure Combined with Radiotherapy on LN18 Cell Proliferation

| Compound No. | $IC_{50}$ (nM) | Compound No. | $IC_{50}$ (nM) |
|---|---|---|---|
| AZD1390 | 2.79 | A-203 | 5.66 |
| A-198 | 5.93 | A-183 | 1.39 |
| A-193 | 10.08 | A-184 | 3.84 |
| A-68 | 6.83 | A-211 | 2.71 |
| A-177 | 5.22 | A-212 | 1.48 |

At the cellular level, the compounds have inhibitory effects on LN18 cell proliferation. Among those, the inhibitory effects of A-183, A-211, and A-212 were higher than that of AZD1390 as positive control.

6 Efficacy Test of the Compounds of the Present Disclosure Combined with Irinotecan Liposome Injection on Inhibiting the Growth of Subcutaneous Xenograft Tumor of Human Non-Small Cell Lung Cancer Cell Line NCI-H441

6.1 Experimental Animals: NU/NU Mice, SPF, Female, 20 to 30 g.

6.2 Experimental Materials

Irinotecan liposome injection (HE072), 43 mg:10 mL, milky white liquid, batch No. B37191202, provided by Preparation Research Institute 2 from CSPC Zhongqi Pharmaceutical Technology (Shijiazhuang) Co., Ltd., diluted to an appropriate concentration with 5% glucose injection while testing.

NCI-H441 cells, provided by Nanjing Kebai Biotechnology Co., Ltd.; 1640 culture medium (gibco Company):fetal bovine serum (Lanzhou Bailing)=90%:10%, 37° C., 5% $CO_2$.

6.3 Experimental Process

NU/NU nude mice were subcutaneously inoculated with NCI-H441 human non-small cell lung cancer cells. When the mean tumor volume reached 170 to 172 $mm^3$ (15 days after inoculation), the animals were evenly divided into groups according to the tumor volume (d0), with 6 mice in each group. 2.5 mg/kg of HE072 was administered intraperitoneally once a week for 2 times. Vehicle control, 25 mg/kg of A-193, 25 mg/kg of A-182, and 25 mg/kg of AZD1390 were administered intragastrically once a day, from Monday to Thursday every week except Friday to Sunday, for 2 weeks (8 times). The tumor volume was measured twice a week, the body weight of mouse was weighed every day, and the data were recorded. The tumor volume (TV) was calculated according to the formula: TV=½×a×b2, wherein a and b represent the long and short diameters of tumor, respectively. Tumor growth inhibitory rate TGI (%)=[1−(Ti−T0)/(Vi−V0)]×100, wherein Ti represents the mean tumor volume of a given treatment group on a certain day; TO represents the mean tumor volume of this treatment group at the beginning of administration; Vi represents the mean tumor volume of the vehicle control group on a certain day (the same day as that in Ti); V0 represents the mean tumor volume of the vehicle control group at the beginning of administration. At the end of the test (d17), the animals were sacrificed, the tumors were stripped and weighed, and the tumor weight inhibitory rates were calculated.

$$\text{Tumor weight inhibitory rate (\%)} = (1 - \text{tumor weight of treatment group}/\text{tumor weight of vehicle control group}) \times 100.$$

6.4 the Efficacy Test Results of the Compounds of the Present Disclosure Combined with Irinotecan Liposome Injection on Inhibiting the Growth of Subcutaneous Xenograft Tumor of Human Non-Small Cell Lung Cancer Cell Line NCI-H441

| Group | Compound dose (mg/kg) | D0 TV (MEAN ± SD, $mm^3$) | D17 TV (MEAN ± SD, $mm^3$) | D17 TGI % | Tumor weight (g) | Tumor weight inhibitory rate % |
|---|---|---|---|---|---|---|
| Vehicle control | 0 | 172.9 ± 30.0 | 605.7 ± 169.6 | — | 0.59 ± 0.13 | — |
| Vehicle control/Irinotecan | 0/2.5 | 170.9 ± 24.8 | 449.9 ± 80.5** | 35.5 | 0.46 ± 0.11* | 21.7 |
| A-193/Irinotecan | 25/2.5 | 171.6 ± 30.9 | 225.9 ± 69.4***### | 87.5 | 0.24 ± 0.06***### | 60.2 |
| A-182/Irinotecan | 25/2.5 | 170.7 ± 31.5 | 278.5 ± 94.1***## | 75.1 | 0.26 ± 0.07***### | 56.1 |
| AZD1390/Irinotecan | 25/2.5 | 171.1 ± 28.5 | 342.8 ± 110.6*** | 60.3 | 0.32 ± 0.09***## | 45.3 |

Compared with the vehicle control, $P < 0.01$, *$P < 0.001$; compared with irinotecan at a dose of 2.5 mpk, ##$P < 0.01$, ###$P < 0.001$.

The efficacy test results of growth inhibition of NCI-H441 subcutaneous xenograft tumor show that the compounds of the present disclosure significantly inhibit the tumor growth, and the inhibitory effects of A-193 and A-182 on both tumor volume and tumor weight are higher than those of AZD1390.

7 Efficacy Test of the Compounds of the Present Disclosure Combined with Irinotecan Liposome Injection on Inhibiting the Growth of Subcutaneous Xenograft Tumor of Human Colon Cancer Cell Line HT-29

7.1 Experimental Animals: NU/NU Mice, SPF, Female, 20 to 30 g.

7.2 Experimental Materials

Irinotecan liposome injection (HE072), 43 mg: 10 mL, milky white liquid, batch No. B37191202, provided by Preparation Research Institute 2 from CSPC Zhongqi Pharmaceutical Technology (Shijiazhuang) Co., Ltd., diluted to an appropriate concentration with 5% glucose injection while testing.

HT-29 cell, provided by Nanjing Kebai Biotechnology Co., Ltd.; 5A culture medium:fetal bovine serum=90%:10%, 37° C., 5% $CO_2$.

7.3 Experimental Process

NU/NU nude mice were subcutaneously inoculated with HT-29 human colon cancer cells. When the mean tumor volume reached about 170 $mm^3$ (9 days after inoculation), the animals were evenly divided into groups according to the tumor volume (d0), with 6 mice in each group. 10 mg/kg of HE072 was administered intraperitoneally once a week for 1 time. Vehicle control, 25 mg/kg of A-6, 25 mg/kg of A-46, and 25 mg/kg of AZD1390 were administered intragastrically once a day, from Monday to Thursday every week except Friday to Sunday, for 1 week (4 times). The tumor volume was measured twice a week, the body weight of mouse was weighed every day, and the data were recorded. The tumor volume (TV) was calculated according to the formula: TV=½×a×b2, wherein a and b represent the long and short diameters of tumor, respectively. Tumor growth inhibitory rate TGI (%)=[1−(Ti−T0)/(Vi−V0)]×100, wherein Ti represents the mean tumor volume of a given treatment group on a certain day; T0 represents the mean tumor volume of this treatment group at the beginning of administration; Vi represents the mean tumor volume of the vehicle control group on a certain day (the same day as that in Ti); V0 represents the mean tumor volume of the vehicle control group at the beginning of administration. At the end of the test (d17), the animals were sacrificed, the tumors were stripped and weighed, and the tumor weight inhibitory rates were calculated.

$$\text{Tumor weight inhibitory rate (\%)} = (1 - \text{tumor weight in treatment group/tumor weight in vehicle control group}) \times 100.$$

7.4 the Efficacy Test Results of the Compounds of the Present Disclosure Combined with Irinotecan Liposome Injection on Inhibiting the Growth of Subcutaneous Xenograft Tumor of Human Colon Cancer Cell Line HT-29

| Group | Compound dose (mg/kg) | D 0 TV (MEAN ± SD, $mm^3$) | D 16 TV (MEAN ± SD, $mm^3$) | D 16 TGI % | Tumor weight (g) | Tumor weight inhibitory rate % |
|---|---|---|---|---|---|---|
| Vehicle control | 0 | 166.4 ± 59.3 | 916.5 ± 412.3 | — | 0.69 ± 0.29 | — |
| Vehicle control/Irinotecan | 0/10 | 166.6 ± 51.3 | 577.4 ± 225.3** | 45.2 | 0.45 ± 0.16** | 34.5 |
| A-6/Irinotecan | 25/10 | 166.9 ± 56.6 | 163.8 ± 62.8***### | 100.4 | 0.12 ± 0.03***### | 82.4 |
| A-46/Irinotecan | 25/10 | 166.2 ± 51.6 | 149.5 ± 67.4***### | 102.2 | 0.12 ± 0.06***### | 82.0 |
| AZD1390/Irinotecan | 25/10 | 166.0 ± 54.9 | 244.2 ± 192.8***### | 89.6 | 0.18 ± 0.18***### | 74.7 |

Compared with the vehicle control, P < 0.01, *P < 0.001; compared with irinotecan at a dose of 10 mpk, ###P < 0.001.

The efficacy test results of growth inhibition of HT-29 subcutaneous xenograft tumor show that the compounds of the present disclosure significantly inhibit the tumor growth, and the inhibitory effects of A-6 and A-46 on both tumor volume and tumor weight are higher than those of AZD1390.

8 Efficacy Test of the Compounds of the Present Disclosure Combined with Radiotherapy in the Intracranial Murine Glioma GL-261-Luc Model 8.1 Experimental Animals: C57BL/6 Mice, SPF, Female, 19 to 22 g.

8.2 Experimental Materials and Instruments

GL-261-Luc tumor cells, DMEM medium:fetal bovine serum=90%:10%, accompanied by adding 4 μM L-Glu, 37° C., 5% $CO_2$.

X-ray irradiator, model: RS2000 X-Ray, supplier: Rad-Source 8.3 Experimental Process (1) Construction of In-Situ Tumor Model Female C57BL/6 mice were anesthetized with Shutai 50 (60 mg/mL) and thiazine (1.5 mg/mL). Buprenorphine (0.1 mg/kg) was injected subcutaneously 30 min before operation and 6 h after operation to relieve pain. The operation area was disinfected with 70% ethanol solution. A sagittal incision was made on the parietal-occipital bone of anesthetized mice with a sterile scalpel, after cleaning the exposed skull surface with 3% hydrogen peroxide solution, tumor cells were injected. After injection, the skull was cleaned with 3% hydrogen peroxide solution, dried with a sterile dry cotton swab, and the incision was sutured. The state of mice was examined continuously to ensure that mice fully recovered from anesthesia.

(2) Bioluminescence Detection

The inoculated mice were weighed and intraperitoneally injected with fluorescein (150 mg/kg). After 10 min injection, the animals were anesthetized with a mixture of oxygen and isoflurane. When the animal was completely anesthetized, it was moved into the imaging room for bioluminescence detection. The bioluminescence signal of the whole animal was measured and recorded for the image.

(3) Grouping

Bioluminescence detection was performed on the second day after operation, and the tumor-bearing mice were randomly divided into groups according to the intensity of bioluminescence. The specific groups were as follows. The administration route was intragastric administration and then JR 1 h after administration.

| No. | Total number | Group | Irradiation dose (Gy) | Compound dose (mg/kg) | Dosing route | Period and frequency |
|---|---|---|---|---|---|---|
| 1 | 7 | Vehicle control | 0 | 0 | Intragastric administration | qd × 5 |
| 2 | 7 | Vehicle control/IR | 2 | 0 | Intragastric administration | qd × 5 |
| 3 | 7 | A-193/IR | 2 | 10 | Intragastric administration | qd × 5 |
| 4 | 7 | A-182/IR | 2 | 10 | Intragastric administration | qd × 5 |
| 5 | 7 | AZD1390/IR | 2 | 10 | Intragastric administration | qd × 5 |

(4) Evaluation Index

After grouping, bioluminescence detection was performed 1 to 2 times a week, according to the bioluminescence data, tumor growth inhibitory rate was calculated as follows: TGI (%)=[1−(Ti−T0)/(Vi−V0)]×100, wherein Ti represents the mean bioluminescence data of a given treatment group on a certain day; T0 represents the mean bioluminescence data of this treatment group at the beginning of administration; Vi represents the mean bioluminescence cence data of the vehicle control group on a certain day (the same day as that in Ti); V0 represents the mean bioluminescence data of the vehicle control group at the beginning of administration.

8.4 the Efficacy Test Results of the Compounds of the Present Disclosure Combined with Radiotherapy in the Intracranial Murine Glioma GL-261-Luc Mode

| Group | Irradiation dose (Gy) | Compound dose (mg/kg) | D 0 BLI (LOG10) | D17 BLI (LOG10) | D 17 TGI % |
|---|---|---|---|---|---|
| Vehicle control | 0 | 0 | 5.49 | 7.93 | — |
| Vehicle control/IR | 2 | 0 | 5.50 | 6.49*** | 59.18 |
| A-193/IR | 2 | 10 | 5.49 | 4.94*** | 122.49 |
| A-182/IR | 2 | 10 | 5.49 | 5.24*** | 110.08 |
| AZD1390/IR | 2 | 10 | 5.49 | 4.90*** | 124.08 |

Note:
Compared with vehicle control,
***P < 0.001.

The efficacy test results in the intracranial GL-261-Luc tumor model show that the compounds of the present disclosure significantly inhibit the tumor growth, and the anti-tumor activities of A-193 and A-182 are equivalent to that of AZD1390.

9 Efficacy Test of the Compounds of the Present Disclosure Combined with Radiotherapy on Inhibiting the Growth of Subcutaneous Xenograft Tumor of Human Glioblastoma LN-18

9.1 Experimental Animals: NOG Mice, SPF, Female, 18 to 22 g.

9.2 Experimental Materials and Instruments

LN-18 tumor cells, DMEM medium:fetal bovine serum=95%:5%, accompanied by adding 100 U/mL penicillin and 100 μg/mL streptomycin, 37° C., 5% $CO_2$.

X-ray irradiator, model: X-RAD 225, supplier: PRECISION.

9.3 Experimental Process (1) Inoculation of Tumor Cells and Grouping

LN18 tumor cells resuspended in serum-free DMEM medium were inoculated subcutaneously in the right costal region of experimental animals at $1.5*10^7$/0.15 mL, and the animals were grouped when the tumor grew to 100 to 150 $mm^3$. The specific administration regimen is shown in table below. Radiotherapy was performed 1 h after administration of compounds.

| No. | Total number | Group | Irradiation dose (Gy) | Compound dose (mg/kg) | Dosing route | Period and frequency |
|---|---|---|---|---|---|---|
| 1 | 6 | Vehicle control | 0 | 0 | Intragastric administration | qd × 5 |
| 2 | 6 | Vehicle control/IR | 1 | 0 | Intragastric administration | qd × 5 |
| 3 | 6 | A-177/IR | 1 | 5 | Intragastric administration | qd × 5 |
| 4 | 6 | A-198/IR | 1 | 5 | Intragastric administration | qd × 5 |
| 5 | 6 | A-193/IR | 1 | 10 | Intragastric administration | qd × 5 |
| 6 | 6 | A-68/IR | 1 | 5 | Intragastric administration | qd × 5 |
| 7 | 6 | A-182/IR | 1 | 20 | Intragastric administration | qd × 5 |
| 8 | 6 | A-203/IR | 1 | 5 | Intragastric administration | qd × 5 |
| 9 | 6 | A-183/IR | 1 | 5 | Intragastric administration | qd × 5 |
| 10 | 6 | A-191/IR | 1 | 10 | Intragastric administration | qd × 5 |
| 11 | 6 | A-192/IR | 1 | 20 | Intragastric administration | qd × 5 |
| 12 | 6 | AZD1390/IR | 1 | 10 | Intragastric administration | qd × 5 |

(2) Detection Index

Tumor volume: The tumor volume was measured twice a week with a vernier caliper, and the long diameter and short diameter of tumor were measured. The tumor volume was calculated as follows: tumor volume (TV)=0.5×long diameter×short diameter$^2$. Tumor growth inhibitory rate (TGI %) was calculated according to the tumor volume. $TV_{Xn}$ represents the mean tumor volume on day n of the treatment group, $TV_{X0}$ represents the mean tumor volume on day 0 of the treatment group, $TV_{Mn}$ represents the mean tumor volume on day n of the control group, and $TV_{M0}$ represents the mean tumor volume on day 0 of the control group.

$$TGI = \left[1 - \frac{(TV_{Xn} - TV_{X0})}{(TV_{Mn} - TV_{M0})}\right] \times 100\%$$

Response of animals after administration: the mice were weighed while the tumor volume was measured. The relationship between body weight change of a mouse and administration time was recorded. At the same time, the survival and health status of mice were observed, such as animal activities, feeding and other general states during the administration.

9.4 the Efficacy Test Results of the Compounds of the Present Disclosure Combined with Radiotherapy on Inhibiting the Growth of Subcutaneous Xenograft Tumor of Human Glioblastoma LN-18

| Group | Irradiation dose (Gy) | Compound dose (mg/kg) | D 0 TV (MEAN ± SD, $mm^3$) | D 17 TV (MEAN ± SD, $mm^3$) | D 17 TGI (%) |
|---|---|---|---|---|---|
| Vehicle control | 0 | 0 | 141 ± 11 | 1029 ± 83 | — |
| Vehicle control/IR | 1 | 0 | 142 ± 7 | 574 ± 110*** | 51.4 |
| A-177/IR | 1 | 5 | 142 ± 8 | 338 ± 67*** | 77.9 |
| A-198/IR | 1 | 5 | 142 ± 11 | 326 ± 77***# | 79.3 |
| A-193/IR | 1 | 10 | 142 ± 6 | 310 ± 61***# | 81.1 |
| A-68/IR | 1 | 5 | 142 ± 7 | 285 ± 61***# | 83.9 |
| A-182/IR | 1 | 20 | 142 ± 7 | 271 ± 107***# | 85.5 |
| A-203/IR | 1 | 5 | 142 ± 10 | 396 ± 121*** | 71.4 |
| A-183/IR | 1 | 5 | 142 ± 7 | 269 ± 89***# | 85.7 |
| A-191/IR | 1 | 10 | 142 ± 8 | 347 ± 64*** | 76.9 |
| A-192/IR | 1 | 20 | 142 ± 6 | 323 ± 114***# | 79.6 |
| AZD1390/IR | 1 | 10 | 141 ± 10 | 294 ± 52***# | 82.8 |

Compared with vehicle control,
***P < 0.001;
compared with vehicle control/IR,
#P < 0.05.

The results of efficacy test of growth inhibition of LN-18 subcutaneous xenograft tumor show that the compounds of the present disclosure significantly inhibit the growth in tumor volume, compared with the vehicle control group.

What is claimed is:

1. A compound as represented by formula (I') or a tautomer, optical isomer, geometric isomer, solvate, isotopic derivative, or pharmaceutically acceptable salt thereof, having the following structure:

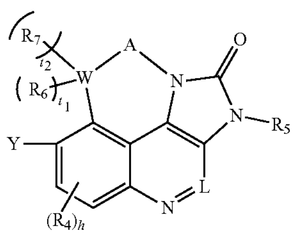

(I')

wherein

Y is

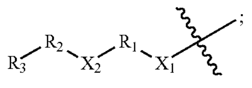

;

$X_1$ is selected from the group consisting of a bond, hydrogen, and halogen;

when $X_1$ is hydrogen or halogen, $R_1$, $X_2$, $R_2$, and $R_3$ are absent;

$R_1$ is absent or an optionally substituted group selected from $C_{2-6}$ alkynyl, 5- to 8-membered heterocyclyl, phenyl, and 5- to 6-membered heteroaryl, wherein the heterocyclyl and heteroaryl represented by $R_1$ contain 1 or 2 heteroatoms selected from N; said optionally substituted means that hydrogen on a group to be substituted is not substituted or hydrogen on one or more substitution sites of a group to be substituted is independently substituted by $R_{1a}$, $R_{1a}$ is, for each presence, independently selected from the group consisting of deuterium, halogen, hydroxyl, amino, oxo, —$R_{1b}$, —C(O)N($R_{1b}$)($R_{1c}$), —N($R_{1b}$)C(O)($R_{1c}$), —S(O)N($R_{1b}$)($R_{1c}$), —$SO_2$N($R_{1b}$)($R_{1c}$), —N($R_{1b}$)S(O)($R_{1c}$), and —N($R_{1b}$)$SO_2$($R_{1c}$);

$R_{1b}$ and $R_{1c}$ are, for each presence, independently selected from the group consisting of hydrogen, and any one of $C_{1-6}$ alkyl, $C_{3-6}$ cycloalkyl, 3- to 8-membered heterocycloalkyl, and phenyl;

$X_2$ is absent or selected from the group consisting of a bond, hydrogen, deuterium, halogen, —O—, and —N($R_{2x}$)—;

$R_{2x}$ is selected from the group consisting of hydrogen and $C_{1-6}$ alkyl;

when $X_2$ is hydrogen or halogen, $R_2$ and $R_3$ are absent;

$R_2$ is absent or selected from the group consisting of $C_{1-6}$ alkyl, $C_{1-6}$ alkoxy, $C_{2-4}$ alkynyl, 5- to 6-membered heterocycloalkyl, wherein the heterocycloalkyl represented by $R_2$ contains 1 or 2 heteroatoms independently selected from N or O;

$R_3$ is absent or selected from the group consisting of —$R_{3b}$, —$OR_{3b}$, and —N($R_{3b}$)($R_{3c}$);

$R_{3b}$ and $R_{3c}$ are, for each presence, independently an optionally substituted $C_{1-6}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 3- to 10-membered heterocycloalkyl and 4- to 12-membered bicyclic heterocyclyl; said optionally substituted means that hydrogen on a group to be substituted is not substituted or hydrogen on one or more substitution sites of a group to be substituted is independently substituted by $R_{3d}$;

$R_{3d}$ is, for each presence, independently selected from the group consisting of deuterium, halogen, hydroxyl, amino, cyano, —$R_{3e}$, —C(O)$R_{3e}$, —C(O)$OR_{3e}$, —N($R_{3e}$)($R_{3f}$), and —C(O)NH($R_{3e}$);

$R_{3e}$ and $R_{3f}$ are, for each presence, independently selected from the group consisting of hydrogen and any one of $C_{1-6}$ alkyl, $C_{1-6}$ alkoxy, $C_{3-6}$ cycloalkyl, 3- to 6-membered heterocycloalkyl, phenyl, and 5- to 6-membered heteroaryl; which is optionally substituted by one or more of halogen, hydroxyl, amino, $C_{1-6}$ alkyl, $C_{3-6}$ cycloalkyl, 3- to 6-membered heterocycloalkyl, phenyl and 5- to 6-membered heteroaryl;

$R_4$ is, for each presence, independently selected from the group consisting of hydrogen, deuterium, halogen, nitro, amino, cyano, hydroxyl, and any one of $C_{1-6}$ alkyl and $C_{1-6}$ alkoxy which is optionally substituted by one or more of deuterium, halogen, hydroxyl, and amino;

h is equal to 1;

$R_5$ is, for each presence, independently selected from the group consisting of hydrogen and $C_{1-6}$ alkyl;

L is CH or N;

A is

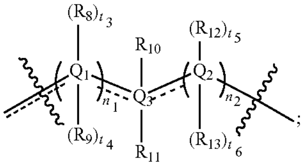

;

wherein ═ represents a single bond or a double bond; $Q_1$ is linked to W;

$t_1$, $t_2$, $t_3$, $t_4$, $t_5$, and $t_6$ are independently equal to 0 or 1;

$n_1$ and $n_2$ are independently equal to 0 or 1; and $n_1$ and $n_2$ are not simultaneously equal to 0;

W is selected from the group consisting of C, O, N, and S;

$Q_1$ is C;

$Q_2$ is C;

$Q_3$ is C; when one of the bonds linked to $Q_3$ is a double bond, $R_{10}$ or $R_{11}$ is absent;

$R_6$, $R_7$, $R_8$, $R_9$, $R_{10}$, $R_{11}$, $R_{12}$, and $R_{13}$ are, for each presence, independently selected from the group consisting of hydrogen, deuterium, halogen, hydroxyl, amino, —$R_{6a}$, and —$N(R_{6a})(R_{6b})$; or any two substituents linked to the same atom among $R_6$, $R_7$, $R_8$, $R_9$, $R_{10}$, $R_{11}$, $R_{12}$, and $R_{13}$ form ═O, ═N—$R_{6a}$, or ═CH—$R_{6a}$; or any two adjacent atoms among W, each present $Q_1$, each present $Q_2$, and $Q_3$, together with the substituents linked thereto, form $C_{3-10}$ carbocyclyl, 3- to 10-membered heterocyclyl, $C_{6-14}$ aryl, or 5- to 12-membered heteroaryl which is optionally substituted by $R_{6e}$, or any one atom among W, each present $Q_1$, each present $Q_2$, and $Q_3$, together with the substituents linked thereto, forms $C_{3-10}$ carbocyclyl or 3- to 10-membered heterocyclyl which is optionally substituted by $R_{6c}$, $R_{6a}$ and $R_{6b}$ are, for each presence, independently selected from the group consisting of hydrogen, deuterium, and any one of $C_{1-6}$ alkyl, $C_{1-6}$ alkoxy, $C_{3-10}$ carbocyclyl, 3- to 10-membered heterocyclyl, $C_{6-14}$ aryl, and 5- to 12-membered heteroaryl, which is optionally substituted by $R_{6c}$; or when $R_{6a}$ and $R_{6b}$ are linked to the same nitrogen atom, $R_{6a}$ and $R_{6b}$, together with the nitrogen atom linked thereto, form 3- to 10-membered heterocyclyl or 5- to 12-membered heteroaryl which is optionally substituted by $R_{6c}$;

$R_{6c}$ is, for each presence, independently selected from the group consisting of hydrogen, deuterium, halogen, hydroxyl, amino, —$R_{6d}$, —$OR_{6d}$, —$N(R_{6d})R_{6e}$, —$C(O)R_{6d}$, —$C(O)N(R_{6d})R_{6e}$, —$N(R_{6d})C(O)R_{6e}$, and —$C(O)OR_{6d}$; said oxo means that two hydrogens on the same substitution site are replaced by the same oxygen to form a double bond; said ═N—$R_{6d}$ means that two hydrogens on the same substitution site are replaced by the same nitrogen to form a double bond, and said nitrogen is substituted by $R_{6d}$; said ═CH—$R_{6d}$ means that two hydrogens on the same substitution site are replaced by the same carbon to form a double bond, and said carbon is substituted by $R_{6d}$;

$R_{6d}$ and $R_{6e}$ are, for each presence, independently selected from the group consisting of hydrogen, $C_{1-6}$ alkyl, $C_{1-6}$ alkoxy, $C_{3-10}$ carbocyclyl, 3- to 10-membered heterocycloalkyl, $C_{6-14}$ aryl, and 5- to 12-membered heteroaryl;

when the heterocycloalkyl, heteroaryl, and/or heterocyclyl, is present, the heteroatom thereof is independently selected from the group consisting of O, N, and S, and the number of the heteroatom is 1, 2, 3, or 4.

2. The compound or the tautomer, optical isomer, geometric isomer, solvate, isotopic derivative, or pharmaceutically acceptable salt thereof according to claim 1, wherein the compound has a structure as represented by formula (I-a):

(I-a)

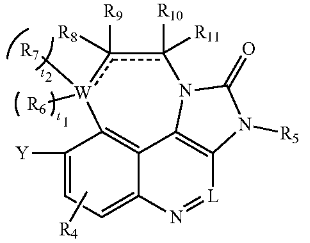

wherein each substituent is as defined in claim 1; or the compound has a structure as represented by formula (I-b) or (I-c):

(I-b)

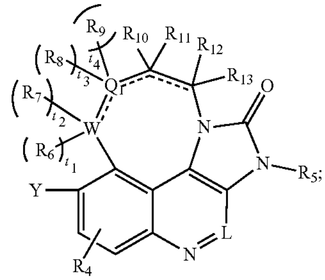

;

(I-c)

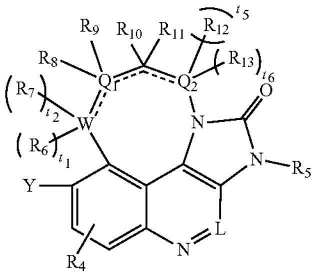

wherein each substituent is as defined in claim 1.

3. The compound or the tautomer, optical isomer, geometric isomer, solvate, isotopic derivative, or pharmaceutically acceptable salt thereof according to claim 1, wherein $X_1$ is a bond.

4. The compound or the tautomer, optical isomer, geometric isomer, solvate, isotopic derivative, or pharmaceutically acceptable salt thereof according to claim 1, wherein $R_1$ is selected from the group consisting of an optionally substituted group selected from ethynyl, phenyl, pyridinyl, pyrimidinyl, pyrazinyl, pyrazolyl, imidazolyl, and pyrrolyl; said optionally substituted represents being optionally substituted by $R_{1a}$; or $R_1$ is an optionally substituted pyridinyl; said optionally substituted represents being optionally substituted by $R_{1a}$; or $R_1$ is an optionally substituted dihydropyridinyl; said optionally substituted represents being optionally substituted by $R_{1a}$, or $R_1$ is selected from the group consisting of the following optionally substituted groups:

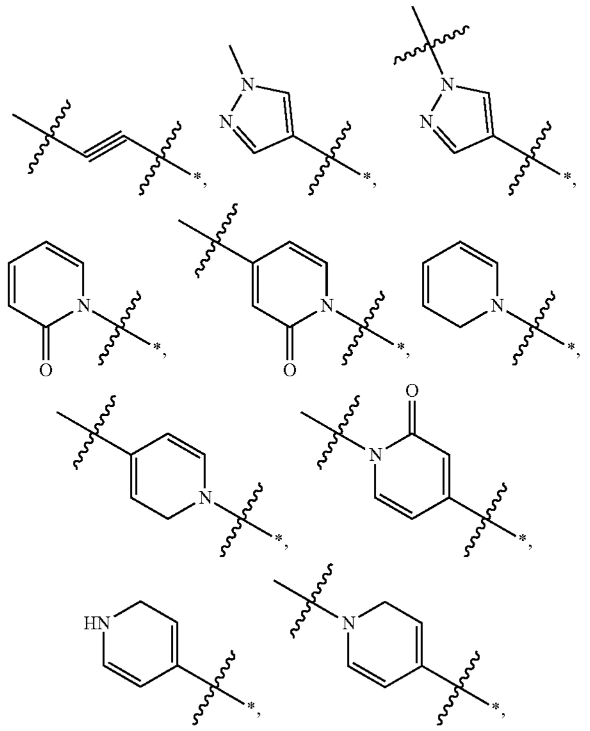

-continued

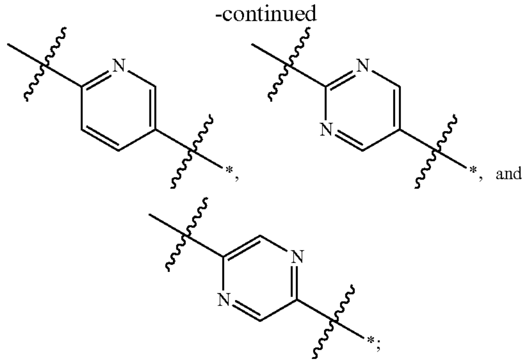

wherein the end with an asterisk "*" is the one linked to $X_1$, and the other end is the one linked to $X_2$; said optionally substituted represents being optionally substituted by $R_{1a}$; or $R_1$ is an optionally substituted

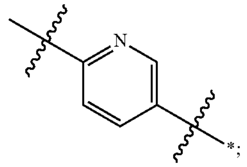

wherein the end with an asterisk "*" is the one linked to $X_1$, and the other end is the one linked to $X_2$; said optionally substituted represents being optionally substituted by $R_{1a}$; or $R_1$ is selected from the group consisting of the following groups:

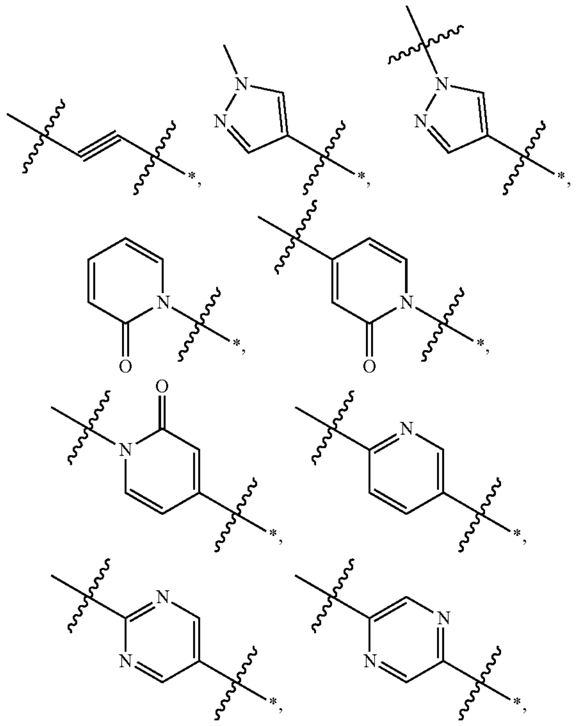

-continued

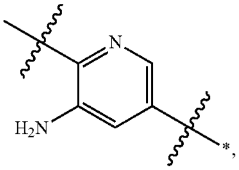,

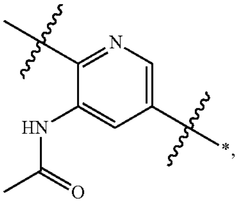,

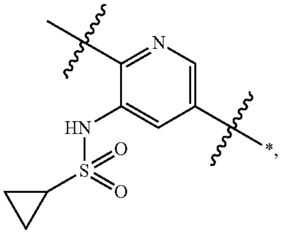,

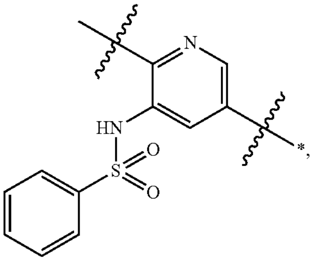,

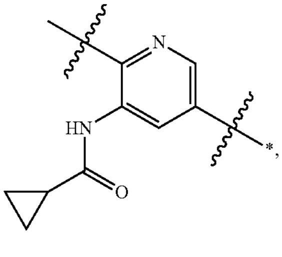,

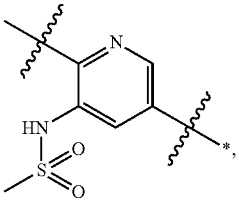,

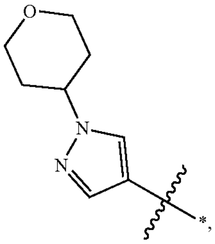, and

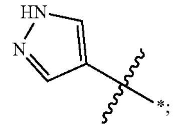;

wherein the end with an asterisk "*" is the one linked to $X_1$, and the other end is the one linked to $X_2$.

5. The compound or the tautomer, optical isomer, geometric isomer, solvate, isotopic derivative, or pharmaceutically acceptable salt thereof according to claim 1, wherein $R_{1a}$ is, for each presence, independently selected from the group consisting of halogen, amino, oxo, —$R_{1b}$, —NHC(O)($R_{1c}$), and —$NHSO_2$($R_{1c}$); or $R_{1a}$ is, for each presence, independently selected from the group consisting of —NHC(O)($R_{1c}$) and —$NHSO_2$($R_{1c}$); or $R_{1a}$ is independently selected from the group consisting of —F, —Cl, —$NH_2$, oxo, —$CH_3$, —$CH_2CH_3$, —NHC(O)$CH_3$, —C(O)$NHCH_3$,

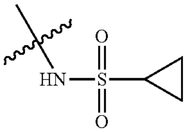,

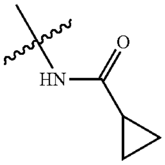,

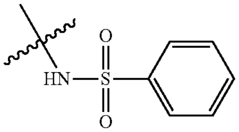, and

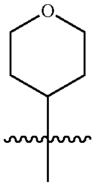.

6. The compound or the tautomer, optical isomer, geometric isomer, solvate, isotopic derivative, or pharmaceutically acceptable salt thereof according to claim 1, wherein $R_{1b}$ and $R_{1c}$ are, for each presence, independently selected from the group consisting of $C_{1-6}$ alkyl and $C_{3-6}$ cycloalkyl; or $R_{1b}$ and $R_{1c}$ are, for each presence, independently selected from the group consisting of $C_{1-4}$ alkyl and $C_{3-4}$ cycloalkyl; or $R_{1b}$ and $R_{1c}$ are, for each presence, independently selected from the group consisting of methyl, ethyl, cyclopropyl, phenyl, and tetrahydropyranyl; or $R_{1b}$ and $R_{1c}$ are, for each presence, independently selected from the group consisting of methyl and cyclopropyl.

7. The compound or the tautomer, optical isomer, geometric isomer, solvate, isotopic derivative, or pharmaceutically acceptable salt thereof according to claim 1, wherein $X_2$ is absent or selected from the group consisting of a bond, hydrogen, halogen, —O—, —NH—, —N($CH_3$)—, and —N($CH_2CH_3$)—; or $X_2$ is absent or selected from the group consisting of a bond, —O—, and —N($CH_3$)—.

8. The compound or the tautomer, optical isomer, geometric isomer, solvate, isotopic derivative, or pharmaceutically acceptable salt thereof according to claim 1, wherein $R_2$ is absent or selected from the group consisting of methyl, ethyl, propyl, butyl, ethynyl, piperidinyl, tetrahydropyrrolyl, and tetrahydropyranyl; or $R_2$ is n-propyl.

9. The compound or the tautomer, optical isomer, geometric isomer, solvate, isotopic derivative, or pharmaceutically acceptable salt thereof according to claim 1, wherein $R_3$ is absent; or $R_3$ is —N($R_{3b}$)($R_{3c}$); or $R_3$ is selected from the group consisting of the following optionally substituted groups:

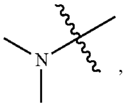,

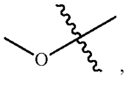,

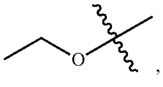,

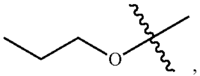,

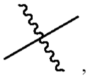,

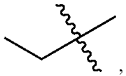,

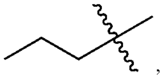,

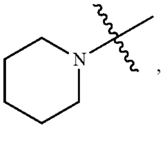,

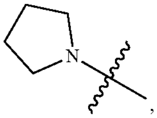,

-continued
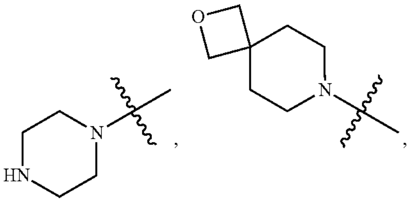
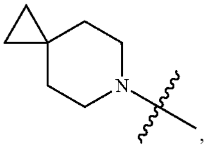, and 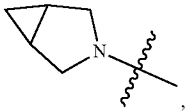,
said optionally substituted represents being optionally substituted by $R_{3d}$; or
$R_3$ is selected from the group consisting of the following groups:
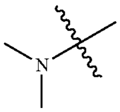, 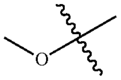, 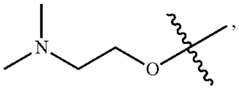,
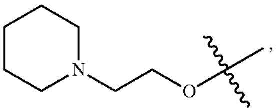,
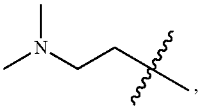, 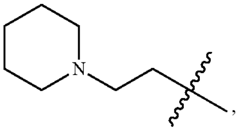,
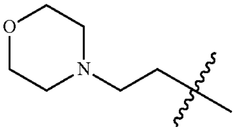, 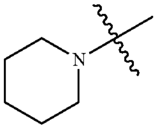,
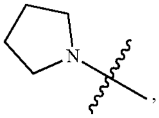, 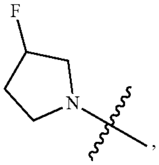, 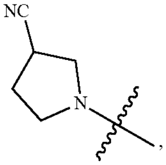,
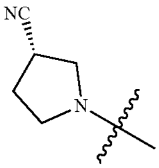, 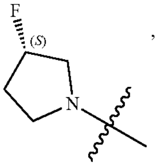, 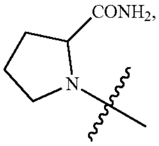
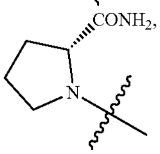 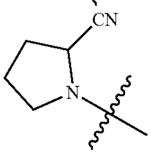, 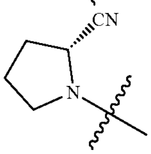,
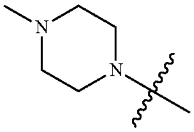, 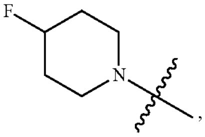,
-continued
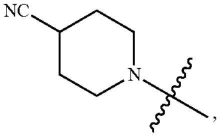, 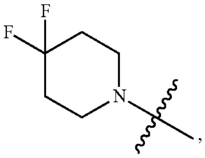,
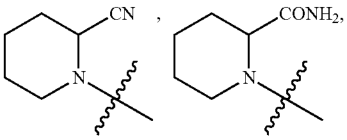
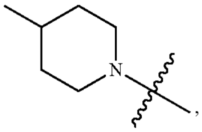, 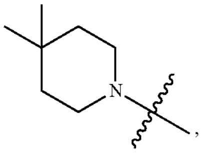,
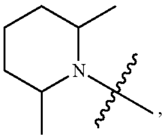, 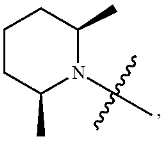, 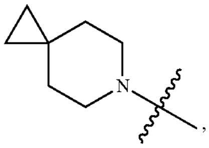,
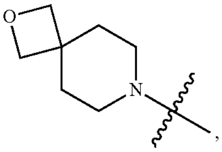, 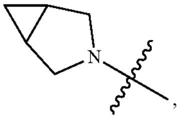,
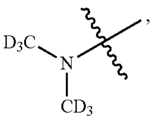, 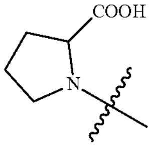,
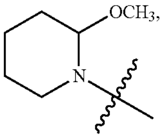 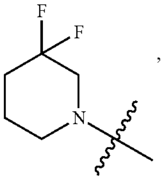,
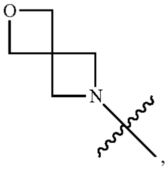, and 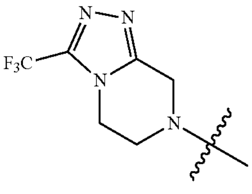;
or
$R_3$ is selected from the group consisting of the following groups:
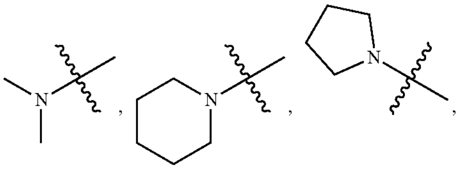

-continued

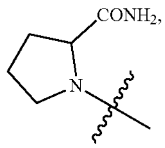, 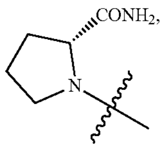, 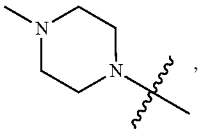,

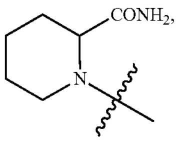, 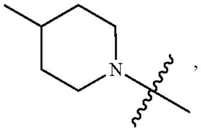,

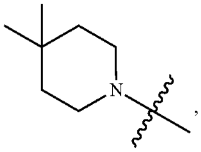, 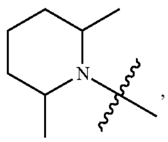, 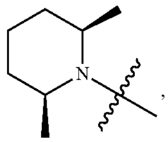,

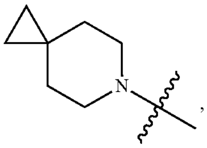, 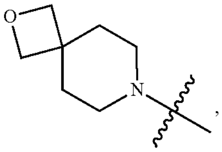,

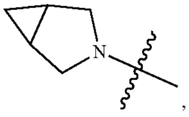, and 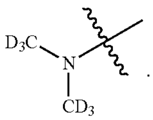.

10. The compound or the tautomer, optical isomer, geometric isomer, solvate, isotopic derivative, or pharmaceutically acceptable salt thereof according to claim 1, wherein $R_{3b}$ and $R_{3c}$ are, for each presence, independently an optionally substituted $C_{1-6}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 4- to 8-membered heterocycloalkyl and 6- to 10-membered bicyclic heterocyclyl; the optionally substituted represents being optionally substituted by $R_{3d}$; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl and 6- to 10-membered bicyclic heterocyclyl, the heteroatom thereof is independently selected from the group consisting of O and N, and the number of the heteroatom is 1, 2, 3, or 4; said optionally substituted represents being optionally substituted by $R_{3d}$; or $R_{3b}$ and $R_{3c}$ are, for each presence, independently an optionally substituted $C_{1-4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl, 3-/4-membered heteromonospiro ring group, 4-/3-membered heteromonospiro ring group, 3-/5-membered heteromonospiro ring group, 5-/3-membered heteromonospiro ring group, 3-/6-membered heteromonospiro ring group, 6-/3-membered heteromonospiro ring group, 4-/5-membered heteromonospiro ring group, 5-/4-membered heteromonospiro ring group, 4-/6-membered heteromonospiro ring group, 6-/4-membered heteromonospiro ring group, 4-/4-membered heteromonospiro ring group, 5-/5-membered heteromonospiro ring group, 5-/6-membered heteromonospiro ring group, 6-/5-membered heteromonospiro ring group, 3-/5-membered fused heterocyclyl, 5-/3-membered fused heterocyclyl, 3-/6-membered fused heterocyclyl, 6-/3-membered fused heterocyclyl, 5-/6-membered fused heterocyclyl, and 6-/5-membered fused heterocyclyl, the heteroatom thereof is independently selected from the group consisting of O and N, and the number of the heteroatom is 1, 2, 3, or 4; the optionally substituted represents being optionally substituted by $R_{3d}$; or $R_{3b}$ and $R_{3c}$ are, for each presence, independently an optionally substituted $C_{1-4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl, 3-/6-membered heteromonospiro ring group, 6-/3-membered heteromonospiro ring group, 4-/6-membered heteromonospiro ring group, 6-/4-membered heteromonospiro ring group, and 4-/4-membered heteromonospiro ring group, the heteroatom thereof is independently selected from the group consisting of O and N, and the number of the heteroatom is 1 or 2; said optionally substituted represents being optionally substituted by $R_{3d}$; or $R_{3b}$ and $R_{3c}$ are, for each presence, independently an optionally substituted $C_{1-4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl and 6- to 10-membered bicyclic heterocyclyl, the heteroatom thereof is independently selected from the group consisting of O and N, and the number of the heteroatom is 1, 2, or 3; said optionally substituted represents being optionally substituted by $R_{3d}$; or $R_{3b}$ and $R_{3c}$ are, for each presence, independently an optionally substituted $C_{1-4}$ alkyl; or when $R_{3b}$ and $R_{3c}$ are linked to the same nitrogen atom, $R_{3b}$ and $R_{3c}$, together with the nitrogen atom linked thereto, form an optionally substituted group selected from 5- to 6-membered heterocycloalkyl, 3-/6-membered heteromonospiro ring group, 4-/6-membered heteromonospiro ring group, and 3-/5-membered fused heterocyclyl, the heteroatom thereof is independently selected from the group consisting of O and N, and the number of the heteroatom is 1, 2, or 3; said optionally substituted represents being optionally substituted by $R_{3d}$; or $R_{3b}$ and $R_{3c}$ are, for each presence, independently an optionally substituted methyl; or when $R_{3b}$ and $R_{3c}$ are linked to the same nitrogen atom, $R_{3b}$ and $R_{3c}$, together with the nitrogen atom linked thereto, form an optionally substituted group selected from pyrrolidinyl, piperazinyl, piperidinyl, 2-oxa-7-azaspiro[3.5]nonanyl, 3-azabicyclo[3.1.0]hexanyl, and 6-azaspiro[2.5]octanyl; said optionally substituted represents being optionally substituted by $R_{3d}$; or a group formed by $R_{3b}$ and $R_{3c}$ together with the nitrogen atom linked thereto is selected from the group consisting of the following groups:

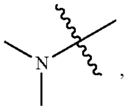, 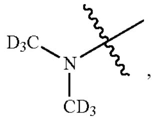, 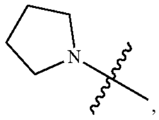, 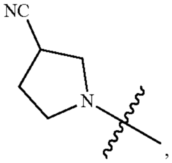, 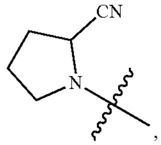, 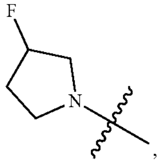, 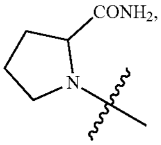 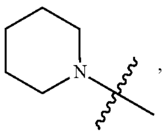, 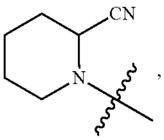, 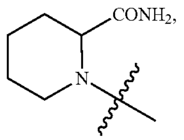 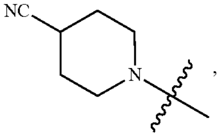, 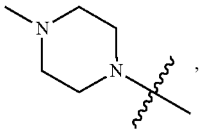, 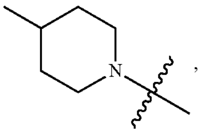, 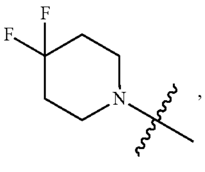, 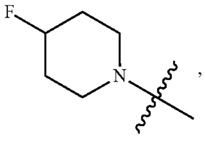, 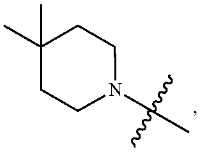, 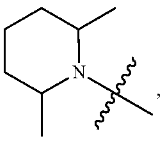, 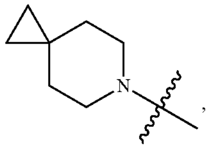, 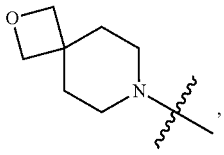, and 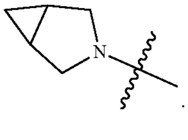.

11. The compound or the tautomer, optical isomer, geometric isomer, solvate, isotopic derivative, or pharmaceutically acceptable salt thereof according to claim 1, wherein $R_{3d}$ is, for each presence, independently selected from the group consisting of deuterium, halogen, hydroxyl, amino, cyano, —CHO, —CO($C_{1-6}$ alkyl), —COOH, —COO($C_{1-6}$ alkyl), —NH($C_{1-6}$ alkyl), —N($C_{1-6}$ alkyl)($C_{1-6}$ alkyl), —C(O)$NH_2$, $C_{1-6}$ alkyl, $C_{1-6}$ alkoxy, and 3- to 6-membered heterocycloalkyl; or $R_{3d}$ is, for each presence, independently selected from the group consisting of deuterium, hydroxyl, amino, —CHO, —CO($C_{1-6}$ alkyl), —COOH, —COO($C_{1-6}$ alkyl), —NH($C_{1-6}$ alkyl), —N($C_{1-6}$ alkyl)($C_{1-6}$ alkyl), —C(O)$NH_2$, $C_{1-6}$ alkyl, $C_{1-6}$ alkoxy, and 5- to 6-membered heterocycloalkyl; or $R_{3d}$ is, for each presence, independently selected from the group consisting of deuterium, fluorine, hydroxyl, amino, cyano, —CHO, —$COCH_3$, —COOH, —$COOCH_3$, —NH($CH_3$), —N($CH_3$)($CH_3$), —C(O)$NH_2$, —$CH_3$, —$CH_2CH_3$, —$CH_2CH_2CH_3$, —$OCH_3$, —$OCH_2CH_3$, —$OCH_2CH_2CH_3$, piperidinyl, piperazinyl, and tetrahydropyrrolyl; or $R_{3d}$ is, for each presence, independently selected from the group consisting of deuterium, fluorine, amino, cyano, —C(O)$NH_2$, —$CH_3$, and piperidinyl; or $R_{3d}$ is selected from the group consisting of methyl, —N(methyl)(methyl), and piperidinyl; or $R_{3d}$ is, for each presence, independently selected from the group consisting of deuterium, fluorine, hydroxyl, amino, cyano, —NH($CH_3$), —N($CH_3$)($CH_3$), —C(O)$NH_2$, —$CH_3$, —$CH_2CH_3$, and —$CH_2CH_2CH_3$; or $R_{3d}$ is, for each presence, independently selected from the group consisting of deuterium, fluorine, cyano, —C(O)$NH_2$, and —$CH_3$.

12. The compound or the tautomer, optical isomer, geometric isomer, solvate, isotopic derivative, or pharmaceutically acceptable salt thereof according to claim 1, wherein the compound has a structure as represented by formula (II-a);

(II-a)

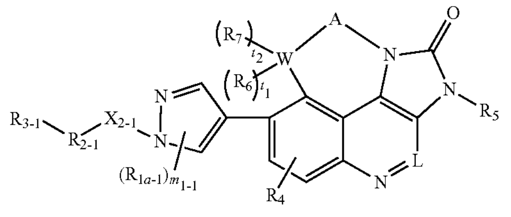

wherein $m_{1-1}$ is selected from the group consisting of 0, 1, and 2, $R_{1a-1}$ is as defined by $R_{1a}$ in claim 1, $X_{2-1}$ is as defined by $X_2$ in claim 1, $R_{2-1}$ is as defined by $R_2$ in claim 1, $R_{3-1}$ is as defined by $R_3$ in claim 1, and $R_4$, $R_5$, $R_6$, $R_7$, A, W, L, $t_1$, and $t_2$ are as defined in claim 1; or the compound has a structure as represented by formula (II-b):

(II-b)

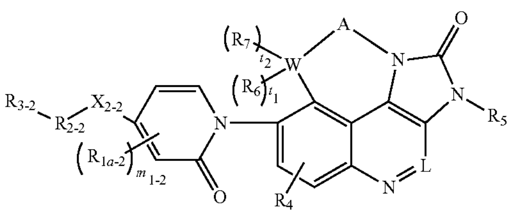

wherein $m_{1-2}$ is selected from the group consisting of 0, 1, 2, and 3, $R_{1a-2}$ is as defined by $R_{1a}$ in claim 1, $X_{2-2}$ is as defined by $X_2$ in claim 1, $R_{2-2}$ is as defined by $R_2$ in claim 1, $R_{3-2}$ is as defined by $R_3$ in claim 1, and $R_4$, $R_5$, $R_6$, $R_7$, A, W, L, $t_1$, and $t_2$ are as defined in claim 1; or the compound has a structure as represented by formula (II-c):

(II-c)

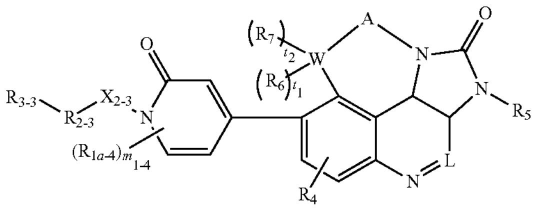

wherein $m_{1-4}$ is selected from the group consisting of 0, 1, 2, and 3, $R_{1a-4}$ is as defined by $R_{1a}$ in claim 1, $X_{2-3}$ is as defined by $X_2$ in claim 1, $R_{2-3}$ is as defined by $R_2$ in claim 1, $R_{3-3}$ is as defined by $R_3$ in claim 1, and $R_4$, $R_5$, $R_6$, $R_7$, A, W, L, $t_1$, and $t_2$ are as defined in claim 1; or the compound has a structure as represented by formula (II-d):

(II-d)

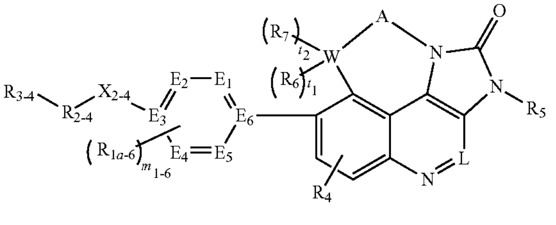

wherein $E_1$, $E_2$, $E_3$, $E_4$, $E_5$, and $E_6$ are independently selected from the group consisting of C and N, $m_{1-6}$ is selected from the group consisting of 0, 1, 2, 3, and 4, $R_{1a-6}$ is as defined by $R_{1a}$ in claim 1, $X_{2-4}$ is as defined by $X_2$ in claim 1, $R_{2-4}$ is as defined by $R_2$ in claim 1, $R_{3-4}$ is as defined by $R_3$ in claim 1, and $R_4$, $R_5$, $R_6$, $R_7$, A, W, L, $t_1$, and $t_2$ are as defined in claim 1; or the compound has a structure as represented by formula (II-e):

(II-e)

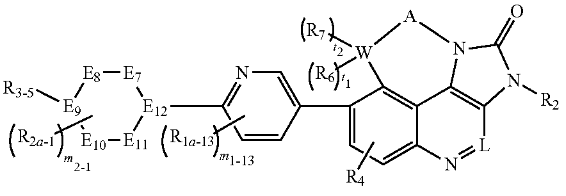

wherein $E_7$, $E_8$, $E_9$, $E_{10}$, $E_{11}$, and $E_{12}$ are independently selected from the group consisting of C and N, $m_{1-13}$ is selected from the group consisting of 0, 1, 2, and 3, $m_{2-1}$ is 0, $R_{1a-13}$ is as defined by $R_{1a}$ in claim 1, $R_{3-5}$ is as defined by $R_3$ in claim 1, and $R_4$, $R_5$, $R_6$, $R_7$, A, W, L, $t_1$, and $t_2$ are as defined in claim 1; or the compound has a structure as represented by formula (II-f):

(II-f)

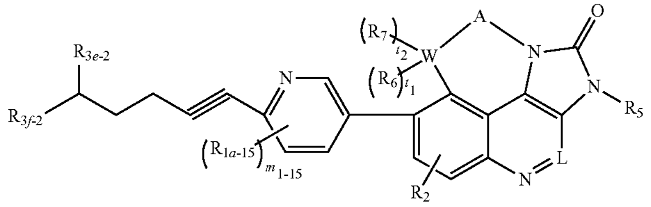

wherein $m_{1-15}$ is selected from the group consisting of 0, 1, 2, and 3, $R_{1a-15}$ is as defined by $R_{1a}$ in claim 1, $R_{3e-2}$ is as defined by $R_{3e}$ in claim 1, $R_{3f-2}$ is as defined by $R_{3f}$ in claim 1, and $R_4$, $R_5$, $R_6$, $R_7$, A, W, L, $t_1$, and $t_2$ are as defined in claim 1; or the compound has a structure as represented by formula (II-g):

(II-g)

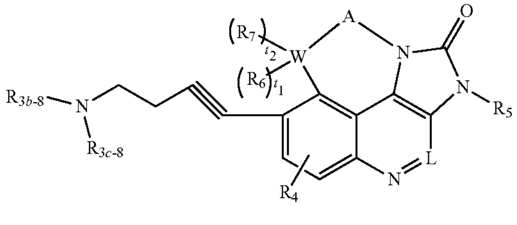

wherein $R_{3b\text{-}8}$ is as defined by $R_{3b}$ in claim 1, $R_{3c\text{-}8}$ is as defined by $R_{3c}$ in claim 1, and $R_4$, $R_5$, $R_6$, $R_7$, A, W, L, $t_1$, and $t_2$ are as defined in claim 1.

13. The compound or the tautomer, optical isomer, geometric isomer, solvate, isotopic derivative, or pharmaceutically acceptable salt thereof according to claim 12, wherein the compound has a structure as represented by formula (II-$a_1$):

(II-$a_1$)

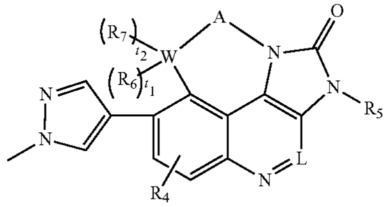

wherein $R_4$, $R_5$, $R_6$, $R_7$, A, W, L, $t_1$, and $t_2$ are as defined in claim 1; or the compound has a structure as represented by formula (II-$a_2$):

(II-$a_2$)

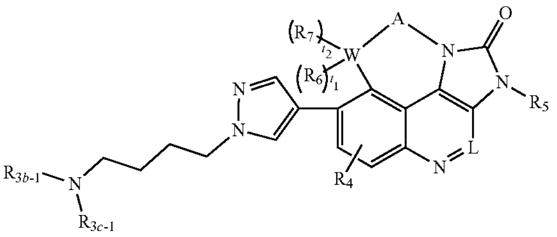

wherein $R_{3b\text{-}1}$ is as defined by $R_{3b}$ in claim 1, $R_{3c\text{-}1}$ is as defined by $R_{3c}$ in claim 1, and $R_4$, $R_5$, $R_6$, $R_7$, A, W, L, $t_1$, and $t_2$ are as defined in claim 1; or the compound has a structure as represented by formula (II-$b_1$):

(II-$b_1$)

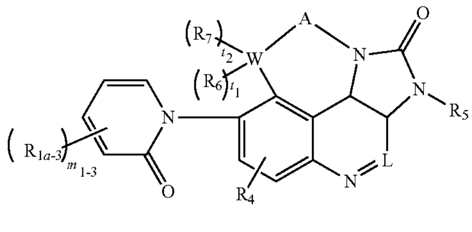

wherein $m_{1\text{-}3}$ is selected from the group consisting of 0, 1, 2, and 3, $R_{1a\text{-}3}$ is as defined by $R_{1a}$ in claim 1, and $R_4$, $R_5$, $R_6$, $R_7$, A, W, L, $t_1$, and $t_2$ are as defined in claim 1; or the compound has a structure as represented by formula (II-$c_1$):

(II-$c_1$)

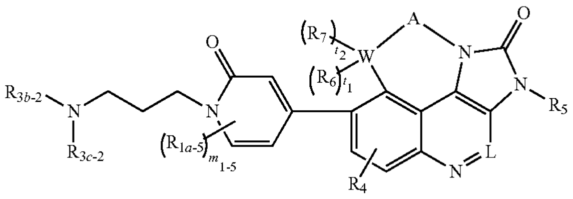

wherein $m_{1\text{-}5}$ is selected from the group consisting of 0, 1, 2, and 3, $R_{1a\text{-}5}$ is as defined by $R_{1a}$ in claim 1, $R_{3b\text{-}2}$ is as defined by $R_{3b}$ in claim 1, $R_{3c\text{-}2}$ is as defined by $R_{3c}$ in claim 1, and $R_4$, $R_5$, $R_6$, $R_7$, A, W, L, $t_1$, and $t_2$ are as defined in claim 1; or the compound has a structure as represented by formula (II-$d_1$):

(II-$d_1$)

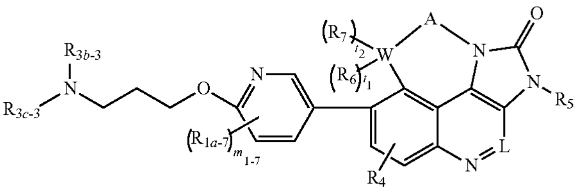

wherein $m_{1\text{-}7}$ is selected from the group consisting of 0, 1, 2, and 3, $R_{1a\text{-}7}$ is as defined by $R_{1a}$ in claim 1, $R_{3b\text{-}3}$ is as defined by $R_{3b}$ in claim 1, $R_{3c\text{-}3}$ is as defined by $R_{3c}$ in claim 1, and $R_4$, $R_5$, $R_6$, $R_7$, A, W, L, $t_1$, and $t_2$ are as defined in claim 1; or the compound has a structure as represented by formula (II-$d_2$):

(II-$d_2$)

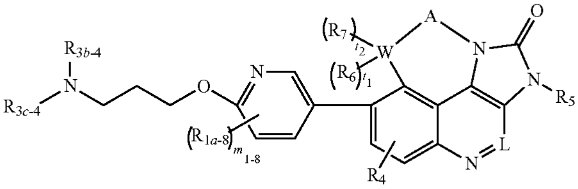

wherein $m_{1\text{-}8}$ is selected from the group consisting of 0, 1, and 2, $R_{1a\text{-}8}$ is as defined by $R_{1a}$ in claim 1, $R_{3b\text{-}4}$ is as defined by $R_{3b}$ in claim 1, $R_{3c\text{-}4}$ is as defined by $R_{3c}$ in claim 1, and $R_4$, $R_5$, $R_6$, $R_7$, A, W, L, $t_1$, and $t_2$ are as defined in claim 1; or the compound has a structure as represented by formula (II-$d_3$):

(II-$d_3$)

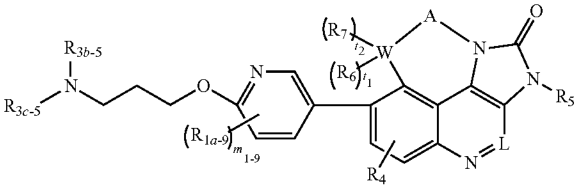

wherein $m_{1-9}$ is selected from the group consisting of 0, 1, and 2, $R_{1a-9}$ is as defined by $R_{1a}$ in claim 1, $R_{3b-5}$ is as defined by $R_{3b}$ in claim 1, $R_{3c-5}$ is as defined by $R_{3c}$ in claim 1, and $R_4$, $R_5$, $R_6$, $R_7$, A, W, L, $t_1$, and $t_2$ are as defined in claim 1; or the compound has a structure as represented by formula (II-$d_4$):

(II-$d_4$)

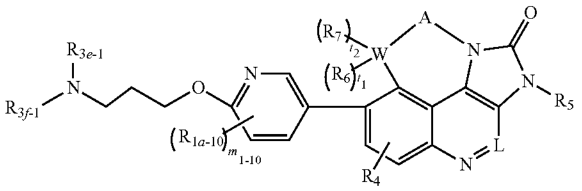

wherein $m_{1-10}$ is selected from the group consisting of 0, 1, 2, and 3, $R_{1a-10}$ is as defined by $R_{1a}$ in claim 1, $R_{3e-1}$ is as defined by $R_{3e}$ in claim 1, $R_{3f-1}$ is as defined by $R_{3f}$ in claim 1, and $R_4$, $R_5$, $R_6$, $R_7$, A, W, L, $t_1$, and $t_2$ are as defined in claim 1; or the compound has a structure as represented by formula (II-$d_5$):

(II-$d_5$)

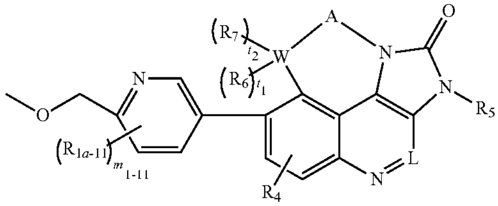

wherein $m_{1-11}$ is selected from the group consisting of 0, 1, 2, and 3, $R_{1a-11}$ is as defined by $R_{1a}$ in claim 1, and $R_4$, $R_5$, $R_6$, $R_7$, A, W, L, $t_1$, and $t_2$ are as defined in claim 1; or the compound has a structure as represented by formula (II-$d_6$):

(II-$d_6$)

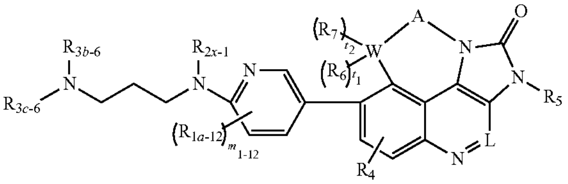

wherein $m_{1-12}$ is selected from the group consisting of 0, 1, 2, and 3, $R_{1a-12}$ is as defined by $R_{1a}$ in claim 1, $R_{2x-1}$ is as defined by $R_{2x}$ in claim 1, $R_{3b-6}$ is as defined by $R_{3b}$ in claim 1, $R_{3c-6}$ is as defined by $R_{3c}$ in claim 1, and $R_4$, $R_5$, $R_6$, $R_7$, A, W, L, $t_1$, and $t_2$ are as defined in claim 1; or the compound has a structure as represented by formula (II-$e_1$):

(II-$e_1$)

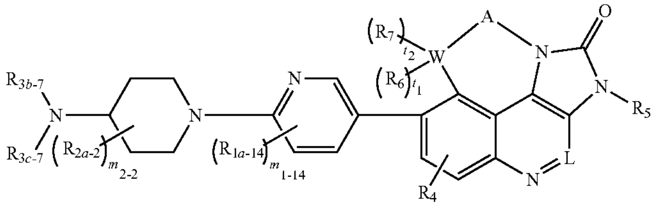

wherein $m_{1-14}$ is selected from the group consisting of 0, 1, 2, and 3, $m_{2-2}$ is 0, $R_{1a-14}$ is as defined by $R_{1a}$ in claim 1, $R_{3b-7}$ is as defined by $R_{3b}$ in claim 1, $R_{3c-7}$ is as defined by $R_{3c}$ in claim 1, and $R_4$, $R_5$, $R_6$, $R_7$, A, W, L, $t_1$, and $t_2$ are as defined in claim 1; or the compound has a structure as represented by formula (III-a):

(III-a)

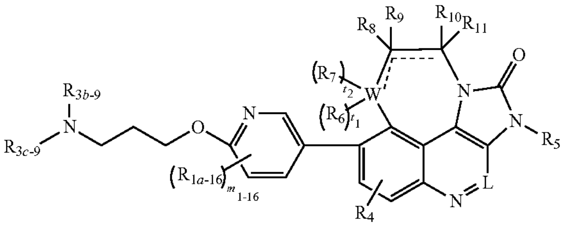

wherein $m_{1-16}$ is selected from the group consisting of 0, 1, 2, and 3, $R_{1a-16}$ is as defined by $R_{1a}$ in claim 1, $R_{3b-9}$ is as defined by $R_{3b}$ in claim 1, $R_{3c-9}$ is as defined by $R_{3c}$ in claim 1, and $R_4$, $R_5$, $R_6$, $R_7$, $R_8$, $R_9$, $R_{10}$, $R_{11}$, W, L, $t_1$, and $t_2$ are as defined in claim 1; or the compound has a structure as represented by formula ($III-a_1$):

($III-a_1$)

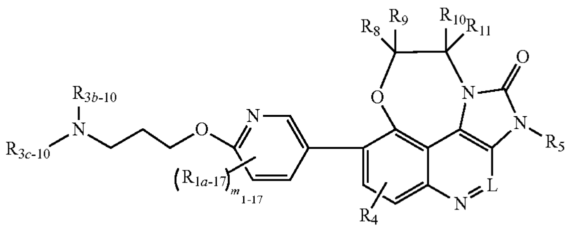

wherein $m_{1-17}$ is selected from the group consisting of 0, 1, 2, and 3, $R_{1a-17}$ is as defined by $R_{1a}$ in claim 1, $R_{3b-10}$ is as defined by $R_{3b}$ in claim 1, $R_{3c-10}$ is as defined by $R_{3c}$ in claim 1, and $R_4$, $R_5$, $R_8$, $R_9$, $R_{10}$, $R_{11}$, and L are as defined in claim 1; or the compound has a structure as represented by formula ($III-a_2$):

($III-a_2$)

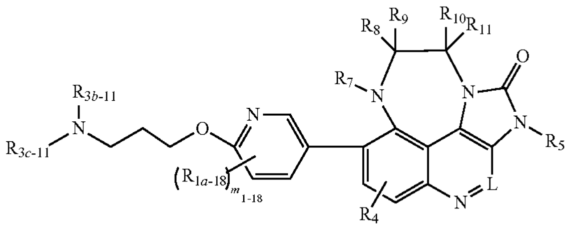

wherein $m_{1-18}$ is selected from the group consisting of 0, 1, 2, and 3, $R_{1a-18}$ is as defined by $R_{1a}$ in claim 1, $R_{3b-11}$ is as defined by $R_{3b}$ in claim 1, $R_{3c-11}$ is as defined by $R_{3c}$ in claim 1, and $R_4$, $R_5$, $R_7$, $R_8$, $R_9$, $R_{10}$, $R_{11}$, and L are as defined in claim 1.

14. The compound or the tautomer, optical isomer, geometric isomer, solvate, isotopic derivative, or pharmaceutically acceptable salt thereof according to claim 1, wherein Y is selected from the group consisting of the following groups:

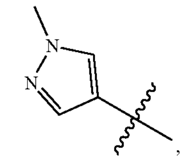

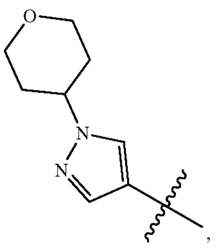

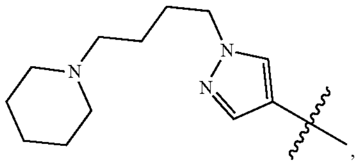

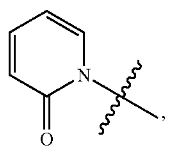

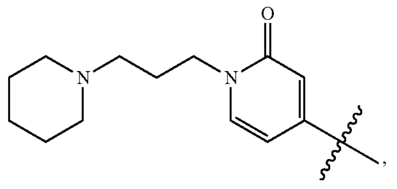

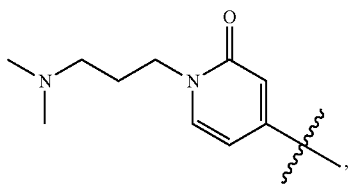

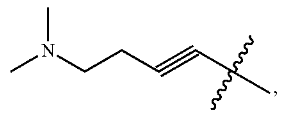

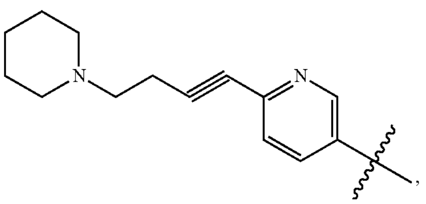

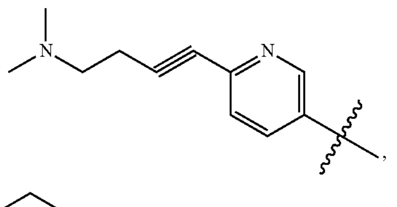

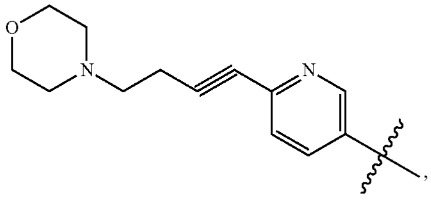

-continued
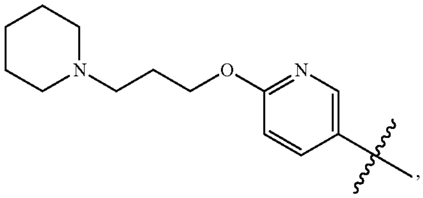
,
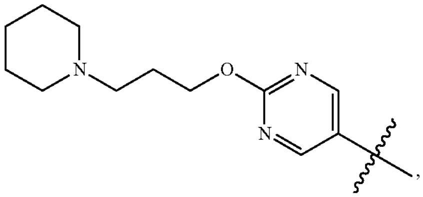
,
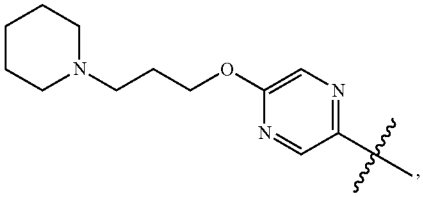
,
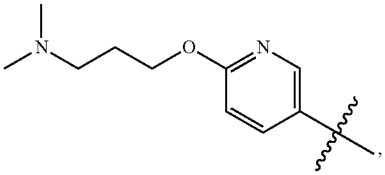
,
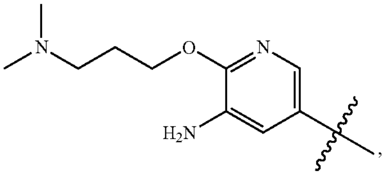
,
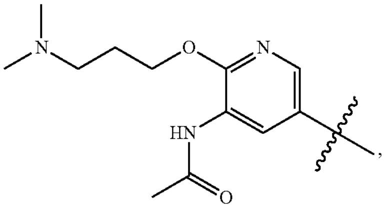
,
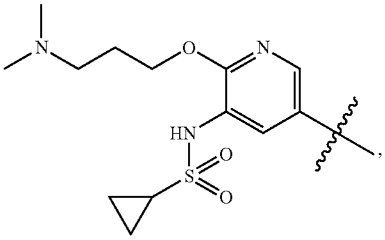
,
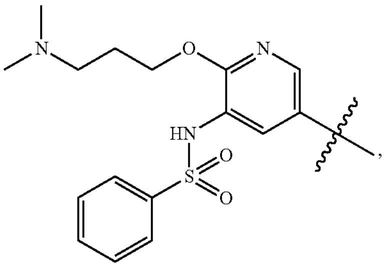
-continued
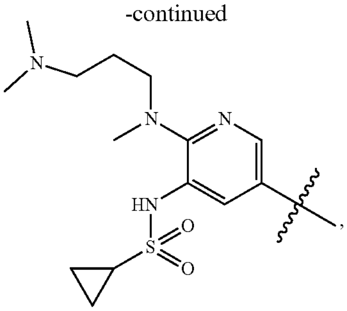
,
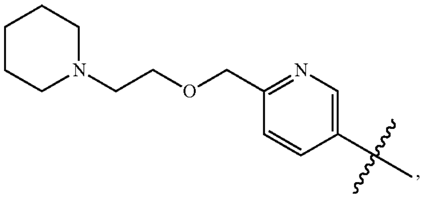
,
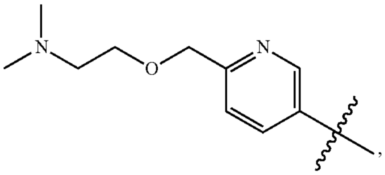
,
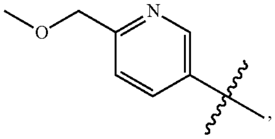
,
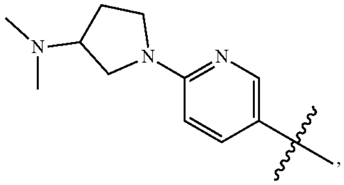
,
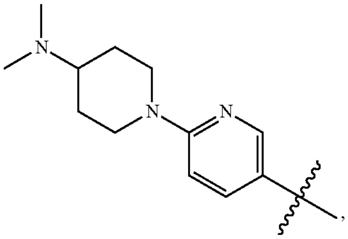
,
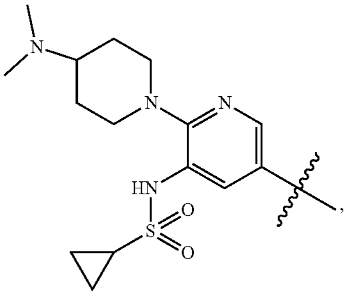
,
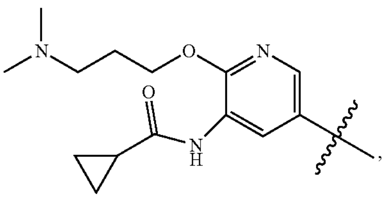
, -continued
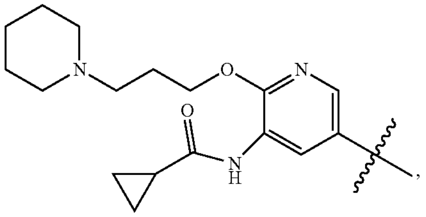
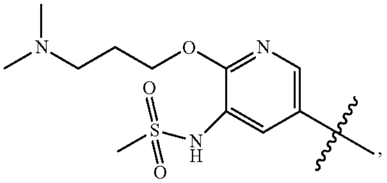
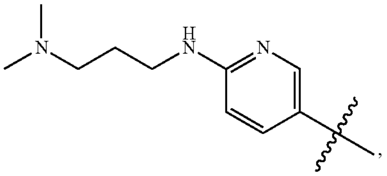
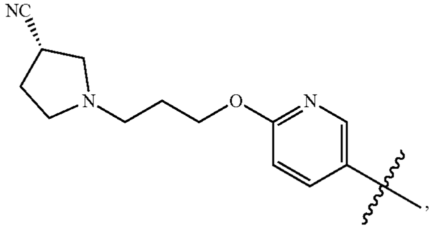
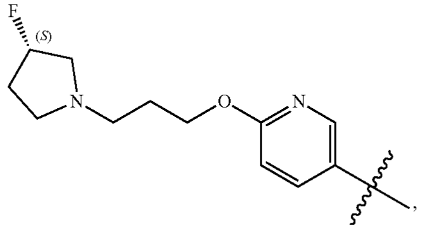
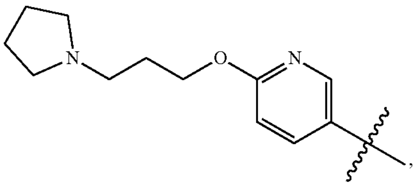
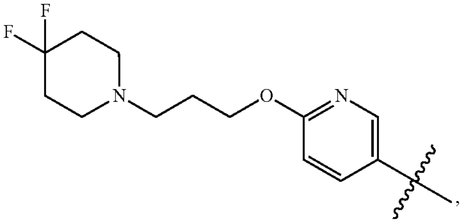
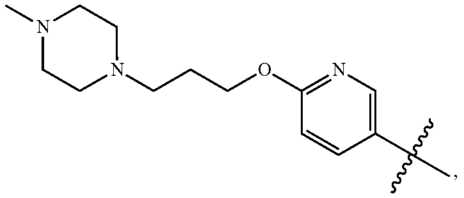
-continued
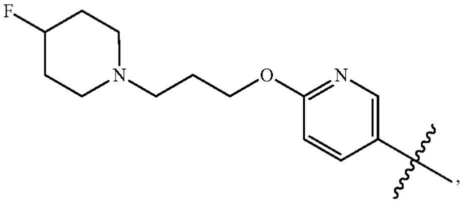
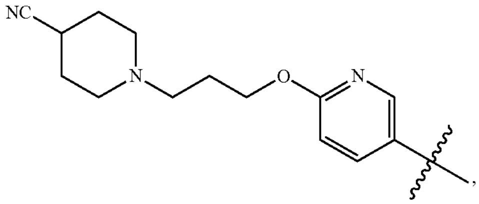
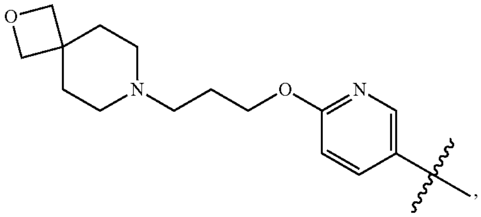
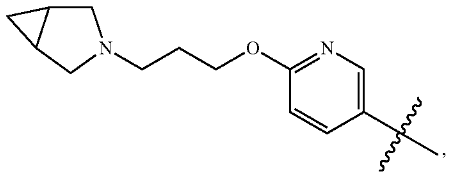
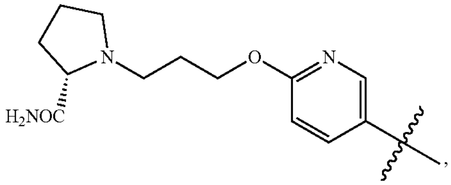
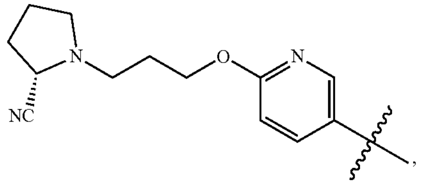
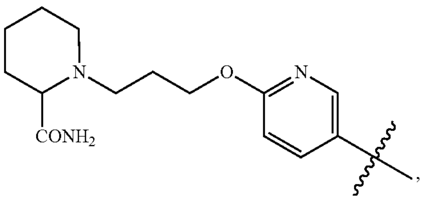
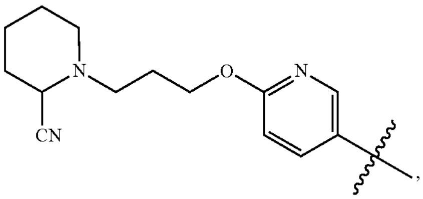

-continued
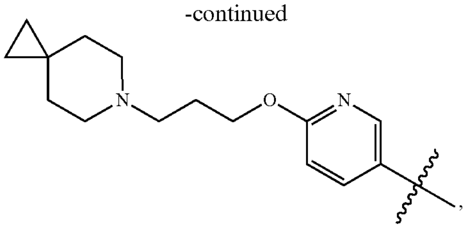
,
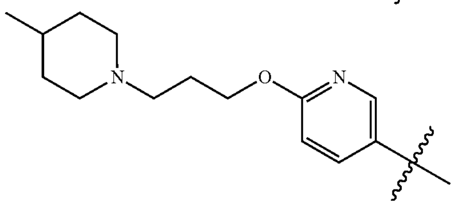
,
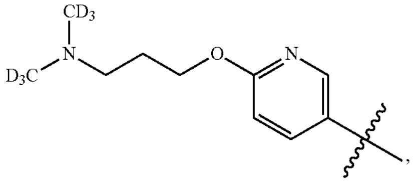
,
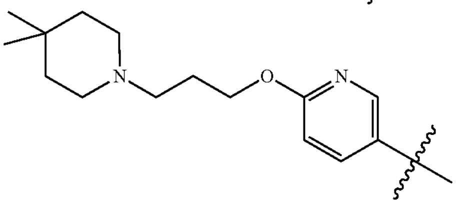
,
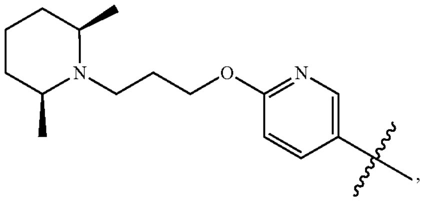
,
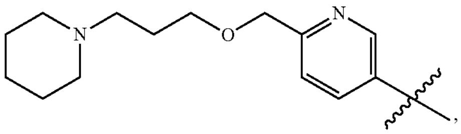
, and
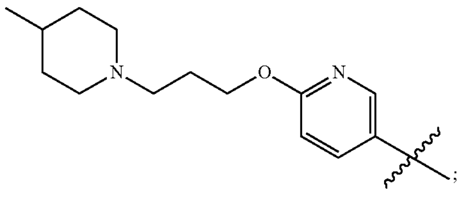
;
or
Y is selected from the group consisting of the following groups:
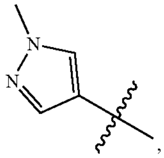
,
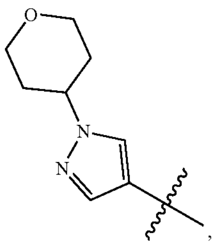
,
-continued
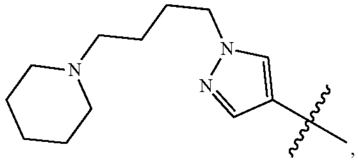
,
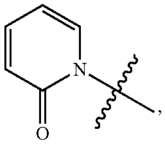
,
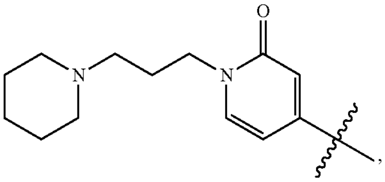
,
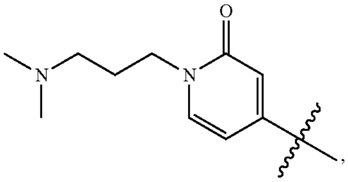
,
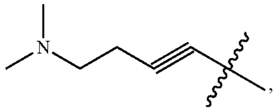
,
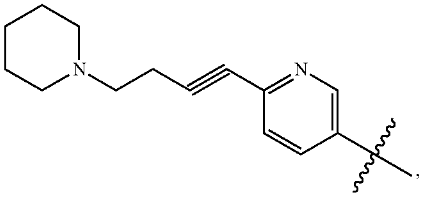
,
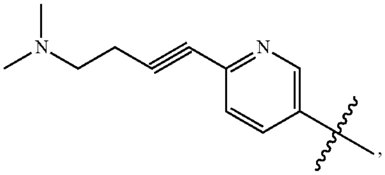
,
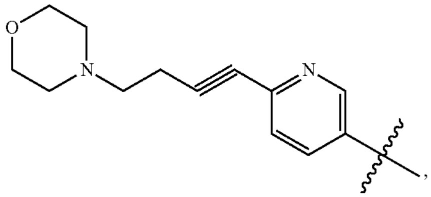
,
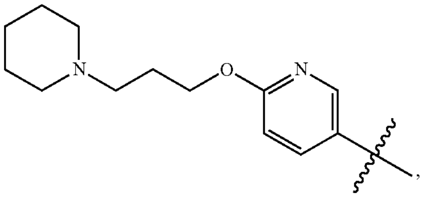
,
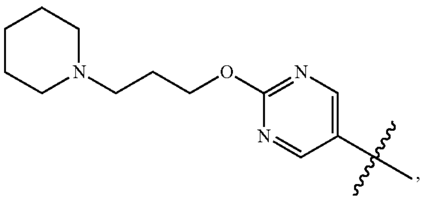
, -continued

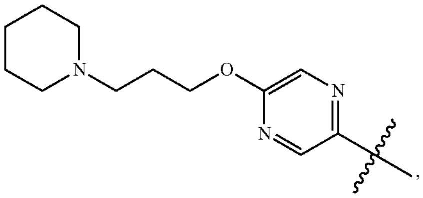

,

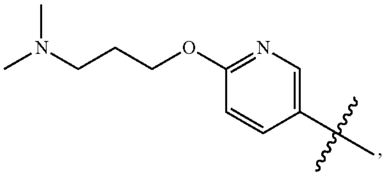

,

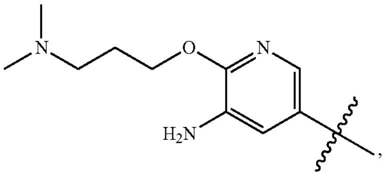

,

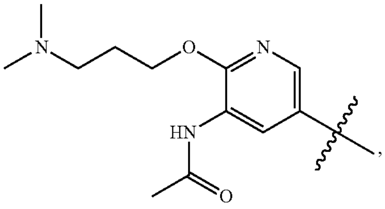

,

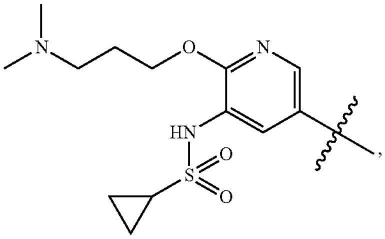

,

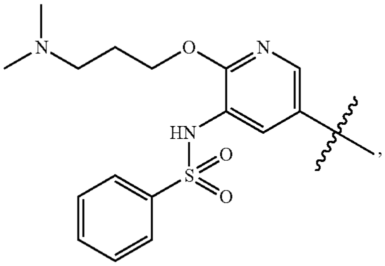

,

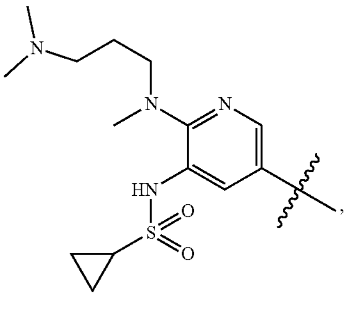

,

-continued

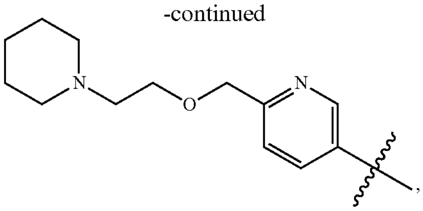

,

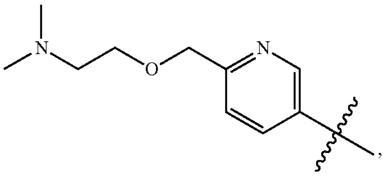

,

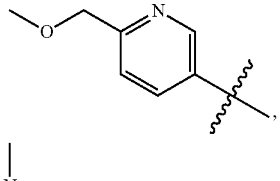

,

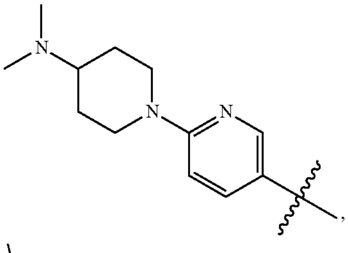

,

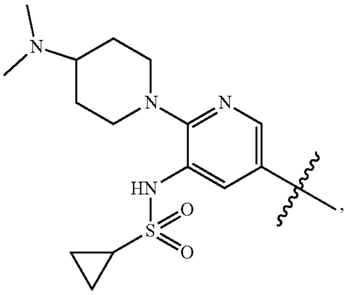

, and

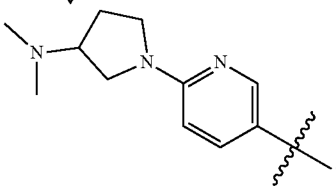

.

15. The compound or the tautomer, optical isomer, geometric isomer, solvate, isotopic derivative, or pharmaceutically acceptable salt thereof according to claim 1, wherein $R_4$ is selected from the group consisting of hydrogen, halogen, amino, and $C_{1-6}$ alkoxy; or $R_4$ is selected from the group consisting of hydrogen, fluorine, and methoxy.

16. The compound or the tautomer, optical isomer, geometric isomer, solvate, isotopic derivative, or pharmaceutically acceptable salt thereof according to claim 1, wherein $R_5$ is $C_{1-6}$ alkyl; or $R_5$ is methyl.

17. The compound or the tautomer, optical isomer, geometric isomer, solvate, isotopic derivative, or pharmaceutically acceptable salt thereof according to claim 1, wherein W is selected from the group consisting of O and N.

18. The compound or the tautomer, optical isomer, geometric isomer, solvate, isotopic derivative, or pharmaceutically acceptable salt thereof according to claim 1, wherein $R_6$, $R_7$, $R_8$, $R_9$, $R_{10}$, $R_1$, $R_{12}$, and $R_{13}$ are, for each presence, independently selected from the group consisting of hydrogen, deuterium, and any one of $C_{1-6}$ alkyl, $C_{1-6}$ alkoxy, $C_{3-6}$ cycloalkyl, 5- to 6-membered heterocycloalkyl, $C_{6-8}$ aryl, 5- to 6-membered heteroaryl, 9- to 10-membered bicyclic heterocyclyl, and 9- to 10-membered bicyclic heteroaryl which is optionally substituted by deuterium, halogen, hydroxyl, amino, $C_{1-6}$ alkyl, $C_{1-6}$ alkoxy, —C(O)($C_{1-6}$ alkyl), —C(O)NH($C_{1-6}$ alkyl), —NHC(O)($C_{1-6}$ alkyl), —C(O)O($C_{1-6}$ alkyl), $C_{3-6}$ cycloalkyl, 5- to 6-membered heterocycloalkyl, phenyl, 5- to 6-membered heteroaryl, 9- to 10-membered bicyclic heterocyclyl, or 9- to 10-membered bicyclic heteroaryl; or $R_6$, $R_7$, $R_8$, $R_9$, $R_{10}$, $R_1$, $R_{12}$, and $R_{13}$ are, for each presence, independently selected from the group consisting of hydrogen and any one of $C_{1-6}$ alkyl, $C_{1-6}$ alkoxy, $C_{3-6}$ cycloalkyl, 5- to 6-membered heterocycloalkyl, $C_{6-8}$ aryl, and 5- to 6-membered heteroaryl which is optionally substituted by halogen, hydroxyl, amino, $C_{1-6}$ alkyl, $C_{1-6}$ alkoxy, —C(O)($C_{1-6}$ alkyl), —C(O)NH($C_{1-6}$ alkyl), —NHC(O)($C_{1-6}$ alkyl), —C(O)O($C_{1-6}$ alkyl), $C_{3-6}$ cycloalkyl, 5- to 6-membered heterocycloalkyl, phenyl, or 5- to 6-membered heteroaryl; or $R_6$, $R_7$, $R_8$, $R_9$, $R_{10}$, $R_{11}$, $R_{12}$, and $R_{13}$ are, for each presence, independently selected from the group consisting of hydrogen and any one of $C_{1-6}$ alkyl and $C_{1-6}$ alkoxy which is optionally substituted by halogen, hydroxyl, amino, $C_{1-6}$ alkyl, or $C_{1-6}$ alkoxy; or $R_6$, $R_7$, $R_8$, $R_9$, $R_{10}$, $R_{11}$, $R_{12}$, and $R_{13}$ are, for each presence, independently selected from the group consisting of hydrogen and any one of $C_{1-3}$ alkyl and $C_{1-3}$ alkoxy which is optionally substituted by halogen, hydroxyl, amino, $C_{1-3}$ alkyl, or $C_{1-3}$ alkoxy; or $R_6$, $R_7$, $R_8$, $R_9$, $R_{10}$, $R_1$, $R_{12}$, and $R_{13}$ are, for each presence, independently selected from the group consisting of the following groups: —H, —F, —Cl, —OH, —$NH_2$, —$CH_3$, —$CH_2CH_3$, —$CH_2CH_2CH_3$, —CH($CH_3$)$CH_3$, —$CH_2CH(CH_3)CH_3$, —$CH_2OH$, —$CH_2CH_2OH$, —$OCH_3$, —$OCH_2CH_3$, —$OCH_2CH_2CH_3$, —$OCH(CH_3)CH_3$, —$CH_2OCH_3$, —$CH_2OCH_2CH_3$, —$CH_2CH_2OCH_3$, —$CH_2CH_2CH_2OCH_3$, —$CH(CH_3)CH_2OCH_3$, —$NHCH_3$, —$N(CH_3)CH_3$, —$CH_2N(CH_3)CH_3$,

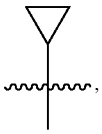,
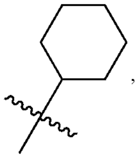,
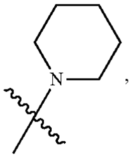,
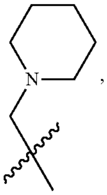,

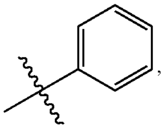,
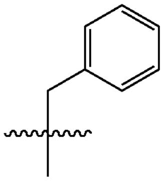,
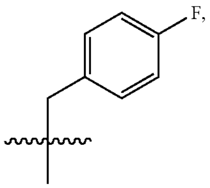

-continued

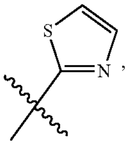,
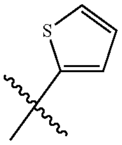,
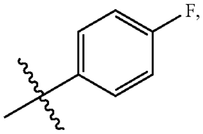

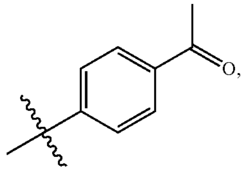
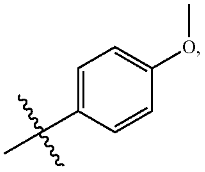

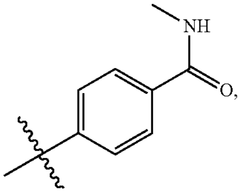
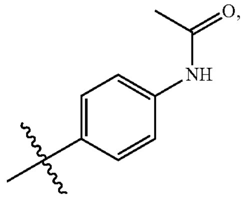

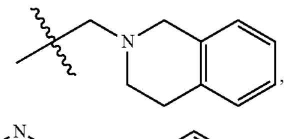,
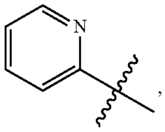,

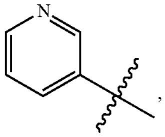,
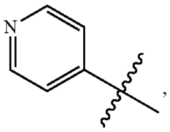,
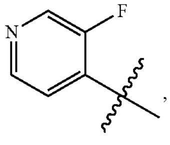,

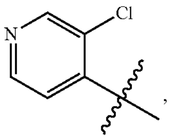,
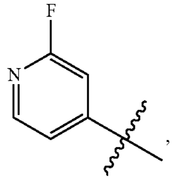, and
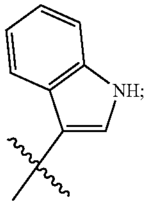

or $R_6$, $R_7$, $R_8$, $R_9$, $R_{10}$, $R_{11}$, $R_{12}$, and $R_{13}$ are, for each presence, independently selected from the group consisting of the following groups: —H, —F, —Cl, —OH, —$NH_2$, —$CH_3$, —$CH_2CH_3$, —$CH_2CH_2CH_3$, —CH($CH_3$)$CH_3$, —$CH_2CH(CH_3)CH_3$, —$CH_2OH$, —$CH_2CH_2OH$, —$OCH_3$, —$OCH_2CH_3$, —$OCH_2CH_2CH_3$, —$OCH(CH_3)CH_3$, —$CH_2OCH_3$, —$CH_2OCH_2CH_3$, —$CH_2CH_2OCH_3$, —$NHCH_3$,

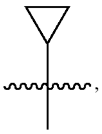,
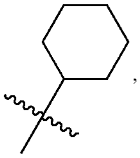,
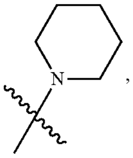,
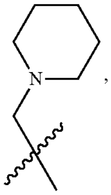,

-continued

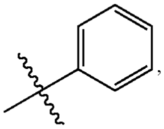, 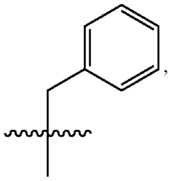, 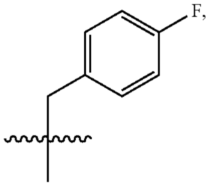

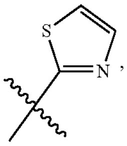, 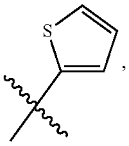, 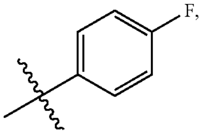

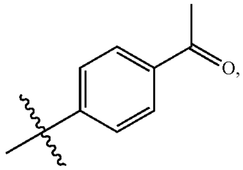 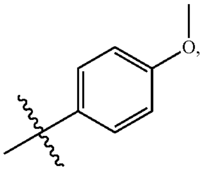

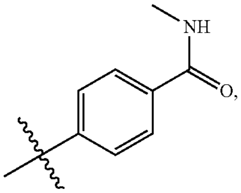 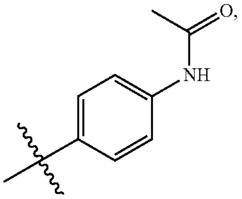

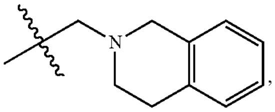,

—$N(CH_3)CH_3$, —$CH_2N(CH_3)CH_3$,

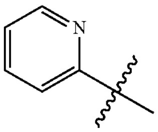, 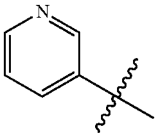,

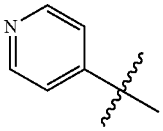, 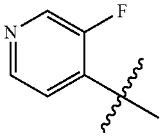,

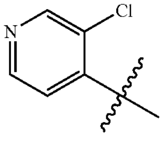, 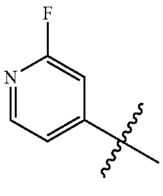, and

-continued

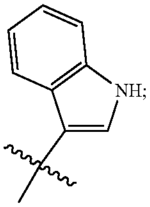

or $R_6$, $R_7$, $R_8$, $R_9$, $R_{10}$, $R_{11}$, $R_{12}$, and $R_{13}$ are, for each presence, independently selected from the group consisting of the following groups: —H, —F, —Cl, —OH, —$NH_2$, —$CH_3$, —$CH_2CH_3$, —$CH_2CH_2CH_3$, —$CH(CH_3)CH_3$, —$CH_2OCH_3$, —$CH_2CH_2OCH_3$, —$CH_2CH_2CH_2OCH_3$, and —$CH(CH_3)CH_2OCH_3$; or any two groups linked to the same atom among $R_6$, $R_7$, $R_8$, $R_9$, $R_{10}$, $R_{11}$, $R_{12}$, and $R_{13}$ form =O or =$CH_2$; or any two adjacent atoms among W, each present $Q_1$, each present $Q_2$, and $Q_3$, together with substituents linked thereto, form $C_{3-10}$ carbocyclyl, 3- to 10-membered heterocycloalkyl, $C_{6-8}$ aryl, or 5- to 10-membered heteroaryl which is optionally substituted by $R_{6c}$, or any two adjacent atoms among W, each present $Q_1$, each present $Q_2$, and $Q_3$, together with the substituents linked thereto, form $C_{3-8}$ cycloalkyl, 3- to 8-membered heterocycloalkyl, $C_{6-8}$ aryl, or 5- to 8-membered heteroaryl which is optionally substituted by $R_{6c}$; or any two adjacent atoms among W, each present $Q_1$, each present $Q_2$, and $Q_3$, together with the substituents linked thereto, form $C_{5-6}$ cycloalkyl, 5- to 6-membered heterocycloalkyl, $C_6$ aryl, or 5- to 6-membered heteroaryl which is optionally substituted by $R_{6c}$, the heteroatom thereof is selected from the group consisting of O and N, and the number of the heteroatom is 1 or 2; or any two adjacent atoms among W, each present $Q_1$, each present $Q_2$, and $Q_3$, together with the substituents linked thereto, form the following groups:

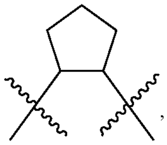, 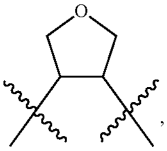, 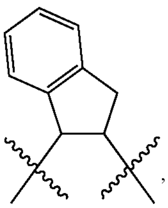,

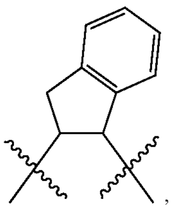, 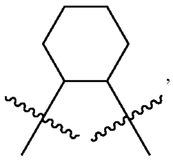, 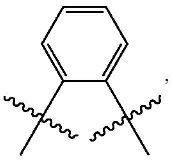,

-continued

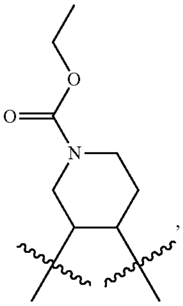,
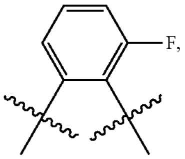
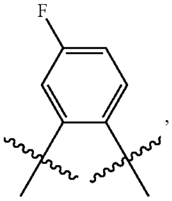,
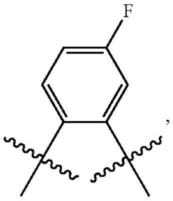,
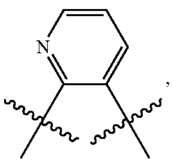,
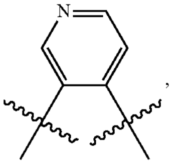,
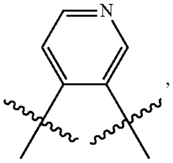,
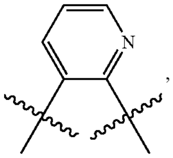,
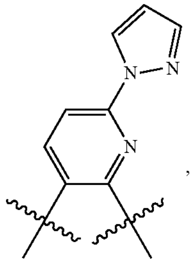,
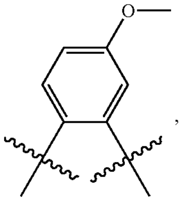,
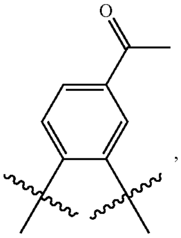,
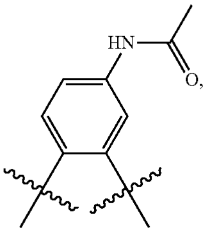 and
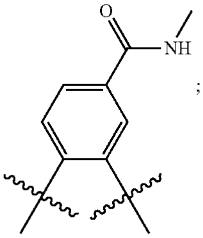;

or any one atom among W, each present $Q_1$, each present $Q_2$, and $Q_3$, together with the substituents linked thereto, forms $C_{3-6}$ cycloalkyl or 3- to 7-membered heterocycloalkyl which is optionally substituted $R_{6c}$, or any one atom among W, each present $Q_1$, each present $Q_2$, and $Q_3$, together with the substituents linked thereto, forms $C_{3-4}$ cycloalkyl or 3- to 6-membered heterocycloalkyl which is optionally substituted by $R_{6c}$, the heteroatom thereof is selected from the group consisting of O and N, and the number of the heteroatom is 1 or 2; or any one atom among W, each present $Q_1$, each present $Q_2$, and $Q_3$, together with the substituents linked thereto, forms the following groups:

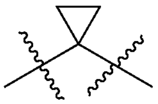,
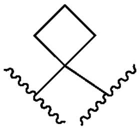,
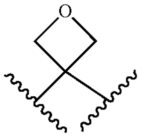,
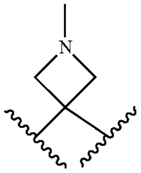,
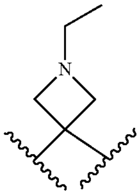,
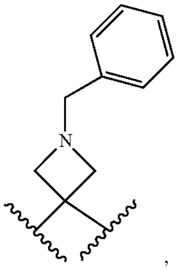, and
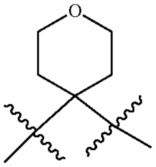;

or any one atom among W, each present $Q_1$, each present $Q_2$, and $Q_3$, together with the substituents linked thereto, forms the following groups:

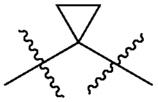,
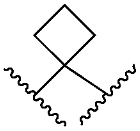,
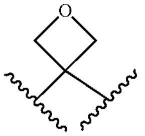,
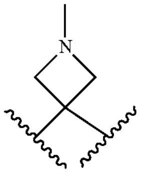,
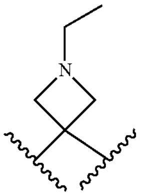,
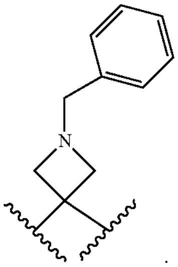.

19. The compound or the tautomer, optical isomer, geometric isomer, solvate, isotopic derivative, or pharmaceutically acceptable salt thereof according to claim 1, wherein $R_{6a}$ and $R_{6b}$ are, for each presence, independently selected from the group consisting of hydrogen and any one of $C_{1-6}$ alkyl, $C_{1-6}$ alkoxy, $C_{3-10}$ carbocyclyl, 3- to 10-membered heterocyclyl, $C_{6-8}$ aryl, and 5- to 10-membered heteroaryl which is optionally substituted by $R_{6c}$, or $R_{6a}$ and $R_{6b}$ are, for each presence, independently selected from the group consisting of hydrogen, deuterium, and any one of $C_{1-6}$ alkyl, $C_{1-6}$ alkoxy, $C_{3-6}$ cycloalkyl, 5- to 6-membered heterocycloalkyl, $C_{6-8}$ aryl, 5- to 6-membered heteroaryl, 9- to 10-membered bicyclic heterocyclyl, and 9- to 10-membered bicyclic heteroaryl which is optionally substituted by $R_{6c}$; or $R_{6a}$ and $R_{6b}$ are, for each presence, independently selected from the group consisting of hydrogen and any one of $C_{1-3}$ alkyl and $C_{1-3}$ alkoxy which is optionally substituted by $R_{6c}$, or $R_{6a}$ and $R_{6b}$ are, for each presence, independently selected from the group consisting of hydrogen and any one of methyl, ethyl, n-propyl, isopropyl, methoxy, ethoxy, n-propoxy, and isopropoxy which is optionally substituted by $R_{6c}$, or $R_{6a}$ and $R_{6b}$ are, for each presence, independently selected from the group consisting of hydrogen and any one of methyl and ethyl which is optionally substituted by $R_{6c}$.

20. The compound or the tautomer, optical isomer, geometric isomer, solvate, isotopic derivative, or pharmaceutically acceptable salt thereof according to claim 1, wherein $R_{6c}$ is, for each presence, independently selected from the group consisting of hydrogen, fluorine, chlorine, hydroxyl, amino, —NH($C_{1-6}$ alkyl), —N($CH_3$)($C_{1-6}$ alkyl), —C(O)($C_{1-6}$ alkyl), —C(O)NH($C_{1-6}$ alkyl), —NHC(O)($C_{1-6}$ alkyl), —C(O)O($C_{1-6}$ alkyl), $C_{1-6}$ alkyl, $C_{1-6}$ alkoxy, $C_{3-10}$ carbocyclyl, 3- to 10-membered heterocyclyl, $C_{6-8}$ aryl, and 5- to 10-membered heteroaryl; or $R_{6c}$ is, for each presence, independently selected from the group consisting of hydrogen, fluorine, chlorine, hydroxyl, amino, —NH($C_{1-6}$ alkyl), —N($CH_3$)($C_{1-6}$ alkyl), —C(O)($C_{1-6}$ alkyl), —C(O)NH($C_{1-6}$ alkyl), —NHC(O)($C_{1-6}$ alkyl), —C(O)O($C_{1-6}$ alkyl), $C_{1-6}$ alkyl, $C_{1-6}$ alkoxy, $C_{3-6}$ cycloalkyl, 3- to 6-membered heterocycloalkyl, $C_{6-8}$ aryl, and 5- to 6-membered heteroaryl, the heteroatom thereof is selected from the group consisting of N and S, and the number of the heteroatom is 1, 2, or 3; or $R_{6c}$ is, for each presence, independently selected from the group consisting of hydrogen, deuterium, halogen, hydroxyl, amino, $C_{1-6}$ alkyl, and $C_{1-6}$ alkoxy; or $R_{6c}$ is, for each presence, independently selected from the group consisting of hydrogen, fluorine, chlorine, hydroxyl, amino, methyl, ethyl, n-propyl, isopropyl, methoxy, ethoxy, n-propoxy, and isopropoxy.

21. The compound or the tautomer, optical isomer, geometric isomer, solvate, isotopic derivative, or pharmaceutically acceptable salt thereof according to claim 1, wherein $R_{6d}$ and $R_{6e}$ are, for each presence, independently selected from the group consisting of hydrogen, $C_{1-6}$ alkyl, $C_{1-6}$ alkoxy, $C_{3-10}$ carbocyclyl, 3- to 10-membered heterocyclyl, $C_{6-8}$ aryl, and 5- to 10-membered heteroaryl.

22. The compound or the tautomer, optical isomer, geometric isomer, solvate, isotopic derivative, or pharmaceutically acceptable salt according to claim 1, wherein the compound is selected from the group consisting of:

A-1

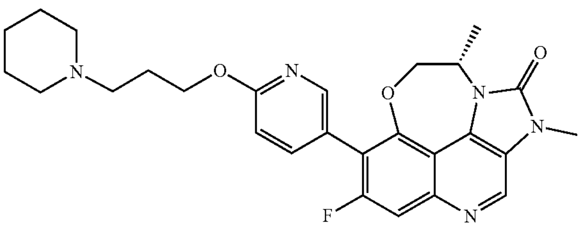

A-2

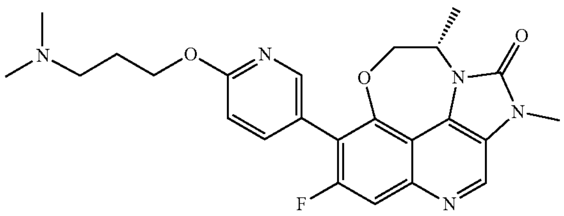

A-3

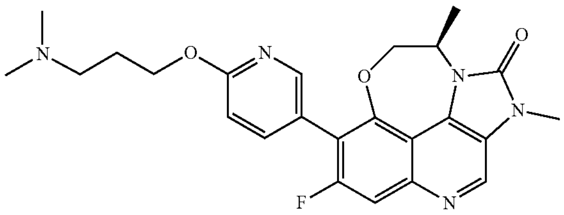

A-4

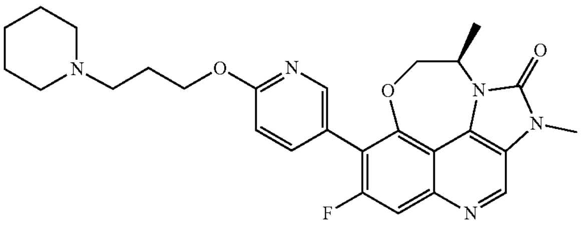

A-5

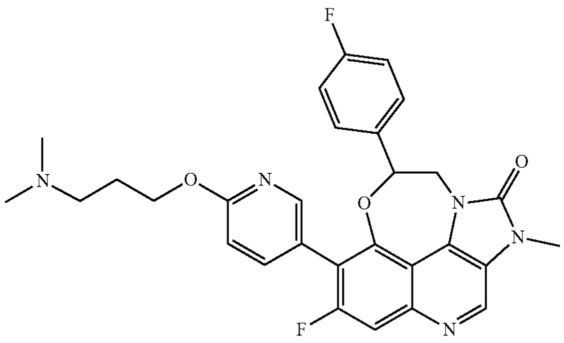

A-6

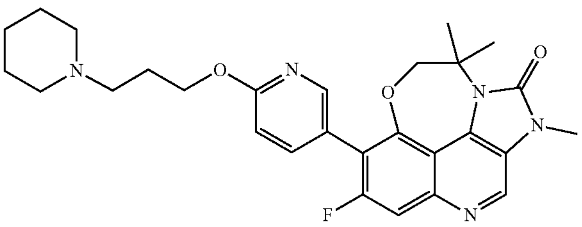

-continued
A-7
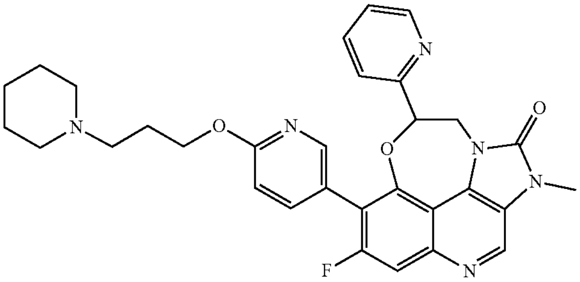
A-8
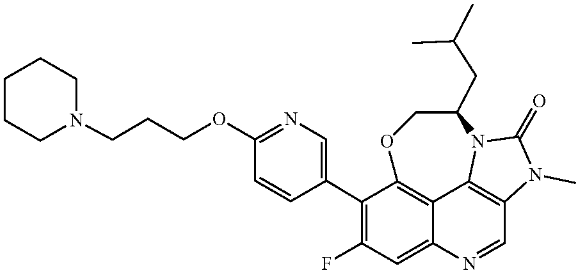
A-9
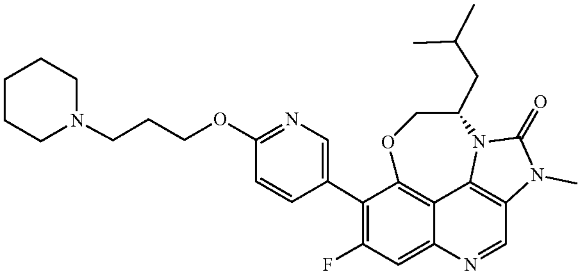
A-10
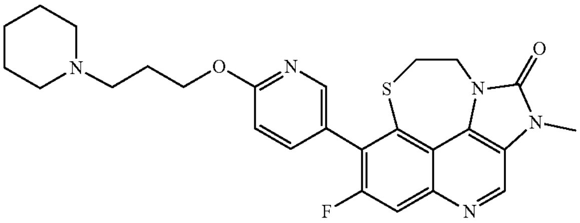
A-11
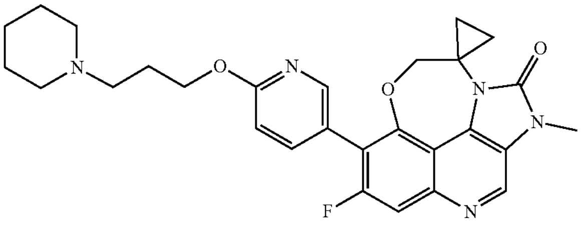
-continued
A-12
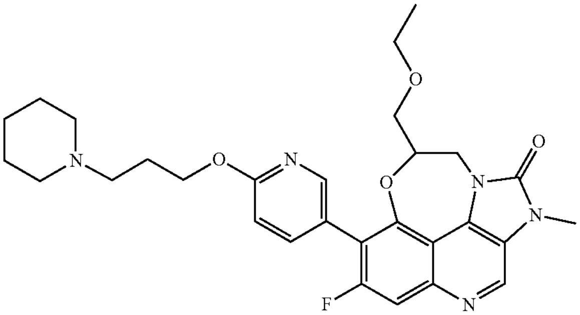
A-13
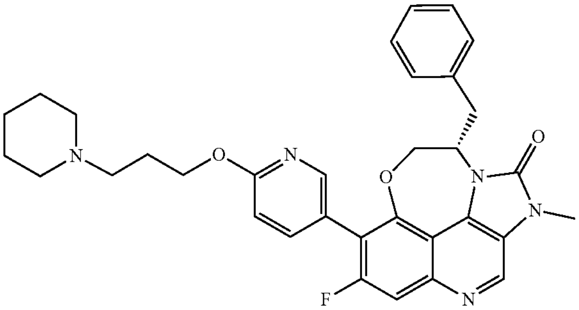
A-14
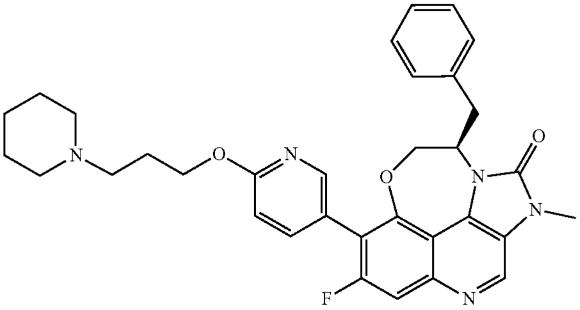
A-15
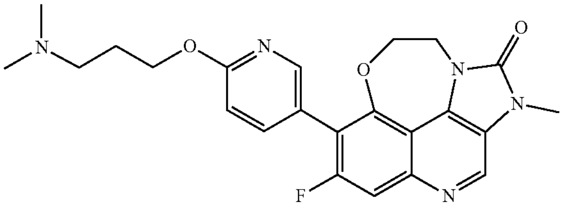
A-16
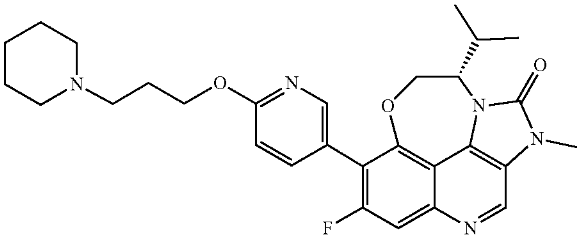

-continued
A-17
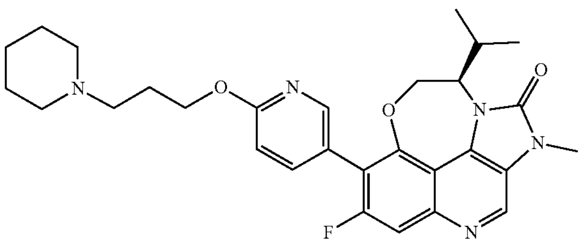
A-18
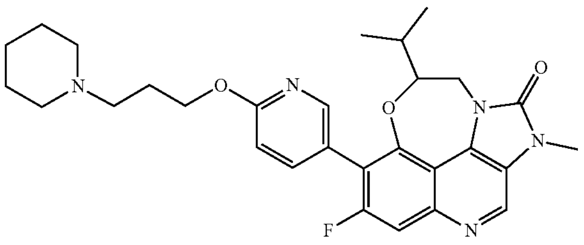
A-19
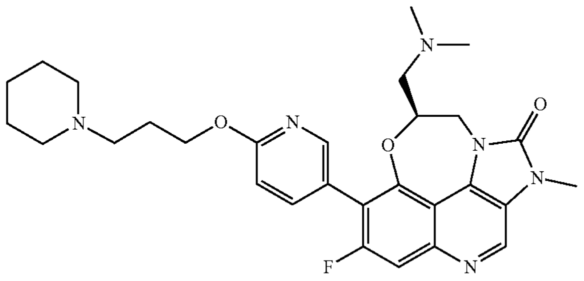
A-20
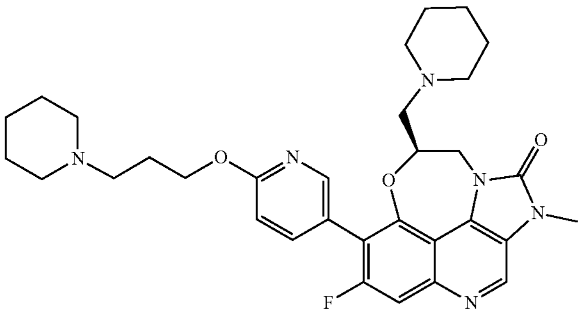
A-21
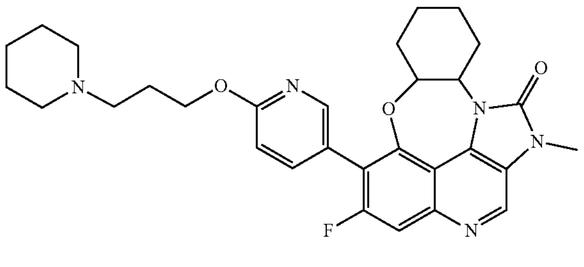
-continued
A-22
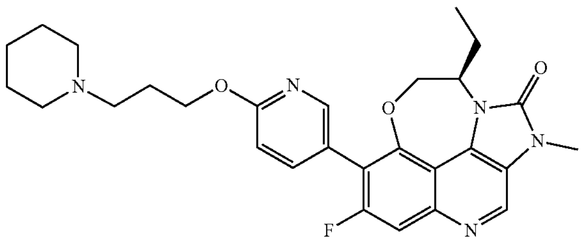
A-23
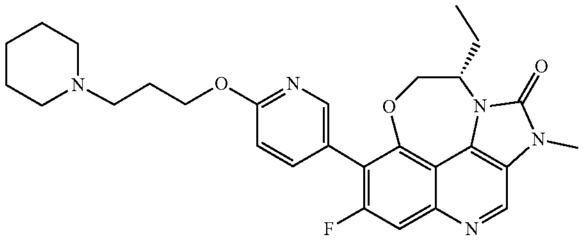
A-24
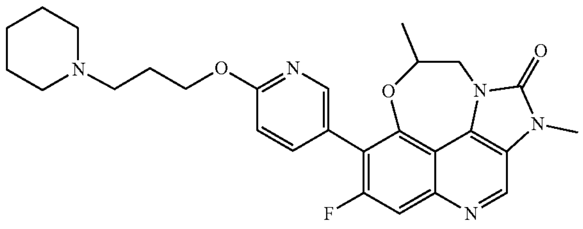
A-25
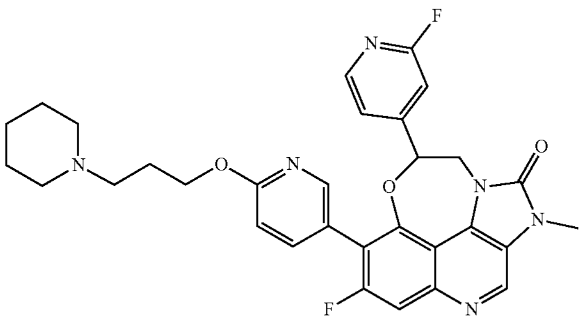
A-26
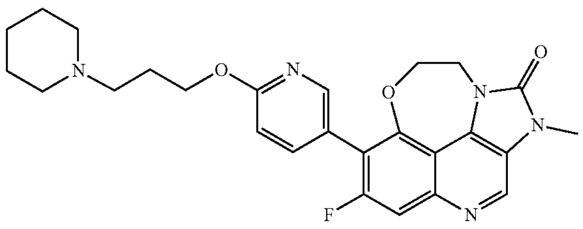
A-27
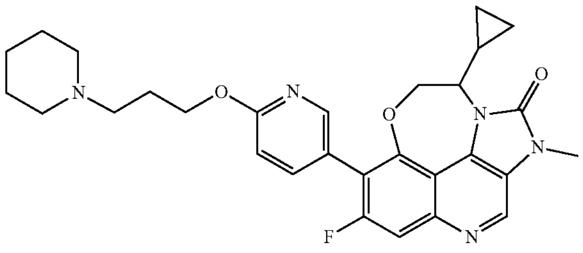

-continued
A-28
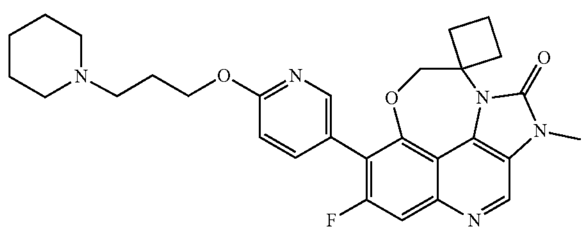
A-29
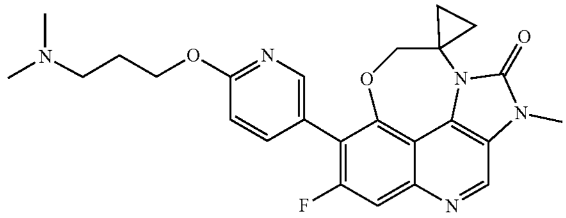
A-30
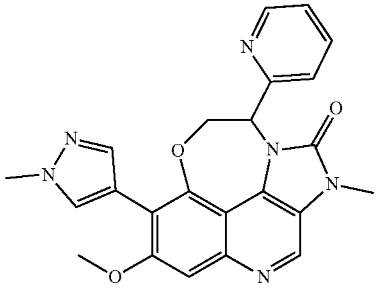
A-31
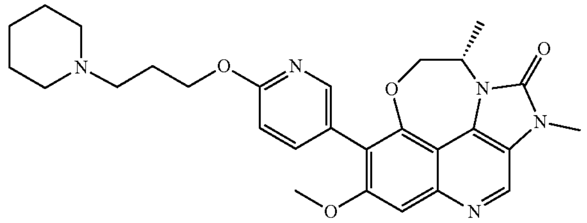
A-32
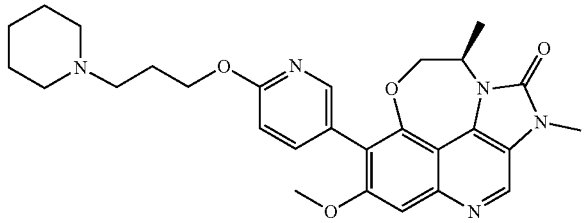
A-33
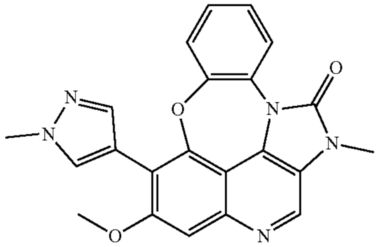
-continued
A-34
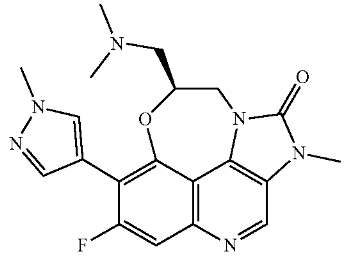
A-35
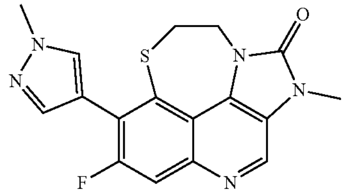
A-36
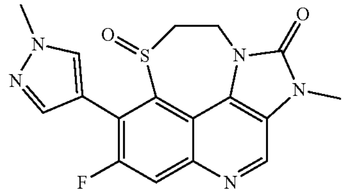
A-37
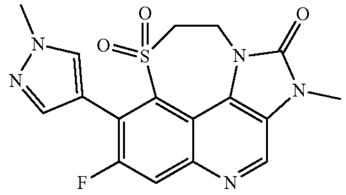
A-38
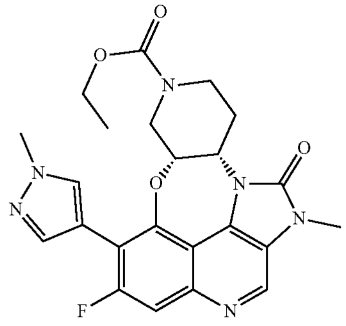
A-39
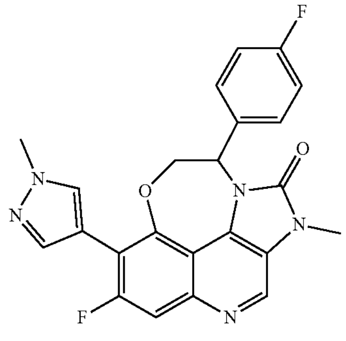

-continued
A-40
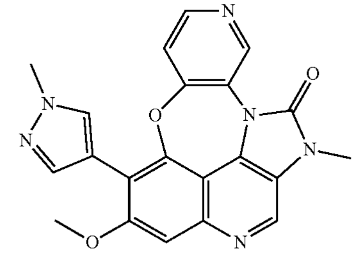
A-41
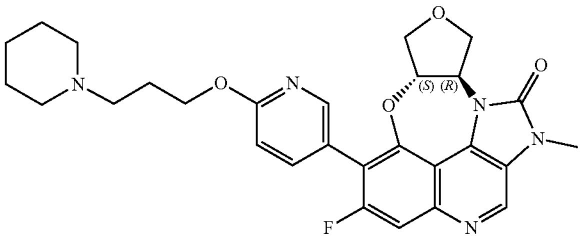
A-42
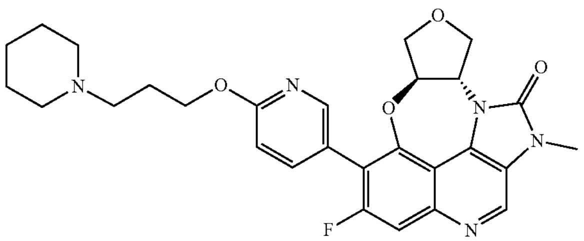
A-43
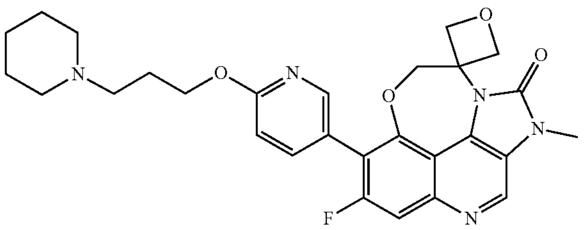
A-44
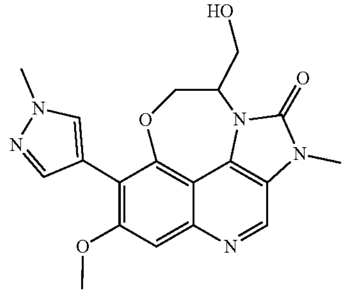
A-45
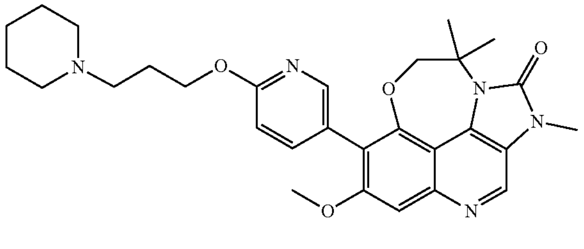
-continued
A-46
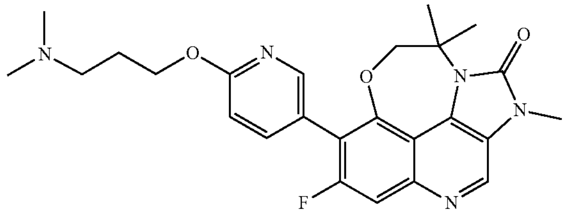
A-47
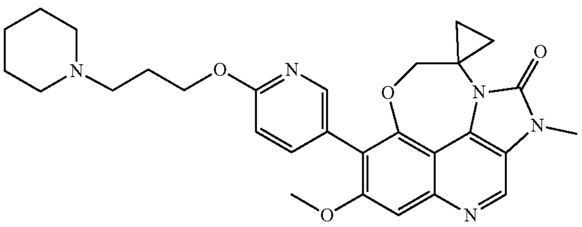
A-48
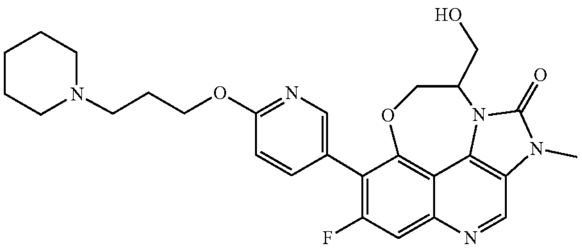
A-49
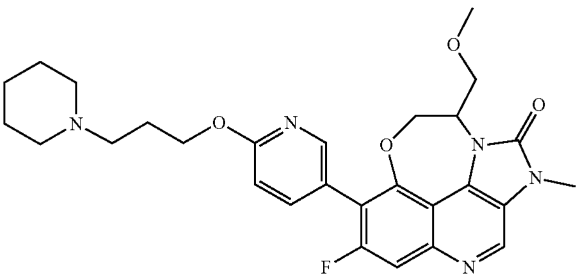
A-50
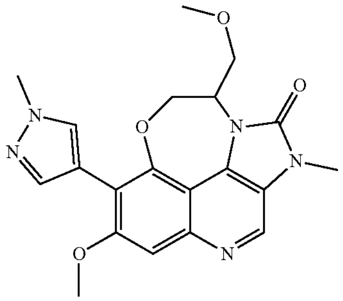
A-51
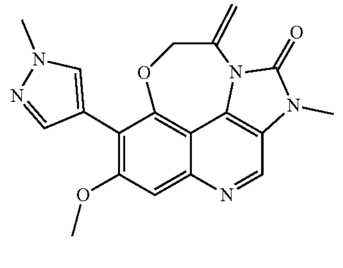

-continued
A-52
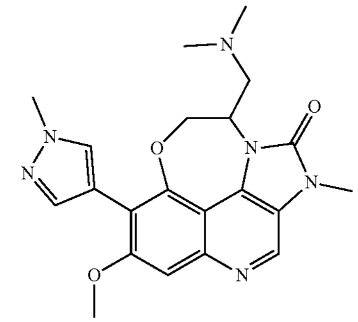
A-53
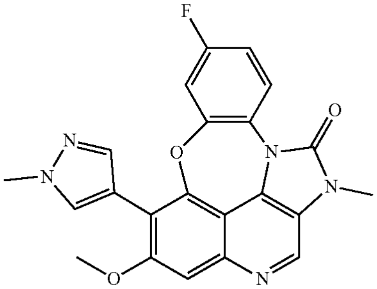
A-54
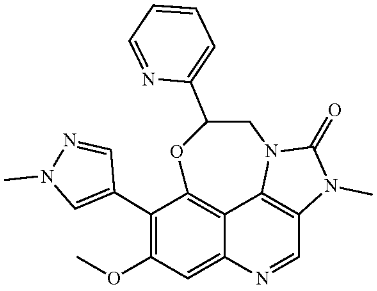
A-55
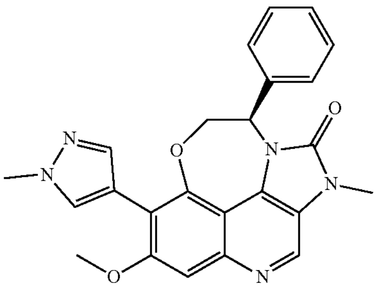
A-56
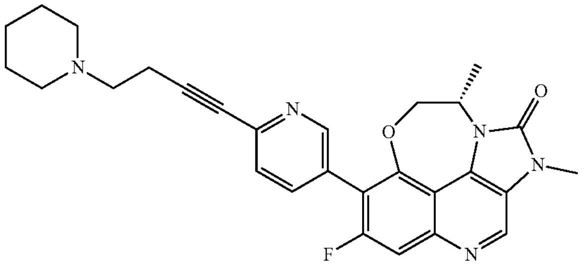
-continued
A-57
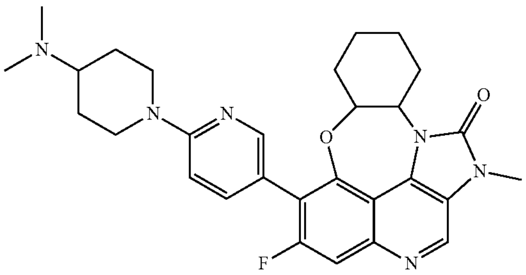
A-58
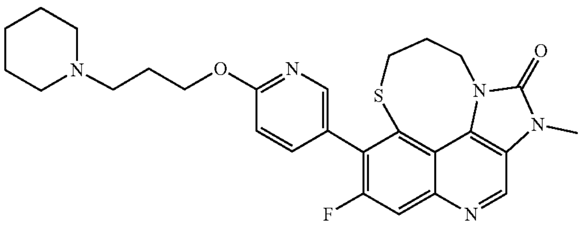
A-59
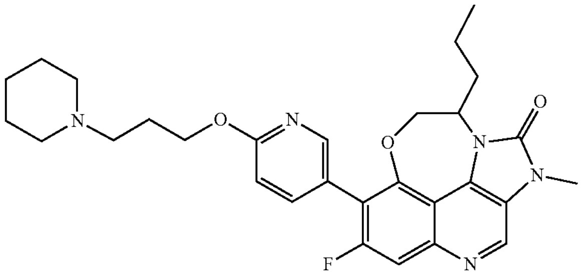
A-60
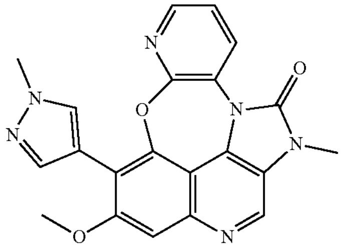
A-61
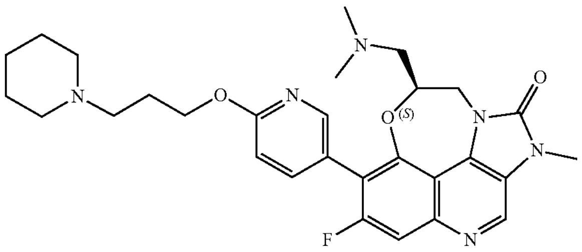
A-62
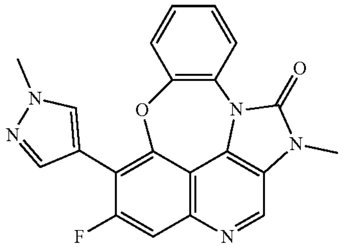

-continued
A-63
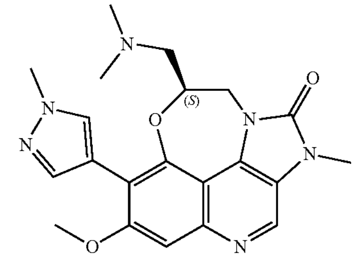
A-64
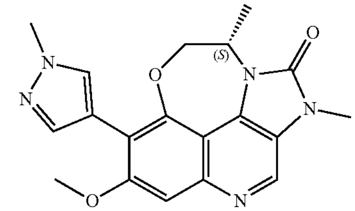
A-65
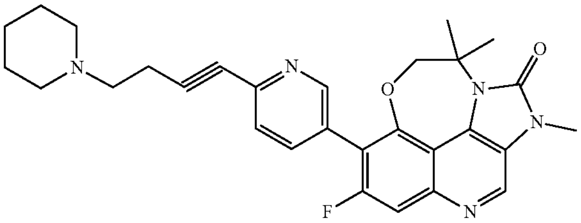
A-66
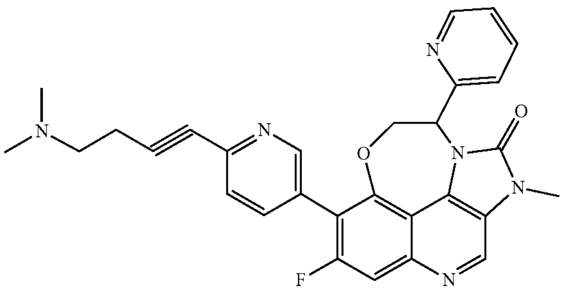
A-67
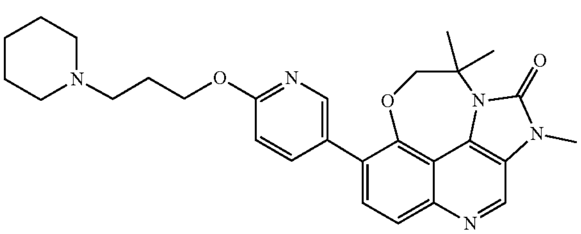
A-68
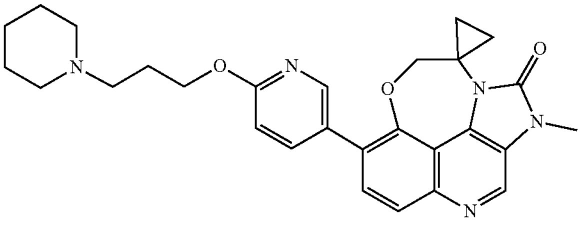
-continued
A-69
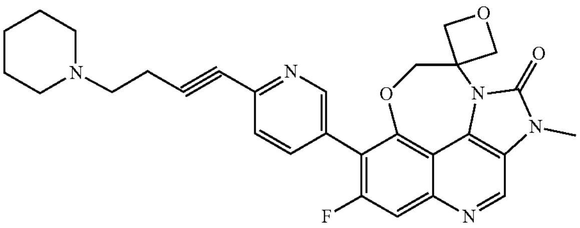
A-70
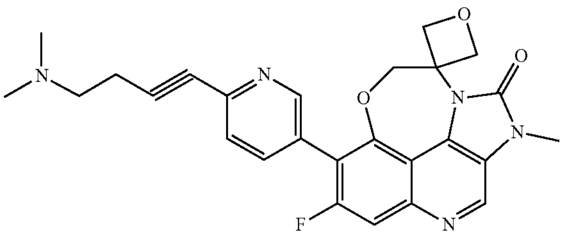
A-71
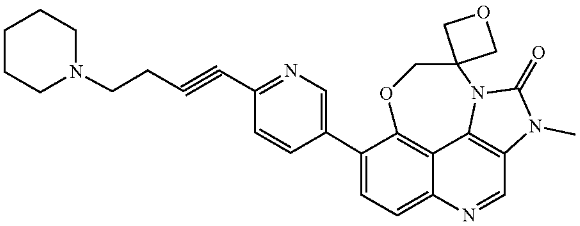
A-72
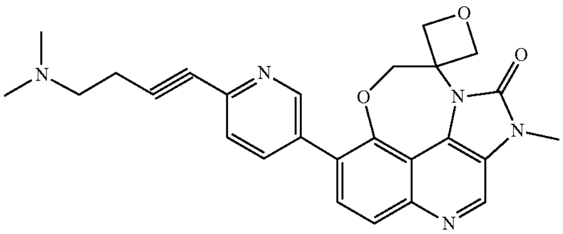
A-73
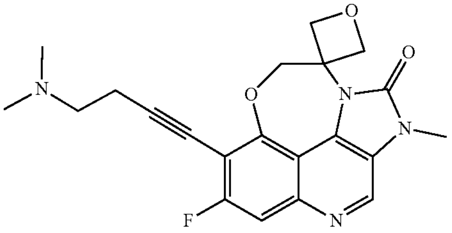
A-74
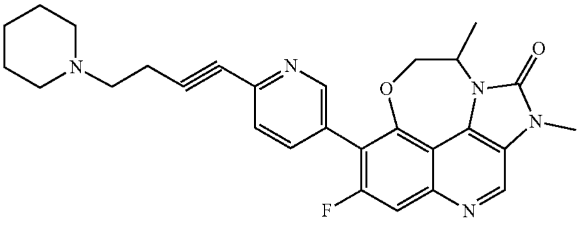

-continued
A-75
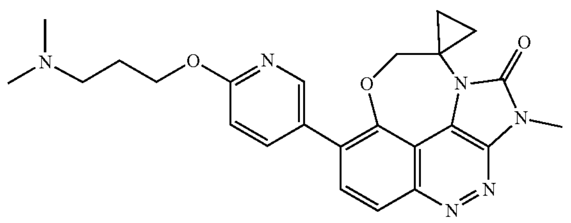
A-76
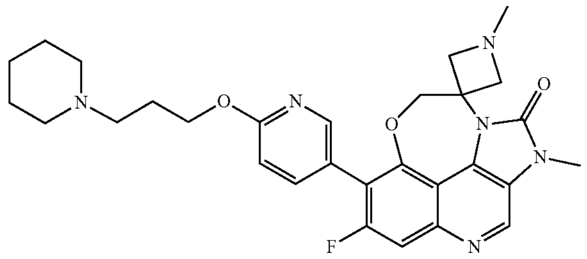
A-77
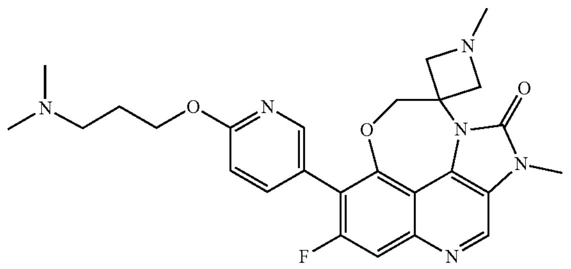
A-78
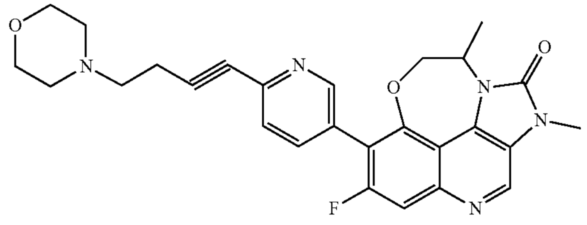
A-79
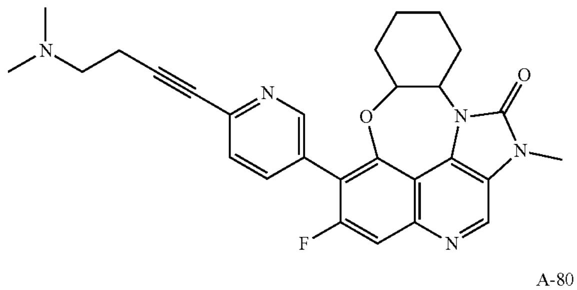
A-80
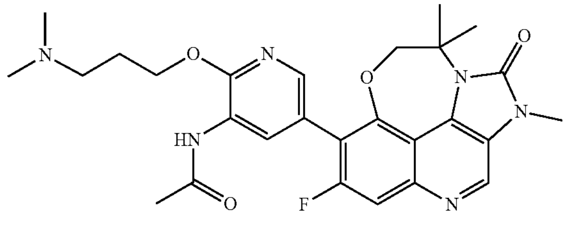
-continued
A-82
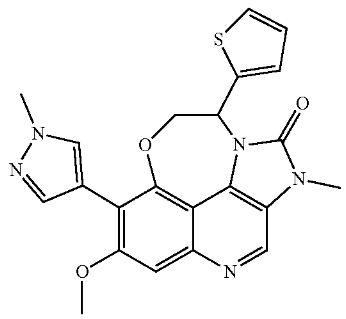
A-83
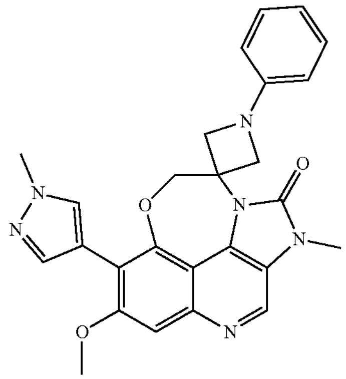
A-84
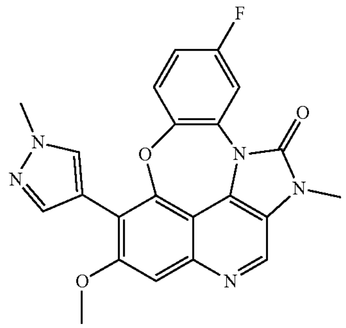
A-85
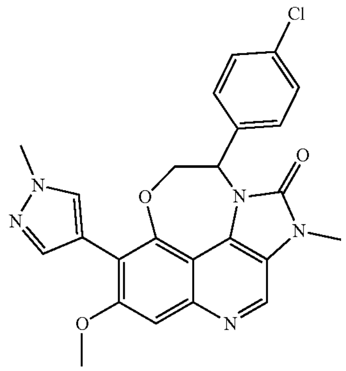

-continued
A-86
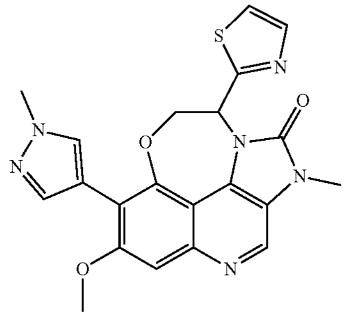
A-87
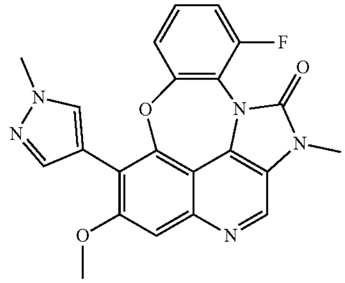
A-88
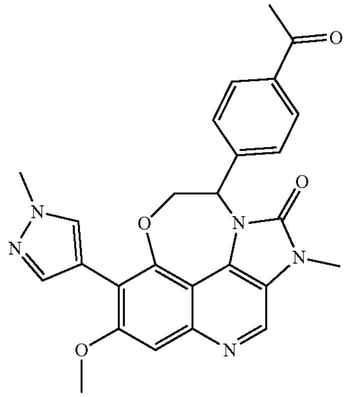
A-89
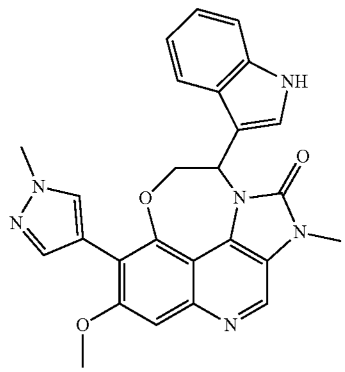
-continued
A-90
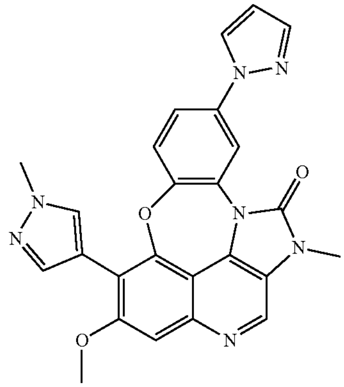
A-91
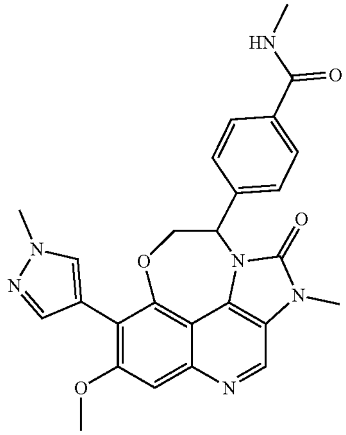
A-92
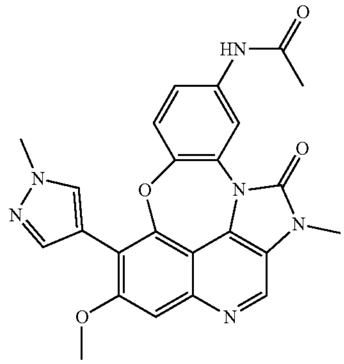
A-93
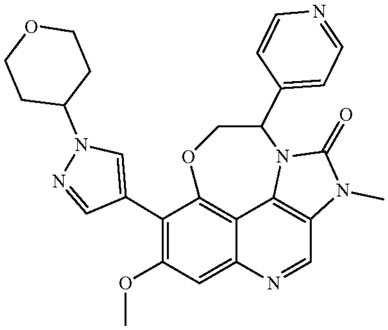

-continued
A-94
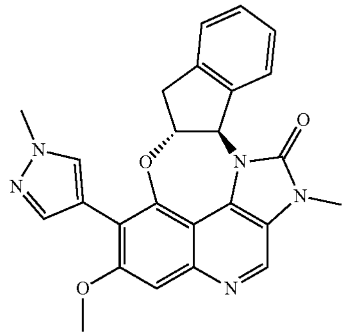
A-95
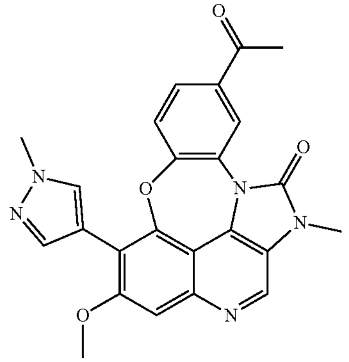
A-96
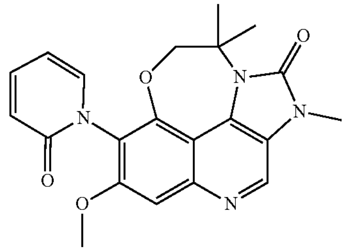
A-97
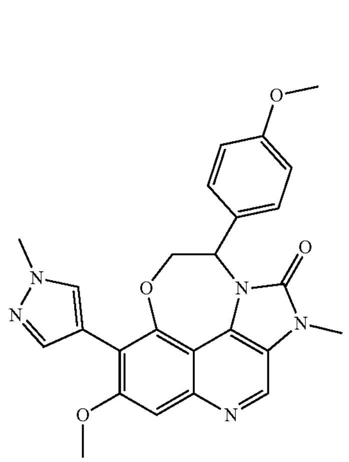
-continued
A-98
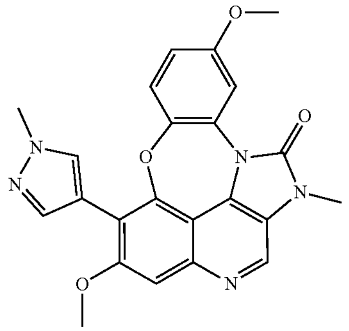
A-99
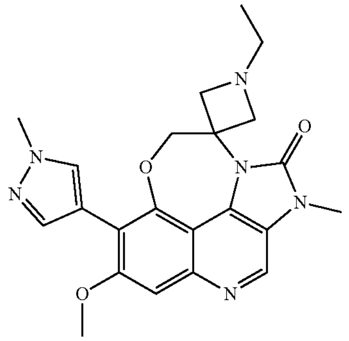
A-100
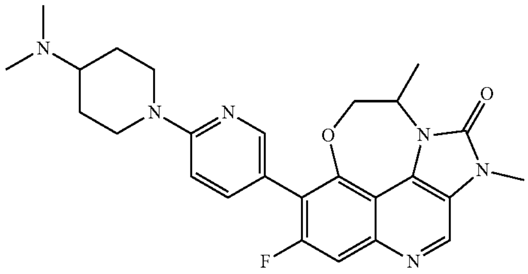
A-101
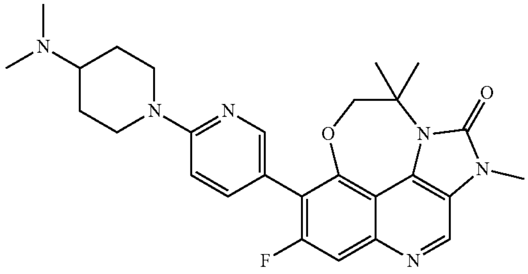
A-102
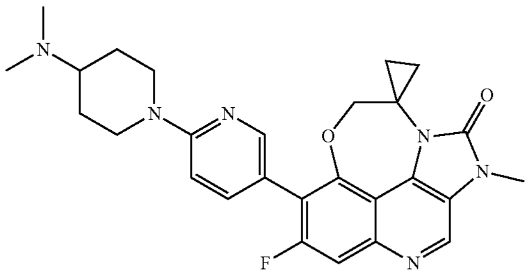

-continued
A-103
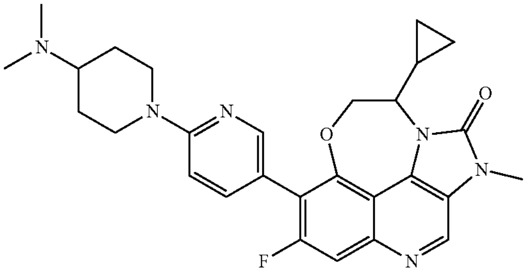
A-104
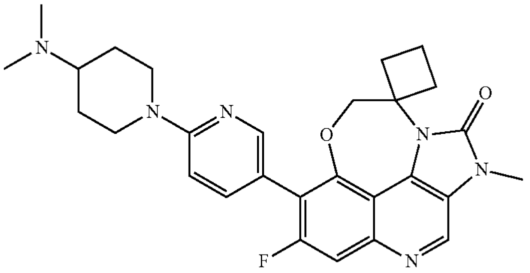
A-105
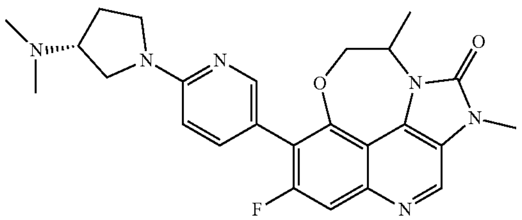
A-106
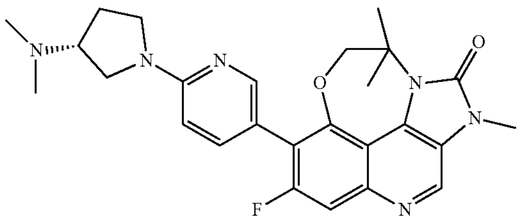
A-107
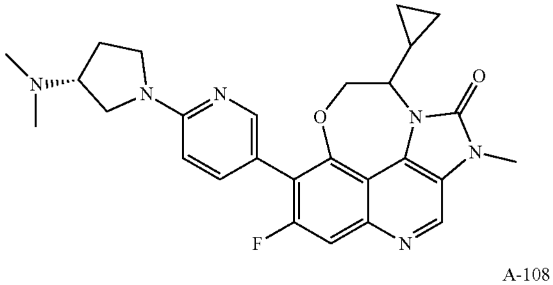
A-108
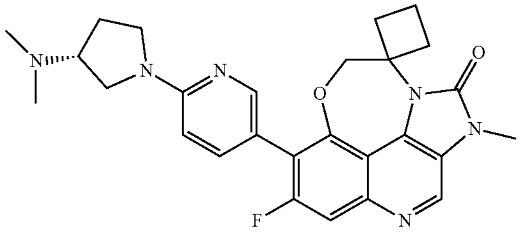
-continued
A-109
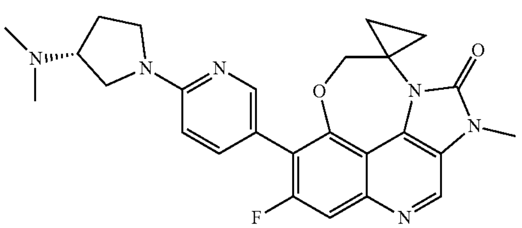
A-110
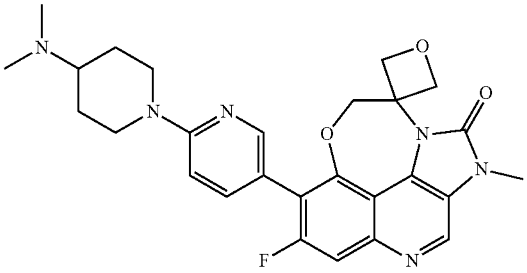
A-111
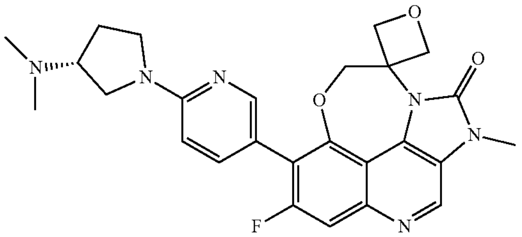
A-112
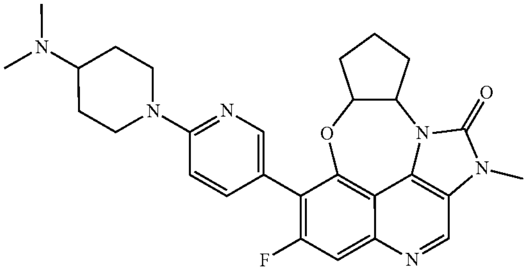
A-113
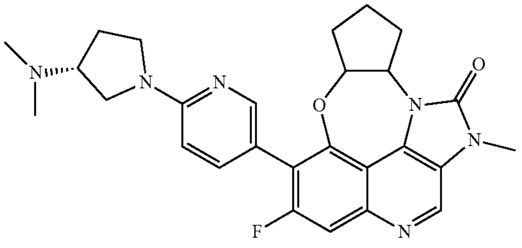

-continued
A-114
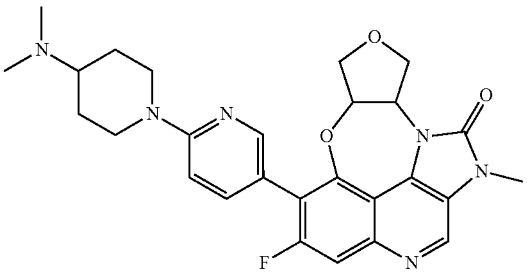
A-115
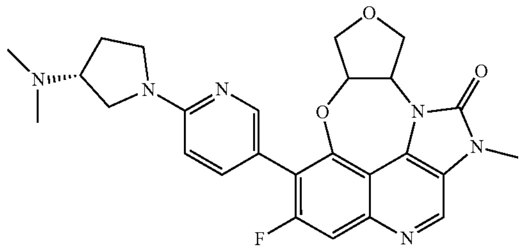
A-116
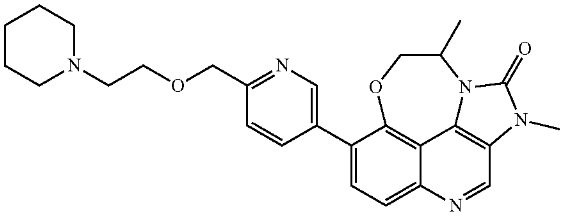
A-117
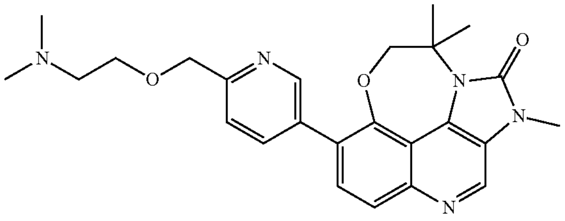
A-118
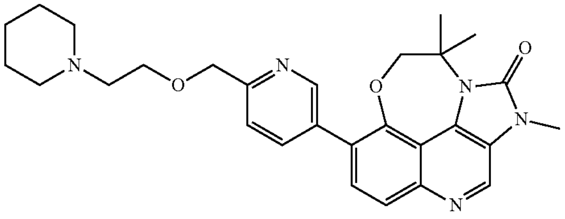
A-119
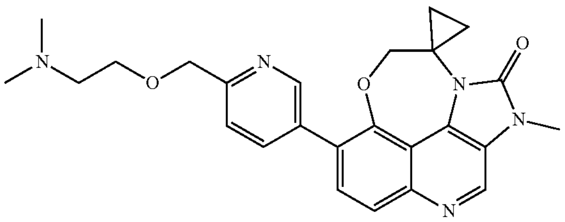
-continued
A-120
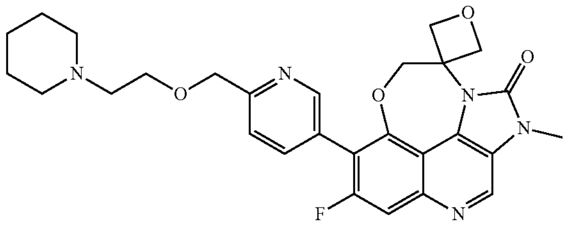
A-121
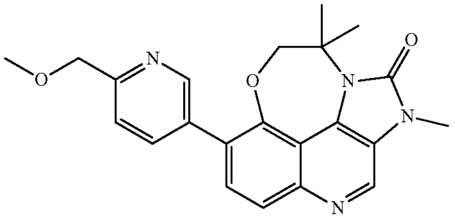
A-122
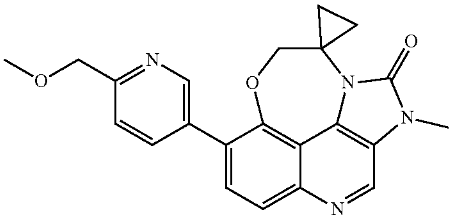
A-123
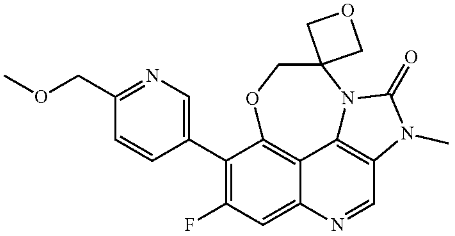
A-124
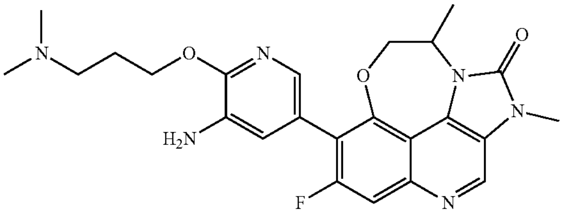
A-125
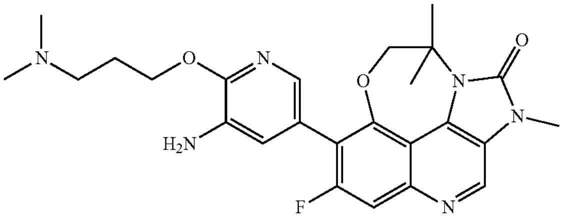

-continued
A-126
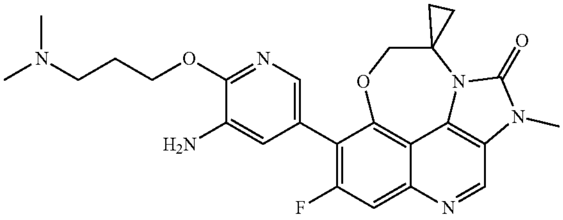
A-127
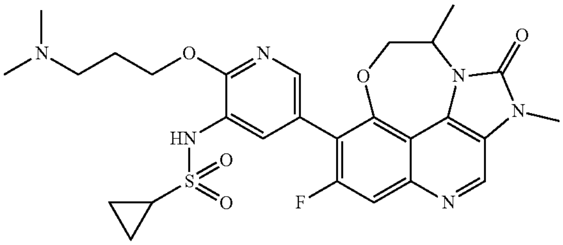
A-128
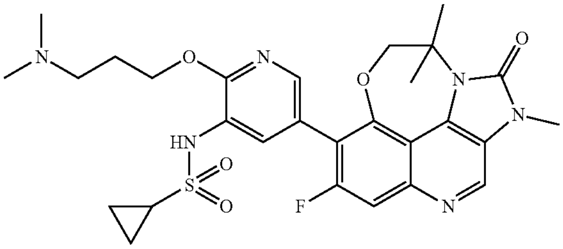
A-129
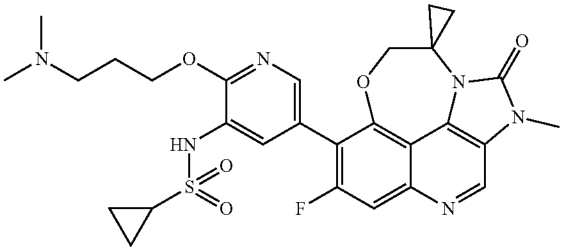
A-130
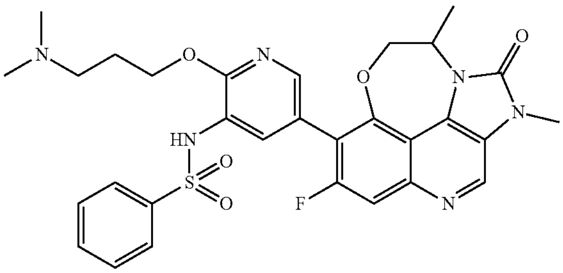
-continued
A-131
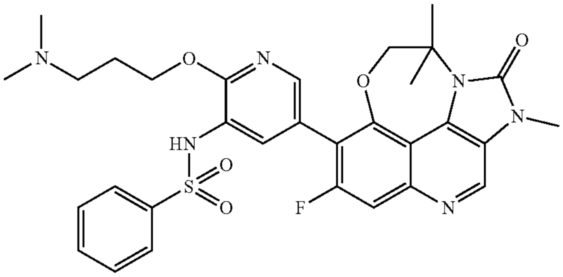
A-132
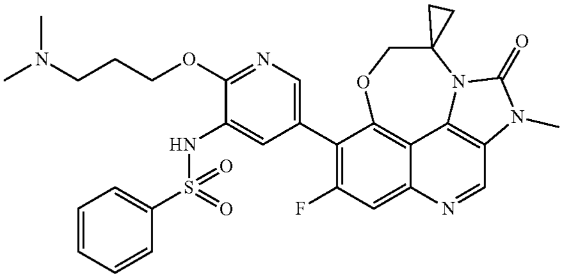
A-133
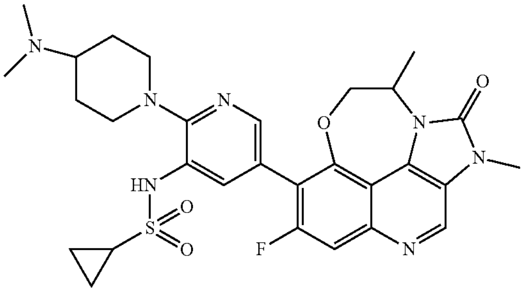
A-134
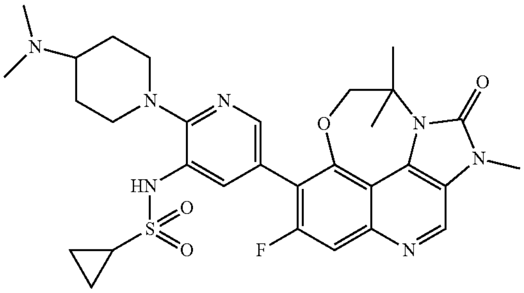
A-135
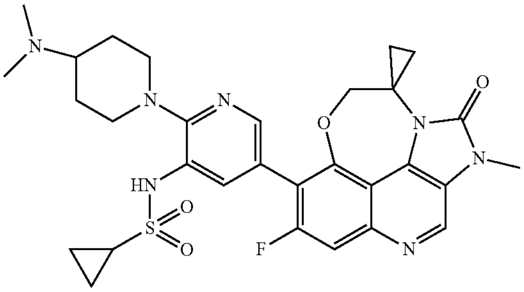

-continued
A-136
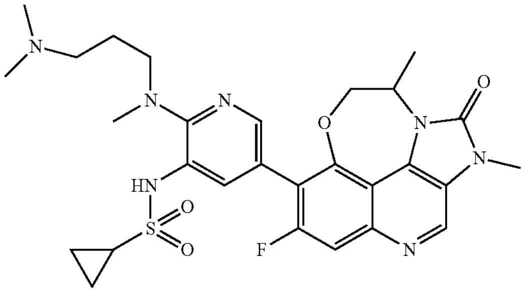
A-137
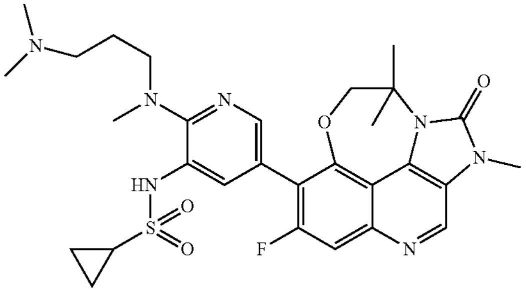
A-138
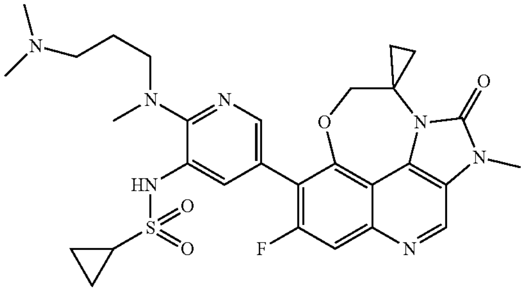
A-139
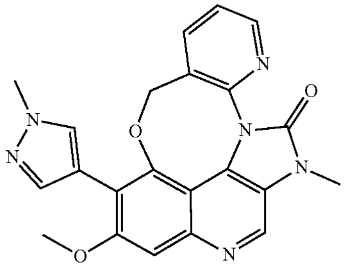
A-140
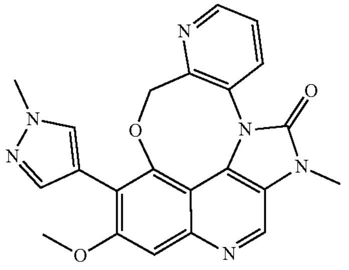
-continued
A-141
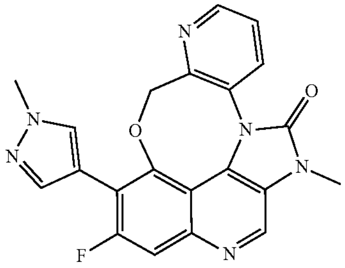
A-142
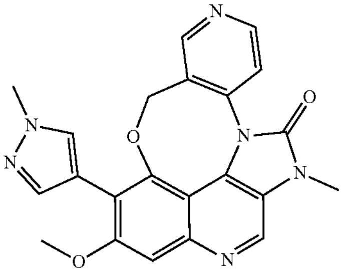
A-143
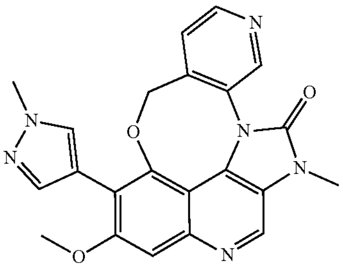
A-144
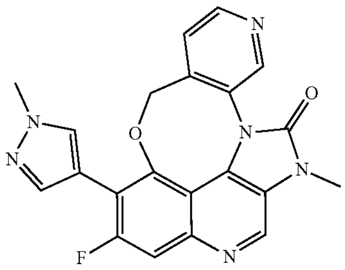
A-145
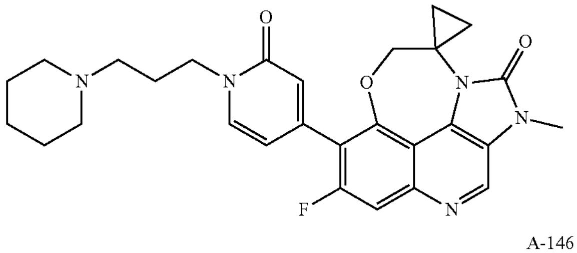
A-146
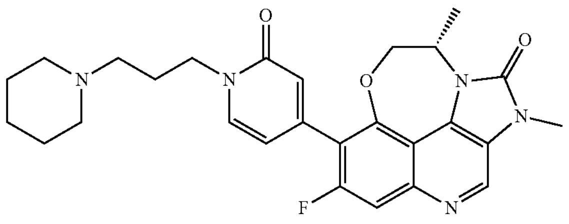

-continued
A-147
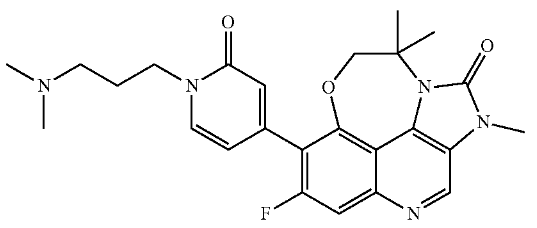
A-148
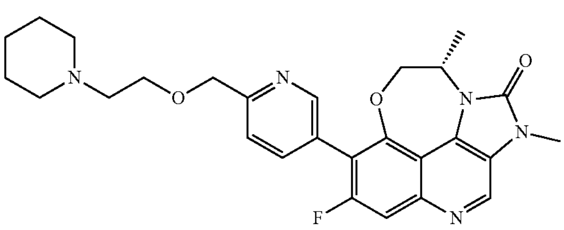
A-149
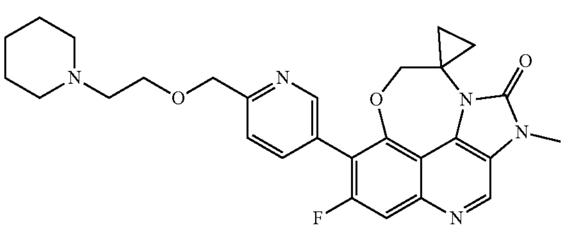
A-150
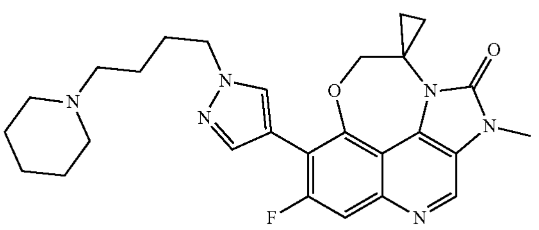
A-151
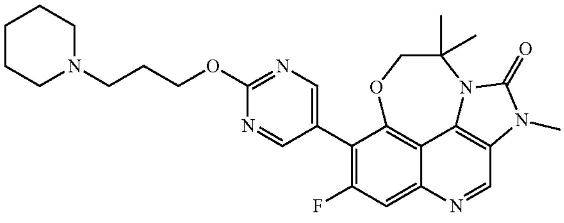
A-152
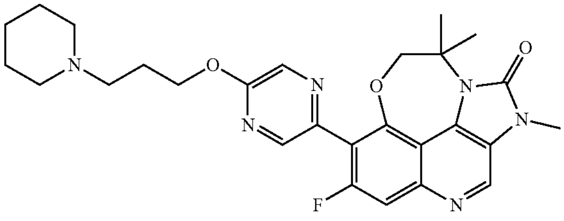
-continued
A-153
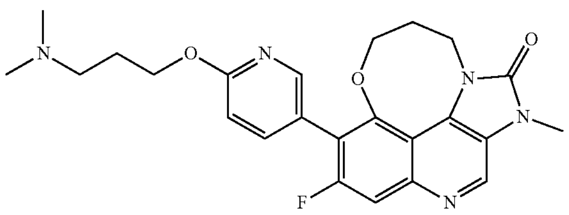
A-154
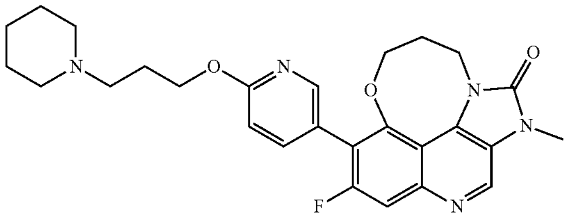
A-155
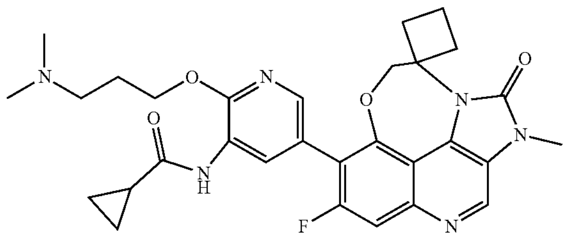
A-156
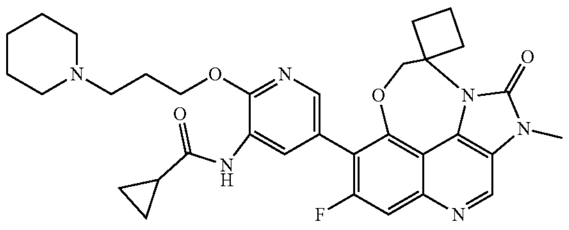
A-157
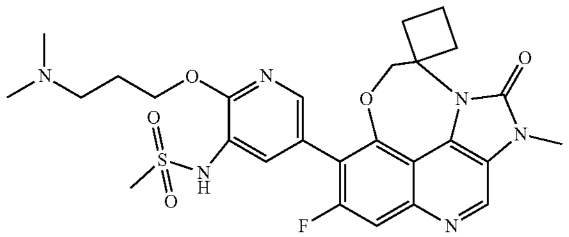
A-158
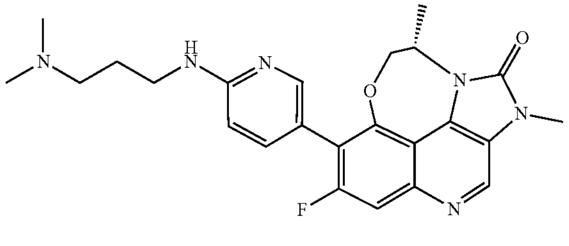

-continued
A-159
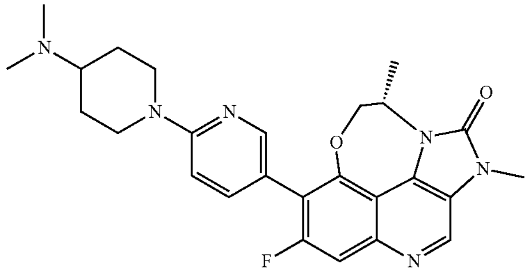
A-160
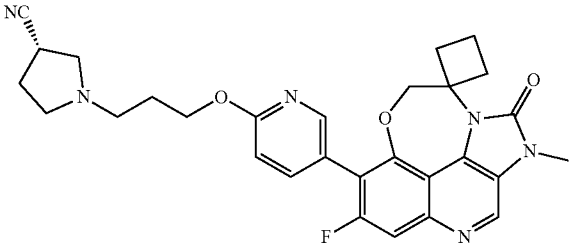
A-161
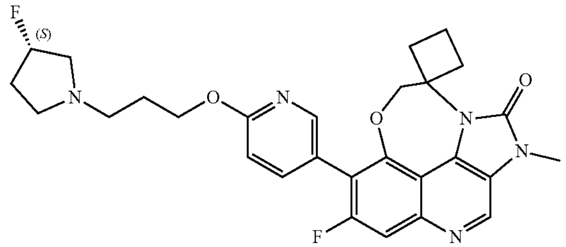
A-162
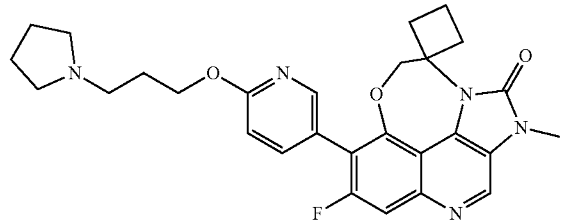
A-163
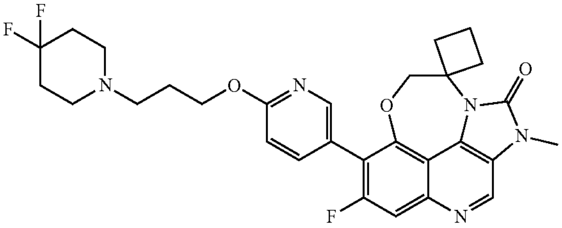
A-164
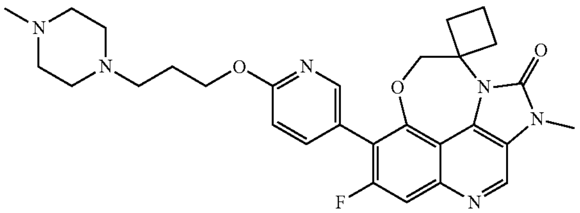
-continued
A-165
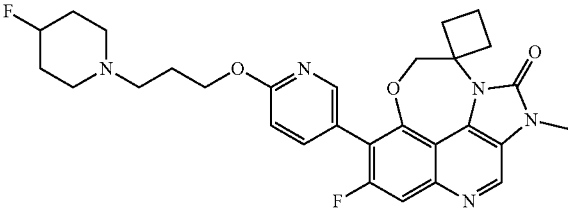
A-166
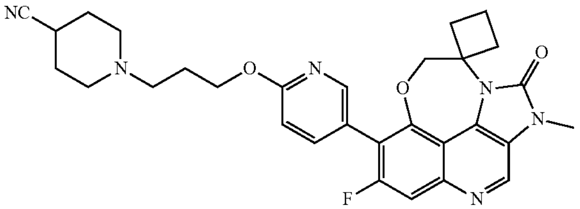
A-167
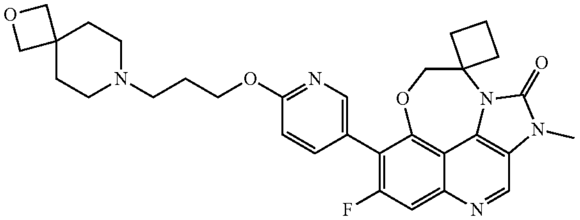
A-168
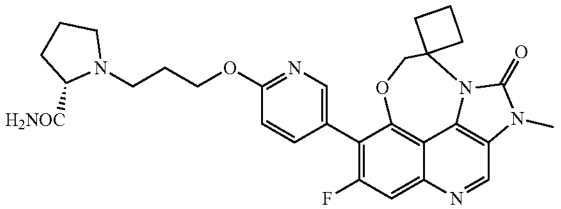
A-169
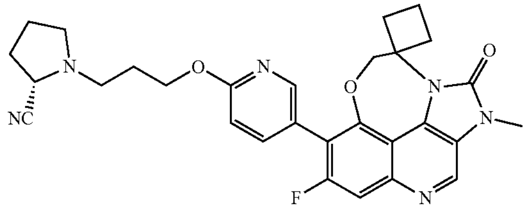
A-170
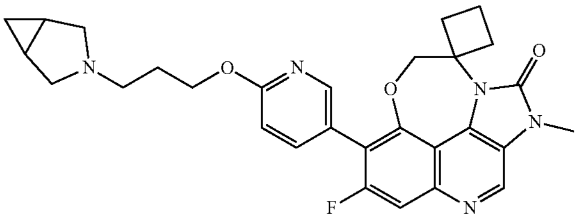

-continued
A-171
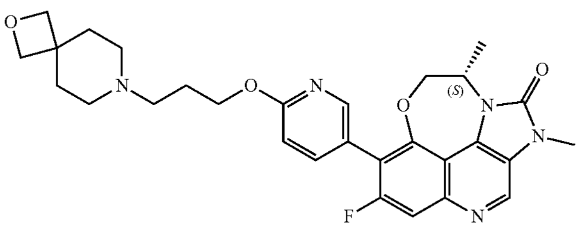
A-172
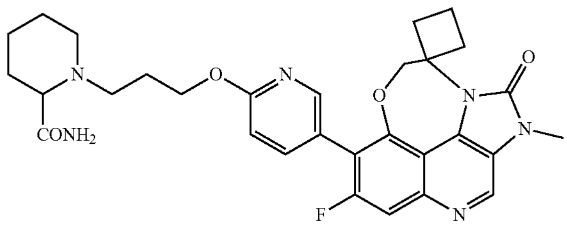
A-173
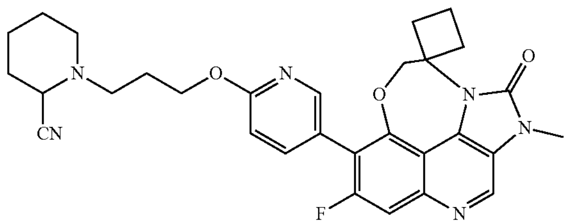
A-174
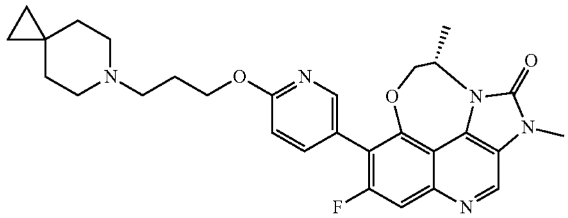
A-175
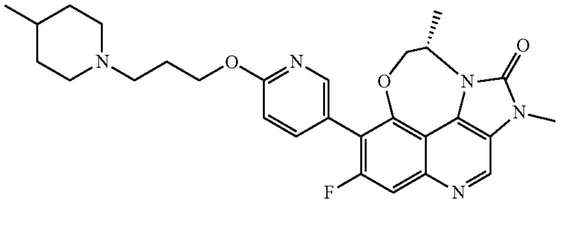
A-176
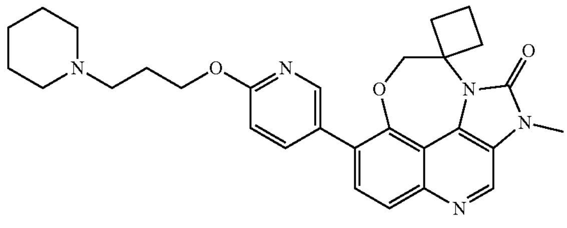
-continued
A-177
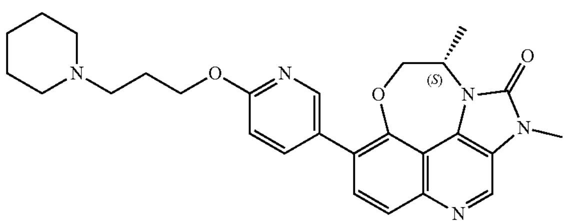
A-178
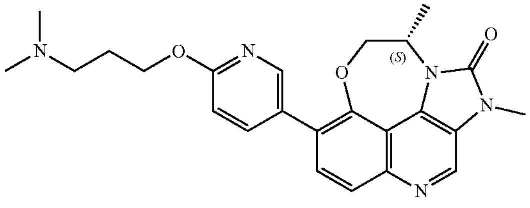
A-179
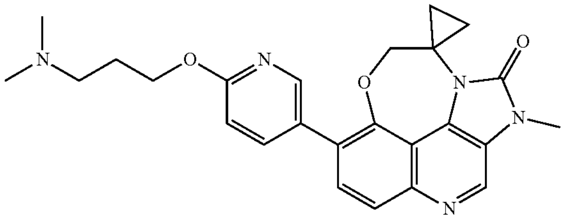
A-180
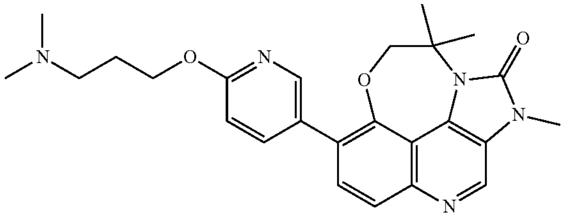
A-181
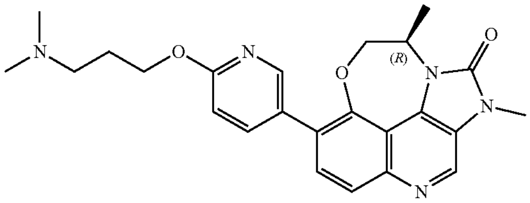
A-182
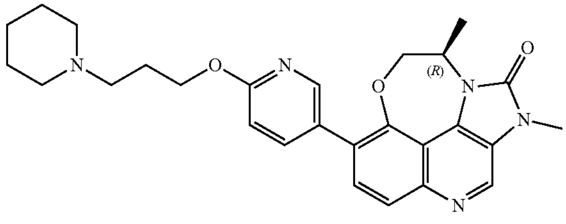

-continued
A-183
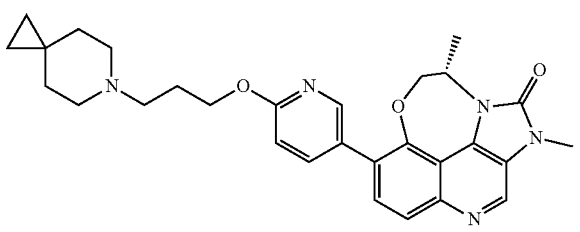
A-184
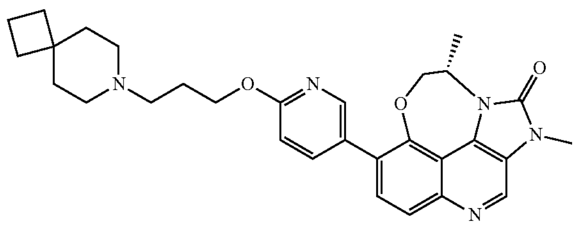
A-185
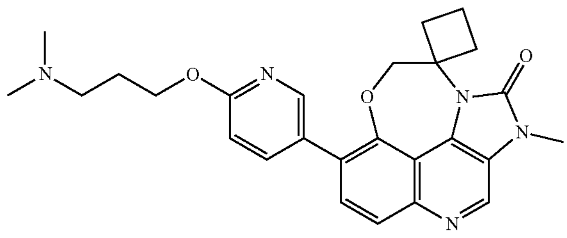
A-186
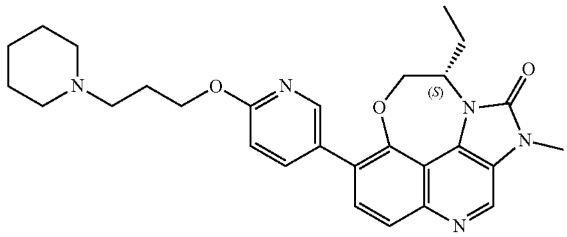
A-187
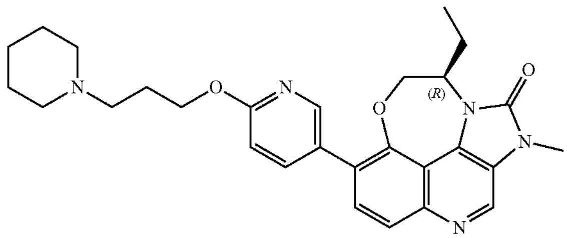
A-188
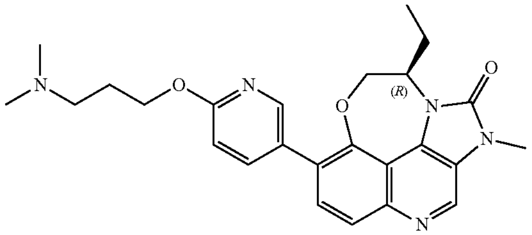
-continued
A-189
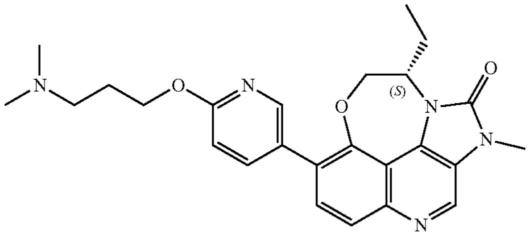
A-190
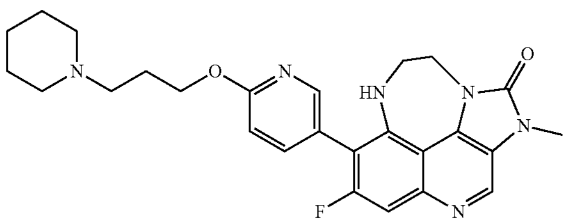
A-191
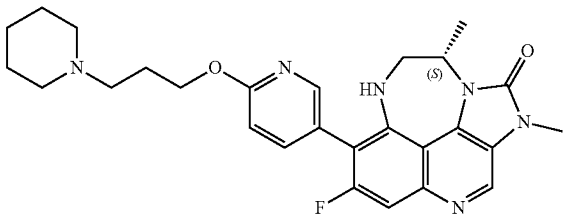
A-192
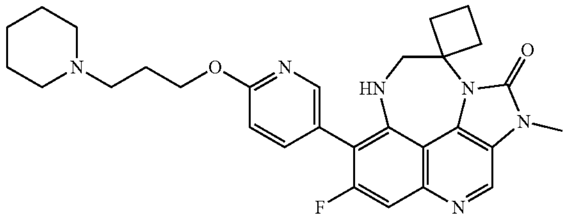
A-193
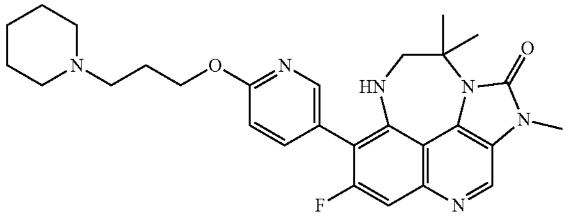
A-194
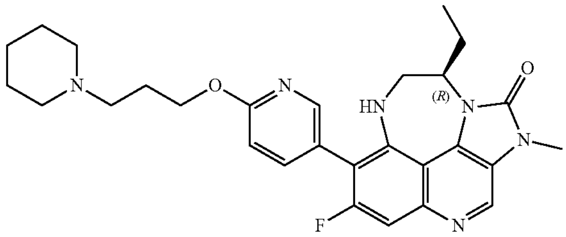

-continued
A-195
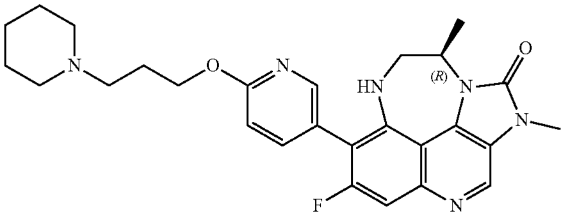
A-196
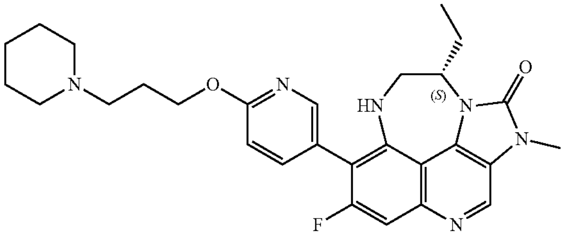
A-197
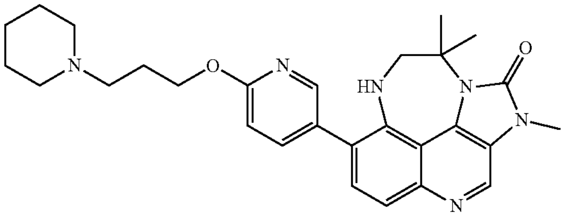
A-198
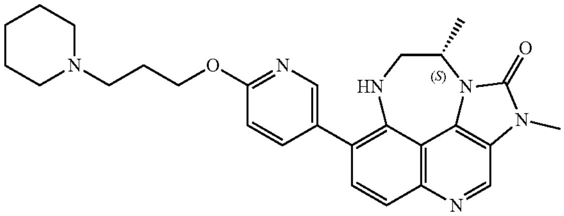
A-199
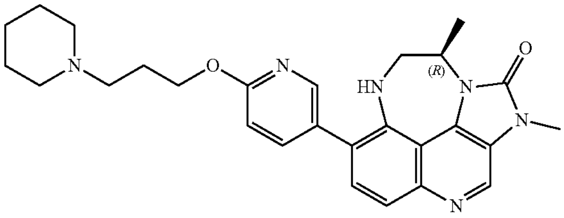
A-200
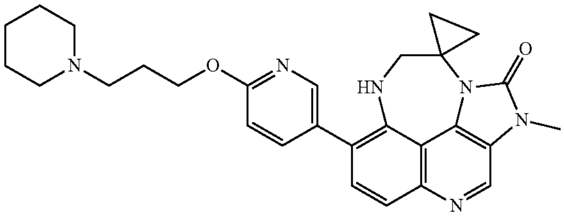
-continued
A-201
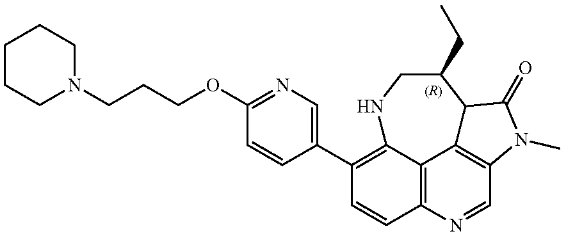
A-202
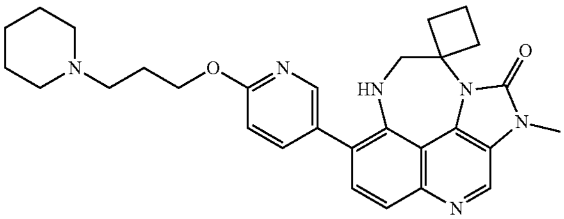
A-203
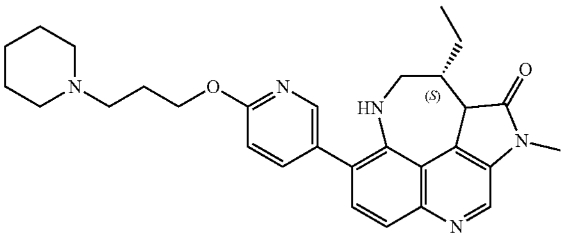
A-204
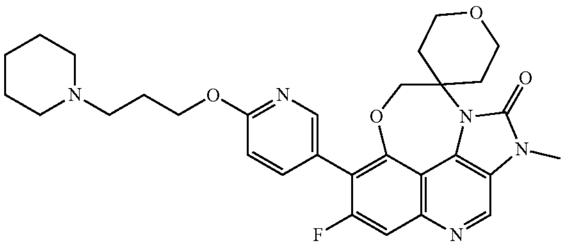
A-205
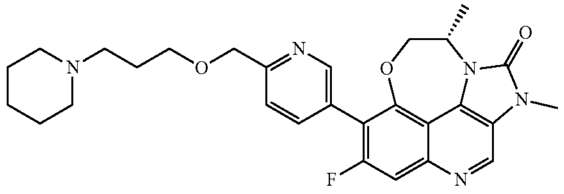
A-206
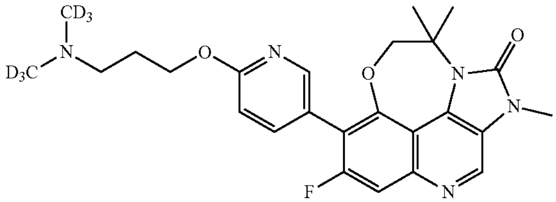

-continued

A-207

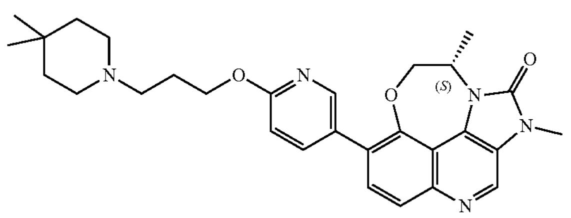

A-208

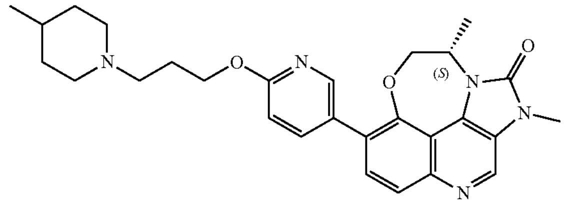

A-209

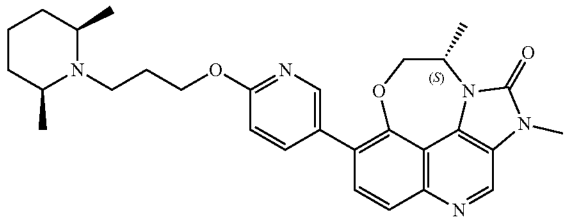

A-210

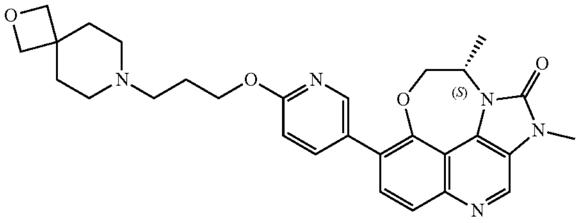

A-211

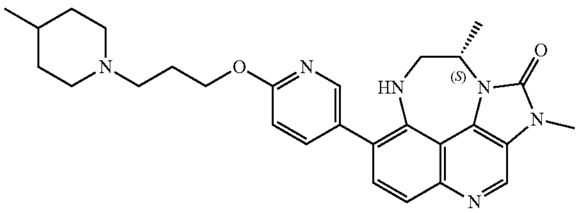

A-212

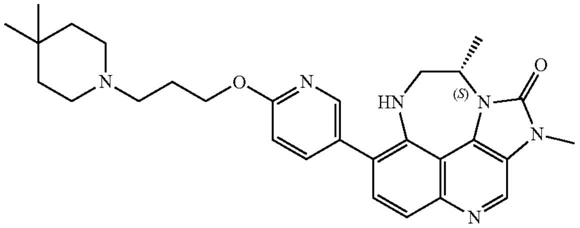

-continued

A-190-6

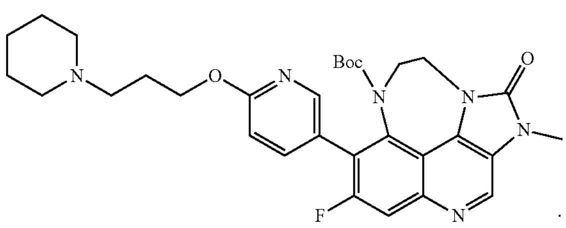

.

23. A pharmaceutical composition, comprising the compound or the tautomer, optical isomer, geometric isomer, solvate, isotopic derivative, or pharmaceutically acceptable salt thereof according to claim 1, and a pharmaceutically acceptable excipient.

24. A pharmaceutical composition, comprising the compound or the tautomer, optical isomer, geometric isomer, solvate, isotopic derivative, or pharmaceutically acceptable salt thereof according to claim 1, as well as at least one additional anti-tumor agent; or a pharmaceutical composition, comprising the compound or the tautomer, optical isomer, geometric isomer, solvate, isotopic derivative, or pharmaceutically acceptable salt thereof according to claim 1, as well as at least one additional anti-tumor agent, said anti-tumor agent being selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738.

25. An intermediate for preparing the compound according to claim 1, having a structure as represented by formula (M-2) or formula (M-3):

(M-2)

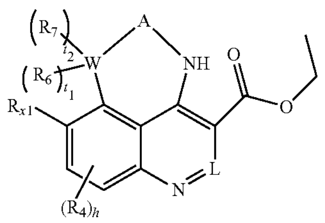

(M-3)

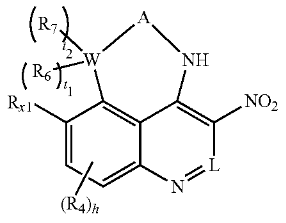

wherein $R_{x1}$ is selected from the group consisting of halogen and hydrogen, and $R_4$, $R_6$, $R_7$, A, W, L, $t_1$, $t_2$, and h are as defined in claim 1;

or having a structure as represented by formula (M-4):

(M-4)

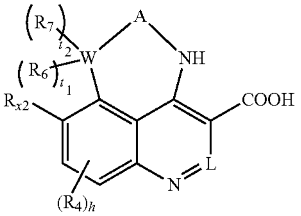

wherein $R_{x2}$ is selected from the group consisting of halogen and hydrogen; and $R_4$, $R_6$, $R_7$, A, W, L, $t_1$, $t_2$, and h are as defined in claim 1; or having a structure as represented by formula (M-5):

(M-5)

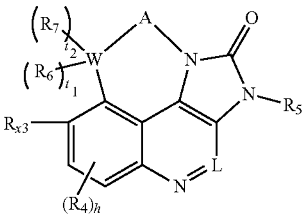

wherein $R_{x3}$ is selected from the group consisting of halogen and hydrogen; and $R_4$, $R_5$, $R_6$, $R_7$, A, W, L, $t_1$, $t_2$, and h are as defined in claim 1; or having a structure as represented by formula (M-6):

(M-6)

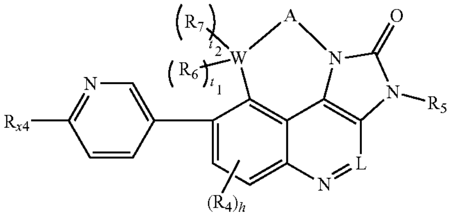

wherein $R_{x4}$ is selected from the group consisting of halogen and hydrogen; and $R_4$, $R_5$, $R_6$, $R_7$, A, W, L, $t_1$, $t_2$, and h are as defined in claim 1.

26. An intermediate as follows for preparing the compound according to claim 1:

M-1

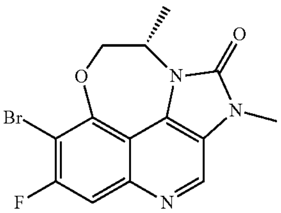

-continued

M-2

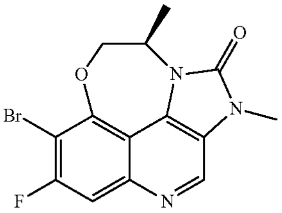

M-3

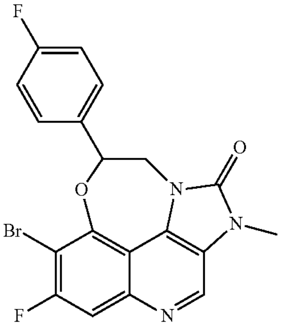

M-4

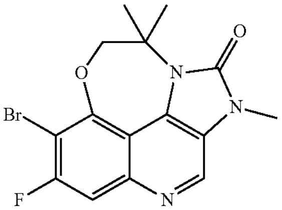

M-5

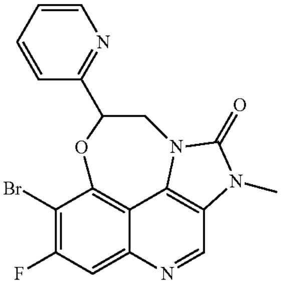

M-6

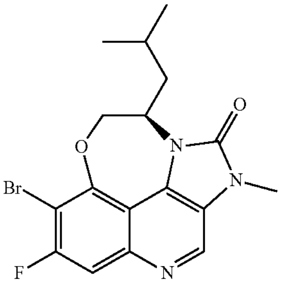

M-7

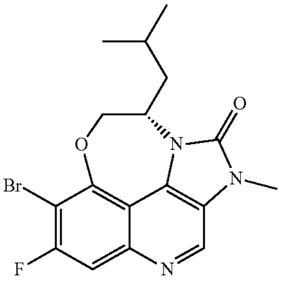

-continued
M-8
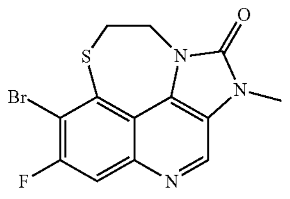
M-9
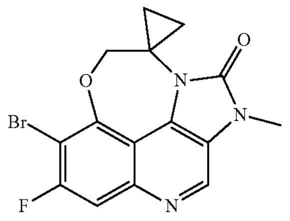
M-10
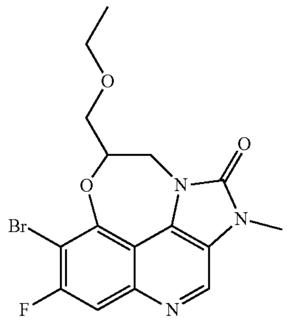
M-11
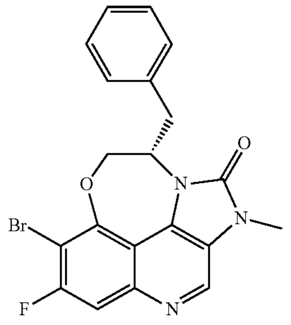
M-12
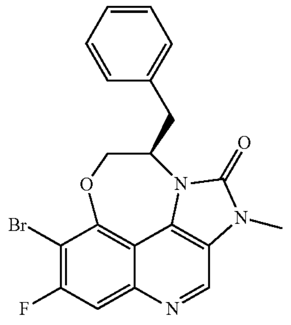
M-13
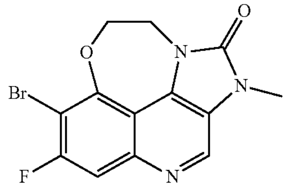
-continued
M-14
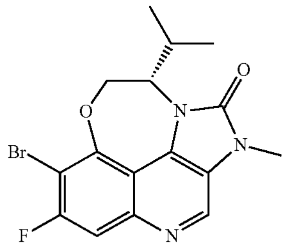
M-15
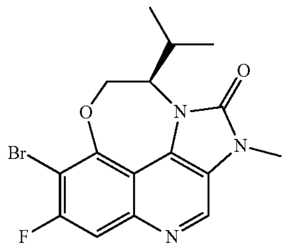
M-16
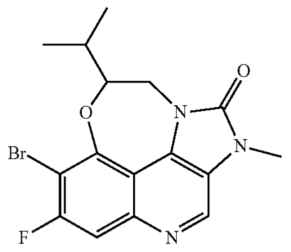
M-17
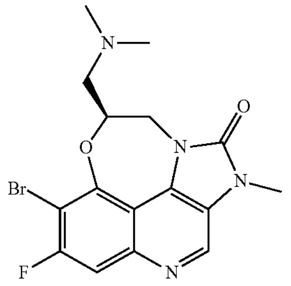
M-18
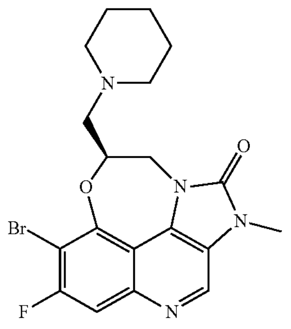
M-19
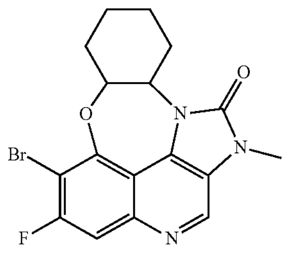

-continued
M-20
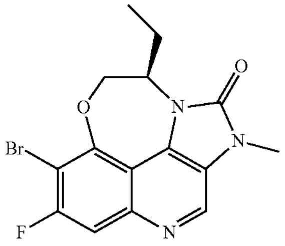
M-21
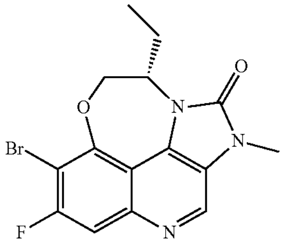
M-22
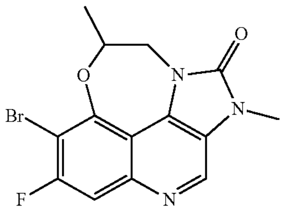
M-23
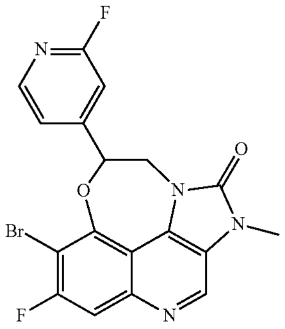
M-24
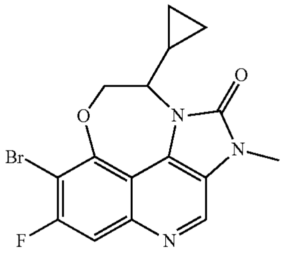
M-25
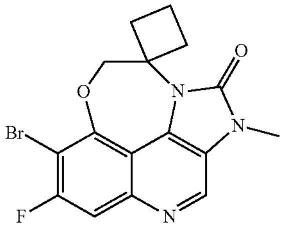
-continued
M-26
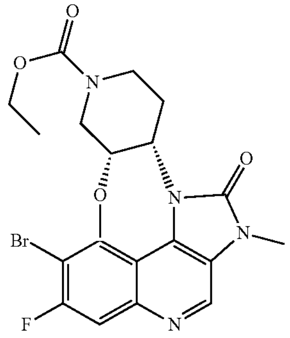
M-27
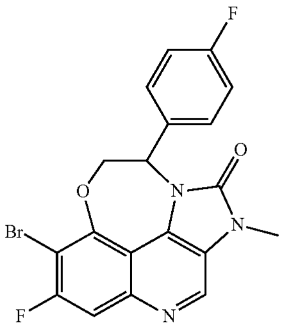
M-28
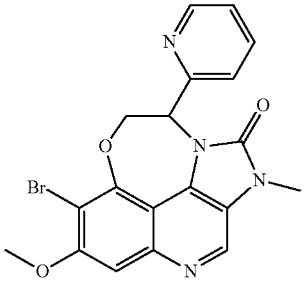
M-29
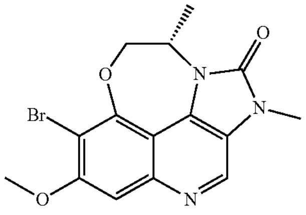
M-30
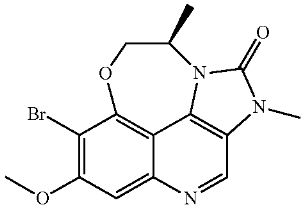

-continued
M-31
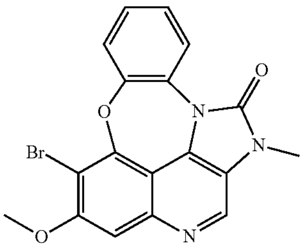
M-32
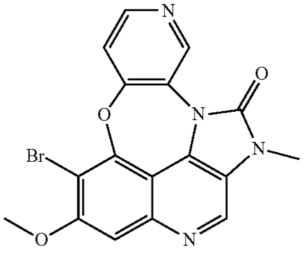
M-33
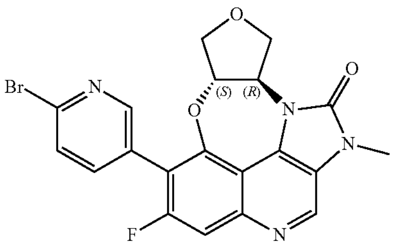
M-34
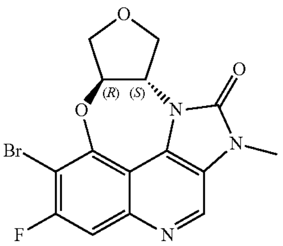
M-35
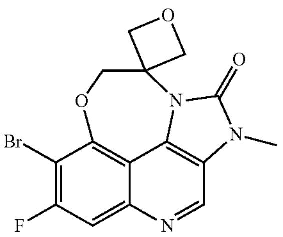
M-36
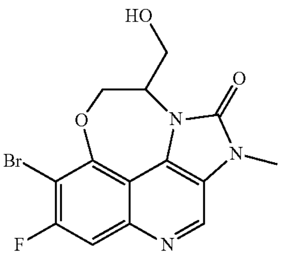
-continued
M-37
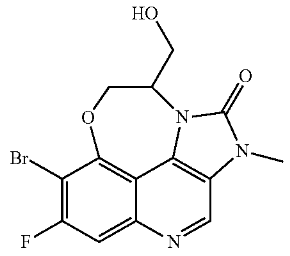
M-38
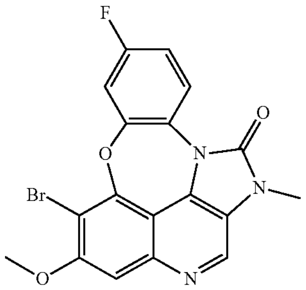
M-39
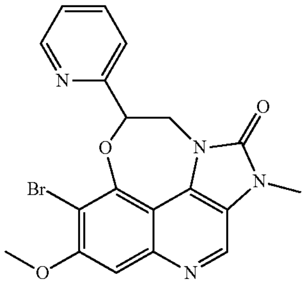
M-40
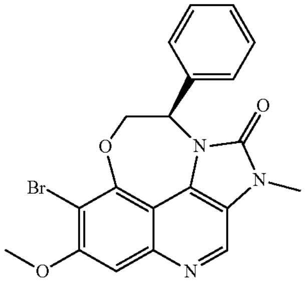
M-1-4
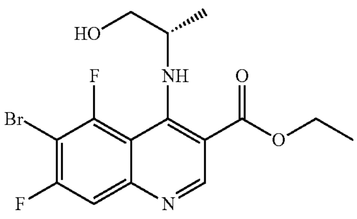
M-1-5
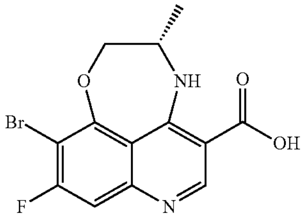

-continued
M-1-6
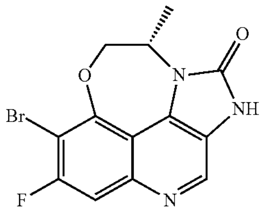
M-28-4
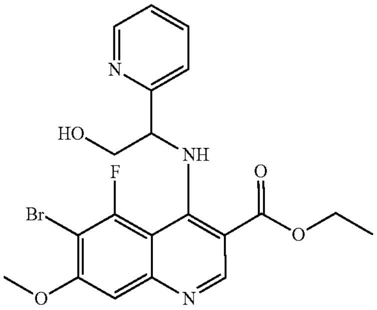
M-28-5
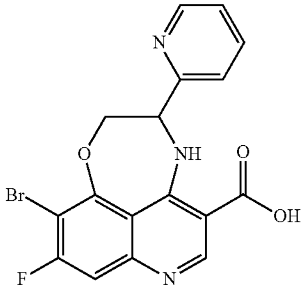
M-28-6
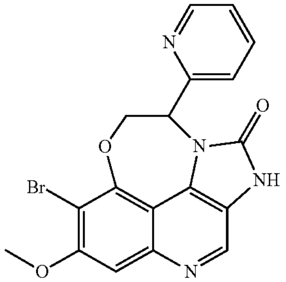
M-31-1
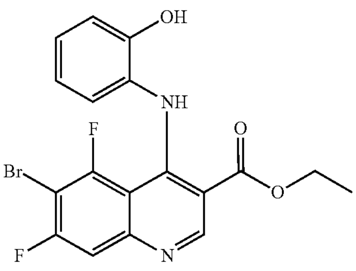
-continued
M-31-2
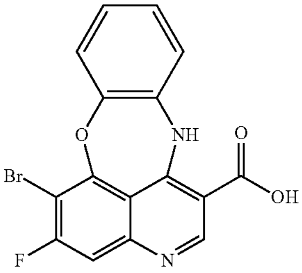
M-31-3
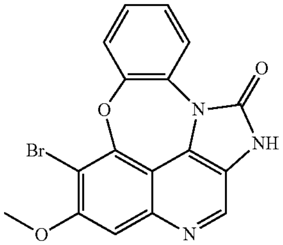
M-31-4
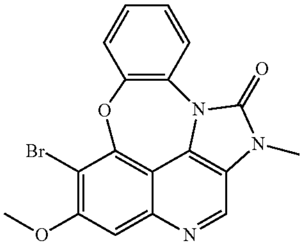
M-41
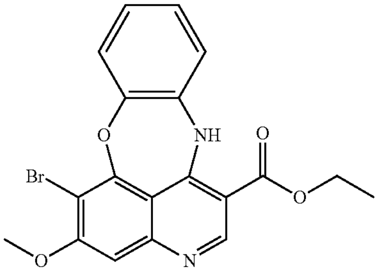
M-42
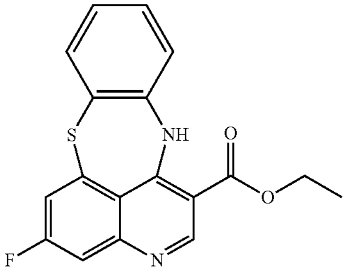
M-43
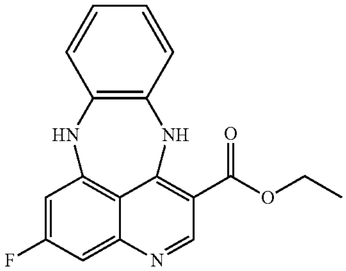

-continued
M-44
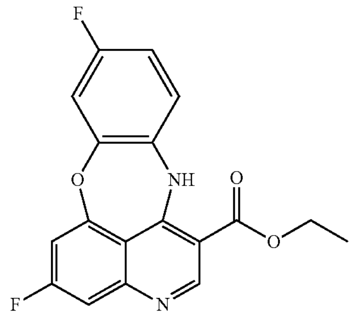
M-45
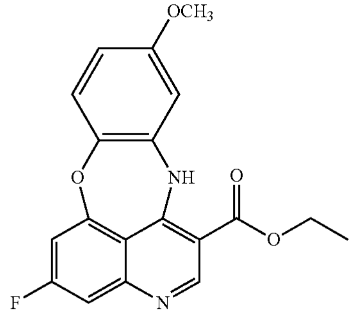
M-46
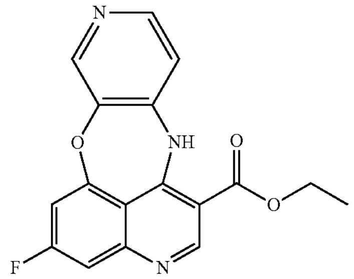
M-47
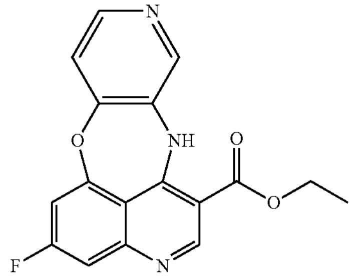
M-48
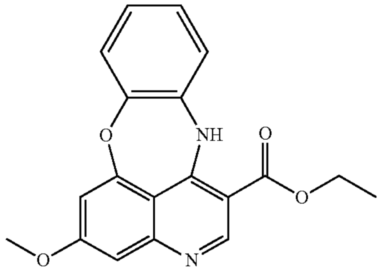
-continued
M-49
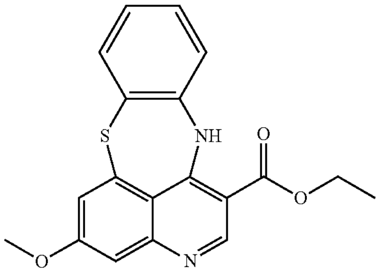
M-50
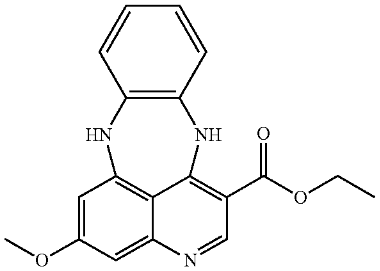
M-51
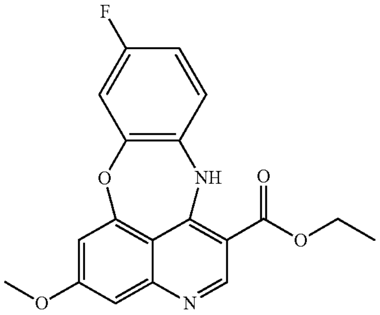
M-52
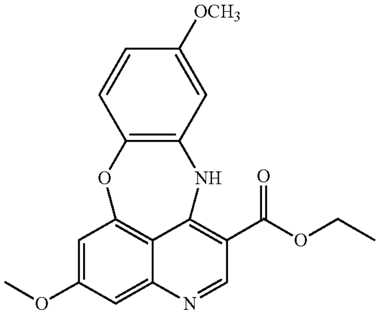
M-53
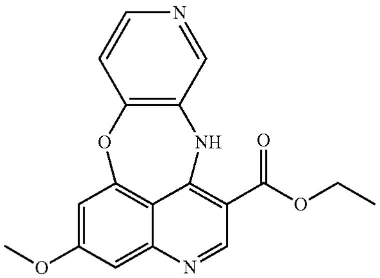

-continued
M-54
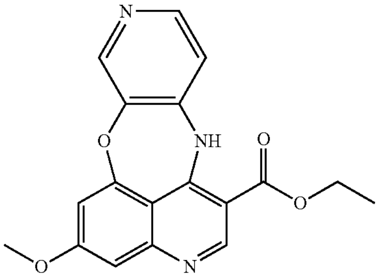
M-55
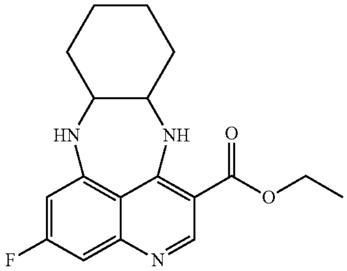
M-56
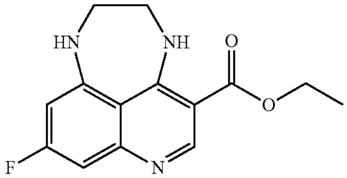
M-57
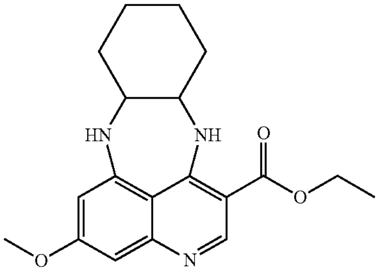
M-58
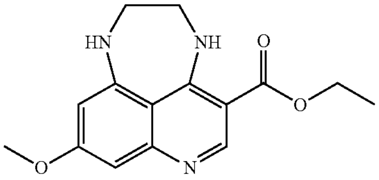
M-59
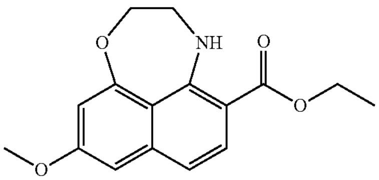
-continued
M-60
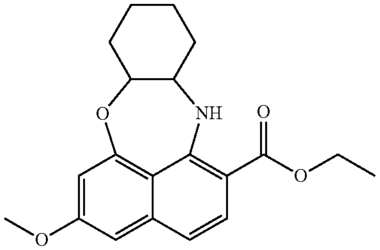
A-1-1
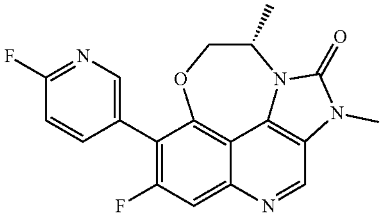
A-3-1
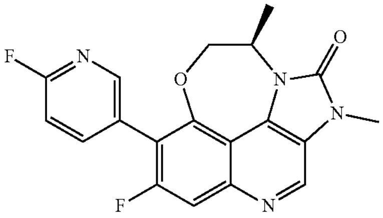
A-5-1
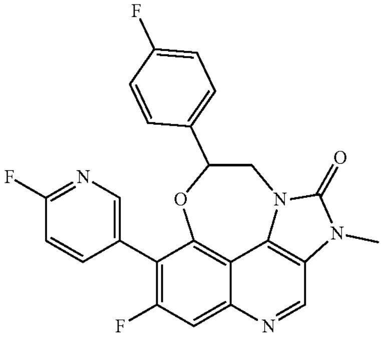
A-6-1
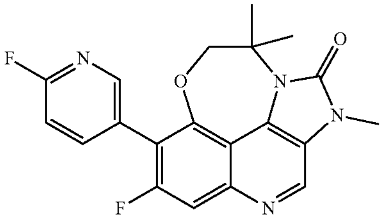
A-7-1
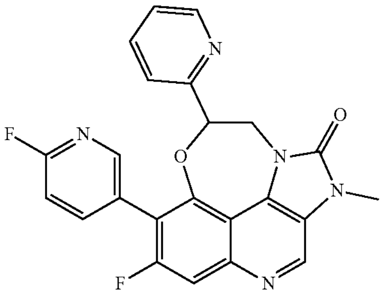

-continued
A-8-1
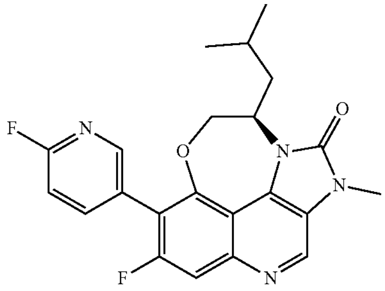
A-9-1
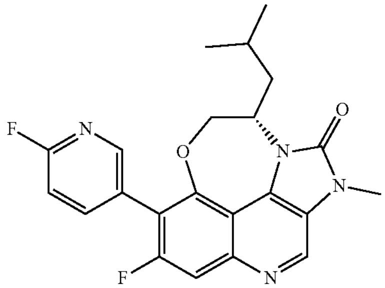
A-10-1
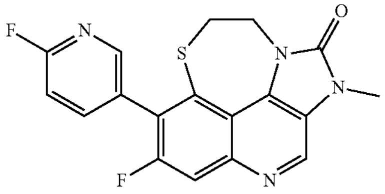
A-11-1
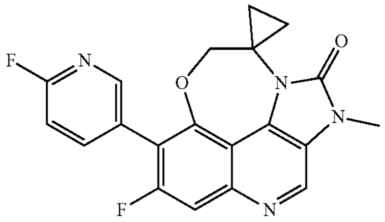
A-12-1
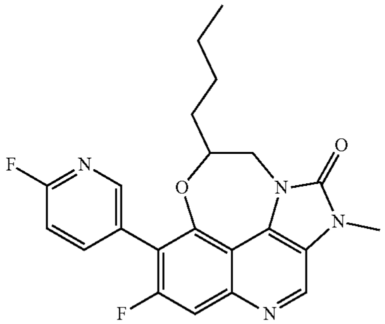
-continued
A-13-1
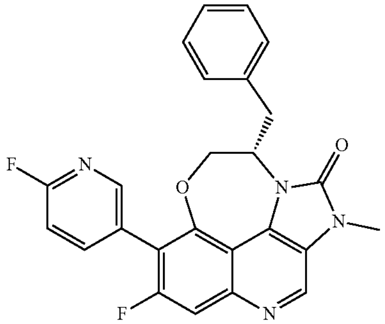
A-14-1
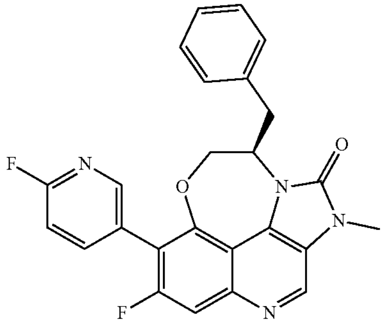
A-15-1
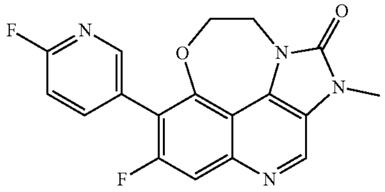
A-16-1
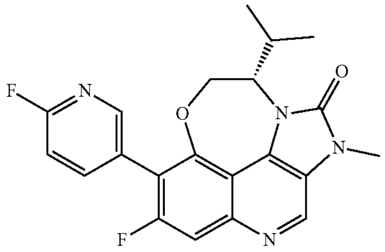
A-17-1
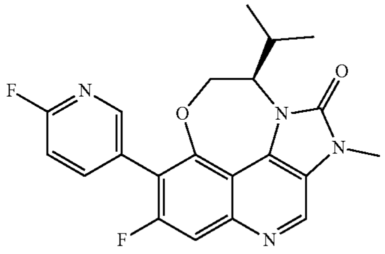
A-18-1
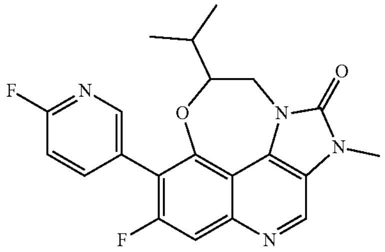

-continued
A-19-1
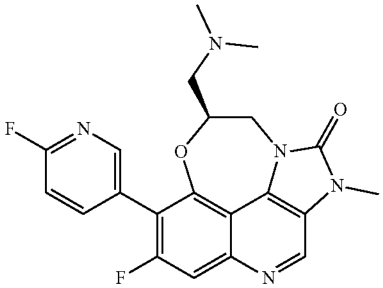
A-20-1
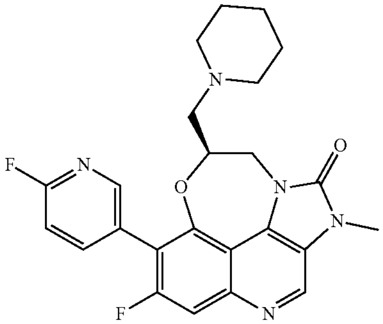
A-21-1
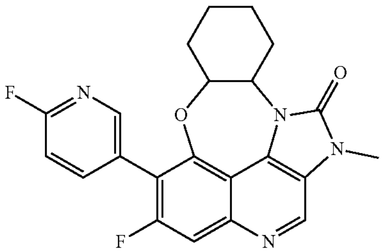
A-22-1
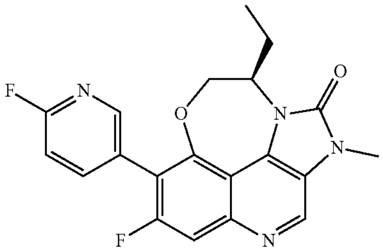
A-23-1
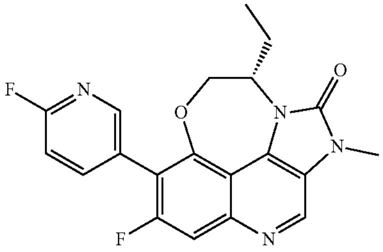
A-24-1
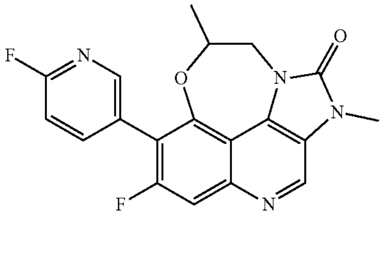
-continued
A-27-1
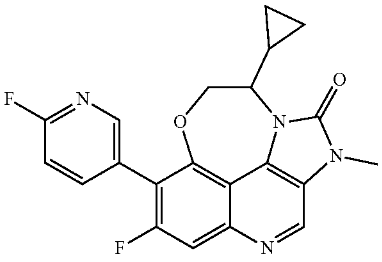
A-28-1
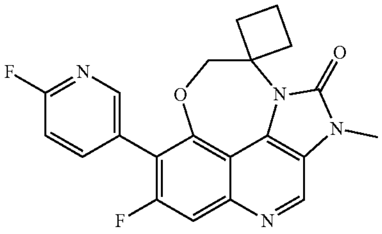
A-31-1
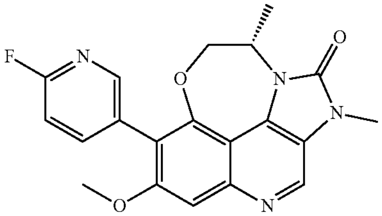
A-32-1
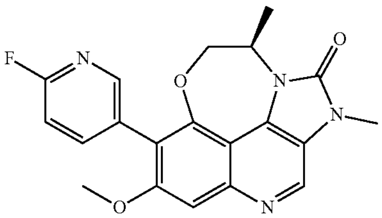
A-41-1
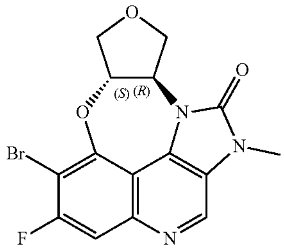
A-41-2
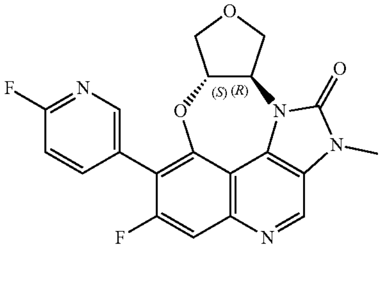

-continued
A-42-1
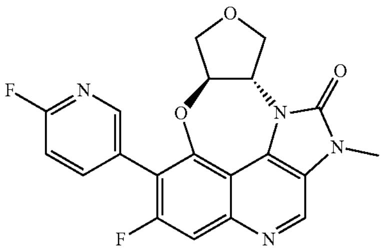
A-43-1
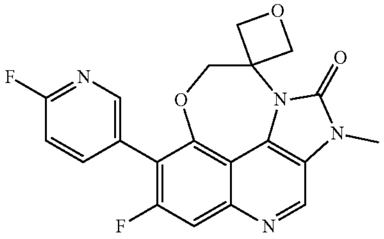
A-49-1
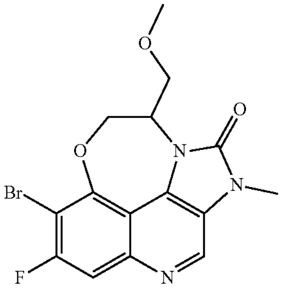
A-52-1
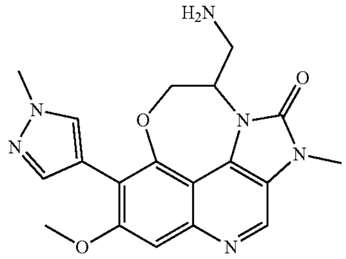
A-67-1
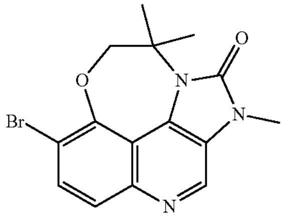
A-67-2
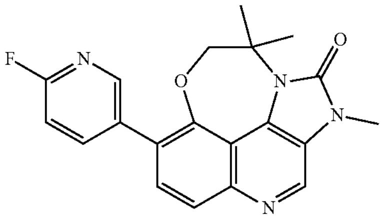
-continued
A-176-1
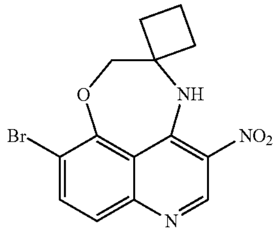
A-176-2
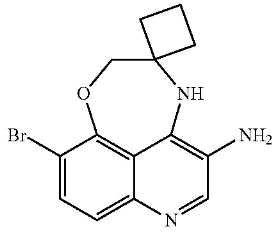
A-176-3
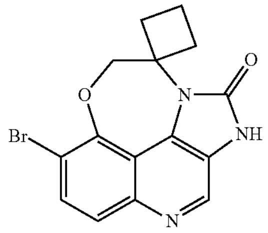
A-176-4
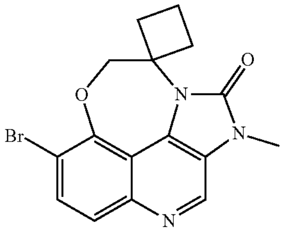
A-181-1
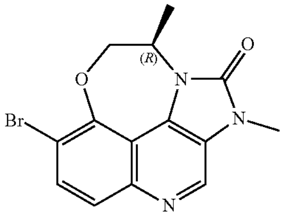
A-181-2
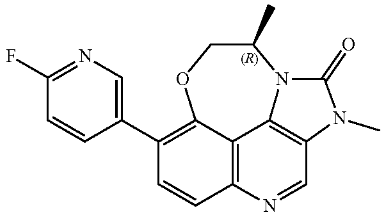
A-183-1
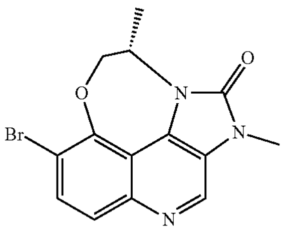

-continued
A-183-2
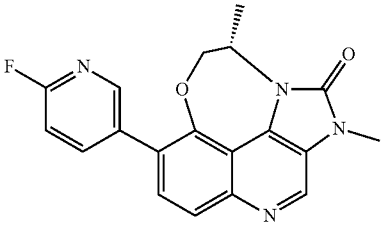
A-190-1
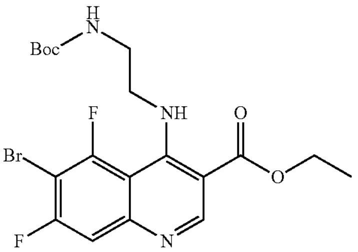
A-190-2
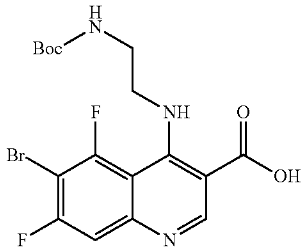
A-190-3
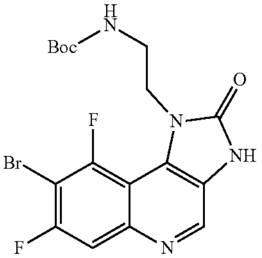
A-190-4
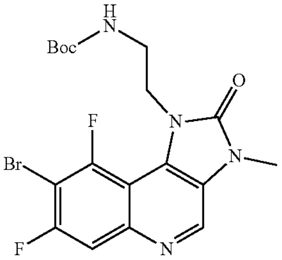
A-190-5
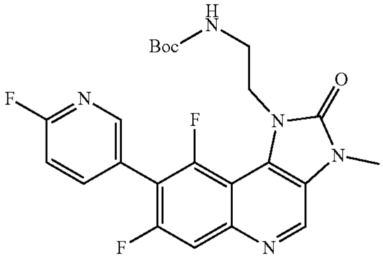
-continued
A-194-1
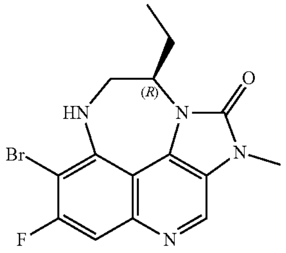
A-197-1
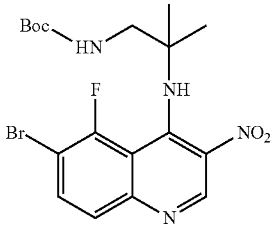
A-197-2
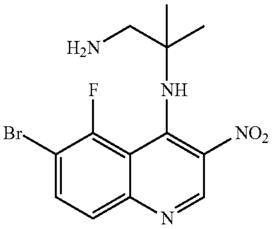
A-197-3
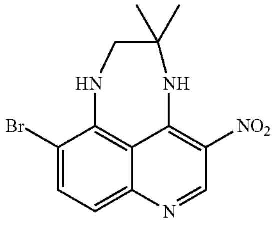
A-197-4
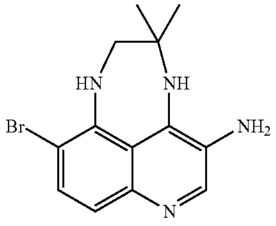
A-197-5
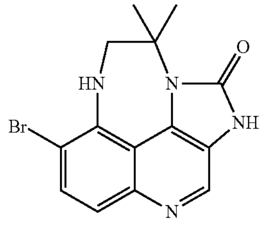

-continued
A-197-6
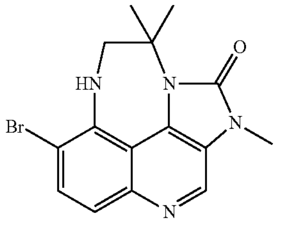
A-200-1
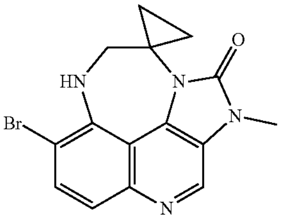
A-201-1
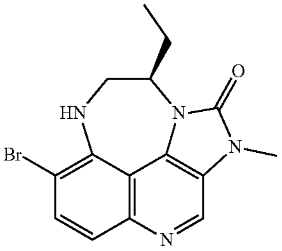
A-204-1
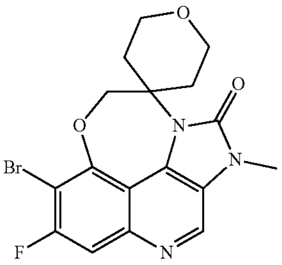
-continued
A-204-1
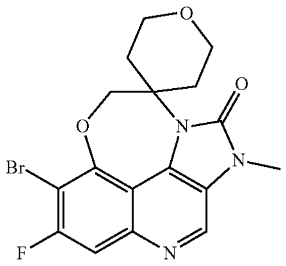
A-204-2
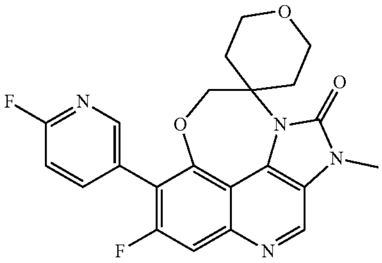
A-211-1
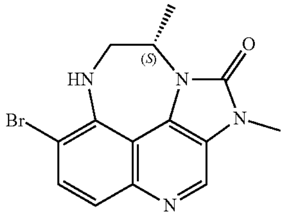
A-211-2
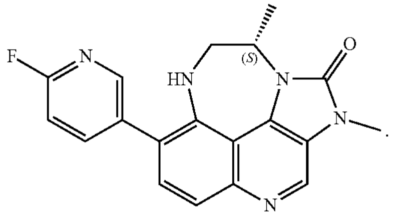
27. A method for preparing the compound according to claim 1, being selected from any one of the following synthetic schemes:
synthetic scheme 1:
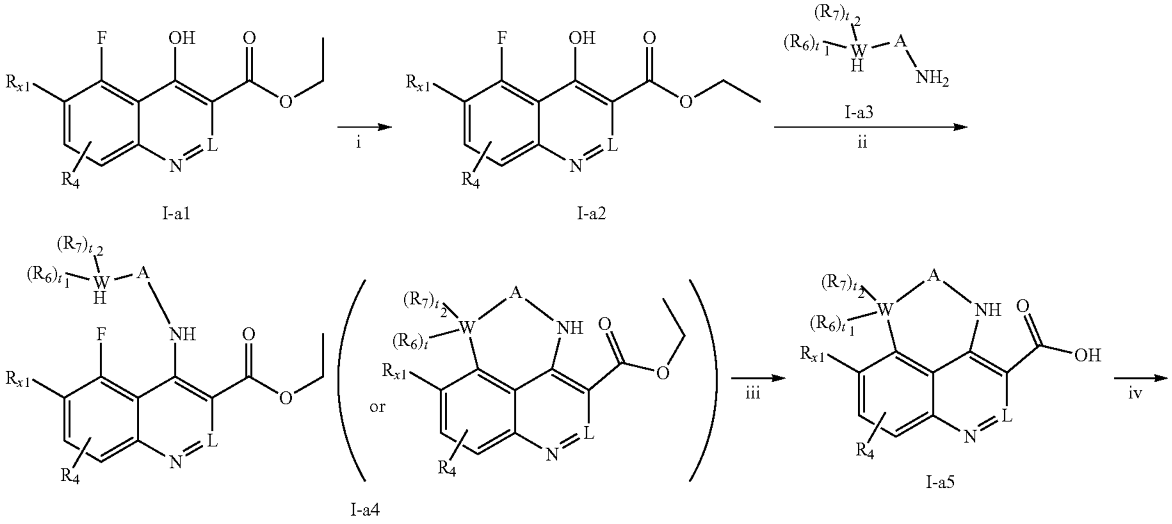

-continued

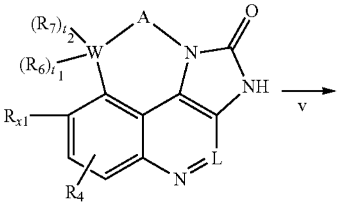

I-a6

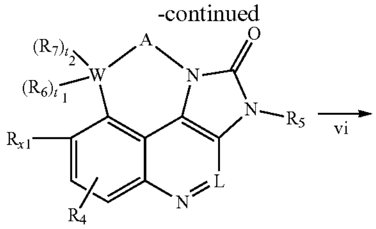

I-a7

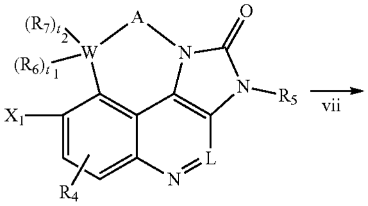

I-a8

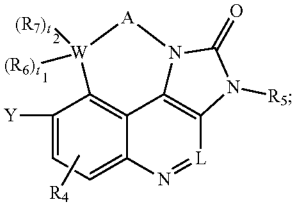

(I)

wherein i) compound I-a1 is converted to compound I-a2 via a substitution reaction;

ii) compound I-a2 is converted to compound I-a4 via a substitution reaction and an optional ring-closing reaction;

iii) compound I-a4 is converted to compound I-a5 via an optional ring-closing reaction and a hydrolysis reaction;

iv) compound I-a5 is converted to compound I-a6 via a ring-closing reaction;

v) compound I-a6 is converted to compound I-a7 via a substitution reaction;

vi) compound I-a7 is converted to compound I-a8 via a coupling reaction;

vii) compound I-a8 is converted to compound of formula I via a substitution reaction;

synthetic scheme 2:

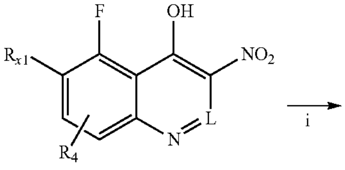

I-b1

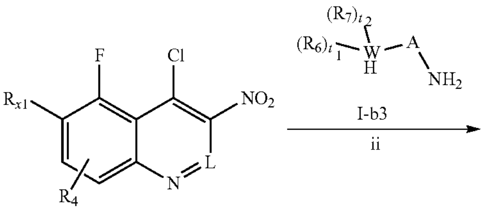

I-b2 I-b3

-continued

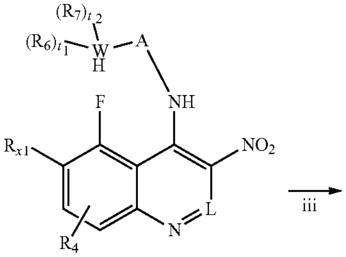

I-b4

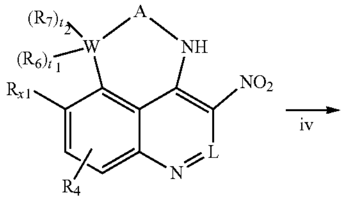

I-b5

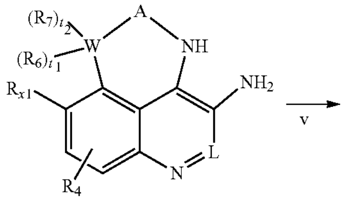

I-b6

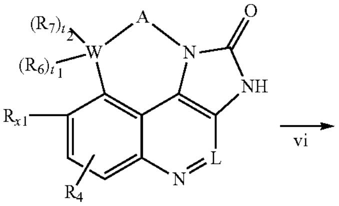

I-b7

-continued

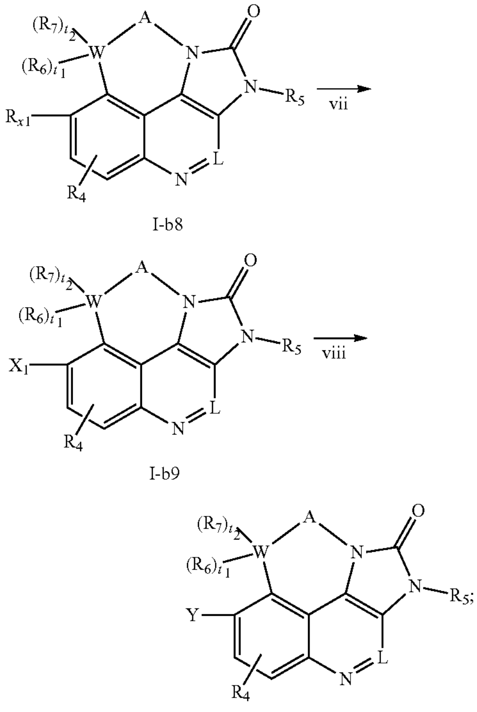

I-b8

I-b9

(I)

wherein i) compound I-b1 is used as a basic starting material to obtain compound I-b2 via a substitution reaction;

ii) compound I-b2 and compound I-b3 are used as basic starting materials to obtain compound I-b4 via a substitution reaction;

iii) compound I-b4 is used as a basic starting material to obtain compound I-b5 via a ring-closing reaction;

iv) compound I-b5 is used as a basic starting material to obtain compound I-b6 via a reduction reaction;

v) compound I-b6 is used as a basic starting material to obtain compound I-b7 via a ring-closing reaction;

vi) compound I-b7 is used as a basic starting material and reacted under basic conditions to obtain compound I-b8 via a substitution reaction;

vii) compound I-b8 is used as a basic starting material to obtain compound I-b9 via a coupling reaction;

viii) compound I-b9 is used as a basic starting material to obtain the compound of formula I via a substitution reaction;

synthetic scheme 3:

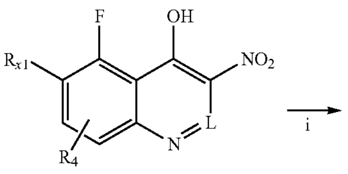

I-b1

-continued

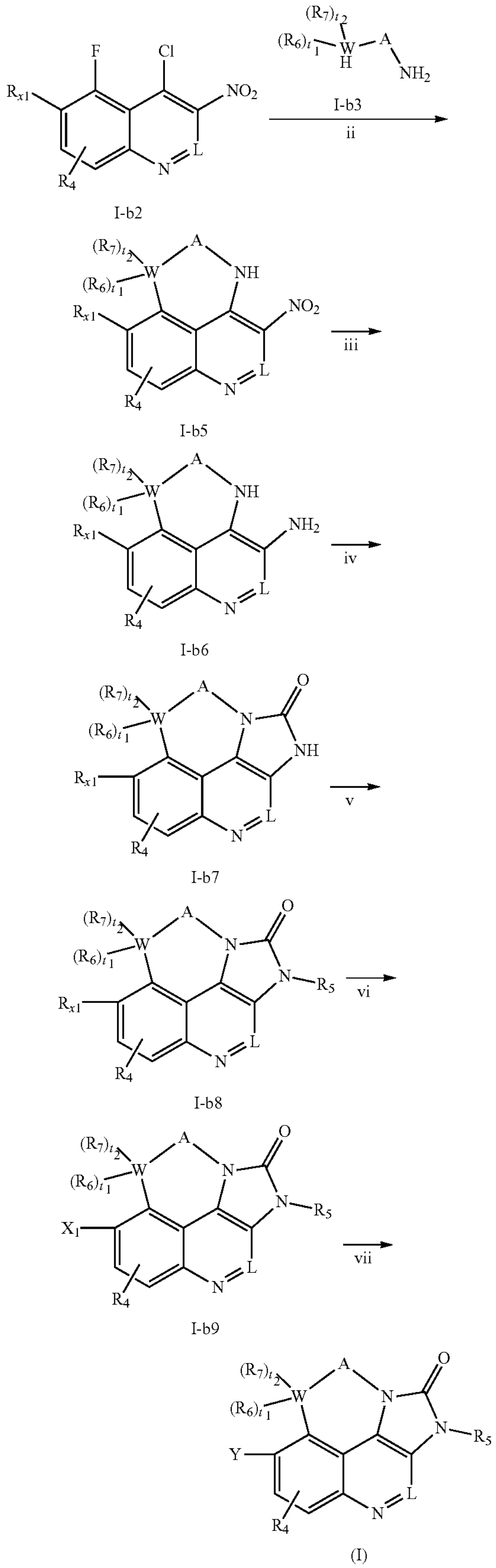

I-b2

I-b5

I-b6

I-b7

I-b8

I-b9

(I)

wherein i) compound I-b1 is used as a basic starting material to obtain compound I-b2 via a substitution reaction;

ii) compound I-b2 and compound I-b3 are used as basic starting materials to obtain compound I-b5 via a substitution reaction and a ring-closing reaction;

iii) compound I-b5 is used as a basic starting material to obtain compound I-b6 via a reduction reaction;

iv) compound I-b6 is used as a basic starting material to obtain compound I-b7 via a ring-closing reaction;

v) compound I-b7 is used as a basic starting material and reacted under basic conditions to obtain compound I-b8 via a substitution reaction;

vi) compound I-b8 is used as a basic starting material to obtain compound I-b9 via a coupling reaction;

vii) compound I-b9 is used as a basic starting material to obtain the compound of formula I via a substitution reaction;

wherein $R_{x1}$ is selected from the group consisting of halogen and hydrogen, and $X_1$, $R_4$, $R_5$, $R_6$, $R_7$, A, W, L, $t_1$, and $t_2$ are as defined in claim 1;

wherein the reaction is carried out in an organic solvent; the organic solvent is selected from the group consisting of ethers, halogenated hydrocarbons, alcohols, alkanes, aromatic hydrocarbons, esters, acetonitrile, N,N-dimethyl formamide, and mixtures thereof, and wherein the base is selected from the group consisting of potassium carbonate, sodium carbonate, magnesium carbonate, sodium bicarbonate, cesium carbonate, lithium carbonate, sodium hydroxide, potassium hydroxide, sodium hydride, lithium hydroxide, magnesium hydroxide, cesium hydroxide, triethylamine, diisopropylethylamine, piperidine, pyrrole, pyridine, dimethylpyridine, and dimethylaminopyridine.

28. A method for treating a cancer, comprising administering the compound or the tautomer, optical isomer, geometric isomer, solvate, isotopic derivative, or pharmaceutically acceptable salt thereof according to claim 1 to a subject in need thereof, wherein said cancer is a solid tumor or wherein said cancer is breast cancer, non-small cell lung cancer, brain glioma, colon cancer, rectal cancer, malignant glioma, gastric cancer, ovarian cancer, head and neck squamous cell carcinoma, small cell lung cancer, or glioblastoma; or a method for treating a disease and/or disorder which is at least partially mediated by ATM kinase, comprising administering the compound or the tautomer, optical isomer, geometric isomer, solvate, isotopic derivative, or pharmaceutically acceptable salt thereof according to claim 1 to a subject in need thereof, wherein said disease and/or disorder which is at least partially mediated by ATM kinase is a cancer; wherein said cancer is a solid tumor or wherein said cancer is breast cancer, non-small cell lung cancer, brain glioma, colon cancer, rectal cancer, malignant glioma, gastric cancer, ovarian cancer, head and neck squamous cell carcinoma, small cell lung cancer, or glioblastoma.

29. The method according to claim 28, wherein the method comprises administering the compound or the tautomer, optical isomer, geometric isomer, solvate, isotopic derivative, or pharmaceutically acceptable salt thereof according to claim 1 with at least one additional anti-tumor agent or therapeutic treatment to a subject in need thereof; or wherein the method comprises administering the compound or the tautomer, optical isomer, geometric isomer, solvate, isotopic derivative, or pharmaceutically acceptable salt thereof according to claim 1 with at least one additional anti-tumor agent to the subject in need thereof, wherein said anti-tumor agent is selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738; or wherein the method comprises administering the compound or the tautomer, optical isomer, geometric isomer, solvate, isotopic derivative, or pharmaceutically acceptable salt thereof according to claim 1 with at least one additional therapeutic treatment to a subject in need thereof, wherein the therapeutic treatment is radiation therapy.

30. A pharmaceutical composition, comprising the compound or the tautomer, optical isomer, geometric isomer, solvate, isotopic derivative, or pharmaceutically acceptable salt thereof according to claim 22 and a pharmaceutically acceptable excipient.

31. A pharmaceutical composition, comprising the compound or the tautomer, optical isomer, geometric isomer, solvate, isotopic derivative, or pharmaceutically acceptable salt thereof according to claim 22, as well as at least one additional anti-tumor agent; or a pharmaceutical composition, comprising the compound or the tautomer, optical isomer, geometric isomer, solvate, isotopic derivative, or pharmaceutically acceptable salt thereof according to claim 22, as well as at least one additional anti-tumor agent, said anti-tumor agent being selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738.

32. A pharmaceutical composition, comprising the pharmaceutical composition according to claim 30, as well as at least one additional anti-tumor agent; or a pharmaceutical composition, comprising the pharmaceutical composition according to claim 30, as well as at least one additional anti-tumor agent, said anti-tumor agent being selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738.

33. A method for treating a cancer, comprising administering the compound or the tautomer, optical isomer, geometric isomer, solvate, isotopic derivative, or pharmaceutically acceptable salt thereof according to claim 22 to a subject in need thereof, wherein said cancer is a solid tumor or wherein said cancer is breast cancer, non-small cell lung cancer, brain glioma, colon cancer, rectal cancer, malignant glioma, gastric cancer, ovarian cancer, head and neck squamous cell carcinoma, small cell lung cancer, or glioblastoma; or a method for treating a disease and/or disorder which is at least partially mediated by ATM kinase, comprising administering the compound or the tautomer, optical isomer, geometric isomer, solvate, isotopic derivative, or pharmaceutically acceptable salt thereof according to claim 22 to a subject in need thereof, wherein said disease and/or disorder which is at least partially mediated by ATM kinase is a cancer, and wherein said cancer is a solid tumor or wherein said cancer is breast cancer, non-small cell lung cancer, brain glioma, colon cancer, rectal cancer, malignant glioma, gastric cancer, ovarian cancer, head and neck squamous cell carcinoma, small cell lung cancer, or glioblastoma.

34. The method according to claim 33, wherein the method comprises administering the compound or the tautomer, optical isomer, geometric isomer, solvate, isotopic derivative, or pharmaceutically acceptable salt thereof according to claim 22 with at least one additional anti-tumor agent or therapeutic treatment to a subject in need thereof; or wherein the method comprises administering the compound or the tautomer, optical isomer, geometric isomer, solvate, isotopic derivative, or pharmaceutically acceptable salt thereof according to claim 22 with at least one additional anti-tumor agent to a subject in need thereof, wherein said anti-tumor agent is selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738; or wherein the method comprises administering the compound or the tautomer, optical isomer, geometric isomer, solvate, isotopic derivative, or pharmaceutically acceptable salt thereof according to claim 22 with at least one additional therapeutic treatment to a subject in need thereof, wherein the therapeutic treatment is radiation therapy.

35. A method for treating a cancer, comprising administering the pharmaceutical composition according to claim 30 to a subject in need thereof, wherein said cancer is a solid tumor or wherein said cancer is breast cancer, non-small cell lung cancer, brain glioma, colon cancer, rectal cancer, malignant glioma, gastric cancer, ovarian cancer, head and neck squamous cell carcinoma, small cell lung cancer, or glioblastoma; or a method for treating a disease and/or disorder which is at least partially mediated by ATM kinase, comprising administering the pharmaceutical composition according to claim 30 to a subject in need thereof, wherein said disease and/or disorder which is at least partially mediated by ATM kinase is a cancer, wherein said cancer is a solid tumor or wherein said cancer is breast cancer, non-small cell lung cancer, brain glioma, colon cancer, rectal cancer, malignant glioma, gastric cancer, ovarian cancer, head and neck squamous cell carcinoma, small cell lung cancer, and glioblastoma.

36. The method according to claim 35, wherein the method comprises administering the pharmaceutical composition according to claim 30 with at least one additional anti-tumor agent or therapeutic treatment to a subject in need thereof, or wherein the method comprises administering the pharmaceutical composition according to claim 30 with at least one additional anti-tumor agent in need thereof, wherein said anti-tumor agent is selected from the group consisting of adriamycin, irinotecan, topotecan, etoposide, mitomycin, bendamustine, chlorambucil, cyclophosphamide, ifosfamide, carmustine, melphalan, bleomycin, cisplatin, oxaliplatin, carboplatin, valrubicin, idarubicin, pirarubicin, amrubicin, epirubicin, olaparib, MEDI4736, AZD1775, and AZD6738; or wherein the method comprises administering the pharmaceutical composition according to claim 30 with at least one additional therapeutic treatment to a subject in need thereof, wherein the therapeutic treatment is radiation therapy.

* * * * *